(12) United States Patent
Segal

(10) Patent No.: US 7,371,387 B2
(45) Date of Patent: *May 13, 2008

(54) VACCINE COMPOSITIONS AND METHODS OF MODULATING IMMUNE RESPONSES

(75) Inventor: Andrew Segal, Cambridge, MA (US)

(73) Assignee: Genitrix LLC, Cambridge, MA (US)

(*) Notice: Subject to any disclaimer, the term of this patent is extended or adjusted under 35 U.S.C. 154(b) by 770 days.

This patent is subject to a terminal disclaimer.

(21) Appl. No.: 10/262,828

(22) Filed: Oct. 2, 2002

(65) Prior Publication Data

US 2003/0133942 A1 Jul. 17, 2003

(51) Int. Cl.
*A61K 39/385* (2006.01)
(52) U.S. Cl. ..................... 424/192.1; 514/44
(58) Field of Classification Search ............ None
See application file for complete search history.

(56) References Cited

U.S. PATENT DOCUMENTS

| | | | | |
|---|---|---|---|---|
| 5,891,432 | A | 4/1999 | Hoo | 424/92.31 |
| 6,277,368 | B1 | 8/2001 | Hiserodt et al. | 424/93.21 |
| 6,632,436 | B2 * | 10/2003 | Segal | 424/192.1 |
| 2002/0076392 | A1 | 6/2002 | Hoo | 424/85.1 |

OTHER PUBLICATIONS

Arvieux, et al. (1988). "Antigen-bound C3b and C4b Enhance Antigen-Presenting Cell Function in Activation of Human T-Cell Clones," *Immunology* 65:229-235.
Baier, et al. (1995). "Immunogenic Targeting of Recombinant Peptide Vaccines to Human Atigen-Presenting Cells by Chimeric Anti-HLA-DR and Anti-Surface Immunoglobulin D Antibody Fab Fragments In Vitro," *Journal of Virology* 69:2357-2365.
Berg, et al. (1994). "Comparing Macrophages and Dendritic Lwukocytes as Antigen-Presenting Cells for Humoral Responses In Vivo by Antigen Targeting," *Eur J Immunol* 24:1262-1268.
Carayanniotis, et al. (1987). "Adjuvant-Free IgG Responses Induced with Antigen Coupled to Antibodies Against Class II MHC," *Nature* 327:59-61.
Chu, et al. (1993). "Receptor-Mediated Antigen Delivery into Macrophages," *Journal of Immunology* 150:48-58.
Chu, et al. (1994). "Adjuvant-Free In Vivo Targeting," *Journal of Immunology* 1538-1545.
Dempsey, et al. (1996). "C3d of Complement as a Molecular Adjubant: Bridging Innate and Acquired Immunity," *Science* 271:348-350.
Estrada, et al. (1995). "Intestinal Immunization of Mice with Antigen Conjugated to Anti-MHC Class II Antibodies," *Vaccine* 13(10):901-907.
Gossselin, et al. (1992). "Enhanced Antigen Presentation Using Human Fcγ Receptor (Monocyte/Macrophage)-Specific Immunogens," *Journal of Immunology* 149(11):3477-3481.
Jacquier-Sarlin, et al. (1995). "Modulation of Antigen Processing and Presentation by Covalently Linked Complement C3b Fragment," *Immunology* 84:164-170.
Liu, et al. (1992). "FCγ RI-Targeted Fusion Proteins Result in Efficient Presentation by Human Monocytes of Antigenic and Antagonis T Cell Epitopes," *J. Clin. Invest.* 98(9):2001-2007.
Snider, et al. (1989). "Efficiency of Antigen Presentation Ater Antigen Targeting to Surface IgD, IgM, MHC, FcγRII and B220 Molecules on Murine Splenic B Cells," *Journal of Immunology* 143:59-65.
Squire, et al. (1994). "Antigen Presentation is Enhanced by Targeting Antigen to the FcεRII by Antigen-Anti-FcεRII Conjugates," *Journal of Immunology* 4388-4396.

* cited by examiner

*Primary Examiner*—David A. Saunders
*Assistant Examiner*—F. Pierre VanderVegt
(74) *Attorney, Agent, or Firm*—Edwards Angell Palmer & Dodge

(57) ABSTRACT

The invention provides compositions and methods for modulating immune responses in subjects. The invention is based, at least in part, on the discovery that an in-frame translation fusion of an antigen with an APC binding domain of an opsonin forms a molecule, that is, a fusion polypeptide, which when administered to a subject modulates an immune response to the antigen.

8 Claims, 2 Drawing Sheets

VACCINE COMPOSITIONS AND METHODS OF MODULATING IMMUNE RESPONSES

FIELD OF THE INVENTION

Figure 1:
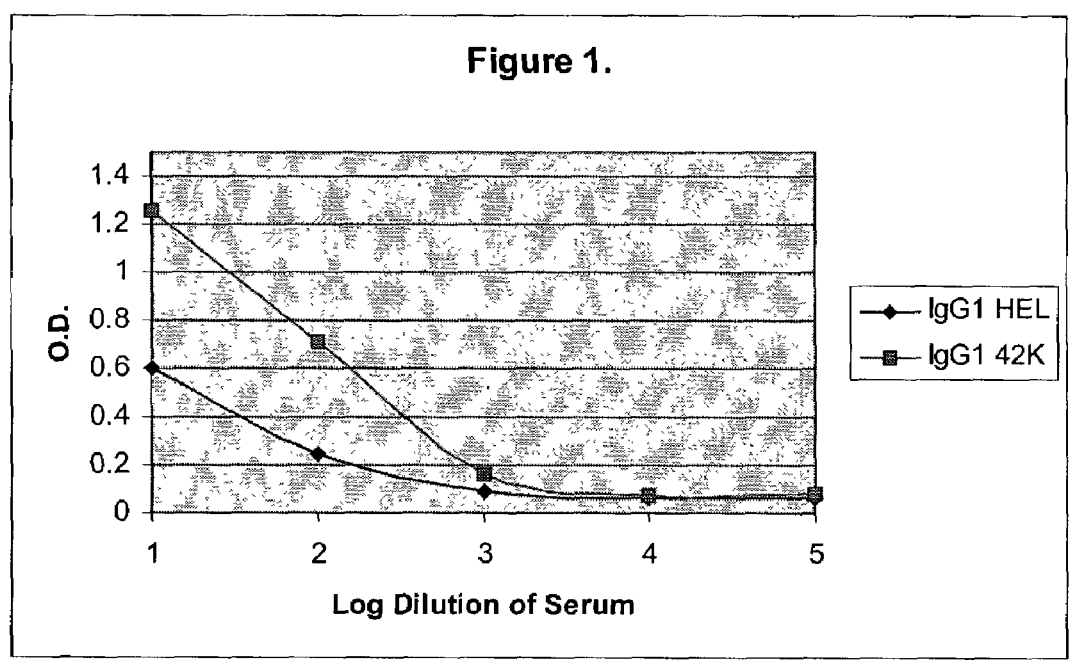

This invention relates to vaccines useful, for example, for modulating immune responses in subjects to a variety of antigens.

BACKGROUND OF THE INVENTION

The innate immune system comprises those mechanisms that have evolved over millennia to provide first line defense against foreign antigens and an antigen recognition repertoire which does not diversify during the ontogeny of the individual. This is in contrast with the acquired immune system which provides later phase defense mechanisms and depends on a repertoire of antigen-specific molecules, e.g., immunoglobulins and T cell receptors that diversify over the ontogeny of the individual. Innate immune mechanisms can contribute to initiation of an antigen-specific response by the acquired immune system, for example by faciltating uptake of antigen by antigen-presenting cells (APCs), which can thereafter stimulate cognate T cells.

Opsonins of the innate immune system ("innate opsonins") are known in the art as secreted polypeptide molecules of the innate immune system and can remain bound to an antigen and to the surface of an APC at the same time. They can thus act as "bridges", and are thought, by virtue of this property, to promote internalization of antigens by APCs. The mode in which opsonins bind to antigens varies among opsonins, and can be covalent or noncovalent. In general, the antigen-binding moieties of innate opsonins differ from the antigen-binding moieties of immunoglobulins in that the former are relatively invariant among members of the same species, and do not undergo diversification during the ontogeny of an individual.

There have been a number of attempts to increase uptake of antigens by APCs by coupling an antigen via a non-peptide linkage to another molecule that can bind to the surface of an APC. Targeting moieties have included, for example, C3b (Jacquier-Sarlin et al., *Immunol* 84:164-70; Arvieux et al., *Immunol* 65:229-35), alpha-2 macroglobulin (Chu et al, *J Immunol* 152:1538-45; Chu and Pizzo, *J. Immunol* 150:48-58), and molecules comprising idiotypes specific for immunoglobulin Fc receptors (Squire et al., *J Immunol* 152:4388-96; Gosselin et al., *J Immunol* 149:3477-81; Snider and Segal, *J Immunol* 143:59-65) or class II MHC molecules (Estrada et al., *Vaccine* 13:901-7; Berg et al., *Eur J Immunol* 24:1262-8; Carayanniotis and Barber, *Nature* 327:59-61).

Another approach to improving uptake of antigen by APCs has been to construct chimeric polypeptides comprising an antigen and an idiotypic portion of an antibody, in which the latter is specific for class II MHC molecules (Baier et al., *J Virol* 69:2357-65) or an immunoglobulin Fc receptor (Liu et al., *JCI* 98:2001-7).

Dempsey et al. (*Science* 271:348-50) constructed fusion proteins between C3d and an antigen, the fusion proteins being capable of binding to CR2-bearing cells such as B cells, reasoning that the B cell costimulation provided by C3d would increase the humoral immune response to the antigen. Marked increases in antibody response were in fact observed, which were abrogated by in vivo antibody blockade of CR2.

SUMMARY OF THE INVENTION

The invention provides compositions and methods for modulating immune responses in subjects. The invention is based, at least in part, on the discovery that an in-frame translation fusion of an antigen with at least a binding domain of a ligand for a cell surface protein forms a molecule, that is, a fusion polypeptide, which when administered to a subject modulates an immune response to the antigen. Preferably, the ligand of the cell surface protein is an opsonin.

Accordingly, the invention also pertains to recombinant nucleic acid molecules which include a nucleotide sequence encoding an antigen and a nucleotide sequence encoding a binding domain of a ligand of a cell surface protein, and thus include a nucleotide sequence encoding a fusion polypeptide comprising the antigen and the binding domain.

As used herein, "modulation" means that a desired/selected response is more efficient, more rapid, greater in magnitude, and/or more easily induced than if the antigen had been used alone. The desired immune response can be stimulation/activation of a selected immune response, e.g., selective enhancement of an immune response to an antigen, or it can be inhibition of a selected immune response e.g., selective suppression, elimination, or attenuation of an immune response to an antigen, or a combination thereof.

As used herein, a binding domain" refers to the whole of a ligand of a cell surface protein, or that portion of a ligand of a cell surface protein that binds to the cell surface protein. In a preferred embodiment, the ligand is an opsonin. An "APC binding domain" therefore, further refers to the whole of a ligand, e.g. an opsonin, e.g. an innate opsonin, or that portion or domain of a ligand that binds to a cell surface protein of an antigen presenting cell.

A "ligand of a cell surface protein" refers to a ligand, useful in the present invention, and which is capable of binding to a cell surface protein including, but not limited to, those cell surface proteins indicated by amino acid sequence in Appendix I or II, or alternatively, those cell surface proteins which are encoded by the nucleic acid sequences indicated in Appendix I or II. Preferably, a "ligand of a cell surface protein" is an opsonin, and the opsonin is capable of binding to a cell surface protein present on the surface of an APC, wherein the cell surface protein includes, but is not limited to, one or more of the proteins indicated by amino acid sequence in Appendix I or II, or those proteins which are encoded by the nucleic acid sequences indicated in Appendix I or II.

In a fusion polypeptide according to the invention, different peptides or polypeptides are linked in-frame to each other to form a contiguous chimeric polypeptide. Thus, a first portion of the fusion polypeptide comprises an antigen and a second portion of the fusion polypeptide, either the amino- or carboxy-terminal to the first portion, comprises a functional binding domain of a ligand for a cell surface protein (e.g. an APC binding domain of an opsonin). It is critical in the fusion polypeptide that the antigen retain its antigenicity and the binding domain retain its ability to facilitate or permit binding of the fusion polypeptide to the cell surface protein; that is, the two portions of the fusion polypeptide must be able to assume their natural structure to the extent that they retain the antigenicity and binding functions necessary to modulate the immune response according to the invention. The amino and carboxy-terminal orientation of the antigen and binding domain will most likely be determined by the location of the binding domain in the ligand for a cell surface protein; that is, in the case wherein the binding domain is the APC binding domain of an opsonin, if the APC binding domain is located near the amino terminus of the opsonin, then the amino-terminal portion of the opsonin may correspond to the amino terminus of the fusion polypeptide; similarly, if the APC binding domain is located near the carboxy terminus of the opsonin, then the amino-terminal portion of the opsonin may correspond to the carboxy terminus of the fusion polypeptide.

Examples of categories of antigens which can be encoded by the nucleic acid molecules include, for example, viral antigens, bacterial antigens, fungal antigens, protozoal and other parasitic antigens, tumor antigens, antigens involved in autoimmune disease, allergy and graft rejection, and other miscellaneous antigens.

APC binding domains of innate opsonins encoded by the nucleic acid molecules can include, for example, an APC binding domain of fibronectin, α2macroglobulin (a2m), C-reactive protein (CRP), complement component C1q, complement fragment C3b, complement component C4b, mannose binding protein, conglutinin, and surfactant proteins A and D.

The nucleic acid molecules of the invention can be used, for example, to modulate an immune response in a mammal to an antigen encoded by the nucleic acid molecule by direct administration of the nucleic acid.

Methods of the invention include the step of administering to an animal a nucleic acid molecule which encodes a fusion polypeptide comprising an antigen and a binding domain of ligand for a cell surface protein, or which encodes a polypeptide complex as defined herein, in an amount and over a period of time effective to modulate an immune response to the antigen in the animal. Preferably, the method includes the step of administering to an animal a nucleic acid molecule which encodes a fusion polypeptide comprising an antigen and an APC binding domain of an opsonin in an amount and over a period of time effective to modulate an immune response to the antigen in the animal.

As used herein, an "animal" refers e.g. to a non-rodent animal, preferably, a non-rodent mammal, more preferably, a primate, and most preferably, a human.

The invention also pertains to vectors which include the nucleic acid molecules of the invention, host cells which are transfected with such vectors, and transgenic animals which include the nucleic acid molecules of the invention.

In another embodiment of the invention, where a first and second portion of a ligand for a cell surface protein (e.g. a ligand which is an opsonin), when covalently associated via a non-peptide bond, form a binding domain, e.g. an APC binding domain, the first or second portion of the ligand may be fused in-frame to the antigen to form a fusion polypeptide. The remaining second or first portion, respectively, may then be covalently associated with the fusion polypeptide via a natural mechanism in the host cell and form a complex.

Therefore, in another aspect, the invention pertains to a multichain polypeptide complex comprising a first portion of a ligand for a cell surface protein which in the presence of a second portion of a ligand for a cell surface protein forms an APC binding domain, and a fusion polypeptide that comprises an antigen and the second portion of the ligand for a cell surface protein. The first portion of the ligand is associated with the fusion polypeptide containing the second portion of the ligand via a covalent linkage. Therefore, the polypeptide complex comprises at least two polypeptide chains which, when covalently associated, form a binding domain. Furthermore, at least one of the chains may comprise an antigen.

Antigens and ligands, e.g. opsonins, which can provide components of the fusion polypeptides are described herein.

In yet another aspect, the invention pertains to vaccine compositions. The vaccine compositions include nucleic acid molecules including nucleotide sequences encoding a fusion polypeptide or a polypeptide complex as described herein and a pharmaceutically acceptable carrier.

The vaccine compositions of the invention can be used for, for example, modulating in an animal an immune response to the antigen.

Methods of administering a vaccine according to the invention include the step of administering naked nucleic acid, which may be RNA or DNA, to the animal. As used herein, "naked" refers to nucleic acid which is substantially free from substances which facilitate entry of the nucleic acid into a host cell, for example, liposomes, ligands specific for cell surface receptors, endosomal disruption agents, etc.

BRIEF DESCRIPTION OF THE FIGURES

FIG. 1 shows the results of an ELISA assay for mouse IgG following administration of DNA constructs of the present invention to mice. "OD" corresponds to IgG1 antibody level; "42K" refers to the construct encoding the IL2 secretory sequence, the 42 N-terminal amino acids of the C3bα' chain, and HEL; "HEL" refers to the construct encoding only the IL2 secretory sequence and the antigen HEL.

FIG. 2 shows the results of an ELISA assay for mouse IgG following administration of DNA constructs of the present invention to mice. "OD" corresponds to IgG1 antibody level; "42K" refers to the construct encoding the IL2 secretory sequence, the 42 N-terminal amino acids of the C3bα' chain, and HEL; "HEL" refers to the construct encoding only the IL2 secretory sequence and the antigen HEL; pCI refers to the expression vector without insert.

DETAILED DESCRIPTION OF THE INVENTION

A composition of the invention comprises a fusion polypeptide which includes an antigen fused to a binding domain of a ligand for a cell surface protein. The fusion polypeptide will bind to a cell surface protein with a binding constant having an affinity that is in the nanomolar range, and the antigen itself (i.e., free of the fusion polypeptide) will not bind to the same or will bind at a significantly lower affinity (at least 10-fold lower). Compositions of the invention preferably comprise a ligand of a cell surface protein or a nucleic acid which comprises such a ligand, wherein the ligand is an opsonin.

A composition of the invention also comprises a multichain polypeptide complex which includes (a) a first portion of an ligand for a cell surface protein which when covalently associated with a second portion of the same ligand for a cell surface protein forms a-binding domain and (b) a fusion polypeptide that includes an antigen and the second portion of the ligand for a cell surface protein. That is, the fusion polypeptide will include an antigen and at least a portion of an ligand for a cell surface protein that, when associated with a binding domain, permits binding of the composition to a cell surface protein. As used herein, "associated with" refers to covalent bonding which is not peptide bonding, the covalent bonding being, for example, disulfide or hydroxyl bonding. The complex also will bind to a cell surface protein with a binding constant having an affinity that is in the nanomolar range, and the antigen itself (i.e., free of association with the binding domain) will not bind to the same cell surface protein or will bind at a significantly lower affinity (at least 10-fold lower).

The compositions of the present invention are distinguished from prior art molecules compositions comprising non-peptide linkages between APC ligand and antigens in that the linkages of the invention can be produced using recombinant DNA techniques. Furthermore, this property allows an animal to be vaccinated with a nucleic acid encoding a fusion polypeptide of the invention, so that, when expressed as a secreted molecule in vivo, the fusion polypeptide is targeted to an APC, regardless of whether a non-APC, e.g. a rhabdomyocyte, expressed it. This is important since, for example, after intramuscular nucleic acid injection a significant amount of the nucleic acid is taken up by rhabdomyocytes, which are not generally considered to be APCs.

In addition, the compositions of the invention are distinguished from fusion polypeptides comprising antibody idiotypes by having an APC-binding portion that is a constituent of the innate immune system, i.e., that is substantially invariant among individuals of a species. Antibody idiotypes, in contrast, are generated and diversified in part by ontogenic processes such as VDJ recombination, junctional diversity, and somatic mutation. Thus, they vary substantially among individuals, and can be unique to individuals. Administration of both an allo-idiotype and another polypeptide, therefore, will often constitute coadministration of at least two foreign antigens. Coadministration of two foreign antigens can result in "antigenic competition" (Hunt et al., *Vaccine* 12:457-64; Rizvi et al., *Int J Exp Path* 71:761-70; Hammerl et al., *Mol Immunol* 25:313-20; Johansson et al., *PNAS* 84:6869-73; Babbitt et al., *PNAS* 83:4509-13), so that the immune response to a fusion polypeptide comprising two foreign antigens, one of which is an idiotype, might be substantially different from the immune response to a polypeptide comprising one foreign antigen and a non-foreign opsonin. In addition, the polypeptides of the invention, unlike immunoglobulins with idiotypes that bind to molecules on the surface of APCs, can bind to antigens that are not expressed on the cell surface.

Ligands Useful According to the Invention

Ligands for cell surface proteins useful in the present invention, include those ligands which bind to cell surface proteins and/or receptors on the surface of antigen presenting cells, preferably APCs of monocytic lineage, including, for example, monocytes, macrophages, and dendritic cells. Ligands which may be included in the compositions and methods of the invention include, but are not limited to those which bind to one or more of the cell surface proteins indicated by amino acid sequence in Appendix I or II, or which are encoded by the nucleic acid molecule indicated in Appendix I or II. In a preferred embodiment, the ligand is an opsonin.

The term "opsonin" is used herein interchangeably with "innate opsonin". Both terms refer to a naturally occurring secreted polypeptide molecule which in nature may become bound to an antigen and also bound to the surface of an APC. Furthermore, in nature the opsonin can be bound contemporaneously to both the antigen and the APC to form a complex that facilitates uptake of the antigen by the APC.

Opsonins particularly useful in the invention are those which bind APCs of monocytic lineage. Monocyte-lineage APCs include, for example, monocytes, macrophages, and dendritic cells.

One particularly useful opsonin is a biologically active fragment of C3 and the APCs are uncultivated peripheral blood monocytes.

If the molecule comprises a fragment of C3, the APC binding domain must bind to CR1 with a greater affinity than it binds to CR2. This definition of a fragment of C3 therefore excludes C3d and C3bi.

An innate opsonin can bind to an antigen other than a molecule that is physiologically expressed on the surface of an APC.

According to the invention, innate opsonins are present in most individuals of a given species, and are structurally invariant among most members of a species, except that allelic variations may exist. During the ontogeny of most individuals, a gene encoding an innate opsonin does not undergo mutation or rearrangement in most of the cells that express the opsonin.

An opsonin can also be a polypeptide molecule, e.g., C3, which can be proteolytically processed such that at least one product of the processing step or steps can be bound stably and contemporaneously to an antigen, via a physiologically occurring linkage, and to the surface of an APC.

Other particularly useful opsonins bind to receptors on monocyte-lineage APCs such as receptors which play a role in innate immunity. Opsonins useful in the present invention include further those opsonins which bind to cell surface proteins including, but not limited to, one or more of those proteins indicated by amino acid sequence in Appendix I or II, or which are encoded by one or more nucleic acid sequences indicated in Appendix I or II. Examples of such receptors include CR1, CR3, the C1q receptors and receptors containing a component of the C1q receptors. Examples of opsonins which can be used in the compositions and methods of the invention include fibronectin (e.g., Genbank accessions X02761, K00799, K02273, X82402, X00307, X00739), CRP (e.g., Genbank accessions X17496, M11880, M11881, M11882), complement components such as C1q (e.g., Genbank accessions X66295, M22531, X03084, X58861, and Swis-Prot accessions P02747, P02745), complement fragments such as C3b (e.g., Genbank accessions K02782, K02765), mannose binding protein (e.g., Genbank accessions S42292, S42294, X15422), conglutinin (e.g., Genbank accession X71774), alpha-2-macroglobulin (e.g., Genbank accessions M93264, M11313), and surfactant proteins A (e.g., Genbank accessions M68519, S48768) and D (e.g., Genbank accessions L40156, X65018, S38981), and their homologues among species.

There are a number of examples of opsonin fragments that comprise APC binding moieties. For example, Las Holtet et al., 1994, *FEBS Lett* 344:242 describe a carboxy-terminal fragment of human a2m (val1299-ala1451) that binds with high affinity to the a2m receptor. Fragments comprising amino acids 1314-1451 of human a2m and the corresponding domain of rat a2m also bind to a2m receptors, albeit with 1-2% of the affinities of native a2m (Van Leuven et al., 1986, *J Biol Chem* 261:11369; Enghild et al., 1989, *Biochemistry* 28:1406; Salvesen et al., 1992, *FEBS Lett* 313:198; Sottrup-Jensen et al., 1986, *FEBS Lett* 205:20).

Becherer and Lambris, 1988, *J Biol Chem* 263:14586 describe fragments of C3b that bind to CR1, e.g., C3c, fragments of C3 generated by elastase treatment and comprising the N-terminal of the alpha' chain of C3b, and a synthetic peptide comprising the 42 N-terminal amino acids of the C3b alpha' chain. A binding sequence in C3 for CR3 has also been described (Wright et al., 1987, *PNAS* 84:4235). "Collagen stalks" of C1q, which are N-terminal fragments obtained by pepsin digestion, bind to the C1q receptor (Reid, 1981, *Methods Enzymol* 80:16; Malhotra et al., 1993, *Biochem J* 293:15). Malhotra et al., ibid., also provide evidence that an APC binding moiety of conglutinin is comprised by its 55 N-terminal amino acids. Ezekowitz (U.S. Pat. No. 5,270,199) offers a putative APC binding site in human mannose binding protein consisting of nucleotides 370-438 of FIG. 2 in the '199 Patent.

Families of Opsonins Useful According to the Invention

Some sets of opsonins can be regarded as structurally and functionally similar. For example, one family comprises fragments of complement components C3 and C4. These two components are highly structurally homologous, and each possesses an intramolecular thiolester bond that is broken when a peptide (C3a or C4a respectively) is proteolytically cleaved from the native molecule. Disruption of the thiolester makes available a chemical structure that can form an ester linkage with an antigen. The moiety of C3 on which this ester bond resides, i.e. the non-C3a moiety, is designated C3b, and C4b is the analogous product of C4 cleavage. C3b can be further proteolysed by proteins such as factor I to yield fragments such as C3bi and C3d, which also remain linked to the antigen via the ester bond.

However, not all biologically active fragments of C3 are opsonins according to the invention. For example, C3d does not bind to surface receptors on peripheral blood monocytes. Its primary biological activity is thought to be to provide costimulatory transmembrane signals directly to B lymphocytes through CR2. Furthermore, such an approach is limited to increasing a humoral immune response, whereas targeting antigens to monocytes can modulate either humoral or cellular immune responses, since APCs of monocytic lineage influence both types of response through their interactions with "helper" T cells.

There are four structurally unique proteins that are known to function as high affinity receptors for biologically active, membrane-bound fragments of C3 and/or C4. CR1 is the major receptor for the C3b fragment of C3 and C4b fragment of C4. It is expressed on monocytes and monocyte-derived APCs, among other cell types. CR2 is the major receptor for the fragment of C3 known as C3d, and is expressed on, e.g., mature B lymphocytes, but not on cells of monocytic lineage. The major role of CR2 on B lymphocytes is believed to be direct costimulation of B cells in concert with their cognate antigens.

CR3 is expressed primarily by neutrophils and monocytes and is also expressed on FDC, Kupffer cells, and NK cells. CR3 is a C3 fragment receptor with a primary specificity for C3bi. CR3 has been proposed as an important organizer of cytoskeletal events necessary for adhesive interactions and membrane reorganization during processes such as phagocytosis.

CR4 is a member of the beta2 integrin family, and its alpha chain is structurally similar to the alpha chain of CR3 and LFA-1. Its primary physiologic ligand is believed to be C3d,g;, however, its biologic activities are less well understood than CR3.

Another example of a family of innate opsonins is the collectins, a group of collagenous C-type lectins that comprises complement component C1q, mannose binding protein, surfactant proteins A and D, and conglutinin. Each molecule comprises a lectin domain that can bind to an antigen, and a collagenous domain that can bind to receptors on phagocytic mononuclear cells, including receptors that are wholly or partially identical to the C1q receptor (Tenner et al., *Immunity* 3:485-93; Guan et al., *J Immunol* 152:4005-16; Geertsma et al., *Am J Physiol* 267:L57-84; Miyamura et al., *Biochem J* 300:237-42; Malhotra et al., *J Exp Med* 172:955-9; Malhotra et al., *Biochem J* 293:15-19). Most known collectins comprise multiple polypeptide chains, in some cases homomeric and in others heteromeric, that are assembled post-translationally, in part by covalent cross-linkage of hydroxyproline and hydroxylysine residues. Collectins are demonstrated to be opsonins in, for example, Pikaar et al., *J Infect Dis* 172:481-9; Alvarez-Dominguez et al., *Infection & Immunity* 61:3664-72; O'Riordan et al., *J Clin Invest* 95:2699-710; Kuhlman et al., *J Exp Med* 169:1733-45; and Geertsma et al., op cit.

Among the other innate opsonins useful according to the invention are C-reactive protein (CRP), alpha-2 macroglobulin (a2m), and fibronectin. CRP, a member of the pentraxin family of molecules, binds to receptors on cells of monocytic lineage and has been shown to be an opsonin (Culley et al., *J Immunol*, 1995, 156;4691). Alpha-2 macroglobulin, like C3 and C4, comprises an internal thiolester bond that can be disrupted when the molecule is proteolysed. Such disruption allows covalent binding of the molecule to an antigen, and binding of alpha-2 macroglobulin to an APC can promote uptake of the conjugate (Straight et al., *Biochemistry* 27:2885-90). Fibronectin binds to the alpha 5 beta 1 integrin and can also bind to various antigens, allowing it to function as an opsonin (Cosio, *J Lab Clin Med* 103:613-9; Czop and Austen, *J Immunol* 129:2678-81).

Fusion polypeptides have previously been constructed between portions of opsonins and relatively limited group of other polypeptides for purposes such as to facilitate isolation and purification of the opsonin or to elucidate structure-function relationships. For example, a portion of alpha-2 macroglobulin has been fused to carbonic anhydrase II to facilitate expression of the a2m moiety in a bacterium (Mottaqui-Tabar et al., *Ann NY Acad Sci* 737 493-5). Short portions of C3 from non-human species have been fused with human C3 to elucidate structure-function relationships (Lambris et al., *J Immunol* 156:4821-32). A heptapeptide recognition site for Tobacco Etch Virus protease was introduced into alpha-2 macroglobulin to investigate the function of the a2m bait region (Van Rompacy et al., *Biochem J* 312:191-5). Carbohydrate recognition domains of opsonins or adhesion molecules have been fused to portions of opsonins in order to demonstrate transfer of ligand specificity (Blanck et al., *J Biol Chem* 271:7289-92; Ogasawara et al., *J Biol Chem* 269:29785-92). Peptides comprising the Arg-Gly-Asp (RGD) APC-binding moiety of fibronectin have been fused to a number of polypeptides in order to study, e.g., structure-function relationships and amphibian cell biology (Alfandari et al., *Mech Dev* 56:83-92; Ramos et al., *J Cell Biol* 134:227-40; Ebeling et al., *Eur J Immunol* 26:2508-16). The invention, in contrast, provides compositions that are useful for preventing or treating disease.

Opsonins are thought to act as a link or coupling agent between the antigen and the APC to allow more efficient binding, engulfinent, and internalization of the antigen. A molecule is defined herein as an opsonin useful in the invention if it binds to a cognate antigen as determined in one or more of the assays of opsonicity described herein. According to the invention, opsonicity is determined in part by detection of binding to an APC and an antigen. For example, fragments of C3 can be bound to sheep red blood cells (SBRC); and opsonins with lectin activity can be directly admixed with microorganisms bearing a cognate carbohydrate.

According to the invention, an "APC binding domain" is a portion of an opsonin which permits binding of a fusion polypeptide containing that domain and an antigen to an APC. A fusion polypeptide or a complex of the invention comprises an APC binding domain if it can bind to a naturally occurring APC surface molecule with an affinity at least in the nanomolar range and if binding to said molecules does not occur via the antigen. Binding via the antigen is easily discernible by testing free antigen for affinity to said surface molecule. Binding via antigen does not occur if the affinity of free antigen is at least 10-fold lower than that of the polypeptide or complex.

A "fusion polypeptide complex" contains first and second portions of an opsonin that together form an APC binding domain and together permit binding of a fusion polypeptide containing one such portion fused in-frame to an antigen to bind to an APC. A first or second portion of an APC binding domain does not correspond to an APC binding domain in itself, but forms an APC binding domain only when covalently associated with the second or first portion, respectively. This complex can be produced when the gene encoding the fusion polypeptide is expressed in a cell and coexpressed with a gene encoding a chain of an opsonin that contains the other portion (first or second portion) of the APC binding domain.

An APC binding domain will also, of course, includes a complete opsonin polypeptide, e.g., C3.

It is particularly preferred according to the invention where the APC binding domain consists essentially of an APC-binding moiety of an innate opsonin.

In one embodiment, the APC binding domain comprises an amino acid sequence which is capable of binding to one or more cell surface proteins, including, but not limited to those indicated by amino acid sequence in Appendix I or II, or encoded by a nucleic acid sequence indicated in Appendix I or II.

A fusion polypeptide according to the invention comprises an "APC binding domain" if the fusion polypeptide can bind to a receptor that is physiologically expressed on an APC with an affinity at least in the nanomolar range. Fusion polypeptides according to the invention do not include chimeric proteins consisting only of a first opsonin or APC binding domain thereof fused to a second different opsonin, or APC binding domain thereof, but may include one or more opsonins or APC binding domains thereof fused to an antigen.

A fision polypeptide or multichain complex of the invention will bind to the cell surface protein via the opsonin portion of the molecule rather than via the antigen. This is easily distinguishable as free antigen will not compete with a fusion polypeptide for binding to the cell surface protein if the polypeptide or complex binds to the protein via the binding domain, whereas free antigen will compete with the fusion polypeptide binding to the cell surface protein if the polypeptide or complex binds to the protein via the antigen portion of the polypeptide or complex. Therefore, a fusion polypeptide of the invention comprises a binding domain, e.g. an APC binding domain of an opsonin, if this binding domain can bind to a receptor that is physiologically expressed on a cell, e.g. an APC, with an affinity at least in the nanomolar range when included in a fusion polypeptide that does not comprise a second portion, heterologous to the first binding domain, which, in isolation, can bind to a receptor that is physiologically expressed on a cell with an affinity at least in the nanomolar range. APC-binding domains that do not comprise entire opsonins have been described, for example, for mannose binding protein (Tenner et al., *Immunity* 3:485-95), C3b (Becherer and Lambris, *J Biol Chem* 263:145891), conglutinin (Malhotra et al., *Biochem J* 293:15-19), and fibronectin (Czop and Austen, *J Immunol* 129:2678-81).

In another preferred embodiment, the APC binding moiety does not require the amino acid sequence RGD in order to bind to an APC receptor.

Assays for Determining Opsonicity According to the Invention

Assay 1

In one assay of opsonicity, as described by O'Rear and Ross in Current Protocols in *Immunology,* 1994, John Wiley & Sons, pp. 13.4.5-9, SRBC bound via a physiologically occurring linkage to the candidate opsonin molecule are obtained. APCs from the species to which the candidate opsonin is native are suspended at $4\times10^6$/ml in ice-cold HBSS with 1% (w/v) Cohn fraction of BSA. If the candidate opsonin is a fragment of C3, the APCs are freshly drawn, uncultivated peripheral blood monocytes. SRBC linked to the candidate opsonin or control SRBC (identical to the former but not linked to the candidate opsonin) are suspended in the same solution at $2\times10^8$/ml. 100 ul of SRBC suspension and 100 ul of APC suspension are mixed in a 10×75 mm plastic tube. The tube is rotated at 40 rpm at 37° C. for 2-20 min. A small drop of the suspension is placed on a slide, covered with a coverslip, and allowed to stand for 5-10 min. Excess fluid can be removed by pressure on the coverslip, and the coverslip can be sealed to the slide, e.g. with clear nail polish. The slide is examined microscopically, and the percentage of APCs visibly adherent to 4 or more SRBCs is determined. If said percentage is 50% or greater when there are up to $4\times10^4$ candidate opsonin molecules/SRBC, the candidate opsonin can be an opsonin.

Assay 2 (for Protease-activated Candidate Opsonin)

Candidate opsonin or radiolabeled Candidate opsonin is treated with a 1.5-3 fold molar excess of protease (0.05 M triethanolamine-0.1 M NaCl, pH 8.0, room temperature overnight). In this assay, the protease can serve as the antigen or an excess of another antigen can be added. Prior to binding studies, the candidate opsonin-antigen complex is dialyzed against HBSS (4° C.).

Candidate opsonin-antigen complex binding to monocytes is measured by incubating labeled ligand at a concentration up to 1.0 M with $(1.5\text{-}4.0)\times10^6$ monocytes in 200 µl volume on ice. Nonspecific binding of radiolabeled ligands is determined in the presence of a 100-fold molar excess labeled candidate opsonin-antigen complex. The unbound ligand is separated from the cells and cell-bound ligand by rapid vacuum filtration on glass fiber filters. Studies are performed on ice to avoid potential complications due to endocytosis. Binding constarts and the number of sites per cell are determined by analysis and by nonlinear curve fit. If candidate opsonin-antigen complex affinity for a monocyte binding site is in at least the nanomolar range, the candidate opsonin is an opsonin.

Assay 3

Part I

To directly evaluate whether candidate opsonin is bound to the surface of *P. carinii*, immunoelectron microscopy is performed. *P. carinii* are isolated from bronchoaveolar lavage (BAL) of moribund infected rats using TBS with 1 mM calcium to preserve surface-bound candidate opsonin. Isolated organisms are fixed in periodate-lysine-paraformaldehyde buffer and embedded in Lowacryl mounting medium (Ted Pella, Inc., Redding, Calif.). Ultrathin sections are obtained, blocked with normal goat serum (2%) for 1 h, and incubated with either rabbit anti-candidate opsonin or non-immune rabbit IgG (25 µg/ml) overnight. After washing, the sections are subsequently incubated with goat and rabbit IgG conjugated to 15 nM colloidal gold (Amersham Corp., Arlington Heights, Ill.). The sections are washed again and examined on a transmission electron microscope (model 6400:JEOL USA, Inc., Peabody, Mass.).

Part II

The attachment of *P. carinii* to cultured alveolar macrophages in the presence or absence of antibody to SP-D or with the addition of purified SP-D is quantified as follows. Adherence of *P. carinii* to alveolar macrophages is assayed by $^{51}$Cr-labeling the organisms. *P. carinii* are isolated from infected rats with TBS containing 1 mM calcium to prevent loss of surface-bound candidate opsonin. The organisms are radiolabeled by incubation for 8 h at 37° C. in 2 ml of DME containing 20% FCS and 200 µCi of $^{51}$Cr-sodium chromate (New England Nuclear). Normal alveolar macrophages are lavaged from healthy rats and plated in tissue culture plates ($1\times10^5$) cells/well) which are been precoated with normal rat IgG (100 µg/ml×60 min) in order to ensure firm adherence of the macrophages. After 1 h, the macrophages are gently washed with HBSS to remove nonadherent cells. >95% of macrophages are adherent after this wash. $^{51}$Cr-*P. carinii* ($1\times10^6$) containing surface-associated candidate opsonin are added to the macrophages and incubated at 37° C. for an additional hour. Subsequently, nonadherent *P. carinii* are removed by washing. The macrophage monolayers containing adherent *P. carinii* are solubilized in 1 N NaOH and quantified. Adherence of *P. carinii* is defined as: percentage of adherence=(A/A+B)×100, where A=$^{51}$Cr-*P. carinii* associated with the monolayer, and B=unattached $^{51}$Cr-*P. carinii*. To assess the effect of candidate opsonin on the attachment of *P. carinii* to alveolar macrophage lung cells in culture, *P. carinii* adherence assays are conducted in the presence or absence of a polyclonal rabbit antibody generated against the candidate opsonin (100 ug/ml).

If candidate opsonin binding to *P. carinii* is apparent in Part I and if, in Part II, % adherence is diminished in the presence of anti-candidate opsonin with statistical significance of P<0.05, the candidate opsonin is an opsonin.

Assay 4

Association of bacteria with adherent monocytes is measured as follows. Endotoxin level in the modified PBS and in all buffers used is below 50 pg/ml as determined by the Limulus assay. $5\times10^3$ monocytes in modified PBS are allowed to adhere to the wells of a Terasaki plate for 2 h at 37° C. After nonadherent cells are removed by three washes with PBS, $5\times10^4$ FITC-labeled bacteria in 0.5 ml buffer with or without 10-50 micrograms/ml of candidate opsonin are added. A bacteria-to-monocyte ratio of 10:1 to 50:1 is used. After 30 min of incubation at 37° C. in the dark, the nonadherent bacteria are removed by five washes with warm PBS. Assays are performed in quadruplicate; in each well, the number of bacteria associated with ≧100 monocytes is counted under a flourescence microscope using ×400 magnification. Results are expressed as the number of bacteria associated with 100 monocytes. If this number with candidate opsonin can be at least twice that without candidate opsonin, the candidate opsonin is an opsonin.

Assay 5

Part I

About $1\times10^7$ to $6\times10^7$ bacteria per ml are incubated (20 min, 0° C.) with 10 mcg/ml of $^{125}$I-candidate opsonin in a total volume of 0.7 ml. of PBS aliquots, 100 ul, of the reaction mixtures are layered over 150 ul of an oil cushion (60% dibutyl phthalate, 40% dioctyl phthalate [Eastman Kodak Co., Rochester, N.Y.]), and the mixtures are centrifuged (10,000×g, 60 s, 4° C.). The tip of the tube, containing the cell pellet, is cut with a Mozart razor blade, and the radioactivity is counted.

Part II

APCs are plated in 96-well tissue culture plates (Costar, Cambridge, Mass.) at $2\times10^5$ cells per ml the evening before use. $2\times10^6$ bacteria per well (0.1 ml per well) are added to the culture plates with or without 100 mcg/ml of candidate opsonin. The plates are then centrifuged at 1,000×g for 7 min. After 15 min at 37° C. to allow the uptake of bacteria, free bacteria are removed by several washes with cold PBS. They are then incubated (45 min, 37° C.) in RPMI 1640 plus an amount of antibiotic that, when present in the culture for 45 min, kills all extracellular bacteria. The end of this incubation period is considered time zero. Monolayers are washed three times with Hanks' balanced saline solution, and the same volume of RPMI 1640 (R0) is added. The cells are lysed by using several cycles of freezing and thawing. The number (CFU) of viable bacteria per well is determined by quantitative plate counts on blood agar plates (Columbia blood agar; Becton Dickinson, San Jose, Calif.) after 24 h of incubation. Each result is given as the mean of three determinations.

If, in Part I, candidate opsonin-treated bacterial pellet has >75 KCPM and this incorporation can be inhibited by unlabeled candidate opsonin, and if in Part II the CFU with candidate opsonin is greater than without (P<0.05), the candidate opsonin can be an opsonin.

Assay 6

200 µl of GHBSS (Hanks Balanced Salt Solution)+0.1% of gelatin containing 10 m mol $CaCl_2$) containing $10^7$ bacteria is prepared. The bacteria are then incubated at 4° C. with 20-100 µg/ml of candidate opsonin. Binding assays are done in the presence or absence of a competitive inhibitor. After incubation for 30 minutes, the bacteria are washed five times in a GHBSS+10 mmol $CaCl_2$ at room temperature in a microfuge at 1,300 g for 3 minutes. Thereafter, a 1:1,000 dilution of rabbit anti-candidate opsonin antiserum is incubated with the bacteria for 1 h in PBS+5% FCS and 10 mmol $CaCl_2$ and then the bacteria are washed three times in GHBSS+10 mmol $CaCl_2$ plus 0.05% Tween 20. Binding of anti-serum to bacteria is detected by a 1:1,000 dilution of goat anti-rabbit IgG conjugated to rhodamine (Fisher Pharmaceuticals, Orangeburg, N.Y.). After incubation, the bacteria are washed five times in GHBSS+10 mmol $CaCl_2$ plus 0.05% Tween 20, smeared onto glass slides and allowed to air dry. Thereafter bacteria are fixed with 100% ice cold methanol for 5 minutes. Negative controls included the absence of candidate opsonin and no first step antibody. Numerous fields of triplicate assays are examined by fluorescence microscopy.

Part II Association of Radiolabeled Bacteria with Cells.

$10^7$ radiolabeled bacteria are resuspended in 200 µl of GHBSS+10 mmol $CaCl_2$ and are incubated with or without candidate opsonin ranging from 2 µg/ml to 40 µg/ml at 4° C. for 30 min. The bacteria are then washed three times in GHBSS+10 mmol $CaCl_2$ for 3 min at room temperature in a microfuge at 1,300 g, resuspended in 50 µl of GHBSS and added to a 1-ml suspension containing on the order of $10^6$ APCs (GHBSS). The bacteria and APCs are gently rocked at 37° C. for 20 min and thereafter the unattached bacteria are removed by five washes using differential centrifugation at 82 g in a microfuge. Before the last wash, an aliquot from each sample is plated on a Labtek slide and cells are adhered for 10 min, fixed in methanol, stained with Geimsa, and scored by light microscopy. To score the cells plated on the Labtek slides, at least 400 cells are counted. The phagocytic index represented the number of attached or ingested particles per 100 PMNs. The pellet from above containing cells and radiolabeled bacteria is then lysed in 100 µl PBS+0.5% Triton X-100 and the radioactivity is measured in a scintillation counter. If, in Part I, specific binding of candidate opsonin to bacteria is evident, and in Part II the specific uptake of bacteria, in cpm, is more than three times greater with candidate opsonin than without, the candidate opsonin can be an opsonin.

Assay 7

Part I

To investigate binding to *L donovani promastigotes* cultures are seeded at $5 \times 10^5$ parasites $ml^{-1}$. At regular time points up to 9 days, a fraction of parasites are counted, washed, and resuspended in 1% BSA, 0.5 mM $Ca^{2+}$. 0.05% $NaN_3$, Tris-buffered saline (TBS), (10 mM Tris-HCl, 0.15 M NaCl, pH 8.0) (diluent) to $2 \times 10^5$ $ml^{-1}$. Fifty microliters of this suspension are then added to 200-µl microfuge tubes containing 70 µl 5 µg/ml radiolabeled C-reactive protein (CRP) (0.12 µCi/µg) in diluent without EDTA, which had been layered over 150 µl of a dinonyl phthalate/dibutyl phthalate (40:60 v/v) oil mixture. Parasites are incubated for 1 h and centrifuged through the oil layer, the cell pellet Is cut off, and associated CRP is detected by gamma counting. Each assay is performed in triplicate. The concentration dependency of CRP binding to promastigotes is also measured as above, using an activity of 0.045 µCi/µg and a twofold dilution series from 60 to 0.015 µg/ml CRP.

Part II

APCs are plated out at $1 \times 10^6$ cells/well on glass coverslips in a 24-well tissue culture plate. Cells are incubated in RPMI 1640 (Life Technologies) supplemented with 10% PCS, 1 mM glutamine, 200 U/ml penicillin and 200 µg/ml streptomycin in a humidified incubator at 37° C. After 24 h, nonadherent cells are removed and remaining cells are used after 6 days. Promastigotes are incubated with or without CRP at 30 µg/ml in RPMI 1640 for 1 h and then washed three times before adding to the APC cultures at $10^6$/well. Promastigotes are allowed to infect APCs for 1 h, then cells are washed, fixed with methanol, and Geimsa stained (BDH, Poole, Dorset, U.K.) before counting. The percentage of APCs infected and the number of parasites/100 macrophages is determined from quadruplicate cultures.

If in Part I the affinity of candidate opsonin for parasites is at least in the nanomolar range and in Part II the number of parasites taken up/100 APCs is, with candidate opsonin, at least twice that without candidate opsonin, the candidate opsonin can be an opsonin.

Assay 8

Part I

Portions (0.5 ml) of [$^{35}$S]methionine-labeled culture medium containing 5 percent fetal calf serum and the candidate opsonin are incubated for 30 minutes at room temperature with 0.1 ml or 0.2 ml of a 10 percent suspension of a microorganism). The microorganisms tested may include, for example, *Salmonella typhimurium, Bacillus subtilis, Staphylococcus aureus, Escherichia coli*, and *Saccharomyces cerevisiae*. Bound proteins are released by boiling in buffer containing 2 percent SDS and 0.1 M dithiothreitol and are analyzed on a 5 percent SDS gel.

Part II

Fixed bacteria (0.1 ml; 10 percent by volume; $10^{10}$ organisms per millileter), labeled with [$^3$H]thymidine, are incubated with 0.1 ml of serum with or without depletion of the candidate opsonin. After being washed with PBS, the bacteria are incubated with on the order of $1 \times 10^7$ APCs in a final volume of 0.9 ml PBS containing divalent cations. At intervals 0.2 ml is removed to ice-cold PBS with N-ethyimaleimide (2 mM) to block further endocytosis, and the cells are washed (at about 100 g for 10 seconds).

If in Part I a band corresponding to the candidate opsonin is apparent, and if in Part II the CPM after 6-10 min of incubation is at least three times greater for undepleted samples with serum than with depleted serum, the candidate opsonin can be an opsonin.

In lieu of results form Parts I of assays 3, 5, 6, 7, 8, a candidate opsonin that satisfies Part II of an assay can be an opsonin if it can bind to the antigen of the assay with an affinity in at least the nanomolar range.

Linkage of Antigen to Ligand for Cell Surface Protein

An antigen is linked to a ligand for a cell surface protein according to the invention via recombinant DNA techniques to form a chimeric gene, and expression of the chimeric gene in a host cell. Therefore, the linkage contemplated in the invention is limited to a peptide linkage for formation of an in-frame fusion polypeptide.

A flexible linker sequence may be inserted into the fusion polypeptide between the antigen and the ligand. For example, a polygylcine/polyserine-containing sequence such as $(Gly_4Ser)_2$. See Huston et al., 1991, *Meth. Enzymol.* 203:46.

Production of Fusion Polypeptide and Fusion Polypeptide Complexes

A fusion polypeptide according to the invention is produced in vivo or in vitro in a host cell by expression of the gene encoding the fusion polypeptide or by coexpression of the gene encoding the fusion polypeptide and a gene encoding a polypeptide chain which when associated with the fusion polypeptide to form a complex, permits binding of the complex to the APC. When two such genes are coexpressed, the fusion polypeptide and the polypeptide chain naturally form an association in the cell, for example, by disulfide bonding or by cross-linking between hydroxylated amino acids, such as via a lysine or proline residue.

Nucleic Acid Sequences

Another aspect of the invention features isolated nucleic acid molecules which include a nucleotide sequence encoding an antigen fused in one reading frame to a nucleotide sequence encoding a binding domain of a ligand for a cell surface protein, e.g. an APC binding domain of an innate opsonin. The nucleic acid molecule also may include a sequence encoding a first or second portion of a ligand for a cell surface protein, which portions correspond to fragments of an ligand that form an APC binding domain. Where the nucleic acid sequence encodes a polypeptide complex according to the invention, the sequence encoding the fusion polypeptide and the sequence encoding the chain which in association with the fusion polypeptide forms a binding domain may be coexpressed and therefore under coordinated or the same gene control elements.

The phrase "nucleic acid molecule" as used herein is intended to include such fragments and refers to DNA molecules (e.g., cDNA or genomic DNA) and RNA molecules (e.g., mRNA). The nucleic acid molecule can be single-stranded or double-stranded, but preferably is double-stranded DNA. An "isolated" nucleic acid molecule is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, can be free of other cellular material. The term "fragment" as used herein refers to a portion of a nucleic acid molecule or polypeptide or other molecule described herein.

Typically, the nucleotide sequence encoding the antigen and the nucleotide sequence encoding the APC binding domain can be fused to form a "fusion gene" according to techniques known in the art. For example, in one embodiment, attachment/linkage of nucleic acid fragments coding for different polypeptide sequences can be performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be performed using anchor primers which give rise to complementary overhangs between two consecutive gene fragments which can subsequently be annealed to generate a chimeric gene sequence (see, e.g., *Current Protocols in Molecular Biology*, eds. Ausubel et al. John Wiley & Sons: 1992).

Antigens Useful According to the Invention

The term "antigen" as used herein refers to a molecule which can initiate a humoral and/or cellular immune response in a recipient of the antigen. The antigen is preferably an agent that causes a disease for which a vaccination would be advantageous treatment. The antigen portion of the fusion polypeptide is preferably at least 8 amino acids, and is preferably no longer than 25 amino acids, and preferably does not include more than 10 contiguous amino acids of an opsonin, or a lectin binding domain of a eukaryotic intercellular adhesion molecule, or a reporter molecule such as β-galactosidase. As used herein, a "lectin binding domain" refers to a carboxy-terminal carbohydrate recognition domain of a protein, for example exon 4, nucleotides 439-813 of human mannose binding protein. "Complement-fixing domain" refers to a collagen-like segment having a repeated pattern of Gly-X-Y (where X and Y represent any amino acid) similar to those of non-fibriallar collagen genes. The structure is consistent with those of an effector region which interacts with complement components; for example, exon 2, nucleotides 253-369 of human mannose binding protein.

Antigens can be any type of biologic molecule including, for example, simple intermediary metabolites, sugars, lipids, and hormones as well as macromolecules such as complex carbohydrates, phospholipids, nucleic acids and proteins. According to the invention, cells that comprise or are attached to a molecule that can elicit an immune response are also considered antigens. Common categories of antigens include, but are not limited to, viral antigens, bacterial antigens, fungal antigens, protozoal and other parasitic antigens, tumor antigens, antigens involved in autoimmune disease, allergy and graft rejection, and other miscellaneous antigens.

Examples of viral antigens include, but are not limited to, retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS1, NS1, NS1-NS2A, 80% E, and other Japanese encephalitis viral antigen components; rabies viral antigens such as rabies glycoprotein, rabies nucleoprotein and other rabies viral antigen components. See Fundamental Virology, Second Edition, eds. Fields, B. N. and Knipe, D. M. (Raven Press, New York, 1991) for additional examples of viral antigens.

Bacterial antigens which can be used in the compositions and methods of the invention include, but are not limited to, pertussis bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; haemophilus influenza bacterial antigens such as capsular polysaccharides and other haemophilus-influenza bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens.

Fungal antigens which can be used in the compositions and methods of the invention include, but are not limited to, candida fungal antigen components; histoplasma fungal antigens such as heat shock protein 60 (HSP60) and other histoplasma fungal antigen components; cryptocoecal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

Examples of protozoal and other parasitic antigens include, but are not limited to, plasmodium falciparum antigens such as merozoite surface antigens, sporozoite surface antigens, circumsporozoite antigens, gametocyte/gamete surface antigens, blood-stage antigen pf 155/RESA and other plasmodial antigen components; toxoplasma antigens such as SAG-1, p30 and other toxoplasmal antigen components; schistosomae antigens such as glutathione-S-transferase, paramyosin, and other schistosomal antigen components; leishmania major and other leishmaniae antigens such as gp63, lipophosphoglycan and its associated protein and other leishmanial antigen components; and trypanosoma cruzi antigens such as the 75-77 kDa antigen, the 56 kDa antigen and other trypanosomal antigen components.

Tumor antigens which can be used in the compositions and methods of the invention include, but are not limited to, telomerase; multidrug resistance proteins such as P-glycoprotein; MAGE-1, alpha fetoprotein, carcinoembryonic antigen, mutant p53, papillomavirus antigens, gangliosides or other carbohydrate-containing components of melanoma or other tumor cells. It is contemplated by the invention that antigens from any type of tumor cell can be used in the compositions and methods described herein.

Antigens involved in autoimmune diseases, allergy, and graft rejection can be used in the compositions and methods of the invention. For example, an antigen involved in any one or more of the following autoimmune diseases or disorders can be used in the present invention: diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis. Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor. Examples of antigens involved in allergy include pollen antigens such as Japanese cedar pollen antigens, ragweed pollen antigens, rye grass pollen antigens, animal derived antigens such as dust mite antigens and feline antigens, histocompatiblity antigens, and penicillin and other therapeutic drugs. Examples of antigens involved in graft rejection include antigenic components of the graft to be transplanted into the graft recipient such as heart, lung, liver, pancreas, kidney, and neural graft components. The antigen may be an altered peptide ligand useful in treating an autoimmune disease.

Examples of miscellaneous antigens which can be can be used in the compositions and methods of the invention include endogenous hormones such as luteinizing hormone, follicular stimulating hormone, testosterone, growth hormone, prolactin, and other hormones, drugs of addiction such as cocaine and heroin, and idiotypic fragments of antigen receptors such as Fab-containing portions of an anti-leptin receptor antibody.

In one embodiment, the antigen comprises an antigen of a bacterium that infects animals. In a preferred embodiment, the antigen comprises an antigen of a virus, fungus, parasite, chlamydia, or rickettsia that infects animals. In another preferred embodiment, the antigen is a target of a pathologic autoimmune response. In yet another embodiment, the antigen comprises greater than seven amino acids. In a further embodiment, the antigen is a short peptide comprising no more than twenty amino acids, or preferably no more than twenty-five. It is preferred that the antigen comprise neither more than ten contiguous amino acids of an opsonin, nor a lectin domain of an adhesion molecule, nor a reporter protein such as a portion of beta galactosidase. If the opsonin moiety is derived from a2m, it is preferred that the antigen is neither carbonic anhydrase nor a heptapeptide comprising a cleavage site for the Tobacco Etch Virus protease. If the opsonin moiety is derived from mannose binding protein, it is preferred that the antigen is neither CD4 nor a toxic portion of a cytotoxin.

Vectors According to the Invention

Yet another aspect of the invention pertains to vectors, preferably expression vectors, containing nucleic acid molecules of the invention (or a portion or fragment thereof). As used herein, the term "vector" refers to a nucleic acid molecule capable of transporting another nucleic acid to which it has been linked. One type of vector is a "plasmid", which refers to a circular double stranded nucleic acid loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant nucleic acid techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce proteins or peptides, including fusion polypeptides or peptides, encoded by nucleic acids as described herein.

The recombinant expression vectors of the invention can be designed for expression of the nucleic acid molecules of the invention in prokaryotic or eukaryotic cells. For example, the polypeptides encoded by the nucleic acid molecules of the invention can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nuc. Acids Res.* 20:2111-2118). Such alteration of nucleic acid sequences of the invention can be carried out by standard nucleic acid synthesis techniques.

In another embodiment, the expression vector is a yeast expression vector. Examples of vectors for expression in yeast *S. cerivisae* include pYepSec1 (Baldari. et al., (1987) *Embo J.* 6:229-234), pMFa (Kutjan and Herskowitz, (1982) *Cell* 30:933-943), pJRY88 (Schultz et al., (1987) *Gene* 54:113-123), and pYES2 (Invitrogen Corporation, San Diego, Calif.).

Alternatively, the polypeptides encoded by the nucleic acid molecules of the invention can be expressed in insect cells using baculovirus expression vectors. Baculovirus vectors available for expression of proteins in cultured insect cells (e.g., Sf9 cells) include the pAc series (Smith et al., (1983) *Mol. Cell Biol.* 3:2156-2165) and the pVL series (Lucklow, V. A., and Summers, M. D., (1989) *Virology* 170:31-39).

In yet another embodiment, the polypeptides encoded by the nucleic acid molecules of the invention are expressed in mammalian cells using a mammalian expression vector. Examples of mammalian expression vectors include pCDM8 (Seed, B., (1987) *Nature* 329:840) and pMT2PC (Kaufman et al. (1987), *EMBO J.* 6:187-195). When used in mammalian cells, the expression vector's control functions are often provided by viral regulatory elements. For example, commonly used promoters are derived from polyoma, adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Baneiji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the -fetoprotein promoter (Campes and Tilghman (1989) *Genes Dev.* 3:537-546).

In one embodiment, a recombinant expression vector containing a nucleic acid molecule encoding a fusion polypeptide of the invention is produced. The fusion polypeptides of the invention, i.e., fusion polypeptides which include an antigen portion and a functional opsonin moiety, can be produced by recombinant expression of a first nucleotide sequence encoding an antigen and a second nucleotide sequence encoding a functional opsonin moiety as described, for example, in U.S. Pat. No. 5,116,964 to Capon et al., the entire contents of which are hereby incorporated by reference. Fusion polypeptides, which include or do not include a linker amino acid sequence or an amino acid sequence directing secretion of the polypeptide which is not native to either the antigen or the opsonin amino acid sequences, produced by recombinant techniques can be secreted and isolated from a mixture of cells and medium containing the protein or peptide. Alternatively, the fusion polypeptide can be retained cytoplasmically and the cells harvested, lysed and the protein isolated. A cell culture typically includes host cells, media and other byproducts. Suitable media for cell culture are well known in the art. Polypeptides and peptides can be isolated from cell culture medium, host cells, or both using techniques known in the art for purifying proteins and peptides. Techniques for transfecting host cells are described in further detail herein.

For example, fusion polypeptides including one or more peptide or polypeptide antigens and one or more functional opsonin moieties can be produced by constructing a fusion gene which includes a nucleotide sequence encoding one or more antigens and a nucleotide sequence encoding one or more functional opsonin moieties. The fusion polypeptide product of the fusion can be expressed and then administered to a recipient mammal, subject etc. as described herein. Libraries of such fusion genes can be generated from microbes, tumor cells, allografts, xenografts, or other gene-containing entities by cloning the entire set of genomic or expressed nucleic acids or any subset thereof into an expression vector which contains one or more nucleotide sequences encoding one or more functional opsonin moieties such that a multitude of fusion genes including one or more opsonins are produced. These fusion genes can also be administered as described herein.

Another aspect of the invention pertains to recombinant host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell may be any prokaryotic or eukaryotic cell. For example, a polypeptides encoded by nucleic acid molecules of the invention can be expressed in bacterial cells such as *E. coli*, insect cells, yeast or mammalian cells (such as Chinese hamster ovary cells (CHO) or COS cells). Other suitable host cells are known to those skilled in the art.

Preparation of Host Cells Containing Nucleic Acid Molecules of the Invention via In Vitro and Ex Vivo Methods Vector nucleic acid can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual*, 2nd Edition, Cold Spring Harbor Laboratory press (1989)), and other laboratory manuals. Additional examples of methods of introducing nucleic acid molecules encoding opsonins and/or opsonin/antigen complexes including an antigen and an opsonin are described below. The cells containing the introduced nucleic acid molecules encoding, for example, an opsonin, can themselves be administered to a subject (as the antigen) according to the methods of the invention, e.g., in a vaccine composition.

A. Introduction of Naked Nucleic Acid into Cells in vitro or ex vivo

1. Transfection mediated by $CaPO_4$: Naked nucleic acid can be introduced into cells by forming a precipitate containing the nucleic acid and calcium phosphate. For example, a HEPES-buffered saline solution can be mixed with a solution containing calcium chloride and nucleic acid to form a precipitate and the precipitate is then incubated with cells. A glycerol or dimethyl sulfoxide shock step can be added to increase the amount of nucleic acid taken up by certain cells. $CaPO_4$-mediated transfection can be used to stably (or transiently) transfect cells and is only applicable to in vitro modification of cells. Protocols for $CaPO_4$-mediated transfection can be found in *Current Protocols in Molecular Biology*, Ausubel, F. M. et al. (eds.) Greene Publishing Associates, (1989), Section 9.1 and in *Molecular Cloning: A Laboratory Manual, 2nd Edition*, Sambrook et al. Cold Spring Harbor Laboratory Press, (1989), Sections 16.32-16.40 or other standard laboratory manuals.

2. Transfection mediated by DEAE-dextran: Naked nucleic acid can be introduced into cells by forming a mixture of the nucleic acid and DEAE-dextran and incubating the mixture with the cells. A dimethylsulfoxide or chloroquine shock step can be added to increase the amount of nucleic acid uptake. DEAE-dextran transfection is only applicable to in vitro modification of cells and can be used to introduce nucleic acid transiently into cells but is not preferred for creating stably transfected cells. Thus, this method can be used for short term production of a gene product but is not a method of choice for long-term production of a gene product. Protocols for DEAE-dextran-mediated transfection can be found in *Current Protocols in Molecular Biology*, Ausubel, F. M. et al. (eds.) Greene Publishing Associates, (1989), Section 9.2 and in *Molecular Cloning: A Laboratory Manual, 2nd Edition*, Sambrook et al. Cold Spring Harbor Laboratory Press, (1989), Sections 16.41-16.46 or other standard laboratory manuals.

3. Electroporation: Naked nucleic acid can also be introduced into cells by incubating the cells and the nucleic acid together in an appropriate buffer and subjecting the cells to a high-voltage electric pulse. The efficiency with which nucleic acid is introduced into cells by electroporation is influenced by the strength of the applied field, the length of the electric pulse, the temperature, the conformation and concentration of the nucleic acid and the ionic composition of the media. Electroporation can be used to stably (or transiently) transfect a wide variety of cell types and is only applicable to in vitro modification of cells. Protocols for electroporating cells can be found in *Current Protocols in Molecular Biology*, Ausubel, F. M. et al. (eds.) Greene Publishing Associates, (1989), Section 9.3 and in *Molecular Cloning: A Laboratory Manual, 2nd Edition*, Sambrook et al. Cold Spring Harbor Laboratory Press, (1989), Sections 16.54-16.55 or other standard laboratory manuals.

4. Liposome-mediated transfection ("lipofection"): Naked nucleic acid can be introduced into cells by mixing the nucleic acid with a liposome suspension containing cationic lipids. The nucleic acid/liposome complex is then incubated with cells. Liposome mediated transfection can be used to stably (or transiently) transfect cells in culture in vitro. Protocols can be found in *Current Protocols in Molecular Biology*, Ausubel, F. M. et al. (eds.) Greene Publishing Associates, (1989), Section 9.4 and other standard laboratory manuals. Additionally, gene delivery in vivo has been accomplished using liposomes. See for example Nicolau et al. (1987) *Meth. Enz.* 149:157-176; Wang and Huang (1987) *Proc. Natl. Acad. Sci. USA* 84:7851-7855; Brigham et al. (1989) *Am. J. Med. Sci.* 298:278; and Gould-Fogerite et al. (1989) *Gene* 84:429-438.

5. Direct Injection: Naked nucleic acid can be introduced into cells by directly injecting the nucleic acid into the cells. For an in vitro culture of cells, nucleic acid can be introduced by microinjection. Since each cell is microinjected individually, this approach is very labor intensive when modifying large numbers of cells. However, a situation wherein microinjection is a method of choice is in the production of transgenic animals (discussed in greater detail below). In this situation, the nucleic acid is stably introduced into a fertilized oocyte which is then allowed to develop into an animal. The resultant animal contains cells carrying the nucleic acid introduced into the oocyte. Direct injection has also been used to introduce naked nucleic acid into cells in vivo (see e.g., Acsadi et al. (1991) *Nature* 332: 815-818; Wolff et al. (1990) *Science* 247:1465-1468). A delivery apparatus (e.g., a "gene gun") for injecting DNA into cells in vivo can be used. Such an apparatus is commercially available (e.g., from BioRad).

6. Receptor-Mediated DNA Uptake: Naked nucleic acid can also be introduced into cells by complexing the nucleic acid to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963-967; and U.S. Pat. No. 5,166,320). Binding of the nucleic acid-ligand complex to the receptor facilitates uptake of the nucleic acid by receptor-mediated endocytosis. Receptors to which a nucleic acid-ligand complex have targeted include the transferrin receptor and the asialoglycoprotein receptor. A nucleic acid-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122-2126). Receptor-mediated nucleic acid uptake can be used to introduce nucleic acid into cells either in vitro or in vivo and, additionally, has the added feature that nucleic acid can be selectively targeted to a particular cell type by use of a ligand which binds to a receptor selectively expressed on a target cell of interest.

Generally, when naked nucleic acid is introduced into cells in culture (e.g., by one of the transfection techniques described above) only a small fraction of cells (about 1 out of $10^5$) typically integrate the transfected nucleic acid into their genomes (i.e., the nucleic acid is maintained in the cell episomally). Thus, in order to identify cells which have taken up exogenous nucleic acid, it is advantageous to transfect nucleic acid encoding a selectable marker into the cell along with the nucleic acid(s) of interest. Preferred selectable markers include those which confer resistance to drugs such as G418, hygromycin and methotrexate. Selectable markers may be introduced on the same plasmid as the gene(s) of interest or may be introduced on a separate plasmid.

B. Viral-Mediated Gene Transfer

A preferred approach for introducing nucleic acid encoding a gene product into a cell is by use of a viral vector containing nucleic acid, e.g. a cDNA, encoding the gene product. Infection of cells with a viral vector has the advantage that a large proportion of cells receive the nucleic acid, which can obviate the need for selection of cells which have received the nucleic acid. Additionally, molecules encoded within the viral vector, e.g., by a cDNA contained in the viral vector, are expressed efficiently in cells which have taken up viral vector nucleic acid and viral vector systems can be used either in vitro or in vivo.

1. Retroviruses: Defective retroviruses are well characterized for use in gene transfer for gene therapy purposes (for a review see Miller, A. D. (1990) *Blood* 76:271). A recombinant retrovirus can be constructed having a nucleic acid encoding a gene product of interest inserted into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include Crip, Cre, 2 and Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150:4104-4115; U.S. Pat. Nos. 4,868,116; 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

2. Adenoviruses: The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482-6486), hepatocytes (Herz and Gerard (1993) *Proc. Natl. Acad. Sci. USA* 90:2812-2816) and muscle cells (Quantin et al. (1992) *Proc. Natl. Acad. Sci. USA* 89:2581-2584). Additionally, introduced adenoviral nucleic acid (and foreign DNA contained therein) is not integrated into the genome of a host cell but remains episomal, thereby avoiding potential problems that can occur as a result of insertional mutagenesis in situations where introduced nucleic acid becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

3. Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as little as 300 base pairs of AAV can be packaged and can integrate. Space for exogenous nucleic acid is limited to about 4.5 kb. An AAV vector such as that described in Tratschin et al. (1985) *Mol. Cell. Biol.* 5:3251-3260 can be used to introduce nucleic acid into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

The efficacy of a particular expression vector system and method of introducing nucleic acid into a cell can be assessed by standard approaches routinely used in the art. For example, nucleic acid introduced into a cell can be detected by a filter hybridization technique (e.g., Southern blotting) and RNA produced by transcription of introduced nucleic acid can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be expressed by a cell is not readily assayable, an expression system can first be optimized using a reporter gene linked to the regulatory elements and vector to be used. The reporter gene encodes a gene product which is easily detectable and, thus, can be used to evaluate the efficacy of the system. Standard reporter genes used in the art include genes encoding β-glactosidase, chloramphenicol acetyl transferase, luciferase and human growth hormone.

A host cell of the invention, such as a prokaryotic or eukaryotic host cell in culture, can be used to produce (i.e., express) fusion polypeptides of the invention. Accordingly, the invention further provides methods for producing polypeptides of the invention using the host cells of the invention. In one embodiment, the method comprises culturing the host cell of invention (into which a recombinant expression vector encoding a polypeptide of the invention has been introduced) in a suitable medium until the polypeptide is produced. In another embodiment, the method further comprises isolating the polypeptide from the medium or the host cell.

Transgenic Animals

The host cells of the invention can also be used to produce nonhuman transgenic animals. For example, in one embodiment, a host cell of the invention is a fertilized oocyte or an embryonic stem cell into which nucleic acid molecules encoding molecules, e.g., polypeptides, of the invention have been introduced. Such host cells can then be used to create non-human transgenic animals in which exogenous nucleic acid molecules encoding the polypeptides of the invention have been introduced into their genome or homologous recombinant animals in which endogenous nucleic acid molecules have been altered. Such animals are useful for studying the function and/or activity of the molecules of the invention and for identifying and/or evaluating modulators of the activity of the molecules of the invention. As used herein, a "transgenic animal" is a non-human animal, preferably a mammal, more preferably a mouse, in which one or more of the cells of the animal includes a transgene. A transgene is exogenous nucleic acid which is integrated into the genome of a cell from which a transgenic animal develops and which remains in the genome of the mature animal, thereby directing the expression of an encoded gene product in one or more cell types or tissues of the transgenic animal.

A transgenic animal of the invention can be created by introducing nucleic acid molecules encoding the polypeptides of the invention into the male pronuclei of a fertilized oocyte, e.g., by microinjection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of a polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the nucleic acid molecule of the invention, e.g., the transgene in its genome and/or expression of the transgene MRNA in tissues or cells of the animals. A transgenic founder animal can then be used to breed additional animals carrying the transgene. Moreover, transgenic animals carrying a transgene encoding polypeptides of the invention can further be bred to other transgenic animals carrying other transgenes.

Vaccine Compositions

Yet another aspect of the invention features vaccine compositions which include the nucleic acid molecules, the vectors containing the nucleic acid molecules, or the fusion polypeptides of the invention and a pharmaceutically acceptable carrier. These vaccine compositions can provide protection against (used as a prophylactic) infection by the antigen encoded by the nucleic acid molecule or included in the fusion polypeptide of the invention. In addition, the vaccine compositions of the invention can be used to treat (used as a therapeutic) infection by the antigen encoded by the nucleic acid molecule or included in the fusion polypeptide of the invention.

The preparation of vaccine compositions which contain the nucleic acid molecules or the fusion polypeptides of the invention as the active ingredient, is known to one skilled in the art. Typically, such vaccines are prepared as injectables, either as liquid solutions or suspensions; solid forms suitable for solution in, or suspension in, liquid prior to infection can also be prepared. The preparation can also be emulsified, or the protein encapsulated in liposomes. The active immunogenic ingredients are often mixed with carriers which are pharmaceutically acceptable and compatible with the active ingredient. The term "pharmaceutically acceptable carrier" refers to a carrier that does not cause an allergic reaction or other untoward effect in subjects to whom it is administered. Suitable pharmaceutically acceptable carriers include, for example, one or more of water, saline, phosphate buffered saline, dextrose, glycerol, ethanol, or the like and combinations thereof. In addition, if desired, the vaccine can contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosporyl lipid A, trehalose dimycolate and cell wall skeleton (MPL+TDM+CWS) in a 2% squalene/Tween 80 emulsion. Other examples of adjuvants include DDA (dimethyldioctadecylammonium bromide), Freund's complete and incomplete adjuvants and QuilA. In addition, immune modulating substances such as lymphokines (e.g., IFN-g, IL-2 and IL-12) or synthetic IFN-g inducers such as poly I:C can be used in combination with adjuvants described herein.

Dosage and Administration

Vaccine or treatment compositions of the invention may be administered parenterally, by injection, for example, either subcutaneously or intramuscularly. Additional formulations which are suitable for other modes of administration include suppositories, and in some cases, oral formulations or formulations suitable for distribution as aerosols. In the case of the oral formulations, the manipulation of T-cell subsets employing adjuvants, antigen packaging, or the addition of individual cytokines to various formulation can result in improved oral vaccines with optimized immune responses. For suppositories, traditional binders and carriers may include, for example, polyalkylene glycols or triglycerides; such suppositories may be formed from mixtures containing the active ingredient in the range of 0.5% to 10%, preferably 1%-2%. Oral formulations include such normally employed excipients as, for example, pharmaceutical grades of mannitol, lactose, starch magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25-70%.

The nucleic acid molecules or fusion polypeptides of the invention can be formulated into the vaccine or treatment compositions as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups can also be derived from inorganic bases such as, for example, sodium, potassium, ammonium, calcium, or ferric hydroides, and such organic bases as isopropylamine, trimethylamine, 2-ethylamino ethanol, histidine, procaine, and the like.

Vaccine or treatment compositions are administered in a manner compatible with the dosage formulation, and in such amount as will be prophylactically-and/or therapeutically effective. The quantity to be administered depends on the subject to be treated, including, e.g., capacity of the subject's immune system to synthesize antibodies, and the degree of protection or treatment desired. Suitable dosage ranges are of the order of several hundred micrograms active ingredient per vaccination with a preferred range from about 0.1 mg to 1000 mg, such as in the range from about 1 mg to 300 mg, and preferably in the range from about 10 mg to 50 mg. Suitable regiments for initial administration and booster shots are also variable but are typified by an initial administration followed by subsequent inoculations or other administrations. Precise amounts of active ingredient required to be administered depend on the judgment of the practitioner and may be peculiar to each subject. It will be apparent to those of skill in the art that the therapeutically effective amount of nucleic acid molecule or fusion polypeptides of this invention will depend, inter alia, upon the administration schedule, the unit dose of antigen administered, whether the nucleic acid molecule or fusion polypeptide is administered in combination with other therapeutic agents, the immune status and health of the recipient, and the therapeutic activity of the particular nucleic acid molecule or fusion polypeptide.

The compositions can be given in a single dose schedule, or preferably in a multiple dose schedule. A multiple dose schedule is one in which a primary course of vaccination can include 1-10 separate doses, followed by other doses given at subsequent time intervals required to maintain and or reinforce the immune response, for example, at 1-4 months for a second dose, and if needed, a subsequent dose(s) after several months. Periodic boosters at intervals of 1-5 years, usually 3 years, are desirable to maintain the desired levels of protective immunity. The course of the immunization can be followed by in vitro proliferation assays of peripheral blood lymphocytes (PBLs) co-cultured with ESAT6 or ST-CF, and by measuring the levels of IFN-g released from the primed lymphocytes. The assays can be performed using conventional labels, such as radionucleotides, enzymes, fluorescent labels and the like. These techniques are known to one skilled in the art and can be found in U.S. Pat. Nos. 3,791,932, 4,174,384 and 3,949,064, which are hereby incorporated by reference.

Intramuscular Injection of Naked DNA

Naked DNA refers to DNA that is free from association with proteins or lipids that enhance introduction of the DNA into a host cell. For direct gene transfer of tibialis anterior (TA) muscle in mice, it is optimal to use 6-8 week old mice (weight 19-21 gm). Females give better immune responses for the hepatitis B surface antigen, and this might be true for some other antigens. The choice of mouse strain will also depend on the antigen. Mice should be anaesthetized since awake mice will contract their muscles and squeeze the DNA solution out. We use either sodium pentobarbital anesthesia (75 mg/kg IP) or halothane inhaled anesthetic (e.g. Metofane form Pittman-Moore). After the mice are asleep the hindlimbs are shaved to better reveal the tibial bone and the access to the TA muscle. Shaving off the limbs allows much greater precision and thus reproducibility for the actual injection step.

In preparation for the intramuscular injection, DNA is dissolved in endotoxin-free injectable PBS (not Tris EDTA) and is best at 0.1-2 mg/ml (depending on how immunogenic your protein is and how rapid a response you want).

To inject plasmid DNA use a 27GX¾" (0.4×20 mm) needle attached to a 1 ml tuberculin syringe. A piece of polyethylene tubing (PE 20, ID-0.38 mm) should be fit over the needle such that only 2-3 mm of needle protrudes (basically just the beveled portion should protrude). Fill the syringe with the DNA solution, attach the needle and then slowly fill the needle so that no air bubbles are trapped. The problem of dead volume is simplified using an insulin syringe (see below).

Alternatively, use a U-100 insulin syringe (1 cc or ³⁄₁₀ cc) which comes with a pre-attached 29G½ needle. Polyethylene tubing is used in the same way as described above. Inject through the skin—the tip of the needle should be about 3 mm lateral to the anterior tibial tuberosity (this is about half way between the knee and the ankle), keeping the needle almost perpendicular to the tibial. Once the needle is in place (push in until the end of the PE tubing rests against the skin with a bit of pressure), inject the 50 µl slowly (over approximately 10 sec), hold the needle in place for another 5-10 sec, then remove the needle slowly. If you accidentally pull the needle out before injection, try to reinsert it in the same hole, otherwise you will experience leakage.

Yet another aspect of the invention pertains to methods for modulating an immune response in an animal, e.g., a non-rodent animal, e.g., a non-rodent mammal, to an antigen. These methods include administering to the animal a nucleic acid molecule or a fusion polypeptide of the invention in an amount and over a period of time effective to modulate an immune response to the antigen in the animal. The term "modulate" as used herein refers to inhibition or activation/stimulation of an immune response to an antigen, a combination of an inhibition and an activation of an immune response (e.g., an inhibition of a humoral immune response and an activation of a cell mediated immune response or vice versa, or an inhibition of a systemic immune response and an activation of a secretory immune response or vice versa), or a change in the character of an immune response to an antigen. Preferably, the modulation of an immune response useful in the present invention is the modulation of a cellular immune response, wherein a "cellular immune response" is an immune response mediated by T-cell activation. Assays are provided herein for determining immune response modulation.

Preferred direct targets of the compositions and methods of the invention include phagocytic leukocytes, e.g., cells of monocyte lineage. The term "non-rodent animal" as used herein refers to any animal which is not a rodent, e.g., a mouse or rat. The term "mammal" as used herein refers to a non-rodent mammal. Examples of preferred mammals include domestic mammals kept for purposes of food production, labor, or companionship, and primates, e.g., humans.

The phrase "in an amount and over a period of time effective to modulate an immune response to the antigen in the mammal" refers to a dosage and period of time in which modulation of an immune response in the recipient mammal or recipient subject occurs. In one embodiment, such an immune response can be observed when the recipient subject exhibits, for example, increased resistance to a challenge by the antigen against which the subject has been immunized using the nucleic acid molecules or the fusion polypeptides of the invention. The nucleic acid molecules and the fusion polypeptides of the invention are typically administered to the recipient animal or subject in the form of a vaccine composition by the routes and in the formulations described herein. In addition, the nucleic acid molecules and the fusion polypeptides of the invention, alone or in the form of a vaccine composition, can be administered in combination with other substances which influence immune responses including, but not limited to, cytokines, anaphylatoxins, cell-death inducing molecules, and cell surface molecules.

Yet another aspect of the invention pertains to antibodies reactive with the fusion polypeptides of the invention. The term "antibody" as used herein refers to monoclonal and polyclonal antibodies. For example, by using the fusion polypeptides of the invention as immunogens, anti-the fusion polypeptide antisera or monoclonal antibodies can be made by standard protocols (See, for example, *Antibodies: A Laboratory Manual* ed. by Harlow and Lane (Cold Spring Harbor Press: 1988)).

Assays for Determining Immune Response Modulation According to the Invention

Fusion polypeptides and multichain complexes are useful according to the invention to modulate an immune response in a mammalian, preferably a human, to an antigen or antigens. The polypeptides or complexes are administered and are taken up (i.e., ingested or phagocytosed) by antigen presenting cells.

An "immune response" refers to stimulation/activation of a selected response involving the immune system, or suppression, elimination, or attenuation of a selected response. Thus, to modulate an immune response means that the desired response is more efficient, more rapid, greater in magnitude, and/or more easily induced than when a control protein is administered in an identical fashion.

The following in vitro and in vivo assays are useful for determining whether an immune response is modulated according to the invention. The assays described in detail below measure stimulation or suppression of cellular or humoral immune responses to an antigen. The antigens referred to in the following assays are representative. It will be apparent to one of skill in the art that an immune response to a selected antigen useful according to the invention may be measured using one or more of the following assays by adapting the assay to that antigen.

I. Detection of Increased Phagocytosis

The following assay may be used in order to determine whether fusion polypeptides or complexes stimulate phagocytosis by antigen presenting cells.

Phagocytosis is examined using monocytes that have been adhered at 37° for 30 min in RPMI without added FCS. Sheep erythrocytes are incubated with a candidate opsonin, or its precursor, under conditions such that there are no more than 300 of such molecules, on average, are deposited on each erythrocyte. If a precursor is used, coated erythrocytes are then processed to convert all precursors to the actual candidate opsonin molecule (e.g., See Carlo et al., *J. Immunol* 123:523-8(1979)). Fresh monocytes are isolated from the subject, and $5 \times 10^4$-$1 \times 10^5$ of these cells suspended in 0.25-0.5 ml of RPMI medium with 1% BSA. This aliquot is placed in a tissue culture well and incubated for 30 min at 37° C. An excess of coated erythrocytes, suspended at $1.2 \times 10^8$ cells/ml, is overlain on the monocytes, the plate is centrifuged for 5 min at 50 g, and incubated for 30 min at 37° C. Non-ingested material is removed in two hypotonic lysis steps using ice-cold lysing buffer before fixing and staining the adherent cells, and examining the cells under light microscopy. Phagocytosis is quantified by determining the percentage of 100 monocytes ingesting one or more target cells, and the total number of ingested E/100 monocyptes (PI) is recorded. Stimulation of phagocytosis according to the invention is indicated by a phagocytic index of equal to or greater than 40.

II. Amplification of the Immune Response Usually Involves Proliferation of Particular Subpopulations of Lymphoid Cells that are Normally in the Resting State.

Proliferative assays have the following applications in clinical studies: (1) Assessment of overall immunologic competence of T cells or B cells as manifested in their ability to respond to polyclonal proliferation signals such as mitogens or anti-CD3 antibodies. Defects in the proliferation may be indicative of fundamental cellular immunologic defect. Low proliferation is often found as a nonspecific secondary effect of chronic disease. (2) Assessment of an individual's response to specific antigens, where low responses are indicative of general or specific immunologic defect. (3) Determination of MHC compatibility by the mixed lymphocyte reaction (MLR).

In addition, proliferative assays are useful for estimating lymphokine production, investigating signal transduction, and assessing growth factor requirements (e.g., lymphokines) for T or B cells. The procedure outlined here measures incorporation of [$^3$H]thymidine into DNA, which usually correlates well with cell growth as measured by changes in cell number. However, when the activation stimulus is toxic, as with chemical activators such as ionomycin plus phorbol myristate acetate (PMA), the burst of new DNA synthesis following activation may not be accompanied with a net increase in viable cells, and, in fact, a decline in cell number may be observed. In this instance, [$^3$H]thymidine incorporation in DNA is more indicative of initial cell stimulation than estimation of cell number. In addition, [$^3$H]thymidine incorporation provides information on cell populations, not on individual cells. Alternate methods, such as flow cytometry may be used for studies requiring that type of information.

Assay for Antigen-Induced T Cell Proliferation

This protocol is designed to test the proliferation of T cells in response to a specific antigen—tetanus toxoid. It can be modified to test T cell proliferation in response to any protein or polysaccharide antigen. Materials: (T cell suspension, autologous antigen-presenting cell suspension (non-T cells), Tetanus toxoid solution (Connaught or State Laboratory Institute of Massachusetts)). (1) Count T cells and adjust to $1 \times 10^6$ cells/ml with complete RPMI-10 AB. (2) Treat antigen-presenting cells with mitomycin C (or irradiate with 2500 rad) as in step 2 of one-way MLR protocol. Adjust concentration of antigen-presenting cells to $2 \times 10^5$ cells/ml. Antigen-presenting cells can consist of autologous non-T cells or autologous monocytes/macrophages. (3) Add 100 ul T cell suspension and 50 ul antigen-presenting cell population to wells; mix just before dispensing. (4) Add 50 ul tetanus toxoid solution to give final concentrations of 0, 1, 5, 10, and 20 ug/ml. Prepare three wells for each dilution. (5) Incubate 6 days in a humidified 37° C., 5% $CO_2$ incubator. (6) Pulse with [$^3$H]thymidine and harvest as described in support protocol.

Assay for Lymphokine-Dependent Cell Proliferation

This protocol assays the lymphokine-dependent proliferation of a lymphocyte population, in this case, the IL-4 dependent proliferation of B cells. Materials: (Tonsil B cell suspension, Anti-IgM cross-linked to Sepharose beads (Bio-Rad), 10,000 U/ml human rIL-4 (Genzyme) in complete RPMI-10). (1) Count tonsil B cells and adjust concentration to $1 \times 10^6$ cells/ml with complete RPMI-10. (2) Dispense 100 ul of tonsil B cells into each well. Prepare three wells for each experimental condition. (3) Dilute 10,000 U/ml rIL-4 solution 1:10, 1:100, and 1:1000. Add 20 ul of the stock or dilution to appropriate wells to yield 1000 U/ml, 100 U/ml, 10 U/ml, and 1 U/ml. Include a control well with no rIL-4. (4) Pipet anti-IgM beads into appropriate wells.

Determine the optimal concentration of beads with pilot experiments. It is best to include several concentrations of beads in each experiment to "bracket" the optimal dose. Prepare wells with tonsil B cells and IL-4 dilutions alone, anti-IgM beads alone, culture medium alone, and all the combinations of IL-4 and anti-IgM bead dilutions. (5) Increase the volume of each well to 200 ul with complete RPMI-10 as necessary. (6) Culture 5 days in a humidified 37° C., 5% $CO_2$ incubator. (7) Pulse with [$^3$H]thymidine and harvest as described in support protocol.

[$^3$H]Thymidine Pulse and Harvest of Cell Cultures

This protocol is used in conjunction with the preceding protocols to complete the [$^3$H] thymidine incorporation assay. (1) Add 20 ul of 50 uCi/ml [$^3$H]thymidine to each culture (1.0 uCi) at a fixed time before terminating the culture (usually 6 or 18 hr). (2) Harvest cell cultures using an automated multiwell harvester that aspirates cells, lyses cells, and transfers DNA onto filter paper, while allowing unincorporated [$^3$H]thymidine to wash out. Fill and aspirate each row of the microtiter plate ten times to ensure complete cell transfer and complete removal of unincorporated thymidine. Wash each filter strip with 100% ethanol to facilitate drying. Transfer to scintillation vials. For semiautomated harvester, transfer filter dots for each well into scintillation counting vials. For manual transfer, dry filters under lamp and transfer to scintillation vial with forceps. Add scintillation fluid to each vial. (3) Count samples in scintillation counter until standard deviation is less than 2%. Calculate mean cpm for background cultures and for each experimental condition. There should be less than 20% variation in replicate cultures.

III. Induction and Measurement of In Vitro Antibody Responses

The capacity of the human immune system to mount an antibody response following in vivo immunization with a protein or polysaccharide antigen is a revealing indication of the overall integrity of both the B and T cell arms of the immune system. As such, in vivo immunization followed by measurement of the antibody response is an appropriate test of immune function in the various acquired and congenital immunodeficiencies and in a host of other conditions affecting the immune system. The following procedures are for in vivo immunization and for the measurement of the subsequent immune response using an ELISA technique.

Immuno-Enzymetric Assay for Cytokines Using NIP- and HRPO-Labeled Antibodies

This protocol describes an immunonoenzymetric assay for cytokines using a heterogeneous, noncompetitive immunoassay reaction in which the cytokine is immobilized by a coating antibody bound to a microtiter plate. Unbound material is washed free, and detection is carried out using a different anti-cytokine antibody labeled with the hapten nitroiodophenyl (NIP). This is in turn detected by a horseradish peroxidase (HRPO) conjugate of an anti-NIP antibody, which is revealed with the chromogenic substrate ABTS. In this noncompetitive immunoassay, the immunoassay signal ($A_{405}$) increases as a direct function of the amount of cytokine present in the sample. Antibodies are prepared as described in Current Protocols in Immunology, 1995, 6.20.2-6.20.10.

Coat assay plate. (1) Using a multichannel pipettor, transfer 100 ul of an appropriate dilution of coating antibody into all wells of the assay plate that are to be used. (2) Seal plates with microtiter plate sealer or Parafilm and incubate 2 hr. At 37° C. Prepare samples and standards in preparation plate. (3) Dilute each sample (or aliquot of conditioned medium) to be assayed with an equal volume of immunoassay diluent. (4) Pipet less than or equal to 1 ml of each diluted sample to be assayed into the upper chamber of a separate Spin-X microfiltration device. Microcentifuge 5 min. At 10,000 rpm and save the filtrates that collect in the lower chambers. (5) Add 65 ul of each diluted sample to the appropriate well of a preparation plate (i.e., a separate 96-well microtiter plate). (6) Thaw an aliquot of cytokine standard at room temperature and make sure that it is well mixed. Pipet 130 ul into the well of the preparation plate representing the highest concentration on the standard curve. Transfer 65 ul from this well into the next, then continue performing serial 1:1 dilutions in immunoassay diluent so that 65 ul of each concentration represented on the standard curve is placed in appropriate well of the preparation plate. (7) Thaw an aliquot of calibrator at room temperature (if used). Dilute with an equal volume of immunoassay diluent, then pipet 65 ul of diluted calibrator into appropriate well or wells of preparation plate.

Incubate with coating antibody. (8) Remove coated assay plate from incubator. Dip in 2-liter beaker filled with 1× wash buffer, then invert over sink and flick to remove liquid. Repeat two more times, then bang dry on paper towel. (9) Transfer 50 ul of solution from each well of preparation plate to corresponding well of the assay plate using multichannel pipettor. (10) Seal plate with microtiter plate sealer or Parafilm and incubate 2 hr. at room temperature.

Incubate with detecting antibody. (11) Dilute NIP-labeled detecting antibody specific to cytokine of interest to 1 ug/ml in detecting buffer. (12) Wash assay plate as in step 8. (13) Add 75 ul diluted detecting antibody from step 11 to all wells of assay plate, including unused outer walls. (14) Reseal plate with microtiter plate sealer or Parafilm and incubate 1 hr. at room temperature.

Incubate with HRPO-conjugated anti-NIP antibody. (15) Dilute HRPO-conjugated anti-NIP Mab 1:3000 in detecting buffer. (16) Wash assay plate as in step 8. (17) Add 75 ul of diluted HRPO-labeled anti-NIP antibody from step 15 to all wells of assay plate. (18) Reseal plate with microtiter plate sealer or Parafilm and incubate 1 hr. at room temperature.

Incubate with chromogenic substrate. (19) Wash assay plate as in step 8. (20) Add 100 ul ABTS substrate working solutions to all wells of assay plate. Cover plate and incubate at room temperature until color development reaches desired level (generally until $A_{405}$ for wells containing the highest concentration of standard is between 1.5 and 2). This protocol usually produces an assay that can be read after 30 to 60 min.

Read plate and analyze data. (21) Using microtiter plate reader with computer interface, measure absorbance in all wells at 405 nm in single-wavelength mode or at 405 and 650 nm in dual-wavelength mode. (22) Fit standard data to a curve described by a first-degree (linear), second degree (quadratic), or four-parameter (nonlinear) mathematical function using curve-fitting software. (23) Interpolate absorbance data from unknown cytokine samples to fitted standard curve, and calculate cytokine concentrations.

IV. Induction of an in vivo Antibody Response Provides an Approach to the Evaluation of the Overall Integrity of the Immune System.

In the protocols presented here, diptheria and tetanus toxoids are used as representative protein antigens and pneumococcal polysaccharides are used as representative polysaccharide antigens because of their safety and availability. It should be noted, however, that the responses elicited by these antigens are likely to be secondary responses because of past vaccination or natural exposure. To obtain a primary response, an unusual antigen such as keyhole limpet hemocyanin should be used.

When antigens are administered by the intramuscular or subcutaneous route, as they are here, a "systemic" immune response is induced and measurement of circulating antibody is most appropriate. It is, however, sometimes of interest to evaluate "local" or mucosal immune responses. In this case, the antigen is given either intranasally to stimulate respiratory lymphoid tissue or orally to stimulate gastrointestinal lymphoid tissue and bronchial washings or intestinal fluids, rather than blood, is assayed for antibody content; in addition, antigens are used that are more appropriate for stimulation of the local/mucosal response (i.e., influenza virus antigen for respiratory responses and cholera toxin for gastrointestinal responses).

In assaying the in vivo antibody response, it is important to determine responses to both protein and polysaccharide antigens because these antigens stimulate different components of the immune system. In this regard, the major antibody response to protein antigen is composed of IgG1 and IgG3 subclass antibodies, whereas the major antibody response to polysaccharide antigen is composed of IgG2 subclass antibody.

A variety of immunoassay techniques have been used to measure antibody responses in materials obtained after in vivo immunization. Of these, the ELISA assay is perhaps the most useful because it yields a stable, easily measurable, reproducible, and safe readout.

Induction of in vivo Antibody Responses to Protein/Polysaccharide Antigens

In this protocol antigens are administered by the intramuscular or subcutaneous route and serum is collected for measurement of responses. (1) Draw preimmunized blood sample, allow blood to clot, and separate serum from clot by centrifugation. Store serum at −20° C. to −70° C. in appropriately labeled plastic tubes. (2) Inject 0.5 ml of toxoid mixture into an appropriately prepared intramuscular site (deltoid or thigh), taking care not to inject material intravenously. (3) Inject 0.5 ml polyvalent pneumococcal vaccine into an appropriately prepared subcutaneous site, taking care not to inject material intravenously. (4) Draw post-immunization blood samples at desired intervals, usually at 1, 2, and 3 weeks. Separate serum and store at −20° C. to −70° C. (5) After all serum samples are collected, assay samples for presence of antibodies using ELISA.

The ELISA offers a rapid, sensitive, reproducible, nonradioactive method for measuring in vivo antibody responses to a variety of antigens, including protein and polysaccharide antigens in sera obtained from individuals vaccinated with tetanus and diphtheria boosters and the polyvalent pneumococcal polysaccharide vaccine. Assays specific for tetanus, diphtheria and the pneumococcal polysaccharide types I, II, and III are detailed in Current Protocols in Immunology, 1995, Vols. 6 and 7.

The invention is further illustrated by the following exemplification which in no way should be construed as being further limiting. The contents of all cited references (including literature references, issued patents, published patent applications, and co-pending patent applications) cited throughout this application are hereby expressly incorporated by reference.

EXEMPLIFICATIONS

Example 1

A fusion gene incorporating sequences for the pneumococcal antigen pneumolysin and for the alpha chain of the opsonin murine C3b is generated using the following method.

The sequence encoding the alpha chain of murine C3b is amplified by PCR from mouse liver cDNA using an upstream primer corresponding to nt 2301-2324 of Genbank K02782, and a downstream primer complementary to nt 5018-5045. The gene for pneumolysin is amplified from pneumococcal DNA using an upstream primer corresponding to nucleotides 207-233 of Genbank M17717 and flanked on the 5' end by 12 bases that correspond to nt 5034-5045 of Genbank K02782 and a downstream primer that corresponds to the sequence complementary to nucleotides 599-1622 of M17717 and flanked at the 5' end by a SphI site. Both products are isolated by agarose gel electrophoresis, eluted using glass beads, and used, in equimolar amounts, in a PCR reaction with excess amounts of the upstream C3b alpha chain primer and the downstream pneumolysin primer. The fusion product is isolated by agarose gel electrophoresis and digested with SphI. A double-stranded DNA sequence corresponding to the mouse IL-2 secretory sequence (nt 48-107 of Genbank X01772) and flanked upstream by a single-stranded HindIII overhang is prepared. The mammalian expression vector pcDNA3 is digested with HindIII and SphI, and the fragments are ligated into the plasmid so that the CMV promoter is upstream of the IL-2 signal sequence, which is upstream of the C3b alpha chain/pneumolysin fusion gene.

Example 2

A fusion gene incorporating sequences for the pneumococcal antigen pneumolysin and for the opsonin murine C3 is generated using the following method.

The sequence encoding murine C3 is amplified by PCR from mouse liver cDNA using an upstream primer corresponding to nt 57-78 of Genbank K02782, and a downstream primer complementary to nt 5018-5045. The gene for pneumolysin is amplified from pneumococcal DNA using an upstream primer corresponding to nucleotides 207-233 of Genbank M17717 and flanked on the 5' end by 12 bases that correspond to nt 5034-5045 of Genbank K02782 and a downstream primer that corresponds to the sequence complementary to nucleotides 599-1622 of M17717 and flanked at the 5' end by a SphI site. Both products are isolated by agarose gel electrophoresis, eluted using glass beads, and used, in equimolar amounts, in a PCR reaction with excess amounts of the upstream C3 primer and the downstream pneumolysin primer. The fusion product is isolated by agarose gel electrophoresis and digested with SphI. The mammalian expression vector pcDNA3 is digested with HindIII, blunted with Klenow, and then digested with SphI, and the fusion gene is ligated into the plasmid so that it is downstream of the CMV promoter.

In Examples 1 and 2, fusion constructs comprising pneumolysin are useful for vaccinating an animal against infection with *S. pneumoniae*, e.g. pneumonia, meningitis, bacteremia, pericarditis, otitis media, or osteomyelitis. Efficacy of the vaccine, administered prophylactically or therapeutically, can be evidenced by a decreased incidence or prevalence of pneumococcal disease, a lower case-mortality rate, fewer complications, or a shorter mean duration of disease (e.g., reduction from 10 to 5 days) in a population.

Example 3

A fusion gene incorporating sequences for the antigen chicken lysozyme and for the opsonin murine mannose binding protein A (MBP) and for a $Gly_3$ linker is generated using the following method.

The sequence encoding MBP is amplified by PCR from mouse liver cDNA using an upstream primer corresponding to nt 121-142 of Genbank S42292 and a downstream primer complementary to nt 818-837 and flanked on its 5' side by 12 residues of poly-C. Lysozyme is amplified from chicken embryo cDNA using an upstream primer corresponding to nt 82-102 of Genbank V00428 and flanked on its 5' side by 12 residues of poly-G, which is itself flanked 5' by a sequence corresponding to nt 829-837 of S42292, and a downstream primer complementary to nt 450-468 of V00428 flanked on the 5' side by an XbaI site. Both products are isolated by agarose gel electrophoresis, eluted using glass beads, and used, in equimolar amounts, in a PCR reaction with excess amounts of the upstream MBP primer and the downstream lysozyme primer. The fusion product is isolated by agarose gel electrophoresis and digested with XbaI. The mammalian expression vector pcDNA3 is digested with HindIII, blunted with Klenow, and then digested with XbaI, and the fusion gene is ligated into the plasmid so that it is downstream of the CMV promoter.

Example 4

A fusion gene incorporating sequences for an immunodominant peptide of chicken lysozyme and for the opsonin murine mannose binding protein A (MBP) is generated using the following method.

The sequence encoding MBP is amplified by PCR from mouse liver cDNA using an upstream primer corresponding to nt 121-142 of Genbank S42292 and a downstream primer complementary to nt 818-837. A double-stranded oligonucleotide is obtained corresponding to nt 196-237 of Genbank V00428 and flanked on its downstream side by a single-stranded XbaI overhang. The pcDNA3 plasmid is digested with HindIII, blunted with Klenow, and digested XbaI. The MBP sequence is ligated to the vector and the product is isolated by agarose gel electrophoresis and glass beads elution. The lysozyme peptide encoding sequence is ligated into the latter product, and, using restriction digest analysis and DNA sequencing, clones are identified in which a single MBP gene in sense orientation is immediately downstream of the promoter and upstream of the lysozyme peptide gene.

Example 5

In this example, the APC binding domain is located at the carboxy terminus of the fusion polypeptide and the antigen is located at the amino terminus of the fusion polypeptide.

A fusion gene incorporating sequences for an immunodominant peptide of chicken lysozyme and for the APC binding moiety of the opsonin murine a2macroglobulin is generated using the following method.

The sequence encoding a2m is amplified by PCR from mouse liver cDNA using an upstream primer corresponding to nt 3683-3709 of Genbank M93264 and a downstream primer complementary to nt 4510-4537 and flanked on its 3' side by an XhoI site. A double-stranded oligonucleotide is obtained corresponding to nt 196-237 of Genbank V00428 and flanked on its downstream side by a sense-strand C paired with an antisense-strand G, followed by a sense-strand G paired with an antisense-strand C, followed by a sense-strand ApaI overhang. A double-stranded DNA molecule corresponding to the mouse IL-2 secretory sequence (nucleotides 48-107 of Genbank Acc. X01772) flanked upstream by a single-stranded HindIII overhang is prepared. The a2m fragment is digested with XhoI and ApaI. The pcDNA3 plasmid is digested with HindIII, and digested with XhoI. The three fragments are ligated into the vector.

In Examples 3-5, Chicken lysozyme is a well-characterized reporter antigen that can be used to evaluate the immunomodulatory effects of a fusion polypeptide comprising it. Animals can be vaccinated with the plasmid encoding the fusion polypeptide (or the polypeptide itself) or a plasmid encoding the antigen (or the antigen itself). The immune responses to the antigen can then be compared by assays for, e.g., antibody production, lymphocyte proliferation, cell-mediated cytotoxicity, or cytokine production. Another type of assay involves challenging the animals with syngeneic tumor cells transfected with a gene encoding the antigen and examining for a reduced incidence of tumor formation (e.g., from 80% to 40%) in animals receiving the fusion vaccine versus those receiving the antigen vaccine.

Example 6

In this example, the molecule comprises an antigen and two different opsonins. A fusion construct comprising the a2m APC binding site and an immunodominant peptide of chicken lysozyme is prepared in a manner similar to that of Example 5. The gene encoding murine MBP-A is then amplified in a manner that allows it to be ligated in-frame upstream of the lysozyme peptide. In this case, the MBP moiety provides a secretory signal for the entire fusion polypeptide, which can be inserted into an appropriate expression vector.

Example 7

In this example, three units of the same opsonin are included in one polypeptide. The sequence encoding the a chain of murine C3b is amplified in three ways: in one reaction, the downstream primer includes a sequence that can be annealed in-frame to the upstream end of the sequence obtained in a second reaction. The downstream end of the second sequence is designed to anneal in-frame to the upstream end of a sequence obtained in a third reaction. The downstream end of the third C3b α encoding sequence is designed to anneeal in-frame to a sequence encoding a polypeptide chain of telomerase, a tumor antigen. The construct can be cloned into a secretory expression vector which places the murine IL-2 secretory sequence in-frame upstream of the first C3b.

Example 8

The following set of experiments demonstrate the efficacy of nucleic acid molecules of the present invention in increasing the immune response as described in the claims.

Figure 2:
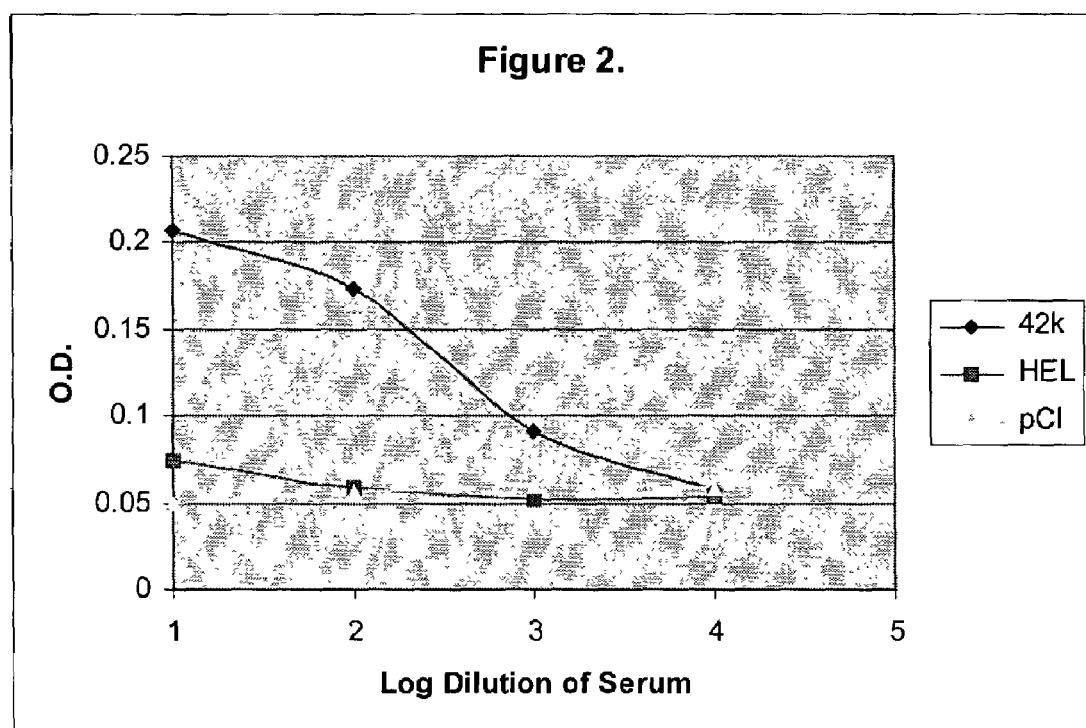

FIGS. 1 and 2 show the results of two experiments following the protocols described hereinbelow, in which various DNA constructs were administered to mice. In these Exhibits, optical density ("OD") corresponds to IgG1 antibody level. In FIGS. 1 and 2, "42K" refers to the construct encoding the IL2 secretory sequence, the 42 N-terminal amino acids of the C3bα' chain (which, as taught above, binds to CR1, a molecule expressed on monocytes), and the antigen HEL. "HEL" refers to the construct encoding only the IL2 secretory sequence and the antigen HEL. In the experiment shown in FIG. 2, a set of mice that received the pCI expression vector without any insert was also included. The data from both experiments shows that the construct comprising the secretory sequence and the amino acid sequence that binds to a molecule on the surface of an APC of monocytic lineage significantly amplifies the IgG1 immune response to HEL.

Experimental Protocols

I. Cloning of a DNA Construct Encoding i) a Secretory Sequence, ii) the 42 N-Terminal Amino Acids of the C3bα' Chain, and iii) Hen Egg Lysozyme (HEL) Fused In-Frame Cloning of the C3bα'-HEL plasmid was a multistep process starting with a plasmid termed C3bα'-GPI. This cloning strategy was chosen because the C3bα'-GPI plasmid had previously been constructed and was readily available. One skilled in the art, though, will recognize that many equivalent strategies are possible.

Construction of the C3bα'-GPI Plasmid

A DNA oligonucleotide sequence encoding a GPI modification signal sequence was cloned into the plasmid pUC19 as follows:

The following two oligonucleotides were purchased:
GTX-5

(SEQ ID NO: 1)
5'pAATTCCGCGCCGGCACAGTGCTCAGAGACAAACTGGTCAAGTGTGAG

GGCATCAGCCTGCTGGCTCAGAACACCTCGTGGCTGCTGCTGCTCCTGCT

GTCCCTCTCCCTCCTCCAGGCCACGGATTTCATGTCCCTGTGACTGGGTA

C

GTX-5 is an oligonucleotide encoding the GPI modification signal sequence found on the human Thy-1 protein. GTX-5 contains:

A 5' EcoRI overhang (bases 1-5)
An NgoMI site for in-frame ligation (bases 9-14)
The coding sequence for the GPI modification signal sequence found on human (bases 15-137)
Termination codon (bases 138-140)
A 3' KpnI overhang (bases 144-148)
GTX-6

(SEQ ID NO: 2)
5'pCCAGTCACAGGGACATGAAATCCGTGGCCTGGAGGAGGGAGAGGGAC

AGCAGGAGCAGCAGCAGCCACGAGGTGTTCTGAGCCAGCAGGCTGATGCC

CTCACACTTGACCAGTTTGTCTCTGAGCACTGTGCCGGCGCGG

GTX-6 is complementary to GTX-5.

GTX-5 and GTX-6 were dissolved in individual tubes in sterile water at a final concentration of 1 microgram/lambda. GTX-5 and GTX-6 were mixed at a final total concentration of 100 ng/lambda and allowed to anneal for 60 minutes at room temperature.

The GTX-5:GTX-6 double stranded oligonucleotide was cloned into pUC19 as follows: pUC19 plasmid was purchased. Four (4) micrograms of plasmid DNA was digested with EcoRI and KpnI. After electrophoresis, the linear DNA was purified from a 0.7% agarose gel using a Qiagen purification kit according to instructions from the manufacturer.

Approximately 100 ng of the GTX-5:GTX-6 oligonucleotide was ligated to 200 ng of the EcoRI-KpnI digested pUC19 in a final volume of 20 microliters. Ligation was at room temperature for 60 minutes.

Competent AG-1 cells were purchased from Stratagene and the plasmid transformed into these cells. Transformation protocols were according to the manufacturer. Transformed *E. coli* were selected on LB-amp plates.

Bacterial colonies growing on LB plates containing ampicillin (100 micrograms/ml) were picked into one ml of LB with amp and grown overnight at 37° with shaking. Plasmid DNA was isolated using alkaline lysis protocol. Plasmid DNA was digested with EcoRI and KpnI. DNA was electrophoresed on 1.6% agaraose gels stained with ethidium bromide.

Colonies containing an EcoRI-KpnI fragment of approximately 148 bp were identified. Colonies were picked into 100 ml of LB with amp and grown overnight. Plasmid DNA was purified using kits purchased from Qiagen. Protocols for DNA isolation were according to the manufacturer.

Plasmid DNA from a Thy-1-GPI positive clone, now called pUC-GPI 21, was sequenced to confirm its identity.

PCR of C3bα' Chain

The C3bα' coding sequence was amplified from a mouse liver cDNA library purchased from Clontech. The primers for PCR are as follows:

Upstream (SEQ ID NO: 3)
5'GCGAATTCCGCCTAGGAGTGAATTGGAGGAAGACATAATTCCAGAAGA

AGATATTATC

Downstream (SEQ ID NO: 4)
5'TAGCCGGCGTTGGGACAACCATAAACCACCATAGATTCTGTGAATGC

PCR parameters were as follows:

| Denaturation | 94° | 1 minute |
| Annealing | 65° | 1 minute |
| Extension | 72° | 1 minute |
| Hold | 72° | 10 minutes |

PCR was done for 35 cycles using Pfu polymerase.

After PCR, the reaction was allowed to cool at 4° for 10 minutes.

The C3bα' chain PCR product was purified after electrophoresis through a 1% agarose gel. The DNA band was excised and the DNA fragment purified using a kit purchased from Qiagen. Protocols were according to the manufacturer.

Construction of C3bα'-GPI 21 Chimeric

The purified C3bα' chain DNA fragment was digested with EcoRI and NgoMI. After digestion, the reaction mix was extracted with phenol:chloroform (1:1) followed by water saturated chloroform. The aqueous phase was adjusted to 0.3M Sodium acetate pH 5.2 and the DNA precipitated with 2 volumes of ethanol at −80° for 2 hours. The DNA was pelleted by centrifugation, ethanol removed, and the pellet rinsed with 70% ethanol. The pellet was dried under vacuum.

The C3bα' chain DNA was resuspended in sterile water and ligated to pUC19-GPI 21 that had been digested with EcoRI-NgoMI. Ligation was for one hour at room temperature. PUC19 GPI 21 ligated to C3bα' chain DNA was used to transform competent AG-1 cells. Transformed AG-1 cells were selected on LB plates with ampicillin.

Transformed colonies were picked individually in one ml of LB containing 100 micrograms/ml of ampicillin. Plasmid DNA was isolated by rapid alkaline lysis method. Restriction digests were done to confirm the pUC 19 C3bα' chain-GPI 21 chimeric. The DNA from a positive clone was isolated and sequenced to confirm its identitiy.

Construction of the pUC 19-42K Plasmid pUC19 C3b alpha-GPI was used to derive the pUC19-42K plasmid that encodes the N-terminal 42 amino acids of the C3bα' chain fused in-frame to a linker sequence. As taught in the iNSTANT specification, this amino acid sequence binds to CR1, which is expressed on APC's of monocytic lineage. pUC19 C3bα'-GPI was partially digested with BspHI. One BspHI site is located just distal to the 42 amino acid sequence at the amino terminus of the C3bα' chain. After the partial digestion, linear DNA was separated by electrophoresis through an agarose gel and purified using a kit manufactured by Qiagen. The linear DNA was then digested to completion with KpnI. This resulted in a plasmid containing the 42 amino acids at the amino terminus of the C3bα' chain (pUC19 42). The pUC19 42 was then ligated to a synthetic double-stranded oligonucleotide coding for GGGGSGGGGS (SEQ ID NO:5), where G represents glycine and S serine, to provide a spacer region. This oligonucleotide was synthesized to have a BspHI restriction site at the 5' end and a KpnI site at the 3' end. The resulting plasmid was used to transform E.coli, which were selected for ampicillin resistance. Clones were analyzed by restriction digests and a clone exhibiting the predicted restriction pattern was sequenced to confirm identity. This clone pUC19 42K, contains the amino terminus 42 amino acids of C3bα' chain upstream of the GGGGSGGGGS (SEQ ID NO: 5) linker.

Cloning of Hen Egg Lysozyme (HEL) into pUC19

A plasmid containing HEL was obtained from Dr. Nelson (Washington University). To generate HEL with suitable restriction sites, PCR was done with the following primers:

(SEQ ID NO: 6)
5'pGCGAATTCGCGCCGGCATGAGGTCTTTGCTAATCTTGGTGCTTTGCT
TCCTGCCCCTG (SEQ ID NO: 7)
5'pGGAAGCTTGCCCTAGGTCACAGCCGGCAGCCTCTGATCCACGCCTG
GACGTCGGTACCCTT

The PCR product was purified from agarose gels, digested with EcoRI and HindIII and cloned into pUC19 that had been digested with EcoRI-HindIII. Transformed E. coli were selected for ampicillin resistance and HEL containing clones were identified by restriction digests.

Construction of pCIL-Mammalian Expression Vector with IL2 Secretory Sequence

The vector pCIL was constructed with a sequence encoding the secretory sequence of murine IL-2. PCI (Promega) is a mammalian expression vector that uses a CMV promoter and an SV40 polyA addition site for constitutive expression of genes cloned downstream of the CMV promoter. A synthetic double-stranded oligonucleotide (GTX 7,8) coding for the mouse IL2 secretory sequence was inserted downstream of this CMV promoter.

GTX-7

(SEQ ID NO: 8)
5'pAATTCATGTACAGCATGCAGCTCGCATCCTGTGTCACATTGACACTT
GTGCTCCTTGTCAACAGCGCTAGCCAGTGGTACCGTTAT

GTX-8

(SEQ ID NO: 9)
5'PCTAGATAACGGTACCACTGGCTAGCGCTGTTGACAAGGAGCACAA
GTGTCAATGTGACACAGGATGCGAGCTGCATGCTGTACATG

An NheI site was included at the downstream end of the sequence coding for the IL2 secretory sequence, allowing in-frame ligation of a sequence immediately downstream.

Construction of pCIL-HEL

To clone HEL into pCIL, the expression vector containing the CMV promoter and the IL2 secretory sequence, the pUC19-HEL was digested with NaeI and a synthetic NheI site was ligated to the HEL fragment. The NheI-ligated HEL fragment was purified by agarose elctrophoresis and ligated to pCIL that had been digested with NheI. Correct orientation was determined by restriction digests. The resulting plasmid, pCIL HEL comprises, progressing downstream, the CMV promoter for mammalian expression, the IL2 secretory sequence coding sequence, and the HEL coding sequence.

Cloning of pCIL-42K-HEL pUC19-42K was purified and digested with AvrII and NheI. This yields a DNA fragment coding for the amino terminal 42 amino acids of the C3bα' chain linked to the GGGGSGGGGS (SEQ ID NO: 5) linker. This fragment was purified after electrophoresis through agarose gels and ligated to pCIL HEL that had been digested with NheI. The plasmid was used to transform E.coli and colonies selected for ampicillin resistance. The resulting plasmid pCIL-42K-HEL comprises, progressing downstream: (i) the CMV promoter for efficient expression in mammalian cells; (ii) the IL2 secretory sequence coding sequence; (iii) a sequence encoding the 42 amino terminal amino acids of the C3bα' chain, which binds to CR1 on APC's of monocytic lineage; (iv) a sequence encoding the GGGGSGGGGS (SEQ ID NO: 5) linker; and (v) the HEL coding sequence.

II. Purification of Vaccine DNA and Injection of Mice with DNA Vaccines

Endotoxin free plasmid DNA was purified using a commercially supplied kit (Qiagen EndoFree Plasmid Maxi Kit). Protocols were according to the manufacturer. Final DNA was resuspended in sterile saline to a final concentration of 2 micrograms per microlitre. The DNA was tested for endotoxin levels using a commercial kit (Charles River and Associates) according to the manufacturer. Final endotoxin level was less than 1.5 EU/sample.

Mice were used to test the immunogenicity of the DNA vaccine. Female Balb/c mice, 3 mice/group, were used.

On Day 1 blood serum was collected from each mouse. This "prebleed" represented baseline antibody levels prior to vaccination. 50 microliters (100 micrograms) of DNA in normal saline was then injected into the tibial muscle of each hind leg (100 micrograms per hind leg; 200 micrograms/ mouse). Each group of mice received either pCI vector DNA alone, a pCI vector encoding HEL operably linked to the murine IL2 secretory sequence, or pCIL-42K-HEL. On day 14, the injections were repeated. On day 28 blood serum was again collected.

III. ELISA Assay for Anti-HEL IgG1

Materials:
Recombinant HEL protein (SIGMA)
96-well flat bottom ELISA plates (Rainin)
96-well plate adhesive tape (Rainin)
8-channel pipetor 20-200 ul (Rainin)
Microplate reader with 405 nm filter (Biorad)
Pipet tips (Rainin)

Reagents:
PBS (8 g NaCl, 0.2 g KCl, 1.44 g $Na_2PO_4$, 0.24 g $KH_2PO_4$, in 1 L pH 7.4)
3 N NaOH in de-ionized water
Coating reagent: 50 ug/ml HEL (Sigma L6876) in sterile PBS pH 7.4 and 0.08% $NaN_3$
Blocking solution: 1% BSA (Sigma A3059) in sterile PBS pH 7.4 and 0.08% $NaN_3$
Wash solution: 1% BSA (Sigma A3059) in sterile PBS pH 7.4 with 0.05% Tween 20 (Mallinckrodt) and 0.08% $NaN_3$
Developing reagent: p-Nitrophenyl Phosphate (PNPP) tablets (Sigma N9389) dilute one tablet in 5 ml of 0.1 M glycine, 1 mM $MgCl_2$, 1 mM $ZnCl_2$, pH 10.4 (combine 7.51 g Glycine, 203 mg $MgCl_2$, 136 $ZnCl_2$ into 1L $dH_2O$)
Alkaline phosphatase-conjugated anti-mouse IgG1 antibody (Southern Biotechnology Associates)

Protocol 50 ul of the coating reagent was added to each well of a 96-well plate. All plates used in the assay were coated with the HEL antigen at the same time under the same conditions. The plates were covered with 96-well plate adhesion tape and incubated overnight at 4° C.

The adhesive tape was removed and the plates washed 4 times with sterile PBS pH 7.4. The washed plates were gently pounded onto absorbent paper. 50 ul of blocking solution was added to each well and the plates were incubated for 1 hour at 37° C.

The plates were washed 3 times with blocking buffer and gently pounded dry as in step 1. Sera from the mice in each group were pooled and diluted in blocking buffer to concentrations ranging from 1:10 to 1:100,000. 50 ul of diluted serum was added to each well.

Samples were incubated for 1 hour at 37° C. Plates were washed four times with wash buffer and gently pounded dry as in step 1.

50 ul of anti-IgG1 was added to each well and the plates were incubated for 1 hour at 37° C.

The plates were washed five times with wash buffer and pounded dry as in step 1.

50 ul of developing reagent was added to each well. Plates were incubated at room temperature and absorbance at 405 nm was periodically measured in the microplate reader.

When the highest diluted sample reached an OD of 0.2, the enzymatic reaction was stopped by adding 3 N NaOH as 1 volume base to 4 volume reaction medium.

The endpoint at 405 nm was read.

Example 9

Since the original filing date of the parent application (U.S. Ser. No. 08/788,143, filed Jan. 24, 1997), the following publications have become available evidencing the operability of the present invention.

Boyle et al (Nature 392:408-411, 1998) was published after the priority date of Jan. 24, 1997, but before the filing date of the present application. Boyle et al. showed that administering a DNA construct encoding a secretory sequence, an antigen, and an amino acid sequence that binds to a polypeptide expressed on the surface of an APC of monocytic lineage increases the immune response to the antigen. Specifically, Boyle et al. administered to mice a construct encoding the CD5 secretory sequence, a portion of human IgG (which is antigenic in mice), and CTLA-4, which binds to the polypeptides B7-1 and B7-2 on the surface of APC's of monocytic lineage (see, for example, Boyle et al., first paragraph; Fleischer et al, Immunology 89:592-598, 1996). FIGS. 2 and 3 in Boyle et al. show that this construct markedly increased the immune response to the antigen human IgG in mice.

Biragyn et al. (Nature Biotechnology, 17:253-258, 1999) was published after the priority date of Jan. 24, 1997, but before the filing date of the present application. Biragyn et al. demonstrate that administering DNA constructs encoding a secretory sequence, an antigen, and an amino acid sequence that binds to a polypeptide expressed on the surface of an APC of monocytic lineage increases the immune response to the antigen. The antigens encoded by these constructs were lymphoma Ig variable regions, which are tumor antigens. The APC binding sequence was MCP-3, which binds to polypeptides expressed on the surface of APC's of monocytic lineage (see, for example, Biragyn et al., first paragraph; Combadiere et al, J Biol Chem 270: 29671-29675, 1995). All constructs also comprised the IP-10 secretory sequence. FIGS. 2B, 2C, 3B, 3C, and 3D in Biragyn et al. show that the constructs markedly increase the immune response to the tumor antigens.

Equivalents

Those skilled in the art will recognize, or be able to ascertain using no more than routine experimentation, many equivalents of the specific embodiments of the invention described herein. Such equivalents are intended to be encompassed by the following claims.

Appendix I

1: NM_017882
Homo sapiens ceroid-lipofuscinosis, neuronal 6, late infantile, variant (CLN6), mRNA
gi|8923531|ref|NM_017882.1|[8923531]

2: BI480800
H2RPE-0436 Human Retinal Pigment Epithelium (2) Homo sapiens cDNA 5' similar to glycoprotein (transmembrane) nmb (GPNMB), mRNA sequence
gi|18998609|gb|BI480800.1|BI480800[18998609]

4: AC096780
Tcc118, complete sequence
gi|18958727|gb|AC096780.1|[18958727]

5: AC113243
Tcc1a22, complete sequence
gi|18958719|gb|AC113243.1|[18958719]

6: AF347029
Homo sapiens transmembrane protein (C6ORF33) mRNA, complete cds
gi|18873730|gb|AF347029.1|[18873730]

8: NM_001183
Homo sapiens ATPase, H+ transporting, lysosomal (vacuolar proton pump), subunit 1 (ATP6S1), mRNA
gi|17136147|ref|NM_001183.2|[17136147]

13: NM_005765
Homo sapiens ATPase, H+ transporting, lysosomal (vacuolar proton pump) membrane sector associated protein M8-9 (ATP6M8-9), mRNA
gi|15011917|ref|NM_005765.2|[15011917]

14: AB028140
Homo sapiens mRNA for spincsin, complete cds
gi|12248916|dbj|AB028140.1|[12248916]

Homo sapiens protein tyrosine phosphatase, receptor type, N (PTPRN), mRNA
gi|18860905|ref|NM_002846.2|[18860905]

16: NM_002845
Homo sapiens protein tyrosine phosphatase, receptor type, M (PTPRM), mRNA
gi|18860903|ref|NM_002845.2|[18860903]

17: NM_002844
Homo sapiens protein tyrosine phosphatase, receptor type, K (PTPRK), mRNA
gi|18860901|ref|NM_002844.2|[18860901]

18: NM_002843
Homo sapiens protein tyrosine phosphatase, receptor type, J (PTPRJ), mRNA
gi|18860899|ref|NM_002843.2|[18860899]

19: NM_002841
Homo sapiens protein tyrosine phosphatase, receptor type, G (PTPRG), mRNA
gi|18860897|ref|NM_002841.2|[18860897]

20: NM_130440
Homo sapiens protein tyrosine phosphatase, receptor type, F (PTPRF), transcript variant 2, mRNA
gi|18860895|ref|NM_130440.1|[18860895]

21: NM_130393
Homo sapiens protein tyrosine phosphatase, receptor type, D (PTPRD), transcript variant 4, mRNA
gi|18860893|ref|NM_130393.1|[18860893]

22: NM_130392
Homo sapiens protein tyrosine phosphatase, receptor type, D (PTPRD), transcript variant 3, mRNA
gi|18860891|ref|NM_130392.1|[18860891]

23: NM_130391
Homo sapiens protein tyrosine phosphatase, receptor type, D (PTPRD), transcript variant 2, mRNA
gi|18860889|ref|NM_130391.1|[18860889]

24: NM_002840
Homo sapiens protein tyrosine phosphatase, receptor type, F (PTPRF), transcript variant 1, mRNA
gi|18860871|ref|NM_002840.2|[18860871]

25: NM_006504
Homo sapiens protein tyrosine phosphatase, receptor type, E (PTPRE), transcript variant 1, mRNA
gi|18860860|ref|NM_006504.2|[18860860]

26: NM_130435
Homo sapiens protein tyrosine phosphatase, receptor type, E (PTPRE), transcript variant 2, mRNA
gi|18860858|ref|NM_130435.1|[18860858]

27: NM_002842
Homo sapiens protein tyrosine phosphatase, receptor type, H (PTPRH), mRNA
gi|4506312|ref|NM_002842.1|[4506312]

28: NM_002839
Homo sapiens protein tyrosine phosphatase, receptor type, D (PTPRD), transcript variant 1, mRNA
gi|4506308|ref|NM_002839.1|[4506308]

29: BC024191
Homo sapiens, Similar to transmembrane protein HTMP10, clone IMAGE:4799785, mRNA
gi|18848306|gb|BC024191.1|[18848306]

30: NM_023068
Homo sapiens sialoadhesin (SN), mRNA
gi|18765743|ref|NM_023068.2|[18765743]

31: NM_032646
Homo sapiens tweety homolog 2 (Drosophila) (TTYH2), mRNA
gi|17939343|ref|NM_032646.4|[17939343]

32: NM_022006
Homo sapiens FXYD domain-containing ion transport regulator 7 (FXYD7), mRNA
gi|11612658|ref|NM_022006.1|[11612658]

33: NM_022003
Homo sapiens FXYD domain-containing ion transport regulator 6 (FXYD6), mRNA
gi|11612654|ref|NM_022003.1|[11612654]

34: NM_002127
Homo sapiens HLA-G histocompatibility antigen, class I, G (HLA-G), mRNA
gi|18765718|ref|NM_002127.2|[18765718]

35: NM_005516
Homo sapiens major histocompatibility complex, class I, E (HLA-E), mRNA
gi|18765717|ref|NM_005516.2|[18765717]

36: NM_002121
Homo sapiens major histocompatibility complex, class II, DP beta 1 (HLA-DPB1), mRNA
gi|18765716|ref|NM_002121.3|[18765716]

37: NM_006120
Homo sapiens major histocompatibility complex, class II, DM alpha (HLA-DMA), mRNA
gi|18765714|ref|NM_006120.2|[18765714]

38: NM_002116
Homo sapiens major histocompatibility complex, class I, A (HLA-A), mRNA
gi|18765713|ref|NM_002116.3|[18765713]

39: NM_130797
Homo sapiens dipeptidylpeptidase VI (DPP6), transcript variant 1, mRNA
gi|18765697|ref|NM_130797.1|[18765697]

40: NM_001936
Homo sapiens dipeptidylpeptidase VI (DPP6), transcript variant 2, mRNA
gi|18765695|ref|NM_001936.2|[18765695]

41: NM_018593
Homo sapiens solute carrier family 16 (monocarboxylic acid transporters), member 10 (SLC16A10), mRNA
gi|18699729|ref|NM_018593.2|[18699729]

42: BM510040
ig97b09.x1 HR85 islet Homo sapiens cDNA clone IMAGE: 3' similar to TR:O60478 O60478 PUTATIVE SEVEN PASS TRANSMEMBRANE PROTEIN. ;, mRNA sequence
gi|18681183|gb|BM510040.1|BM510040[18681183]

43: BM509858
ig94h01.y1 HR85 islet Homo sapiens cDNA clone IMAGE: 5' similar to SW:MTRP_HUMAN Q15012 GOLGI 4-TRANSMEMBRANE SPANNING TRANSPORTER MTP ;, mRNA sequence
gi|18681001|gb|BM509858.1|BM509858[18681001]

44: BM509717
ig93b05.y1 HR85 islet Homo sapiens cDNA clone IMAGE: 5' similar to SW:MTRP_HUMAN Q15012 GOLGI 4-TRANSMEMBRANE SPANNING TRANSPORTER MTP ;, mRNA sequence
gi|18680860|gb|BM509717.1|BM509717[18680860]

45: BM508064
ij38f06.x1 Human insulinoma Homo sapiens cDNA clone IMAGE:5633410 3' similar to TR:P97544 P97544 ER TRANSMEMBRANE PROTEIN. ;, mRNA sequence
gi|18679207|gb|BM508064.1|BM508064[18679207]

46: NM_033543
Homo sapiens hypothetical protein R29124_1 (R29124_1), mRNA
gi|16117774|ref|NM_033543.1|[16117774]

47: NM_032732
Homo sapiens hypothetical protein MGC10763 (IL17RL), mRNA
gi|14249349|ref|NM_032732.1|[14249349]

48: NM_018676
Homo sapiens TMTSP for transmembrane molecule with thrombospondin module (LOC55901), mRNA gi|8923893|ref|NM_018676.1|[8923893]

49: NM_016372
Homo sapiens seven transmembrane domain orphan receptor (TPRA40), mRNA
gi|7705964|ref|NM_016372.1|[7705964]

50: L47337
Homo sapiens transmembrane protein (TMC) mRNA, complete cds
gi|18654193|gb|L47337.1|HUMTMC[18654193]

56: Y13567
Homo sapiens HLA-B*07022 gene exon 1-5
gi|4007617|emb|Y13567.1|HSY13567[4007617]

57: NM_032027
Homo sapiens beta-amyloid binding protein precursor (BBP), mRNA
gi|17738309|ref|NM_032027.2|[17738309]

58: NM_030913
Homo sapiens sema domain, transmembrane domain (TM), and cytoplasmic domain, (semaphorin) 6C (SEMA6C), mRNA
gi|16306551|ref|NM_030913.2|[16306551]

59: NM_021203
Homo sapiens APMCF1 protein (APMCF1), mRNA
gi|14917112|ref|NM_021203.2|[14917112]

60: NM_006854
Homo sapiens KDEL (Lys-Asp-Glu-Leu) endoplasmic reticulum protein retention receptor 2 (KDELR2), mRNA
gi|8051609|ref|NM_006854.2|[8051609]

61: NM_014394
Homo sapiens growth hormone inducible transmembrane protein (GHITM), mRNA
gi|7657479|ref|NM_014394.1|[7657479]

62: NM_014399

Homo sapiens tetraspan NET-6 protein (NET-6), mRNA
gi|7657372|ref|NM_014399.1|[7657372]

63: NM_014478
Homo sapiens calcitonin gene-related peptide-receptor component protein (CGRP-RCP), mRNA
gi|7656976|ref|NM_014478.1|[7656976]

64: NM_007324
Homo sapiens MAD, mothers against decapentaplegic homolog (Drosophila) interacting protein, receptor activation anchor (MADHIP), transcript variant 1, mRNA
gi|6552338|ref|NM_007324.1|[6552338]

65: NM_007323
Homo sapiens MAD, mothers against decapentaplegic homolog (Drosophila) interacting protein, receptor activation anchor (MADHIP), transcript variant 2, mRNA
gi|6552336|ref|NM_007323.1|[6552336]

66: NM_006876
Homo sapiens UDP-GlcNAc:betaGal beta-1,3-N-acetylglucosaminyltransferase 6 (B3GNT6), mRNA
gi|5802983|ref|NM_006876.1|[5802983]

67: NM_006675
Homo sapiens tetraspan transmembrane 4 super family (NET-5), mRNA
gi|5729940|ref|NM_006675.1|[5729940]

68: NM_006405
Homo sapiens transmembrane 9 superfamily member 1 (TM9SF1), mRNA
gi|5453741|ref|NM_006405.1|[5453741]

69: NM_005761
Homo sapiens plexin C1 (PLXNC1), mRNA
gi|5032222|ref|NM_005761.1|[5032222]

70: NM_005814

Homo sapiens glycoprotein A33 (transmembrane) (GPA33), mRNA
gi|5031560|ref|NM_005814.1|[5031560]

71: NM_004799
Homo sapiens MAD, mothers against decapentaplegic homolog (Drosophila) interacting protein, receptor activation anchor (MADHIP), transcript variant 3, mRNA
gi|4759059|ref|NM_004799.1|[4759059]

72: NM_003764
Homo sapiens syntaxin 11 (STX11), mRNA
gi|4507286|ref|NM_003764.1|[4507286]

73: NM_003622
Homo sapiens PTPRF interacting protein, binding protein 1 (liprin beta 1) (PPFIBP1), mRNA
gi|4505986|ref|NM_003622.1|[4505986]

74: NM_003626
Homo sapiens protein tyrosine phosphatase, receptor type, f polypeptide (PTPRF), interacting protein (liprin), alpha 1 (PPFIA1), mRNA
gi|4505982|ref|NM_003626.1|[4505982]

75: NM_033266
Homo sapiens ER to nucleus signalling 2 (ERN2), mRNA
gi|15149481|ref|NM_033266.1|[15149481]

76: NM_030780
Homo sapiens folate transporter/carrier (LOC81034), mRNA
gi|13540550|ref|NM_030780.1|[13540550]

77: NM_025179
Homo sapiens plexin A2 (PLXNA2), mRNA
gi|13378152|ref|NM_025179.1|[13378152]

78: NM_022097
Homo sapiens hepatocellular carcinoma antigen gene 520 (LOC63928), mRNA
gi|11545810|ref|NM_022097.1|[11545810]

79: NM_019111
Homo sapiens major histocompatibility complex, class II, DR alpha (HLA-DRA), mRNA
gi|18641378|ref|NM_019111.2|[18641378]

80: NM_002120
Homo sapiens major histocompatibility complex, class II, DO beta (HLA-DOB), mRNA
gi|18641377|ref|NM_002120.2|[18641377]

81: NM_002118
Homo sapiens major histocompatibility complex, class II, DM beta (HLA-DMB), mRNA
gi|18641376|ref|NM_002118.3|[18641376]

82: NM_002125
Homo sapiens major histocompatibility complex, class II, DR beta 5 (HLA-DRB5), mRNA
gi|18641374|ref|NM_002125.2|[18641374]

83: NM_021983
Homo sapiens major histocompatibility complex, class II, DR beta 4 (HLA-DRB4), mRNA
gi|18641372|ref|NM_021983.3|[18641372]

84: NM_022555
Homo sapiens major histocompatibility complex, class II, DR beta 3 (HLA-DRB3), mRNA
gi|18641371|ref|NM_022555.3|[18641371]

85: NM_080923
Homo sapiens protein tyrosine phosphatase, receptor type, C (PTPRC), transcript variant 4, mRNA
gi|18641365|ref|NM_080923.1|[18641365]

86: NM_080922
Homo sapiens protein tyrosine phosphatase, receptor type, C (PTPRC), transcript variant 3, mRNA
gi|18641363|ref|NM_080922.1|[18641363]

87: NM_080921
Homo sapiens protein tyrosine phosphatase, receptor type, C (PTPRC), transcript variant 2, mRNA
gi|18641361|ref|NM_080921.1|[18641361]

88: NM_130778
Homo sapiens collagen, type XVII, alpha 1 (COL17A1), transcript variant short, mRNA
gi|18641355|ref|NM_130778.1|[18641355]

89: NM_000494
Homo sapiens collagen, type XVII, alpha 1 (COL17A1), transcript variant long, mRNA
gi|18641353|ref|NM_000494.2|[18641353]

90: NM_002838
Homo sapiens protein tyrosine phosphatase, receptor type, C (PTPRC), transcript variant 1, mRNA
gi|18641346|ref|NM_002838.2|[18641346]

91: NM_030950
Homo sapiens ret finger protein (RFP), transcript variant beta, mRNA
gi|18641280|ref|NM_030950.2|[18641280]

92: NM_130785
Homo sapiens TPTE and PTEN homologous inositol lipid phosphatase (TPIP), mRNA
gi|18640755|ref|NM_130785.1|[18640755]

93: AB057445
Homo sapiens hTAT1 mRNA for aromatic amino acid transporter, complete cds
gi|18640046|dbj|AB057445.1|[18640046]

94: NM_006510
Homo sapiens ret finger protein (RFP), transcript variant alpha, mRNA
gi|17105396|ref|NM_006510.3|[17105396]

95: NM_033554
Homo sapiens major histocompatibility complex, class II, DP alpha 1 (HLA-DPA1), mRNA
gi|15809045|ref|NM_033554.1|[15809045]

96: NM_005608
Homo sapiens protein tyrosine phosphatase, receptor type, C-associated protein (PTPRCAP), mRNA
gi|5032004|ref|NM_005608.1|[5032004]

97: BM491907
pgp2n.pk007.m20 Normalized Chicken Pituitary/Hypothalamus/Pineal Library (pgp2n) Gallus gallus cDNA clone pgp2n.pk007.m20 5' similar to gb|AAH17476.1|AAH17476 (BC017476) sema domain, immunoglobulin domain (Ig), transmembrane domain TM) and short cytoplasmic domain, (semaphorin) 4C [Homo sapiens], mRNA sequence
gi|18612838|gb|BM491907.1|BM491907[18612838]

98: BM491823
pgp2n.pk007.i6 Normalized Chicken Pituitary/Hypothalamus/Pineal Library (pgp2n) Gallus gallus cDNA clone pgp2n.pk007.i6 5' similar to ref|NP_055070.1 (NM_014255) transmembrane protein 4; putative type II membrane protein [Homo sapiens] dbj|BAA76498.1| (AB015631) type II membrane protein [Homo sapiens], mRNA sequence
gi|18612754|gb|BM491823.1|BM491823[18612754]

99: BM491746
pgp2n.pk007.f14 Normalized Chicken Pituitary/Hypothalamus/Pineal Library (pgp2n) Gallus gallus cDNA clone pgp2n.pk007.f14 5' similar to ref|XP_044533.2 (XM_044533) sema domain, immunoglobulin domain (Ig), transmembrane domain (TM) and short cytoplasmic domain, (semaphorin) 4B [Homo sapiens], mRNA sequence
gi|18612677|gb|BM491746.1|BM491746[18612677]

100: BM491722
pgp2n.pk007.d9 Normalized Chicken Pituitary/Hypothalamus/Pineal Library (pgp2n) Gallus gallus cDNA clone pgp2n.pk007.d9 5' similar to ref|XP_032285.1 (XM_032285) similar to putative transmembrane protein; homolog of yeast Golgi membrane protein Yif1p (Yip1p-interacting factor) [Homo sapiens], mRNA sequence
gi|18612653|gb|BM491722.1|BM491722[18612653]

101: BM491453 pgp2n.pk006.h11 Normalized Chicken Pituitary/Hypothalamus/Pineal Library (pgp2n)
Gallus gallus cDNA clone pgp2n.pk006.h11 5' similar to ref|XP_058189.1
(XM_058189) similar to Similar to transmembrane 4 superfamily member 1 (H.
sapiens) [Homo sapiens] gb|AAH14339.1|AAH14339 (BC014339) Similar to
transmembrane 4 superfamily member 1 [Homo sapiens], mRNA sequence
gi|18612384|gb|BM491453.1|BM491453[18612384]

102: BM490974
pgp2n.pk005.a11 Normalized Chicken Pituitary/Hypothalamus/Pineal Library (pgp2n)
Gallus gallus cDNA clone pgp2n.pk005.a11 5' similar to ref|XP_008022.1
(XM_008022) chromosome 16 open reading frame 5 [Homo sapiens]
gb|AAG35583.1|AF195661_1 (AF195661) transmembrane protein I1 [Homo sapiens]
gb|AAH02882.1|AAH02882 (BC002882) chromosome 16 open reading frame 5 [Homo
sapiens], mRNA sequence
gi|18611905|gb|BM490974.1|BM490974[18611905]

103: BM490515
pgp2n.pk003.k2 Normalized Chicken Pituitary/Hypothalamus/Pineal Library (pgp2n)
Gallus gallus cDNA clone pgp2n.pk003.k2 5' similar to ref|NP_055070.1
(NM_014255) transmembrane protein 4; putative type II membrane protein [Homo
sapiens] dbj|BAA76498.1| (AB015631) type II membrane protein [Homo sapiens],
mRNA sequence
gi|18611446|gb|BM490515.1|BM490515[18611446]

104: BM490496
pgp2n.pk003.j21 Normalized Chicken Pituitary/Hypothalamus/Pineal Library (pgp2n)
Gallus gallus cDNA clone pgp2n.pk003.j21 5' similar to ref|XP_015557.1
(XM_015557) transmembrane gamma-carboxyglutamic acid protein 3 [Homo sapiens],
mRNA sequence
gi|18611427|gb|BM490496.1|BM490496[18611427]

105: BM490381
pgp2n.pk003.e10 Normalized Chicken Pituitary/Hypothalamus/Pineal Library (pgp2n)
Gallus gallus cDNA clone pgp2n.pk003.e10 5' similar to ref|NP_057641.1
(NM_016557) orphan seven-transmembrane receptor, chemokine related [Homo
sapiens] ref|XP_016022.1| (XM_016022) orphan seven-transmembrane receptor,
chemokine related [Homo sapiens] sp|Q9NPB9|CKRB_HUMAN C-C CHEMOKINE
RECEPTOR
TYPE, mRNA sequence
gi|18611312|gb|BM490381.1|BM490381[18611312]

106: BM489618 pgm2n.pk011.h5 Normalized Chicken Breast Muscle, Leg Muscle, and Epiphyseal Growth Plate cDNA library (pgm2n) Gallus gallus cDNA clone pgm2n.pk011.h5 5' similar to ref|NP_114131.1 (NM_031925) transmembrane protein induced by tumor necrosis factor alpha [Homo sapiens] gb|AAK16442.1|AF327923_1 (AF327923) transmembrane protein induced by tumor necrosis factor alpha [Homo sapiens], mRNA sequence
gi|18610549|gb|BM489618.1|BM489618[18610549]

107: BM489501 pgm2n.pk011.b24 Normalized Chicken Breast Muscle, Leg Muscle, and Epiphyseal Growth Plate cDNA library (pgm2n) Gallus gallus cDNA clone pgm2n.pk011.b24 5' similar to ref|NP_055070.1 (NM_014255) transmembrane protein 4; putative type II membrane protein [Homo sapiens] dbj|BAA76498.1| (AB015631) type II membrane protein [Homo sapiens], mRNA sequence
gi|18610432|gb|BM489501.1|BM489501[18610432]

108: BM489487 pgm2n.pk011.a8 Normalized Chicken Breast Muscle, Leg Muscle, and Epiphyseal Growth Plate cDNA library (pgm2n) Gallus gallus cDNA clone pgm2n.pk011.a8 5' similar to gb|AAC64943.1 (AF084481) transmembrane protein [Homo sapiens], mRNA sequence
gi|18610418|gb|BM489487.1|BM489487[18610418]

109: BM489466 pgm2n.pk010.p5 Normalized Chicken Breast Muscle, Leg Muscle, and Epiphyseal Growth Plate cDNA library (pgm2n) Gallus gallus cDNA clone pgm2n.pk010.p5 5' similar to dbj|AK056595.1|AK056595 Homo sapiens cDNA FLJ32033 fis, clone NTONG2000265, weakly similar to Probable transmembrane protein of fission yeast, mRNA sequence
gi|18610397|gb|BM489466.1|BM489466[18610397]

110: BM489443 pgm2n.pk010.o4 Normalized Chicken Breast Muscle, Leg Muscle, and Epiphyseal Growth Plate cDNA library (pgm2n) Gallus gallus cDNA clone pgm2n.pk010.o4 5' similar to ref|XP_008022.1 (XM_008022) chromosome 16 open reading frame 5 [Homo sapiens] gb|AAG35583.1|AF195661_1 (AF195661) transmembrane protein I1 [Homo sapiens] gb|AAH02882.1|AAH02882 (BC002882) chromosome 16 open reading frame 5 [Homo sapiens], mRNA sequence
gi|18610374|gb|BM489443.1|BM489443[18610374]

111: BM489432
pgm2n.pk010.o15 Normalized Chicken Breast Muscle, Leg Muscle, and Epiphyseal
Growth Plate cDNA library (pgm2n) Gallus gallus cDNA clone pgm2n.pk010.o15 5'
similar to ref|NP_055070.1 (NM_014255) transmembrane protein 4; putative type II
membrane protein [Homo sapiens] dbj|BAA76498.1| (AB015631) type II membrane
protein [Homo sapiens], mRNA sequence
gi|18610363|gb|BM489432.1|BM489432[18610363]

112: BM489389
pgm2n.pk010.m15 Normalized Chicken Breast Muscle, Leg Muscle, and Epiphyseal
Growth Plate cDNA library (pgm2n) Gallus gallus cDNA clone pgm2n.pk010.m15 5'
similar to ref|XP_028438.1 (XM_028438) CGI-101 protein [Homo sapiens]
gb|AAF99603.1|AF242523_1 (AF242523) hypothetical transmembrane protein SBBI53
[Homo sapiens] gb|AAG43049.1|AF132289_1 (AF132289) F-LAN-1 [Homo sapiens]
gb|AAH10890.1|AAH10890 (BC010890), mRNA sequence
gi|18610320|gb|BM489389.1|BM489389[18610320]

113: BM489272
pgm2n.pk010.g4 Normalized Chicken Breast Muscle, Leg Muscle, and Epiphyseal
Growth Plate cDNA library (pgm2n) Gallus gallus cDNA clone pgm2n.pk010.g4 5'
similar to ref|NP_055070.1 (NM_014255) transmembrane protein 4; putative type II
membrane protein [Homo sapiens] dbj|BAA76498.1| (AB015631) type II membrane
protein [Homo sapiens], mRNA sequence
gi|18610203|gb|BM489272.1|BM489272[18610203]

114: BM489267
pgm2n.pk010.g2 Normalized Chicken Breast Muscle, Leg Muscle, and Epiphyseal
Growth Plate cDNA library (pgm2n) Gallus gallus cDNA clone pgm2n.pk010.g2 5'
similar to ref|NP_055070.1 (NM_014255) transmembrane protein 4; putative type II
membrane protein [Homo sapiens] dbj|BAA76498.1| (AB015631) type II membrane
protein [Homo sapiens], mRNA sequence
gi|18610198|gb|BM489267.1|BM489267[18610198]

115: BM488196
pgm2n.pk006.n2 Normalized Chicken Breast Muscle, Leg Muscle, and Epiphyseal
Growth Plate cDNA library (pgm2n) Gallus gallus cDNA clone pgm2n.pk006.n2 5'
similar to ref|NP_114434.1 (NM_032045) kringle-containing transmembrane protein;
kringle-coding gene marking the eye and the nose [Homo sapiens] dbj|BAB40969.1|
(AB059618) kringle-containing transmembrane protein [Homo sapiens], mRNA
sequence
gi|18609127|gb|BM488196.1|BM488196[18609127]

116: BM488072
pgm2n.pk006.h15 Normalized Chicken Breast Muscle, Leg Muscle, and Epiphyseal Growth Plate cDNA library (pgm2n) Gallus gallus cDNA clone pgm2n.pk006.h15 5' similar to ref|XP_044533.2 (XM_044533) sema domain, immunoglobulin domain (Ig), transmembrane domain (TM) and short cytoplasmic domain, (semaphorin) 4B [Homo sapiens], mRNA sequence
gi|18609003|gb|BM488072.1|BM488072[18609003]

117: BM487945
pgm2n.pk006.b16 Normalized Chicken Breast Muscle, Leg Muscle, and Epiphyseal Growth Plate cDNA library (pgm2n) Gallus gallus cDNA clone pgm2n.pk006.b16 5' similar to ref|NP_055070.1 (NM_014255) transmembrane protein 4; putative type II membrane protein [Homo sapiens] dbj|BAA76498.1| (AB015631) type II membrane protein [Homo sapiens], mRNA sequence
gi|18608876|gb|BM487945.1|BM487945[18608876]

118: BM487175
pgm2n.pk003.m18 Normalized Chicken Breast Muscle, Leg Muscle, and Epiphyseal Growth Plate cDNA library (pgm2n) Gallus gallus cDNA clone pgm2n.pk003.m18 5' similar to ref|NP_055070.1 (NM_014255) transmembrane protein 4; putative type II membrane protein [Homo sapiens] dbj|BAA76498.1| (AB015631) type II membrane protein [Homo sapiens], mRNA sequence
gi|18608105|gb|BM487175.1|BM487175[18608105]

119: BM487035
pgm2n.pk003.f7 Normalized Chicken Breast Muscle, Leg Muscle, and Epiphyseal Growth Plate cDNA library (pgm2n) Gallus gallus cDNA clone pgm2n.pk003.f7 5' similar to emb|CAC88191.1 (AL136141) bA138E2.2 (novel protein (lung seven transmembrane receptor 1 (LUSTR1), KIAA1623, FLJ22591, MGC15440) ) [Homo sapiens], mRNA sequence
gi|18607965|gb|BM487035.1|BM487035[18607965]

120: BM486914
pgm2n.pk003.a11 Normalized Chicken Breast Muscle, Leg Muscle, and Epiphyseal Growth Plate cDNA library (pgm2n) Gallus gallus cDNA clone pgm2n.pk003.a11 5' similar to ref|NP_055070.1 (NM_014255) transmembrane protein 4; putative type II membrane protein [Homo sapiens] dbj|BAA76498.1| (AB015631) type II membrane protein [Homo sapiens], mRNA sequence
gi|18607844|gb|BM486914.1|BM486914[18607844]

121: NT_009151
Homo sapiens chromosome 11 working draft sequence segment
gi|18604868|ref|NT_009151.8|Hs11_9308[18604868]

122: NT_010823
Homo sapiens chromosome 17 working draft sequence segment
gi|18604211|ref|NT_010823.8|Hs17_10980[18604211]

123: XM_008517
Homo sapiens similar to transmembrane 4 superfamily member 5 (H. sapiens)
(LOC147059), mRNA
gi|18604159|ref|XM_008517.4|[18604159]

124: NT_009482
Homo sapiens chromosome 12 working draft sequence segment
gi|18601829|ref|NT_009482.8|Hs12_9639[18601829]

125: NT_009458
Homo sapiens chromosome 12 working draft sequence segment
gi|18601539|ref|NT_009458.7|Hs12_9615[18601539]

126: NT_005428
Homo sapiens chromosome 2 working draft sequence segment
gi|18600405|ref|NT_005428.7|Hs2_5585[18600405]

127: XM_087234
Homo sapiens sema domain, immunoglobulin domain (Ig), transmembrane domain (TM)
and short cytoplasmic domain, (semaphorin) 4F (SEMA4F), mRNA
gi|18600294|ref|XM_087234.1|[18600294]

128: NT_030593
Homo sapiens chromosome 2 working draft sequence segment
gi|18599598|ref|NT_030593.2|Hs2_30849[18599598]

129: XM_092364
Homo sapiens similar to seven transmembrane receptor (LOC165082), mRNA
gi|18599578|ref|XM_092364.1|[18599578]

130: NT_025667
Homo sapiens chromosome 3 working draft sequence segment
gi|18599563|ref|NT_025667.2|Hs3_25823[18599563]

131: NT_010478
Homo sapiens chromosome 16 working draft sequence segment
gi|18598685|ref|NT_010478.8|Hs16_10635[18598685]

132: NT_010422
Homo sapiens chromosome 16 working draft sequence segment
gi|18598469|ref|NT_010422.8|Hs16_10579[18598469]

133: NT_030136
Homo sapiens chromosome 14 working draft sequence segment
gi|18597657|ref|NT_030136.3|Hs14_30391[18597657]

134: XM_090902
Homo sapiens similar to transmembrane 9 superfamily member 1 (H. sapiens) (LOC161426), mRNA
gi|18597655|ref|XM_090902.1|[18597655]

135: XM_085169
Homo sapiens similar to seven transmembrane receptor BLTR2; leukotriene B4 receptor BLT2 (H. sapiens) (LOC145549), mRNA
gi|18597626|ref|XM_085169.1|[18597626]

136: NT_026437
Homo sapiens chromosome 14 working draft sequence segment
gi|18597566|ref|NT_026437.6|Hs14_26604[18597566]

137: XM_085149
Homo sapiens similar to fibronectin leucine rich transmembrane protein 2 (H. sapiens) (LOC145535), mRNA
gi|18597448|ref|XM_085149.1|[18597448]

138: NT_025892
Homo sapiens chromosome 14 working draft sequence segment gi|18597282|ref|NT_025892.7|Hs14_26048[18597282]

139: NT_019583
Homo sapiens chromosome 14 working draft sequence segment
gi|18596851|ref|NT_019583.8|Hs14_19739[18596851]

140: XM_093204
Homo sapiens similar to G protein-coupled receptor 64; G protein-coupled
receptor, epididymis-specific (seven transmembrane family) (LOC170247), mRNA
gi|18596481|ref|XM_093204.1|[18596481]

141: NT_025319
Homo sapiens chromosome X working draft sequence segment
gi|18596220|ref|NT_025319.8|HsX_25475[18596220]

142: NT_011719
Homo sapiens chromosome X working draft sequence segment
gi|18595448|ref|NT_011719.6|HsX_11876[18595448]

143: XM_093073
Homo sapiens similar to TRANSMEMBRANE 9 SUPERFAMILY PROTEIN MEMBER 2
PRECURSOR
(LOC170048), mRNA
gi|18595444|ref|XM_093073.1|[18595444]

144: XM_060026
Homo sapiens similar to transmembrane 9 superfamily member 2; 76 kDa membrane
protein; transmembrane protein 9 superfamily member 2 (LOC139375), mRNA
gi|18595426|ref|XM_060026.2|[18595426]

145: NT_011687
Homo sapiens chromosome X working draft sequence segment
gi|18595291|ref|NT_011687.8|HsX_11844[18595291]

146: NT_011657
Homo sapiens chromosome X working draft sequence segment
gi|18595178|ref|NT_011657.8|HsX_11814[18595178]

147: XM_032382
Homo sapiens transmembrane 4 superfamily member 2 (TM4SF2), mRNA
gi|18595108|ref|XM_032382.3|[18595108]

148: XM_055073
Homo sapiens similar to transmembrane phosphatase with tensin homology (H. sapiens) (LOC150132), mRNA
gi|18593511|ref|XM_055073.3|[18593511]

149: XM_009671
Homo sapiens transmembrane, prostate androgen induced RNA (TMEPAI), mRNA
gi|18591987|ref|XM_009671.7|[18591987]

150: NT_011296
Homo sapiens chromosome 19 working draft sequence segment
gi|18591133|ref|NT_011296.8|Hs19_11453[18591133]

151: NT_011295
Homo sapiens chromosome 19 working draft sequence segment
gi|18591086|ref|NT_011295.5|Hs19_11452[18591086]

152: NT_011294
Homo sapiens chromosome 19 working draft sequence segment
gi|18591029|ref|NT_011294.7|Hs19_11451[18591029]

153: NT_011255
Homo sapiens chromosome 19 working draft sequence segment
gi|18590680|ref|NT_011255.8|Hs19_11412[18590680]

154: NT_011233
Homo sapiens chromosome 19 working draft sequence segment
gi|18590500|ref|NT_011233.8|Hs19_11390[18590500]

155: XM_032285
Homo sapiens similar to putative transmembrane protein; homolog of yeast Golgi membrane protein Yif1p (Yip1p-interacting factor) (LOC90522), mRNA
gi|18590452|ref|XM_032285.2|[18590452]

156: NT_011151
Homo sapiens chromosome 19 working draft sequence segment
gi|18590324|ref|NT_011151.8|Hs19_11308[18590324]

157: NT_011109
Homo sapiens chromosome 19 working draft sequence segment
gi|18589940|ref|NT_011109.8|Hs19_11266[18589940]

158: NT_030157
Homo sapiens chromosome 17 working draft sequence segment
gi|18588299|ref|NT_030157.3|Hs17_30412[18588299]

159: XM_096100
Homo sapiens transmembrane activator and CAML interactor (TACI), mRNA
gi|18588295|ref|XM_096100.1|[18588295]

160: NT_010672
Homo sapiens chromosome 17 working draft sequence segment
gi|18586808|ref|NT_010672.8|Hs17_10829[18586808]

161: NT_024776
Homo sapiens chromosome 16 working draft sequence segment
gi|18585964|ref|NT_024776.4|Hs16_24932[18585964]

162: NT_015360
Homo sapiens chromosome 16 working draft sequence segment
gi|18585813|ref|NT_015360.8|Hs16_15516[18585813]

163: NT_010552
Homo sapiens chromosome 16 working draft sequence segment
gi|18585429|ref|NT_010552.8|Hs16_10709[18585429]

164: NT_010356
Homo sapiens chromosome 15 working draft sequence segment
gi|18584698|ref|NT_010356.8|Hs15_10513[18584698]

165: NT_010351
Homo sapiens chromosome 15 working draft sequence segment
gi|18584556|ref|NT_010351.8|Hs15_10508[18584556]

166: NT_010224
Homo sapiens chromosome 15 working draft sequence segment
gi|18583998|ref|NT_010224.7|Hs15_10381[18583998]

167: XM_083914
Homo sapiens transmembrane 6 superfamily member 1 (TM6SF1), mRNA
gi|18583986|ref|XM_083914.1|[18583986]

168: XM_083903
Homo sapiens transmembrane 9 superfamily member 1 (TM9SF1), mRNA
gi|18583350|ref|XM_083903.1|[18583350]

169: NT_010036
Homo sapiens chromosome 14 working draft sequence segment
gi|18583080|ref|NT_010036.8|Hs14_10193[18583080]

170: XM_028295
Homo sapiens calponin like transmembrane domain protein (calmin), mRNA
gi|18582992|ref|XM_028295.3|[18582992]

171: NT_029430
Homo sapiens chromosome 13 working draft sequence segment
gi|18582622|ref|NT_029430.4|Hs13_29589[18582622]

172: NT_009967
Homo sapiens chromosome 13 working draft sequence segment
gi|18582005|ref|NT_009967.8|Hs13_10124[18582005]

173: NT_009952
Homo sapiens chromosome 13 working draft sequence segment
gi|18581926|ref|NT_009952.8|Hs13_10109[18581926]

174: NT_009917
Homo sapiens chromosome 13 working draft sequence segment
gi|18581517|ref|NT_009917.8|Hs13_10074[18581517]

175: XM_084974
Homo sapiens transmembrane phosphatase with tensin homology (TPTE), mRNA
gi|18581435|ref|XM_084974.1|[18581435]

176: NT_009910
Homo sapiens chromosome 13 working draft sequence segment
gi|18581383|ref|NT_009910.8|Hs13_10067[18581383]

177: NT_009711
Homo sapiens chromosome 12 working draft sequence segment
gi|18580591|ref|NT_009711.8|Hs12_9868[18580591]

178: NT_009540
Homo sapiens chromosome 12 working draft sequence segment
gi|18579972|ref|NT_009540.8|Hs12_9697[18579972]

179: NT_009487
Homo sapiens chromosome 12 working draft sequence segment
gi|18579817|ref|NT_009487.8|Hs12_9644[18579817]

180: XM_084852
Homo sapiens similar to transmembrane protein induced by tumor necrosis factor alpha (LOC144404), mRNA
gi|18579801|ref|XM_084852.1|[18579801]

181: NT_009471
Homo sapiens chromosome 12 working draft sequence segment
gi|18579778|ref|NT_009471.8|Hs12_9628[18579778]

182: XM_084845
Homo sapiens similar to interferon induced transmembrane protein 3 (1-8U) (LOC144383), mRNA
gi|18579688|ref|XM_084845.1|[18579688]

183: XM_006748
Homo sapiens seven transmembrane protein TM7SF3 (TM7SF3), mRNA
gi|18579647|ref|XM_006748.5|[18579647]

184: NT_030809
Homo sapiens chromosome 12 working draft sequence segment
gi|18579377|ref|NT_030809.2|Hs12_31065[18579377]

185: NT_024394
Homo sapiens chromosome 12 working draft sequence segment
gi|18579035|ref|NT_024394.7|Hs12_24550[18579035]

186: NT_009237
Homo sapiens chromosome 11 working draft sequence segment
gi|18578641|ref|NT_009237.8|Hs11_9394[18578641]

187: NT_009215
Homo sapiens chromosome 11 working draft sequence segment
gi|18578584|ref|NT_009215.8|Hs11_9372[18578584]

188: NT_008992
Homo sapiens chromosome 11 working draft sequence segment
gi|18578338|rcf|NT_008992.7|Hs11_9149[18578338]

189: XM_055266
Homo sapiens putative transmembrane protein; homolog of yeast Golgi membrane
protein Yif1p (Yip1p-interacting factor) (54TM), mRNA
gi|18578177|ref|XM_055266.2|[18578177]

190: XM_045525
Homo sapiens transmembrane 7 superfamily member 2 (TM7SF2), mRNA
gi|18578063|ref|XM_045525.4|[18578063]

191: XM_006111
Homo sapiens fibronectin leucine rich transmembrane protein 1 (FLRT1), mRNA
gi|18578050|ref|XM_006111.5|[18578050]

192: NT_008804
Homo sapiens chromosome 10 working draft sequence segment
gi|18576536|ref|NT_008804.8|Hs10_8961[18576536]

193: XM_084484
Homo sapiens similar to sema domain, immunoglobulin domain (Ig), transmembrane domain (TM) and short cytoplasmic domain, (semaphorin) 4G; sema domain, immunoglobulin domain (Ig), transmembrane domain (TM) and short cytoplasmic domain, 4G (LOC143288), mRNA
gi|18576428|ref|XM_084484.1|[18576428]

194: NT_008609
Homo sapiens chromosome 10 working draft sequence segment
gi|18575857|ref|NT_008609.8|Hs10_8766[18575857]

195: NT_029394
Homo sapiens chromosome 10 working draft sequence segment
gi|18574577|ref|NT_029394.3|Hs10_29553[18574577]

196: NT_024089
Homo sapiens chromosome 10 working draft sequence segment
gi|18574182|ref|NT_024089.8|Hs10_24245[18574182]

197: NT_024064
Homo sapiens chromosome 10 working draft sequence segment
gi|18574077|ref|NT_024064.8|Hs10_24220[18574077]

198: XM_084331
Homo sapiens similar to growth hormone inducible transmembrane protein (H. sapiens) (LOC170427), mRNA
gi|18574063|ref|XM_084331.1|[18574063]

199: XM_043589
Homo sapiens growth hormone inducible transmembrane protein (GHITM), mRNA
gi|18574061|ref|XM_043589.3|[18574061]

200: NT_008554

Homo sapiens chromosome 9 working draft sequence segment
gi|18573734|ref|NT_008554.8|Hs9_8711[18573734]

201: XM_071188
Homo sapiens similar to mucin 1, transmembrane (LOC138940), mRNA
gi|18573702|ref|XM_071188.2|[18573702]

202: NT_008476
Homo sapiens chromosome 9 working draft sequence segment
gi|18573649|ref|NT_008476.8|Hs9_8633[18573649]

203: NT_008421
Homo sapiens chromosome 9 working draft sequence segment
gi|18573390|ref|NT_008421.8|Hs9_8578[18573390]

204: NT_031831
Homo sapiens chromosome 9 working draft sequence segment
gi|18572946|ref|NT_031831.1|Hs9_32002[18572946]

205: NT_031830
Homo sapiens chromosome 9 working draft sequence segment
gi|18572933|ref|NT_031830.1|Hs9_32001[18572933]

206: NT_029366
Homo sapiens chromosome 9 working draft sequence segment
gi|18572447|ref|NT_029366.4|Hs9_29525[18572447]

207: NT_027082
Homo sapiens chromosome 9 working draft sequence segment
gi|18572282|ref|NT_027082.5|Hs9_27242[18572282]

208: NT_024010
Homo sapiens chromosome 9 working draft sequence segment
gi|18572162|ref|NT_024010.7|Hs9_24166[18572162]

209: XM_108898
Homo sapiens sema domain, immunoglobulin domain (Ig), transmembrane domain (TM)

and short cytoplasmic domain, (semaphorin) 4D (SEMA4D), mRNA
gi|18572160|ref|XM_108898.1|[18572160]

210: NT_023967
Homo sapiens chromosome 9 working draft sequence segment
gi|18571929|ref|NT_023967.8|Hs9_24123[18571929]

211: XM_095756
Homo sapiens similar to transmembrane protein 2 (H. sapiens) (LOC169529), mRNA
gi|18571901|ref|XM_095756.1|[18571901]

212: NT_008253
Homo sapiens chromosome 8 working draft sequence segment
gi|18571429|ref|NT_008253.8|Hs8_8410[18571429]

213: NT_008079
Homo sapiens chromosome 8 working draft sequence segment
gi|18570812|ref|NT_008079.8|Hs8_8236[18570812]

214: NT_007997
Homo sapiens chromosome 8 working draft sequence segment
gi|18570417|ref|NT_007997.8|Hs8_8154[18570417]

215: XM_095564
Homo sapiens similar to transmembrane trafficking protein (LOC169193), mRNA
gi|18570401|ref|XM_095564.1|[18570401]

216: NT_007978
Homo sapiens chromosome 8 working draft sequence segment
gi|18570256|ref|NT_007978.8|Hs8_8135[18570256]

217: NT_030735
Homo sapiens chromosome 8 working draft sequence segment
gi|18569963|ref|NT_030735.2|Hs8_30991[18569963]

218: NT_007905
Homo sapiens chromosome 7 working draft sequence segment gi|18568542|ref|NT_007905.8|Hs7_8062[18568542]

219: NT_007902
Homo sapiens chromosome 7 working draft sequence segment
gi|18568515|ref|NT_007902.8|Hs7_8059[18568515]

220: AF132746
Homo sapiens transmembrane protein mRNA, complete cds
gi|18568116|gb|AF132746.1|[18568116]

221: NT_007867
Homo sapiens chromosome 7 working draft sequence segment
gi|18568101|ref|NT_007867.8|Hs7_8024[18568101]

222: NT_007751
Homo sapiens chromosome 7 working draft sequence segment
gi|18567173|ref|NT_007751.8|Hs7_7908[18567173]

223: NT_031815
Homo sapiens chromosome 7 working draft sequence segment
gi|18566709|ref|NT_031815.1|Hs7_31986[18566709]

224: NT_031811
Homo sapiens chromosome 7 working draft sequence segment
gi|18566667|ref|NT_031811.1|Hs7_31982[18566667]

225: XM_095132
Homo sapiens similar to dM538M10.1 (novel 7 transmembrane receptor (rhodopsin family) (olfactory receptor like) protein similar to human HS6M1-21) (LOC154958), mRNA
gi|18566661|ref|XM_095132.1|[18566661]

226: NT_031807
Homo sapiens chromosome 7 working draft sequence segment
gi|18566613|ref|NT_031807.1|Hs7_31978[18566613]

227: NT_030004

Homo sapiens chromosome 7 working draft sequence segment
gi|18566403|ref|NT_030004.3|Hs7_30259[18566403]

228: NT_027064
Homo sapiens chromosome 7 working draft sequence segment
gi|18566143|ref|NT_027064.5|Hs7_27224[18566143]

229: NT_017168
Homo sapiens chromosome 7 working draft sequence segment
gi|18565551|ref|NT_017168.8|Hs7_17324[18565551]

230: NT_007592
Homo sapiens chromosome 6 working draft sequence segment
gi|18565438|ref|NT_007592.8|Hs6_7749[18565438]

231: XM_094938
Homo sapiens similar to 573K1.2 (mm17M1-3 (novel 7 transmembrane receptor (rhodopsin family) (olfactory receptor LIKE) protein)) (LOC168233), mRNA
gi|18565395|ref|XM_094938.1|[18565395]

232: XM_094903
Homo sapiens similar to 573K1.15 (mm17M1-6 (novel 7 transmembrane receptor (rhodopsin family) (olfactory receptor LIKE) protein)) (LOC168189), mRNA
gi|18565249|ref|XM_094903.1|[18565249]

233: XM_094939
Homo sapiens similar to dM538M10.7 (novel 7 transmembrane receptor (rhodopsin family) (olfactory receptor like) protein) (LOC154634), mRNA
gi|18565093|ref|XM_094939.1|[18565093]

234: NT_007402
Homo sapiens chromosome 6 working draft sequence segment
gi|18564193|ref|NT_007402.8|Hs6_7559[18564193]

235: XM_069322
Homo sapiens similar to transmembrane protein 2 (LOC135381), mRNA
gi|18564165|ref|XM_069322.2|[18564165]

236: XM_087914
Homo sapiens similar to dJ402H5.1 (novel 7 transmembrane receptor of the rhodopsin family) (LOC154354), mRNA
gi|18564052|ref|XM_087914.1|[18564052]

237: XM_087917
Homo sapiens similar to embryonic seven-span transmembrane protein-like protein (LOC154344), mRNA
gi|18564031|ref|XM_087917.1|[18564031]

238: XM_094741
Homo sapiens similar to 573K1.15 (mm17M1-6 (novel 7 transmembrane receptor (rhodopsin family) (olfactory receptor LIKE) protein)) (LOC167905), mRNA
gi|18563541|ref|XM_094741.1|[18563541]

239: NT_025741
Homo sapiens chromosome 6 working draft sequence segment
gi|18563240|ref|NT_025741.7|Hs6_25897[18563240]

240: NT_023451
Homo sapiens chromosome 6 working draft sequence segment
gi|18563080|ref|NT_023451.8|Hs6_23607[18563080]

241: XM_069021
Homo sapiens similar to putative transmembrane protein PTG (LOC134801), mRNA
gi|18563039|ref|XM_069021.2|[18563039]

242: NT_006725
Homo sapiens chromosome 5 working draft sequence segment
gi|18561712|ref|NT_006725.8|Hs5_6882[18561712]

243: XM_094515
Homo sapiens similar to transmembrane receptor Unc5H1 (LOC167476), mRNA
gi|18561698|ref|XM_094515.1|[18561698]

244: NT_006576
Homo sapiens chromosome 5 working draft sequence segment

245: XM_004042
Homo sapiens sema domain, seven thrombospondin repeats (type 1 and type 1-like), transmembrane domain (TM) and short cytoplasmic domain, (semaphorin) 5A (SEMA5A), mRNA
gi|18561264|ref|XM_004042.7|[18561264]

246: XM_087665
Homo sapiens similar to semaphorin 6A1; sema domain, transmembrane domain (TM), and cytoplasmic domain, 6A; semaphorin 6A-1 (LOC153420), mRNA
gi|18560683|ref|XM_087665.1|[18560683]

247: NT_006169
Homo sapiens chromosome 4 working draft sequence segment
gi|18558377|ref|NT_006169.8|Hs4_6326[18558377]

248: NT_022836
Homo sapiens chromosome 4 working draft sequence segment
gi|18557125|ref|NT_022836.7|Hs4_22992[18557125]

249: XM_093891
Homo sapiens similar to interferon induced transmembrane protein 3 (1-8U) (LOC166482), mRNA
gi|18557119|ref|XM_093891.1|[18557119]

250: AF456925
Homo sapiens USH3 region, partial sequence
gi|17901944|gb|AF456925.1|AF411849S2[17901944]

251: AF411849
Homo sapiens USH3 region, partial sequence
gi|17901943|gb|AF411849.1|AF411849S1[17901943]

252: AH011260
Homo sapiens
gi|17901942|gb|AH011260.1|SEG_AF411849S[17901942]

253: XM_064062
Homo sapiens similar to putative transmembrane receptor (LOC124274), mRNA
gi|17488065|ref|XM_064062.1|[17488065]

254: XM_063875
Homo sapiens similar to interferon induced transmembrane protein 3 (1-8U) (LOC123862), mRNA
gi|17487213|ref|XM_063875.1|[17487213]

255: XM_066655
Homo sapiens similar to G protein-coupled receptor 64; G protein-coupled receptor, epididymis-specific (seven transmembrane family) (LOC139378), mRNA
gi|17485715|ref|XM_066655.1|[17485715]

256: NT_011519
Homo sapiens chromosome 22 working draft sequence segment
gi|17484914|ref|NT_011519.9|Hs22_11676[17484914]

257: NT_011362
Homo sapiens chromosome 20 working draft sequence segment
gi|17484369|ref|NT_011362.7|Hs20_11519[17484369]

258: XM_063355
Homo sapiens similar to transmembrane 7 superfamily member 1 (upregulated in kidney); transmembrane 7 superfamily member 1 (upregulated in (LOC122791), mRNA
gi|17476790|ref|XM_063355.1|[17476790]

259: XM_062544
Homo sapiens similar to transmembrane protein 4; putative secreted protein ZSIG9 (LOC121255), mRNA
gi|17474559|ref|XM_062544.1|[17474559]

260: XM_062443
Homo sapiens similar to interferon induced transmembrane protein 3 (1-8U) (LOC121062), mRNA
gi|17474137|ref|XM_062443.1|[17474137]

261: XM_070446
Homo sapiens similar to interferon induced transmembrane protein 3 (1-8U) (LOC137474), mRNA
gi|17466780|ref|XM_070446.1|[17466780]

262: XM_070130
Homo sapiens similar to transmembrane protein 4; putative secreted protein ZSIG9 (LOC136903), mRNA
gi|17465836|ref|XM_070130.1|[17465836]

263: XM_069635
Homo sapiens similar to interferon induced transmembrane protein 3 (1-8U) (LOC135982), mRNA
gi|17465065|ref|XM_069635.1|[17465065]

264: XM_069633
Homo sapiens similar to interferon induced transmembrane protein 3 (1-8U); interferon-inducible (LOC135976), mRNA
gi|17465055|ref|XM_069633.1|[17465055]

265: XM_069470
Homo sapiens similar to interferon induced transmembrane protein 3 (1-8U) (LOC135637), mRNA
gi|17464370|ref|XM_069470.1|[17464370]

266: XM_069460
Homo sapiens similar to dM538M10.7 (novel 7 transmembrane receptor (rhodopsin family) (olfactory receptor like) protein) (LOC135626), mRNA
gi|17464346|ref|XM_069460.1|[17464346]

267: XM_064220
Homo sapiens similar to putative transmembrane receptor (LOC124601), mRNA
gi|17457972|ref|XM_064220.1|[17457972]

268: XM_063652
Homo sapiens similar to leucine zipper-EF-hand containing transmembrane protein 1; leucine zipper-EF-hand containing transmembrane protein 1 (LOC123430), mRNA
gi|17456715|ref|XM_063652.1|[17456715]

269: XM_062703
Homo sapiens similar to tetraspan transmembrane 4 super family (LOC121590), mRNA
gi|17456679|ref|XM_062703.1|[17456679]

270: XM_051362
Homo sapiens transmembrane 6 superfamily member 2 (TM6SF2), mRNA
gi|17456138|ref|XM_051362.2|[17456138]

271: NT_011288
Homo sapiens chromosome 19 working draft sequence segment
gi|17455923|ref|NT_011288.7|Hs19_11445[17455923]

272: XM_031933
Homo sapiens transmembrane protein vezatin (VEZATIN), mRNA
gi|17454769|ref|XM_031933.3|[17454769]

273: XM_068785
Homo sapiens similar to transmembrane receptor Unc5H1 (LOC134307), mRNA
gi|17446928|ref|XM_068785.1|[17446928]

274: NT_030685
Homo sapiens chromosome 5 working draft sequence segment
gi|17443457|ref|NT_030685.1|Hs5_30941[17443457]

275: NT_011387
Homo sapiens chromosome 20 working draft sequence segment
gi|16195112|ref|NT_011387.6|Hs20_11544[16195112]

276: NT_011512
Homo sapiens chromosome 21 working draft sequence segment
gi|16170824|ref|NT_011512.4|Hs21_11669[16170824]

277: XM_049793
Homo sapiens transmembrane protease, serine 2 (TMPRSS2), mRNA
gi|16170797|ref|XM_049793.2|[16170797]

278: NT_011520
Homo sapiens chromosome 22 working draft sequence segment
gi|16168698|ref|NT_011520.8|Hs22_11677[16168698]

279: NT_030188
Homo sapiens chromosome 21 working draft sequence segment
gi|16166749|ref|NT_030188.1|Hs21_30443[16166749]

280: NT_029490
Homo sapiens chromosome 21 working draft sequence segment
gi|16166567|ref|NT_029490.2|Hs21_29649[16166567]

281: NT_011515
Homo sapiens chromosome 21 working draft sequence segment
gi|16166537|ref|NT_011515.6|Hs21_11672[16166537]

282: XM_009794
Homo sapiens transmembrane protein 1 (TMEM1), mRNA
gi|16166381|ref|XM_009794.4|[16166381]

283: NT_009407
Homo sapiens chromosome 11 working draft sequence segment
gi|16164445|ref|NT_009407.5|Hs11_9564[16164445]

284: NT_027220
Homo sapiens chromosome X working draft sequence segment
gi|16163830|ref|NT_027220.2|HsX_27380[16163830]

285: XM_055222
Homo sapiens region containing sema domain, immunoglobulin domain (Ig), transmembrane domain (TM) and short cytoplasmic domain, (semaphorin) 4G; mitochondrial ribosomal protein L32 (LOC143289), mRNA
gi|16156787|ref|XM_055222.1|[16156787]

286: XM_008123
Homo sapiens tryptase gamma 1 (TPSG1), mRNA
gi|15317318|ref|XM_008123.5|[15317318]

287: NT_009738
Homo sapiens chromosome 12 working draft sequence segment
gi|15307319|ref|NT_009738.5|Hs12_9895[15307319]

288: XM_006991
Homo sapiens tetraspan transmembrane 4 super family (NET-5), mRNA
gi|15307297|ref|XM_006991.5|[15307297]

289: NT_009513
Homo sapiens chromosome 12 working draft sequence segment
gi|15303938|ref|NT_009513.5|Hs12_9670[15303938]

290: NT_029317
Homo sapiens chromosome 6 working draft sequence segment
gi|15300889|ref|NT_029317.1|Hs6_29476[15300889]

291: XM_040419
Homo sapiens transmembrane trafficking protein (TMP21), mRNA
gi|14784589|ref|XM_040419.1|[14784589]

292: XM_030300
Homo sapiens similar to transmembrane receptor Unc5H1 (LOC90249), mRNA
gi|14781377|ref|XM_030300.1|[14781377]

293: XM_036570
Homo sapiens type I transmembrane protein Fn14 (FN14), mRNA
gi|14777984|ref|XM_036570.1|[14777984]

294: XM_027469
Homo sapiens transmembrane protein 8 (five membrane-spanning domains) (TMEM8), mRNA
gi|14777199|ref|XM_027469.1|[14777199]

295: XM_009839
Homo sapiens claudin 5 (transmembrane protein deleted in velocardiofacial syndrome) (CLDN5), mRNA
gi|14777026|ref|XM_009839.4|[14777026]

296: NT_025911
Homo sapiens chromosome 17 working draft sequence segment
gi|14776336|ref|NT_025911.3|Hs17_26067[14776336]

297: XM_041427
Homo sapiens transmembrane protease, serine 5 (spinesin) (TMPRSS5), mRNA
gi|14770562|ref|XM_041427.1|[14770562]

298: XM_006940
Homo sapiens cytoskeleton-associated protein 4 (CKAP4), mRNA
gi|14766392|ref|XM_006940.4|[14766392]

299: NT_011598
Homo sapiens chromosome X working draft sequence segment
gi|14759313|ref|NT_011598.4|HsX_11755[14759313]

300: XM_033157
Homo sapiens transmembrane 4 superfamily member 6 (TM4SF6), mRNA
gi|14757314|ref|XM_033157.1|[14757314]

301: XM_044358
Homo sapiens similar to cleft lip and palate associated transmembrane protein 1 (LOC92330), mRNA
gi|14755905|ref|XM_044358.1|[14755905]

302: XM_004980
Homo sapiens cystic fibrosis transmembrane conductance regulator, ATP-binding cassette (sub-family C, member 7) (CFTR), mRNA
gi|14753226|ref|XM_004980.4|[14753226]

303: XM_002838
Homo sapiens similar to orphan seven-transmembrane receptor, chemokine related (H. sapiens) (LOC154103), mRNA
gi|14750021|ref|XM_002838.6|[14750021]

304: XM_005949

Homo sapiens sema domain, immunoglobulin domain (Ig), transmembrane domain (TM) and short cytoplasmic domain, (semaphorin) 4G (SEMA4G), mRNA
gi|14747317|ref|XM_005949.4|[14747317]

305: XM_035329
Homo sapiens similar to transmembrane trafficking protein (LOC90981), mRNA
gi|14744677|ref|XM_035329.1|[14744677]

306: XM_038156
Homo sapiens transmembrane protein 2 (TMEM2), mRNA
gi|14743733|ref|XM_038156.1|[14743733]

307: XM_005346
Homo sapiens transmembrane protein with EGF-like and two follistatin-like domains 1 (TMEFF1), mRNA
gi|14738782|ref|XM_005346.4|[14738782]

308: XM_045505
Homo sapiens transmembrane 4 superfamily member (tetraspan NET-7) (NET-7), mRNA
gi|14738519|ref|XM_045505.1|[14738519]

311: NT_026472
Homo sapiens chromosome 17 working draft sequence segment
gi|13654226|ref|NT_026472.1|Hs17_26639[13654226]

312: XM_012718
Homo sapiens secreted and transmembrane 1 (SECTM1), mRNA
gi|13654161|ref|XM_012718.2|[13654161]

313: XM_016506
Homo sapiens fibronectin leucine rich transmembrane protein 2 (FLRT2), mRNA
gi|13648109|ref|XM_016506.1|[13648109]

314: XM_005187
Homo sapiens ankyrin-like with transmembrane domains 1 (ANKTM1), mRNA
gi|13645787|ref|XM_005187.3|[13645787]

315: NT_025803

Homo sapiens chromosome 8 working draft sequence segment
gi|13642635|ref|NT_025803.2|Hs8_25959[13642635]

316: XM_017003
Homo sapiens interferon induced transmembrane protein 3 (1-8U) (IFITM3), mRNA
gi|13642630|ref|XM_017003.1|[13642630]

317: NT_022761
Homo sapiens chromosome 4 working draft sequence segment
gi|18556805|ref|NT_022761.8|Hs4_22917[18556805]

318: XM_093853
Homo sapiens similar to transmembrane tryptase (LOC166415), mRNA
gi|18556799|ref|XM_093853.1|[18556799]

319: NT_005997
Homo sapiens chromosome 3 working draft sequence segment
gi|18556520|ref|NT_005997.8|Hs3_6154[18556520]

320: XM_087464
Homo sapiens similar to transmembrane protein 7 (LOC152408), mRNA
gi|18556483|ref|XM_087464.1|[18556483]

321: NT_005986
Homo sapiens chromosome 3 working draft sequence segment
gi|18556440|ref|NT_005986.8|Hs3_6143[18556440]

322: NT_005678
Homo sapiens chromosome 3 working draft sequence segment
gi|18555423|ref|NT_005678.7|Hs3_5835[18555423]

323: XM_093638
Homo sapiens similar to orphan seven transmembrane receptor (LOC166071), mRNA
gi|18555421|ref|XM_093638.1|[18555421]

324: XM_093637
Homo sapiens similar to orphan seven transmembrane receptor (LOC166070), mRNA gi|18555419|ref|XM_093637.1|[18555419]

325: NT_005654
Homo sapiens chromosome 3 working draft sequence segment
gi|18555355|ref|NT_005654.8|Hs3_5811[18555355]

326: NT_005616
Homo sapiens chromosome 3 working draft sequence segment
gi|18555281|ref|NT_005616.8|Hs3_5773[18555281]

327: NT_005543
Homo sapiens chromosome 3 working draft sequence segment
gi|18555061|ref|NT_005543.7|Hs3_5700[18555061]

328: XM_098155
Homo sapiens similar to seven transmembrane domain orphan receptor (H. sapiens) (LOC152010), mRNA
gi|18555022|ref|XM_098155.1|[18555022]

329: NT_022531
Homo sapiens chromosome 3 working draft sequence segment
gi|18554079|ref|NT_022531.4|Hs3_22687[18554079]

330: XM_096181
Homo sapiens transmembrane 4 superfamily member 4 (TM4SF4), mRNA
gi|18554072|ref|XM_096181.1|[18554072]

331: NT_022412
Homo sapiens chromosome 3 working draft sequence segment
gi|18553606|ref|NT_022412.6|Hs3_22568[18553606]

332: NT_022393
Homo sapiens chromosome 3 working draft sequence segment
gi|18553572|ref|NT_022393.7|Hs3_22549[18553572]

333: NT_005423
Homo sapiens chromosome 2 working draft sequence segment gi|18553407|ref|NT_005423.8|Hs2_5580[18553407]

334: NT_005387
Homo sapiens chromosome 2 working draft sequence segment
gi|18553071|ref|NT_005387.8|Hs2_5544[18553071]

335: NT_005289
Homo sapiens chromosome 2 working draft sequence segment
gi|18552655|ref|NT_005289.8|Hs2_5446[18552655]

336: NT_005214
Homo sapiens chromosome 2 working draft sequence segment
gi|18552351|ref|NT_005214.8|Hs2_5371[18552351]

337: NT_005138
Homo sapiens chromosome 2 working draft sequence segment
gi|18552129|ref|NT_005138.8|Hs2_5295[18552129]

338: NT_022180
Homo sapiens chromosome 2 working draft sequence segment
gi|18550124|ref|NT_022180.8|Hs2_22336[18550124]

339: NT_004858
Homo sapiens chromosome 1 working draft sequence segment
gi|18549451|ref|NT_004858.8|Hs1_5015[18549451]

340: XM_053256
Homo sapiens mucin 1, transmembrane (MUC1), mRNA
gi|18549380|ref|XM_053256.4|[18549380]

341: NT_004836
Homo sapiens chromosome 1 working draft sequence segment
gi|18549182|ref|NT_004836.8|Hs1_4993[18549182]

342: NT_004811
Homo sapiens chromosome 1 working draft sequence segment
gi|18549145|ref|NT_004811.8|Hs1_4968[18549145]

343: XM_041879
Homo sapiens similar to AF1Q protein; transmembrane protein (LOC149430), mRNA
gi|18549121|ref|XM_041879.2|[18549121]

344: NT_004668
Homo sapiens chromosome 1 working draft sequence segment
gi|18548894|ref|NT_004668.8|Hs1_4825[18548894]

345: NT_004441
Homo sapiens chromosome 1 working draft sequence segment
gi|18547758|ref|NT_004441.8|Hs1_4598[18547758]

346: NT_004434
Homo sapiens chromosome 1 working draft sequence segment
gi|18547724|ref|NT_004434.8|Hs1_4591[18547724]

347: NT_004391
Homo sapiens chromosome 1 working draft sequence segment
gi|18547557|ref|NT_004391.8|Hs1_4548[18547557]

348: NT_021907
Homo sapiens chromosome 1 working draft sequence segment
gi|18544452|ref|NT_021907.8|Hs1_22063[18544452]

349: XM_053163
Homo sapiens sema domain, transmembrane domain (TM), and cytoplasmic domain, (semaphorin) 6C (SEMA6C), mRNA
gi|18544383|ref|XM_053163.4|[18544383]

350: NM_016155
Homo sapiens matrix metalloproteinase 17 (membrane-inserted) (MMP17), mRNA
gi|18543372|ref|NM_016155.2|[18543372]

351: XM_060507
Homo sapiens similar to putative integral membrane transporter; lysosomal-associated transmembrane protein 4 beta (LOC127480), mRNA gi|17443784|ref|XM_060507.1|[17443784]

352: XM_060501
Homo sapiens similar to bM332P19.3 (novel 7 transmembrane receptor (rhodopsin family) (olfactory receptor like) protein (mm17M1-14)) (LOC127469), mRNA
gi|17443690|ref|XM_060501.1|[17443690]

353: XM_060442
Homo sapiens similar to interferon induced transmembrane protein 3 (1-8U); interferon-inducible (LOC127360), mRNA
gi|17441370|ref|XM_060442.1|[17441370]

354: XM_065294
Homo sapiens similar to Transmembrane protease, serine 3 (Serine protease TADG-12) (Tumor associated differentially-expressed gene-12 protein) (LOC129566), mRNA
gi|17439790|ref|XM_065294.1|[17439790]

355: XM_032249
Homo sapiens sema domain, seven thrombospondin repeats (type 1 and type 1-like), transmembrane domain (TM) and short cytoplasmic domain, (semaphorin) 5B (SEMA5B), mRNA
gi|17438489|ref|XM_032249.3|[17438489]

356: XM_058189
Homo sapiens similar to TRANSMEMBRANE 4 SUPERFAMILY, MEMBER 1 (TUMOR-ASSOCIATED
ANTIGEN L6) (MEMBRANE COMPONENT, SURFACE MARKER 1) (M3S1) (LOC116441), mRNA
gi|17437690|ref|XM_058189.2|[17437690]

357: NT_011903
Homo sapiens chromosome Y working draft sequence segment
gi|17433681|ref|NT_011903.8|HsY_12060[17433681]

358: XM_034757
Homo sapiens similar to transmembrane phosphatase with tensin homology (H. sapiens) (LOC159185), mRNA
gi|16164045|ref|XM_034757.2|[16164045]

359: XM_003025
Homo sapiens mucin 13, epithelial transmembrane (MUC13), mRNA
gi|16159511|ref|XM_003025.5|[16159511]

360: NT_015169
Homo sapiens chromosome 4 working draft sequence segment
gi|16156888|ref|NT_015169.5|Hs4_15325[16156888]

361: NM_002837
Homo sapiens protein tyrosine phosphatase, receptor type, B (PTPRB), mRNA
gi|18491009|ref|NM_002837.2|[18491009]

362: BC022439
Homo sapiens, interferon induced transmembrane protein 3 (1-8U), clone MGC:24755
IMAGE:4282809, mRNA, complete cds
gi|18490258|gb|BC022439.1|[18490258]

363: NM_005031
Homo sapiens FXYD domain containing ion transport regulator 1 (phospholemman)
(FXYD1), transcript variant a, mRNA
gi|11612671|ref|NM_005031.2|[11612671]

364: NM_021902
Homo sapiens FXYD domain containing ion transport regulator 1 (phospholemman)
(FXYD1), transcript variant b, mRNA
gi|11612669|ref|NM_021902.1|[11612669]

365: NM_014164
Homo sapiens FXYD domain-containing ion transport regulator 5 (FXYD5), mRNA
gi|11612664|ref|NM_014164.2|[11612664]

366: NM_020399
Homo sapiens PDZ/coiled-coil domain binding partner for the rho-family GTPase
TC10 (PIST), mRNA
gi|9966876|ref|NM_020399.1|[9966876]

367: BM439879
pgr1n.pk001.i17 Normalized Chicken Reproductive Tract cDNA Library (pgr1n)
Gallus gallus cDNA clone pgr1n.pk001.i17 5' similar to gi|7657373
ref|NP_055214.1| tetraspan NET-6 protein; transmembrane 4 superfamily protein
[Homo sapiens] gi|13628481 ref|XP_004793.3| tetraspan NET-6 protein [Homo
sapiens] gi|14747013 ref|XP_049585.1| tetraspan NET-6 protein [Homo sapiens]
gi|14, mRNA sequence
gi|18470654|gb|BM439879.1|BM439879[18470654]

368: BM439852
pgr1n.pk001.h13 Normalized Chicken Reproductive Tract cDNA Library (pgr1n)
Gallus gallus cDNA clone pgr1n.pk001.h13 5' similar to gi|7657176
ref|NP_055070.1| transmembrane protein 4; putative type II membrane protein
[Homo sapiens] dbj|BAA76498.1| (AB015631) type II membrane protein [Homo
sapiens], mRNA sequence
gi|18470627|gb|BM439852.1|BM439852[18470627]

369: BM439375
pgr1c.pk001.a9 Primary Chicken Reproductive Tract cDNA Library (pgr1c) Gallus
gallus cDNA clone pgr1c.pk001.a9 5' similar to gi|13994300 ref|NP_114131.1|
transmembrane protein induced by tumor necrosis factor alpha [Homo sapiens]
gb|AAK16442.1|AF327923_1 (AF327923) transmembrane protein induced by tumor
necrosis factor alpha [Homo sapiens], mRNA sequence
gi|18470150|gb|BM439375.1|BM439375[18470150]

370: NM_080841
Homo sapiens protein tyrosine phosphatase, receptor type, A (PTPRA), transcript
variant 3, mRNA
gi|18450370|ref|NM_080841.1|[18450370]

371: NM_080840
Homo sapiens protein tyrosine phosphatase, receptor type, A (PTPRA), transcript
variant 2, mRNA
gi|18450368|ref|NM_080840.1|[18450368]

372: NM_002836
Homo sapiens protein tyrosine phosphatase, receptor type, A (PTPRA), transcript
variant 1, mRNA
gi|18450367|ref|NM_002836.2|[18450367]

373: NM_018490
Homo sapiens G protein-coupled receptor 48 (GPR48), mRNA
gi|8923700|ref|NM_018490.1|[8923700]

374: NM_006065
Homo sapiens signal-regulatory protein beta 1 (SIRPB1), mRNA
gi|5174678|ref|NM_006065.1|[5174678]

375: NM_004648
Homo sapiens protein tyrosine phosphatase, non-receptor type substrate 1
(PTPNS1), mRNA
gi|4758977|ref|NM_004648.1|[4758977]

376: NM_003667
Homo sapiens G protein-coupled receptor 49 (GPR49), mRNA
gi|4504378|ref|NM_003667.1|[4504378]

377: BM427439
pgf2n.pk006.m15 Normalized Chicken Abdominal Fat Library (pgf2n) Gallus gallus
cDNA clone pgf2n.pk006.m15 5' similar to gi|13994300 ref|NP_114131.1|
transmembrane protein induced by tumor necrosis factor alpha [Homo sapiens]
gb|AAK16442.1|AF327923_1 (AF327923) transmembrane protein induced by tumor
necrosis factor alpha [Homo sapiens], mRNA sequence
gi|18432616|gb|BM427439.1|BM427439[18432616]

378: BM427410
pgf2n.pk006.k5 Normalized Chicken Abdominal Fat Library (pgf2n) Gallus gallus
cDNA clone pgf2n.pk006.k5 5' similar to gi|13994300 ref|NP_114131.1|
transmembrane protein induced by tumor necrosis factor alpha [Homo sapiens]
gb|AAK16442.1|AF327923_1 (AF327923) transmembrane protein induced by tumor
necrosis factor alpha [Homo sapiens], mRNA sequence
gi|18432562|gb|BM427410.1|BM427410[18432562]

379: BM427358
pgf2n.pk006.i13 Normalized Chicken Abdominal Fat Library (pgf2n) Gallus gallus
cDNA clone pgf2n.pk006.i13 5' similar to gi|7705965 ref|NP_057456.1| seven
transmembrane domain orphan receptor [Homo sapiens] dbj|BAA89782.1| (AB037108)
seven transmembrane domain orphan receptor [Homo sapiens], mRNA sequence
gi|18432475|gb|BM427358.1|BM427358[18432475]

380: NM_002122
Homo sapiens major histocompatibility complex, class II, DQ alpha 1 (HLA-DQA1), mRNA
gi|18426974|ref|NM_002122.2|[18426974]

381: NM_080815
Homo sapiens collagen, type XIII, alpha 1 (COL13A1), transcript variant 19, mRNA
gi|18426960|ref|NM_080815.1|[18426960]

382: NM_080814
Homo sapiens collagen, type XIII, alpha 1 (COL13A1), transcript variant 18, mRNA
gi|18426958|ref|NM_080814.1|[18426958]

383: NM_080813
Homo sapiens collagen, type XIII, alpha 1 (COL13A1), transcript variant 17, mRNA
gi|18426956|ref|NM_080813.1|[18426956]

384: NM_080812
Homo sapiens collagen, type XIII, alpha 1 (COL13A1), transcript variant 16, mRNA
gi|18426954|ref|NM_080812.1|[18426954]

385: NM_080811
Homo sapiens collagen, type XIII, alpha 1 (COL13A1), transcript variant 15, mRNA
gi|18426952|ref|NM_080811.1|[18426952]

386: NM_080810
Homo sapiens collagen, type XIII, alpha 1 (COL13A1), transcript variant 14, mRNA
gi|18426950|ref|NM_080810.1|[18426950]

387: NM_080809
Homo sapiens collagen, type XIII, alpha 1 (COL13A1), transcript variant 13, mRNA
gi|18426948|ref|NM_080809.1|[18426948]

388: NM_080808
Homo sapiens collagen, type XIII, alpha 1 (COL13A1), transcript variant 12, mRNA
gi|18426946|ref|NM_080808.1|[18426946]

389: NM_080807
Homo sapiens collagen, type XIII, alpha 1 (COL13A1), transcript variant 11, mRNA
gi|18426944|ref|NM_080807.1|[18426944]

390: NM_080806
Homo sapiens collagen, type XIII, alpha 1 (COL13A1), transcript variant 10, mRNA
gi|18426942|ref|NM_080806.1|[18426942]

391: NM_080805
Homo sapiens collagen, type XIII, alpha 1 (COL13A1), transcript variant 9, mRNA
gi|18426940|ref|NM_080805.1|[18426940]

392: NM_080804
Homo sapiens collagen, type XIII, alpha 1 (COL13A1), transcript variant 8, mRNA
gi|18426938|ref|NM_080804.1|[18426938]

393: NM_080803
Homo sapiens collagen, type XIII, alpha 1 (COL13A1), transcript variant 7, mRNA
gi|18426936|ref|NM_080803.1|[18426936]

394: NM_080802
Homo sapiens collagen, type XIII, alpha 1 (COL13A1), transcript variant 6, mRNA
gi|18426934|ref|NM_080802.1|[18426934]

395: NM_080801
Homo sapiens collagen, type XIII, alpha 1 (COL13A1), transcript variant 5, mRNA
gi|18426932|ref|NM_080801.1|[18426932]

396: NM_080800
Homo sapiens collagen, type XIII, alpha 1 (COL13A1), transcript variant 4, mRNA
gi|18426930|ref|NM_080800.1|[18426930]

397: NM_080799
Homo sapiens collagen, type XIII, alpha 1 (COL13A1), transcript variant 3, mRNA
gi|18426928|ref|NM_080799.1|[18426928]

398: NM_080798
Homo sapiens collagen, type XIII, alpha 1 (COL13A1), transcript variant 2, mRNA
gi|18426926|ref|NM_080798.1|[18426926]

399: NM_005203
Homo sapiens collagen, type XIII, alpha 1 (COL13A1), transcript variant 1, mRNA
gi|18426924|ref|NM_005203.2|[18426924]

400: NM_080792
Homo sapiens brain-immunoglobulin-like molecule with tyrosine-based activation motifs (BIT), mRNA
gi|18426910|ref|NM_080792.1|[18426910]

401: NM_080816
Homo sapiens signal-regulatory protein beta 2 (SIRPB2), transcript variant 2, mRNA
gi|18426908|ref|NM_080816.1|[18426908]

402: NM_018556
Homo sapiens signal-regulatory protein beta 2 (SIRPB2), transcript variant 1, mRNA
gi|18426907|ref|NM_018556.2|[18426907]

406: AF367761
Homo sapiens transmembrane protein HTMP10 (HTMP10) mRNA, complete cds
gi|16356924|gb|AF367761.2|[16356924]

409: NM_002124
Homo sapiens major histocompatibility complex, class II, DR beta 1 (HLA-DRB1), mRNA
gi|4504410|ref|NM_002124.1|[4504410]

411: NM_016235
Homo sapiens G protein-coupled receptor, family C, group 1, member B (GPRC5B), mRNA
gi|7706450|ref|NM_016235.1|[7706450]

412: NM_003105
Homo sapiens sortilin-related receptor, L(DLR class) A repeats-containing (SORL1), mRNA
gi|18379347|ref|NM_003105.3|[18379347]

413: NM_004843
Homo sapiens class I cytokine receptor (WSX1), mRNA
gi|18379338|ref|NM_004843.2|[18379338]

414: AF450008
Homo sapiens CFTR-associated ligand (CAL) mRNA, complete cds
gi|17865153|gb|AF450008.1|AF450008[17865153]

415: NM_033056
Homo sapiens protocadherin 15 (PCDH15), mRNA
gi|16933554|ref|NM_033056.2|[16933554]

416: NM_022349
Homo sapiens membrane-spanning 4-domains, subfamily A, member 6A (MS4A6A), mRNA
gi|11641258|ref|NM_022349.1|[11641258]

417: NM_005438
Homo sapiens FOS-like antigen 1 (FOSL1), mRNA
gi|4885242|ref|NM_005438.1|[4885242]

418: BC021208
Homo sapiens, leucine zipper-EF-hand containing transmembrane protein 1, clone MGC:12631 IMAGE:4126510, mRNA, complete cds
gi|18204588|gb|BC021208.1|BC021208[18204588]

419: BC021557
Homo sapiens, transmembrane protein 8 (five membrane-spanning domains), clone MGC:31822 IMAGE:4899167, mRNA, complete cds
gi|18204291|gb|BC021557.1|BC021557[18204291]

420: BC020870
Homo sapiens, fibronectin leucine rich transmembrane protein 3, clone MGC:24073 IMAGE:4606852, mRNA, complete cds
gi|18088787|gb|BC020870.1|BC020870[18088787]

421: BC020960

Homo sapiens, sema domain, immunoglobulin domain (Ig), transmembrane domain (TM) and short cytoplasmic domain, (semaphorin) 4G, clone MGC:8849 IMAGE:3851526, mRNA, complete cds
gi|18088075|gb|BC020960.1|BC020960[18088075]

422: AF444779

Homo sapiens myocyte inner nuclear membrane protein (MYNE1) mRNA, complete cds
gi|17227153|gb|AF444779.1|AF444779[17227153]

423: AF329637

Homo sapiens mitofusin 1 mRNA, nuclear gene for mitochondrial protein, complete cds
gi|12744895|gb|AF329637.1|AF329637[12744895]

424: NM_019074

Homo sapiens delta-like 4 (Drosophila) (DLL4), mRNA
gi|9506544|ref|NM_019074.1|[9506544]

425: NM_017789

Homo sapiens sema domain, immunoglobulin domain (Ig), transmembrane domain (TM) and short cytoplasmic domain, (semaphorin) 4C (SEMA4C), mRNA
gi|8923345|ref|NM_017789.1|[8923345]

426: NM_003836

Homo sapiens delta-like 1 homolog (Drosophila) (DLK1), mRNA
gi|4503338|ref|NM_003836.1|[4503338]

427: NM_024021

Homo sapiens membrane-spanning 4-domains, subfamily A, member 4 (MS4A4A), mRNA
gi|13430865|ref|NM_024021.1|[13430865]

432: NM_021950

Homo sapiens membrane-spanning 4-domains, subfamily A, member 2 (Fc fragment of IgE, high affinity I, receptor for; beta polypeptide) (MS4A1), mRNA
gi|11386186|ref|NM_021950.1|[11386186]

433: AY046529
Homo sapiens melanocortin 1 receptor mutant V122M (MC1R) gene, complete cds
gi|18138241|gb|AY046529.1|[18138241]

434: AY046528
Homo sapiens melanocortin 1 receptor mutant I40T (MC1R) gene, complete cds
gi|18138239|gb|AY046528.1|[18138239]

436: AY028261
Homo sapiens delta transmembrane LIGHT mRNA, complete cds, alternatively spliced
gi|14278834|gb|AY028261.1|[14278834]

437: AF296875
Gallus gallus fas ligand receptor soluble form mRNA, partial cds
gi|9931641|gb|AF296875.1|AF296875[9931641]

439: BM315073
ig43b07.y1 HR85 islet Homo sapiens cDNA 5' similar to SW:MTRP_HUMAN Q15012 GOLGI 4-TRANSMEMBRANE SPANNING TRANSPORTER MTP ;, mRNA sequence
gi|18049418|gb|BM315073.1|BM315073[18049418]

440: BM314493
ig51c05.y1 HR85 islet Homo sapiens cDNA 5' similar to TR:Q9Y287 Q9Y287 TRANSMEMBRANE PROTEIN BRI. ;, mRNA sequence
gi|18048838|gb|BM314493.1|BM314493[18048838]

441: BM313985
ih05d09.y1 Human insulinoma Homo sapiens cDNA 5' similar to SW:MTRP_HUMAN Q15012 GOLGI 4-TRANSMEMBRANE SPANNING TRANSPORTER MTP ;, mRNA sequence
gi|18048330|gb|BM313985.1|BM313985[18048330]

442: AF267740
Homo sapiens transmembrane protein H4 mRNA, complete cds
gi|18032260|gb|AF267740.1|AF267740[18032260]

443: AF350504
Homo sapiens four-span transmembrane protein 4 (4SPAN4) mRNA, complete cds
gi|18028935|gb|AF350504.1|AF350504[18028935]

444: AF350503
Homo sapiens four-span transmembrane protein 3.2 (4SPAN3) mRNA, complete cds
gi|18028933|gb|AF350503.1|AF350503[18028933]

445: AF350502
Homo sapiens four-span transmembrane protein 3.1 (4SPAN3) mRNA, complete cds
gi|18028931|gb|AF350502.1|AF350502[18028931]

446: AF350501
Homo sapiens four-span transmembrane protein 2 (4SPAN2) mRNA, complete cds
gi|18028929|gb|AF350501.1|AF350501[18028929]

447: AF350500
Homo sapiens four-span transmembrane protein 1 (4SPAN1) mRNA, complete cds
gi|18028927|gb|AF350500.1|AF350500[18028927]

448: NM_078470
Homo sapiens COX15 homolog, cytochrome c oxidase assembly protein (yeast) (COX15), nuclear gene encoding mitochondrial protein, transcript variant 1, mRNA
gi|17921984|ref|NM_078470.1|[17921984]

449: NM_004375
Homo sapiens COX11 homolog, cytochrome c oxidase assembly protein (yeast) (COX11), nuclear gene encoding mitochondrial protein, mRNA
gi|17921983|ref|NM_004375.2|[17921983]

450: NM_001303
Homo sapiens COX10 homolog, cytochrome c oxidase assembly protein, heme A: farnesyltransferase (yeast) (COX10), nuclear gene encoding mitochondrial protein, mRNA
gi|17921981|ref|NM_001303.2|[17921981]

451: NM_031999
Mus musculus transmembrane 7 superfamily member 1 (Tm7sf1), mRNA
gi|14269573|ref|NM_031999.1|[14269573]

452: NM_020659
Homo sapiens tweety homolog 1 (Drosophila) (TTYH1), mRNA
gi|10257436|ref|NM_020659.1|[10257436]

453: NM_052945
Homo sapiens BAFF receptor (BAFFR), mRNA
gi|17978517|ref|NM_052945.2|[17978517]

454: NM_078481
Homo sapiens CD97 antigen (CD97), transcript variant 1, mRNA
gi|17978490|ref|NM_078481.1|[17978490]

455: NM_001784
Homo sapiens CD97 antigen (CD97), transcript variant 2, mRNA
gi|17978488|ref|NM_001784.2|[17978488]

456: NM_004444
Homo sapiens EphB4 (EPHB4), mRNA
gi|17975769|ref|NM_004444.2|[17975769]

457: NM_004443
Homo sapiens EphB3 (EPHB3), mRNA
gi|17975767|ref|NM_004443.2|[17975767]

458: NM_004442
Homo sapiens EphB2 (EPHB2), transcript variant 1, mRNA
gi|17975766|ref|NM_004442.2|[17975766]

459: NM_017449
Homo sapiens EphB2 (EPHB2), transcript variant 2, mRNA
gi|17975764|ref|NM_017449.1|[17975764]

460: BM273281
if28f09.y1 Melton Normalized Human Islet 4 N4-HIS 1 Homo sapiens cDNA 5' similar
to TR:Q9Z112 Q9Z112 SEVEN TRANSMEMBRANE DOMAIN ORPHAN RECEPTOR. ;,
mRNA sequence
gi|17966574|gb|BM273281.1|BM273281[17966574]

461: BM271899
ig36e08.y1 HR85 islet Homo sapiens cDNA 5' similar to SW:MTRP_HUMAN Q15012 GOLGI 4-TRANSMEMBRANE SPANNING TRANSPORTER MTP ;, mRNA sequence
gi|17965175|gb|BM271899.1|BM271899[17965175]

462: BM271817
ig35e06.y1 HR85 islet Homo sapiens cDNA 5' similar to SW:MTRP_HUMAN Q15012 GOLGI 4-TRANSMEMBRANE SPANNING TRANSPORTER MTP ;, mRNA sequence
gi|17965091|gb|BM271817.1|BM271817[17965091]

463: BM271771
ig38h09.x1 HR85 islet Homo sapiens cDNA 3' similar to TR:O08721 O08721 TRANSMEMBRANE RECEPTOR UNC5H1. ;, mRNA sequence
gi|17965045|gb|BM271771.1|BM271771[17965045]

464: BC019314
Homo sapiens, transmembrane 4 superfamily member 7, clone MGC:4337 IMAGE:2821236, mRNA, complete cds
gi|17939509|gb|BC019314.1|BC019314[17939509]

465: BM263743
ig29h12.y1 HR85 islet Homo sapiens cDNA 5' similar to SW:NMB_HUMAN Q14956 PUTATIVE TRANSMEMBRANE PROTEIN NMB PRECURSOR. ;, mRNA sequence
gi|17926783|gb|BM263743.1|BM263743[17926783]

466: NM_004376
Homo sapiens COX15 homolog, cytochrome c oxidase assembly protein (yeast) (COX15), nuclear gene encoding mitochondrial protein, transcript variant 2, mRNA
gi|17921986|ref|NM_004376.2|[17921986]

467: AY062295
Homo sapiens prolactin receptor (PRLR) mRNA, partial cds; alternatively spliced
gi|17887307|gb|AY062295.1|[17887307]

468: NM_078474
Homo sapiens BBP-like protein 2 (BLP2), transcript variant 1, mRNA
gi|17865799|ref|NM_078474.1|[17865799]

469: NM_025141
Homo sapiens BBP-like protein 2 (BLP2), transcript variant 2, mRNA
gi|17865798|ref|NM_025141.2|[17865798]

470: NM_078473
Homo sapiens BBP-like protein 1 (BLP1), transcript variant 1, mRNA
gi|17865796|ref|NM_078473.1|[17865796]

471: NM_031940
Homo sapiens BBP-like protein 1 (BLP1), transcript variant 2, mRNA
gi|17865794|ref|NM_031940.2|[17865794]

472: NM_003728
Homo sapiens unc-5 homolog B (C. elegans) (UNC5C), mRNA
gi|16933524|ref|NM_003728.2|[16933524]

473: NM_054027
Homo sapiens ankylosis, progressive homolog (mouse) (ANKH), transcript variant 2, mRNA
gi|16905506|ref|NM_054027.1|[16905506]

474: NM_019847
Homo sapiens ankylosis, progressive homolog (mouse) (ANKH), transcript variant 1, mRNA
gi|16905505|ref|NM_019847.3|[16905505]

475: NM_018440
Homo sapiens phosphoprotein associated with glycosphingolipid-enriched microdomains (PAG), mRNA
gi|16753228|ref|NM_018440.2|[16753228]

478: NM_019894
Homo sapiens transmembrane protease, serine 4 (TMPRSS4), mRNA
gi|15451939|ref|NM_019894.1|[15451939]

479: NM_006577

Homo sapiens UDP-GlcNAc:betaGal beta-1,3-N-acetylglucosaminyltransferase 1 (B3GNT1), transcript variant 1, mRNA
gi|15451893|ref|NM_006577.3|[15451893]

480: NM_033252
Homo sapiens UDP-GlcNAc:betaGal beta-1,3-N-acetylglucosaminyltransferase 1 (B3GNT1), transcript variant 2, mRNA
gi|15451863|ref|NM_033252.1|[15451863]

481: NM_014302
Homo sapiens Sec61 gamma (SEC61G), mRNA
gi|14591933|ref|NM_014302.2|[14591933]

482: NM_014459
Homo sapiens protocadherin 17 (PCDH17), mRNA
gi|14589926|ref|NM_014459.2|[14589926]

483: NM_032961
Homo sapiens protocadherin 10 (PCDH10), transcript variant 1, mRNA
gi|14589915|ref|NM_032961.1|[14589915]

484: NM_020815
Homo sapiens protocadherin 10 (PCDH10), transcript variant 2, mRNA
gi|14589913|ref|NM_020815.1|[14589913]

485: NM_032966
Homo sapiens Burkitt lymphoma receptor 1, GTP binding protein (BLR1), transcript variant 2, mRNA
gi|14589868|ref|NM_032966.1|[14589868]

486: NM_001716
Homo sapiens Burkitt lymphoma receptor 1, GTP binding protein (BLR1), transcript variant 1, mRNA
gi|14589867|ref|NM_001716.2|[14589867]

487: NM_031866
Homo sapiens frizzled homolog 8 (Drosophila) (FZD8), mRNA
gi|13994189|ref|NM_031866.1|[13994189]

488: NM_030770
Homo sapiens transmembrane protease, serine 5 (spinesin) (TMPRSS5), mRNA
gi|13540534|ref|NM_030770.1|[13540534]

489: NM_001407
Homo sapiens cadherin, EGF LAG seven-pass G-type receptor 3 (flamingo homolog, Drosophila) (CELSR3), mRNA
gi|13325065|ref|NM_001407.1|[13325065]

490: NM_001408
Homo sapiens cadherin, EGF LAG seven-pass G-type receptor 2 (flamingo homolog, Drosophila) (CELSR2), mRNA
gi|13325063|ref|NM_001408.1|[13325063]

491: NM_005971
Homo sapiens FXYD domain-containing ion transport regulator 3 (FXYD3), transcript variant 1, mRNA
gi|11612675|ref|NM_005971.2|[11612675]

492: NM_021910
Homo sapiens FXYD domain-containing ion transport regulator 3 (FXYD3), transcript variant 2, mRNA
gi|11612673|ref|NM_021910.1|[11612673]

493: NM_021778
Homo sapiens a disintegrin and metalloproteinase domain 28 (ADAM28), transcript variant 2, mRNA
gi|11496995|ref|NM_021778.1|[11496995]

494: NM_021777
Homo sapiens a disintegrin and metalloproteinase domain 28 (ADAM28), transcript variant 3, mRNA
gi|11496993|ref|NM_021777.1|[11496993]

495: NM_021783
Homo sapiens ectodysplasin A2 isoform receptor (XEDAR), mRNA
gi|11140822|ref|NM_021783.1|[11140822]

496: NM_020182
Homo sapiens transmembrane, prostate androgen induced RNA (TMEPAI), mRNA
gi|9910497|ref|NM_020182.1|[9910497]

497: NM_003857
Homo sapiens galanin receptor 2 (GALR2), mRNA
gi|8051600|ref|NM_003857.2|[8051600]

498: NM_015727
Homo sapiens tachykinin receptor 1 (TACR1), transcript variant short, mRNA
gi|7669545|ref|NM_015727.1|[7669545]

499: NM_001058
Homo sapiens tachykinin receptor 1 (TACR1), transcript variant long, mRNA
gi|7669544|ref|NM_001058.2|[7669544]

501: NM_014246
Homo sapiens cadherin, EGF LAG seven-pass G-type receptor 1 (flamingo homolog, Drosophila) (CELSR1), mRNA
gi|7656966|ref|NM_014246.1|[7656966]

502: NM_014265
Homo sapiens a disintegrin and metalloproteinase domain 28 (ADAM28), transcript variant 1, mRNA
gi|7656862|ref|NM_014265.1|[7656862]

503: NM_007264
Homo sapiens adrenomedullin receptor (ADMR), mRNA
gi|6466448|ref|NM_007264.2|[6466448]

504: NM_004733
Homo sapiens acetyl-Coenzyme A transporter (ACATN), mRNA
gi|6042194|ref|NM_004733.2|[6042194]

505: NM_003801
Homo sapiens GPAA1P anchor attachment protein 1 homolog (yeast) (GPAA1), mRNA
gi|6031166|ref|NM_003801.2|[6031166]

506: NM_007197
Homo sapiens frizzled homolog 10 (Drosophila) (FZD10), mRNA
gi|6005761|ref|NM_007197.1|[6005761]

507: NM_001466
Homo sapiens frizzled homolog 2 (Drosophila) (FZD2), mRNA
gi|5922012|ref|NM_001466.2|[5922012]

508: NM_006579
Homo sapiens emopamil binding protein (sterol isomerase) (EBP), mRNA
gi|5729809|ref|NM_006579.1|[5729809]

509: NM_006017
Homo sapiens prominin-like 1 (mouse) (PROML1), mRNA
gi|5174386|ref|NM_006017.1|[5174386]

510: NM_005228
Homo sapiens epidermal growth factor receptor (erythroblastic leukemia viral
(v-erb-b) oncogene homolog, avian) (EGFR), mRNA
gi|4885198|ref|NM_005228.1|[4885198]

511: NM_004617
Homo sapiens transmembrane 4 superfamily member 4 (TM4SF4), mRNA
gi|4759239|ref|NM_004617.1|[4759239]

512: NM_004787
Homo sapiens slit homolog 2 (Drosophila) (SLIT2), mRNA
gi|4759145|ref|NM_004787.1|[4759145]

513: NM_004445
Homo sapiens EphB6 (EPHB6), mRNA
gi|4758291|ref|NM_004445.1|[4758291]

514: NM_004338
Homo sapiens chromosome 18 open reading frame 1 (C18orf1), mRNA
gi|4757883|ref|NM_004338.1|[4757883]

515: NM_002982
Homo sapiens small inducible cytokine A2 (monocyte chemotactic protein 1) (SCYA2), mRNA
gi|4506840|ref|NM_002982.1|[4506840]

516: NM_002944
Homo sapiens v-ros UR2 sarcoma virus oncogene homolog 1 (avian) (ROS1), mRNA
gi|4506578|ref|NM_002944.1|[4506578]

517: NM_000264
Homo sapiens patched homolog (Drosophila) (PTCH), mRNA
gi|4506246|ref|NM_000264.1|[4506246]

518: NM_003508
Homo sapiens frizzled homolog 9 (Drosophila) (FZD9), mRNA
gi|4503834|ref|NM_003508.1|[4503834]

519: NM_003507
Homo sapiens frizzled homolog 7 (Drosophila) (FZD7), mRNA
gi|4503832|ref|NM_003507.1|[4503832]

520: NM_003506
Homo sapiens frizzled homolog 6 (Drosophila) (FZD6), mRNA
gi|4503830|ref|NM_003506.1|[4503830]

521: NM_003468
Homo sapiens frizzled homolog 5 (Drosophila) (FZD5), mRNA
gi|4503828|ref|NM_003468.1|[4503828]

522: NM_003505
Homo sapiens frizzled homolog 1 (Drosophila) (FZD1), mRNA
gi|4503824|ref|NM_003505.1|[4503824]

523: NM_001982
Homo sapiens v-erb-b2 erythroblastic leukemia viral oncogene homolog 3 (avian) (ERBB3), mRNA
gi|4503596|ref|NM_001982.1|[4503596]

524: NM_003859
Homo sapiens dolichyl-phosphate mannosyltransferase polypeptide 1, catalytic subunit (DPM1), mRNA
gi|4503362|ref|NM_003859.1|[4503362]

525: NM_003915
Homo sapiens copine I (CPNE1), mRNA
gi|4503012|ref|NM_003915.1|[4503012]

527: NM_052959
Homo sapiens pannexin 3 (PANX3), mRNA
gi|16418452|ref|NM_052959.1|[16418452]

528: NM_052859
Homo sapiens putative endoplasmic reticulum multispan transmembrane protein (RFT1), mRNA
gi|16418360|ref|NM_052859.1|[16418360]

531: NM_032108
Homo sapiens sema domain, transmembrane domain (TM), and cytoplasmic domain, (semaphorin) 6B (SEMA6B), mRNA
gi|14165267|ref|NM_032108.1|[14165267]

532: NM_031925

Homo sapiens transmembrane protein induced by tumor necrosis factor alpha (TMPIT), mRNA
gi|13994299|ref|NM_031925.1|[13994299]

533: NM_030960
Homo sapiens sperm acrosome associated 1 (SPACA1), mRNA
gi|13569933|ref|NM_030960.1|[13569933]

534: NM_030755
Homo sapiens thioredoxin domain-containing (TXNDC), mRNA
gi|13559515|ref|NM_030755.1|[13559515]

535: NM_024734
Homo sapiens calponin like transmembrane domain protein (calmin), mRNA
gi|13376053|ref|NM_024734.1|[13376053]

536: NM_023003
Homo sapiens transmembrane 6 superfamily member 1 (TM6SF1), mRNA
gi|13194198|ref|NM_023003.1|[13194198]

537: NM_021034
Homo sapiens interferon induced transmembrane protein 3 (1-8U) (IFITM3), mRNA
gi|11995467|ref|NM_021034.1|[11995467]

538: NM_006435
Homo sapiens interferon induced transmembrane protein 2 (1-8D) (IFITM2), mRNA
gi|10835237|ref|NM_006435.1|[10835237]

539: NM_016326
Homo sapiens chemokine-like factor 1 (CKLF1), mRNA
gi|10092611|ref|NM_016326.2|[10092611]

540: NM_016951
Homo sapiens chemokine-like factor 1 (CKLF1), mRNA
gi|10092593|ref|NM_016951.2|[10092593]

541: NM_000888

Homo sapiens integrin, beta 6 (ITGB6), mRNA
gi|9966771|ref|NM_000888.3|[9966771]

542: NM_020241
Homo sapiens sema domain, transmembrane domain (TM), and cytoplasmic domain, (semaphorin) 6B (SEMA6B), mRNA
gi|9910379|ref|NM_020241.1|[9910379]

543: NM_018407
Homo sapiens putative integral membrane transporter (LC27), mRNA
gi|8923827|ref|NM_018407.1|[8923827]

544: NM_017514
Homo sapiens SEX gene (HSSEXGENE), mRNA
gi|8923792|ref|NM_017514.1|[8923792]

545: NM_017893
Homo sapiens sema domain, immunoglobulin domain (Ig), transmembrane domain (TM) and short cytoplasmic domain, (semaphorin) 4G (SEMA4G), mRNA
gi|8923550|ref|NM_017893.1|[8923550]

546: NM_017599
Homo sapiens transmembrane protein vezatin (VEZATIN), mRNA
gi|8922162|ref|NM_017599.1|[8922162]

547: NM_014254
Homo sapiens transmembrane protein 5 (TMEM5), mRNA
gi|7657177|ref|NM_014254.1|[7657177]

548: NM_012339
Homo sapiens transmembrane 4 superfamily member (tetraspan NET-7) (NET-7), mRNA
gi|6912529|ref|NM_012339.1|[6912529]

549: NM_012338
Homo sapiens transmembrane 4 superfamily member (tetraspan NET-2) (NET-2), mRNA
gi|6912527|ref|NM_012338.1|[6912527]

550: NM_002673
Homo sapiens plexin B1 (PLXNB1), mRNA
gi|6631105|ref|NM_002673.1|[6631105]

551: NM_006825
Homo sapiens cytoskeleton-associated protein 4 (CKAP4), mRNA
gi|5803112|ref|NM_006825.1|[5803112]

552: NM_004785
Homo sapiens solute carrier family 9 (sodium/hydrogen exchanger), isoform 3 regulatory factor 2 (SLC9A3R2), mRNA
gi|4759141|ref|NM_004785.1|[4759141]

553: NM_004263
Homo sapiens sema domain, immunoglobulin domain (Ig), transmembrane domain (TM) and short cytoplasmic domain, (semaphorin) 4F (SEMA4F), mRNA
gi|4759093|ref|NM_004263.1|[4759093]

554: NM_004800
Homo sapiens transmembrane 9 superfamily member 2 (TM9SF2), mRNA
gi|4758873|ref|NM_004800.1|[4758873]

555: NM_000950
Homo sapiens proline-rich Gla (G-carboxyglutamic acid) polypeptide 1 (PRRG1), mRNA
gi|4506134|ref|NM_000950.1|[4506134]

556: NM_003625
Homo sapiens protein tyrosine phosphatase, receptor type, f polypeptide (PTPRF), interacting protein (liprin), alpha 2 (PPFIA2), mRNA
gi|4505984|ref|NM_003625.1|[4505984]

558: NM_032518
Homo sapiens collagen-like Alzheimer amyloid plaque component precursor (LOC84570), mRNA
gi|14210525|ref|NM_032518.1|[14210525]

559: NM_023945

Homo sapiens membrane-spanning 4-domains, subfamily A, member 5 (MS4A5), mRNA
gi|12965204|ref|NM_023945.1|[12965204]

560: NM_016158
Homo sapiens erythrocyte transmembrane protein (LOC51145), mRNA
gi|7705856|ref|NM_016158.1|[7705856]

561: AK056649
Homo sapiens cDNA FLJ32087 fis, clone OCBBF2000467, highly similar to
Fibronectin leucine rich transmembrane protein 2
gi|16552109|dbj|AK056649.1|AK056649[16552109]

562: AK056595
Homo sapiens cDNA FLJ32033 fis, clone NTONG2000265, weakly similar to Probable
transmembrane protein of fission yeast
gi|16552042|dbj|AK056595.1|AK056595[16552042]

563: AK055648
Homo sapiens cDNA FLJ31086 fis, clone IMR321000044, highly similar to Human
transmembrane receptor precursor (PTK7) mRNA
gi|16550428|dbj|AK055648.1|AK055648[16550428]

564: AK055208
Homo sapiens cDNA FLJ30646 fis, clone CTONG2004716, weakly similar to Rattus
norvegicus mRNA for seven transmembrane receptor
gi|16549884|dbj|AK055208.1|AK055208[16549884]

565: AK054712
Homo sapiens cDNA FLJ30150 fis, clone BRACE2000300, highly similar to
TRANSMEMBRANE PROTEIN PFT27
gi|16549313|dbj|AK054712.1|AK054712[16549313]

566: AK054646
Homo sapiens cDNA FLJ30084 fis, clone BGGI12001682, highly similar to Homo
sapiens transmembrane protein TENB2 (TENB2) mRNA
gi|16549231|dbj|AK054646.1|AK054646[16549231]

567: NM_019035

Homo sapiens protocadherin 18 (PCDH18), mRNA
gi|14589928|ref|NM_019035.1|[14589928]

568: NM_030943
Homo sapiens amnionless protein (AMN), mRNA
gi|13569914|ref|NM_030943.1|[13569914]

570: BC018361
Homo sapiens, sema domain, immunoglobulin domain (Ig), transmembrane domain (TM) and short cytoplasmic domain, (semaphorin) 4F, clone MGC:21849 IMAGE:4215248, mRNA, complete cds
gi|17390842|gb|BC018361.1|BC018361[17390842]

571: AF214006
Homo sapiens TDC1 (TDC1) mRNA, complete cds
gi|17221828|gb|AF214006.1|AF214006[17221828]

572: NM_021201
Homo sapiens membrane-spanning 4-domains, subfamily A, member 7 (MS4A7), mRNA
gi|11139298|ref|NM_021201.1|[11139298]

573: AF289028
Homo sapiens transmembrane protein B7-H2 ICOS ligand mRNA, complete cds
gi|9858866|gb|AF289028.1|AF289028[9858866]

574: NM_016941
Homo sapiens delta-like 3 (Drosophila) (DLL3), mRNA
gi|8393263|ref|NM_016941.1|[8393263]

575: NM_014450
Homo sapiens SHP2 interacting transmembrane adaptor (SIT), mRNA
gi|7657576|ref|NM_014450.1|[7657576]

576: NM_021259
Homo sapiens transmembrane protein 8 (five membrane-spanning domains) (TMEM8), mRNA
gi|10864068|ref|NM_021259.1|[10864068]

577: NM_002959
Homo sapiens sortilin 1 (SORT1), mRNA
gi|17149833|ref|NM_002959.3|[17149833]

578: NM_000675
Homo sapiens adenosine A2a receptor (ADORA2A), mRNA
gi|17136146|ref|NM_000675.3|[17136146]

579: BM128846
if17e06.x1 Melton Normalized Human Islet 4 N4-HIS 1 Homo sapiens cDNA 3' similar
to SW:PF27_MOUSE P52875 TRANSMEMBRANE PROTEIN PFT27. [1] ;, mRNA sequence
gi|17123398|gb|BM128846.1|BM128846[17123398]

580: BM127423
ie95b07.y1 Melton Normalized Human Islet 4 N4-HIS 1 Homo sapiens cDNA 5' similar
to TR:O60639 O60639 PUTATIVE TRANSMEMBRANE GTPASE ;, mRNA sequence
gi|17121975|gb|BM127423.1|BM127423[17121975]

581: AY016020
Gallus gallus alpha globin gene cluster, complete sequence
gi|17104478|gb|AY016020.1|[17104478]

582: M86631
Homo sapiens (clone ST-18-5(9/16)) cystic fibrosis transmembrane conductance
regulator (CFTR) gene, 3' end intron 17B; complete exon 18; complete intron 18
gi|180296|gb|M86631.1|HUMCFTR[180296]

584: BC017476
Homo sapiens, sema domain, immunoglobulin domain (Ig), transmembrane domain TM)
and short cytoplasmic domain, (semaphorin) 4C, clone MGC:15189 IMAGE:3528227,
mRNA, complete cds
gi|17028345|gb|BC017476.1|BC017476[17028345]

585: NM_000420
Homo sapiens Kell blood group (KEL), mRNA
gi|17025233|ref|NM_000420.2|[17025233]

586: BM090614 ig16b09.y1 Human Fetal Pancreas 1A Homo sapiens cDNA 5' similar to TR:Q9Y287
Q9Y287 TRANSMEMBRANE PROTEIN BRI. ;, mRNA sequence
gi|17019580|gb|BM090614.1|BM090614[17019580]

587: AF217288
Homo sapiens protocadherin-S mRNA, complete cds, alternatively spliced
gi|15054520|gb|AF217288.1|AF217288[15054520]

588: AF206516
Homo sapiens protocadherin-S mRNA, complete cds
gi|15054518|gb|AF206516.1|AF206516[15054518]

589: NM_021153
Homo sapiens cadherin 19, type 2 (CDH19), mRNA
gi|16306535|ref|NM_021153.2|[16306535]

590: AY048509
Homo sapiens pannexin 1 (PANX1) gene, partial cds
gi|15808666|gb|AY048509.1|[15808666]

591: NG_000012
Homo sapiens genomic protocadherin gamma cluster (PCDHG@) on chromosome 5
gi|14861871|ref|NG_000012.1|[14861871]

592: AE006466
Homo sapiens 16p13.3 sequence section 5 of 8
gi|14336735|gb|AE006466.1|AE006466[14336735]

593: AF376725
Homo sapiens lung seven transmembrane receptor 1 (LUSTR1) mRNA, complete cds
gi|14248996|gb|AF376725.1|AF376725[14248996]

594: NM_004776
Homo sapiens UDP-Gal:betaGlcNAc beta 1,4- galactosyltransferase, polypeptide 5
(B4GALT5), mRNA
gi|13929470|ref|NM_004776.2|[13929470]

595: NM_030587
Homo sapiens UDP-Gal:betaGlcNAc beta 1,4- galactosyltransferase, polypeptide 2 (B4GALT2), transcript variant 1, mRNA
gi|13929464|ref|NM_030587.1|[13929464]

596: NM_003780
Homo sapiens UDP-Gal:betaGlcNAc beta 1,4- galactosyltransferase, polypeptide 2 (B4GALT2), transcript variant 2, mRNA
gi|13929463|ref|NM_003780.2|[13929463]

597: NM_002590
Homo sapiens protocadherin 8 (PCDH8), transcript variant 1, mRNA
gi|6631101|ref|NM_002590.2|[6631101]

598: L42572
Homo sapiens transmembrane protein (p87/89) mRNA, complete cds
gi|1160962|gb|L42572.1|HUMP8789R[1160962]

599: AF106202
Homo sapiens endothelial cell protein C receptor precursor (EPCR) gene, promoter region and complete cds
gi|16950557|gb|AF106202.2|AF106202[16950557]

600: NM_033207
Homo sapiens transmembrane protein HTMP10 (HTMP10), mRNA
gi|16945967|ref|NM_033207.2|[16945967]

601: AF153440
Mus musculus Nma (Nma) mRNA, complete cds
gi|14328906|gb|AF153440.1|AF153440[14328906]

604: NM_005086
Homo sapiens sarcospan (Kras oncogene-associated gene) (SSPN), mRNA
gi|16933560|ref|NM_005086.3|[16933560]

605: NM_018153
Homo sapiens tumor endothelial marker 8 (TEM8), transcript variant 3, mRNA
gi|16933552|ref|NM_018153.2|[16933552]

606: NM_053034
Homo sapiens tumor endothelial marker 8 (TEM8), transcript variant 2, mRNA
gi|16933550|ref|NM_053034.1|[16933550]

607: NM_032208
Homo sapiens tumor endothelial marker 8 (TEM8), transcript variant 1, mRNA
gi|14149903|ref|NM_032208.1|[14149903]

608: AV225853
AV225853 RIKEN full-length enriched, 18 days pregnant, placenta and extra embryonic tissue Mus musculus cDNA clone 3830432D01 3' similar to X69910 H.sapiens p63 mRNA for transmembrane protein, mRNA sequence
gi|6177168|dbj|AV225853.1|AV225853[6177168]

609: AV222771
AV222771 RIKEN full-length enriched, 18 days pregnant, placenta and extra embryonic tissue Mus musculus cDNA clone 3830404C12 3' similar to X69910 H.sapiens p63 mRNA for transmembrane protein, mRNA sequence
gi|6171948|dbj|AV222771.1|AV222771[6171948]

611: BC017058
Homo sapiens, Similar to seven transmembrane domain orphan receptor, clone MGC:9442 IMAGE:3904719, mRNA, complete cds
gi|16877618|gb|BC017058.1|BC017058[16877618]

612: BM055437
ie94h04.y1 Melton Normalized Human Islet 4 N4-HIS 1 Homo sapiens cDNA 5' similar
to SW:CFTR_HUMAN P13569 CYSTIC FIBROSIS TRANSMEMBRANE CONDUCTANCE REGULATOR ;,
mRNA sequence
gi|16813328|gb|BM055437.1|BM055437[16813328]

614: AF328788
Homo sapiens amnionless mRNA, complete cds
gi|13507258|gb|AF328788.1|AF328788[13507258]

615: NM_052836

Homo sapiens cadherin related 23 (CDH23), transcript variant 2, mRNA
gi|16507963|ref|NM_052836.1|[16507963]

616: NM_022124
Homo sapiens cadherin related 23 (CDH23), transcript variant 1, mRNA
gi|16507961|ref|NM_022124.2|[16507961]

617: NM_004063
Homo sapiens cadherin 17, LI cadherin (liver-intestine) (CDH17), mRNA
gi|16507959|ref|NM_004063.2|[16507959]

618: NM_004062
Homo sapiens cadherin 16, KSP-cadherin (CDH16), mRNA
gi|16507958|ref|NM_004062.2|[16507958]

619: NM_004933
Homo sapiens cadherin 15, M-cadherin (myotubule) (CDH15), mRNA
gi|16507957|ref|NM_004933.2|[16507957]

620: NM_001257
Homo sapiens cadherin 13, H-cadherin (heart) (CDH13), mRNA
gi|16507956|ref|NM_001257.2|[16507956]

621: BC009704
Homo sapiens, transmembrane 4 superfamily member 9, clone MGC:9300
IMAGE:3895933, mRNA, complete cds
gi|16307230|gb|BC009704.1|BC009704[16307230]

622: BC001496
Homo sapiens, transmembrane trafficking protein, clone MGC:1979 IMAGE:2959718,
mRNA, complete cds
gi|16306639|gb|BC001496.1|BC001496[16306639]

623: BC013577
Homo sapiens, claudin 11 (oligodendrocyte transmembrane protein), clone MGC:9232
IMAGE:3895040, mRNA, complete cds
gi|15488893|gb|BC013577.1|BC013577[15488893]

624: NM_053002
Homo sapiens no opposite paired repeat protein (NOPAR), mRNA
gi|16506292|ref|NM_053002.1|[16506292]

625: NM_052995
Homo sapiens Usher syndrome 3A (USH3A), mRNA
gi|16506280|ref|NM_052995.1|[16506280]

639: NM_014879
Homo sapiens G protein-coupled receptor 105 (GPR105), mRNA
gi|7661847|ref|NM_014879.1|[7661847]

640: NM_052891
Homo sapiens peptidoglycan recognition protein-I-alpha precursor (PGLYRPIalpha), mRNA
gi|16418404|ref|NM_052891.1|[16418404]

642: BI964203
ie66b09.y1 Melton Normalized Human Islet 4 N4-HIS 1 Homo sapiens cDNA 5' similar to TR:Q99989 Q99989 TRANSMEMBRANE CHLORIDE CONDUCTOR PROTEIN ;, mRNA sequence
gi|16338608|gb|BI964203.1|BI964203[16338608]

643: BI963913
ie66e08.x1 Melton Normalized Human Islet 4 N4-HIS 1 Homo sapiens cDNA 3' similar to SW:PF27_MOUSE P52875 TRANSMEMBRANE PROTEIN PFT27. [1] ;, mRNA sequence
gi|16338318|gb|BI963913.1|BI963913[16338318]

644: AF293372
Pan troglodytes sialic acid-binding lectin Siglec-L1 mRNA, complete cds
gi|15824309|gb|AF293372.1|AF293372[15824309]

645: BC009696
Homo sapiens, interferon induced transmembrane protein 2 (1-8D), clone MGC:9196 IMAGE:3876542, mRNA, complete cds
gi|16307214|gb|BC009696.1|BC009696[16307214]

646: NM_031891
Homo sapiens cadherin 20, type 2 (CDH20), mRNA
gi|16306536|ref|NM_031891.2|[16306536]

647: NM_004361
Homo sapiens cadherin 7, type 2 (CDH7), transcript variant b, mRNA
gi|16306488|ref|NM_004361.2|[16306488]

648: NM_033646
Homo sapiens cadherin 7, type 2 (CDH7), transcript variant a, mRNA
gi|16306486|ref|NM_033646.1|[16306486]

649: AF319952
Homo sapiens tweety-like protein 2 mRNA, complete cds
gi|16303747|gb|AF319952.1|AF319952[16303747]

651: NM_005756
Homo sapiens G protein-coupled receptor 64 (GPR64), mRNA
gi|5031732|ref|NM_005756.1|[5031732]

652: AF416903
Homo sapiens SH2 domain-containing phosphatase anchor protein 2c mRNA, complete cds, alternatively spliced
gi|16033593|gb|AF416903.1|AF416903[16033593]

653: AF416902
Homo sapiens SH2 domain-containing phosphatase anchor protein 2b mRNA, complete cds, alternatively spliced
gi|16033590|gb|AF416902.1|AF416902[16033590]

654: AF416901
Homo sapiens SH2 domain-containing phosphatase anchor protein 2a mRNA, complete cds, alternatively spliced
gi|16033587|gb|AF416901.1|AF416901[16033587]

655: AF264740
Homo sapiens MHC class I chain-related protein A (MICA) gene, MICA*015 allele, exon 6 and partial cds gi|16032983|gb|AF264740.1|AF264738S3[16032983]

656: AF264739
Homo sapiens MHC class I chain-related protein A (MICA) gene, MICA*015 allele, exons 4 and 5
gi|16032982|gb|AF264739.1|AF264738S2[16032982]

657: AF264738
Homo sapiens MHC class I chain-related protein A (MICA) gene, MICA*015 allele, exons 2 and 3
gi|16032981|gb|AF264738.1|AF264738S1[16032981]

658: AH011143
Homo sapiens MHC class I chain-related protein A (MICA) gene, MICA*015 allele, partial cds
gi|16032980|gb|AH011143.1|SEG_AF264738S[16032980]

659: NM_033467
Homo sapiens membrane metallo-endopeptidase-like 2 (MMEL2), mRNA
gi|15991812|ref|NM_033467.1|[15991812]

660: AF378755
Homo sapiens tumor endothelial marker 5 precursor (TEM5) mRNA, complete cds
gi|15987490|gb|AF378755.1|AF378755[15987490]

661: NM_016227
Homo sapiens chromosome 1 open reading frame 9 (C1orf9), mRNA
gi|7705321|ref|NM_016227.1|[7705321]

662: NM_014283
Homo sapiens chromosome 1 open reading frame 9 (C1orf9), mRNA
gi|7656939|ref|NM_014283.1|[7656939]

663: NM_018475
Homo sapiens TPA regulated locus (TPARL), mRNA
gi|8923860|ref|NM_018475.1|[8923860]

664: D83783
Human mRNA for KIAA0192 gene, partial cds
gi|1663693|dbj|D83783.1|D83783[1663693]

665: D79997
Human mRNA for KIAA0175 gene, complete cds
gi|1136409|dbj|D79997.1|D79997[1136409]

666: D13626
Human mRNA for KIAA0001 gene, complete cds
gi|285994|dbj|D13626.1|HUMRSC338[285994]

679: BI793175
ie48h08.y1 Melton Normalized Human Islet 4 N4-HIS 1 Homo sapiens cDNA 5' similar to SW:NMB_HUMAN Q14956 PUTATIVE TRANSMEMBRANE PROTEIN NMB PRECURSOR. ;, mRNA
sequence
gi|15820900|gb|BI793175.1|BI793175[15820900]

680: U40271
Homo sapiens transmembrane receptor precursor (PTK7) mRNA, complete cds
gi|15808058|gb|U40271.2|HSU40271[15808058]

681: BC014554
Homo sapiens, calponin like transmembrane domain protein, clone IMAGE:3837453, mRNA
gi|15778950|gb|BC014554.1|BC014554[15778950]

682: NM_018916
Homo sapiens protocadherin gamma subfamily A, 3 (PCDHGA3), transcript variant 1, mRNA
gi|14589879|ref|NM_018916.3|[14589879]

683: NM_032407
Homo sapiens protocadherin gamma subfamily C, 5 (PCDHGC5), transcript variant 2, mRNA
gi|14277684|ref|NM_032407.1|[14277684]

684: NM_018929
Homo sapiens protocadherin gamma subfamily C, 5 (PCDHGC5), transcript variant 1, mRNA
gi|14277683|ref|NM_018929.2|[14277683]

685: NM_032406
Homo sapiens protocadherin gamma subfamily C, 4 (PCDHGC4), transcript variant 2, mRNA
gi|14277681|ref|NM_032406.1|[14277681]

686: NM_018928
Homo sapiens protocadherin gamma subfamily C, 4 (PCDHGC4), transcript variant 1, mRNA
gi|14277680|ref|NM_018928.2|[14277680]

687: NM_032101
Homo sapiens protocadherin gamma subfamily B, 7 (PCDHGB7), transcript variant 2, mRNA
gi|14270507|ref|NM_032101.1|[14270507]

688: NM_018927
Homo sapiens protocadherin gamma subfamily B, 7 (PCDHGB7), transcript variant 1, mRNA
gi|14270506|ref|NM_018927.2|[14270506]

689: NM_032099
Homo sapiens protocadherin gamma subfamily B, 5 (PCDHGB5), transcript variant 2, mRNA
gi|14270504|ref|NM_032099.1|[14270504]

690: NM_018925
Homo sapiens protocadherin gamma subfamily B, 5 (PCDHGB5), transcript variant 1, mRNA
gi|14270503|ref|NM_018925.2|[14270503]

691: NM_032100
Homo sapiens protocadherin gamma subfamily B, 6 (PCDHGB6), transcript variant 2, mRNA
gi|14270501|ref|NM_032100.1|[14270501]

692: NM_018926
Homo sapiens protocadherin gamma subfamily B, 6 (PCDHGB6), transcript variant 1, mRNA
gi|14270500|ref|NM_018926.2|[14270500]

693: NM_032097
Homo sapiens protocadherin gamma subfamily B, 3 (PCDHGB3), transcript variant 2, mRNA
gi|14270495|ref|NM_032097.1|[14270495]

694: NM_018924
Homo sapiens protocadherin gamma subfamily B, 3 (PCDHGB3), transcript variant 1, mRNA
gi|14270494|ref|NM_018924.2|[14270494]

695: NM_032096
Homo sapiens protocadherin gamma subfamily B, 2 (PCDHGB2), transcript variant 2, mRNA
gi|14270492|ref|NM_032096.1|[14270492]

696: NM_018923
Homo sapiens protocadherin gamma subfamily B, 2 (PCDHGB2), transcript variant 1, mRNA
gi|14270491|ref|NM_018923.2|[14270491]

697: NM_032095
Homo sapiens protocadherin gamma subfamily B, 1 (PCDHGB1), transcript variant 2, mRNA
gi|14270489|ref|NM_032095.1|[14270489]

698: NM_018922
Homo sapiens protocadherin gamma subfamily B, 1 (PCDHGB1), transcript variant 1, mRNA
gi|14270488|ref|NM_018922.2|[14270488]

699: NM_032089
Homo sapiens protocadherin gamma subfamily A, 9 (PCDHGA9), transcript variant 2, mRNA
gi|14270486|ref|NM_032089.1|[14270486]

700: NM_018921
Homo sapiens protocadherin gamma subfamily A, 9 (PCDHGA9), transcript variant 1, mRNA
gi|14270485|ref|NM_018921.2|[14270485]

701: NM_032088
Homo sapiens protocadherin gamma subfamily A, 8 (PCDHGA8), transcript variant 1, mRNA
gi|14270483|ref|NM_032088.1|[14270483]

702: NM_014004
Homo sapiens protocadherin gamma subfamily A, 8 (PCDHGA8), transcript variant 2, mRNA
gi|14270482|ref|NM_014004.2|[14270482]

703: NM_032087
Homo sapiens protocadherin gamma subfamily A, 7 (PCDHGA7), transcript variant 2, mRNA
gi|14196476|ref|NM_032087.1|[14196476]

704: NM_018920
Homo sapiens protocadherin gamma subfamily A, 7 (PCDHGA7), transcript variant 1, mRNA
gi|14196475|ref|NM_018920.2|[14196475]

705: NM_032086
Homo sapiens protocadherin gamma subfamily A, 6 (PCDHGA6), transcript variant 2, mRNA
gi|14196473|ref|NM_032086.1|[14196473]

706: NM_018919
Homo sapiens protocadherin gamma subfamily A, 6 (PCDHGA6), transcript variant 1, mRNA
gi|14196472|ref|NM_018919.2|[14196472]

707: NM_032054
Homo sapiens protocadherin gamma subfamily A, 5 (PCDHGA5), transcript variant 2, mRNA
gi|14196470|ref|NM_032054.1|[14196470]

708: NM_018918
Homo sapiens protocadherin gamma subfamily A, 5 (PCDHGA5), transcript variant 1, mRNA
gi|14196469|ref|NM_018918.2|[14196469]

709: NM_032053
Homo sapiens protocadherin gamma subfamily A, 4 (PCDHGA4), transcript variant 2, mRNA
gi|14196467|ref|NM_032053.1|[14196467]

710: NM_018917
Homo sapiens protocadherin gamma subfamily A, 4 (PCDHGA4), transcript variant 1, mRNA
gi|14196466|ref|NM_018917.2|[14196466]

711: NM_032011
Homo sapiens protocadherin gamma subfamily A, 3 (PCDHGA3), transcript variant 2, mRNA
gi|14196464|ref|NM_032011.1|[14196464]

712: NM_032009
Homo sapiens protocadherin gamma subfamily A, 2 (PCDHGA2), transcript variant 2, mRNA
gi|14196461|ref|NM_032009.1|[14196461]

713: NM_018915
Homo sapiens protocadherin gamma subfamily A, 2 (PCDHGA2), transcript variant 1, mRNA
gi|14196460|ref|NM_018915.2|[14196460]

714: NM_031993
Homo sapiens protocadherin gamma subfamily A, 1 (PCDHGA1), transcript variant 2, mRNA
gi|14196458|ref|NM_031993.1|[14196458]

715: NM_032092
Homo sapiens protocadherin gamma subfamily A, 11 (PCDHGA11), transcript variant 3, mRNA
gi|14196454|ref|NM_032092.1|[14196454]

716: NM_018912
Homo sapiens protocadherin gamma subfamily A, 1 (PCDHGA1), transcript variant 1, mRNA
gi|14196453|ref|NM_018912.2|[14196453]

717: NM_032091
Homo sapiens protocadherin gamma subfamily A, 11 (PCDHGA11), transcript variant 2, mRNA
gi|14196450|ref|NM_032091.1|[14196450]

718: NM_018914
Homo sapiens protocadherin gamma subfamily A, 11 (PCDHGA11), transcript variant 1, mRNA
gi|14196449|ref|NM_018914.2|[14196449]

719: NM_032090
Homo sapiens protocadherin gamma subfamily A, 10 (PCDHGA10), transcript variant 2, mRNA
gi|14196447|ref|NM_032090.1|[14196447]

720: NM_018913
Homo sapiens protocadherin gamma subfamily A, 10 (PCDHGA10), transcript variant 1, mRNA
gi|14196446|ref|NM_018913.2|[14196446]

721: NM_031411
Homo sapiens protocadherin alpha 1 (PCDHA1), transcript variant 3, mRNA
gi|14165401|ref|NM_031411.1|[14165401]

722: NM_031849
Homo sapiens protocadherin alpha 6 (PCDHA6), transcript variant 3, mRNA
gi|14165393|ref|NM_031849.1|[14165393]

723: NM_031860
Homo sapiens protocadherin alpha 10 (PCDHA10), transcript variant 3, mRNA
gi|14165382|ref|NM_031860.1|[14165382]

724: NM_031442
Homo sapiens brain cell membrane protein 1 (BCMP1), mRNA
gi|13899272|ref|NM_031442.1|[13899272]

725: NM_007000
Homo sapiens uroplakin 1A (UPK1A), mRNA
gi|5902147|ref|NM_007000.1|[5902147]

726: NM_003332
Homo sapiens TYRO protein tyrosine kinase binding protein (TYROBP), mRNA
gi|4507754|ref|NM_003332.1|[4507754]

727: AF264747
Homo sapiens MHC class I chain-related protein A (MICA) gene, MICA*00901 allele, exon 6 and partial cds
gi|14279228|gb|AF264747.1|AF264744S3[14279228]

728: AF264746
Homo sapiens MHC class I chain-related protein A (MICA) gene, MICA*00901 allele, exons 4 and 5
gi|14279227|gb|AF264746.1|AF264744S2[14279227]

729: AF264744
Homo sapiens MHC class I chain-related protein A (MICA) gene, MICA*00901 allele, exons 2 and 3
gi|14279226|gb|AF264744.1|AF264744S1[14279226]

730: AH010821
Homo sapiens MHC class I chain-related protein A (MICA) gene, MICA*00901 allele, partial cds
gi|14279225|gb|AH010821.1|SEG_AF264744S[14279225]

731: AF264743
Homo sapiens MHC class I chain-related protein A (MICA) gene, MICA*048 allele, exon 6 and partial cds
gi|14279223|gb|AF264743.1|AF264741S3[14279223]

732: AF264742
Homo sapiens MHC class I chain-related protein A (MICA) gene, MICA*048 allele, exons 4 and 5
gi|14279222|gb|AF264742.1|AF264741S2[14279222]

733: AF264741
Homo sapiens MHC class I chain-related protein A (MICA) gene, MICA*048 allele, exons 2 and 3
gi|14279221|gb|AF264741.1|AF264741S1[14279221]

734: AH010820
Homo sapiens MHC class I chain-related protein A (MICA) gene, MICA*048 allele, partial cds
gi|14279220|gb|AH010820.1|SEG_AF264741S[14279220]

735: AF264737
Homo sapiens MHC class I chain-related protein A (MICA) gene, MICA*017 allele, exon 6 and partial cds
gi|14279218|gb|AF264737.1|AF264735S3[14279218]

736: AF264736
Homo sapiens MHC class I chain-related protein A (MICA) gene, MICA*017 allele, exons 4 and 5
gi|14279217|gb|AF264736.1|AF264735S2[14279217]

737: AF264735
Homo sapiens MHC class I chain-related protein A (MICA) gene, MICA*017 allele, exons 2 and 3
gi|14279216|gb|AF264735.1|AF264735S1[14279216]

738: AH010819
Homo sapiens MHC class I chain-related protein A (MICA) gene, MICA*017 allele, partial cds
gi|14279215|gb|AH010819.1|SEG_AF264735S[14279215]

739: AF336080
Homo sapiens MHC class I chain-related protein A (MICA) gene, MICA*019 allele, exon 6 and partial cds
gi|13469855|gb|AF336080.1|AF336079S2[13469855]

740: AF336079
Homo sapiens MHC class I chain-related protein A (MICA) gene, MICA*019 allele, exons 2 through 5
gi|13469854|gb|AF336079.1|AF336079S1[13469854]

741: AH010587
Homo sapiens MHC class I chain-related protein A (MICA) gene, MICA*019 allele, partial cds
gi|13469853|gb|AH010587.1|SEG_AF336079S[13469853]

742: AF336086
Homo sapiens MHC class I chain-related protein A (MICA) gene, MICA*001 allele, exon 6 and partial cds
gi|13445651|gb|AF336086.1|AF336085S2[13445651]

743: AF336085
Homo sapiens MHC class I chain-related protein A (MICA) gene, MICA*001 allele, exons 2 through 5
gi|13445650|gb|AF336085.1|AF336085S1[13445650]

744: AH010572
Homo sapiens MHC class I chain-related protein A (MICA) gene, MICA*001 allele, partial cds
gi|13445649|gb|AH010572.1|SEG_AF336085S[13445649]

745: AF336084
Homo sapiens MHC class I chain-related protein A (MICA) gene, MICA*002 allele, exon 6 and partial cds
gi|13445647|gb|AF336084.1|AF336083S2[13445647]

746: AF336083
Homo sapiens MHC class I chain-related protein A (MICA) gene, MICA*002 allele, exons 2 through 5
gi|13445646|gb|AF336083.1|AF336083S1[13445646]

747: AH010571
Homo sapiens MHC class I chain-related protein A (MICA) gene, MICA*002 allele, partial cds
gi|13445645|gb|AH010571.1|SEG_AF336083S[13445645]

748: AF336070
Homo sapiens MHC class I chain-related protein A (MICA) gene, MICA*009 allele, exon 6 and partial cds
gi|13430213|gb|AF336070.1|AF336069S2[13430213]

749: AF336069
Homo sapiens MHC class I chain-related protein A (MICA) gene, MICA*009 allele, exons 2 through 5
gi|13430212|gb|AF336069.1|AF336069S1[13430212]

750: AH010569
Homo sapiens MHC class I chain-related protein A (MICA) gene, MICA*009 allele, partial cds
gi|13430211|gb|AH010569.1|SEG_AF336069S[13430211]

751: AF336068
Homo sapiens MHC class I chain-related protein A (MICA) gene, MICA*008 allele, exon 6
gi|13430209|gb|AF336068.1|AF336067S2[13430209]

752: AF336067
Homo sapiens MHC class I chain-related protein A (MICA) gene, MICA*008 allele, exons 2 through 5 and partial cds
gi|13430208|gb|AF336067.1|AF336067S1[13430208]

753: AH010568
Homo sapiens MHC class I chain-related protein A (MICA) gene, MICA*008 allele, partial cds
gi|13430207|gb|AH010568.1|SEG_AF336067S[13430207]

754: AF336082
Homo sapiens MHC class I chain-related protein A (MICA) gene, MICA*012 allele, exon 6 and partial cds
gi|13378046|gb|AF336082.1|AF336081S2[13378046]

755: AF336081
Homo sapiens MHC class I chain-related protein A (MICA) gene, MICA*012 allele, exons 2 through 5
gi|13378045|gb|AF336081.1|AF336081S1[13378045]

756: AH010562
Homo sapiens MHC class I chain-related protein A (MICA) gene, MICA*012 allele, partial cds
gi|13378044|gb|AH010562.1|SEG_AF336081S[13378044]

757: AF336078
Homo sapiens MHC class I chain-related protein A (MICA) gene, MICA*018 allele, exon 6 and partial cds
gi|13378042|gb|AF336078.1|AF336077S2[13378042]

758: AF336077
Homo sapiens MHC class I chain-related protein A (MICA) gene, MICA*018 allele, exons 2 through 5
gi|13378041|gb|AF336077.1|AF336077S1[13378041]

759: AH010561
Homo sapiens MHC class I chain-related protein A (MICA) gene, MICA*018 allele, partial cds
gi|13378040|gb|AH010561.1|SEG_AF336077S[13378040]

760: AF336076
Homo sapiens MHC class I chain-related protein A (MICA) gene, MICA*016 allele, exon 6 and partial cds
gi|13378038|gb|AF336076.1|AF336075S2[13378038]

761: AF336075
Homo sapiens MHC class I chain-related protein A (MICA) gene, MICA*016 allele, exons 2 through 5
gi|13378037|gb|AF336075.1|AF336075S1[13378037]

762: AH010560
Homo sapiens MHC class I chain-related protein A (MICA) gene, MICA*016 allele, partial cds
gi|13378036|gb|AH010560.1|SEG_AF336075S[13378036]

763: AF336074
Homo sapiens MHC class I chain-related protein A (MICA) gene, MICA*011 allele, exon 6 and partial cds
gi|13346205|gb|AF336074.1|AF336073S2[13346205]

764: AF336073
Homo sapiens MHC class I chain-related protein A (MICA) gene, MICA*011 allele, exons 2 through 5
gi|13346204|gb|AF336073.1|AF336073S1[13346204]

765: AH010546
Homo sapiens MHC class I chain-related protein A (MICA) gene, MICA*011 allele, partial cds
gi|13346203|gb|AH010546.1|SEG_AF336073S[13346203]

766: AF336064
Homo sapiens MHC class I chain-related protein A (MICA) gene, MICA*002 allele, exon 6 and partial cds
gi|13346201|gb|AF336064.1|AF336063S2[13346201]

767: AF336063
Homo sapiens MHC class I chain-related protein A (MICA) gene, MICA*002 allele, exons 2 through 5
gi|13346200|gb|AF336063.1|AF336063S1[13346200]

768: AH010545
Homo sapiens MHC class I chain-related protein A (MICA) gene, MICA*002 allele, partial cds
gi|13346199|gb|AH010545.1|SEG_AF336063S[13346199]

769: AF336072
Homo sapiens MHC class I chain-related protein A (MICA) gene, MICA*010 allele, exon 6 and partial cds
gi|13310419|gb|AF336072.1|AF336071S2[13310419]

770: AF336071
Homo sapiens MHC class I chain-related protein A (MICA) gene, MICA*010 allele,
exons 2 through 5
gi|13310418|gb|AF336071.1|AF336071S1[13310418]

771: AH010532
Homo sapiens MHC class I chain-related protein A (MICA) gene, MICA*010 allele,
partial cds
gi|13310417|gb|AH010532.1|SEG_AF336071S[13310417]

772: AF336066
Homo sapiens MHC class I chain-related protein A (MICA) gene, MICA*006 allele,
exon 6 and partial cds
gi|13274608|gb|AF336066.1|AF336065S2[13274608]

773: AF336065
Homo sapiens MHC class I chain-related protein A (MICA) gene, MICA*006 allele,
exons 2 through 5
gi|13274607|gb|AF336065.1|AF336065S1[13274607]

774: AH010526
Homo sapiens MHC class I chain-related protein A (MICA) gene, MICA*006 allele,
partial cds
gi|13274606|gb|AH010526.1|SEG_AF336065S[13274606]

775: NM_022059
Homo sapiens chemokine (C-X-C motif) ligand 16 (CXCL16), mRNA
gi|11545764|ref|NM_022059.1|[11545764]

776: NM_000024
Homo sapiens adrenergic, beta-2-, receptor, surface (ADRB2), mRNA
gi|15718673|ref|NM_000024.3|[15718673]

777: AF257472
Homo sapiens transmembrane protein MT75 mRNA, complete cds gi|15718477|gb|AF257472.1|AF257472[15718477]

778: AJ301609
Homo sapiens partial mRNA for GluR6 kainate receptor (GRIK2 gene), exons 10, 11 and 13
gi|15485589|emb|AJ301609.1|HSA301609[15485589]

779: AJ301608
Homo sapiens partial mRNA for GluR6 kainate receptor (GRIK2 gene), exons 11, 13 and 14
gi|15485587|emb|AJ301608.1|HSA301608[15485587]

780: BI713761
ie03f09.y1 HR85 islet Homo sapiens cDNA 5' similar to TR:Q9Y287 Q9Y287 TRANSMEMBRANE PROTEIN BRI. ;, mRNA sequence
gi|15689456|gb|BI713761.1|BI713761[15689456]

781: BI713497
ie03f09.x1 HR85 islet Homo sapiens cDNA 3' similar to TR:Q9Y287 Q9Y287 TRANSMEMBRANE PROTEIN BRI. ;, mRNA sequence
gi|15689192|gb|BI713497.1|BI713497[15689192]

782: BI712829
ie09g03.y1 HR85 islet Homo sapiens cDNA 5' similar to TR:Q9Y287 Q9Y287 TRANSMEMBRANE PROTEIN BRI. ;, mRNA sequence
gi|15688524|gb|BI712829.1|BI712829[15688524]

783: BI712748
ie08g08.y1 HR85 islet Homo sapiens cDNA 5' similar to SW:TM21_RAT Q63584 TRANSMEMBRANE PROTEIN TMP21 PRECURSOR ;, mRNA sequence
gi|15688443|gb|BI712748.1|BI712748[15688443]

784: BI711750
id97b10.y1 Human insulinoma Homo sapiens cDNA 5' similar to TR:Q9Y287 Q9Y287 TRANSMEMBRANE PROTEIN BRI. ;, mRNA sequence
gi|15687445|gb|BI711750.1|BI711750[15687445]

785: BI711468 id97b10.x1 Human insulinoma Homo sapiens cDNA 3' similar to TR:Q9Y287 Q9Y287 TRANSMEMBRANE PROTEIN BRI. ;, mRNA sequence
gi|15687163|gb|BI711468.1|BI711468[15687163]

786: BI711211
id93c12.x1 Human insulinoma Homo sapiens cDNA 3' similar to TR:P97544 P97544 ER TRANSMEMBRANE PROTEIN. ;, mRNA sequence
gi|15686906|gb|BI711211.1|BI711211[15686906]

787: BI710795
id92a02.y1 Human insulinoma Homo sapiens cDNA 5' similar to SW:NMB_HUMAN Q14956 PUTATIVE TRANSMEMBRANE PROTEIN NMB PRECURSOR. ;, mRNA sequence
gi|15686490|gb|BI710795.1|BI710795[15686490]

788: BC014500
Homo sapiens, Similar to leucine zipper-EF-hand containing transmembrane protein 1, clone MGC:23613 IMAGE:4860194, mRNA, complete cds
gi|15680274|gb|BC014500.1|BC014500[15680274]

789: BC014443
Homo sapiens, Similar to transmembrane protein vezatin, clone IMAGE:4851150, mRNA
gi|15680188|gb|BC014443.1|BC014443[15680188]

790: BC014339
Homo sapiens, Similar to transmembrane 4 superfamily member 1, clone MGC:23935 IMAGE:3828466, mRNA, complete cds
gi|15680043|gb|BC014339.1|BC014339[15680043]

791: NM_032405
Homo sapiens transmembrane protease, serine 3 (TMPRSS3), transcript variant D, mRNA
gi|14602456|ref|NM_032405.1|[14602456]

792: NM_032404
Homo sapiens transmembrane protease, serine 3 (TMPRSS3), transcript variant C, mRNA
gi|14602454|ref|NM_032404.1|[14602454]

793: NM_032401
Homo sapiens transmembrane protease, serine 3 (TMPRSS3), transcript variant B, mRNA
gi|14602452|ref|NM_032401.1|[14602452]

794: NM_024022
Homo sapiens transmembrane protease, serine 3 (TMPRSS3), transcript variant A, mRNA
gi|13173470|ref|NM_024022.1|[13173470]

795: AF325418
Ovis aries cystic fibrosis transmembrane conductance regulator (CFTR) gene, intron 21
gi|15637182|gb|AF325418.1|F325416S08[15637182]

796: AF325419
Ovis aries cystic fibrosis transmembrane conductance regulator (CFTR) gene, intron 10
gi|15637180|gb|AF325419.1|F325416S06[15637180]

797: AH011064
Ovis aries
gi|15637174|gb|AH011064.1|SEG_F325416S[15637174]

798: NM_022570
Homo sapiens C-type (calcium dependent, carbohydrate-recognition domain) lectin, superfamily member 12 (CLECSF12), mRNA
gi|13384603|ref|NM_022570.2|[13384603]

799: AF360695
Homo sapiens keratinocyte growth factor receptor 2 (FGFR2) gene, exons 3 through 22 and complete cds, alternatively spliced
gi|15620559|gb|AF360695.3|AF410480S2[15620559]

800: AH010989
Homo sapiens keratinocyte growth factor receptor 2 (FGFR2) gene, complete cds, alternatively spliced
gi|15620558|gb|AH010989.3|SEG_AF410480S[15620558]

801: AY035377
Homo sapiens peptidoglycan recognition protein-I-beta precursor (PGLYRPIbeta) mRNA, complete cds
gi|15590685|gb|AY035377.1|[15590685]

802: AY035376
Homo sapiens peptidoglycan recognition protein-I-alpha precursor (PGLYRPIalpha) mRNA, complete cds
gi|15590683|gb|AY035376.1|[15590683]

803: NM_013317
Homo sapiens lung type-I cell membrane-associated glycoprotein (T1A-2), transcript variant 1, mRNA
gi|7019416|ref|NM_013317.1|[7019416]

804: AJ318099
Homo sapiens mRNA for putative endoplasmic reticulum multispan transmembrane protein (RFT1 gene)
gi|15558857|emb|AJ318099.1|HSA318099[15558857]

807: NM_021808
Homo sapiens UDP-N-acetyl-alpha-D-galactosamine:polypeptide N-acetylgalactosaminyltransferase 9 (GalNAc-T9) (GALNT9), mRNA
gi|11141878|ref|NM_021808.1|[11141878]

808: AF275150
Homo sapiens transmembrane-type protein tyrosine phosphatase H (PTPRH) gene, exon 20 and complete cds
gi|9652146|gb|AF275150.1|F275131S20[9652146]

809: AF275149
Homo sapiens transmembrane-type protein tyrosine phosphatase H (PTPRH) gene, exon 19
gi|9652145|gb|AF275149.1|F275131S19[9652145]

810: AF275148
Homo sapiens transmembrane-type protein tyrosine phosphatase H (PTPRH) gene, exon 18 gi|9652144|gb|AF275148.1|F275131S18[9652144]

811: AF275147
Homo sapiens transmembrane-type protein tyrosine phosphatase H (PTPRH) gene, exon 17
gi|9652143|gb|AF275147.1|F275131S17[9652143]

812: AF275146
Homo sapiens transmembrane-type protein tyrosine phosphatase H (PTPRH) gene, exon 16
gi|9652142|gb|AF275146.1|F275131S16[9652142]

813: AF275145
Homo sapiens transmembrane-type protein tyrosine phosphatase H (PTPRH) gene, exon 15
gi|9652141|gb|AF275145.1|F275131S15[9652141]

814: AF275144
Homo sapiens transmembrane-type protein tyrosine phosphatase H (PTPRH) gene, exon 14
gi|9652140|gb|AF275144.1|F275131S14[9652140]

815: AF275143
Homo sapiens transmembrane-type protein tyrosine phosphatase H (PTPRH) gene, exon 13
gi|9652139|gb|AF275143.1|F275131S13[9652139]

816: AF275142
Homo sapiens transmembrane-type protein tyrosine phosphatase H (PTPRH) gene, exon 12
gi|9652138|gb|AF275142.1|F275131S12[9652138]

817: AF275141
Homo sapiens transmembrane-type protein tyrosine phosphatase H (PTPRH) gene, exon 11
gi|9652137|gb|AF275141.1|F275131S11[9652137]

818: AF275140

Homo sapiens transmembrane-type protein tyrosine phosphatase H (PTPRH) gene, exon 10
gi|9652136|gb|AF275140.1|F275131S10[9652136]

819: AF275139
Homo sapiens transmembrane-type protein tyrosine phosphatase H (PTPRH) gene, exon 9
gi|9652135|gb|AF275139.1|F275131S09[9652135]

820: AF275138
Homo sapiens transmembrane-type protein tyrosine phosphatase H (PTPRH) gene, exon 8
gi|9652134|gb|AF275138.1|F275131S08[9652134]

821: AF275137
Homo sapiens transmembrane-type protein tyrosine phosphatase H (PTPRH) gene, exon 7
gi|9652133|gb|AF275137.1|F275131S07[9652133]

822: AF275136
Homo sapiens transmembrane-type protein tyrosine phosphatase H (PTPRH) gene, exon 6
gi|9652132|gb|AF275136.1|F275131S06[9652132]

823: AF275135
Homo sapiens transmembrane-type protein tyrosine phosphatase H (PTPRH) gene, exon 5
gi|9652131|gb|AF275135.1|F275131S05[9652131]

824: AF275134
Homo sapiens transmembrane-type protein tyrosine phosphatase H (PTPRH) gene, exon 4
gi|9652130|gb|AF275134.1|F275131S04[9652130]

825: AF275133
Homo sapiens transmembrane-type protein tyrosine phosphatase H (PTPRH) gene, exon 3
gi|9652129|gb|AF275133.1|F275131S03[9652129]

826: AF275132
Homo sapiens transmembrane-type protein tyrosine phosphatase H (PTPRH) gene, exon 2
gi|9652128|gb|AF275132.1|F275131S02[9652128]

827: AF275131
Homo sapiens transmembrane-type protein tyrosine phosphatase H (PTPRH) gene, exon 1
gi|9652127|gb|AF275131.1|F275131S01[9652127]

828: AH009676
Homo sapiens transmembrane-type protein tyrosine phosphatase H (PTPRH) gene, complete cds
gi|9652126|gb|AH009676.1|SEG_F275131S[9652126]

829: NM_017417
Homo sapiens UDP-N-acetyl-alpha-D-galactosamine:polypeptide N-acetylgalactosaminyltransferase 8 (GalNAc-T8) (GALNT8), mRNA
gi|8393411|ref|NM_017417.1|[8393411]

830: NM_033346
Homo sapiens bone morphogenetic protein receptor, type II (serine/threonine kinase) (BMPR2), transcript variant 2, mRNA
gi|15451917|ref|NM_033346.1|[15451917]

831: NM_001204
Homo sapiens bone morphogenetic protein receptor, type II (serine/threonine kinase) (BMPR2), transcript variant 1, mRNA
gi|15451915|ref|NM_001204.3|[15451915]

832: NM_003933
Homo sapiens BAI1-associated protein 3 (BAIAP3), mRNA
gi|15451913|ref|NM_003933.3|[15451913]

833: NM_014256
Homo sapiens UDP-GlcNAc:betaGal beta-1,3-N-acetylglucosaminyltransferase 3 (B3GNT3), mRNA
gi|15451894|ref|NM_014256.2|[15451894]

834: NM_033274
Homo sapiens a disintegrin and metalloproteinase domain 19 (meltrin beta) (ADAM19), transcript variant 2, mRNA
gi|15451843|ref|NM_033274.1|[15451843]

835: NM_023038
Homo sapiens a disintegrin and metalloproteinase domain 19 (meltrin beta) (ADAM19), transcript variant 1, mRNA
gi|15451841|ref|NM_023038.2|[15451841]

836: NM_030765
Homo sapiens UDP-GlcNAc:betaGal beta-1,3-N-acetylglucosaminyltransferase 4 (B3GNT4), mRNA
gi|13540526|ref|NM_030765.1|[13540526]

837: AB048207
Homo sapiens mRNA for TIGA1, complete cds
gi|15425668|dbj|AB048207.1|AB048207[15425668]

838: NM_006005
Homo sapiens Wolfram syndrome 1 (wolframin) (WFS1), mRNA
gi|13376995|ref|NM_006005.2|[13376995]

839: NM_015722
Homo sapiens calcyon; D1 dopamine receptor-interacting protein (CALCYON), mRNA
gi|9257200|ref|NM_015722.2|[9257200]

840: AY038990
Homo sapiens ER-localized type I transmembrane adaptor precursor (CAPER) mRNA, complete cds
gi|15418959|gb|AY038990.1|[15418959]

841: BB226825
BB226825 RIKEN full-length enriched, adult male aorta and vein Mus musculus cDNA clone A530098L04 3' similar to AF169676 Homo sapiens leucine-rich repeat transmembrane protein FLRT2 (FLRT2) mRNA, mRNA sequence
gi|15410201|dbj|BB226825.2|BB226825[15410201]

843: AF059274
Homo sapiens neuroglycan C mRNA, complete cds
gi|3820499|gb|AF059274.1|AF059274[3820499]

844: BC013152
Homo sapiens, Similar to transmembrane protein 5, clone MGC:17085 IMAGE:3919181, mRNA, complete cds
gi|15341928|gb|BC013152.1|BC013152[15341928]

845: AH011005
Homo sapiens
gi|15341629|gb|AH011005.1|SEG_L11671S[15341629]

846: AF406650
Homo sapiens putative gap junction protein pannexin 3 (PANX3) mRNA, complete cds
gi|15341531|gb|AF406650.1|AF406650[15341531]

847: L11671
Homo sapiens transmembrane glycoprotein (CD53) gene, exon 1
gi|291896|gb|L11671.1|L11671S1[291896]

848: L11670
Homo sapiens transmembrane glycoprotein (CD53) gene, exons 2 through 8
gi|180145|gb|L11670.1|L11671S2[180145]

849: BI468287
id87a04.y1 Human insulinoma Homo sapiens cDNA 5' similar to TR:Q9Y287 Q9Y287 TRANSMEMBRANE PROTEIN BRI. ;, mRNA sequence
gi|15284396|gb|BI468287.1|BI468287[15284396]

850: BI468286
id87a04.x1 Human insulinoma Homo sapiens cDNA 3' similar to TR:Q9Y287 Q9Y287 TRANSMEMBRANE PROTEIN BRI. ;, mRNA sequence
gi|15284395|gb|BI468286.1|BI468286[15284395]

Appendix II

4: BC025704 Homo sapiens, leukocyte immunoglobulin-like receptor, subfamily B (with TM and ITIM domains), member 5, clone MGC:34418 IMAGE:5223581, mRNA, complete cds
gi|19344005|gb|BC025704.1|[19344005]

5: BC025713 Homo sapiens, T-cell receptor interacting molecule, clone MGC:34314 IMAGE:5227396, mRNA, complete cds
gi|19343996|gb|BC025713.1|[19343996]

6: BC025722 Homo sapiens, adenosine A2b receptor, clone MGC:34640 IMAGE:5198898, mRNA,complete cds
gi|19343938|gb|BC025722.1|[19343938]

7: BC025717 Homo sapiens, chemokine (C-C motif) receptor-like 2, clone MGC:34104 IMAGE:5228561, mRNA, complete cds
gi|19343936|gb|BC025717.1|[19343936]

8: BC025695 Homo sapiens, endothelial differentiation, lysophosphatidic acid G-protein-coupled receptor, 4, clone MGC:34227 IMAGE:5209267, mRNA, complete cds
gi|19343926|gb|BC025695.1|[19343926]

9: BC025727 Homo sapiens, Similar to T cell receptor alpha locus, clone MGC:34712 IMAGE:5201547, mRNA, complete cds
gi|19343616|gb|BC025727.1|[19343616]

10: BC025691 Homo sapiens, interleukin 2 receptor, beta, clone MGC:34584 IMAGE:5207833, mRNA, complete cds
gi|19343610|gb|BC025691.1|[19343610]

11: AF474992 Homo sapiens G protein-coupled receptor SNSR6 gene, complete cds
gi|19338917|gb|AF474992.1|[19338917]

12: AF474991 Homo sapiens G protein-coupled receptor SNSR5 gene, complete cds
gi|19338915|gb|AF474991.1|[19338915]

13: AF474990 Homo sapiens G protein-coupled receptor SNSR4 gene, complete cds gi|19338913|gb|AF474990.1|[19338913]

14: AF474989 Homo sapiens G protein-coupled receptor SNSR3 gene, complete cds
gi|19338911|gb|AF474989.1|[19338911]

15: AF474988 Homo sapiens G protein-coupled receptor SNSR2 gene, complete cds
gi|19338909|gb|AF474988.1|[19338909]

71: AF453877 Homo sapiens neuronal nicotinic receptor beta 4 subunit precursor, gene, exon 1 and partial cds
gi|18042122|gb|AF453877.1|[18042122]

73: U62556 Homo sapiens chemokine receptor-like protein (TER1) gene, complete cds
gi|1468978|gb|U62556.1|HSU62556[1468978]

74: AF449218 Homo sapiens 43kDa acetylcholine receptor-associated protein (RAPSN) mRNA, complete cds
gi|19310212|gb|AF449218.1|[19310212]

84: AJ437349 Homo sapiens partial mRNA for T-cell receptor beta chain (V14-D-J-C) (TCRB gene), clone 11
gi|19262919|emb|AJ437349.1|HSA437349[19262919]

85: AJ011371 Homo sapiens mRNA for serotonin 4 receptor, splice variant h5-HT4(e)
gi|3646277|emb|AJ011371.1|HSAJ1371[3646277]

88: BC025294 Homo sapiens, Similar to toll-like receptor 4, clone IMAGE:4868078, mRNA
gi|19263693|gb|BC025294.1|[19263693]

89: BM875542 ij54d02.y1 Human insulinoma Homo sapiens cDNA clone IMAGE:5634842 5' similar to TR:O00559 O00559 RECEPTOR-BINDING CANCER ANTIGEN EXPRESSED ON SISO CELLS ;, mRNA sequence
gi|19243208|gb|BM875542.1|BM875542[19243208]

99: AY059419 Homo sapiens killer-cell immunoglobulin-like receptor (KIR3DL1) mRNA, KIR3DL1*011 allele, partial cds
gi|19224338|gb|AY059419.1|[19224338]

100: AY059418 Homo sapiens killer-cell immunoglobulin-like receptor (KIR3DL2) mRNA, KIR3DL2*010 allele, partial cds
gi|19224336|gb|AY059418.1|[19224336]

101: AY059417 Homo sapiens killer-cell immunoglobulin-like receptor KIR3DL1/2v mRNA, partial cds
gi|19224334|gb|AY059417.1|[19224334]

102: AY059420 Homo sapiens killer-cell immunoglobulin-like receptor (KIR3DL2) mRNA,KIR3DL2*012 allele, partial cds
gi|19224332|gb|AY059420.1|[19224332]

103: AC079385 Homo sapiens 12q BAC RP11-482D24 (Roswell Park Cancer Institute Human BAC Library) complete sequence
gi|14670063|gb|AC079385.18|[14670063]

104: AC078889 Homo sapiens 12q BAC RP11-335I12 (Roswell Park Cancer Institute Human BAC Library) complete sequence
gi|11072039|gb|AC078889.20|[11072039]

105: AC010168 Homo sapiens 12p12-31.7-32.2 BAC RP11-174G6 (Rosewell Park Cancer Institute Human Bac Library) complete sequence
gi|6855156|gb|AC010168.6|[6855156]

106: U14188 Homo sapiens LERK-4 (EPLG4) mRNA, complete cds
gi|642834|gb|U14188.1|HSU14188[642834]

107: U14187 Homo sapiens LERK-3 (EPLG3) mRNA, complete cds
gi|642832|gb|U14187.1|HSU14187[642832]

108: U15637 Homo sapiens CD40 binding protein (CD40BP) mRNA, complete cds
gi|595910|gb|U15637.1|HSU15637[595910]

109: AF262304 Homo sapiens clone 7 CC chemokine receptor 3-like mRNA, partial sequence, alternatively spliced
gi|19171650|gb|AF262304.1|[19171650]

110: AF262303 Homo sapiens clone 6 CC chemokine receptor 3 (CCR3) mRNA, partial cds
gi|19171648|gb|AF262303.1|[19171648]

111: AF262302 Homo sapiens clone 5 CC chemokine receptor 3 (CCR3) mRNA, partial cds
gi|19171646|gb|AF262302.1|[19171646]

112: AF262301 Homo sapiens clone 4 CC chemokine receptor 3 (CCR3) mRNA, partial cds
gi|19171644|gb|AF262301.1|[19171644]

113: AF262300 Homo sapiens clone 2 CC chemokine receptor 3 (CCR3) mRNA, partial cds
gi|19171642|gb|AF262300.1|[19171642]

114: AF262299 Homo sapiens clone 1 CC chemokine receptor 3 (CCR3) mRNA, partial cds
gi|19171640|gb|AF262299.1|[19171640]

118: AF247361 Homo sapiens CC chemokine receptor 3 (CCR3) gene, complete cds
gi|19110542|gb|AF247361.1|[19110542]

122: AF416619 Homo sapiens prolactin receptor short isoform 1a (PRLR) mRNA, complete cds, alternatively spliced
gi|16506717|gb|AF416619.1|[16506717]

123: AF416618 Homo sapiens prolactin receptor short isoform 1b (PRLR) mRNA, complete cds, alternatively spliced
gi|16506715|gb|AF416618.1|[16506715]

125: AJ303165 Homo sapiens partial gene for putative transmembrane receptor
gi|13162199|emb|AJ303165.1|HSA303165[13162199]

126: NM_017451 Homo sapiens BAI1-associated protein 2 (BAIAP2) transcript variant 2, mRNA
gi|9257198|ref|NM_017451.1|[9257198]

127: NM_017450 Homo sapiens BAI1-associated protein 2 (BAIAP2) transcript variant 1, mRNA
gi|9257196|ref|NM_017450.1|[9257196]

128: NM_006340 Homo sapiens BAI1-associated protein 2 (BAIAP2) transcript variant 3, mRNA
gi|5453564|ref|NM_006340.1|[5453564]

131: AF350881 Homo sapiens channel kinase 2 (CHAK2) mRNA, complete cds
gi|18860923|gb|AF350881.2|[18860923]

132: AF022044 Homo sapiens natural killer cell receptor KIR3DS1 variant mRNA, complete cds
gi|2760894|gb|AF022044.1|[2760894]

133: AF034773 Homo sapiens natural killer cell inhibitory receptor (KIR2DL4) mRNA, variant 3,complete cds
gi|2739181|gb|AF034773.1|[2739181]

134: AF034772 Homo sapiens natural killer cell inhibitory receptor (KIR2DL4) mRNA, variant 2,complete cds
gi|2739179|gb|AF034772.1|[2739179]

135: AF034771 Homo sapiens natural killer cell inhibitory receptor (KIR2DL4) mRNA, variant 1,complete cds
gi|2739177|gb|AF034771.1|[2739177]

136: AF022047 Homo sapiens natural killer cell inhibitory receptor KIR2DS3 variant mRNA,complete cds
gi|2738966|gb|AF022047.1|[2738966]

137: AF022046 Homo sapiens natural killer cell inhibitory receptor KIR2DS1 variant mRNA,complete cds
gi|2738964|gb|AF022046.1|[2738964]

138: AF022045 Homo sapiens natural killer cell receptor KIR2DL1 variant mRNA, complete cds
gi|2738962|gb|AF022045.1|[2738962]

139: U56255 Homo sapiens CW-1 mRNA, complete cds gi|1399688|gb|U56255.1|HSU56255[1399688]

140: AJ422056 Homo sapiens partial GRM5 gene for metabotrophic glutamate receptor, exon 1A
gi|19069804|emb|AJ422056.1|HSA422056[19069804]

141: AY028912 Homo sapiens ectodysplasin A receptor associated death domain (EDARADD) gene,exon 7 and complete cds, alternatively spliced
gi|19067944|gb|AY028912.1|AY028906S7[19067944]

142: AY028911 Homo sapiens ectodysplasin A receptor associated death domain (EDARADD) gene,exon 6
gi|19067943|gb|AY028911.1|AY028906S6[19067943]

143: AY028910 Homo sapiens ectodysplasin A receptor associated death domain (EDARADD) gene,exon 5
gi|19067942|gb|AY028910.1|AY028906S5[19067942]

144: AY028909 Homo sapiens ectodysplasin A receptor associated death domain (EDARADD) gene,exon 4
gi|19067941|gb|AY028909.1|AY028906S4[19067941]

145: AY028908 Homo sapiens ectodysplasin A receptor associated death domain (EDARADD) gene,exon 3
gi|19067940|gb|AY028908.1|AY028906S3[19067940]

146: AY028907 Homo sapiens ectodysplasin A receptor associated death domain (EDARADD) gene, exon 2
gi|19067939|gb|AY028907.1|AY028906S2[19067939]

147: AY028906 Homo sapiens ectodysplasin A receptor associated death domain (EDARADD) gene, exon 1
gi|19067938|gb|AY028906.1|AY028906S1[19067938]

148: AH010677 Homo sapiens ectodysplasin A receptor associated death domain (EDARADD) gene, complete cds, alternatively spliced
gi|19067937|gb|AH010677.1|SEG_AY028906S[19067937]

149: AY028913 Homo sapiens ectodysplasia A receptor associated death domain A (EDARADD) mRNA, complete cds; alternatively spliced
gi|19067935|gb|AY028913.1|[19067935]

150: BM735809 06E08 Canine Brain cDNA Library Canis familiaris cDNA 5' similar to Homo sapiens glycine receptor, beta, mRNA sequence
gi|19057142|gb|BM735809.1|BM735809[19057142]

151: BM735756 06A09 Canine Brain cDNA Library Canis familiaris cDNA 5' similar to Homo sapiens glycine receptor, beta subunit, mRNA sequence
gi|19057089|gb|BM735756.1|BM735756[19057089]

152: BM735711 10E11 Canine Brain cDNA Library Canis familiaris cDNA 5' similar to Homo sapiens protein tyrosine phosphatase, receptor-type, Z polypeptide 1, mRNA sequence
gi|19057044|gb|BM735711.1|BM735711[19057044]

155: AC007165 Homo sapiens BAC clone RP11-451C2 from 2, complete sequence
gi|19033999|gb|AC007165.4|[19033999]

156: AF245699 Homo sapiens type 1 angiotensin II receptor (AGTR1) gene, complete cds
gi|7862074|gb|AF245699.1|[7862074]

157: BC024229 Homo sapiens, prostaglandin E receptor 3 (subtype EP3), clone MGC:27302 IMAGE:4660371, mRNA, complete cds
gi|18999476|gb|BC024229.1|[18999476]

176: AJ417555 Homo sapiens partial mRNA for killer cell immunoglobulin receptor (KIR2DS4 gene), strain 4053
gi|18958228|emb|AJ417555.1|HSA417555[18958228]

177: AJ417554 Homo sapiens partial mRNA for killer cell immunoglobulin receptor (KIR2DS4 gene), strain 3321
gi|18958226|emb|AJ417554.1|HSA417554[18958226]

179: NM_003877 Homo sapiens STAT induced STAT inhibitor-2 (STATI2), mRNA
gi|18921206|ref|NM_003877.2|[18921206]

180: NM_017662 Homo sapiens transient receptor potential cation channel, subfamily M, member 6(TRPM6), mRNA
gi|18921092|ref|NM_017662.3|[18921092]

191: NM_016148 Homo sapiens SH3 and multiple ankyrin repeat domains 1 (SHANK1), mRNA
gi|11968151|ref|NM_016148.1|[11968151]

193: NM_017729 Homo sapiens epidermal growth factor receptor pathway substrate 8 related protein 1 (EPS8R1), mRNA
gi|8923231|ref|NM_017729.1|[8923231]

195: M13824 Homo sapiens T cell receptor gamma chain variable region (TCRG) gene, partial cds
gi|339169|gb|M13824.1|HUMTCGXL[339169]

196: M12960 Homo sapiens T-cell receptor gamma-chain J1, partial cds
gi|339144|gb|M12960.1|HUMTCGJB[339144]

197: M13823 Homo sapiens T cell receptor gamma chain (TCRG) gene, partial cds
gi|292736|gb|M13823.1|HUMTCGXK[292736]

198: L12398 Homo sapiens dopamine receptor D4 (DRD4) mRNA, complete cds
gi|291945|gb|L12398.1|HUMD4C[291945]

199: M86383 Homo sapiens nicotinic acetylcholine receptor alpha 3 subunit precursor, mRNA,complete cds
gi|177897|gb|M86383.1|HUMA3NARSP[177897]

202: NM_012245 Homo sapiens SKI-interacting protein (SNW1), mRNA
gi|18860912|ref|NM_012245.2|[18860912]

203: NM_006750 Homo sapiens syntrophin, beta 2 (dystrophin-associated protein A1, 59kD, basiccomponent 2) (SNTB2), transcript variant 1, mRNA
gi|18860911|ref|NM_006750.2|[18860911]

204: NM_130845 Homo sapiens syntrophin, beta 2 (dystrophin-associated protein A1, 59kD, basic component 2) (SNTB2), transcript variant 2, mRNA
gi|18860909|ref|NM_130845.1|[18860909]

205: NM_002846 Homo sapiens protein tyrosine phosphatase, receptor type, N (PTPRN), mRNA
gi|18860905|ref|NM_002846.2|[18860905]

206: NM_002845 Homo sapiens protein tyrosine phosphatase, receptor type, M (PTPRM), mRNA
gi|18860903|ref|NM_002845.2|[18860903]

207: NM_002844 Homo sapiens protein tyrosine phosphatase, receptor type, K (PTPRK), mRNA
gi|18860901|ref|NM_002844.2|[18860901]

208: NM_002843 Homo sapiens protein tyrosine phosphatase, receptor type, J (PTPRJ), mRNA
gi|18860899|ref|NM_002843.2|[18860899]

209: NM_002841 Homo sapiens protein tyrosine phosphatase, receptor type, G (PTPRG), mRNA
gi|18860897|ref|NM_002841.2|[18860897]

210: NM_130440 Homo sapiens protein tyrosine phosphatase, receptor type, F (PTPRF), transcript variant 2, mRNA
gi|18860895|ref|NM_130440.1|[18860895]

211: NM_130393 Homo sapiens protein tyrosine phosphatase, receptor type, D (PTPRD), transcript variant 4, mRNA
gi|18860893|ref|NM_130393.1|[18860893]

212: NM_130392 Homo sapiens protein tyrosine phosphatase, receptor type, D (PTPRD), transcript variant 3, mRNA
gi|18860891|ref|NM_130392.1|[18860891]

213: NM_130391 Homo sapiens protein tyrosine phosphatase, receptor type, D (PTPRD), transcript variant 2, mRNA
gi|18860889|ref|NM_130391.1|[18860889]

214: NM_003682 Homo sapiens MAP-kinase activating death domain (MADD), transcript variant 4, mRNA
gi|18860876|ref|NM_003682.2|[18860876]

215: NM_130476 Homo sapiens MAP-kinase activating death domain (MADD), transcript variant 8, mRNA
gi|18860874|ref|NM_130476.1|[18860874]

216: NM_130475 Homo sapiens MAP-kinase activating death domain (MADD), transcript variant 7, mRNA
gi|18860872|ref|NM_130475.1|[18860872]

217: NM_002840 Homo sapiens protein tyrosine phosphatase, receptor type, F (PTPRF), transcript variant 1, mRNA
gi|18860871|ref|NM_002840.2|[18860871]

218: NM_130474 Homo sapiens MAP-kinase activating death domain (MADD), transcript variant 6, mRNA
gi|18860869|ref|NM_130474.1|[18860869]

219: NM_130473 Homo sapiens MAP-kinase activating death domain (MADD), transcript variant 5, mRNA
gi|18860867|ref|NM_130473.1|[18860867]

220: NM_130472 Homo sapiens MAP-kinase activating death domain (MADD), transcript variant 3, mRNA
gi|18860865|ref|NM_130472.1|[18860865]

221: NM_130471 Homo sapiens MAP-kinase activating death domain (MADD), transcript variant 2, mRNA
gi|18860863|ref|NM_130471.1|[18860863]

222: NM_130470 Homo sapiens MAP-kinase activating death domain (MADD), transcript variant 1, mRNA
gi|18860861|ref|NM_130470.1|[18860861]

223: NM_006504 Homo sapiens protein tyrosine phosphatase, receptor type, E (PTPRE), transcript variant 1, mRNA
gi|18860860|ref|NM_006504.2|[18860860]

224: NM_130435 Homo sapiens protein tyrosine phosphatase, receptor type, E (PTPRE), transcript variant 2, mRNA
gi|18860858|ref|NM_130435.1|[18860858]

225: AJ431177 Homo sapiens mRNA for WIRE protein
gi|18857713|emb|AJ431177.1|HSA431177[18857713]

226: NM_006474 Homo sapiens lung type-I cell membrane-associated glycoprotein (T1A-2), mRNA
gi|18767663|ref|NM_006474.2|[18767663]

228: NM_006794 Homo sapiens G protein-coupled receptor 75 (GPR75), mRNA
gi|5803024|ref|NM_006794.1|[5803024]

229: NM_002842 Homo sapiens protein tyrosine phosphatase, receptor type, H (PTPRH), mRNA
gi|4506312|ref|NM_002842.1|[4506312]

230: NM_002839 Homo sapiens protein tyrosine phosphatase, receptor type, D (PTPRD), transcript variant 1, mRNA
gi|4506308|ref|NM_002839.1|[4506308]

231: BC024145 Homo sapiens, TNF receptor-associated factor 1, clone MGC:10353 IMAGE:3832475,mRNA, complete cds
gi|18848176|gb|BC024145.1|[18848176]

232: AF469756 Homo sapiens clone S9 interleukin-1 receptor type I (IL1R1) gene, partial sequence
gi|18846656|gb|AF469756.1|[18846656]

233: AF469755 Homo sapiens clone S8 interleukin-1 receptor type I (IL1R1) gene, partial sequence
gi|18846655|gb|AF469755.1|[18846655]

234: AF469754 Homo sapiens clone S7 interleukin-1 receptor type I (IL1R1) gene, partial sequence
gi|18845036|gb|AF469754.1|[18845036]

237: AF416711 Homo sapiens Fc-gamma receptor IIc5 mRNA, partial cds
gi|18765992|gb|AF416711.1|[18765992]

238: NM_023068 Homo sapiens sialoadhesin (SN), mRNA
gi|18765743|ref|NM_023068.2|[18765743]

239: NM_004782 Homo sapiens synaptosomal-associated protein, 29kD (SNAP29), mRNA
gi|18765736|ref|NM_004782.2|[18765736]

240: NM_130798 Homo sapiens synaptosomal-associated protein, 23kD (SNAP23), transcript variant 2, mRNA
gi|18765730|ref|NM_130798.1|[18765730]

241: NM_003825 Homo sapiens synaptosomal-associated protein, 23kD (SNAP23), transcript variant 1, mRNA
gi|18765728|ref|NM_003825.2|[18765728]

245: AF439409 Homo sapiens G-protein-coupled receptor kinase 7 (GRK7) mRNA, GRK7-S allele,complete cds
gi|17933258|gb|AF439409.1|[17933258]

246: NM_032211 Homo sapiens lysyl oxidase-like 4 (LOXL4), mRNA
gi|16933522|ref|NM_032211.4|[16933522]

247: AF411122 Homo sapiens importin 4 mRNA, complete cds
gi|18700634|gb|AF411122.1|[18700634]

289: NM_130441 Homo sapiens C-type (calcium dependent, carbohydrate-recognition domain) lectin, superfamily member 11 (CLECSF11), mRNA
gi|18466805|ref|NM_130441.1|[18466805]

290: NM_030876 Homo sapiens olfactory receptor, family 5, subfamily V, member 1 (OR5V1), mRNA
gi|14495550|ref|NM_030876.2|[14495550]

291: NM_032732 Homo sapiens hypothetical protein MGC10763 (IL17RL), mRNA
gi|14249349|ref|NM_032732.1|[14249349]

292: NM_030959 Homo sapiens olfactory receptor, family 12, subfamily D, member 3 (OR12D3), mRNA
gi|13624334|ref|NM_030959.1|[13624334]

294: NM_018844 Homo sapiens B-cell receptor-associated protein BAP29 (BAP29), mRNA
gi|9994198|ref|NM_018844.1|[9994198]

295: NM_002825 Homo sapiens pleiotrophin (heparin binding growth factor 8, neurite growth-promoting factor 1) (PTN), mRNA
gi|18656935|ref|NM_002825.2|[18656935]

299: NM_016372 Homo sapiens seven transmembrane domain orphan receptor (TPRA40), mRNA
gi|7705964|ref|NM_016372.1|[7705964]

300: NM_014288 Homo sapiens integrin beta 3 binding protein (beta3-endonexin) (ITGB3BP), mRNA
gi|7657205|ref|NM_014288.1|[7657205]

301: L43588 Homo sapiens T cell antigen receptor mRNA, partial cds
gi|18654191|gb|L43588.1|HUMTCARF[18654191]

318: U77589 Homo sapiens MHC class II HLA-DQ-alpha chain (HLA-DQA1) mRNA, HLA-DQA1*0104 allele, complete cds
gi|1916744|gb|U77589.1|HSU77589[1916744]

319: AF410465 Homo sapiens importin 9 mRNA, complete cds
gi|15529702|gb|AF410465.1|[15529702]

320: AF332759 Homo sapiens partially duplicated CHRNA7 gene, hybrid intron A/4 and partial exon 5
gi|13345792|gb|AF332759.1|[13345792]

321: AF332758 Homo sapiens alpha-7 nicotinic cholinergic receptor subunit (CHRNA7) gene, partial intron 4 and partial cds
gi|13345790|gb|AF332758.1|[13345790]

322: NM_003744 Homo sapiens numb homolog (Drosophila) (NUMB), mRNA
gi|18644887|ref|NM_003744.2|[18644887]

323: NM_003681 Homo sapiens pyridoxal (pyridoxine, vitamin B6) kinase (PDXK), mRNA
gi|18644884|ref|NM_003681.2|[18644884]

324: NM_080706 Homo sapiens transient receptor potential cation channel, subfamily V, member 1(TRPV1), transcript variant 3, mRNA
gi|18375670|ref|NM_080706.1|[18375670]

325: NM_080705 Homo sapiens transient receptor potential cation channel, subfamily V, member 1(TRPV1), transcript variant 4, mRNA
gi|18375668|ref|NM_080705.1|[18375668]

326: NM_080704 Homo sapiens transient receptor potential cation channel, subfamily V, member 1(TRPV1), transcript variant 1, mRNA
gi|18375666|ref|NM_080704.1|[18375666]

327: NM_018727 Homo sapiens transient receptor potential cation channel, subfamily V, member 1(TRPV1), transcript variant 2, mRNA
gi|18375664|ref|NM_018727.3|[18375664]

328: NM_080819
Homo sapiens G protein-coupled receptor 78 (GPR78), mRNA
gi|18201873|ref|NM_080819.1|[18201873]

329: NM_080738
Homo sapiens EDAR-associated death domain (EDARADD), mRNA
gi|18152768|ref|NM_080738.1|[18152768]

330: NM_080491 Homo sapiens GRB2-associated binding protein 2 (GAB2), transcript variant 1,mRNA
gi|18105041|ref|NM_080491.1|[18105041]

331: NM_012296 Homo sapiens GRB2-associated binding protein 2 (GAB2), transcript variant 2,mRNA
gi|18105040|ref|NM_012296.2|[18105040]

332: NM_032027 Homo sapiens beta-amyloid binding protein precursor (BBP), mRNA
gi|17738309|ref|NM_032027.2|[17738309]

333: NM_057159 Homo sapiens endothelial differentiation, lysophosphatidic acid G-protein-coupled receptor, 2 (EDG2), transcript variant 2, mRNA
gi|16950637|ref|NM_057159.1|[16950637]

334: NM_001401 Homo sapiens endothelial differentiation, lysophosphatidic acid G-protein-coupled receptor, 2 (EDG2), transcript variant 1, mRNA
gi|16950635|ref|NM_001401.2|[16950635]

335: NM_007070 Homo sapiens FKBP-associated protein (FAP48), transcript variant 2, mRNA
gi|16933538|ref|NM_007070.2|[16933538]

336: NM_053274 Homo sapiens FKBP-associated protein (FAP48), transcript variant 1, mRNA
gi|16933536|ref|NM_053274.1|[16933536]

337: NM_003726 Homo sapiens src family associated phosphoprotein 1 (SCAP1), mRNA
gi|16753209|ref|NM_003726.2|[16753209]

338: NM_033632 Homo sapiens F-box and WD-40 domain protein 7 (archipelago homolog, Drosophila)(FBXW7), transcript variant 1, mRNA
gi|16117780|ref|NM_033632.1|[16117780]

339: NM_018315 Homo sapiens F-box and WD-40 domain protein 7 (archipelago homolog, Drosophila)(FBXW7), transcript variant 2, mRNA
gi|16117778|ref|NM_018315.2|[16117778]

340: NM_021203 Homo sapiens APMCF1 protein (APMCF1), mRNA
gi|14917112|ref|NM_021203.2|[14917112]

341: NM_002927 Homo sapiens regulator of G-protein signalling 13 (RGS13), mRNA
gi|14589857|ref|NM_002927.2|[14589857]

344: NM_020167 Homo sapiens neuromedin U receptor 2 (NMU2R), mRNA
gi|9910461|ref|NM_020167.1|[9910461]

346: AF190052 Homo sapiens interleukin 1 receptor type I (IL1R1) gene, exon 1C sequence
gi|9719300|gb|AF190052.1|[9719300]

347: NM_018965 Homo sapiens triggering receptor expressed on myeloid cells 2 (TREM2), mRNA
gi|9507202|ref|NM_018965.1|[9507202]

348: NM_018643 Homo sapiens triggering receptor expressed on myeloid cells 1 (TREM1), mRNA
gi|8924261|ref|NM_018643.1|[8924261]

349: NM_018647 Homo sapiens tumor necrosis factor receptor superfamily, member 19 (TNFRSF19),mRNA
gi|8924251|ref|NM_018647.1|[8924251]

350: NM_018695 Homo sapiens erbb2 interacting protein (ERBB2IP), mRNA
gi|8923908|ref|NM_018695.1|[8923908]

351: NM_017636 Homo sapiens transient receptor potential cation channel, subfamily M, member 4(TRPM4), mRNA
gi|8923048|ref|NM_017636.1|[8923048]

353: NM_016559 Homo sapiens PXR2b protein (PXR2b), mRNA gi|7706670|ref|NM_016559.1|[7706670]

354: NM_016382 Homo sapiens natural killer cell receptor 2B4 (CD244), mRNA
gi|7706528|ref|NM_016382.1|[7706528]

357: NM_015986 Homo sapiens cytokine receptor-like factor 3 (CRLF3), mRNA
gi|7705331|ref|NM_015986.1|[7705331]

358: NM_014815 Homo sapiens KIAA0130 gene product (KIAA0130), mRNA
gi|7661929|ref|NM_014815.1|[7661929]

359: NM_014053 Homo sapiens FLVCR protein (FLVCR), mRNA
gi|7661707|ref|NM_014053.1|[7661707]

360: NM_014478 Homo sapiens calcitonin gene-related peptide-receptor component protein (CGRP-RCP), mRNA
gi|7656976|ref|NM_014478.1|[7656976]

361: NM_012470 Homo sapiens transportin-SR (TRN-SR), mRNA
gi|6912733|ref|NM_012470.1|[6912733]

362: NM_007357 Homo sapiens low density lipoprotein receptor defect C complementing (LDLC), mRNA
gi|6678675|ref|NM_007357.1|[6678675]

366: NM_005162 Homo sapiens angiotensin receptor-like 2 (AGTRL2), mRNA
gi|6031157|ref|NM_005162.2|[6031157]

367: NM_005501 Homo sapiens integrin, alpha 3 (antigen CD49C, alpha 3 subunit of VLA-3 receptor) (ITGA3), transcript variant b, mRNA
gi|6006010|ref|NM_005501.1|[6006010]

370: NM_007053 Homo sapiens natural killer cell receptor, immunoglobulin superfamily member(BY55), mRNA
gi|5901909|ref|NM_007053.1|[5901909]

371: NM_006653 Homo sapiens suc1-associated neurotrophic factor target 2 (FGFR signalling adaptor) (SNT-2), mRNA
gi|5730058|ref|NM_006653.1|[5730058]

374: NM_005761 Homo sapiens plexin C1 (PLXNC1), mRNA
gi|5032222|ref|NM_005761.1|[5032222]

375: NM_005866 Homo sapiens sigma receptor (SR31747 binding protein 1) (SR-BP1), mRNA
gi|5032116|ref|NM_005866.1|[5032116]

377: NM_005506 Homo sapiens CD36 antigen (collagen type I receptor, thrombospondin receptor)-like 2 (lysosomal integral membrane protein II) (CD36L2), mRNA
gi|5031630|ref|NM_005506.1|[5031630]

379: NM_004799 Homo sapiens MAD, mothers against decapentaplegic homolog (Drosophila)interacting protein, receptor activation anchor (MADHIP), transcript variant 3,mRNA
gi|4759059|ref|NM_004799.1|[4759059]

380: NM_004292 Homo sapiens ras inhibitor (RIN1), mRNA
gi|4759039|ref|NM_004292.1|[4759039]

381: NM_004828 Homo sapiens lymphocyte antigen 95 (activating NK-receptor; NK-p44) (LY95), mRNA
gi|4758693|ref|NM_004828.1|[4758693]

382: NM_004767 Homo sapiens endothelin type b receptor-like protein 2 (ET(B)R-LP-2), mRNA
gi|4758309|ref|NM_004767.1|[4758309]

383: NM_004440 Homo sapiens EphA7 (EPHA7), mRNA
gi|4758281|ref|NM_004440.1|[4758281]

384: NM_003999 Homo sapiens oncostatin M receptor (OSMR), mRNA
gi|4557039|ref|NM_003999.1|[4557039]

386: NM_003305 Homo sapiens transient receptor potential cation channel, subfamily C, member 3(TRPC3), mRNA
gi|4507686|ref|NM_003305.1|[4507686]

388: NM_003626 Homo sapiens protein tyrosine phosphatase, receptor type, f polypeptide (PTPRF),interacting protein (liprin), alpha 1 (PPFIA1), mRNA
gi|4505982|ref|NM_003626.1|[4505982]

389: NM_003876 Homo sapiens putative receptor protein (PMI), mRNA
gi|4505900|ref|NM_003876.1|[4505900]

390: NM_003559 Homo sapiens phosphatidylinositol-4-phosphate 5-kinase, type II, beta (PIP5K2B),mRNA
gi|4505818|ref|NM_003559.1|[4505818]

391: NM_003629 Homo sapiens phosphoinositide-3-kinase, regulatory subunit, polypeptide 3 (p55,gamma) (PIK3R3), mRNA
gi|4505804|ref|NM_003629.1|[4505804]

392: NM_003676 Homo sapiens degenerative spermatocyte homolog, lipid desaturase (Drosophila)(DEGS), mRNA
gi|4505192|ref|NM_003676.1|[4505192]

393: NM_002270 Homo sapiens karyopherin (importin) beta 2 (KPNB2), mRNA
gi|4504906|ref|NM_002270.1|[4504906]

394: NM_002204 Homo sapiens integrin, alpha 3 (antigen CD49C, alpha 3 subunit of VLA-3 receptor) (ITGA3), transcript variant a, mRNA
gi|4504746|ref|NM_002204.1|[4504746]

395: NM_001560 Homo sapiens interleukin 13 receptor, alpha 1 (IL13RA1), mRNA
gi|4504646|ref|NM_001560.1|[4504646]

396: NM_000842 Homo sapiens glutamate receptor, metabotropic 5 (GRM5), mRNA
gi|4504142|ref|NM_000842.1|[4504142]

397: NM_001883 Homo sapiens corticotropin releasing hormone receptor 2 (CRHR2), mRNA
gi|4503044|ref|NM_001883.1|[4503044]

398: NM_001873 Homo sapiens carboxypeptidase E (CPE), mRNA
gi|4503008|ref|NM_001873.1|[4503008]

400: L29395 Homo sapiens v-erbB-related protein gene, partial cds
gi|459807|gb|L29395.1|HUMERBB[459807]

401: L08584 Homo sapiens T cell receptor beta chain (TCRB) mRNA, partial cds
gi|307497|gb|L08584.1|HUMTCVB7A[307497]

403: NM_015638 Homo sapiens chromosome 20 open reading frame 188 (C20orf188), mRNA
gi|18158415|ref|NM_015638.1|[18158415]

405: NM_054032 Homo sapiens G protein-coupled receptor MRGX4 (MRGX4), mRNA
gi|16876454|ref|NM_054032.1|[16876454]

406: NM_054031 Homo sapiens G protein-coupled receptor MRGX3 (MRGX3), mRNA
gi|16876452|ref|NM_054031.1|[16876452]

407: NM_054030 Homo sapiens G protein-coupled receptor MRGX2 (MRGX2), mRNA
gi|16876450|ref|NM_054030.1|[16876450]

408: NM_052931 Homo sapiens activating NK receptor (KALI), mRNA
gi|16418406|ref|NM_052931.1|[16418406]

409: NM_032871 Homo sapiens tumor necrosis factor receptor superfamily, member 19-like(TNFRSF19L), mRNA
gi|14249611|ref|NM_032871.1|[14249611]

410: NM_032553 Homo sapiens putative purinergic receptor (FKSG79), mRNA
gi|14211848|ref|NM_032553.1|[14211848]

411: NM_025179 Homo sapiens plexin A2 (PLXNA2), mRNA gi|13378152|ref|NM_025179.1|[13378152]

413: NM_021249 Homo sapiens sorting nexin 6 (SNX6), mRNA
gi|13027619|ref|NM_021249.1|[13027619]

414: NM_014045 Homo sapiens DKFZP564C1940 protein (DKFZP564C1940), mRNA
gi|13027587|ref|NM_014045.1|[13027587]

415: NM_080923 Homo sapiens protein tyrosine phosphatase, receptor type, C (PTPRC), transcript variant 4, mRNA
gi|18641365|ref|NM_080923.1|[18641365]

416: NM_080922 Homo sapiens protein tyrosine phosphatase, receptor type, C (PTPRC), transcript variant 3, mRNA
gi|18641363|ref|NM_080922.1|[18641363]

417: NM_080921 Homo sapiens protein tyrosine phosphatase, receptor type, C (PTPRC), transcript variant 2, mRNA
gi|18641361|ref|NM_080921.1|[18641361]

418: NM_130386 Homo sapiens collectin sub-family member 12 (COLEC12), transcript variant I, mRNA
gi|18641359|ref|NM_130386.1|[18641359]

419: NM_030781 Homo sapiens collectin sub-family member 12 (COLEC12), transcript variant II, mRNA
gi|18641357|ref|NM_030781.2|[18641357]

420: NM_002838 Homo sapiens protein tyrosine phosphatase, receptor type, C (PTPRC), transcript variant 1, mRNA
gi|18641346|ref|NM_002838.2|[18641346]

421: NM_130770 Homo sapiens 5-hydroxytryptamine receptor 3 subunit C (HTR3C), mRNA
gi|18640739|ref|NM_130770.1|[18640739]

430: BD010218 Novel hemopoietin receptor protein, NR12 gi|18638591|dbj|BD010218.1|[18638591]

431: BD010217 Novel hemopoietin receptor protein, NR12
gi|18638590|dbj|BD010217.1|[18638590]

432: BD010216 Novel hemopoietin receptor protein, NR12
gi|18638589|dbj|BD010216.1|[18638589]

433: BD010215 Novel hemopoietin receptor protein, NR12
gi|18638588|dbj|BD010215.1|[18638588]

434: BD010214 Novel hemopoietin receptor protein, NR12
gi|18638587|dbj|BD010214.1|[18638587]

435: BD010125 Peptide leukotriene receptor
gi|18638498|dbj|BD010125.1|[18638498]

436: BD010114 Novel receptor and gene encoding the same
gi|18638487|dbj|BD010114.1|[18638487]

437: BD010057 Novel G protein coupled receptor protein and its DNA
gi|18638430|dbj|BD010057.1|[18638430]

438: BD010056 Novel G protein coupled receptor protein and its DNA
gi|18638429|dbj|BD010056.1|[18638429]

439: BD010055 Novel G protein coupled receptor protein and its DNA
gi|18638428|dbj|BD010055.1|[18638428]

440: BD010054 Novel G protein coupled receptor protein and its DNA
gi|18638427|dbj|BD010054.1|[18638427]

441: BD010053 Novel G protein coupled receptor protein and its DNA
gi|18638426|dbj|BD010053.1|[18638426]

442: BD010052 Novel G protein coupled receptor protein and its DNA
gi|18638425|dbj|BD010052.1|[18638425]

443: BD010051 Novel G protein coupled receptor protein and its DNA
gi|18638424|dbj|BD010051.1|[18638424]

444: BD010050 Novel G protein coupled receptor protein and its DNA
gi|18638423|dbj|BD010050.1|[18638423]

445: BD010049 Novel G protein coupled receptor protein and its DNA
gi|18638422|dbj|BD010049.1|[18638422]

446: BD010046 Novel G protein coupled receptor protein and its DNA
gi|18638419|dbj|BD010046.1|[18638419]

447: BD010035 Novel G protein coupled receptor protein and its DNA
gi|18638408|dbj|BD010035.1|[18638408]

448: BD010034 Novel G protein coupled receptor protein and its DNA
gi|18638407|dbj|BD010034.1|[18638407]

449: BD010028 Novel G protein coupled receptor protein and its DNA
gi|18638401|dbj|BD010028.1|[18638401]

450: BD010022 Novel G protein coupled receptor protein and its DNA
gi|18638395|dbj|BD010022.1|[18638395]

451: BD009263 GABAA receptor subunit epsilon-related protein
gi|18637636|dbj|BD009263.1|[18637636]

452: BD009262 GABAA receptor subunit epsilon-related protein
gi|18637635|dbj|BD009262.1|[18637635]

453: BD009261 GABAA receptor subunit epsilon-related protein gi|18637634|dbj|BD009261.1|[18637634]

454: BD009260 GABAA receptor subunit epsilon-related protein
gi|18637633|dbj|BD009260.1|[18637633]

455: BD006753 Human G protein chemokine receptor HDGNR10
gi|18635124|dbj|BD006753.1|[18635124]

460: E51301 Novel G protein-coupled receptor protein and gene of said G protein-coupled receptor protein
gi|18633577|dbj|E51301.1|[18633577]

461: E51300 Novel G protein-coupled receptor protein and gene of said G protein-coupled receptor protein
gi|18633576|dbj|E51300.1|[18633576]

462: E51299 Novel G protein-coupled receptor protein and gene of said G protein-coupled receptor protein gi|18633575|dbj|E51299.1|[18633575]

463: E51298 Novel G protein-coupled receptor protein and gene of said G protein-coupled receptor protein gi|18633574|dbj|E51298.1|[18633574]

464: E51297 Novel G protein-coupled receptor protein and gene of said G protein-coupled receptor protein gi|18633573|dbj|E51297.1|[18633573]

465: E51296 Novel G protein-coupled receptor protein and gene of said G protein-coupled receptor protein gi|18633572|dbj|E51296.1|[18633572]

466: E50838 Novel G protein-coupled receptor
gi|18633543|dbj|E50838.1|[18633543]

467: E50837 Novel G protein-coupled receptor
gi|18633542|dbj|E50837.1|[18633542]

468: E50836 Novel G protein-coupled receptor gi|18633541|dbj|E50836.1|[18633541]

469: E50835 Novel G protein-coupled receptor
gi|18633540|dbj|E50835.1|[18633540]

470: E50834 Novel G protein-coupled receptor
gi|18633539|dbj|E50834.1|[18633539]

471: E50833 Novel G protein-coupled receptor
gi|18633538|dbj|E50833.1|[18633538]

490: BD003056 Novel G protein-coupled receptor protein and DNA thereof
gi|18631017|dbj|BD003056.1|[18631017]

491: E55122 Novel G protein-coupled receptor and the G protein-coupled receptor gene
gi|18629753|dbj|E55122.1|[18629753]

492: E55121 Novel G protein-coupled receptor and the G protein-coupled receptor gene
gi|18629752|dbj|E55121.1|[18629752]

493: E55120 Novel G protein-coupled receptor and the G protein-coupled receptor gene
gi|18629751|dbj|E55120.1|[18629751]

494: E55119 Novel G protein-coupled receptor and the G protein-coupled receptor gene
gi|18629750|dbj|E55119.1|[18629750]

495: E55118 Novel G protein-coupled receptor and the G protein-coupled receptor gene
gi|18629749|dbj|E55118.1|[18629749]

496: E55117 Novel G protein-coupled receptor and the G protein-coupled receptor gene
gi|18629748|dbj|E55117.1|[18629748]

497: E49128 Novel G protein-conjugated receptor protein
gi|18629265|dbj|E49128.1|[18629265]

498: E49127 Novel G protein-conjugated receptor protein
gi|18629264|dbj|E49127.1|[18629264]

499: E49126 Novel G protein-conjugated receptor protein
gi|18629263|dbj|E49126.1|[18629263]

500: E49125 Novel G protein-conjugated receptor protein gi|18629262|dbj|E49125.1|[18629262]

501: D21847
Human mRNA for T cell receptor alpha chain TcHST2Va7, V segment, J segment and C region
gi|431140|dbj|D21847.1|HUMTCHST24[431140]

502: D21846
Human mRNA for T cell receptor beta chain HPBL3xVb20, V segment, D segment, J segment and C region
gi|431139|dbj|D21846.1|HUMHPBL3X3[431139]

503: D21845
Human mRNA for T cell receptor alpha chain HPBL3xVa7, V segment, J segment and C region
gi|431138|dbj|D21845.1|HUMHPBL3X2[431138]

504: D21844
Human mRNA for T cell receptor alpha chain HPBL(-)Va7, V segment, J segment and C region
gi|431137|dbj|D21844.1|HUMCHPBL1[431137]

505: D13083
Human mRNA for T-cell receptor beta-chain V region, partial cds, clone WBDM19C
gi|407766|dbj|D13083.1|HUMVB73B[407766]

506: D13085
Human mRNA for T-cell receptor beta-chain V region, partial cds, clone WBDM28A
gi|407764|dbj|D13085.1|HUMVB69B[407764]

507: D13088
Human TCRBV2.3a mRNA for T-cell receptor beta-chain V region, partial cds
gi|407762|dbj|D13088.1|HUMVB23A[407762]

508: D13087
Human TCRBV2.1c mRNA for T-cell receptor beta-chain V region, partial cds
gi|407760|dbj|D13087.1|HUMVB21C[407760]

509: D13082
Human mRNA for T-cell receptor beta-chain V region, partial cds, clone WBDM17A
gi|407758|dbj|D13082.1|HUMVB21AA[407758]

510: D13086
Human TCRBV20.1a mRNA for T-cell receptor beta-chain V region, partial cds
gi|407756|dbj|D13086.1|HUMVB201A[407756]

511: D13084
Human TCRBV12.5a mRNA for T-cell receptor beta-chain V region, partial cds
gi|407754|dbj|D13084.1|HUMVB125A[407754]

512: D13073
Human TCRAVN1 mRNA for T-cell receptor alpha-chain V region, partial cds
gi|407752|dbj|D13073.1|HUMVAN1[407752]

513: D13079
Human TCRAV8.1a mRNA for T-cell receptor alpha-chain V region, partial cds
gi|407750|dbj|D13079.1|HUMVA81A[407750]

514: D13069
Human TCRAV5.1a mRNA for T-cell receptor alpha-chain V region, partial cds
gi|407748|dbj|D13069.1|HUMVA51A[407748]

515: D13078
Human TCRAV2.5a mRNA for T-cell receptor alpha-chain V region, partial cds
gi|407746|dbj|D13078.1|HUMVA25A[407746]

516: D13072

Human mRNA for T-cell receptor alpha-chain V-J-C, partial cds, clone WADM13D
gi|407744|dbj|D13072.1|HUMVA221AJ[407744]

517: D13076
Human TCRAV21.1a mRNA for T-cell receptor alpha-chain V region, partial cds
gi|407742|dbj|D13076.1|HUMVA211A[407742]

518: D13071
Human mRNA for T-cell receptor alpha-chain V region, partial cds, clone WADM11H
gi|407740|dbj|D13071.1|HUMVA171A[407740]

519: D13074
Human TCRAV14.1a mRNA for T-cell receptor alpha-chain V region, partial cds
gi|407738|dbj|D13074.1|HUMVA141A[407738]

520: D13070
Human TCRAV1.3a mRNA for T-cell receptor alpha-chain V region, partial cds
gi|407736|dbj|D13070.1|HUMVA13A[407736]

521: D13077
Human TCRAV1.2a mRNA for T-cell receptor alpha-chain V region, partial cds
gi|407734|dbj|D13077.1|HUMVA12A[407734]

522: D13075
Human TCRAV10.1a mRNA for T-cell receptor alpha-chain V region, partial cds
gi|407732|dbj|D13075.1|HUMVA101A[407732]

523: D13081
Human mRNA for T-cell receptor alpha-chain J segment, partial cds, clone WADM36G
gi|407730|dbj|D13081.1|HUMJAAC17[407730]

524: D13080
Human mRNA for T-cell receptor alpha-chain J segment, partial cds, clone WADM36A
gi|407728|dbj|D13080.1|HUMJAAB19[407728]

525: D16584
Homo sapiens mRNA for T cell receptor beta chain, N-terminal gi|391732|dbj|D16584.1|HUMTCRB17[391732]

526: D16586
Homo sapiens mRNA for T cell receptor alpha chain, N-terminal
gi|391731|dbj|D16586.1|HUMTCRA17[391731]

527: D16585
Homo sapiens mRNA for T cell receptor alpha chain, N-terminal
gi|391730|dbj|D16585.1|HUMTCRA32[391730]

528: NM_003268
Homo sapiens toll-like receptor 5 (TLR5), mRNA
gi|19718736|ref|NM_003268.3|[19718736]

529: NM_003265
Homo sapiens toll-like receptor 3 (TLR3), mRNA
gi|19718735|ref|NM_003265.2|[19718735]

530: NM_003264
Homo sapiens toll-like receptor 2 (TLR2), mRNA
gi|19718733|ref|NM_003264.2|[19718733]

531: NM_003263
Homo sapiens toll-like receptor 1 (TLR1), mRNA
gi|19718732|ref|NM_003263.2|[19718732]

534: NM_020350
Homo sapiens angiotensin II, type I receptor-associated protein (ATRAP), mRNA
gi|19705427|ref|NM_020350.2|[19705427]

535: AY081843
Homo sapiens GnRH receptor II 5TM mRNA, complete cds
gi|19697895|gb|AY081843.1|[19697895]

539: NM_016511
Homo sapiens C-type lectin-like receptor-1 (LOC51267), mRNA
gi|7706062|ref|NM_016511.1|[7706062]

540: NM_016509
Homo sapiens C-type lectin-like receptor-2 (LOC51266), mRNA
gi|7706060|ref|NM_016509.1|[7706060]

546: AL713657
Homo sapiens mRNA; cDNA DKFZp547G1215 (from clone DKFZp547G1215)
gi|19584339|emb|AL713657.1|HSM802985[19584339]

547: AJ438313
Homo sapiens partial mRNA for KIT protein
gi|19571549|emb|AJ438313.1|HSA438313[19571549]

575: AF390036
Homo sapiens FCRLd mRNA, partial cds
gi|16611715|gb|AF390036.1|[16611715]

576: AF329495
Homo sapiens FCRLe mRNA, complete cds
gi|16506270|gb|AF329495.1|[16506270]

577: AF329494
Homo sapiens FCRLc1 mRNA, complete cds
gi|16506268|gb|AF329494.1|[16506268]

578: AF329493
Homo sapiens FCRLb mRNA, complete cds
gi|16506266|gb|AF329493.1|[16506266]

579: AF329491
Homo sapiens FCRLc2 mRNA, complete cds
gi|16506262|gb|AF329491.1|[16506262]

580: AF329489
Homo sapiens FCRLa mRNA, complete cds
gi|16506258|gb|AF329489.1|[16506258]

582: AB060695
Homo sapiens TLR5 mRNA for Toll-like receptor 5, complete cds
gi|13810567|dbj|AB060695.1|[13810567]

583: AJ276429
Homo sapiens mRNA for 19A protein
gi|12619176|emb|AJ276429.2|HSA276429[12619176]

584: AL136801
Homo sapiens mRNA; cDNA DKFZp434K0220 (from clone DKFZp434K0220); complete cds
gi|12053114|emb|AL136801.1|HSM801769[12053114]

585: AL136652
Homo sapiens mRNA; cDNA DKFZp564O1762 (from clone DKFZp564O1762); complete cds
gi|12052829|emb|AL136652.1|HSM801622[12052829]

587: AB012911
Homo sapiens mRNA for Frizzled-6, complete cds
gi|3062802|dbj|AB012911.1|[3062802]

589: AY071862
Homo sapiens crinkled (CR) mRNA, complete cds
gi|19568064|gb|AY071862.1|[19568064]

596: NM_133169
Homo sapiens osteoclast-associated receptor (OSCAR), transcript variant 2, mRNA
gi|19557667|ref|NM_133169.1|[19557667]

597: NM_133168
Homo sapiens osteoclast-associated receptor (OSCAR), transcript variant 3, mRNA
gi|19557663|ref|NM_133168.1|[19557663]

598: NM_130771
Homo sapiens osteoclast-associated receptor (OSCAR), transcript variant 1, mRNA
gi|19557659|ref|NM_130771.1|[19557659]

599: AF426461
Homo sapiens FREB mRNA, complete cds
gi|18056674|gb|AF426461.1|[18056674]

600: AF428134
Homo sapiens T-cell receptor beta-chain (TCRVb13.1-Jb1.5) mRNA, partial cds
gi|16566700|gb|AF428134.1|[16566700]

601: AF428133
Homo sapiens T-cell receptor beta-chain (TCRVb13.1-Jb1.2) mRNA, partial cds
gi|16566697|gb|AF428133.1|[16566697]

602: AF428132
Homo sapiens T-cell receptor beta-chain (TCRVb8.1-Jb2.3) mRNA, partial cds
gi|16566694|gb|AF428132.1|[16566694]

603: AF428131
Homo sapiens T-cell receptor beta-chain (TCRVb8.2-Jb2.7) mRNA, partial cds
gi|16566691|gb|AF428131.1|[16566691]

604: AF428130
Homo sapiens T-cell receptor beta-chain (TCRVb8.1-Jb2.3) mRNA, partial cds
gi|16566688|gb|AF428130.1|[16566688]

605: AF428129
Homo sapiens T-cell receptor beta-chain (TCRVb7.1-Jb1.2) mRNA, partial cds
gi|16566685|gb|AF428129.1|[16566685]

606: AF428128
Homo sapiens T-cell receptor beta-chain (TCRVb7.2-Jb1.6) mRNA, partial cds
gi|16566682|gb|AF428128.1|[16566682]

607: AF428127
Homo sapiens T-cell receptor beta-chain (TCRVb7.1-Jb1.2) mRNA, partial cds
gi|16566679|gb|AF428127.1|[16566679]

608: AF428126
Homo sapiens T-cell receptor beta-chain (TCRVb7.2-Jb1.2) mRNA, partial cds
gi|16566676|gb|AF428126.1|[16566676]

609: AF428125
Homo sapiens T-cell receptor beta-chain (TCRVb7.1-Jb1.5) mRNA, partial cds
gi|16566673|gb|AF428125.1|[16566673]

611: AF242456
Homo sapiens interleukin 13 receptor alpha 1-binding protein-1 mRNA, complete cds
gi|19548138|gb|AF242456.1|[19548138]

616: S57283
Homo sapiens endothelin ET-B receptor mRNA, complete cds
gi|298321|gb|S57283.1|[298321]

617: L14854
Homo sapiens T cell receptor TCR-beta D38 (TCRB) mRNA, partial cds
gi|292794|gb|L14854.1|HUMTCRD38[292794]

618: NM_024080
Homo sapiens transient receptor potential cation channel, subfamily M, member 8 (TRPM8), mRNA
gi|13129071|ref|NM_024080.1|[13129071]

619: AY069961
Homo sapiens lymphocyte effector toxicity activation ligand (LETAL) mRNA, complete cds
gi|19525539|gb|AY069961.1|[19525539]

620: U43901
Homo sapiens 37 kD laminin receptor precursor/p40 ribosome associated protein (LAMR1) gene, complete cds; and E2 small nuclear RNA gene, complete sequence
gi|19483807|gb|U43901.2|HSU43901[19483807]

621: NM_021044
Homo sapiens desert hedgehog homolog (Drosophila) (DHH), mRNA gi|19482157|ref|NM_021044.1|[19482157]

622: AC078860
Homo sapiens 12q BAC RP11-186F10 (Roswell Park Cancer Institute Human BAC Library) complete sequence
gi|13491193|gb|AC078860.19|[13491193]

623: AC003683
Homo sapiens x BAC RP1-147H15 (Roswell Park Cancer Institute Human BAC Library) complete sequence
gi|13489135|gb|AC003683.2|[13489135]

624: AC007397
Homo sapiens 12p13 BAC RPCI11-439G16 (Roswell Park Cancer Institute Human BAC Library) complete sequence
gi|5685879|gb|AC007397.21|[5685879]

625: AC007784
Homo sapiens 12p13 BAC RPCI11-1092P21 (Roswell Park Cancer Library Human BAC Library) complete sequence
gi|5597031|gb|AC007784.7|[5597031]

627: AF451730
Homo sapiens isolate R5255 T cell receptor delta chain (TRD@) mRNA, partial cds
gi|19401669|gb|AF451730.1|[19401669]

628: AF451729
Homo sapiens isolate Q5252 T cell receptor delta chain (TRD@) mRNA, partial cds
gi|19401667|gb|AF451729.1|[19401667]

629: AF451728
Homo sapiens isolate P5739 T cell receptor delta chain (TRD@) mRNA, partial cds
gi|19401665|gb|AF451728.1|[19401665]

630: AF451727
Homo sapiens isolate P5742 T cell receptor delta chain (TRD@) mRNA, partial cds
gi|19401663|gb|AF451727.1|[19401663]

631: AF451726
Homo sapiens isolate P5738 T cell receptor delta chain (TRD@) mRNA, partial cds
gi|19401661|gb|AF451726.1|[19401661]

632: AF451725
Homo sapiens isolate O581 T cell receptor delta chain (TRD@) mRNA, partial cds
gi|19401658|gb|AF451725.1|[19401658]

633: AF451724
Homo sapiens isolate N505 T cell receptor delta chain (TRD@) mRNA, partial cds
gi|19401656|gb|AF451724.1|[19401656]

634: AF451723
Homo sapiens isolate N504 T cell receptor delta chain (TRD@) mRNA, partial cds
gi|19401653|gb|AF451723.1|[19401653]

635: AF451722
Homo sapiens isolate P5729 T cell receptor delta chain (TRD@) mRNA, partial cds
gi|19401650|gb|AF451722.1|[19401650]

636: AF451721
Homo sapiens isolate P5728 T cell receptor delta chain (TRD@) mRNA, partial cds
gi|19401647|gb|AF451721.1|[19401647]

637: AF451720
Homo sapiens isolate O268 T cell receptor delta chain (TRD@) mRNA, partial cds
gi|19401645|gb|AF451720.1|[19401645]

638: AF451719
Homo sapiens isolate O38 T cell receptor delta chain (TRD@) mRNA, partial cds
gi|19401642|gb|AF451719.1|[19401642]

639: AF451718
Homo sapiens isolate O37 T cell receptor delta chain (TRD@) mRNA, partial cds
gi|19401640|gb|AF451718.1|[19401640]

640: AF449218
Homo sapiens 43kDa acetylcholine receptor-associated protein (RAPSN) mRNA, complete cds
gi|19310212|gb|AF449218.1|[19310212]

644: BC025704
Homo sapiens, leukocyte immunoglobulin-like receptor, subfamily B (with TM and ITIM domains), member 5, clone MGC:34418 IMAGE:5223581, mRNA, complete cds
gi|19344005|gb|BC025704.1|[19344005]

645: BC025713
Homo sapiens, T-cell receptor interacting molecule, clone MGC:34314 IMAGE:5227396, mRNA, complete cds
gi|19343996|gb|BC025713.1|[19343996]

646: BC025722
Homo sapiens, adenosine A2b receptor, clone MGC:34640 IMAGE:5198898, mRNA, complete cds
gi|19343938|gb|BC025722.1|[19343938]

647: BC025717
Homo sapiens, chemokine (C-C motif) receptor-like 2, clone MGC:34104 IMAGE:5228561, mRNA, complete cds
gi|19343936|gb|BC025717.1|[19343936]

648: BC025695
Homo sapiens, endothelial differentiation, lysophosphatidic acid G-protein-coupled receptor, 4, clone MGC:34227 IMAGE:5209267, mRNA, complete cds
gi|19343926|gb|BC025695.1|[19343926]

650: BC025691
Homo sapiens, interleukin 2 receptor, beta, clone MGC:34584 IMAGE:5207833, mRNA, complete cds
gi|19343610|gb|BC025691.1|[19343610]

651: AF474992
Homo sapiens G protein-coupled receptor SNSR6 gene, complete cds
gi|19338917|gb|AF474992.1|[19338917]

652: AF474991
Homo sapiens G protein-coupled receptor SNSR5 gene, complete cds
gi|19338915|gb|AF474991.1|[19338915]

653: AF474990
Homo sapiens G protein-coupled receptor SNSR4 gene, complete cds
gi|19338913|gb|AF474990.1|[19338913]

654: AF474989
Homo sapiens G protein-coupled receptor SNSR3 gene, complete cds
gi|19338911|gb|AF474989.1|[19338911]

655: AF474988
Homo sapiens G protein-coupled receptor SNSR2 gene, complete cds
gi|19338909|gb|AF474988.1|[19338909]

656: AF474987
Homo sapiens G protein-coupled receptor SNSR1 gene, complete cds
gi|19338907|gb|AF474987.1|[19338907]

695: AF453877
Homo sapiens neuronal nicotinic receptor beta 4 subunit precursor, gene, exon 1 and partial cds
gi|18042122|gb|AF453877.1|[18042122]

697: U62556
Homo sapiens chemokine receptor-like protein (TER1) gene, complete cds
gi|1468978|gb|U62556.1|HSU62556[1468978]

698: AJ011371
Homo sapiens mRNA for serotonin 4 receptor, splice variant h5-HT4(e)
gi|3646277|emb|AJ011371.1|HSAJ1371[3646277]

712: AY059419
Homo sapiens killer-cell immunoglobulin-like receptor (KIR3DL1) mRNA, KIR3DL1*011 allele, partial cds gi|19224338|gb|AY059419.1|[19224338]

713: AY059418
Homo sapiens killer-cell immunoglobulin-like receptor (KIR3DL2) mRNA, KIR3DL2*010 allele, partial cds
gi|19224336|gb|AY059418.1|[19224336]

714: AY059417
Homo sapiens killer-cell immunoglobulin-like receptor KIR3DL1/2v mRNA, partial cds
gi|19224334|gb|AY059417.1|[19224334]

715: AY059420
Homo sapiens killer-cell immunoglobulin-like receptor (KIR3DL2) mRNA, KIR3DL2*012 allele, partial cds
gi|19224332|gb|AY059420.1|[19224332]

716: AC079385
Homo sapiens 12q BAC RP11-482D24 (Roswell Park Cancer Institute Human BAC Library) complete sequence
gi|14670063|gb|AC079385.18|[14670063]

717: AC078889
Homo sapiens 12q BAC RP11-335I12 (Roswell Park Cancer Institute Human BAC Library) complete sequence
gi|11072039|gb|AC078889.20|[11072039]

718: AC010168
Homo sapiens 12p12-31.7-32.2 BAC RP11-174G6 (Rosewell Park Cancer Institute Human Bac Library) complete sequence
gi|6855156|gb|AC010168.6|[6855156]

719: U14188
Homo sapiens LERK-4 (EPLG4) mRNA, complete cds
gi|642834|gb|U14188.1|HSU14188[642834]

720: U14187
Homo sapiens LERK-3 (EPLG3) mRNA, complete cds gi|642832|gb|U14187.1|HSU14187[642832]

721: U15637
Homo sapiens CD40 binding protein (CD40BP) mRNA, complete cds
gi|595910|gb|U15637.1|HSU15637[595910]

722: AF262304
Homo sapiens clone 7 CC chemokine receptor 3-like mRNA, partial sequence, alternatively spliced
gi|19171650|gb|AF262304.1|[19171650]

723: AF262303
Homo sapiens clone 6 CC chemokine receptor 3 (CCR3) mRNA, partial cds
gi|19171648|gb|AF262303.1|[19171648]

724: AF262302
Homo sapiens clone 5 CC chemokine receptor 3 (CCR3) mRNA, partial cds
gi|19171646|gb|AF262302.1|[19171646]

725: AF262301
Homo sapiens clone 4 CC chemokine receptor 3 (CCR3) mRNA, partial cds
gi|19171644|gb|AF262301.1|[19171644]

726: AF262300
Homo sapiens clone 2 CC chemokine receptor 3 (CCR3) mRNA, partial cds
gi|19171642|gb|AF262300.1|[19171642]

727: AF262299
Homo sapiens clone 1 CC chemokine receptor 3 (CCR3) mRNA, partial cds
gi|19171640|gb|AF262299.1|[19171640]

729: AF247361
Homo sapiens CC chemokine receptor 3 (CCR3) gene, complete cds
gi|19110542|gb|AF247361.1|[19110542]

730: AF247360
Homo sapiens CC chemokine receptor 3 (CCR3) gene, promoter region and partial sequence
gi|19110541|gb|AF247360.1|[19110541]

731: AF247359
Homo sapiens CC chemokine receptor 3 (CCR3) gene, promoter region and partial sequence
gi|19110540|gb|AF247359.1|[19110540]

733: AF416619
Homo sapiens prolactin receptor short isoform 1a (PRLR) mRNA, complete cds, alternatively spliced
gi|16506717|gb|AF416619.1|[16506717]

734: AF416618
Homo sapiens prolactin receptor short isoform 1b (PRLR) mRNA, complete cds, alternatively spliced
gi|16506715|gb|AF416618.1|[16506715]

736: AJ303165
Homo sapiens partial gene for putative transmembrane receptor
gi|13162199|emb|AJ303165.1|HSA303165[13162199]

738: AF350881
Homo sapiens channel kinase 2 (CHAK2) mRNA, complete cds
gi|18860923|gb|AF350881.2|[18860923]

739: AF022044
Homo sapiens natural killer cell receptor KIR3DS1 variant mRNA, complete cds
gi|2760894|gb|AF022044.1|[2760894]

740: AF034773
Homo sapiens natural killer cell inhibitory receptor (KIR2DL4) mRNA, variant 3, complete cds
gi|2739181|gb|AF034773.1|[2739181]

741: AF034772
Homo sapiens natural killer cell inhibitory receptor (KIR2DL4) mRNA, variant 2, complete cds gi|2739179|gb|AF034772.1|[2739179]

742: AF034771
Homo sapiens natural killer cell inhibitory receptor (KIR2DL4) mRNA, variant 1, complete cds
gi|2739177|gb|AF034771.1|[2739177]

743: AF022047
Homo sapiens natural killer cell inhibitory receptor KIR2DS3 variant mRNA, complete cds
gi|2738966|gb|AF022047.1|[2738966]

744: AF022046
Homo sapiens natural killer cell inhibitory receptor KIR2DS1 variant mRNA, complete cds
gi|2738964|gb|AF022046.1|[2738964]

745: AF022045
Homo sapiens natural killer cell receptor KIR2DL1 variant mRNA, complete cds
gi|2738962|gb|AF022045.1|[2738962]

746: U56255
Homo sapiens CW-1 mRNA, complete cds
gi|1399688|gb|U56255.1|HSU56255[1399688]

747: AJ422056
Homo sapiens partial GRM5 gene for metabotrophic glutamate receptor, exon 1A
gi|19069804|emb|AJ422056.1|HSA422056[19069804]

748: AY028912
Homo sapiens ectodysplasin A receptor associated death domain (EDARADD) gene, exon 7 and complete cds, alternatively spliced
gi|19067944|gb|AY028912.1|AY028906S7[19067944]

749: AY028911
Homo sapiens ectodysplasin A receptor associated death domain (EDARADD) gene, exon 6
gi|19067943|gb|AY028911.1|AY028906S6[19067943]

750: AY028910
Homo sapiens ectodysplasin A receptor associated death domain (EDARADD) gene, exon 5
gi|19067942|gb|AY028910.1|AY028906S5[19067942]

751: AY028909
Homo sapiens ectodysplasin A receptor associated death domain (EDARADD) gene, exon 4
gi|19067941|gb|AY028909.1|AY028906S4[19067941]

752: AY028908
Homo sapiens ectodysplasin A receptor associated death domain (EDARADD) gene, exon 3
gi|19067940|gb|AY028908.1|AY028906S3[19067940]

753: AY028907
Homo sapiens ectodysplasin A receptor associated death domain (EDARADD) gene, exon 2
gi|19067939|gb|AY028907.1|AY028906S2[19067939]

754: AY028906
Homo sapiens ectodysplasin A receptor associated death domain (EDARADD) gene, exon 1
gi|19067938|gb|AY028906.1|AY028906S1[19067938]

755: AH010677
Homo sapiens ectodysplasin A receptor associated death domain (EDARADD) gene, complete cds, alternatively spliced
gi|19067937|gb|AH010677.1|SEG_AY028906S[19067937]

756: AY028913
Homo sapiens ectodysplasia A receptor associated death domain A (EDARADD) mRNA, complete cds; alternatively spliced
gi|19067935|gb|AY028913.1|[19067935]

757: BM735809
06E08 Canine Brain cDNA Library Canis familiaris cDNA 5' similar to Homo sapiens glycine receptor, beta, mRNA sequence
gi|19057142|gb|BM735809.1|BM735809[19057142]

758: BM735756
06A09 Canine Brain cDNA Library Canis familiaris cDNA 5' similar to Homo sapiens glycine receptor, beta subunit, mRNA sequence
gi|19057089|gb|BM735756.1|BM735756[19057089]

759: BM735711
10E11 Canine Brain cDNA Library Canis familiaris cDNA 5' similar to Homo sapiens protein tyrosine phosphatase, receptor-type, Z polypeptide 1, mRNA sequence
gi|19057044|gb|BM735711.1|BM735711[19057044]

762: AC007165
Homo sapiens BAC clone RP11-451C2 from 2, complete sequence
gi|19033999|gb|AC007165.4|[19033999]

763: AF245699
Homo sapiens type 1 angiotensin II receptor (AGTR1) gene, complete cds
gi|7862074|gb|AF245699.1|[7862074]

764: BC024229
Homo sapiens, prostaglandin E receptor 3 (subtype EP3), clone MGC:27302 IMAGE:4660371, mRNA, complete cds
gi|18999476|gb|BC024229.1|[18999476]

783: AJ417555
Homo sapiens partial mRNA for killer cell immunoglobulin receptor (KIR2DS4 gene), strain 4053
gi|18958228|emb|AJ417555.1|HSA417555[18958228]

784: AJ417554
Homo sapiens partial mRNA for killer cell immunoglobulin receptor (KIR2DS4 gene), strain 3321
gi|18958226|emb|AJ417554.1|HSA417554[18958226]

786: NM_003877
Homo sapiens STAT induced STAT inhibitor-2 (STATI2), mRNA gi|18921206|ref|NM_003877.2|[18921206]

787: NM_017662
Homo sapiens transient receptor potential cation channel, subfamily M, member 6 (TRPM6), mRNA
gi|18921092|ref|NM_017662.3|[18921092]

788: NM_133181
Homo sapiens epidermal growth factor receptor pathway substrate 8 related protein 3 (EPS8R3), mRNA
gi|18874727|ref|NM_133181.1|[18874727]

802: M13823
Homo sapiens T cell receptor gamma chain (TCRG) gene, partial cds
gi|292736|gb|M13823.1|HUMTCGXK[292736]

803: L12398
Homo sapiens dopamine receptor D4 (DRD4) mRNA, complete cds
gi|291945|gb|L12398.1|HUMD4C[291945]

804: M86383
Homo sapiens nicotinic acetylcholine receptor alpha 3 subunit precursor, mRNA, complete cds
gi|177897|gb|M86383.1|HUMA3NARSP[177897]

805: NG_000019
Homo sapiens chorionic gonadotropin beta region (CGB@) on chromosome 19
gi|18860921|ref|NG_000019.2|[18860921]

807: NM_012245
Homo sapiens SKI-interacting protein (SNW1), mRNA
gi|18860912|ref|NM_012245.2|[18860912]

808: NM_006750
Homo sapiens syntrophin, beta 2 (dystrophin-associated protein A1, 59kD, basic component 2) (SNTB2), transcript variant 1, mRNA
gi|18860911|ref|NM_006750.2|[18860911]

809: NM_130845
Homo sapiens syntrophin, beta 2 (dystrophin-associated protein A1, 59kD, basic component 2) (SNTB2), transcript variant 2, mRNA
gi|18860909|ref|NM_130845.1|[18860909]

810: NM_002846
Homo sapiens protein tyrosine phosphatase, receptor type, N (PTPRN), mRNA
gi|18860905|ref|NM_002846.2|[18860905]

811: NM_002845
Homo sapiens protein tyrosine phosphatase, receptor type, M (PTPRM), mRNA
gi|18860903|ref|NM_002845.2|[18860903]

812: NM_002844
Homo sapiens protein tyrosine phosphatase, receptor type, K (PTPRK), mRNA
gi|18860901|ref|NM_002844.2|[18860901]

813: NM_002843
Homo sapiens protein tyrosine phosphatase, receptor type, J (PTPRJ), mRNA
gi|18860899|ref|NM_002843.2|[18860899]

814: NM_002841
Homo sapiens protein tyrosine phosphatase, receptor type, G (PTPRG), mRNA
gi|18860897|ref|NM_002841.2|[18860897]

815: NM_130440
Homo sapiens protein tyrosine phosphatase, receptor type, F (PTPRF), transcript variant 2, mRNA
gi|18860895|ref|NM_130440.1|[18860895]

816: NM_130393
Homo sapiens protein tyrosine phosphatase, receptor type, D (PTPRD), transcript variant 4, mRNA
gi|18860893|ref|NM_130393.1|[18860893]

817: NM_130392

Homo sapiens protein tyrosine phosphatase, receptor type, D (PTPRD), transcript variant 3, mRNA
gi|18860891|ref|NM_130392.1|[18860891]

818: NM_130391
Homo sapiens protein tyrosine phosphatase, receptor type, D (PTPRD), transcript variant 2, mRNA
gi|18860889|ref|NM_130391.1|[18860889]

819: NM_003682
Homo sapiens MAP-kinase activating death domain (MADD), transcript variant 4, mRNA
gi|18860876|ref|NM_003682.2|[18860876]

820: NM_130476
Homo sapiens MAP-kinase activating death domain (MADD), transcript variant 8, mRNA
gi|18860874|ref|NM_130476.1|[18860874]

821: NM_130475
Homo sapiens MAP-kinase activating death domain (MADD), transcript variant 7, mRNA
gi|18860872|ref|NM_130475.1|[18860872]

822: NM_002840
Homo sapiens protein tyrosine phosphatase, receptor type, F (PTPRF), transcript variant 1, mRNA
gi|18860871|ref|NM_002840.2|[18860871]

823: NM_130474
Homo sapiens MAP-kinase activating death domain (MADD), transcript variant 6, mRNA
gi|18860869|ref|NM_130474.1|[18860869]

824: NM_130473
Homo sapiens MAP-kinase activating death domain (MADD), transcript variant 5, mRNA
gi|18860867|ref|NM_130473.1|[18860867]

825: NM_130472
Homo sapiens MAP-kinase activating death domain (MADD), transcript variant 3, mRNA
gi|18860865|ref|NM_130472.1|[18860865]

826: NM_130471
Homo sapiens MAP-kinase activating death domain (MADD), transcript variant 2, mRNA
gi|18860863|ref|NM_130471.1|[18860863]

827: NM_130470
Homo sapiens MAP-kinase activating death domain (MADD), transcript variant 1, mRNA
gi|18860861|ref|NM_130470.1|[18860861]

828: NM_006504
Homo sapiens protein tyrosine phosphatase, receptor type, E (PTPRE), transcript variant 1, mRNA
gi|18860860|ref|NM_006504.2|[18860860]

829: NM_130435
Homo sapiens protein tyrosine phosphatase, receptor type, E (PTPRE), transcript variant 2, mRNA
gi|18860858|ref|NM_130435.1|[18860858]

830: AJ431177
Homo sapiens mRNA for WIRE protein
gi|18857713|emb|AJ431177.1|HSA431177[18857713]

831: NM_006474
Homo sapiens lung type-I cell membrane-associated glycoprotein (T1A-2), mRNA
gi|18767663|ref|NM_006474.2|[18767663]

833: NM_006794
Homo sapiens G protein-coupled receptor 75 (GPR75), mRNA
gi|5803024|ref|NM_006794.1|[5803024]

834: NM_002842
Homo sapiens protein tyrosine phosphatase, receptor type, H (PTPRH), mRNA
gi|4506312|ref|NM_002842.1|[4506312]

835: NM_002839
Homo sapiens protein tyrosine phosphatase, receptor type, D (PTPRD), transcript variant 1, mRNA
gi|4506308|ref|NM_002839.1|[4506308]

836: BC024145
Homo sapiens, TNF receptor-associated factor 1, clone MGC:10353 IMAGE:3832475, mRNA, complete cds
gi|18848176|gb|BC024145.1|[18848176]

837: AF469756
Homo sapiens clone S9 interleukin-1 receptor type I (IL1R1) gene, partial sequence
gi|18846656|gb|AF469756.1|[18846656]

838: AF469755
Homo sapiens clone S8 interleukin-1 receptor type I (IL1R1) gene, partial sequence
gi|18846655|gb|AF469755.1|[18846655]

839: AF469754
Homo sapiens clone S7 interleukin-1 receptor type I (IL1R1) gene, partial sequence
gi|18845036|gb|AF469754.1|[18845036]

841: BM565570
ih27b03.x1 Human insulinoma Homo sapiens cDNA clone IMAGE: 3' similar to SW:FCEG_HUMAN P30273 HIGH AFFINITY IMMUNOGLOBULIN EPSILON RECEPTOR GAMMA-SUBUNIT
PRECURSOR ;, mRNA sequence
gi|18825852|gb|BM565570.1|BM565570[18825852]

842: AF416711
Homo sapiens Fc-gamma receptor IIc5 mRNA, partial cds gi|18765992|gb|AF416711.1|[18765992]

843: NM_023068
Homo sapiens sialoadhesin (SN), mRNA
gi|18765743|ref|NM_023068.2|[18765743]

844: NM_004782
Homo sapiens synaptosomal-associated protein, 29kD (SNAP29), mRNA
gi|18765736|ref|NM_004782.2|[18765736]

845: NM_130798
Homo sapiens synaptosomal-associated protein, 23kD (SNAP23), transcript variant 2, mRNA
gi|18765730|ref|NM_130798.1|[18765730]

846: NM_003825
Homo sapiens synaptosomal-associated protein, 23kD (SNAP23), transcript variant 1, mRNA
gi|18765728|ref|NM_003825.2|[18765728]

850: AF439409
Homo sapiens G-protein-coupled receptor kinase 7 (GRK7) mRNA, GRK7-S allele, complete cds
gi|17933258|gb|AF439409.1|[17933258]

851: NM_032211
Homo sapiens lysyl oxidase-like 4 (LOXL4), mRNA
gi|16933522|ref|NM_032211.4|[16933522]

852: AF411122
Homo sapiens importin 4 mRNA, complete cds
gi|18700634|gb|AF411122.1|[18700634]

894: NM_130441
Homo sapiens C-type (calcium dependent, carbohydrate-recognition domain) lectin, superfamily member 11 (CLECSF11), mRNA
gi|18466805|ref|NM_130441.1|[18466805]

895: NM_030876
Homo sapiens olfactory receptor, family 5, subfamily V, member 1 (OR5V1), mRNA
gi|14495550|ref|NM_030876.2|[14495550]

896: NM_032732
Homo sapiens hypothetical protein MGC10763 (IL17RL), mRNA
gi|14249349|ref|NM_032732.1|[14249349]

897: NM_030959
Homo sapiens olfactory receptor, family 12, subfamily D, member 3 (OR12D3), mRNA
gi|13624334|ref|NM_030959.1|[13624334]

898: NM_018842
Homo sapiens insulin receptor tyrosine kinase substrate (LOC55971), mRNA
gi|10047119|ref|NM_018842.1|[10047119]

899: NM_018844
Homo sapiens B-cell receptor-associated protein BAP29 (BAP29), mRNA
gi|9994198|ref|NM_018844.1|[9994198]

900: NM_002825
Homo sapiens pleiotrophin (heparin binding growth factor 8, neurite
growth-promoting factor 1) (PTN), mRNA
gi|18656935|ref|NM_002825.2|[18656935]

904: NM_016372
Homo sapiens seven transmembrane domain orphan receptor (TPRA40), mRNA
gi|7705964|ref|NM_016372.1|[7705964]

905: NM_014288
Homo sapiens integrin beta 3 binding protein (beta3-endonexin) (ITGB3BP), mRNA
gi|7657205|ref|NM_014288.1|[7657205]

906: L43588
Homo sapiens T cell antigen receptor mRNA, partial cds
gi|18654191|gb|L43588.1|HUMTCARF[18654191]

907: AB050954
Homo sapiens irs-2 gene for insulin receptor substrate-2, partial cds
gi|18652856|dbj|AB050954.1|[18652856]

923: U77589
Homo sapiens MHC class II HLA-DQ-alpha chain (HLA-DQA1) mRNA, HLA-DQA1*0104 allele, complete cds
gi|1916744|gb|U77589.1|HSU77589[1916744]

924: AF410465
Homo sapiens importin 9 mRNA, complete cds
gi|15529702|gb|AF410465.1|[15529702]

925: AF332759
Homo sapiens partially duplicated CHRNA7 gene, hybrid intron A/4 and partial exon 5
gi|13345792|gb|AF332759.1|[13345792]

926: AF332758
Homo sapiens alpha-7 nicotinic cholinergic receptor subunit (CHRNA7) gene, partial intron 4 and partial cds
gi|13345790|gb|AF332758.1|[13345790]

927: NM_003744
Homo sapiens numb homolog (Drosophila) (NUMB), mRNA
gi|18644887|ref|NM_003744.2|[18644887]

928: NM_003681
Homo sapiens pyridoxal (pyridoxine, vitamin B6) kinase (PDXK), mRNA
gi|18644884|ref|NM_003681.2|[18644884]

929: NM_080706
Homo sapiens transient receptor potential cation channel, subfamily V, member 1 (TRPV1), transcript variant 3, mRNA
gi|18375670|ref|NM_080706.1|[18375670]

930: NM_080705

Homo sapiens transient receptor potential cation channel, subfamily V, member 1 (TRPV1), transcript variant 4, mRNA
gi|18375668|ref|NM_080705.1|[18375668]

931: NM_080704
Homo sapiens transient receptor potential cation channel, subfamily V, member 1 (TRPV1), transcript variant 1, mRNA
gi|18375666|ref|NM_080704.1|[18375666]

932: NM_018727
Homo sapiens transient receptor potential cation channel, subfamily V, member 1 (TRPV1), transcript variant 2, mRNA
gi|18375664|ref|NM_018727.3|[18375664]

933: NM_080819
Homo sapiens G protein-coupled receptor 78 (GPR78), mRNA
gi|18201873|ref|NM_080819.1|[18201873]

934: NM_080738
Homo sapiens EDAR-associated death domain (EDARADD), mRNA
gi|18152768|ref|NM_080738.1|[18152768]

935: NM_080491 Homo sapiens GRB2-associated binding protein 2 (GAB2), transcript variant 1,mRNA gi|18105041|ref|NM_080491.1|[18105041]

936: NM_012296 Homo sapiens GRB2-associated binding protein 2 (GAB2), transcript variant 2,mRNA gi|18105040|ref|NM_012296.2|[18105040]

937: NM_032027 Homo sapiens beta-amyloid binding protein precursor (BBP), mRNA
gi|17738309|ref|NM_032027.2|[17738309]

938: NM_057159 Homo sapiens endothelial differentiation, lysophosphatidic acid G-protein-coupled receptor, 2 (EDG2), transcript variant 2, mRNA
gi|16950637|ref|NM_057159.1|[16950637]

939: NM_001401 Homo sapiens endothelial differentiation, lysophosphatidic acid G-protein-coupled receptor, 2 (EDG2), transcript variant 1, mRNA gi|16950635|ref|NM_001401.2|[16950635]

940: NM_007070 Homo sapiens FKBP-associated protein (FAP48), transcript variant 2, mRNA
gi|16933538|ref|NM_007070.2|[16933538]

941: NM_053274 Homo sapiens FKBP-associated protein (FAP48), transcript variant 1, mRNA
gi|16933536|ref|NM_053274.1|[16933536]

942: NM_003726 Homo sapiens src family associated phosphoprotein 1 (SCAP1), mRNA
gi|16753209|ref|NM_003726.2|[16753209]

943: NM_033632 Homo sapiens F-box and WD-40 domain protein 7 (archipelago homolog, Drosophila)(FBXW7), transcript variant 1, mRNA
gi|16117780|ref|NM_033632.1|[16117780]

944: NM_018315 Homo sapiens F-box and WD-40 domain protein 7 (archipelago homolog, Drosophila)(FBXW7), transcript variant 2, mRNA
gi|16117778|ref|NM_018315.2|[16117778]

945: NM_021203 Homo sapiens APMCF1 protein (APMCF1), mRNA
gi|14917112|ref|NM_021203.2|[14917112]

946: NM_002927 Homo sapiens regulator of G-protein signalling 13 (RGS13), mRNA
gi|14589857|ref|NM_002927.2|[14589857]

949: NM_020167 Homo sapiens neuromedin U receptor 2 (NMU2R), mRNA
gi|9910461|ref|NM_020167.1|[9910461]

950: NM_020149 Homo sapiens Meis1, myeloid ecotropic viral integration site 1 homolog 2 (mouse)(MEIS2), mRNA
gi|9910355|ref|NM_020149.1|[9910355]

951: AF190052 Homo sapiens interleukin 1 receptor type I (IL1R1) gene, exon 1C sequence
gi|9719300|gb|AF190052.1|[9719300]

952: NM_018965 Homo sapiens triggering receptor expressed on myeloid cells 2 (TREM2), mRNA gi|9507202|ref|NM_018965.1|[9507202]

953: NM_018643 Homo sapiens triggering receptor expressed on myeloid cells 1 (TREM1), mRNA gi|8924261|ref|NM_018643.1|[8924261]

954: NM_018647 Homo sapiens tumor necrosis factor receptor superfamily, member 19 (TNFRSF19),mRNA gi|8924251|ref|NM_018647.1|[8924251]

955: NM_018695 Homo sapiens erbb2 interacting protein (ERBB2IP), mRNA gi|8923908|ref|NM_018695.1|[8923908]

956: NM_017636 Homo sapiens transient receptor potential cation channel, subfamily M, member 4(TRPM4), mRNA gi|8923048|ref|NM_017636.1|[8923048]

958: NM_016559 Homo sapiens PXR2b protein (PXR2b), mRNA gi|7706670|ref|NM_016559.1|[7706670]

959: NM_016382 Homo sapiens natural killer cell receptor 2B4 (CD244), mRNA gi|7706528|ref|NM_016382.1|[7706528]

962: NM_015986 Homo sapiens cytokine receptor-like factor 3 (CRLF3), mRNA gi|7705331|ref|NM_015986.1|[7705331]

963: NM_014815 Homo sapiens KIAA0130 gene product (KIAA0130), mRNA gi|7661929|ref|NM_014815.1|[7661929]

964: NM_014053 Homo sapiens FLVCR protein (FLVCR), mRNA gi|7661707|ref|NM_014053.1|[7661707]

965: NM_014478 Homo sapiens calcitonin gene-related peptide-receptor component protein(CGRP-RCP), mRNA gi|7656976|ref|NM_014478.1|[7656976]

966: NM_012470
Homo sapiens transportin-SR (TRN-SR), mRNA gi|6912733|ref|NM_012470.1|[6912733]

967: NM_007357 Homo sapiens low density lipoprotein receptor defect C complementing (LDLC), mRNA gi|6678675|ref|NM_007357.1|[6678675]

969: NM_007324 Homo sapiens MAD, mothers against decapentaplegic homolog (Drosophila)interacting protein, receptor activation anchor (MADHIP), transcript variant 1, mRNA gi|6552338|ref|NM_007324.1|[6552338]

970: NM_007323 Homo sapiens MAD, mothers against decapentaplegic homolog (Drosophila)interacting protein, receptor activation anchor (MADHIP), transcript variant 2,mRNA gi|6552336|ref|NM_007323.1|[6552336]

971: NM_005162 Homo sapiens angiotensin receptor-like 2 (AGTRL2), mRNA gi|6031157|ref|NM_005162.2|[6031157]

972: NM_005501 Homo sapiens integrin, alpha 3 (antigen CD49C, alpha 3 subunit of VLA-3 receptor) (ITGA3), transcript variant b, mRNA gi|6006010|ref|NM_005501.1|[6006010]

975: NM_007053 Homo sapiens natural killer cell receptor, immunoglobulin superfamily member(BY55), mRNA gi|5901909|ref|NM_007053.1|[5901909]

978: NM_006254 Homo sapiens protein kinase C, delta (PRKCD), mRNA gi|5453969|ref|NM_006254.1|[5453969]

979: NM_005761 Homo sapiens plexin C1 (PLXNC1), mRNA gi|5032222|ref|NM_005761.1|[5032222]

980: NM_005866 Homo sapiens sigma receptor (SR31747 binding protein 1) (SR-BP1), mRNA gi|5032116|ref|NM_005866.1|[5032116]

982: NM_005506 Homo sapiens CD36 antigen (collagen type I receptor, thrombospondin receptor)-like 2 (lysosomal integral membrane protein II) (CD36L2), mRNA gi|5031630|ref|NM_005506.1|[5031630]

984: NM_004799 Homo sapiens MAD, mothers against decapentaplegic homolog (Drosophila)interacting protein, receptor activation anchor (MADHIP), transcript variant 3, mRNA gi|4759059|ref|NM_004799.1|[4759059]

985: NM_004292 Homo sapiens ras inhibitor (RIN1), mRNA gi|4759039|ref|NM_004292.1|[4759039]

986: NM_004828 Homo sapiens lymphocyte antigen 95 (activating NK-receptor; NK-p44) (LY95), mRNA gi|4758693|ref|NM_004828.1|[4758693]

987: NM_004767 Homo sapiens endothelin type b receptor-like protein 2 (ET(B)R-LP-2), mRNA gi|4758309|ref|NM_004767.1|[4758309]

988: NM_004440 Homo sapiens EphA7 (EPHA7), mRNA gi|4758281|ref|NM_004440.1|[4758281]

989: NM_003999 Homo sapiens oncostatin M receptor (OSMR), mRNA gi|4557039|ref|NM_003999.1|[4557039]

990: NM_003904 Homo sapiens zinc finger protein 259 (ZNF259), mRNA gi|4508020|ref|NM_003904.1|[4508020]

991: NM_003305 Homo sapiens transient receptor potential cation channel, subfamily C, member 3(TRPC3), mRNA gi|4507686|ref|NM_003305.1|[4507686]

992: NM_003804 Homo sapiens receptor (TNFRSF)-interacting serine-threonine kinase 1 (RIPK1), mRNA gi|4506538|ref|NM_003804.1|[4506538]

993: NM_003626 Homo sapiens protein tyrosine phosphatase, receptor type, f polypeptide (PTPRF),interacting protein (liprin), alpha 1 (PPFIA1), mRNA gi|4505982|ref|NM_003626.1|[4505982]

994: NM_003876 Homo sapiens putative receptor protein (PMI), mRNA gi|4505900|ref|NM_003876.1|[4505900]

995: NM_003559 Homo sapiens phosphatidylinositol-4-phosphate 5-kinase, type II, beta (PIP5K2B),mRNA gi|4505818|ref|NM_003559.1|[4505818]

996: NM_003629 Homo sapiens phosphoinositide-3-kinase, regulatory subunit, polypeptide 3 (p55,gamma) (PIK3R3), mRNA gi|4505804|ref|NM_003629.1|[4505804]

997: NM_003676 Homo sapiens degenerative spermatocyte homolog, lipid desaturase (Drosophila)(DEGS), mRNA gi|4505192|ref|NM_003676.1|[4505192]

998: NM_002270 Homo sapiens karyopherin (importin) beta 2 (KPNB2), mRNA gi|4504906|ref|NM_002270.1|[4504906]

999: NM_002204 Homo sapiens integrin, alpha 3 (antigen CD49C, alpha 3 subunit of VLA-3 receptor) (ITGA3), transcript variant a, mRNA gi|4504746|ref|NM_002204.1|[4504746]

1000: NM_001560 Homo sapiens interleukin 13 receptor, alpha 1 (IL13RA1), mRNA gi|4504646|ref|NM_001560.1|[4504646]

■■■■■■■■■■■■■■■■■■■■■■■■■■■■■■■■■■■■■■■■■■■■■■■■■■■■■■■■■■■■■■■■■■■■■■■■■■■■■■ı sapiens AND receptor NOT similar NOT non-receptor NOT nuclear NOT receptor-associated NOT "thyroid hormone" NOT "steroid receptor"

779: NM_000842
Homo sapiens glutamate receptor, metabotropic 5 (GRM5), mRNA
gi|4504142|ref|NM_000842.1|[4504142]

780: NM_001883
Homo sapiens corticotropin releasing hormone receptor 2 (CRHR2), mRNA
gi|4503044|ref|NM_001883.1|[4503044]

781: NM_001873
Homo sapiens carboxypeptidase E (CPE), mRNA
gi|4503008|ref|NM_001873.1|[4503008]

783: L29395
Homo sapiens v-erbB-related protein gene, partial cds
gi|459807|gb|L29395.1|HUMERBB[459807]

784: L08584
Homo sapiens T cell receptor beta chain (TCRB) mRNA, partial cds
gi|307497|gb|L08584.1|HUMTCVB7A[307497]

786: NM_015638
Homo sapiens chromosome 20 open reading frame 188 (C20orf188), mRNA
gi|18158415|ref|NM_015638.1|[18158415]

787: NM_058167
Homo sapiens ubiquitin conjugating enzyme 6 (Ubc6p), mRNA
gi|17157996|ref|NM_058167.1|[17157996]

788: NM_054032
Homo sapiens G protein-coupled receptor MRGX4 (MRGX4), mRNA
gi|16876454|ref|NM_054032.1|[16876454]

789: NM_054031
Homo sapiens G protein-coupled receptor MRGX3 (MRGX3), mRNA
gi|16876452|ref|NM_054031.1|[16876452]

790: NM_054030
Homo sapiens G protein-coupled receptor MRGX2 (MRGX2), mRNA
gi|16876450|ref|NM_054030.1|[16876450]

791: NM_052931
Homo sapiens activating NK receptor (KALI), mRNA
gi|16418406|ref|NM_052931.1|[16418406]

792: NM_032871
Homo sapiens tumor necrosis factor receptor superfamily, member 19-like (TNFRSF19L), mRNA
gi|14249611|ref|NM_032871.1|[14249611]

793: NM_032553
Homo sapiens putative purinergic receptor (FKSG79), mRNA
gi|14211848|ref|NM_032553.1|[14211848]

794: NM_025179
Homo sapiens plexin A2 (PLXNA2), mRNA
gi|13378152|ref|NM_025179.1|[13378152]

795: NM_024419
Homo sapiens Phosphatidylglycerophosphate Synthase (PGS1), mRNA
gi|13259369|ref|NM_024419.1|[13259369]

796: NM_021249
Homo sapiens sorting nexin 6 (SNX6), mRNA
gi|13027619|ref|NM_021249.1|[13027619]

797: NM_014045
Homo sapiens DKFZP564C1940 protein (DKFZP564C1940), mRNA
gi|13027587|ref|NM_014045.1|[13027587]

798: NM_080923
Homo sapiens protein tyrosine phosphatase, receptor type, C (PTPRC), transcript variant 4, mRNA
gi|18641365|ref|NM_080923.1|[18641365]

799: NM_080922
Homo sapiens protein tyrosine phosphatase, receptor type, C (PTPRC), transcript variant 3, mRNA
gi|18641363|ref|NM_080922.1|[18641363]

800: NM_080921
Homo sapiens protein tyrosine phosphatase, receptor type, C (PTPRC), transcript variant 2, mRNA
gi|18641361|ref|NM_080921.1|[18641361]

801: NM_130386
Homo sapiens collectin sub-family member 12 (COLEC12), transcript variant I, mRNA
gi|18641359|ref|NM_130386.1|[18641359]

802: NM_030781
Homo sapiens collectin sub-family member 12 (COLEC12), transcript variant II, mRNA
gi|18641357|ref|NM_030781.2|[18641357]

803: NM_002838
Homo sapiens protein tyrosine phosphatase, receptor type, C (PTPRC), transcript variant 1, mRNA
gi|18641346|ref|NM_002838.2|[18641346]

804: NM_130770
Homo sapiens 5-hydroxytryptamine receptor 3 subunit C (HTR3C), mRNA
gi|18640739|ref|NM_130770.1|[18640739]

813: BD010218
Novel hemopoietin receptor protein, NR12
gi|18638591|dbj|BD010218.1|[18638591]

814: BD010217
Novel hemopoietin receptor protein, NR12
gi|18638590|dbj|BD010217.1|[18638590]

815: BD010216
Novel hemopoietin receptor protein, NR12
gi|18638589|dbj|BD010216.1|[18638589]

816: BD010215
Novel hemopoietin receptor protein, NR12
gi|18638588|dbj|BD010215.1|[18638588]

817: BD010214
Novel hemopoietin receptor protein, NR12
gi|18638587|dbj|BD010214.1|[18638587]

818: BD010125
Peptide leukotrien receptor
gi|18638498|dbj|BD010125.1|[18638498]

819: BD010114
Novel receptor and gene encoding the same
gi|18638487|dbj|BD010114.1|[18638487]

820: BD010057
Novel G protein coupled receptor protein and its DNA
gi|18638430|dbj|BD010057.1|[18638430]

821: BD010056
Novel G protein coupled receptor protein and its DNA
gi|18638429|dbj|BD010056.1|[18638429]

822: BD010055
Novel G protein coupled receptor protein and its DNA
gi|18638428|dbj|BD010055.1|[18638428]

823: BD010054
Novel G protein coupled receptor protein and its DNA
gi|18638427|dbj|BD010054.1|[18638427]

824: BD010053
Novel G protein coupled receptor protein and its DNA
gi|18638426|dbj|BD010053.1|[18638426]

825: BD010052
Novel G protein coupled receptor protein and its DNA
gi|18638425|dbj|BD010052.1|[18638425]

826: BD010051
Novel G protein coupled receptor protein and its DNA
gi|18638424|dbj|BD010051.1|[18638424]

827: BD010050

Novel G protein coupled receptor protein and its DNA
gi|18638423|dbj|BD010050.1|[18638423]

828: BD010049
Novel G protein coupled receptor protein and its DNA
gi|18638422|dbj|BD010049.1|[18638422]

829: BD010046
Novel G protein coupled receptor protein and its DNA
gi|18638419|dbj|BD010046.1|[18638419]

830: BD010035
Novel G protein coupled receptor protein and its DNA
gi|18638408|dbj|BD010035.1|[18638408]

831: BD010034
Novel G protein coupled receptor protein and its DNA
gi|18638407|dbj|BD010034.1|[18638407]

832: BD010028
Novel G protein coupled receptor protein and its DNA
gi|18638401|dbj|BD010028.1|[18638401]

833: BD010022
Novel G protein coupled receptor protein and its DNA
gi|18638395|dbj|BD010022.1|[18638395]

834: BD009263
GABAA receptor subunit epsilon-related protein
gi|18637636|dbj|BD009263.1|[18637636]

835: BD009262
GABAA receptor subunit epsilon-related protein
gi|18637635|dbj|BD009262.1|[18637635]

836: BD009261
GABAA receptor subunit epsilon-related protein gi|18637634|dbj|BD009261.1|[18637634]

837: BD009260
GABAA receptor subunit epsilon-related protein
gi|18637633|dbj|BD009260.1|[18637633]

838: BD006753
Human G protein chemokine receptor HDGNR10
gi|18635124|dbj|BD006753.1|[18635124]

843: E51301
Novel G protein-coupled receptor protein and gene of said G protein-coupled receptor protein
gi|18633577|dbj|E51301.1|[18633577]

844: E51300
Novel G protein-coupled receptor protein and gene of said G protein-coupled receptor protein
gi|18633576|dbj|E51300.1|[18633576]

845: E51299
Novel G protein-coupled receptor protein and gene of said G protein-coupled receptor protein
gi|18633575|dbj|E51299.1|[18633575]

846: E51298
Novel G protein-coupled receptor protein and gene of said G protein-coupled receptor protein
gi|18633574|dbj|E51298.1|[18633574]

847: E51297
Novel G protein-coupled receptor protein and gene of said G protein-coupled receptor protein
gi|18633573|dbj|E51297.1|[18633573]

848: E51296
Novel G protein-coupled receptor protein and gene of said G protein-coupled receptor protein gi|18633572|dbj|E51296.1|[18633572]

849: E50838
Novel G protein-coupled receptor
gi|18633543|dbj|E50838.1|[18633543]

850: E50837
Novel G protein-coupled receptor
gi|18633542|dbj|E50837.1|[18633542]

851: E50836
Novel G protein-coupled receptor
gi|18633541|dbj|E50836.1|[18633541]

852: E50835
Novel G protein-coupled receptor
gi|18633540|dbj|E50835.1|[18633540]

853: E50834
Novel G protein-coupled receptor
gi|18633539|dbj|E50834.1|[18633539]

854: E50833
Novel G protein-coupled receptor
gi|18633538|dbj|E50833.1|[18633538]

873: BD003056
Novel G protein-coupled receptor protein and DNA thereof
gi|18631017|dbj|BD003056.1|[18631017]

874: E55122
Novel G protein-coupled receptor and the G protein-coupled receptor gene
gi|18629753|dbj|E55122.1|[18629753]

875: E55121
Novel G protein-coupled receptor and the G protein-coupled receptor gene
gi|18629752|dbj|E55121.1|[18629752]

876: E55120
Novel G protein-coupled receptor and the G protein-coupled receptor gene
gi|18629751|dbj|E55120.1|[18629751]

877: E55119
Novel G protein-coupled receptor and the G protein-coupled receptor gene
gi|18629750|dbj|E55119.1|[18629750]

878: E55118
Novel G protein-coupled receptor and the G protein-coupled receptor gene
gi|18629749|dbj|E55118.1|[18629749]

879: E55117
Novel G protein-coupled receptor and the G protein-coupled receptor gene
gi|18629748|dbj|E55117.1|[18629748]

880: E49128
Novel G protein-conjugated receptor protein
gi|18629265|dbj|E49128.1|[18629265]

881: E49127
Novel G protein-conjugated receptor protein
gi|18629264|dbj|E49127.1|[18629264]

882: E49126
Novel G protein-conjugated receptor protein
gi|18629263|dbj|E49126.1|[18629263]

883: E49125
Novel G protein-conjugated receptor protein
gi|18629262|dbj|E49125.1|[18629262]

884: E49124
Novel G protein-conjugated receptor protein
gi|18629261|dbj|E49124.1|[18629261]

885: E49123
Novel G protein-conjugated receptor protein
gi|18629260|dbj|E49123.1|[18629260]

887: E58499
Novel G protein-coupled receptor protein, DNA and utilization thereof
gi|18628416|dbj|E58499.1|[18628416]

888: E58495
Novel G protein-coupled receptor protein, DNA and utilization thereof
gi|18628412|dbj|E58495.1|[18628412]

889: E58494
Novel G protein-coupled receptor protein, DNA and utilization thereof
gi|18628411|dbj|E58494.1|[18628411]

890: E58488
Novel G protein-coupled receptor protein, DNA and utilization thereof
gi|18628405|dbj|E58488.1|[18628405]

891: E58485
Novel G protein-coupled receptor protein, DNA and utilization thereof
gi|18628402|dbj|E58485.1|[18628402]

892: E58484
Novel G protein-coupled receptor protein, DNA and utilization thereof
gi|18628401|dbj|E58484.1|[18628401]

893: E58479
Novel G protein-coupled receptor protein, DNA and utilization thereof
gi|18628396|dbj|E58479.1|[18628396]

902: E43451
Novel protein G-coupled receptor protein and DNA thereof
gi|18627717|dbj|E43451.1|[18627717]

903: E43450

Novel protein G-coupled receptor protein and DNA thereof
gi|18627716|dbj|E43450.1|[18627716]

904: E41270
Novel G protein-conjugate receptor protein and its DNA
gi|18627502|dbj|E41270.1|[18627502]

905: E41269
Novel G protein-conjugate receptor protein and its DNA
gi|18627501|dbj|E41269.1|[18627501]

906: E41268
Novel G protein-conjugate receptor protein and its DNA
gi|18627500|dbj|E41268.1|[18627500]

907: E40003
Novel G protein-conjugate receptor protein and its DNA
gi|18627119|dbj|E40003.1|[18627119]

908: E40000
Novel G protein-conjugate receptor protein and its DNA
gi|18627116|dbj|E40000.1|[18627116]

909: E39999
Novel G protein-conjugate receptor protein and its DNA
gi|18627115|dbj|E39999.1|[18627115]

910: E39824
Novel guanosine triphospate (GTP)-binding protein-conjugate receptor protein
gi|18627105|dbj|E39824.1|[18627105]

911: E39817
Novel guanosine triphospate (GTP)-binding protein-conjugate receptor protein
gi|18627098|dbj|E39817.1|[18627098]

912: E39816
Novel guanosine triphospate (GTP)-binding protein-conjugate receptor protein gi|18627097|dbj|E39816.1|[18627097]

913: E39815
Novel guanosine triphospate (GTP)-binding protein-conjugate receptor protein
gi|18627096|dbj|E39815.1|[18627096]

929: E34464
Novel Toll-like receptor and gene thereof
gi|18624350|dbj|E34464.1|[18624350]

930: E33807
Human splice mutant CXCR4B of CXCR4 chemokine receptor
gi|18624164|dbj|E33807.1|[18624164]

931: E33806
Human splice mutant CXCR4B of CXCR4 chemokine receptor
gi|18624163|dbj|E33806.1|[18624163]

941: E63757
Human nurse cell receptor gene
gi|18622844|dbj|E63757.1|[18622844]

942: E63756
Human nurse cell receptor gene
gi|18622843|dbj|E63756.1|[18622843]

943: E63754
Human nurse cell receptor gene
gi|18622841|dbj|E63754.1|[18622841]

944: E49275
Novel G protein-conjugated receptor protein and DNA thereof
gi|18622037|dbj|E49275.1|[18622037]

945: E44151

Novel G protein-coupled receptor protein and DNA thereof
gi|18622012|dbj|E44151.1|[18622012]

946: E44032
Novel G protein-coupled receptor protein and DNA and ligand of the same
gi|18621998|dbj|E44032.1|[18621998]

947: AX350990
Sequence 24 from Patent WO0190358
gi|18616366|emb|AX350990.1|[18616366]

948: AX350988
Sequence 22 from Patent WO0190358
gi|18616364|emb|AX350988.1|[18616364]

949: AX350984
Sequence 18 from Patent WO0190358
gi|18616360|emb|AX350984.1|[18616360]

950: AX350982
Sequence 16 from Patent WO0190358
gi|18616358|emb|AX350982.1|[18616358]

951: AX350981
Sequence 15 from Patent WO0190358
gi|18616357|emb|AX350981.1|[18616357]

952: AX350979
Sequence 13 from Patent WO0190358
gi|18616355|emb|AX350979.1|[18616355]

953: AX350975
Sequence 9 from Patent WO0190358
gi|18616351|emb|AX350975.1|[18616351]

954: AX350973
Sequence 7 from Patent WO0190358 gi|18616349|emb|AX350973.1|[18616349]

955: AX350969
Sequence 3 from Patent WO0190358
gi|18616345|emb|AX350969.1|[18616345]

956: AX350967
Sequence 1 from Patent WO0190358
gi|18616343|emb|AX350967.1|[18616343]

957: NM_005608
Homo sapiens protein tyrosine phosphatase, receptor type, C-associated protein (PTPRCAP), mRNA
gi|5032004|ref|NM_005608.1|[5032004]

958: XM_012097
Homo sapiens olfactory receptor, family 6, subfamily A, member 1 (OR6A1), mRNA
gi|18605332|ref|XM_012097.3|[18605332]

959: XM_090173
Homo sapiens olfactory receptor, family 5, subfamily L, member 2 (OR5L2), mRNA
gi|18605181|ref|XM_090173.1|[18605181]

960: XM_055369
Homo sapiens pro-oncosis receptor inducing membrane injury gene (PORIMIN), mRNA
gi|18604484|ref|XM_055369.2|[18604484]

961: XM_041961
Homo sapiens PYK2 N-terminal domain-interacting receptor 1 (NIR1), mRNA
gi|18604126|ref|XM_041961.2|[18604126]

962: XM_040037
Homo sapiens adrenergic, beta, receptor kinase 1 (ADRBK1), mRNA
gi|18604053|ref|XM_040037.3|[18604053]

963: XM_045532
Homo sapiens olfactory receptor, family 51, subfamily E, member 2 (OR51E2), mRNA 964: XM_091465
Homo sapiens olfactory receptor, family 4, subfamily D, member 1 (OR4D1), mRNA
gi|18603196|ref|XM_091465.1|[18603196]

965: XM_036784
Homo sapiens phosphatidylserine receptor (KIAA0585), mRNA
gi|18603024|ref|XM_036784.3|[18603024]

966: XM_036728
Homo sapiens ryanodine receptor 3 (RYR3), mRNA
gi|18602746|ref|XM_036728.3|[18602746]

967: XM_084025
Homo sapiens complement component 5 receptor 1 (C5a ligand) (C5R1), mRNA
gi|18601827|ref|XM_084025.1|[18601827]

968: XM_009107
Homo sapiens KDEL (Lys-Asp-Glu-Leu) endoplasmic reticulum protein retention receptor 1 (KDELR1), mRNA
gi|18601740|ref|XM_009107.6|[18601740]

969: XM_027883
Homo sapiens protein tyrosine phosphatase, receptor type, f polypeptide (PTPRF), interacting protein (liprin), alpha 3 (PPFIA3), mRNA
gi|18601690|ref|XM_027883.2|[18601690]

970: XM_027904
Homo sapiens Fc fragment of IgG, receptor, transporter, alpha (FCGRT), mRNA
gi|18601656|ref|XM_027904.4|[18601656]

971: XM_049229
Homo sapiens dopamine receptor interacting protein (DRIP78), mRNA
gi|18601498|ref|XM_049229.3|[18601498]

972: XM_040709

Homo sapiens prostaglandin F2 receptor negative regulator (PTGFRN), mRNA
gi|18601130|ref|XM_040709.2|[18601130]

973: XM_003091
Homo sapiens G protein-coupled receptor 105 (GPR105), mRNA
gi|18600688|ref|XM_003091.5|[18600688]

975: XM_010533
Homo sapiens interleukin 12 receptor, beta 2 (IL12RB2), mRNA
gi|18600602|ref|XM_010533.4|[18600602]

976: NT_006318
Homo sapiens chromosome 4 working draft sequence segment
gi|18600353|ref|NT_006318.7|Hs4_6475[18600353]

977: XM_039145
Homo sapiens cholinergic receptor, nicotinic, alpha polypeptide 3 (CHRNA3), mRNA
gi|18597785|ref|XM_039145.3|[18597785]

978: XM_039151
Homo sapiens cholinergic receptor, nicotinic, beta polypeptide 4 (CHRNB4), mRNA
gi|18597777|ref|XM_039151.2|[18597777]

979: XM_007392
Homo sapiens G protein-coupled receptor 65 (GPR65), mRNA
gi|18597722|ref|XM_007392.4|[18597722]

980: XM_007315
Homo sapiens receptor-interacting serine-threonine kinase 3 (RIPK3), mRNA
gi|18597625|ref|XM_007315.2|[18597625]

981: NT_024675
Homo sapiens chromosome 15 working draft sequence segment
gi|18597616|ref|NT_024675.7|Hs15_24831[18597616]

982: XM_051711
Homo sapiens prostaglandin D2 receptor (DP) (PTGDR), mRNA gi|18597012|ref|XM_051711.2|[18597012]

983: XM_007337
Homo sapiens kinectin 1 (kinesin receptor) (KTN1), mRNA
gi|18596970|ref|XM_007337.7|[18596970]

984: XM_096782
Homo sapiens putative leukocyte platelet-activating factor receptor (HUMNPIIY20), mRNA
gi|18596920|ref|XM_096782.1|[18596920]

985: XM_055898
Homo sapiens nerve growth factor receptor (TNFRSF16) associated protein 1 (NGFRAP1), mRNA
gi|18596422|ref|XM_055898.3|[18596422]

986: XM_018505
Homo sapiens G protein-coupled receptor 23 (GPR23), mRNA
gi|18594906|ref|XM_018505.3|[18594906]

987: XM_096288
Homo sapiens G protein-coupled receptor 64 (GPR64), mRNA
gi|18594854|ref|XM_096288.1|[18594854]

988: XM_096154
Homo sapiens angiotensin receptor-like 2 (AGTRL2), mRNA
gi|18593950|ref|XM_096154.1|[18593950]

989: XM_015620
Homo sapiens nogo receptor (NOGOR), mRNA
gi|18593698|ref|XM_015620.5|[18593698]

990: XM_048563
Homo sapiens interferon gamma receptor 2 (interferon gamma transducer 1) (IFNGR2), mRNA
gi|18593096|ref|XM_048563.2|[18593096]

991: XM_086754

Homo sapiens coxsackie virus and adenovirus receptor (CXADR), mRNA
gi|18592977|ref|XM_086754.1|[18592977]

992: XM_056242

Homo sapiens protein C receptor, endothelial (EPCR) (PROCR), mRNA
gi|18592822|ref|XM_056242.3|[18592822]

993: XM_097415

Homo sapiens leukocyte receptor cluster (LRC) member 8 (LENG8), mRNA
gi|18591238|ref|XM_097415.1|[18591238]

994: XM_044314

Homo sapiens leukocyte immunoglobulin-like receptor, subfamily A (without TM domain), member 4 (ILT7), mRNA
gi|18591234|ref|XM_044314.4|[18591234]

995: XM_092068

Homo sapiens olfactory receptor, family 7, subfamily C, member 1 (OR7C1), mRNA
gi|18591224|ref|XM_092068.1|[18591224]

996: XM_084042

Homo sapiens egf-like module containing, mucin-like, hormone receptor-like sequence 2 (EMR2), mRNA
gi|18591222|ref|XM_084042.1|[18591222]

997: XM_012893

Homo sapiens endothelial differentiation, lysophosphatidic acid G-protein-coupled receptor, 4 (EDG4), mRNA
gi|18591032|ref|XM_012893.5|[18591032]

998: XM_103288

Homo sapiens polycythemia rubra vera 1; cell surface receptor (PRV1), mRNA
gi|18590882|ref|XM_103288.1|[18590882]

999: XM_046103

Homo sapiens protein tyrosine phosphatase, receptor type, S (PTPRS), mRNA
gi|18590850|ref|XM_046103.3|[18590850]

1000: XM_047633
Homo sapiens thromboxane A2 receptor (TBXA2R), mRNA
gi|18590817|ref|XM_047633.2|[18590817]

1001: XM_030637
Homo sapiens G protein-coupled receptor kinase 7 (GPRK7), mRNA
gi|18590749|ref|XM_030637.3|[18590749]

1002: XM_086017
Homo sapiens plasminogen activator, urokinase receptor (PLAUR), mRNA
gi|18590707|ref|XM_086017.1|[18590707]

1003: XM_029455
Homo sapiens ryanodine receptor 1 (skeletal) (RYR1), mRNA
gi|18590460|ref|XM_029455.2|[18590460]

1004: XM_085976
Homo sapiens leukocyte receptor cluster (LRC) member 3 (LENG3), mRNA
gi|18590428|ref|XM_085976.1|[18590428]

1005: XM_084028
Homo sapiens killer cell immunoglobulin-like receptor, three domains, long cytoplasmic tail, 1 (KIR3DL1), mRNA
gi|18590419|ref|XM_084028.1|[18590419]

1006: XM_097304
Homo sapiens leukocyte receptor cluster (LRC) member 1 (LENG1), mRNA
gi|18590235|ref|XM_097304.1|[18590235]

1007: XM_050582
Homo sapiens leukocyte immunoglobulin-like receptor, subfamily B (with TM and ITIM domains), member 3 (LILRB3), mRNA
gi|18590233|ref|XM_050582.3|[18590233]

1008: XM_041258
Homo sapiens leukocyte immunoglobulin-like receptor, subfamily B (with TM and ITIM domains), member 2 (LILRB2), mRNA
gi|18590231|ref|XM_041258.3|[18590231]

1009: XM_050236
Homo sapiens leukocyte receptor cluster (LRC) member 4 (LENG4), mRNA
gi|18590224|ref|XM_050236.3|[18590224]

1010: XM_048346
Homo sapiens insulin receptor (INSR), mRNA
gi|18590185|ref|XM_048346.3|[18590185]

1011: XM_044591
Homo sapiens G protein-coupled receptor 108 (GPR108), mRNA
gi|18590160|ref|XM_044591.3|[18590160]

1012: XM_085864
Homo sapiens endothelial differentiation, sphingolipid G-protein-coupled receptor, 8 (EDG8), mRNA
gi|18589990|ref|XM_085864.1|[18589990]

1013: XM_044320
Homo sapiens poliovirus receptor-related 2 (herpesvirus entry mediator B) (PVRL2), mRNA
gi|18589873|ref|XM_044320.4|[18589873]

1014: XM_012671
Homo sapiens olfactory receptor, family 1, subfamily E, member 2 (OR1E2), mRNA
gi|18588331|ref|XM_012671.5|[18588331]

1015: XM_085745
Homo sapiens somatostatin receptor 2 (SSTR2), mRNA
gi|18588314|ref|XM_085745.1|[18588314]

1016: XM_008646
Homo sapiens cytokine receptor-like factor 3 (CRLF3), mRNA
gi|18588105|ref|XM_008646.5|[18588105]

1017: XM_008509
Homo sapiens purinergic receptor P2X, ligand-gated ion channel, 5 (P2RX5), mRNA
gi|18587692|ref|XM_008509.6|[18587692]

1018: XM_030851
Homo sapiens G protein-coupled receptor kinase-interactor 1 (GIT1), mRNA
gi|18587652|ref|XM_030851.2|[18587652]

1019: XM_048233
Homo sapiens autocrine motility factor receptor (AMFR), mRNA
gi|18585872|ref|XM_048233.3|[18585872]

1020: NT_010280
Homo sapiens chromosome 15 working draft sequence segment
gi|18584150|ref|NT_010280.8|Hs15_10437[18584150]

1021: XM_039208
Homo sapiens gamma-aminobutyric acid (GABA) A receptor, gamma 3 (GABRG3), mRNA
gi|18584141|ref|XM_039208.5|[18584141]

1022: XM_030709
Homo sapiens transient receptor potential cation channel, subfamily M, member 7 (TRPM7), mRNA
gi|18583756|ref|XM_030709.3|[18583756]

1023: XM_085103
Homo sapiens G protein-coupled receptor (G2A), mRNA
gi|18583332|ref|XM_085103.1|[18583332]

1024: XM_040854
Homo sapiens bradykinin receptor B2 (BDKRB2), mRNA
gi|18582977|ref|XM_040854.2|[18582977]

1025: XM_007275
Homo sapiens bradykinin receptor B1 (BDKRB1), mRNA
gi|18582976|ref|XM_007275.4|[18582976]

1027: XM_083897
Homo sapiens Epstein-Barr virus induced gene 2 (lymphocyte-specific G protein-coupled receptor) (EBI2), mRNA
gi|18581588|ref|XM_083897.1|[18581588]

1029: XM_062656
Homo sapiens C-type lectin-like receptor (CLEC-6), mRNA
gi|18580484|ref|XM_062656.2|[18580484]

1031: XM_084785
Homo sapiens protein tyrosine phosphatase, receptor type, f polypeptide (PTPRF), interacting protein (liprin), alpha 2 (PPFIA2), mRNA
gi|18579245|ref|XM_084785.1|[18579245]

1032: XM_043322
Homo sapiens peroxisome receptor 1 (PXR1), mRNA
gi|18579222|ref|XM_043322.3|[18579222]

1033: XM_090117
Homo sapiens olfactory receptor, family 8, subfamily G, member 2 (OR8G2), mRNA
gi|18578560|ref|XM_090117.1|[18578560]

1034: XM_090109
Homo sapiens olfactory receptor, family 8, subfamily G, member 1 (OR8G1), mRNA
gi|18578546|ref|XM_090109.1|[18578546]

1035: XM_035095
Homo sapiens cortical thymocyte receptor (X. laevis CTX) like (CTXL), mRNA
gi|18578508|ref|XM_035095.4|[18578508]

1036: XM_084690
Homo sapiens olfactory receptor, family 8, subfamily B, member 8 (OR8B8), mRNA
gi|18578501|ref|XM_084690.1|[18578501]

1037: XM_012064
Homo sapiens glutamate receptor, ionotropic, kainate 4 (GRIK4), mRNA
gi|18578454|ref|XM_012064.6|[18578454]

1039: XM_031348
Homo sapiens glutamate receptor, metabotropic 5 (GRM5), mRNA
gi|18577875|ref|XM_031348.2|[18577875]

1040: XM_089965
Homo sapiens olfactory receptor, family 10, subfamily A, member 3 (OR10A3), mRNA
gi|18577828|ref|XM_089965.1|[18577828]

1041: NT_030791
Homo sapiens chromosome 11 working draft sequence segment
gi|18577645|ref|NT_030791.2|Hs11_31047[18577645]

1042: XM_006549
Homo sapiens G protein-coupled receptor 48 (GPR48), mRNA
gi|18577644|ref|XM_006549.5|[18577644]

1043: XM_054215
Homo sapiens purinergic receptor P2Y, G-protein coupled, 2 (P2RY2), mRNA
gi|18577261|ref|XM_054215.4|[18577261]

1044: XM_038024
Homo sapiens protein tyrosine phosphatase, receptor type, J (PTPRJ), mRNA
gi|18577179|ref|XM_038024.4|[18577179]

1045: XM_049296
Homo sapiens GDNF family receptor alpha 1 (GFRA1), mRNA
gi|18576832|ref|XM_049296.4|[18576832]

1046: XM_005781
Homo sapiens protein tyrosine phosphatase, receptor type, E (PTPRE), mRNA
gi|18576581|ref|XM_005781.5|[18576581]

1047: XM_011904
Homo sapiens cubilin (intrinsic factor-cobalamin receptor) (CUBN), mRNA
gi|18576082|ref|XM_011904.6|[18576082]

1048: XM_005969
Homo sapiens G protein-coupled receptor kinase 5 (GPRK5), mRNA
gi|18575440|ref|XM_005969.6|[18575440]

1049: XM_089569
Homo sapiens VPS10 domain receptor protein SORCS 1 (SORCS1), mRNA
gi|18574995|ref|XM_089569.1|[18574995]

1050: XM_005830
Homo sapiens mannose receptor, C type 1 (MRC1), mRNA
gi|18574297|ref|XM_005830.7|[18574297]

1051: XM_005747
Homo sapiens tachykinin receptor 2 (TACR2), mRNA
gi|18574167|ref|XM_005747.5|[18574167]

1052: XM_043613
Homo sapiens glutamate receptor, ionotropic, delta 1 (GRID1), mRNA
gi|18574031|ref|XM_043613.4|[18574031]

1053: XM_028830
Homo sapiens transient receptor potential cation channel, subfamily M, member 6 (TRPM6), mRNA
gi|18573768|ref|XM_028830.3|[18573768]

1054: XM_095961
Homo sapiens olfactory receptor, family 2, subfamily K, member 2 (OR2K2), mRNA
gi|18573486|ref|XM_095961.1|[18573486]

1055: XM_096286
Homo sapiens receptor tyrosine kinase-like orphan receptor 2 (ROR2), mRNA
gi|18573067|ref|XM_096286.1|[18573067]

1056: XM_095815
Homo sapiens olfactory receptor, family 1, subfamily J, member 5 (OR1J5), mRNA
gi|18572435|ref|XM_095815.1|[18572435]

1057: XM_095814
Homo sapiens olfactory receptor, family 1, subfamily J, member 4 (OR1J4), mRNA
gi|18572433|ref|XM_095814.1|[18572433]

1059: XM_011695
Homo sapiens leptin receptor overlapping transcript-like 1 (LEPROTL1), mRNA
gi|18570296|ref|XM_011695.3|[18570296]

1061: XM_088035
Homo sapiens transient receptor potential cation channel, subfamily V, member 6 (TRPV6), mRNA
gi|18565882|ref|XM_088035.1|[18565882]

1062: XM_004696
Homo sapiens EphB6 (EPHB6), mRNA
gi|18565881|ref|XM_004696.5|[18565881]

1063: XM_096245
Homo sapiens olfactory receptor, family 2, subfamily H, member 3 (OR2H3), mRNA
gi|18564780|ref|XM_096245.1|[18564780]

1064: XM_084200
Homo sapiens olfactory receptor, family 11, subfamily A, member 1 (OR11A1), mRNA
gi|18563692|ref|XM_084200.1|[18563692]

1065: XM_084190
Homo sapiens olfactory receptor, family 2, subfamily A, member 4 (OR2A4), mRNA
gi|18563106|ref|XM_084190.1|[18563106]

1066: XM_004341
Homo sapiens opioid receptor, mu 1 (OPRM1), mRNA
gi|18562969|ref|XM_004341.6|[18562969]

1067: XM_084185
Homo sapiens dopamine receptor D1 (DRD1), mRNA
gi|18561988|ref|XM_084185.1|[18561988]

1069: XM_049570

Homo sapiens dioxin receptor repressor (AHRR), mRNA
gi|18560847|ref|XM_049570.4|[18560847]

1070: XM_084176
Homo sapiens coagulation factor II (thrombin) receptor-like 1 (F2RL1), mRNA
gi|18560787|ref|XM_084176.1|[18560787]

1071: NT_029289
Homo sapiens chromosome 5 working draft sequence segment
gi|18560495|ref|NT_029289.4|Hs5_29448[18560495]

1072: XR_000069
Homo sapiens neuropeptide Y receptor Y6 (psuedogene) (NPY6R), misc RNA
gi|18560235|ref|XR_000069.1|[18560235]

1073: NT_025716
Homo sapiens chromosome 5 working draft sequence segment
gi|18560224|ref|NT_025716.6|Hs5_25872[18560224]

1074: XM_094306
Homo sapiens gamma-aminobutyric acid (GABA) A receptor, alpha 1 (GABRA1), mRNA
gi|18560222|ref|XM_094306.1|[18560222]

1075: XM_096226
Homo sapiens interleukin 7 receptor (IL7R), mRNA
gi|18560176|ref|XM_096226.1|[18560176]

1076: XM_031131
Homo sapiens leukemia inhibitory factor receptor (LIFR), mRNA
gi|18559952|ref|XM_031131.2|[18559952]

1077: XM_011222
Homo sapiens gamma-aminobutyric acid (GABA) A receptor, beta 2 (GABRB2), mRNA
gi|18559788|ref|XM_011222.6|[18559788]

1078: XM_003519
Homo sapiens gamma-aminobutyric acid (GABA) A receptor, beta 1 (GABRB1), mRNA gi|18558473|ref|XM_003519.3|[18558473]

1079: XM_038446
Homo sapiens melatonin receptor 1A (MTNR1A), mRNA
gi|18558343|ref|XM_038446.2|[18558343]

1080: XM_084160
Homo sapiens gamma-aminobutyric acid (GABA) A receptor, alpha 2 (GABRA2), mRNA
gi|18558328|ref|XM_084160.1|[18558328]

1081: XM_011169
Homo sapiens neuropeptide Y receptor Y2 (NPY2R), mRNA
gi|18558281|ref|XM_011169.3|[18558281]

1082: XM_044120
Homo sapiens fibroblast growth factor receptor 3 (achondroplasia, thanatophoric dwarfism) (FGFR3), mRNA
gi|18558241|ref|XM_044120.2|[18558241]

1083: NT_030654
Homo sapiens chromosome 4 working draft sequence segment
gi|18557828|ref|NT_030654.2|Hs4_30910[18557828]

1084: NT_030650
Homo sapiens chromosome 4 working draft sequence segment
gi|18557822|ref|NT_030650.2|Hs4_30906[18557822]

1085: XM_011173
Homo sapiens glutamate receptor, ionotropic, delta 2 (GRID2), mRNA
gi|18557816|ref|XM_011173.4|[18557816]

1086: NT_029955
Homo sapiens chromosome 4 working draft sequence segment
gi|18557687|ref|NT_029955.3|Hs4_30210[18557687]

1087: NT_025693
Homo sapiens chromosome 4 working draft sequence segment

1088: NM_019841
Homo sapiens transient receptor potential cation channel, subfamily V, member 5 (TRPV5), mRNA
gi|17505199|ref|NM_019841.2|[17505199]

1089: NT_030778
Homo sapiens chromosome 10 working draft sequence segment
gi|17489667|ref|NT_030778.1|Hs10_31034[17489667]

1090: NT_010591
Homo sapiens chromosome 16 working draft sequence segment
gi|17487829|ref|NT_010591.6|Hs16_10748[17487829]

1091: NT_030889
Homo sapiens chromosome X working draft sequence segment
gi|17486981|ref|NT_030889.1|HsX_31145[17486981]

1092: XM_066104
Homo sapiens G protein-coupled receptor 73-like 1 (GPR73L1), mRNA
gi|17484462|ref|XM_066104.1|[17484462]

1093: XM_056414
Homo sapiens killer cell immunoglobulin-like receptor, two domains, long cytoplasmic tail, 4 (KIR2DL4), mRNA
gi|17483039|ref|XM_056414.2|[17483039]

1094: XM_053166
Homo sapiens somatostatin receptor-interacting protein (SSTRIP), mRNA
gi|17482811|ref|XM_053166.3|[17482811]

1096: XM_008489
Homo sapiens acetyl LDL receptor; SREC=scavenger receptor expressed by endothelial cells (SREC), mRNA
gi|17481055|ref|XM_008489.7|[17481055]

1097: XM_044091
Homo sapiens cholinergic receptor, nicotinic, alpha polypeptide 7 (CHRNA7), mRNA
gi|17477913|ref|XM_044091.2|[17477913]

1098: NT_010258
Homo sapiens chromosome 15 working draft sequence segment
gi|17477780|ref|NT_010258.7|Hs15_10415[17477780]

1099: XM_038336
Homo sapiens neurotrophic tyrosine kinase, receptor, type 3 (NTRK3), mRNA
gi|17477779|ref|XM_038336.2|[17477779]

1101: XM_027181
Homo sapiens transient receptor potential cation channel, subfamily V, member 4 (TRPV4), mRNA
gi|17475007|ref|XM_027181.2|[17475007]

1102: XM_047362
Homo sapiens Glutamate receptor interacting protein (GRIP1), mRNA
gi|17474492|ref|XM_047362.3|[17474492]

1104: XM_006372
Homo sapiens aryl hydrocarbon receptor interacting protein (AIP), mRNA
gi|17472888|ref|XM_006372.4|[17472888]

1105: XM_004893
Homo sapiens receptor (calcitonin) activity modifying protein 3 (RAMP3), mRNA
gi|17464777|ref|XM_004893.4|[17464777]

1107: XM_004559
Homo sapiens discoidin domain receptor family, member 1 (DDR1), mRNA
gi|17464405|ref|XM_004559.5|[17464405]

1108: XM_004237
Homo sapiens insulin-like growth factor 2 receptor (IGF2R), mRNA
gi|17463326|ref|XM_004237.4|[17463326]

1109: XM_051214
Homo sapiens type 1 tumor necrosis factor receptor shedding aminopeptidase regulator (ARTS-1), mRNA
gi|17462792|ref|XM_051214.2|[17462792]

1110: XM_059645
Homo sapiens neuropeptide Y receptor Y1 (NPY1R), mRNA
gi|17462720|ref|XM_059645.1|[17462720]

1111: XM_044493
Homo sapiens cholecystokinin B receptor (CCKBR), mRNA
gi|17461537|ref|XM_044493.2|[17461537]

1112: XM_048562
Homo sapiens interferon (alpha, beta and omega) receptor 1 (IFNAR1), mRNA
gi|17460140|ref|XM_048562.3|[17460140]

1113: XM_040307
Homo sapiens low density lipoprotein receptor defect B complementing (LDLB), mRNA
gi|17459160|ref|XM_040307.2|[17459160]

1114: XM_046949
Homo sapiens glutamate receptor, ionotropic, N-methyl D-aspartate 2C (GRIN2C), mRNA
gi|17457940|ref|XM_046949.3|[17457940]

1115: XM_050937
Homo sapiens galanin receptor 1 (GALR1), mRNA
gi|17457665|ref|XM_050937.2|[17457665]

1116: XM_058224
Homo sapiens protein tyrosine phosphatase, receptor type, M (PTPRM), mRNA
gi|17457059|ref|XM_058224.1|[17457059]

1117: XM_059877
Homo sapiens scavenger receptor cysteine rich domain containing, group B (4 domains) (SRCRB4D), mRNA gi|17452620|ref|XM_059877.1|[17452620]

1118: XM_030074
Homo sapiens corticotropin releasing hormone receptor 2 (CRHR2), mRNA
gi|17451624|ref|XM_030074.2|[17451624]

1119: XM_036899
Homo sapiens paired immunoglobulin-like receptor alpha (PILR(ALPHA)), mRNA
gi|17450024|ref|XM_036899.2|[17450024]

1120: XM_040292
Homo sapiens glutamate receptor, ionotropic, AMPA 1 (GRIA1), mRNA
gi|17447971|ref|XM_040292.3|[17447971]

1121: XM_003913
Homo sapiens integrin, alpha 2 (CD49B, alpha 2 subunit of VLA-2 receptor) (ITGA2), mRNA
gi|17447767|ref|XM_003913.5|[17447767]

1122: XM_052621
Homo sapiens VPS10 domain receptor protein (SORCS2), mRNA
gi|17447359|ref|XM_052621.2|[17447359]

1123: XM_011186
Homo sapiens platelet-derived growth factor receptor, alpha polypeptide (PDGFRA), mRNA
gi|17446713|ref|XM_011186.5|[17446713]

1124: XM_037260
Homo sapiens coagulation factor II (thrombin) receptor (F2R), mRNA
gi|17446698|ref|XM_037260.3|[17446698]

1125: XM_068231
Homo sapiens G protein-coupled receptor 78 (GPR78), mRNA
gi|17446518|ref|XM_068231.1|[17446518]

1126: XM_003896

Homo sapiens growth hormone receptor (GHR), mRNA
gi|17446516|ref|XM_003896.5|[17446516]

1127: XM_003883
Homo sapiens prolactin receptor (PRLR), mRNA
gi|17446302|ref|XM_003883.4|[17446302]

1128: XM_003423
Homo sapiens toll-like receptor 6 (TLR6), mRNA
gi|17443462|ref|XM_003423.5|[17443462]

1129: XM_050674
Homo sapiens kinase insert domain receptor (a type III receptor tyrosine kinase) (KDR), mRNA
gi|17443063|ref|XM_050674.2|[17443063]

1130: XM_016537
Homo sapiens low density lipoprotein receptor-related protein 8, apolipoprotein e receptor (LRP8), mRNA
gi|17438001|ref|XM_016537.4|[17438001]

1131: XM_050512
Homo sapiens activin A receptor, type I (ACVR1), mRNA
gi|17437640|ref|XM_050512.3|[17437640]

1132: XM_011248
Homo sapiens adrenergic, alpha-1B-, receptor (ADRA1B), mRNA
gi|17437111|ref|XM_011248.5|[17437111]

1133: XM_057299
Homo sapiens very large G protein-coupled receptor 1 (VLGR1), mRNA
gi|17436651|ref|XM_057299.2|[17436651]

1134: XM_042825
Homo sapiens luteinizing hormone/choriogonadotropin receptor (LHCGR), mRNA
gi|17433844|ref|XM_042825.3|[17433844]

1135: XM_039993
Homo sapiens fms-related tyrosine kinase 1 (vascular endothelial growth factor/vascular permeability factor receptor) (FLT1), mRNA
gi|16188964|ref|XM_039993.2|[16188964]

1136: XM_028642
Homo sapiens integrin, alpha 5 (fibronectin receptor, alpha polypeptide) (ITGA5), mRNA
gi|16186750|ref|XM_028642.2|[16186750]

1137: XM_057337
Homo sapiens cholinergic receptor, muscarinic 1 (CHRM1), mRNA
gi|16184321|ref|XM_057337.1|[16184321]

1138: XM_006447
Homo sapiens interleukin 10 receptor, alpha (IL10RA), mRNA
gi|16183626|ref|XM_006447.5|[16183626]

1139: XM_057984
Homo sapiens G protein-coupled receptor 51 (GPR51), mRNA
gi|16181083|ref|XM_057984.1|[16181083]

1140: XM_057452
Homo sapiens toll-like receptor 4 (TLR4), mRNA
gi|16179752|ref|XM_057452.1|[16179752]

1141: XM_051505
Homo sapiens opioid receptor, kappa 1 (OPRK1), mRNA
gi|16179331|ref|XM_051505.2|[16179331]

1142: XM_027651
Homo sapiens tumor necrosis factor receptor superfamily, member 10b (TNFRSF10B), mRNA
gi|16178146|ref|XM_027651.2|[16178146]

1144: XM_028141
Homo sapiens killer cell immunoglobulin-like receptor, three domains, long cytoplasmic tail, 2 (KIR3DL2), mRNA gi|16176785|ref|XM_028141.2|[16176785]

1145: XM_004872
Homo sapiens atrophin-1 interacting protein 1; activin receptor interacting protein 1 (KIAA0705), mRNA
gi|16175845|ref|XM_004872.6|[16175845]

1146: XM_057372
Homo sapiens tumor necrosis factor receptor superfamily, member 5 (TNFRSF5), mRNA
gi|16174074|ref|XM_057372.1|[16174074]

1147: XM_056391
Homo sapiens BAFF receptor (BAFFR), mRNA
gi|16168558|ref|XM_056391.1|[16168558]

1148: XM_054949
Homo sapiens transient receptor potential cation channel, subfamily V, member 2 (TRPV2), mRNA
gi|16165271|ref|XM_054949.1|[16165271]

1149: XM_009219
Homo sapiens endothelial differentiation, G-protein-coupled receptor 6 (EDG6), mRNA
gi|16163259|ref|XM_009219.5|[16163259]

1150: XM_057188
Homo sapiens transient receptor potential cation channel, subfamily M, member 4 (TRPM4), mRNA
gi|16162857|ref|XM_057188.1|[16162857]

1151: XM_033762
Homo sapiens growth factor receptor-bound protein 10 (GRB10), mRNA
gi|16162156|ref|XM_033762.2|[16162156]

1152: XM_037256
Homo sapiens protein tyrosine phosphatase, receptor type, N polypeptide 2 (PTPRN2), mRNA gi|16162004|ref|XM_037256.2|[16162004]

1153: XM_007662
Homo sapiens transient receptor potential cation channel, subfamily M, member 1 (TRPM1), mRNA
gi|16161643|ref|XM_007662.6|[16161643]

1154: XM_011327
Homo sapiens hepatitis A virus cellular receptor 1 (HAVCR-1), mRNA
gi|16159892|ref|XM_011327.4|[16159892]

1155: XM_034331
Homo sapiens endothelin receptor type A (EDNRA), mRNA
gi|16158485|ref|XM_034331.2|[16158485]

1156: XM_002212
Homo sapiens follicle stimulating hormone receptor (FSHR), mRNA
gi|16158251|ref|XM_002212.4|[16158251]

1157: XM_003736
Homo sapiens G protein-coupled receptor kinase 6 (GPRK6), mRNA
gi|16157601|ref|XM_003736.4|[16157601]

1158: XM_038350
Homo sapiens platelet-derived growth factor receptor, beta polypeptide (PDGFRB), mRNA
gi|16157449|ref|XM_038350.2|[16157449]

1159: XM_003789
Homo sapiens colony stimulating factor 1 receptor, formerly McDonough feline sarcoma viral (v-fms) oncogene homolog (CSF1R), mRNA
gi|16157447|ref|XM_003789.4|[16157447]

1160: XM_054659
Homo sapiens olfactory receptor, family 3, subfamily A, member 3 (OR3A3), mRNA
gi|15314104|ref|XM_054659.1|[15314104]

1161: XM_054658
Homo sapiens olfactory receptor, family 1, subfamily E, member 1 (OR1E1), mRNA
gi|15314100|ref|XM_054658.1|[15314100]

1162: XM_006275
Homo sapiens membrane-spanning 4-domains, subfamily A, member 1 (MS4A2), mRNA
gi|15311761|ref|XM_006275.4|[15311761]

1163: XM_012695
Homo sapiens growth factor receptor-bound protein 7 (GRB7), mRNA
gi|15310219|ref|XM_012695.4|[15310219]

1164: XM_045812
Homo sapiens G protein-coupled receptor 72 (GPR72), mRNA
gi|15308293|ref|XM_045812.2|[15308293]

1165: XM_033995
Homo sapiens histamine H4 receptor (HRH4), mRNA
gi|15305825|ref|XM_033995.2|[15305825]

1166: XM_036978
Homo sapiens tumor necrosis factor receptor superfamily, member 11a, activator of NFKB (TNFRSF11A), mRNA
gi|15305343|ref|XM_036978.2|[15305343]

1167: XM_015355
Homo sapiens protein tyrosine phosphatase, receptor type, R (PTPRR), mRNA
gi|15304370|ref|XM_015355.2|[15304370]

1168: XM_006738
Homo sapiens CD36 antigen (collagen type I receptor, thrombospondin receptor)-like 1 (CD36L1), mRNA
gi|15303296|ref|XM_006738.5|[15303296]

1169: XM_049255
Homo sapiens Fc fragment of IgE, low affinity II, receptor for (CD23A) (FCER2), mRNA
gi|15302967|ref|XM_049255.2|[15302967]

1170: XM_008930
Homo sapiens coagulation factor II (thrombin) receptor-like 3 (F2RL3), mRNA
gi|15302724|ref|XM_008930.4|[15302724]

1171: NT_029418
Homo sapiens chromosome 12 working draft sequence segment
gi|15302021|ref|NT_029418.1|Hs12_29577[15302021]

1173: XM_054004
Homo sapiens glutamate receptor, metabotropic 1 (GRM1), mRNA
gi|15299786|ref|XM_054004.1|[15299786]

1174: XM_046588
Homo sapiens G protein-coupled receptor slt (SLT), mRNA
gi|15299770|ref|XM_046588.2|[15299770]

1175: XM_032592
Homo sapiens VPS10 domain receptor protein SORCS 3 (SORCS3), mRNA
gi|15299687|ref|XM_032592.2|[15299687]

1176: XM_054157
Homo sapiens G protein-coupled receptor 35 (GPR35), mRNA
gi|15298180|ref|XM_054157.1|[15298180]

1177: XM_042907
Homo sapiens bone morphogenetic protein receptor, type IB (BMPR1B), mRNA
gi|15296528|ref|XM_042907.2|[15296528]

1178: XM_033031
Homo sapiens peroxisome proliferative activated receptor, gamma, coactivator 1 (PPARGC1), mRNA
gi|15295682|ref|XM_033031.2|[15295682]

1179: XM_003708
Homo sapiens gamma-aminobutyric acid (GABA) A receptor, pi (GABRP), mRNA
gi|15294866|ref|XM_003708.5|[15294866]

1180: XM_008189
Homo sapiens CMRF35 leukocyte immunoglobulin-like receptor (CMRF35), mRNA
gi|14785569|ref|XM_008189.4|[14785569]

1182: XM_033305
Homo sapiens lymphotoxin beta receptor (TNFR superfamily, member 3) (LTBR), mRNA
gi|14784387|ref|XM_033305.1|[14784387]

1183: XM_004350
Homo sapiens cannabinoid receptor 1 (brain) (CNR1), mRNA
gi|14783266|ref|XM_004350.4|[14783266]

1184: XM_004285
Homo sapiens peroxisome proliferative activated receptor, delta (PPARD), mRNA
gi|14782955|ref|XM_004285.4|[14782955]

1185: XM_042636
Homo sapiens inositol 1,4,5-triphosphate receptor, type 3 (ITPR3), mRNA
gi|14782869|ref|XM_042636.1|[14782869]

1187: XM_050142
Homo sapiens integrin, alpha M (complement component receptor 3, alpha; also known as CD11b (p170), macrophage antigen alpha polypeptide) (ITGAM), mRNA
gi|14779440|ref|XM_050142.1|[14779440]

1188: XM_037826
Homo sapiens adrenergic, beta, receptor kinase 2 (ADRBK2), mRNA
gi|14777914|ref|XM_037826.1|[14777914]

1189: XM_036497
Homo sapiens olfactory receptor, family 1, subfamily F, member 2 (OR1F2), mRNA
gi|14777865|ref|XM_036497.1|[14777865]

1190: XM_036891
Homo sapiens purinergic receptor P2X-like 1, orphan receptor (P2RXL1), mRNA
gi|14777537|ref|XM_036891.1|[14777537]

1191: XM_007986
Homo sapiens apolipoprotein B48 receptor (APOB48R), mRNA
gi|14777420|ref|XM_007986.4|[14777420]

1192: XM_047456
Homo sapiens melanocortin 1 receptor (alpha melanocyte stimulating hormone receptor) (MC1R), mRNA
gi|14776693|ref|XM_047456.1|[14776693]

1193: XM_030214
Homo sapiens glutamate receptor, ionotropic, N-methyl D-aspartate 2A (GRIN2A), mRNA
gi|14776459|ref|XM_030214.1|[14776459]

1194: XM_049959
Homo sapiens chemokine (C-C motif) receptor 7 (CCR7), mRNA
gi|14775963|ref|XM_049959.1|[14775963]

1196: XM_048049
Homo sapiens G protein-coupled receptor 56 (GPR56), mRNA
gi|14775189|ref|XM_048049.1|[14775189]

1197: XM_046488
Homo sapiens glucagon receptor (GCGR), mRNA
gi|14775175|ref|XM_046488.1|[14775175]

1198: XM_040635
Homo sapiens purinergic receptor P2X, ligand-gated ion channel, 1 (P2RX1), mRNA
gi|14774341|ref|XM_040635.1|[14774341]

1199: XM_018451
Homo sapiens cholinergic receptor, nicotinic, beta polypeptide 1 (muscle) (CHRNB1), mRNA
gi|14773487|ref|XM_018451.2|[14773487]

1201: XM_008432

Homo sapiens integrin, alpha 3 (antigen CD49C, alpha 3 subunit of VLA-3 receptor) (ITGA3), mRNA
gi|14773206|ref|XM_008432.4|[14773206]

1202: XM_047339
Homo sapiens opiate receptor-like 1 (OPRL1), mRNA
gi|14772199|ref|XM_047339.1|[14772199]

1203: XM_006349
Homo sapiens angiotensin receptor-like 1 (AGTRL1), mRNA
gi|14771894|ref|XM_006349.2|[14771894]

1204: XM_046182
Homo sapiens purinergic receptor P2X, ligand-gated ion channel, 3 (P2RX3), mRNA
gi|14771633|ref|XM_046182.1|[14771633]

1205: XM_006312
Homo sapiens sortilin-related receptor, L(DLR class) A repeats-containing (SORL1), mRNA
gi|14771251|ref|XM_006312.4|[14771251]

1206: XM_012936
Homo sapiens protein tyrosine phosphatase, receptor type, T (PTPRT), mRNA
gi|14770881|ref|XM_012936.3|[14770881]

1207: XM_040842
Homo sapiens cullin 5 (CUL5), mRNA
gi|14770334|ref|XM_040842.1|[14770334]

1208: XM_045103
Homo sapiens G protein coupled receptor interacting protein, complement-c1q tumor necrosis factor-related (ZSIG37), mRNA
gi|14770190|ref|XM_045103.1|[14770190]

1209: XM_040699
Homo sapiens transient receptor potential cation channel, subfamily C, member 6 (TRPC6), mRNA
gi|14770156|ref|XM_040699.1|[14770156]

1210: XM_040922

Homo sapiens interleukin 13 receptor, alpha 2 (IL13RA2), mRNA
gi|14769890|ref|XM_040922.1|[14769890]

1211: XM_028854

Homo sapiens cholinergic receptor, nicotinic, alpha polypeptide 4 (CHRNA4), mRNA
gi|14769881|ref|XM_028854.1|[14769881]

1212: XM_028783

Homo sapiens opioid growth factor receptor (OGFR), mRNA
gi|14769761|ref|XM_028783.1|[14769761]

1213: XM_050577

Homo sapiens leukocyte immunoglobulin-like receptor, subfamily B (with TM and ITIM domains), member 7 (ILT11), mRNA
gi|14769454|ref|XM_050577.1|[14769454]

1215: XM_045929

Homo sapiens purinergic receptor P2X, ligand-gated ion channel, 4 (P2RX4), mRNA
gi|14768232|ref|XM_045929.1|[14768232]

1216: XM_006929

Homo sapiens complement component 3a receptor 1 (C3AR1), mRNA
gi|14765892|ref|XM_006929.2|[14765892]

1217: XM_030897

Homo sapiens angiotensin receptor 2 (AGTR2), mRNA
gi|14765825|ref|XM_030897.1|[14765825]

1218: XM_037563

Homo sapiens G protein-coupled receptor 54 (GPR54), mRNA
gi|14765555|ref|XM_037563.1|[14765555]

1219: XM_045549

Homo sapiens FGF receptor activating protein 1 (FRAG1), mRNA
gi|14765112|ref|XM_045549.1|[14765112]

1220: XM_045706
Homo sapiens toll-like receptor 8 (TLR8), mRNA
gi|14764423|ref|XM_045706.1|[14764423]

1221: XM_013100
Homo sapiens G protein-coupled receptor 34 (GPR34), mRNA
gi|14764061|ref|XM_013100.3|[14764061]

1222: XM_012862
Homo sapiens cargo selection protein (mannose 6 phosphate receptor binding protein) (TIP47), mRNA
gi|14764025|ref|XM_012862.3|[14764025]

1223: XM_035037
Homo sapiens low density lipoprotein receptor-related protein 4 (LRP4), mRNA
gi|14763920|ref|XM_035037.1|[14763920]

1224: XM_050707
Homo sapiens activin A receptor type II-like 1 (ACVRL1), mRNA
gi|14763806|ref|XM_050707.1|[14763806]

1225: XM_036573
Homo sapiens low density lipoprotein receptor-related protein 3 (LRP3), mRNA
gi|14763070|ref|XM_036573.1|[14763070]

1226: XM_012843
Homo sapiens protein tyrosine phosphatase, receptor type, H (PTPRH), mRNA
gi|14762603|ref|XM_012843.3|[14762603]

1227: XM_006789
Homo sapiens protein tyrosine phosphatase, receptor type, B (PTPRB), mRNA
gi|14762249|ref|XM_006789.4|[14762249]

1229: XM_034808
Homo sapiens interleukin 1 receptor accessory protein-like 2 (IL1RAPL2), mRNA
gi|14760985|ref|XM_034808.1|[14760985]

1230: XM_006747

Homo sapiens inositol 1,4,5-triphosphate receptor, type 2 (ITPR2), mRNA
gi|14760648|ref|XM_006747.4|[14760648]

1231: XM_015921

Homo sapiens putative chemokine receptor; GTP-binding protein (HM74), mRNA
gi|14760439|ref|XM_015921.2|[14760439]

1232: XM_009008

Homo sapiens egf-like module containing, mucin-like, hormone receptor-like sequence 1 (EMR1), mRNA
gi|14759169|ref|XM_009008.4|[14759169]

1233: XM_028274

Homo sapiens prostaglandin I2 (prostacyclin) receptor (IP) (PTGIR), mRNA
gi|14758807|ref|XM_028274.1|[14758807]

1234: XM_007123

Homo sapiens 5-hydroxytryptamine (serotonin) receptor 2A (HTR2A), mRNA
gi|14757796|ref|XM_007123.4|[14757796]

1235: XM_049518

Homo sapiens intercellular adhesion molecule 1 (CD54), human rhinovirus receptor (ICAM1), mRNA
gi|14756651|ref|XM_049518.1|[14756651]

1236: XM_049496

Homo sapiens purinergic receptor P2Y, G-protein coupled, 11 (P2RY11), mRNA
gi|14756601|ref|XM_049496.1|[14756601]

1237: XM_007577

Homo sapiens cholinergic receptor, nicotinic, alpha polypeptide 5 (CHRNA5), mRNA
gi|14756537|ref|XM_007577.2|[14756537]

1238: XM_006636

Homo sapiens glutamate receptor, ionotropic, N-methyl D-aspartate 2B (GRIN2B), mRNA
gi|14756111|ref|XM_006636.4|[14756111]

1239: XM_044309
Homo sapiens poliovirus receptor (PVR), mRNA
gi|14755769|ref|XM_044309.1|[14755769]

1240: XM_004134
Homo sapiens 5-hydroxytryptamine (serotonin) receptor 1E (HTR1E), mRNA
gi|14755675|ref|XM_004134.4|[14755675]

1241: XM_033838
Homo sapiens chemokine (C-C motif) receptor 6 (CCR6), mRNA
gi|14755122|ref|XM_033838.1|[14755122]

1242: XM_031082
Homo sapiens formyl peptide receptor-like 1 (FPRL1), mRNA
gi|14754918|ref|XM_031082.1|[14754918]

1243: XM_028205
Homo sapiens glucagon-like peptide 1 receptor (GLP1R), mRNA
gi|14754205|ref|XM_028205.1|[14754205]

1244: XM_051710
Homo sapiens prostaglandin E receptor 2 (subtype EP2), 53kD (PTGER2), mRNA
gi|14753577|ref|XM_051710.1|[14753577]

1245: XM_048918
Homo sapiens met proto-oncogene (hepatocyte growth factor receptor) (MET), mRNA
gi|14752543|ref|XM_048918.1|[14752543]

1246: XM_045352
Homo sapiens receptor-interacting serine-threonine kinase 2 (RIPK2), mRNA
gi|14751723|ref|XM_045352.1|[14751723]

1247: XM_049463
Homo sapiens fibroblast growth factor receptor 1 (fms-related tyrosine kinase 2, Pfeiffer syndrome) (FGFR1), mRNA
gi|14750712|ref|XM_049463.1|[14750712]

1248: XM_033240
Homo sapiens leukotriene b4 receptor (chemokine receptor-like 1) (LTB4R), mRNA
gi|14750696|ref|XM_033240.1|[14750696]

1249: XM_046720
Homo sapiens gamma-aminobutyric acid (GABA) receptor, rho 1 (GABRR1), mRNA
gi|14750531|ref|XM_046720.1|[14750531]

1250: XM_050434
Homo sapiens interferon gamma receptor 1 (IFNGR1), mRNA
gi|14750131|ref|XM_050434.1|[14750131]

1251: XM_035832
Homo sapiens cholinergic receptor, nicotinic, beta polypeptide 3 (CHRNB3), mRNA
gi|14749978|ref|XM_035832.1|[14749978]

1252: XM_034142
Homo sapiens CD36 antigen (collagen type I receptor, thrombospondin receptor) (CD36), mRNA
gi|14749875|ref|XM_034142.1|[14749875]

1253: XM_030066
Homo sapiens growth hormone releasing hormone receptor (GHRHR), mRNA
gi|14749610|ref|XM_030066.1|[14749610]

1254: XM_007383
Homo sapiens G protein-coupled receptor 68 (GPR68), mRNA
gi|14748827|ref|XM_007383.2|[14748827]

1255: XM_004117
Homo sapiens 5-hydroxytryptamine (serotonin) receptor 1B (HTR1B), mRNA
gi|14747779|ref|XM_004117.2|[14747779]

1256: XM_036123

Homo sapiens transient receptor potential cation channel, subfamily M, member 3 (TRPM3), mRNA
gi|14743665|ref|XM_036123.1|[14743665]

1257: XM_011817
Homo sapiens muscle, skeletal, receptor tyrosine kinase (MUSK), mRNA
gi|14742818|ref|XM_011817.3|[14742818]

1258: XM_044653
Homo sapiens epidermal growth factor receptor (erythroblastic leukemia viral (v-erb-b) oncogene homolog, avian) (EGFR), mRNA
gi|14741797|ref|XM_044653.1|[14741797]

1259: XM_033529
Homo sapiens G protein-coupled receptor 85 (GPR85), mRNA
gi|14741568|ref|XM_033529.1|[14741568]

1260: XM_011916
Homo sapiens pancreatic polypeptide receptor 1 (PPYR1), mRNA
gi|14740172|ref|XM_011916.2|[14740172]

1261: XM_005486
Homo sapiens neurotrophic tyrosine kinase, receptor, type 2 (NTRK2), mRNA
gi|14740022|ref|XM_005486.4|[14740022]

1262: XM_042740
Homo sapiens region containing Sulfonylurea receptor; KIAA1674 (LOC142781), mRNA
gi|14739341|ref|XM_042740.1|[14739341]

1263: XM_045386
Homo sapiens very low density lipoprotein receptor (VLDLR), mRNA
gi|14736403|ref|XM_045386.1|[14736403]

1264: XM_004002
Homo sapiens hyaluronan-mediated motility receptor (RHAMM) (HMMR), mRNA
gi|14734503|ref|XM_004002.4|[14734503]

1265: XM_034451
Homo sapiens olfactory receptor, family 7, subfamily A, member 120 (OR7E120), mRNA
gi|14733406|ref|XM_034451.1|[14733406]

1266: XM_029284
Homo sapiens cholecystokinin A receptor (CCKAR), mRNA
gi|14733138|ref|XM_029284.1|[14733138]

1267: XM_052171
Homo sapiens 5-hydroxytryptamine (serotonin) receptor 4 (HTR4), mRNA
gi|14732310|ref|XM_052171.1|[14732310]

1268: XM_042695
Homo sapiens fibroblast growth factor receptor-like 1 (FGFRL1), mRNA
gi|14728655|ref|XM_042695.1|[14728655]

1269: XM_041933
Homo sapiens Ig superfamily receptor LNIR (LNIR), mRNA
gi|14723974|ref|XM_041933.1|[14723974]

1270: XM_032738
Homo sapiens glycine receptor, alpha 1 (startle disease/hyperekplexia, stiff man syndrome) (GLRA1), mRNA
gi|14722750|ref|XM_032738.1|[14722750]

1271: XM_032682
Homo sapiens gamma-aminobutyric acid (GABA) A receptor, alpha 6 (GABRA6), mRNA
gi|14722636|ref|XM_032682.1|[14722636]

1272: XM_017228
Homo sapiens low density lipoprotein-related protein 1 (alpha-2-macroglobulin receptor) (LRP1), mRNA
gi|13654580|ref|XM_017228.1|[13654580]

1273: XM_008538
Homo sapiens aryl hydrocarbon receptor interacting protein-like 1 (AIPL1), mRNA
gi|13653245|ref|XM_008538.3|[13653245]

1274: XM_007046
Homo sapiens vitamin D (1,25- dihydroxyvitamin D3) receptor (VDR), mRNA
gi|13653215|ref|XM_007046.3|[13653215]

1275: XM_007751
Homo sapiens gamma-aminobutyric acid (GABA) A receptor, beta 3 (GABRB3), mRNA
gi|13653090|ref|XM_007751.3|[13653090]

1276: XM_007719
Homo sapiens paired basic amino acid cleaving enzyme (furin, membrane associated receptor protein) (PACE), mRNA
gi|13652501|ref|XM_007719.2|[13652501]

1277: XM_010296
Homo sapiens transient receptor potential cation channel, subfamily C, member 5 (TRPC5), mRNA
gi|13652451|ref|XM_010296.2|[13652451]

1278: XM_006950
Homo sapiens tumor necrosis factor receptor superfamily, member 1A (TNFRSF1A), mRNA
gi|13652420|ref|XM_006950.3|[13652420]

1279: XM_008206
Homo sapiens receptor (calcitonin) activity modifying protein 2 (RAMP2), mRNA
gi|13652390|ref|XM_008206.3|[13652390]

1280: XM_013114
Homo sapiens interleukin 1 receptor accessory protein-like 1 (IL1RAPL1), mRNA
gi|13652318|ref|XM_013114.2|[13652318]

1281: XM_015989
Homo sapiens interleukin 9 receptor (IL9R), mRNA
gi|13652206|ref|XM_015989.1|[13652206]

1282: XM_006934

Homo sapiens arginine vasopressin receptor 1A (AVPR1A), mRNA
gi|13652044|ref|XM_006934.3|[13652044]

1283: XM_012441
Homo sapiens gamma-aminobutyric acid (GABA) A receptor, alpha 5 (GABRA5), mRNA
gi|13651536|ref|XM_012441.2|[13651536]

1284: XM_008193
Homo sapiens putative receptor protein (PMI), mRNA
gi|13650873|ref|XM_008193.2|[13650873]

1285: XM_009108
Homo sapiens glutamate receptor, ionotropic, N-methyl D-aspartate 2D (GRIN2D), mRNA
gi|13650682|ref|XM_009108.3|[13650682]

1286: XM_015505
Homo sapiens AXL receptor tyrosine kinase (AXL), mRNA
gi|13650099|ref|XM_015505.1|[13650099]

1287: XM_006145
Homo sapiens dopamine receptor D4 (DRD4), mRNA
gi|13647063|ref|XM_006145.2|[13647063]

1288: XM_009803
Homo sapiens transient receptor potential cation channel, subfamily M, member 2 (TRPM2), mRNA
gi|13646881|ref|XM_009803.3|[13646881]

1289: XM_004030
Homo sapiens adrenergic, beta-2-, receptor, surface (ADRB2), mRNA
gi|13645597|ref|XM_004030.2|[13645597]

1290: XM_011703
Homo sapiens tumor necrosis factor receptor superfamily, member 10a (TNFRSF10A), mRNA
gi|13644652|ref|XM_011703.2|[13644652]

1291: XM_003986
Homo sapiens gamma-aminobutyric acid (GABA) A receptor, gamma 2 (GABRG2), mRNA
gi|13643024|ref|XM_003986.2|[13643024]

1292: XM_004253
Homo sapiens gamma-aminobutyric acid (GABA) receptor, rho 2 (GABRR2), mRNA
gi|13642452|ref|XM_004253.2|[13642452]

1293: XM_006233
Homo sapiens glutamate receptor, ionotrophic, AMPA 4 (GRIA4), mRNA
gi|13639643|ref|XM_006233.3|[13639643]

1294: XM_005384
Homo sapiens RAR-related orphan receptor B (RORB), mRNA
gi|13639481|ref|XM_005384.3|[13639481]

1295: XM_004988
Homo sapiens aryl hydrocarbon receptor (AHR), mRNA
gi|13631520|ref|XM_004988.2|[13631520]

1296: XM_011364
Homo sapiens lymphocyte antigen 95 (activating NK-receptor; NK-p44) (LY95), mRNA
gi|13630600|ref|XM_011364.2|[13630600]

1297: XM_009612
Homo sapiens neurotensin receptor 1 (high affinity) (NTSR1), mRNA
gi|13630500|ref|XM_009612.2|[13630500]

1298: XM_003417
Homo sapiens CD36 antigen (collagen type I receptor, thrombospondin
receptor)-like 2 (lysosomal integral membrane protein II) (CD36L2), mRNA
gi|13630130|ref|XM_003417.3|[13630130]

1299: XM_007817
Homo sapiens tumor necrosis factor receptor superfamily, member 17 (TNFRSF17), mRNA
gi|13627219|ref|XM_007817.3|[13627219]

1300: XM_012949
Homo sapiens complement component 1, q subcomponent, receptor 1 (C1QR1), mRNA
gi|12742414|ref|XM_012949.1|[12742414]

1301: XM_009594
Homo sapiens somatostatin receptor 4 (SSTR4), mRNA
gi|12742412|ref|XM_009594.2|[12742412]

1302: XM_008512
Homo sapiens vanilloid receptor subtype 1 (VR1), mRNA
gi|12740624|ref|XM_008512.2|[12740624]

1303: XM_006931
Homo sapiens oxidised low density lipoprotein (lectin-like) receptor 1 (OLR1), mRNA
gi|12737735|ref|XM_006931.2|[12737735]

1304: XM_006933
Homo sapiens C-type lectin-like receptor-1 (LOC51267), mRNA
gi|12737731|ref|XM_006933.2|[12737731]

1305: XM_004438
Homo sapiens interleukin 20 receptor, alpha (IL20RA), mRNA
gi|12732139|ref|XM_004438.2|[12732139]

1306: XM_003692
Homo sapiens 5-hydroxytryptamine (serotonin) receptor 1A (HTR1A), mRNA
gi|12731011|ref|XM_003692.2|[12731011]

1307: XM_010228
Homo sapiens G protein-coupled receptor 50 (GPR50), mRNA
gi|12719157|ref|XM_010228.2|[12719157]

1308: XM_009082
Homo sapiens low density lipoprotein receptor (familial hypercholesterolemia) (LDLR), mRNA gi|11525992|ref|XM_009082.1|[11525992]

1309: XM_006296
Homo sapiens cholinergic receptor, muscarinic 4 (CHRM4), mRNA
gi|11437838|ref|XM_006296.1|[11437838]

1310: NT_009784
Homo sapiens chromosome 12 working draft sequence segment
gi|11436706|ref|NT_009784.1|Hs12_9941[11436706]

1311: XM_003386
Homo sapiens gonadotropin-releasing hormone receptor (GNRHR), mRNA
gi|11435615|ref|XM_003386.1|[11435615]

1312: NT_024131
Homo sapiens chromosome 10 working draft sequence segment
gi|11430625|ref|NT_024131.1|Hs10_24287[11430625]

1313: XM_009373
Homo sapiens formyl peptide receptor-like 2 (FPRL2), mRNA
gi|11426996|ref|XM_009373.1|[11426996]

1314: XM_008520
Homo sapiens cholinergic receptor, nicotinic, epsilon polypeptide (CHRNE), mRNA
gi|11426945|ref|XM_008520.1|[11426945]

1315: XM_009140
Homo sapiens G protein-coupled receptor 4 (GPR4), mRNA
gi|11425489|ref|XM_009140.1|[11425489]

1316: XM_008279
Homo sapiens adenosine A2b receptor (ADORA2B), mRNA
gi|11425432|ref|XM_008279.1|[11425432]

1317: XM_010321
Homo sapiens glycine receptor, alpha 2 (GLRA2), mRNA
gi|11421007|ref|XM_010321.1|[11421007]

1318: XM_004808
Homo sapiens taste receptor, type 2, member 4 (TAS2R4), mRNA
gi|11420322|ref|XM_004808.1|[11420322]

1319: XM_004807
Homo sapiens taste receptor, type 2, member 5 (TAS2R5), mRNA
gi|11420320|ref|XM_004807.1|[11420320]

1320: XM_011092
Homo sapiens glycine receptor, alpha 3 (GLRA3), mRNA
gi|18556859|ref|XM_011092.4|[18556859]

1321: XM_003324
Homo sapiens transient receptor potential cation channel, subfamily C, member 3 (TRPC3), mRNA
gi|18556760|ref|XM_003324.5|[18556760]

1322: XM_011068
Homo sapiens macrophage stimulating 1 receptor (c-met-related tyrosine kinase) (MST1R), mRNA
gi|18556611|ref|XM_011068.4|[18556611]

1323: XM_011064
Homo sapiens protein tyrosine phosphatase, receptor type, G (PTPRG), mRNA
gi|18556526|ref|XM_011064.7|[18556526]

1324: XM_003207
Homo sapiens glutamate receptor, metabotropic 2 (GRM2), mRNA
gi|18556346|ref|XM_003207.5|[18556346]

1325: XM_036436
Homo sapiens interleukin 1 receptor accessory protein (IL1RAP), mRNA
gi|18555803|ref|XM_036436.4|[18555803]

1326: XM_031246
Homo sapiens roundabout, axon guidance receptor, homolog 2 (Drosophila) (ROBO2), mRNA
gi|18555796|ref|XM_031246.2|[18555796]

1327: XM_003226
Homo sapiens vasoactive intestinal peptide receptor 1 (VIPR1), mRNA
gi|18555693|ref|XM_003226.7|[18555693]

1328: NT_005824
Homo sapiens chromosome 3 working draft sequence segment
gi|18555677|ref|NT_005824.7|Hs3_5981[18555677]

1329: XM_093692
Homo sapiens RYK receptor-like tyrosine kinase (RYK), mRNA
gi|18555675|ref|XM_093692.1|[18555675]

1332: NT_005564
Homo sapiens chromosome 3 working draft sequence segment
gi|18555104|ref|NT_005564.8|Hs3_5721[18555104]

1333: XM_010943
Homo sapiens inositol 1,4,5-triphosphate receptor, type 1 (ITPR1), mRNA
gi|18554594|ref|XM_010943.7|[18554594]

1334: XM_052730
Homo sapiens transferrin receptor (p90, CD71) (TFRC), mRNA
gi|18553906|ref|XM_052730.3|[18553906]

1335: XM_032666
Homo sapiens calcium-sensing receptor (hypocalciuric hypercalcemia 1, severe neonatal hyperparathyroidism) (CASR), mRNA
gi|18553576|ref|XM_032666.3|[18553576]

1336: XM_002686
Homo sapiens interleukin 1 receptor, type I (IL1R1), mRNA
gi|18553052|ref|XM_002686.6|[18553052]

1337: XM_002596

Homo sapiens protein tyrosine phosphatase, receptor type, N (PTPRN), mRNA
gi|18552617|ref|XM_002596.6|[18552617]

1338: XM_087110
Homo sapiens macrophage receptor with collagenous structure (MARCO), mRNA
gi|18552038|ref|XM_087110.1|[18552038]

1340: XM_087047
Homo sapiens G protein-coupled receptor 66 (GPR66), mRNA
gi|18551251|ref|XM_087047.1|[18551251]

1341: XM_086954
Homo sapiens G protein-coupled receptor 45 (GPR45), mRNA
gi|18549982|ref|XM_086954.1|[18549982]

1342: XM_029434
Homo sapiens toll-like receptor 5 (TLR5), mRNA
gi|18549454|ref|XM_029434.2|[18549454]

1344: XM_089355
Homo sapiens LDL receptor adaptor protein (ARH), mRNA
gi|18549097|ref|XM_089355.1|[18549097]

1346: XM_086483
Homo sapiens Fc fragment of IgG, low affinity IIa, receptor for (CD32) (FCGR2A), mRNA
gi|18548731|ref|XM_086483.1|[18548731]

1347: XM_046751
Homo sapiens protein tyrosine phosphatase, receptor type, f polypeptide (PTPRF), interacting protein (liprin), alpha 4 (PPFIA4), mRNA
gi|18548679|ref|XM_046751.3|[18548679]

1348: XM_001821
Homo sapiens glutamate receptor, ionotropic, kainate 3 (GRIK3), mRNA
gi|18548332|ref|XM_001821.7|[18548332]

1349: XM_002205
Homo sapiens colony stimulating factor 3 receptor (granulocyte) (CSF3R), mRNA
gi|18548330|ref|XM_002205.2|[18548330]

1350: XM_033690
Homo sapiens protein tyrosine phosphatase, receptor type, U (PTPRU), mRNA
gi|18548204|ref|XM_033690.2|[18548204]

1351: XM_001795
Homo sapiens lamin B receptor (LBR), mRNA
gi|18548051|ref|XM_001795.6|[18548051]

1352: XM_058179
Homo sapiens natural killer cell receptor 2B4 (CD244), mRNA
gi|18547600|ref|XM_058179.3|[18547600]

1353: XM_086356
Homo sapiens cannabinoid receptor 2 (macrophage) (CNR2), mRNA
gi|18547399|ref|XM_086356.1|[18547399]

1354: XM_001499
Homo sapiens endothelial differentiation, sphingolipid G-protein-coupled receptor, 1 (EDG1), mRNA
gi|18547249|ref|XM_001499.5|[18547249]

1355: NT_031737
Homo sapiens chromosome 1 working draft sequence segment
gi|18547126|ref|NT_031737.1|Hs1_31908[18547126]

1356: XM_010608
Homo sapiens G-protein coupled receptor 88 (GPR88), mRNA
gi|18547116|ref|XM_010608.6|[18547116]

1357: XM_089029
Homo sapiens olfactory receptor, family 2, subfamily L, member 2 (OR2L2), mRNA
gi|18547000|ref|XM_089029.1|[18547000]

1358: XM_089028
Homo sapiens olfactory receptor, family 2, subfamily L, member 1 (OR2L1), mRNA
gi|18546996|ref|XM_089028.1|[18546996]

1359: XM_089016
Homo sapiens olfactory receptor, family 1, subfamily C, member 1 (OR1C1), mRNA
gi|18546895|ref|XM_089016.1|[18546895]

1360: XM_001289
Homo sapiens xenotropic and polytropic retrovirus receptor (XPR1), mRNA
gi|18546688|ref|XM_001289.7|[18546688]

1361: XM_049849
Homo sapiens tumor necrosis factor receptor superfamily, member 14 (herpesvirus entry mediator) (TNFRSF14), mRNA
gi|18546661|ref|XM_049849.3|[18546661]

1362: XM_001667
Homo sapiens natural killer cell receptor, immunoglobulin superfamily member (BY55), mRNA
gi|18546631|ref|XM_001667.5|[18546631]

1364: XM_086285
Homo sapiens leucine-rich repeat-containing G protein-coupled receptor 6 (LGR6), mRNA
gi|18546477|ref|XM_086285.1|[18546477]

1365: XM_016748
Homo sapiens protein tyrosine phosphatase, receptor type, C (PTPRC), mRNA
gi|18546353|ref|XM_016748.4|[18546353]

1366: XM_088942
Homo sapiens olfactory receptor, family 2, subfamily M, member 4 (OR2M4), mRNA
gi|18546222|ref|XM_088942.1|[18546222]

1367: XM_086242
Homo sapiens receptor tyrosine kinase-like orphan receptor 1 (ROR1), mRNA
gi|18546174|ref|XM_086242.1|[18546174]

1368: XM_086232
Homo sapiens G protein-coupled receptor 61 (GPR61), mRNA
gi|18546070|ref|XM_086232.1|[18546070]

1369: XM_042739
Homo sapiens cadherin, EGF LAG seven-pass G-type receptor 2 (flamingo homolog, Drosophila) (CELSR2), mRNA
gi|18546045|ref|XM_042739.2|[18546045]

1370: XM_002008
Homo sapiens complement component (3d/Epstein Barr virus) receptor 2 (CR2), mRNA
gi|18545768|ref|XM_002008.6|[18545768]

1371: XM_052013
Homo sapiens polymeric immunoglobulin receptor (PIGR), mRNA
gi|18545758|ref|XM_052013.2|[18545758]

1372: XM_001320
Homo sapiens low density lipoprotein receptor defect C complementing (LDLC), mRNA
gi|18545223|ref|XM_001320.4|[18545223]

1373: NT_030585
Homo sapiens chromosome 1 working draft sequence segment
gi|18544898|ref|NT_030585.2|Hs1_30841[18544898]

1374: XM_084053
Homo sapiens complement component (3b/4b) receptor 1, including Knops blood group system (CR1), mRNA
gi|18544845|ref|XM_084053.1|[18544845]

1376: XM_039685
Homo sapiens putative G-protein coupled receptor (SH120), mRNA
gi|17488963|ref|XM_039685.3|[17488963]

1377: XM_001687

Homo sapiens adenosine A1 receptor (ADORA1), mRNA
gi|17488879|ref|XM_001687.5|[17488879]

1378: XM_002700
Homo sapiens cytochrome c oxidase subunit VIIa polypeptide 2 like (COX7A2L), mRNA
gi|17462137|ref|XM_002700.3|[17462137]

1379: XM_002673
Homo sapiens calcitonin receptor-like (CALCRL), mRNA
gi|17447546|ref|XM_002673.5|[17447546]

1380: XM_001924
Homo sapiens transforming growth factor, beta receptor III (betaglycan, 300kD) (TGFBR3), mRNA
gi|17446897|ref|XM_001924.6|[17446897]

1381: XM_001744
Homo sapiens tumor necrosis factor receptor superfamily, member 8 (TNFRSF8), mRNA
gi|17444362|ref|XM_001744.6|[17444362]

1382: XM_054837
Homo sapiens tumor necrosis factor receptor superfamily, member 1B (TNFRSF1B), mRNA
gi|17444359|ref|XM_054837.2|[17444359]

1383: XM_037011
Homo sapiens T-cell receptor interacting molecule (TRIM), mRNA
gi|17438759|ref|XM_037011.2|[17438759]

1384: NT_022773
Homo sapiens chromosome 4 working draft sequence segment
gi|17438611|ref|NT_022773.6|Hs4_22929[17438611]

1385: XM_051522
Homo sapiens G protein-coupled receptor (RDC1), mRNA
gi|17437231|ref|XM_051522.2|[17437231]

1386: NT_029249
Homo sapiens chromosome 2 working draft sequence segment
gi|17436701|ref|NT_029249.2|Hs2_29408[17436701]

1387: XM_050043
Homo sapiens gamma-aminobutyric acid (GABA) A receptor, alpha 4 (GABRA4), mRNA
gi|17436698|ref|XM_050043.2|[17436698]

1388: XM_001857
Homo sapiens platelet-activating factor receptor (PTAFR), mRNA
gi|17435918|ref|XM_001857.3|[17435918]

1389: XM_001630
Homo sapiens prostaglandin F receptor (FP) (PTGFR), mRNA
gi|17434349|ref|XM_001630.5|[17434349]

1390: XM_058183
Homo sapiens activating NK receptor (KALI), mRNA
gi|16165765|ref|XM_058183.1|[16165765]

1391: XM_003177
Homo sapiens oxytocin receptor (OXTR), mRNA
gi|16164840|ref|XM_003177.5|[16164840]

1392: XM_001778
Homo sapiens ryanodine receptor 2 (cardiac) (RYR2), mRNA
gi|16161568|ref|XM_001778.6|[16161568]

1393: XM_039118
Homo sapiens phospholipase A2 receptor 1, 180kD (PLA2R1), mRNA
gi|16160858|ref|XM_039118.2|[16160858]

1394: NT_005791
Homo sapiens chromosome 3 working draft sequence segment
gi|16159942|ref|NT_005791.5|Hs3_5948[16159942]

1395: NT_029941

Homo sapiens chromosome 3 working draft sequence segment
gi|16158541|ref|NT_029941.1|Hs3_30196[16158541]

1396: XM_056760

Homo sapiens tumor necrosis factor receptor superfamily, member 9 (TNFRSF9), mRNA
gi|16158007|ref|XM_056760.1|[16158007]

1397: XM_010871

Homo sapiens adrenergic, alpha-2B-, receptor (ADRA2B), mRNA
gi|16157882|ref|XM_010871.5|[16157882]

1398: XM_055737

Homo sapiens interleukin 6 receptor (IL6R), mRNA
gi|16157271|ref|XM_055737.1|[16157271]

1399: XM_043563

Homo sapiens insulin receptor-related receptor (INSRR), mRNA
gi|15299156|ref|XM_043563.2|[15299156]

1400: XM_001466

Homo sapiens protein tyrosine phosphatase, receptor type, F (PTPRF), mRNA
gi|15299050|ref|XM_001466.5|[15299050]

1401: XM_002888

Homo sapiens activin A receptor, type IIB (ACVR2B), mRNA
gi|15298060|ref|XM_002888.3|[15298060]

1402: XM_049427

Homo sapiens interleukin 5 receptor, alpha (IL5RA), mRNA
gi|15297287|ref|XM_049427.2|[15297287]

1404: XM_047502

Homo sapiens chemokine (C-X3-C) receptor 1 (CX3CR1), mRNA
gi|15295593|ref|XM_047502.2|[15295593]

1405: XM_041048
Homo sapiens chemokine (C-C motif) receptor 8 (CCR8), mRNA
gi|15295589|ref|XM_041048.2|[15295589]

1406: XM_052155
Homo sapiens adenosine A3 receptor (ADORA3), mRNA
gi|14739381|ref|XM_052155.1|[14739381]

1407: XM_002926
Homo sapiens chemokine (C-C motif) receptor-like 2 (CCRL2), mRNA
gi|14736663|ref|XM_002926.3|[14736663]

1408: XM_030397
Homo sapiens chemokine (C-C motif) receptor 5 (CCR5), mRNA
gi|14736645|ref|XM_030397.1|[14736645]

1409: XM_040605
Homo sapiens interleukin 17B receptor (IL17BR), mRNA
gi|14735848|ref|XM_040605.1|[14735848]

1410: XM_003199
Homo sapiens growth hormone secretagogue receptor (GHSR), mRNA
gi|14735283|ref|XM_003199.4|[14735283]

1411: XM_041399
Homo sapiens glutamate receptor, metabotropic 7 (GRM7), mRNA
gi|14734683|ref|XM_041399.1|[14734683]

1412: XM_039011
Homo sapiens integrin, alpha 4 (antigen CD49D, alpha 4 subunit of VLA-4 receptor) (ITGA4), mRNA
gi|14733147|ref|XM_039011.1|[14733147]

1413: XM_033709
Homo sapiens opioid receptor, delta 1 (OPRD1), mRNA
gi|14732044|ref|XM_033709.1|[14732044]

1414: XM_033469
Homo sapiens transforming growth factor, beta receptor II (70-80kD) (TGFBR2), mRNA
gi|14732004|ref|XM_033469.1|[14732004]

1415: XM_017782
Homo sapiens ectodysplasin 1, anhidrotic receptor (EDAR), mRNA
gi|14731094|ref|XM_017782.2|[14731094]

1416: XM_002475
Homo sapiens insulin receptor substrate 1 (IRS1), mRNA
gi|14730385|ref|XM_002475.4|[14730385]

1417: XM_051470
Homo sapiens angiotensin receptor 1 (AGTR1), mRNA
gi|14729512|ref|XM_051470.1|[14729512]

1418: XM_001542
Homo sapiens 5-hydroxytryptamine (serotonin) receptor 1D (HTR1D), mRNA
gi|14726872|ref|XM_001542.4|[14726872]

1419: XM_052382
Homo sapiens histamine receptor H1 (HRH1), mRNA
gi|14726259|ref|XM_052382.1|[14726259]

1420: XM_032349
Homo sapiens interleukin 22 receptor (IL22R), mRNA
gi|14725224|ref|XM_032349.1|[14725224]

1421: XM_002792
Homo sapiens APMCF1 protein (APMCF1), mRNA
gi|14720925|ref|XM_002792.4|[14720925]

1422: XM_045070
Homo sapiens immunoglobulin superfamily receptor translocation associated 2 (IRTA2), mRNA
gi|14720460|ref|XM_045070.1|[14720460]

1423: XM_045067
Homo sapiens immunoglobulin superfamily receptor translocation associated 1 (IRTA1), mRNA
gi|14720452|ref|XM_045067.1|[14720452]

1425: XM_002685
Homo sapiens interleukin 1 receptor-like 2 (IL1RL2), mRNA
gi|12728885|ref|XM_002685.2|[12728885]

1426: XM_002624
Homo sapiens G protein-coupled receptor 75 (GPR75), mRNA
gi|11430331|ref|XM_002624.1|[11430331]

1427: XM_001907
Homo sapiens G protein-coupled receptor 25 (GPR25), mRNA
gi|11425714|ref|XM_001907.1|[11425714]

1428: XM_001543
Homo sapiens G protein-coupled receptor 52 (GPR52), mRNA
gi|11423045|ref|XM_001543.1|[11423045]

1429: NM_016113
Homo sapiens transient receptor potential cation channel, subfamily V, member 2 (TRPV2), mRNA
gi|7706766|ref|NM_016113.1|[7706766]

1430: NM_002837
Homo sapiens protein tyrosine phosphatase, receptor type, B (PTPRB), mRNA
gi|18491009|ref|NM_002837.2|[18491009]

1431: NM_017625
Homo sapiens intelectin (ITLN), mRNA
gi|8923027|ref|NM_017625.1|[8923027]

1432: NM_000651
Homo sapiens complement component (3b/4b) receptor 1, including Knops blood group system (CR1), transcript variant S, mRNA
gi|18490997|ref|NM_000651.2|[18490997]

1433: NM_000573
Homo sapiens complement component (3b/4b) receptor 1, including Knops blood group system (CR1), transcript variant F, mRNA
gi|18490996|ref|NM_000573.2|[18490996]

1435: BC022501
Homo sapiens, neurotensin receptor 2, clone MGC:26447 IMAGE:4792730, mRNA, complete cds
gi|18490911|gb|BC022501.1|[18490911]

1436: BC022447
Homo sapiens, angiotensin receptor 1, clone MGC:25987 IMAGE:4799755, mRNA, complete cds
gi|18490885|gb|BC022447.1|[18490885]

1437: BC022317
Homo sapiens, T cell receptor delta diversity 3, clone MGC:22624 IMAGE:4732634, mRNA, complete cds
gi|18490613|gb|BC022317.1|[18490613]

1438: BC022304
Homo sapiens, receptor (calcitonin) activity modifying protein 3, clone MGC:22548 IMAGE:4717934, mRNA, complete cds
gi|18490610|gb|BC022304.1|[18490610]

1439: BC022496
Homo sapiens, glutamate receptor, metabotropic 3, clone MGC:26392 IMAGE:4792430, mRNA, complete cds
gi|18490393|gb|BC022496.1|[18490393]

1440: BC022511
Homo sapiens, endothelin receptor type A, clone MGC:26548 IMAGE:4812050, mRNA, complete cds
gi|18490297|gb|BC022511.1|[18490297]

1441: BC022502
Homo sapiens, glycine receptor, beta, clone IMAGE:4792516, mRNA
gi|18490294|gb|BC022502.1|[18490294]

1442: BC022449
Homo sapiens, gamma-aminobutyric acid (GABA) A receptor, beta 1, clone MGC:25991 IMAGE:4797401, mRNA, complete cds
gi|18490266|gb|BC022449.1|[18490266]

1443: BC022295
Homo sapiens, oxidised low density lipoprotein (lectin-like) receptor 1, clone MGC:22491 IMAGE:4722086, mRNA, complete cds
gi|18490152|gb|BC022295.1|[18490152]

1444: BC022279
Homo sapiens, CMRF35 leukocyte immunoglobulin-like receptor, clone MGC:22395 IMAGE:4692025, mRNA, complete cds
gi|18490142|gb|BC022279.1|[18490142]

1448: AH011463
Homo sapiens chromosome 7 map 7q22
gi|18483169|gb|AH011463.1|SEG_AF461188S[18483169]

1449: AF453828
Homo sapiens G protein-coupled receptor affecting testicular descent (GREAT) mRNA, complete cds
gi|18483167|gb|AF453828.1|[18483167]

1450: AY072912
Homo sapiens coxsackie-adenovirus-receptor isoform CAR4/7 (CXADR) mRNA, complete cds; alternatively spliced
gi|18482481|gb|AY072912.1|[18482481]

1451: AY072911
Homo sapiens coxsackie-adenovirus-receptor isoform CAR3/7 (CXADR) mRNA, complete cds; alternatively spliced
gi|18482479|gb|AY072911.1|[18482479]

1452: AY072910
Homo sapiens soluble coxsackie-adenovirus-receptor isoform CAR2/7 (CXADR) mRNA, complete cds; alternatively spliced
gi|18482477|gb|AY072910.1|[18482477]

1453: NM_020399
Homo sapiens PDZ/coiled-coil domain binding partner for the rho-family GTPase TC10 (PIST), mRNA
gi|9966876|ref|NM_020399.1|[9966876]

1454: NM_017935
Homo sapiens hypothetical protein FLJ20706 (BANK), mRNA
gi|8923635|ref|NM_017935.1|[8923635]

1455: NM_002438
Homo sapiens mannose receptor, C type 1 (MRC1), mRNA
gi|4505244|ref|NM_002438.1|[4505244]

1456: AF321913
Homo sapiens histamine H3 receptor isoform 4 (HRH3) mRNA, complete cds, alternatively spliced
gi|18461386|gb|AF321913.1|[18461386]

1457: AF321912
Homo sapiens histamine H3 receptor isoform 3 (HRH3) mRNA, complete cds, alternatively spliced
gi|18461384|gb|AF321912.1|[18461384]

1458: AF321911
Homo sapiens histamine H3 receptor isoform 2 (HRH3) mRNA, complete cds, alternatively spliced
gi|18461382|gb|AF321911.1|[18461382]

1459: AF321910
Homo sapiens histamine H3 receptor isoform 1 (HRH3) mRNA, complete cds, alternatively spliced
gi|18461380|gb|AF321910.1|[18461380]

1460: NM_080841
Homo sapiens protein tyrosine phosphatase, receptor type, A (PTPRA), transcript variant 3, mRNA
gi|18450370|ref|NM_080841.1|[18450370]

1461: NM_080840
Homo sapiens protein tyrosine phosphatase, receptor type, A (PTPRA), transcript variant 2, mRNA
gi|18450368|ref|NM_080840.1|[18450368]

1462: NM_002836
Homo sapiens protein tyrosine phosphatase, receptor type, A (PTPRA), transcript variant 1, mRNA
gi|18450367|ref|NM_002836.2|[18450367]

1463: NM_023915
Homo sapiens G protein-coupled receptor 87 (GPR87), mRNA
gi|13236505|ref|NM_023915.1|[13236505]

1464: NM_003029
Homo sapiens SHC (Src homology 2 domain containing) transforming protein 1 (SHC1), mRNA
gi|10835030|ref|NM_003029.1|[10835030]

1465: NM_018490
Homo sapiens G protein-coupled receptor 48 (GPR48), mRNA
gi|8923700|ref|NM_018490.1|[8923700]

1466: NM_006065
Homo sapiens signal-regulatory protein beta 1 (SIRPB1), mRNA
gi|5174678|ref|NM_006065.1|[5174678]

1467: NM_003667
Homo sapiens G protein-coupled receptor 49 (GPR49), mRNA
gi|4504378|ref|NM_003667.1|[4504378]

1468: NM_080816

Homo sapiens signal-regulatory protein beta 2 (SIRPB2), transcript variant 2, mRNA
gi|18426908|ref|NM_080816.1|[18426908]

1469: NM_018556
Homo sapiens signal-regulatory protein beta 2 (SIRPB2), transcript variant 1, mRNA
gi|18426907|ref|NM_018556.2|[18426907]

1470: NM_080914
Homo sapiens asialoglycoprotein receptor 2 (ASGR2), transcript variant 3, mRNA
gi|18426876|ref|NM_080914.1|[18426876]

1471: NM_080913
Homo sapiens asialoglycoprotein receptor 2 (ASGR2), transcript variant 2, mRNA
gi|18426874|ref|NM_080913.1|[18426874]

1472: NM_080912
Homo sapiens asialoglycoprotein receptor 2 (ASGR2), transcript variant H2', mRNA
gi|18426872|ref|NM_080912.1|[18426872]

1473: NM_001181
Homo sapiens asialoglycoprotein receptor 2 (ASGR2), transcript variant 1, mRNA
gi|18426871|ref|NM_001181.2|[18426871]

1474: NM_001671
Homo sapiens asialoglycoprotein receptor 1 (ASGR1), mRNA
gi|18426870|ref|NM_001671.2|[18426870]

1475: NM_014978
Homo sapiens VPS10 domain receptor protein SORCS 3 (SORCS3), mRNA
gi|18379345|ref|NM_014978.1|[18379345]

1476: NM_021625
Homo sapiens transient receptor potential cation channel, subfamily V, member 4 (TRPV4), mRNA
gi|13699862|ref|NM_021625.2|[13699862]

1477: NM_020960
Homo sapiens G protein-coupled receptor 107 (GPR107), mRNA
gi|13470087|ref|NM_020960.1|[13470087]

1478: NM_021634
Homo sapiens leucine-rich repeat-containing G protein-coupled receptor 7 (LGR7), mRNA
gi|11056007|ref|NM_021634.1|[11056007]

1479: NM_016179
Homo sapiens transient receptor potential cation channel, subfamily C, member 4 (TRPC4), mRNA
gi|7706746|ref|NM_016179.1|[7706746]

1480: NM_004621
Homo sapiens transient receptor potential cation channel, subfamily C, member 6 (TRPC6), mRNA
gi|5730101|ref|NM_004621.2|[5730101]

1481: NM_003304
Homo sapiens transient receptor potential cation channel, subfamily C, member 1 (TRPC1), mRNA
gi|4507684|ref|NM_003304.1|[4507684]

1485: NM_016235
Homo sapiens G protein-coupled receptor, family C, group 1, member B (GPRC5B), mRNA
gi|7706450|ref|NM_016235.1|[7706450]

1487: AF024642
Homo sapiens luteinizing hormone receptor gene, exon 1 and partial cds
gi|2655113|gb|AF024642.1|AF024642[2655113]

1488: NM_007128
Homo sapiens pre-B lymphocyte gene 1 (VPREB1), mRNA
gi|18379350|ref|NM_007128.2|[18379350]

1489: NM_020777
Homo sapiens VPS10 domain receptor protein (SORCS2), mRNA
gi|18379343|ref|NM_020777.1|[18379343]

1490: NM_052918
Homo sapiens VPS10 domain receptor protein SORCS 1 (SORCS1), mRNA
gi|18379341|ref|NM_052918.2|[18379341]

1491: AF391164
Homo sapiens osteoclast-associated receptor hOSCAR-M3 (OSCAR) mRNA, complete cds
gi|18376830|gb|AF391164.1|AF391164[18376830]

1492: AF391163
Homo sapiens osteoclast-associated receptor hOSCAR-M2 (OSCAR) mRNA, complete cds
gi|18376828|gb|AF391163.1|AF391163[18376828]

1493: AF391162
Homo sapiens osteoclast-associated receptor hOSCAR-M1 (OSCAR) mRNA, complete cds
gi|18376826|gb|AF391162.1|AF391162[18376826]

1494: AJ421783
Homo sapiens mRNA for short transient receptor potential channel 7 (TRP7 gene)
gi|18376628|emb|AJ421783.1|HSA421783[18376628]

1497: AF410902
Homo sapiens neurotrophin receptor tyrosine kinase type 2 (NTRK2) gene, promoter region and partial cds; alternatively spliced
gi|18369868|gb|AF410902.1|AF410902[18369868]

1498: AF410901
Homo sapiens neurotrophin receptor tyrosine kinase type 2 truncated isoform (NTRK2) mRNA, complete cds; alternatively spliced
gi|18369866|gb|AF410901.1|AF410901[18369866]

1499: AF410900
Homo sapiens neurotrophin receptor tyrosine kinase type 2 truncated isoform (NTRK2) mRNA, complete cds; alternatively spliced gi|18369864|gb|AF410900.1|AF410900[18369864]

1500: AF410899
Homo sapiens neurotrophin receptor tyrosine kinase type 2 (NTRK2) mRNA, complete cds; alternatively spliced
gi|18369862|gb|AF410899.1|AF410899[18369862]

1501: AF410898
Homo sapiens clone DKFZp547L014 neurotrophin receptor tyrosine kinase type 2 truncated isoform (NTRK2) mRNA, partial cds; alternatively spliced
gi|18369860|gb|AF410898.1|AF410898[18369860]

1502: AY071830
Homo sapiens interleukin 9 receptor (IL9R) gene, complete cds
gi|18071671|gb|AY071830.1|[18071671]

1503: AF421362
Homo sapiens transient receptor potential channel 4 zeta splice variant (TRPC4) mRNA, complete cds; alternatively spliced
gi|16517177|gb|AF421362.1|AF421362[16517177]

1504: AF421361
Homo sapiens transient receptor potential channel 4 eta splice variant (TRPC4) mRNA, complete cds; alternatively spliced
gi|16517175|gb|AF421361.1|AF421361[16517175]

1505: AF421360
Homo sapiens transient receptor potential channel 4 epsilon splice variant (TRPC4) mRNA, complete cds; alternatively spliced
gi|16517173|gb|AF421360.1|AF421360[16517173]

1506: AF421359
Homo sapiens transient receptor potential channel 4 beta splice variant (TRPC4) mRNA, complete cds; alternatively spliced
gi|16517171|gb|AF421359.1|AF421359[16517171]

1507: AF421358
Homo sapiens transient receptor potential channel 4 alpha splice variant (TRPC4)

mRNA, complete cds; alternatively spliced
gi|16517169|gb|AF421358.1|AF421358[16517169]

1508: AF359246
Homo sapiens fibroblast growth factor receptor 4 variant mRNA, complete cds
gi|13991617|gb|AF359246.1|AF359246[13991617]

1509: NM_022349
Homo sapiens membrane-spanning 4-domains, subfamily A, member 6A (MS4A6A), mRNA
gi|11641258|ref|NM_022349.1|[11641258]

1510: NM_006055
Homo sapiens LanC lantibiotic synthetase component C-like 1 (bacterial) (LANCL1), mRNA
gi|5174444|ref|NM_006055.1|[5174444]

1511: NM_005716
Homo sapiens regulator of G-protein signalling 19 interacting protein 1 (RGS19IP1), mRNA
gi|5031714|ref|NM_005716.1|[5031714]

1512: NM_003307
Homo sapiens transient receptor potential cation channel, subfamily M, member 2 (TRPM2), mRNA
gi|4507688|ref|NM_003307.1|[4507688]

1513: NM_003807
Homo sapiens tumor necrosis factor (ligand) superfamily, member 14 (TNFSF14), mRNA
gi|4507600|ref|NM_003807.1|[4507600]

1514: NM_002984
Homo sapiens small inducible cytokine A4 (SCYA4), mRNA
gi|4506844|ref|NM_002984.1|[4506844]

1515: NM_021181
Homo sapiens 19A24 protein (CRACC), mRNA
gi|12711663|ref|NM_021181.2|[12711663]

1516: BC021892
Homo sapiens, CD36 antigen (collagen type I receptor, thrombospondin receptor)-like 2 (lysosomal integral membrane protein II), clone MGC:9392 IMAGE:3872778, mRNA, complete cds
gi|18257311|gb|BC021892.1|BC021892[18257311]

1517: AF459285
Homo sapiens 5-hydroxytryptamine receptor 3 subunit C (HTR3C) mRNA, complete cds
gi|18251965|gb|AF459285.1|AF459285[18251965]

1518: BC021553
Homo sapiens, G protein coupled receptor interacting protein, complement-c1q tumor necrosis factor-related, clone MGC:31795 IMAGE:4622952, mRNA, complete cds
gi|18204860|gb|BC021553.1|BC021553[18204860]

1519: BC021195
Homo sapiens, dopamine receptor D2, clone MGC:10521 IMAGE:3939741, mRNA, complete cds
gi|18203702|gb|BC021195.1|BC021195[18203702]

1520: BC020752
Homo sapiens, Epstein-Barr virus induced gene 2 (lymphocyte-specific G protein-coupled receptor), clone MGC:22599 IMAGE:4722289, mRNA, complete cds
gi|18089130|gb|BC020752.1|BC020752[18089130]

1521: BC020614
Homo sapiens, G protein-coupled receptor 84, clone MGC:22224 IMAGE:4279185, mRNA, complete cds
gi|18089044|gb|BC020614.1|BC020614[18089044]

1522: BC021104
Homo sapiens, apelin; peptide ligand for APJ receptor, clone MGC:31846 IMAGE:4586949, mRNA, complete cds
gi|18088893|gb|BC021104.1|BC021104[18088893]

1523: BC020805
Homo sapiens, leukocyte receptor cluster (LRC) member 5, clone MGC:23828

IMAGE:4277870, mRNA, complete cds
gi|18088780|gb|BC020805.1|BC020805[18088780]

1524: BC020742
Homo sapiens, complement component 3a receptor 1, clone MGC:22570 IMAGE:4690283, mRNA, complete cds
gi|18088764|gb|BC020742.1|BC020742[18088764]

1525: BC020815
Homo sapiens, putative receptor protein, clone MGC:23860 IMAGE:4296149, mRNA, complete cds
gi|18088747|gb|BC020815.1|BC020815[18088747]

1526: BC020768
Homo sapiens, olfactory receptor, family 51, subfamily E, member 2, clone MGC:22638 IMAGE:4249775, mRNA, complete cds
gi|18088468|gb|BC020768.1|BC020768[18088468]

1527: BC020739
Homo sapiens, interleukin 13 receptor, alpha 2, clone MGC:22566 IMAGE:4807603, mRNA, complete cds
gi|18088440|gb|BC020739.1|BC020739[18088440]

1528: BC020678
Homo sapiens, G protein-coupled receptor 34, clone MGC:22389 IMAGE:4770479, mRNA, complete cds
gi|18088371|gb|BC020678.1|BC020678[18088371]

1529: BC020669
Homo sapiens, advanced glycosylation end product-specific receptor, clone MGC:22357 IMAGE:4718076, mRNA, complete cds
gi|18088362|gb|BC020669.1|BC020669[18088362]

1530: BC020968
Homo sapiens, chemokine (C-X-C motif), receptor 4 (fusin), clone MGC:9199 IMAGE:3846345, mRNA, complete cds
gi|18088082|gb|BC020968.1|BC020968[18088082]

1531: BC019610
Homo sapiens, somatostatin receptor 2, clone MGC:24950 IMAGE:3875163, mRNA, complete cds
gi|18043108|gb|BC019610.1|BC019610[18043108]

1532: BC020079
Homo sapiens, lamin B receptor, clone MGC:9041 IMAGE:3925138, mRNA, complete cds
gi|18042833|gb|BC020079.1|BC020079[18042833]

1715: NM_001364
Homo sapiens discs, large homolog 2, chapsyn-110 (Drosophila) (DLG2), mRNA
gi|4557526|ref|NM_001364.1|[4557526]

1716: NM_080744
Homo sapiens scavenger receptor cysteine rich domain containing, group B (4 domains) (SRCRB4D), mRNA
gi|18152778|ref|NM_080744.1|[18152778]

1717: AB063170
Homo sapiens mRNA for BANK, complete cds
gi|17646091|dbj|AB063170.1|AB063170[17646091]

1718: NM_022760
Homo sapiens chromosome 20 open reading frame 81 (C20orf81), mRNA
gi|16163672|ref|NM_022760.2|[16163672]

1719: NM_032554
Homo sapiens G protein-coupled receptor 81 (GPR81), mRNA
gi|14211850|ref|NM_032554.1|[14211850]

1720: AB054004
Homo sapiens DR5 gene for death receptor 5, promoter and partial cds
gi|13429873|dbj|AB054004.1|AB054004[13429873]

1721: NM_000668
Homo sapiens alcohol dehydrogenase IB (class I), beta polypeptide (ADH1B), mRNA
gi|11496887|ref|NM_000668.2|[11496887]

1722: NM_018697
Homo sapiens LanC lantibiotic synthetase component C-like 2 (bacterial) (LANCL2), mRNA
gi|8923910|ref|NM_018697.1|[8923910]

1723: NM_016610
Homo sapiens toll-like receptor 8 (TLR8), mRNA
gi|7706147|ref|NM_016610.1|[7706147]

1725: NM_015833
Homo sapiens adenosine deaminase, RNA-specific, B1 (RED1 homolog rat) (ADARB1), transcript variant DRABA2b, mRNA
gi|7669476|ref|NM_015833.1|[7669476]

1727: NM_007184
Homo sapiens nischarin (NISCH), mRNA
gi|6005787|ref|NM_007184.1|[6005787]

1728: NM_000139
Homo sapiens membrane-spanning 4-domains, subfamily A, member 1 (MS4A2), mRNA
gi|4503676|ref|NM_000139.1|[4503676]

1730: NM_080681
Homo sapiens collagen, type XI, alpha 2 (COL11A2), transcript variant 2, mRNA
gi|18201918|ref|NM_080681.1|[18201918]

1731: NM_080680
Homo sapiens collagen, type XI, alpha 2 (COL11A2), transcript variant 1, mRNA
gi|18201916|ref|NM_080680.1|[18201916]

1732: NM_080679
Homo sapiens collagen, type XI, alpha 2 (COL11A2), transcript variant 3, mRNA
gi|18201914|ref|NM_080679.1|[18201914]

1733: NM_006115
Homo sapiens preferentially expressed antigen in melanoma (PRAME), mRNA
gi|18201906|ref|NM_006115.2|[18201906]

1734: NM_020526
Homo sapiens EphA8 (EPHA8), mRNA
gi|18201903|ref|NM_020526.2|[18201903]

1735: NM_080818
Homo sapiens G protein-coupled receptor 80 (GPR80), mRNA
gi|18201871|ref|NM_080818.1|[18201871]

1736: NM_080817
Homo sapiens G protein-coupled receptor 82 (GPR82), mRNA
gi|18201869|ref|NM_080817.1|[18201869]

1737: AF400075
Homo sapiens coagulation factor II (thrombin) receptor-like 1 (F2RL1) gene, complete cds
gi|15021772|gb|AF400075.1|AF400075[15021772]

1738: NM_024021
Homo sapiens membrane-spanning 4-domains, subfamily A, member 4 (MS4A4A), mRNA
gi|13430865|ref|NM_024021.1|[13430865]

1739: AB066218
Homo sapiens RYR1 gene for ryanodine receptor type1, partial cds, clone:4-101
gi|18181961|dbj|AB066218.1|AB066218[18181961]

1740: AB066217
Homo sapiens RYR1 gene for ryanodine receptor type1, partial cds, clone:4-96
gi|18181959|dbj|AB066217.1|AB066217[18181959]

1741: NM_021950
Homo sapiens membrane-spanning 4-domains, subfamily A, member 2 (Fc fragment of IgE, high affinity I, receptor for; beta polypeptide) (MS4A1), mRNA
gi|11386186|ref|NM_021950.1|[11386186]

1742: NM_012323
Homo sapiens v-maf musculoaponeurotic fibrosarcoma oncogene homolog F (avian)

(MAFF), mRNA
gi|6912489|ref|NM_012323.1|[6912489]

1743: AJ298292
Homo sapiens mRNA for histamine receptor H4 (HRH4 gene)
gi|18152452|emb|AJ298292.1|HSA298292[18152452]

1744: AB070621
Homo sapiens HTR4 gene for 5-hydroxytryptamine 4 receptor, promoter and exon 1
gi|18149171|dbj|AB070621.1|AB070621[18149171]

1745: AB070620
Homo sapiens HTR4 mRNA for 5-hydroxytryptamine 4 receptor, partial cds
gi|18149169|dbj|AB070620.1|AB070620[18149169]

1746: AB050774
Homo sapiens N27C7-4 gene, complete cds
gi|18147104|dbj|AB050774.1|AB050774[18147104]

1747: AB048946
Homo sapiens PrRPR gene for prolactin releasing peptide receptor, complete cds
gi|18147078|dbj|AB048946.1|AB048946[18147078]

1748: NM_030760
Homo sapiens endothelial differentiation, sphingolipid G-protein-coupled receptor, 8 (EDG8), mRNA
gi|18141314|ref|NM_030760.2|[18141314]

1749: NM_032556
Homo sapiens interleukin-1 HY2 (IL1HY2), mRNA
gi|18141307|ref|NM_032556.2|[18141307]

1750: AF459634
Homo sapiens immunoglobulin superfamily receptor translocation associated 5 mRNA, complete cds
gi|18140080|gb|AF459634.1|AF459634[18140080]

1751: AF459633
Homo sapiens immunoglobulin superfamily receptor translocation associated 4 mRNA, complete cds
gi|18140078|gb|AF459633.1|AF459633[18140078]

1752: AY046529
Homo sapiens melanocortin 1 receptor mutant V122M (MC1R) gene, complete cds
gi|18138241|gb|AY046529.1|[18138241]

1753: AY046528
Homo sapiens melanocortin 1 receptor mutant I40T (MC1R) gene, complete cds
gi|18138239|gb|AY046528.1|[18138239]

1754: AX338549
Sequence 1 from Patent WO0185790
gi|18128949|emb|AX338549.1|AX338549[18128949]

1755: NM_001745
Homo sapiens calcium modulating ligand (CAMLG), mRNA
gi|18105008|ref|NM_001745.2|[18105008]

1756: NM_001128
Homo sapiens adaptor-related protein complex 1, gamma 1 subunit (AP1G1), mRNA
gi|18104997|ref|NM_001128.2|[18104997]

1757: NM_080545
Homo sapiens adaptor-related protein complex 1, gamma 2 subunit (AP1G2), transcript variant 2, mRNA
gi|18104995|ref|NM_080545.1|[18104995]

1758: NM_003917
Homo sapiens adaptor-related protein complex 1, gamma 2 subunit (AP1G2), transcript variant 1, mRNA
gi|18104994|ref|NM_003917.2|[18104994]

1759: AF459027
Homo sapiens immunoglobulin superfamily receptor translocation associated protein 3 mRNA, complete cds gi|18092654|gb|AF459027.1|AF459027[18092654]

1760: AY069943
Homo sapiens TCP11b protein mRNA, complete cds
gi|18091790|gb|AY069943.1|[18091790]

1761: AY063126
Homo sapiens Fc alpha/mu receptor mRNA, partial cds; alternatively spliced
gi|18032043|gb|AY063126.1|[18032043]

1762: AY063125
Homo sapiens Fc alpha/mu receptor mRNA, complete cds; alternatively spliced
gi|18032041|gb|AY063125.1|[18032041]

1763: AF395264
Homo sapiens clone EIII48bpVNTR55 dopamine receptor D4 (DRD4) gene, partial cds
gi|17063763|gb|AF395264.1|AF395264[17063763]

1764: AF395263
Homo sapiens clone EIII48bpVNTR54 dopamine receptor D4 (DRD4) gene, partial cds
gi|17063761|gb|AF395263.1|AF395263[17063761]

1765: AF395262
Homo sapiens clone EIII48bpVNTR53 dopamine receptor D4 (DRD4) gene, partial cds
gi|17063759|gb|AF395262.1|AF395262[17063759]

1766: AF395261
Homo sapiens clone EIII48bpVNTR52 dopamine receptor D4 (DRD4) gene, partial cds
gi|17063757|gb|AF395261.1|AF395261[17063757]

1767: AF395260
Homo sapiens clone EIII48bpVNTR51 dopamine receptor D4 (DRD4) gene, partial cds
gi|17063755|gb|AF395260.1|AF395260[17063755]

1768: AF395259
Homo sapiens clone EIII48bpVNTR50 dopamine receptor D4 (DRD4) gene, partial cds
gi|17063753|gb|AF395259.1|AF395259[17063753]

1769: AF395258
Homo sapiens clone EIII48bpVNTR49 dopamine receptor D4 (DRD4) gene, partial cds
gi|17063751|gb|AF395258.1|AF395258[17063751]

1770: AF395257
Homo sapiens clone EIII48bpVNTR48 dopamine receptor D4 (DRD4) gene, partial cds
gi|17063749|gb|AF395257.1|AF395257[17063749]

1771: AF395256
Homo sapiens clone EIII48bpVNTR47 dopamine receptor D4 (DRD4) gene, partial cds
gi|17063747|gb|AF395256.1|AF395256[17063747]

1772: AF395255
Homo sapiens clone EIII48bpVNTR46 dopamine receptor D4 (DRD4) gene, partial cds
gi|17063745|gb|AF395255.1|AF395255[17063745]

1773: AF395254
Homo sapiens clone EIII48bpVNTR45 dopamine receptor D4 (DRD4) gene, partial cds
gi|17063743|gb|AF395254.1|AF395254[17063743]

1774: AF395253
Homo sapiens clone EIII48bpVNTR44 dopamine receptor D4 (DRD4) gene, partial cds
gi|17063741|gb|AF395253.1|AF395253[17063741]

1775: AF395252
Homo sapiens clone EIII48bpVNTR43 dopamine receptor D4 (DRD4) gene, partial cds
gi|17063739|gb|AF395252.1|AF395252[17063739]

1776: AF395251
Homo sapiens clone EIII48bpVNTR42 dopamine receptor D4 (DRD4) gene, partial cds
gi|17063737|gb|AF395251.1|AF395251[17063737]

1777: AF395250
Homo sapiens clone EIII48bpVNTR41 dopamine receptor D4 (DRD4) gene, partial cds
gi|17063735|gb|AF395250.1|AF395250[17063735]

1778: AF395249
Homo sapiens clone EIII48bpVNTR40 dopamine receptor D4 (DRD4) gene, partial cds
gi|17063733|gb|AF395249.1|AF395249[17063733]

1779: AF395248
Homo sapiens clone EIII48bpVNTR39 dopamine receptor D4 (DRD4) gene, partial cds
gi|17063731|gb|AF395248.1|AF395248[17063731]

1780: AF395247
Homo sapiens clone EIII48bpVNTR38 dopamine receptor D4 (DRD4) gene, partial cds
gi|17063729|gb|AF395247.1|AF395247[17063729]

1781: AF395246
Homo sapiens clone EIII48bpVNTR37 dopamine receptor D4 (DRD4) gene, partial cds
gi|17063727|gb|AF395246.1|AF395246[17063727]

1782: AF395245
Homo sapiens clone EIII48bpVNTR36 dopamine receptor D4 (DRD4) gene, partial cds
gi|17063725|gb|AF395245.1|AF395245[17063725]

1783: AF395244
Homo sapiens clone EIII48bpVNTR35 dopamine receptor D4 (DRD4) gene, partial cds
gi|17063723|gb|AF395244.1|AF395244[17063723]

1784: AF395243
Homo sapiens clone EIII48bpVNTR34 dopamine receptor D4 (DRD4) gene, partial cds
gi|17063721|gb|AF395243.1|AF395243[17063721]

1785: AF395242
Homo sapiens clone EIII48bpVNTR33 dopamine receptor D4 (DRD4) gene, partial cds
gi|17063719|gb|AF395242.1|AF395242[17063719]

1786: AF395241
Homo sapiens clone EIII48bpVNTR32 dopamine receptor D4 (DRD4) gene, partial cds
gi|17063717|gb|AF395241.1|AF395241[17063717]

1787: AF395240
Homo sapiens clone EIII48bpVNTR31 dopamine receptor D4 (DRD4) gene, partial cds
gi|17063715|gb|AF395240.1|AF395240[17063715]

1788: AF395239
Homo sapiens clone EIII48bpVNTR30 dopamine receptor D4 (DRD4) gene, partial cds
gi|17063713|gb|AF395239.1|AF395239[17063713]

1789: AF395238
Homo sapiens clone EIII48bpVNTR29 dopamine receptor D4 (DRD4) gene, partial cds
gi|17063711|gb|AF395238.1|AF395238[17063711]

1790: AF395237
Homo sapiens clone EIII48bpVNTR28 dopamine receptor D4 (DRD4) gene, partial cds
gi|17063709|gb|AF395237.1|AF395237[17063709]

1791: AF395236
Homo sapiens clone EIII48bpVNTR27 dopamine receptor D4 (DRD4) gene, partial cds
gi|17063707|gb|AF395236.1|AF395236[17063707]

1792: AF395235
Homo sapiens clone EIII48bpVNTR26 dopamine receptor D4 (DRD4) gene, partial cds
gi|17063705|gb|AF395235.1|AF395235[17063705]

1793: AF395234
Homo sapiens clone EIII48bpVNTR25 dopamine receptor D4 (DRD4) gene, partial cds
gi|17063703|gb|AF395234.1|AF395234[17063703]

1794: AF395233
Homo sapiens clone EIII48bpVNTR24 dopamine receptor D4 (DRD4) gene, partial cds
gi|17063701|gb|AF395233.1|AF395233[17063701]

1795: AF395232
Homo sapiens clone EIII48bpVNTR23 dopamine receptor D4 (DRD4) gene, partial cds
gi|17063699|gb|AF395232.1|AF395232[17063699]

1796: AF395231

Homo sapiens clone EIII48bpVNTR22 dopamine receptor D4 (DRD4) gene, partial cds
gi|17063697|gb|AF395231.1|AF395231[17063697]

1797: AF395230
Homo sapiens clone EIII48bpVNTR21 dopamine receptor D4 (DRD4) gene, partial cds
gi|17063695|gb|AF395230.1|AF395230[17063695]

1798: AF395229
Homo sapiens clone EIII48bpVNTR20 dopamine receptor D4 (DRD4) gene, partial cds
gi|17063693|gb|AF395229.1|AF395229[17063693]

1799: AF395228
Homo sapiens clone EIII48bpVNTR19 dopamine receptor D4 (DRD4) gene, partial cds
gi|17063691|gb|AF395228.1|AF395228[17063691]

1800: AF395227
Homo sapiens clone EIII48bpVNTR18 dopamine receptor D4 (DRD4) gene, partial cds
gi|17063689|gb|AF395227.1|AF395227[17063689]

1801: AF395226
Homo sapiens clone EIII48bpVNTR17 dopamine receptor D4 (DRD4) gene, partial cds
gi|17063687|gb|AF395226.1|AF395226[17063687]

1802: AF395225
Homo sapiens clone EIII48bpVNTR16 dopamine receptor D4 (DRD4) gene, partial cds
gi|17063685|gb|AF395225.1|AF395225[17063685]

1803: AF395224
Homo sapiens clone EIII48bpVNTR15 dopamine receptor D4 (DRD4) gene, partial cds
gi|17063683|gb|AF395224.1|AF395224[17063683]

1804: AF395223
Homo sapiens clone EIII48bpVNTR14 dopamine receptor D4 (DRD4) gene, partial cds
gi|17063681|gb|AF395223.1|AF395223[17063681]

1805: AF395222
Homo sapiens clone EIII48bpVNTR13 dopamine receptor D4 (DRD4) gene, partial cds gi|17063679|gb|AF395222.1|AF395222[17063679]

1806: AF395221
Homo sapiens clone EIII48bpVNTR12 dopamine receptor D4 (DRD4) gene, partial cds
gi|17063677|gb|AF395221.1|AF395221[17063677]

1807: AF395220
Homo sapiens clone EIII48bpVNTR11 dopamine receptor D4 (DRD4) gene, partial cds
gi|17063675|gb|AF395220.1|AF395220[17063675]

1808: AF395219
Homo sapiens clone EIII48bpVNTR10 dopamine receptor D4 (DRD4) gene, partial cds
gi|17063673|gb|AF395219.1|AF395219[17063673]

1809: AF395218
Homo sapiens clone EIII48bpVNTR9 dopamine receptor D4 (DRD4) gene, partial cds
gi|17063671|gb|AF395218.1|AF395218[17063671]

1810: AF395217
Homo sapiens clone EIII48bpVNTR8 dopamine receptor D4 (DRD4) gene, partial cds
gi|17063669|gb|AF395217.1|AF395217[17063669]

1811: AF395216
Homo sapiens clone EIII48bpVNTR7 dopamine receptor D4 (DRD4) gene, partial cds
gi|17063667|gb|AF395216.1|AF395216[17063667]

1812: AF395215
Homo sapiens clone EIII48bpVNTR6 dopamine receptor D4 (DRD4) gene, partial cds
gi|17063665|gb|AF395215.1|AF395215[17063665]

1813: AF395214
Homo sapiens clone EIII48bpVNTR5 dopamine receptor D4 (DRD4) gene, partial cds
gi|17063663|gb|AF395214.1|AF395214[17063663]

1814: AF395213
Homo sapiens clone EIII48bpVNTR4 dopamine receptor D4 (DRD4) gene, partial cds
gi|17063661|gb|AF395213.1|AF395213[17063661]

1815: AF395212

Homo sapiens clone EIII48bpVNTR3 dopamine receptor D4 (DRD4) gene, partial cds
gi|17063659|gb|AF395212.1|AF395212[17063659]

1816: AF395211

Homo sapiens clone EIII48bpVNTR2 dopamine receptor D4 (DRD4) gene, partial cds
gi|17063657|gb|AF395211.1|AF395211[17063657]

1817: AF395210

Homo sapiens clone EIII48bpVNTR1 dopamine receptor D4 (DRD4) gene, partial cds
gi|17063655|gb|AF395210.1|AF395210[17063655]

1818: AF258342

Homo sapiens biogenic amine receptor-like protein mRNA, complete cds
gi|15428321|gb|AF258342.1|AF258342[15428321]

1819: AJ278982

Homo sapiens mRNA for 5-hydroxytryptamine4 receptor (HTR4 gene), splice variant h5-HT4(n)
gi|12274905|emb|AJ278982.1|HSA278982[12274905]

1820: AJ278981

Homo sapiens mRNA for 5-hydroxytryptamine4 receptor (HTR4 gene), splice variant h5-HT4(g)
gi|12274903|emb|AJ278981.1|HSA278981[12274903]

1821: AJ278980

Homo sapiens mRNA for 5-hydroxytryptamine4 receptor (HTR4 gene), splice variant h5-HT4(b)
gi|12274901|emb|AJ278980.1|HSA278980[12274901]

1822: AJ278979

Homo sapiens mRNA for 5-hydroxytryptamine4 receptor (HTR4 gene), splice variant h5-HT4(a)
gi|12274899|emb|AJ278979.1|HSA278979[12274899]

1823: NM_014555
Homo sapiens transient receptor potential cation channel, subfamily M, member 5 (TRPM5), mRNA
gi|11225265|ref|NM_014555.1|[11225265]

1824: AF200627
Homo sapiens putative catecholamine receptor gene, complete cds
gi|10441576|gb|AF200627.1|AF200627[10441576]

1825: AF257789
Homo sapiens urokinase-type plasminogen activator receptor mRNA, partial cds
gi|8050814|gb|AF257789.1|AF257789[8050814]

1826: NM_002335
Homo sapiens low density lipoprotein receptor-related protein 5 (LRP5), mRNA
gi|4505018|ref|NM_002335.1|[4505018]

1827: Y00508
H. sapiens M1 gene for muscarinic acetylcholine receptor
gi|297405|emb|Y00508.1|HSMIMAR[297405]

1828: AF457599
Homo sapiens killer cell immunoglobulin-like receptor (KIR3DL1) gene, KIR3DL1-NKB1-like allele, promoter region and exon 1
gi|18087432|gb|AF457599.1|AF457599[18087432]

1829: AF457598
Homo sapiens killer cell immunoglobulin-like receptor (KIR3DL1) gene, KIR3DL1-NKB1-like allele, promoter region and exon 1
gi|18087431|gb|AF457598.1|AF457598[18087431]

1830: AF457597
Homo sapiens killer cell immunoglobulin-like receptor (KIR3DL1) gene, KIR3DL1-NKAT3-like allele, promoter region and exon 1
gi|18087430|gb|AF457597.1|AF457597[18087430]

1831: AJ312755
Homo sapiens mRNA for scavenger receptor cysteine-rich protein SRCRB-S4D, (SRCRB-S4D gene)
gi|18073905|emb|AJ312755.1|HSA312755[18073905]

1832: AF331842
Homo sapiens SPPR-2 mRNA, complete cds, alternatively spliced
gi|18033260|gb|AF331842.1|AF331842[18033260]

1833: AF331841
Homo sapiens SPPR-1 mRNA, complete cds, alternatively spliced
gi|18033258|gb|AF331841.1|AF331841[18033258]

1834: AF331840
Homo sapiens SPPR mRNA, complete cds, alternatively spliced
gi|18033256|gb|AF331840.1|AF331840[18033256]

1835: AF284756
Homo sapiens VPS10 domain receptor SorCS mRNA, complete cds
gi|18032274|gb|AF284756.1|AF284756[18032274]

1836: AF328684
Homo sapiens Fc-epsilon receptor III mRNA, complete cds
gi|18028292|gb|AF328684.1|AF328684[18028292]

1837: AY029413
Homo sapiens interleukin-1 receptor antagonist-like FIL1 theta (FIL1-theta) mRNA, complete cds
gi|18025343|gb|AY029413.1|[18025343]

1838: AF126470
Homo sapiens KOR-3D (KOR-3) mRNA, complete cds
gi|18000078|gb|AF126470.1|AF126470[18000078]

1839: AF435925
Homo sapiens very large G protein-coupled receptor 1b (VLGR1) mRNA, complete cds
gi|16904207|gb|AF435925.1|AF435925[16904207]

1840: G67431

D7S3125 GRB10 Homo sapiens STS genomic, sequence tagged site
gi|12025489|gb|G67431.1|G67431[12025489]

1841: AF260136
Homo sapiens NK cell receptor D (NKG2-D) mRNA, NKG2-D*03 allele, complete cds
gi|9295444|gb|AF260136.1|AF260136[9295444]

1842: AF260135
Homo sapiens NK cell receptor D (NKG2-D) mRNA, NKG2-D*02 allele, complete cds
gi|9295442|gb|AF260135.1|AF260135[9295442]

1843: AF260134
Homo sapiens NK cell receptor C (NKG2-C) mRNA, NKG2-C*02 allele, complete cds
gi|9295440|gb|AF260134.1|AF260134[9295440]

1844: NM_015891
Homo sapiens pre-mRNA splicing factor 17 (PRP17), mRNA
gi|7706656|ref|NM_015891.1|[7706656]

1845: L12397
Homo sapiens Dopamine D4 receptor (DRD4) gene, partial cds
gi|291947|gb|L12397.1|HUMD4G[291947]

1846: NM_019888
Homo sapiens melanocortin 3 receptor (MC3R), mRNA
gi|17986278|ref|NM_019888.2|[17986278]

1847: NM_000795
Homo sapiens dopamine receptor D2 (DRD2), transcript variant 1, mRNA
gi|17986271|ref|NM_000795.2|[17986271]

1848: NM_016574
Homo sapiens dopamine receptor D2 (DRD2), transcript variant 2, mRNA
gi|17986269|ref|NM_016574.2|[17986269]

1849: AY070269
Homo sapiens hypocretin receptor 1 (HCRTR1) gene, complete cds gi|17979217|gb|AY070269.1|[17979217]

1850: NM_052945
Homo sapiens BAFF receptor (BAFFR), mRNA
gi|17978517|ref|NM_052945.2|[17978517]

1851: NM_054026
Homo sapiens CCR4-NOT transcription complex, subunit 7 (CNOT7), transcript variant 2, mRNA
gi|17978499|ref|NM_054026.1|[17978499]

1852: NM_013354
Homo sapiens CCR4-NOT transcription complex, subunit 7 (CNOT7), transcript variant 1, mRNA
gi|17978498|ref|NM_013354.3|[17978498]

1853: NM_004444
Homo sapiens EphB4 (EPHB4), mRNA
gi|17975769|ref|NM_004444.2|[17975769]

1854: NM_004443
Homo sapiens EphB3 (EPHB3), mRNA
gi|17975767|ref|NM_004443.2|[17975767]

1855: NM_004442
Homo sapiens EphB2 (EPHB2), transcript variant 1, mRNA
gi|17975766|ref|NM_004442.2|[17975766]

1856: NM_017449
Homo sapiens EphB2 (EPHB2), transcript variant 2, mRNA
gi|17975764|ref|NM_017449.1|[17975764]

1857: BC019278
Homo sapiens, cargo selection protein (mannose 6 phosphate receptor binding protein), clone MGC:3816 IMAGE:2905275, mRNA, complete cds
gi|17939468|gb|BC019278.1|BC019278[17939468]

1858: NM_080387
Homo sapiens C-type lectin-like receptor (CLEC-6), mRNA
gi|17933769|ref|NM_080387.1|[17933769]

1859: NM_007200
Homo sapiens A kinase (PRKA) anchor protein 13 (AKAP13), mRNA
gi|17933491|ref|NM_007200.1|[17933491]

1861: AF373878
Homo sapiens herpesvirus entry mediator (TNFRSF14) mRNA, TNFRSF14-V241I allele, complete cds
gi|17901872|gb|AF373878.1|AF373878[17901872]

1862: AF373877
Homo sapiens herpesvirus entry mediator (TNFRSF14) mRNA, TNFRSF14-R17K allele, complete cds
gi|17901869|gb|AF373877.1|AF373877[17901869]

1863: AF373876
Homo sapiens nectin-1 (PVRL1) gene, PVRL1-R199W allele, partial cds
gi|17901866|gb|AF373876.1|AF373876[17901866]

1864: AY065844
Homo sapiens truncated receptor tyrosine kinase TrkC mRNA, partial cds
gi|17887448|gb|AY065844.1|[17887448]

1865: AY062295
Homo sapiens prolactin receptor (PRLR) mRNA, partial cds; alternatively spliced
gi|17887307|gb|AY062295.1|[17887307]

1866: NM_078474
Homo sapiens BBP-like protein 2 (BLP2), transcript variant 1, mRNA
gi|17865799|ref|NM_078474.1|[17865799]

1867: NM_025141
Homo sapiens BBP-like protein 2 (BLP2), transcript variant 2, mRNA
gi|17865798|ref|NM_025141.2|[17865798]

1868: NM_078473
Homo sapiens BBP-like protein 1 (BLP1), transcript variant 1, mRNA
gi|17865796|ref|NM_078473.1|[17865796]

1869: NM_020749
Homo sapiens AT2 receptor-interacting protein 1 (ATIP1), mRNA
gi|17865631|ref|NM_020749.1|[17865631]

1870: NM_002088
Homo sapiens glutamate receptor, ionotropic, kainate 5 (GRIK5), mRNA
gi|17864085|ref|NM_002088.2|[17864085]

1871: AY064474
Homo sapiens interleukin 21 receptor (IL21R) gene, complete cds
gi|17863086|gb|AY064474.1|[17863086]

1872: AY036093
Homo sapiens lysyl oxidase-like 4 mRNA, complete cds
gi|17861371|gb|AY036093.1|[17861371]

1873: AF369653
Homo sapiens corticotropin releasing hormone receptor variant 1g (CRHR1) mRNA, partial cds, alternatively spliced
gi|17834100|gb|AF369653.1|AF369653[17834100]

1874: AF369652
Homo sapiens corticotropin releasing hormone receptor variant 1f (CRHR1) mRNA, partial cds, alternatively spliced
gi|17834097|gb|AF369652.1|AF369652[17834097]

1875: AF369651
Homo sapiens corticotropin releasing hormone receptor variant 1e (CRHR1) mRNA, partial cds, alternatively spliced
gi|17834094|gb|AF369651.1|AF369651[17834094]

1876: NM_001239
Homo sapiens cyclin H (CCNH), mRNA gi|17738313|ref|NM_001239.2|[17738313]

1877: NM_014286
Homo sapiens frequenin homolog (Drosophila) (FREQ), mRNA
gi|17738307|ref|NM_014286.2|[17738307]

1878: NM_006650
Homo sapiens complexin 2 (CPLX2), mRNA
gi|17738306|ref|NM_006650.2|[17738306]

1879: NM_006651
Homo sapiens complexin 1 (CPLX1), mRNA
gi|17738305|ref|NM_006651.2|[17738305]

1880: AF416558
Homo sapiens N-methyl-D-aspartate receptor 3A (GRIN3A) mRNA, complete cds
gi|17530176|gb|AF416558.1|AF416558[17530176]

1882: BC018926
Homo sapiens, vanilloid receptor-like protein, clone MGC:12549 IMAGE:4298484, mRNA, complete cds
gi|17511937|gb|BC018926.1|BC018926[17511937]

1883: BC018778
Homo sapiens, KDEL (Lys-Asp-Glu-Leu) endoplasmic reticulum protein retention receptor 1, clone MGC:32075 IMAGE:4870476, mRNA, complete cds
gi|17511855|gb|BC018778.1|BC018778[17511855]

1884: NM_004625
Homo sapiens wingless-type MMTV integration site family, member 7A (WNT7A), mRNA
gi|17505190|ref|NM_004625.2|[17505190]

1885: L78805
Homo sapiens G protein-coupled receptor gene, partial cds
gi|17466993|gb|L78805.1|HUMGPCRE[17466993]

1886: NM_003602

Homo sapiens FK506 binding protein 6 (36kD) (FKBP6), mRNA
gi|17149848|ref|NM_003602.2|[17149848]

1887: NM_000801
Homo sapiens FK506 binding protein 1A (12kD) (FKBP1A), transcript variant 12B, mRNA
gi|17149837|ref|NM_000801.2|[17149837]

1888: NM_054014
Homo sapiens FK506 binding protein 1A (12kD) (FKBP1A), transcript variant 12A, mRNA
gi|17149835|ref|NM_054014.1|[17149835]

1889: AF411044
Homo sapiens DnaJ protein Tid-1 mRNA, complete cds
gi|17066574|gb|AF411044.1|AF411044[17066574]

1890: NM_003728
Homo sapiens unc-5 homolog B (C. elegans) (UNC5C), mRNA
gi|16933524|ref|NM_003728.2|[16933524]

1891: NM_005633
Homo sapiens son of sevenless homolog 1 (Drosophila) (SOS1), mRNA
gi|15529995|ref|NM_005633.2|[15529995]

1892: AJ308539
Homo sapiens partial mRNA for T-cell receptor beta chain V-D-J region (TCRBV7BJ2S4 gene)
gi|14787781|emb|AJ308539.1|HSA308539[14787781]

1893: AJ308538
Homo sapiens partial mRNA for T-cell receptor beta chain V-D-J region (TCRBV14BJ1S1 gene)
gi|14787779|emb|AJ308538.1|HSA308538[14787779]

1894: AJ308537
Homo sapiens partial mRNA for T-cell receptor beta chain V-D-J region (TCRBV17BJ2S7 gene)

gi|14787777|emb|AJ308537.1|HSA308537[14787777]

1895: AJ308536
Homo sapiens partial mRNA for T-cell receptor beta chain V-D-J region (TCRBV23BJ2S2 gene)
gi|14787775|emb|AJ308536.1|HSA308536[14787775]

1896: AJ308535
Homo sapiens partial mRNA for T-cell receptor beta chain V-D-J region (TCRBV12BJ1S5 gene)
gi|14787773|emb|AJ308535.1|HSA308535[14787773]

1897: AJ308534
Homo sapiens partial mRNA for T-cell receptor beta chain, V-D-J region (TCRBV1BJ2S1 gene)
gi|14787771|emb|AJ308534.1|HSA308534[14787771]

1898: AJ308533
Homo sapiens partial mRNA for T-cell receptor beta chain, V-D-J region (TCRBV25BJ2S7 gene)
gi|14787769|emb|AJ308533.1|HSA308533[14787769]

1899: AJ308532
Homo sapiens partial mRNA for T-cell receptor beta chain, V-D-J region (TCRBV22BJ2S7 gene)
gi|14787767|emb|AJ308532.1|HSA308532[14787767]

1900: NM_014459
Homo sapiens protocadherin 17 (PCDH17), mRNA
gi|14589926|ref|NM_014459.2|[14589926]

1901: NM_032961
Homo sapiens protocadherin 10 (PCDH10), transcript variant 1, mRNA
gi|14589915|ref|NM_032961.1|[14589915]

1902: NM_020815
Homo sapiens protocadherin 10 (PCDH10), transcript variant 2, mRNA
gi|14589913|ref|NM_020815.1|[14589913]

1903: NM_032966
Homo sapiens Burkitt lymphoma receptor 1, GTP binding protein (BLR1), transcript variant 2, mRNA
gi|145

2001: AF011513
Homo sapiens isolate MwCCR5-1553 CCR5 receptor (CCR5) mRNA, partial cds
gi|2305143|gb|AF011513.1|AF011513[2305143]

2002: AF011512
Homo sapiens isolate MwCCR5-107 CCR5 receptor (CCR5) mRNA, partial cds
gi|2305141|gb|AF011512.1|AF011512[2305141]

2003: AF011511
Homo sapiens isolate KeCCR5-3b CCR5 receptor (CCR5) mRNA, partial cds
gi|2305139|gb|AF011511.1|AF011511[2305139]

2004: AF011510
Homo sapiens isolate KeCCR5-3a CCR5 receptor (CCR5) mRNA, partial cds
gi|2305137|gb|AF011510.1|AF011510[2305137]

2005: AF011509
Homo sapiens isolate KeCCR5-116 CCR5 receptor (CCR5) mRNA, partial cds
gi|2305135|gb|AF011509.1|AF011509[2305135]

2006: AF011508
Homo sapiens isolate KeCCR5-111 CCR5 receptor (CCR5) mRNA, partial cds
gi|2305133|gb|AF011508.1|AF011508[2305133]

2007: AF011507
Homo sapiens isolate InCCR5-72a CCR5 receptor (CCR5) mRNA, partial cds
gi|2305131|gb|AF011507.1|AF011507[2305131]

2008: AF011506
Homo sapiens isolate InCCR5-71b CCR5 receptor (CCR5) mRNA, partial cds
gi|2305129|gb|AF011506.1|AF011506[2305129]

2009: AF011505
Homo sapiens isolate InCCR5-71a CCR5 receptor (CCR5) mRNA, partial cds
gi|2305127|gb|AF011505.1|AF011505[2305127]

2010: AF011504
Homo sapiens isolate InCCR5-46 CCR5 receptor (CCR5) mRNA, partial cds
gi|2305125|gb|AF011504.1|AF011504[2305125]

2011: AF011503
Homo sapiens isolate InCCR5-467 CCR5 receptor (CCR5) mRNA, partial cds
gi|2305123|gb|AF011503.1|AF011503[2305123]

2012: AF011502
Homo sapiens isolate InCCR5-463 CCR5 receptor (CCR5) mRNA, partial cds
gi|2305121|gb|AF011502.1|AF011502[2305121]

2013: AF011501
Homo sapiens isolate InCCR5-45c CCR5 receptor (CCR5) mRNA, partial cds
gi|2305119|gb|AF011501.1|AF011501[2305119]

2014: AF011500
Homo sapiens isolate HtCCR5-104 CCR5 receptor (CCR5) mRNA, partial cds
gi|2305117|gb|AF011500.1|AF011500[2305117]

2015: U77732
Homo sapiens glycine receptor alpha 1 subunit gene, partial cds
gi|1718390|gb|U77732.1|HSU77732[1718390]

2016: NM_033519
Homo sapiens olfactory receptor sdolf (sdolf), mRNA
gi|15723373|ref|NM_033519.1|[15723373]

2017: NM_032192
Homo sapiens hypothetical protein FLJ20940 (FLJ20940), mRNA
gi|14149882|ref|NM_032192.1|[14149882]

2018: NM_032152
Homo sapiens PRAM-1 protein (PRAM-1), mRNA
gi|14149826|ref|NM_032152.1|[14149826]

2019: NM_032142
Homo sapiens hypothetical protein FLJ10352 (FLJ10352), mRNA
gi|14149808|ref|NM_032142.1|[14149808]

2020: NM_004801
Homo sapiens neurexin 1 (NRXN1), mRNA
gi|14149612|ref|NM_004801.1|[14149612]

2021: NM_031936
Homo sapiens G protein-coupled receptor 61 (GPR61), mRNA
gi|13994319|ref|NM_031936.1|[13994319]

2022: NM_030901
Homo sapiens olfactory receptor, family 7, subfamily A, member 17 (OR7A17), mRNA
gi|13775161|ref|NM_030901.1|[13775161]

2023: NM_024681
Homo sapiens hypothetical protein FLJ12242 (FLJ12242), mRNA
gi|13489098|ref|NM_024681.1|[13489098]

2024: NM_022571
Homo sapiens putative leukocyte platelet-activating factor receptor (HUMNPIIY20), mRNA
gi|12007653|ref|NM_022571.1|[12007653]

2025: NM_022065
Homo sapiens hypothetical protein FLJ21877 (FLJ21877), mRNA
gi|11545774|ref|NM_022065.1|[11545774]

2026: NM_020806
Homo sapiens gephyrin (GPHN), mRNA
gi|10880982|ref|NM_020806.1|[10880982]

2027: NM_021258
Homo sapiens interleukin 22 receptor (IL22R), mRNA
gi|10864066|ref|NM_021258.1|[10864066]

2029: NM_020400
Homo sapiens G protein-coupled receptor 92 (GPR92), mRNA
gi|9966878|ref|NM_020400.1|[9966878]

2030: NM_000888
Homo sapiens integrin, beta 6 (ITGB6), mRNA
gi|9966771|ref|NM_000888.3|[9966771]

2032: NM_018113
Homo sapiens lipocalin-interacting membrane receptor (LIMR), mRNA
gi|8922462|ref|NM_018113.1|[8922462]

2033: NM_018423
Homo sapiens hypothetical protein DKFZp761P1010 (DKFZp761P1010), mRNA
gi|8922178|ref|NM_018423.1|[8922178]

2034: AF257182
Homo sapiens G-protein-coupled receptor 48 (GPR48) mRNA, complete cds
gi|7739736|gb|AF257182.1|AF257182[7739736]

2035: NM_016442
Homo sapiens type 1 tumor necrosis factor receptor shedding aminopeptidase regulator (ARTS-1), mRNA
gi|7706544|ref|NM_016442.1|[7706544]

2036: NM_015364
Homo sapiens MD-2 protein (MD-2), mRNA
gi|7662503|ref|NM_015364.1|[7662503]

2037: NM_014380
Homo sapiens nerve growth factor receptor (TNFRSF16) associated protein 1 (NGFRAP1), mRNA
gi|7657043|ref|NM_014380.1|[7657043]

2038: NM_013308
Homo sapiens platelet activating receptor homolog (H963), mRNA
gi|7019400|ref|NM_013308.1|[7019400]

2039: NM_013333
Homo sapiens EH domain-binding mitotic phosphoprotein (EPSIN), mRNA
gi|7019368|ref|NM_013333.1|[7019368]

2040: NM_007369
Homo sapiens G-protein coupled receptor (RE2), mRNA
gi|6677700|ref|NM_007369.1|[6677700]

2041: NM_002673
Homo sapiens plexin B1 (PLXNB1), mRNA
gi|6631105|ref|NM_002673.1|[6631105]

2042: NM_007115
Homo sapiens tumor necrosis factor, alpha-induced protein 6 (TNFAIP6), mRNA
gi|6005905|ref|NM_007115.1|[6005905]

2044: NM_007223
Homo sapiens putative G protein coupled receptor (GPR), mRNA
gi|6005771|ref|NM_007223.1|[6005771]

2045: NM_006748
Homo sapiens Src-like-adaptor (SLA), mRNA
gi|5803170|ref|NM_006748.1|[5803170]

2046: NM_006681
Homo sapiens neuromedin U (NMU), mRNA
gi|5729946|ref|NM_006681.1|[5729946]

2047: NM_006068
Homo sapiens toll-like receptor 6 (TLR6), mRNA
gi|5174720|ref|NM_006068.1|[5174720]

2048: NM_006018
Homo sapiens putative chemokine receptor; GTP-binding protein (HM74), mRNA
gi|5174460|ref|NM_006018.1|[5174460]

2049: NM_006098
Homo sapiens guanine nucleotide binding protein (G protein), beta polypeptide 2-like 1 (GNB2L1), mRNA
gi|5174446|ref|NM_006098.1|[5174446]

2050: NM_005879
Homo sapiens TRAF interacting protein (TRIP), mRNA
gi|5032194|ref|NM_005879.1|[5032194]

2051: NM_005843
Homo sapiens signal transducing adaptor molecule (SH3 domain and ITAM motif) 2 (STAM2), mRNA
gi|5032126|ref|NM_005843.1|[5032126]

2052: NM_005505
Homo sapiens CD36 antigen (collagen type I receptor, thrombospondin receptor)-like 1 (CD36L1), mRNA
gi|5031628|ref|NM_005505.1|[5031628]

2053: NM_005795
Homo sapiens calcitonin receptor-like (CALCRL), mRNA
gi|5031620|ref|NM_005795.1|[5031620]

2054: NM_005400
Homo sapiens protein kinase C, epsilon (PRKCE), mRNA
gi|4885562|ref|NM_005400.1|[4885562]

2057: NM_004488
Homo sapiens glycoprotein V (platelet) (GP5), mRNA
gi|4758459|ref|NM_004488.1|[4758459]

2058: NM_004122
Homo sapiens growth hormone secretagogue receptor (GHSR), mRNA
gi|4758433|ref|NM_004122.1|[4758433]

2059: NM_004438
Homo sapiens EphA4 (EPHA4), mRNA
gi|4758279|ref|NM_004438.1|[4758279]

2060: NM_004198
Homo sapiens cholinergic receptor, nicotinic, alpha polypeptide 6 (CHRNA6), mRNA
gi|4757981|ref|NM_004198.1|[4757981]

2061: NM_004054
Homo sapiens complement component 3a receptor 1 (C3AR1), mRNA
gi|4757887|ref|NM_004054.1|[4757887]

2062: NM_003955
Homo sapiens STAT induced STAT inhibitor 3 (SSI-3), mRNA
gi|4507234|ref|NM_003955.1|[4507234]

2063: NM_003693
Homo sapiens acetyl LDL receptor; SREC=scavenger receptor expressed by endothelial cells (SREC), mRNA
gi|4507202|ref|NM_003693.1|[4507202]

2064: NM_003625
Homo sapiens protein tyrosine phosphatase, receptor type, f polypeptide (PTPRF), interacting protein (liprin), alpha 2 (PPFIA2), mRNA
gi|4505984|ref|NM_003625.1|[4505984]

2065: NM_000286
Homo sapiens peroxisomal biogenesis factor 12 (PEX12), mRNA
gi|4505720|ref|NM_000286.1|[4505720]

2066: NM_002563
Homo sapiens purinergic receptor P2Y, G-protein coupled, 1 (P2RY1), mRNA
gi|4505556|ref|NM_002563.1|[4505556]

2067: NM_000913
Homo sapiens opiate receptor-like 1 (OPRL1), mRNA
gi|4505512|ref|NM_000913.1|[4505512]

2068: NM_002333
Homo sapiens low density lipoprotein receptor-related protein 3 (LRP3), mRNA
gi|4505014|ref|NM_002333.1|[4505014]

2069: NM_001957
Homo sapiens endothelin receptor type A (EDNRA), mRNA
gi|4503464|ref|NM_001957.1|[4503464]

2070: L34726
Homo sapiens T-cell receptor beta (TCRB) mRNA (HLA-A3, 29; B7, 44; DR 2, 7), partial cds
gi|1100206|gb|L34726.1|HUMTCRBZ[1100206]

2071: L34725
Homo sapiens T-cell receptor beta (TCRB) mRNA (HLA-A1, 24; B7, 8; DR 1, 3), partial cds
gi|1100204|gb|L34725.1|HUMTCRBY[1100204]

2072: L34724
Homo sapiens T-cell receptor beta (TCRB) mRNA (HLA-A3, 29; B7, 44; DR 2, 7), partial cds
gi|1100202|gb|L34724.1|HUMTCRBU[1100202]

2073: L34723
Homo sapiens T-cell receptor beta (TCRB) mRNA (HLA-A3, 29; B7, 44; DR 2, 7), partial cds
gi|1100200|gb|L34723.1|HUMTCRBT[1100200]

2074: L34722
Homo sapiens T-cell receptor beta (TCRB) mRNA (HLA-A1, 24; B7, 8; DR 1, 3), partial cds
gi|1100198|gb|L34722.1|HUMTCRBS[1100198]

2075: L34721
Homo sapiens T-cell receptor beta (TCRB) mRNA (HLA-A3, 29; B7, 44; DR 2, 7). partial cds
gi|1100196|gb|L34721.1|HUMTCRBQ[1100196]

2076: L34719
Homo sapiens T-cell receptor beta (TCRB) mRNA (HLA-A1, 24; B7, 8; DR 1, 3), partial cds
gi|1100192|gb|L34719.1|HUMTCRBO[1100192]

2077: L34737
Homo sapiens T-cell receptor beta (TCRB) mRNA (HLA-A3, 29; B7, 44; DR2, 7), partial cds
gi|1100188|gb|L34737.1|HUMTCRBAO[1100188]

2078: L34736
Homo sapiens T-cell receptor beta (TCRB) mRNA (HLA-A3, 29; B7, 44; DR2, 7), partial cds
gi|1100186|gb|L34736.1|HUMTCRBAN[1100186]

2079: L34735
Homo sapiens T-cell receptor beta (TCRB) mRNA (HLA-A1, 24; B7, 8; DR 1, 3), partial cds
gi|1100184|gb|L34735.1|HUMTCRBAM[1100184]

2080: L34733
Homo sapiens T-cell receptor beta (TCRB) mRNA (HLA-A3, 29; B7, 44; DR 2, 7), partial cds
gi|1100179|gb|L34733.1|HUMTCRBAK[1100179]

2081: L34732
Homo sapiens T-cell receptor beta (TCRB) mRNA (HLA-A3, 29; B7, 44; DR 2, 7), partial cds
gi|1100177|gb|L34732.1|HUMTCRBAJ[1100177]

2082: L34731
Homo sapiens T-cell receptor beta (TCRB) mRNA (HLA-A3, 29; B7, 44; DR 2, 7), partial cds
gi|1100175|gb|L34731.1|HUMTCRBAI[1100175]

2083: L34730
Homo sapiens T-cell receptor beta (TCRB) mRNA (HLA-A1, 24; B7, 8; DR 1, 3), partial cds
gi|1100173|gb|L34730.1|HUMTCRBAH[1100173]

2084: L34728
Homo sapiens T-cell receptor beta (TCRB) mRNA (HLA-A3, 29; B7, 44; DR 2, 7), partial cds
gi|1100169|gb|L34728.1|HUMTCRBAF[1100169]

2085: L34727
Homo sapiens T-cell receptor beta (TCRB) mRNA (HLA-A3, 29; B7, 44; DR 2, 7), partial cds
gi|1100167|gb|L34727.1|HUMTCRBAE[1100167]

2086: L34703
Homo sapiens T-cell receptor alpha chain (TCRA) mRNA (HLA-A1, 24; B7, 8; DR 1, 3), complete cds
gi|1100165|gb|L34703.1|HUMTCRAZ[1100165]

2087: L34702
Homo sapiens T-cell receptor alpha (TCRA) mRNA (HLA-A3, 29; B7, 44; DR 2, 7), partial cds
gi|1100163|gb|L34702.1|HUMTCRAY[1100163]

2088: L34701
Homo sapiens T-cell receptor alpha (TCRA) mRNA (HLA-A3, 29; B7, 44; DR 2, 7), partial cds
gi|1100161|gb|L34701.1|HUMTCRAV[1100161]

2089: L34700
Homo sapiens T-cell receptor alpha (TCRA) mRNA (HLA-A3, 29; B7, 44; DR 2, 7), partial cds
gi|1100159|gb|L34700.1|HUMTCRAU[1100159]

2090: L34699
Homo sapiens T-cell receptor alpha (TCRA) mRNA (HLA-A1, 24; B7, 8; C7; DR 1, 3), partial cds
gi|1100157|gb|L34699.1|HUMTCRAT[1100157]

2091: L34698
Homo sapiens T-cell receptor alpha (TCRA) mRNA (HLA-A3, 29; B7, 44; DR 2, 7), complete cds
gi|1100155|gb|L34698.1|HUMTCRAQ[1100155]

2092: L34695
Homo sapiens T-cell receptor alpha (TCRA) mRNA (HLA-A3, 29; B7, 44; DR2, 7), partial cds
gi|1100153|gb|L34695.1|HUMTCRAP[1100153]

2093: L34694
Homo sapiens T-cell receptor alpha (TCRA) mRNA (HLA-A1, 24; B7, 8; C7; DR 1, 3), partial cds
gi|1100151|gb|L34694.1|HUMTCRAO[1100151]

2094: L34738
Homo sapiens T-cell receptor beta (TCRB) mRNA (HLA-A1, 24; B7, 8; C7; DR 1, 3), partial cds
gi|1100149|gb|L34738.1|HUMTCRAAX[1100149]

2095: L34718
Homo sapiens T-cell receptor alpha (TCRA) mRNA (HLA-A3, 29; B7, 44; DR 2, 7), partial cds
gi|1100147|gb|L34718.1|HUMTCRAAW[1100147]

2096: L34717
Homo sapiens T-cell receptor alpha (TCRA) mRNA (HLA-A3, 29; B7, 44; DR 2, 7), partial cds
gi|1100145|gb|L34717.1|HUMTCRAAV[1100145]

2097: L34716
Homo sapiens T-cell receptor alpha (TCRA) mRNA (HLA-A1, 24; B7, 8; DR 1, 3), partial cds
gi|1100143|gb|L34716.1|HUMTCRAAU[1100143]

2098: L34715
Homo sapiens T-cell receptor alpha (TCRA) mRNA (HLA-A1, 24; B7, 8; DR 1, 3), partial cds
gi|1100141|gb|L34715.1|HUMTCRAAT[1100141]

2099: L34714
Homo sapiens T-cell receptor alpha (TCRA) mRNA (HLA-A1, 24; B7, 8; DR 1, 3), partial cds
gi|1100139|gb|L34714.1|HUMTCRAAS[1100139]

2100: L34713
Homo sapiens T-cell receptor alpha (TCRA) mRNA (HLA-A3, 29; B7, 44; DR 2, 7), partial cds
gi|1100137|gb|L34713.1|HUMTCRAAR[1100137]

2101: L34712
Homo sapiens T-cell receptor alpha (TCRA) mRNA (HLA-A3, 29; B7, 44; DR 2, 7), partial cds
gi|1100135|gb|L34712.1|HUMTCRAAQ[1100135]

2102: L34711
Homo sapiens T-cell receptor alpha (TCRA) mRNA (HLA-A3, 29; B7, 44; DR 2, 7), partial cds
gi|1100133|gb|L34711.1|HUMTCRAAP[1100133]

2103: L34710
Homo sapiens T-cell receptor alpha (TCRA) mRNA (HLA-A3, 29; B7, 44; DR 2, 7), partial cds
gi|1100131|gb|L34710.1|HUMTCRAAO[1100131]

2104: L34709
Homo sapiens T-cell receptor alpha (TCRA) mRNA (HLA-A3, 29; B7, 44; DR 2, 7), partial cds
gi|1100129|gb|L34709.1|HUMTCRAAN[1100129]

2105: L34708
Homo sapiens T-cell receptor alpha (TCRA) mRNA (HLA-A1, 24; B7, 8; DR1, 3), partial cds
gi|1100127|gb|L34708.1|HUMTCRAAM[1100127]

2106: L34707
Homo sapiens T-cell receptor alpha (TCRA) mRNA (HLA-A3, 29; B7, 44; DR 2, 7), partial cds
gi|1100125|gb|L34707.1|HUMTCRAAL[1100125]

2107: L34706
Homo sapiens T-cell receptor alpha (TCRA) mRNA (HLA-A3, 29; B7, 44; DR 2, 7), partial cds
gi|1100123|gb|L34706.1|HUMTCRAAK[1100123]

2108: L34705
Homo sapiens T-cell receptor alpha (TCRA) mRNA (HLA-A3, 29; B7, 44; DR 2, 7), partial cds
gi|1100121|gb|L34705.1|HUMTCRAAJ[1100121]

2109: L34704
Homo sapiens T-cell receptor alpha (TCRA) mRNA (HLA-A3, 29; B7, 44; DR 2, 7), partial cds
gi|1100119|gb|L34704.1|HUMTCRAAI[1100119]

2110: L29037
Human T-cell antigen receptor mRNA
gi|517066|gb|L29037.1|HUMTCRBW[517066]

2111: L29038
Human T-cell antigen receptor mRNA
gi|456432|gb|L29038.1|HUMTCRBX[456432]

2112: L29036
Human T-cell antigen receptor mRNA
gi|456431|gb|L29036.1|HUMTCRAX[456431]

2113: L29035
Human T-cell antigen receptor mRNA
gi|456430|gb|L29035.1|HUMTCRAW[456430]

2114: AF106913
Homo sapiens CRL3 protein (CRL3) mRNA, complete cds
gi|17221662|gb|AF106913.1|AF106913[17221662]

2115: AB055881
Homo sapiens NKp30 mRNA for natural killer cell receptor, complete cds
gi|17221621|dbj|AB055881.1|AB055881[17221621]

2116: AJ417149
Homo sapiens partial mRNA for T cell receptor beta chain (TCRB gene), clone 21
gi|17154680|emb|AJ417149.1|HSA417149[17154680]

2117: AJ417148
Homo sapiens partial mRNA for T cell receptor beta chain (TCRB gene), clone 17
gi|17148484|emb|AJ417148.1|HSA417148[17148484]

2118: NM_054021
Homo sapiens G protein-coupled receptor 101 (GPR101), mRNA
gi|16876434|ref|NM_054021.1|[16876434]

2119: NM_052939
Homo sapiens Fc receptor-like protein 3 (FCRH3), mRNA
gi|16418420|ref|NM_052939.1|[16418420]

2120: NM_052938
Homo sapiens Fc receptor-like protein 1 (FCRH1), mRNA
gi|16418418|ref|NM_052938.1|[16418418]

2121: NM_003823
Homo sapiens tumor necrosis factor receptor superfamily, member 6b, decoy (TNFRSF6B), transcript variant M68E, mRNA
gi|14790166|ref|NM_003823.2|[14790166]

2122: NM_006470
Homo sapiens tripartite motif-containing 16 (TRIM16), mRNA
gi|14577927|ref|NM_006470.2|[14577927]

2123: NM_031918
Homo sapiens Kruppel-like factor 16 (KLF16), mRNA
gi|13994286|ref|NM_031918.1|[13994286]

2124: NM_023945
Homo sapiens membrane-spanning 4-domains, subfamily A, member 5 (MS4A5), mRNA
gi|12965204|ref|NM_023945.1|[12965204]

2125: NM_018485
Homo sapiens G protein-coupled receptor C5L2 (LOC55868), mRNA
gi|8923872|ref|NM_018485.1|[8923872]

2126: NM_016562
Homo sapiens toll-like receptor 7 (TLR7), mRNA
gi|7706092|ref|NM_016562.1|[7706092]

2130: NM_006138
Homo sapiens membrane-spanning 4-domains, subfamily A, member 3 (hematopoietic cell-specific) (MS4A3), mRNA
gi|5453608|ref|NM_006138.1|[5453608]

2131: AF447176
Homo sapiens protein tyrosine kinase-7 (PTK7) gene, exon 20 and complete cds
gi|17432420|gb|AF447176.1|F447157S11[17432420]

2132: AF447175
Homo sapiens protein tyrosine kinase-7 (PTK7) gene, exon 19
gi|17432419|gb|AF447175.1|F447157S10[17432419]

2133: AF447174
Homo sapiens protein tyrosine kinase-7 (PTK7) gene, exon 18
gi|17432418|gb|AF447174.1|F447157S09[17432418]

2134: AF447173
Homo sapiens protein tyrosine kinase-7 (PTK7) gene, exon 17
gi|17432417|gb|AF447173.1|F447157S08[17432417]

2135: AF447171
Homo sapiens protein tyrosine kinase-7 (PTK7) gene, exons 15 and 16
gi|17432416|gb|AF447171.1|F447157S07[17432416]

2136: AF447170
Homo sapiens protein tyrosine kinase-7 (PTK7) gene, exon 14
gi|17432415|gb|AF447170.1|F447157S06[17432415]

2137: AF447167
Homo sapiens protein tyrosine kinase-7 (PTK7) gene, exons 11, 12, and 13
gi|17432414|gb|AF447167.1|F447157S05[17432414]

2138: AF447164
Homo sapiens protein tyrosine kinase-7 (PTK7) gene, exons 8, 9, and 10
gi|17432413|gb|AF447164.1|F447157S04[17432413]

2139: AF447162
Homo sapiens protein tyrosine kinase-7 (PTK7) gene, exons 6 and 7
gi|17432412|gb|AF447162.1|F447157S03[17432412]

2140: AF447158
Homo sapiens protein tyrosine kinase-7 (PTK7) gene, exons 2, 3, 4, and 5
gi|17432411|gb|AF447158.1|F447157S02[17432411]

2141: AF447157
Homo sapiens protein tyrosine kinase-7 (PTK7) gene, exon 1
gi|17432410|gb|AF447157.1|F447157S01[17432410]

2142: AH011239
Homo sapiens protein tyrosine kinase-7 (PTK7) gene, complete cds
gi|17432409|gb|AH011239.1|SEG_F447157S[17432409]

2143: AF374231
Homo sapiens corticotropin releasing hormone receptor variant 1h mRNA, partial
cds, alternatively spliced
gi|17432316|gb|AF374231.1|AF374231[17432316]

2145: AY013309
Homo sapiens clone FM1-3.3.12A immunoglobulin heavy chain variable region gene,
partial cds
gi|17220530|gb|AY013309.1|[17220530]

2146: AY013308
Homo sapiens clone FL1-2.4.2G immunoglobulin heavy chain variable region gene, partial cds
gi|17220528|gb|AY013308.1|[17220528]

2147: AY013307
Homo sapiens clone FL1-2.4.12A immunoglobulin heavy chain variable region gene, partial cds
gi|17220526|gb|AY013307.1|[17220526]

2148: AY013306
Homo sapiens clone FL3-3.4.4G immunoglobulin heavy chain variable region gene, partial cds
gi|17220524|gb|AY013306.1|[17220524]

2149: AB062787
Homo sapiens mRNA for triggering receptor TREM-2V, complete cds
gi|17425161|dbj|AB062787.1|AB062787[17425161]

2150: NM_003392
Homo sapiens wingless-type MMTV integration site family, member 5A (WNT5A), mRNA
gi|17402917|ref|NM_003392.2|[17402917]

2152: AJ421518
Homo sapiens mRNA for tumor necrosis factor-stimulated gene 6 (TSG-6) protein, G431 allele
gi|17402491|emb|AJ421518.1|HSA421518[17402491]

2153: NM_053049
Homo sapiens stresscopin (SPC), mRNA
gi|16596691|ref|NM_053049.1|[16596691]

2154: AF430697
Homo sapiens T cell receptor beta variable region, Vbeta 13S3-KRGAYETQYF-Jbeta 2.5 mRNA, partial cds
gi|16566919|gb|AF430697.1|AF430697[16566919]

2155: AF430696
Homo sapiens T cell receptor beta variable region, Vbeta 13S2A1T-SEVRETQYF-Jbeta
2.5 mRNA, partial cds
gi|16566916|gb|AF430696.1|AF430696[16566916]

2156: AF430695
Homo sapiens T cell receptor beta variable region, Vbeta 13S3-EKVTGGETQYF-Jbeta
2.5 mRNA, partial cds
gi|16566913|gb|AF430695.1|AF430695[16566913]

2157: AF430694
Homo sapiens T cell receptor beta variable region, Vbeta
13S2A1T-QGRTSVIETQYF-Jbeta 2.5 mRNA, partial cds
gi|16566910|gb|AF430694.1|AF430694[16566910]

2158: AF430693
Homo sapiens T cell receptor beta variable region, Vbeta
13S2A1T-RSDRRKTRYF-Jbeta2.5 mRNA, partial cds
gi|16566907|gb|AF430693.1|AF430693[16566907]

2159: AF430692
Homo sapiens T cell receptor beta variable region, Vbeta 13S3-GRGAQETQYF-Jbeta
2.5 mRNA, partial cds
gi|16566904|gb|AF430692.1|AF430692[16566904]

2160: AF430691
Homo sapiens T cell receptor beta variable region, Vbeta 13S2A1T-GGQTYF-Jbeta
2.5 mRNA, partial cds
gi|16566901|gb|AF430691.1|AF430691[16566901]

2161: AF430690
Homo sapiens T cell receptor beta variable region, Vbeta
1S1A1N1-SGLTPNTGELFF-Jbeta 2.2 mRNA, partial cds
gi|16566898|gb|AF430690.1|AF430690[16566898]

2162: AF430689
Homo sapiens T cell receptor beta variable region, Vbeta
13S6A1N1-TSPVPIGTDTQYF-Jbeta 2.3 mRNA, partial cds gi|16566895|gb|AF430689.1|AF430689[16566895]

2163: AF430688
Homo sapiens T cell receptor beta variable region, Vbeta 13S3-MFGGSTGELFF-Jbeta 2.2 mRNA, partial cds
gi|16566892|gb|AF430688.1|AF430688[16566892]

2164: AF430687
Homo sapiens T cell receptor beta variable region, Vbeta 13S3-AQGKGTQYF-Jbeta 2.5 mRNA, partial cds
gi|16566889|gb|AF430687.1|AF430687[16566889]

2165: AF430686
Homo sapiens T cell receptor beta variable region, Vbeta 13 S3-EQGLLSTDTQYF-Jbeta 2.3 mRNA, partial cds
gi|16566886|gb|AF430686.1|AF430686[16566886]

2166: AF430685
Homo sapiens T cell receptor beta variable region, Vbeta 13S5-ETPGQGAGELFF-Jbeta 2.2 mRNA, partial cds
gi|16566883|gb|AF430685.1|AF430685[16566883]

2167: AF430684
Homo sapiens T cell receptor beta variable region, Vbeta 13S5-RLAGASYNEQYF-Jbeta 2.1 mRNA, partial cds
gi|16566880|gb|AF430684.1|AF430684[16566880]

2168: AF430683
Homo sapiens T cell receptor beta variable region, Vbeta 13S5-DTAGSTDTQYF-Jbeta 2.3 mRNA, partial cds
gi|16566877|gb|AF430683.1|AF430683[16566877]

2169: AF430682
Homo sapiens T cell receptor beta variable region, Vbeta 13S5-EVASGTDTQYF-Jbeta 2.3 mRNA, partial cds
gi|16566874|gb|AF430682.1|AF430682[16566874]

2170: AF430681

Homo sapiens T cell receptor beta variable region, Vbeta
S6A3N2T-ASSGGYEQYF-Jbeta 2.7 mRNA, partial cds
gi|16566871|gb|AF430681.1|AF430681[16566871]

2171: AF430680
Homo sapiens T cell receptor beta variable region, Vbeta 5
S3A1T/S1A1T-RRSDTQYF-Jbeta 2.3 mRNA, partial cds
gi|16566868|gb|AF430680.1|AF430680[16566868]

2172: AF430679
Homo sapiens T cell receptor beta variable region, Vbeta
5S1A1T-FGGEDTDTQYF-Jbeta 2.3 mRNA, partial cds
gi|16566865|gb|AF430679.1|AF430679[16566865]

2173: AF430678
Homo sapiens T cell receptor beta variable region, Vbeta 5 S2-FGTRGNEQFF-Jbeta
2.7 mRNA, partial cds
gi|16566862|gb|AF430678.1|AF430678[16566862]

2174: AF430677
Homo sapiens T cell receptor beta variable region, Vbeta 5-FQGARETQYF-Jbeta 2.5
mRNA, partial cds
gi|16566859|gb|AF430677.1|AF430677[16566859]

2175: AF430676
Homo sapiens T cell receptor beta variable region, Vbeta
5S6A3N2T-FTGTGIYGYTF-Jbeta 1.2 mRNA, partial cds
gi|16566856|gb|AF430676.1|AF430676[16566856]

2176: AF430675
Homo sapiens T cell receptor beta variable region, Vbeta
5S1A1T-APLTGDSGNTIYF-Jbeta 1.3 mRNA, partial cds
gi|16566853|gb|AF430675.1|AF430675[16566853]

2177: AF430674
Homo sapiens T cell receptor beta variable region, Vbeta 5S1A1TSDLSGANVLTF-Jbeta
2.6 mRNA, partial cds
gi|16566850|gb|AF430674.1|AF430674[16566850]

2178: AF430673
Homo sapiens T cell receptor beta variable region, Vbeta 5S6A3N2T-GQGKGTF-Jbeta
1.2 mRNA, partial cds
gi|16566847|gb|AF430673.1|AF430673[16566847]

2179: AF430672
Homo sapiens T cell receptor beta variable region, Vbeta
5S6A3N2T-YTGGVWRNQYF-Jbeta 2.5 mRNA, partial cds
gi|16566844|gb|AF430672.1|AF430672[16566844]

2180: AF430671
Homo sapiens T cell receptor beta variable region, Vbeta 5S2-FSGGAHTQYF-Jbeta
2.3 mRNA, partial cds
gi|16566841|gb|AF430671.1|AF430671[16566841]

2181: AF430670
Homo sapiens T cell receptor beta variable region, Vbeta
5S2/S6A3N2T-SGQGKTEAFF-Jbeta 1.1 mRNA, partial cds
gi|16566838|gb|AF430670.1|AF430670[16566838]

2182: AF430669
Homo sapiens T cell receptor beta variable region, Vbeta 5S1A1T-FSKGVTEAFF-Jbeta
1.1 mRNA, partial cds
gi|16566835|gb|AF430669.1|AF430669[16566835]

2183: AF430668
Homo sapiens T cell receptor beta variable region, Vbeta 5S2-SSPTGRSGNTIYF-Jbeta
1.3 mRNA, partial cds
gi|16566832|gb|AF430668.1|AF430668[16566832]

2184: AF430667
Homo sapiens T cell receptor beta variable region, Vbeta
5S4A2T-PLLGQGRDEQFF-Jbeta 2.1 mRNA, partial cds
gi|16566829|gb|AF430667.1|AF430667[16566829]

2185: AF430666
Homo sapiens T cell receptor beta variable region, Vbeta 5S1A1T-FDFPGELFF-Jbeta
2.2 mRNA, partial cds gi|16566827|gb|AF430666.1|AF430666[16566827]

2186: AF430665
Homo sapiens T cell receptor beta variable region, Vbeta 5S1A1T-DPSGGYNEQFF-Jbeta 2.1 mRNA, partial cds
gi|16566824|gb|AF430665.1|AF430665[16566824]

2187: AF430664
Homo sapiens T cell receptor beta variable region, Vbeta 5S1A1T-DATGNLNEQYF-Jbeta 2.7 mRNA, partial cds
gi|16566821|gb|AF430664.1|AF430664[16566821]

2188: AF430663
Homo sapiens T cell receptor beta variable region, Vbeta 5S1A1T-SGQVTGELFF-Jbeta 2.2 mRNA, partial cds
gi|16566818|gb|AF430663.1|AF430663[16566818]

2189: AF430662
Homo sapiens T cell receptor beta variable region, Vbeta 5S1A1T-AWWGAGYEGYF-Jbeta 2.7 mRNA, partial cds
gi|16566815|gb|AF430662.1|AF430662[16566815]

2190: AF430661
Homo sapiens T cell receptor beta variable region, Vbeta 5S1A1T-RRLAGVYNEQFF-Jbeta 2.1 mRNA, partial cds
gi|16566812|gb|AF430661.1|AF430661[16566812]

2191: AF430660
Homo sapiens T cell receptor beta variable region, Vbeta 5S1A1T-EFQAPYGYTF-Jbeta1.2 mRNA, partial cds
gi|16566809|gb|AF430660.1|AF430660[16566809]

2192: AF430659
Homo sapiens T cell receptor beta variable region, Vbeta 5S6A3N2T-TGTESPDTQYF-Jbeta 2.3 mRNA, partial cds
gi|16566806|gb|AF430659.1|AF430659[16566806]

2193: AF430658

Homo sapiens T cell receptor beta variable region, Vbeta
5S6A3N2T-TFGTPTYNEQFF-Jbeta 2.1 mRNA, partial cds
gi|16566803|gb|AF430658.1|AF430658[16566803]

2194: AF430657
Homo sapiens T cell receptor beta variable region, Vbeta 5-SGPSTDTQYF-Jbeta 2.3
mRNA, partial cds
gi|16566800|gb|AF430657.1|AF430657[16566800]

2195: AF430656
Homo sapiens T cell receptor beta variable region, Vbeta 5S2-NPGGNYGYTF-Jbeta
1.2 mRNA, partial cds
gi|16566797|gb|AF430656.1|AF430656[16566797]

2196: AF430655
Homo sapiens T cell receptor beta variable region, Vbeta 5S1A1T-VIGTYEQYF-Jbeta
2.7 mRNA, partial cds
gi|16566794|gb|AF430655.1|AF430655[16566794]

2197: AF430654
Homo sapiens T cell receptor beta variable region, Vbeta 5S2-AGGETQYF-J beta 2.5
mRNA, partial cds
gi|16566791|gb|AF430654.1|AF430654[16566791]

2198: AF430653
Homo sapiens T cell receptor beta variable region, Vbeta
5S1A1T-VSGRGSYEQYF-Jbeta 2.7 mRNA, partial cds
gi|16566788|gb|AF430653.1|AF430653[16566788]

2199: AF430652
Homo sapiens T cell receptor beta variable region, Vbeta 5S2-VRSEAFF-JBeta 1.1
mRNA, partial cds
gi|16566785|gb|AF430652.1|AF430652[16566785]

2200: AF430651
Homo sapiens T cell receptor beta variable region, Vbeta
5S1A1T-RTRTGETNTGELFF-JBeta2.2 mRNA, partial cds
gi|16566782|gb|AF430651.1|AF430651[16566782]

2201: AF430650
Homo sapiens T cell receptor beta variable region, Vbeta 5S6A3N2T-GAGPSGELFF-JBeta 2.2 mRNA, partial cds
gi|16566779|gb|AF430650.1|AF430650[16566779]

2202: AF430649
Homo sapiens T cell receptor beta variable region, Vbeta 5S1A1T-GGGTGELFF-Jbeta2.2 mRNA, partial cds
gi|16566776|gb|AF430649.1|AF430649[16566776]

2203: AF430648
Homo sapiens T cell receptor beta variable region, Vbeta 5S1AT-PGQGAYEQYF-2.7 mRNA, partial cds
gi|16566773|gb|AF430648.1|AF430648[16566773]

2204: AF430647
Homo sapiens T cell receptor beta variable region, Vbeta 5S2-RPDSGYTF-Jeta1.2 mRNA, partial cds
gi|16566770|gb|AF430647.1|AF430647[16566770]

2205: AF411117
Homo sapiens G protein-coupled receptor (GPR103) mRNA, complete cds
gi|16566346|gb|AF411117.1|AF411117[16566346]

2206: AF411116
Homo sapiens G protein-coupled receptor (GPR102) gene, complete cds
gi|16566343|gb|AF411116.1|AF411116[16566343]

2207: AF411115
Homo sapiens G protein-coupled receptor (GPR101) gene, complete cds
gi|16566340|gb|AF411115.1|AF411115[16566340]

2208: AF411114
Homo sapiens G protein-coupled receptor (GPR95) mRNA, complete cds
gi|16566337|gb|AF411114.1|AF411114[16566337]

2209: AF411113

Homo sapiens G protein-coupled receptor (GPR94) gene, complete cds
gi|16566334|gb|AF411113.1|AF411113[16566334]

2210: AF411112
Homo sapiens G protein-coupled receptor (GPR93) gene, complete cds
gi|16566331|gb|AF411112.1|AF411112[16566331]

2211: AF411111
Homo sapiens G protein-coupled receptor (GPR82) gene, complete cds
gi|16566328|gb|AF411111.1|AF411111[16566328]

2212: AF411110
Homo sapiens G protein-coupled receptor (GPR81) gene, complete cds
gi|16566325|gb|AF411110.1|AF411110[16566325]

2213: AF411109
Homo sapiens G protein-coupled receptor (GPR80) gene, complete cds
gi|16566322|gb|AF411109.1|AF411109[16566322]

2215: AF411107
Homo sapiens G protein-coupled receptor (GPR78) mRNA, complete cds
gi|16566318|gb|AF411107.1|AF411107[16566318]

2216: AF406692
Homo sapiens G protein-coupled receptor GPR86 mRNA, complete cds
gi|15487985|gb|AF406692.1|AF406692[15487985]

2217: NM_019035
Homo sapiens protocadherin 18 (PCDH18), mRNA
gi|14589928|ref|NM_019035.1|[14589928]

2218: AF214012
Homo sapiens prolactin receptor gene, exon 11 and partial sequence
gi|14328908|gb|AF214012.1|AF214012[14328908]

2219: NM_030943
Homo sapiens amnionless protein (AMN), mRNA gi|13569914|ref|NM_030943.1|[13569914]

2220: NM_023922
Homo sapiens taste receptor, type 2, member 14 (TAS2R14), mRNA
gi|12965181|ref|NM_023922.1|[12965181]

2221: NM_023921
Homo sapiens taste receptor, type 2, member 10 (TAS2R10), mRNA
gi|12965179|ref|NM_023921.1|[12965179]

2222: NM_023920
Homo sapiens taste receptor, type 2, member 13 (TAS2R13), mRNA
gi|12965177|ref|NM_023920.1|[12965177]

2223: NM_023919
Homo sapiens taste receptor, type 2, member 7 (TAS2R7), mRNA
gi|12965175|ref|NM_023919.1|[12965175]

2224: NM_023918
Homo sapiens taste receptor, type 2, member 8 (TAS2R8), mRNA
gi|12965173|ref|NM_023918.1|[12965173]

2225: NM_023917
Homo sapiens taste receptor, type 2, member 9 (TAS2R9), mRNA
gi|12965171|ref|NM_023917.1|[12965171]

2226: AF206696
Homo sapiens interleukin-1 epsilon (IL1E) mRNA, complete cds
gi|11493847|gb|AF206696.1|AF206696[11493847]

2227: AF230377
Homo sapiens interleukin-1 delta mRNA, complete cds
gi|9651788|gb|AF230377.1|AF230377[9651788]

2228: BC018284
Homo sapiens, triggering receptor expressed on myeloid cells 2, clone IMAGE:4151400, mRNA gi|17390669|gb|BC018284.1|BC018284[17390669]

2229: BC018130
Homo sapiens, coagulation factor II (thrombin) receptor-like 1, clone MGC:9298 IMAGE:3895653, mRNA, complete cds
gi|17390291|gb|BC018130.1|BC018130[17390291]

2230: BC017898
Homo sapiens, Purinergic receptor P2Y, G protein-coupled, 12, clone MGC:23802 IMAGE:4251263, mRNA, complete cds
gi|17389766|gb|BC017898.1|BC017898[17389766]

2231: BC017865
Homo sapiens, Fc fragment of IgG, low affinity IIIa, receptor for (CD16), clone MGC:22630 IMAGE:4690249, mRNA, complete cds
gi|17389687|gb|BC017865.1|BC017865[17389687]

2232: BC017852
Homo sapiens, tumor necrosis factor receptor superfamily, member 10c, decoy without an intracellular domain, clone IMAGE:4700855, mRNA
gi|17389657|gb|BC017852.1|BC017852[17389657]

2233: BC017784
Homo sapiens, killer cell lectin-like receptor subfamily C, member 4, clone MGC:22279 IMAGE:4619154, mRNA, complete cds
gi|17389488|gb|BC017784.1|BC017784[17389488]

2234: BC017773
Homo sapiens, triggering receptor expressed on myeloid cells 1, clone MGC:22242 IMAGE:4692680, mRNA, complete cds
gi|17389458|gb|BC017773.1|BC017773[17389458]

2235: BC017730
Homo sapiens, tumor necrosis factor receptor superfamily, member 21, clone MGC:21476 IMAGE:3847246, mRNA, complete cds
gi|17389378|gb|BC017730.1|BC017730[17389378]

2237: AJ252246
Homo sapiens mRNA for kainate receptor subunit (GRIK2 gene)
gi|17384623|emb|AJ252246.1|HSA252246[17384623]

2238: AJ249210
Homo sapiens mRNA for glutamate/kainate receptor subtype GluR7 (GRIK3 gene)
gi|17384612|emb|AJ249210.1|HSA249210[17384612]

2239: AJ249209
Homo sapiens mRNA for glutamate/kainate receptor subunit KA2a (GRIK5 gene)
gi|17384610|emb|AJ249209.1|HSA249209[17384610]

2240: AJ249208
Homo sapiens mRNA for glutamate receptor subunit GluR5 (GRIK1 gene)
gi|17384608|emb|AJ249208.1|HSA249208[17384608]

2241: AJ415410
Homo sapiens partial IGVK1-O14 gene for immunoglobulin kappa chain variable region, donor MF, cell24
gi|17384019|emb|AJ415410.2|HSA415410[17384019]

2242: AJ415291
Homo sapiens partial IGVH3-33 gene for immunoglobulin heavy chain variable region, donor TG, cell46
gi|17384018|emb|AJ415291.2|HSA415291[17384018]

2243: AJ414840
Homo sapiens partial IGVKA30 gene for immunoglobulin kappa chain variable region, donor MF, cell2
gi|17384017|emb|AJ414840.2|HSA414840[17384017]

2244: NM_000623
Homo sapiens bradykinin receptor B2 (BDKRB2), mRNA
gi|17352499|ref|NM_000623.2|[17352499]

2246: AJ347709
Homo sapiens mRNA for FKBP-associated protein
gi|15620770|emb|AJ347709.1|HSA347709[15620770]

2247: AF356518
Homo sapiens junctional adhesion molecule 3 precursor, mRNA, complete cds
gi|13448824|gb|AF356518.1|AF356518[13448824]

2248: NM_021201
Homo sapiens membrane-spanning 4-domains, subfamily A, member 7 (MS4A7), mRNA
gi|11139298|ref|NM_021201.1|[11139298]

2249: NM_015344
Homo sapiens leptin receptor overlapping transcript-like 1 (LEPROTL1), mRNA
gi|7662509|ref|NM_015344.1|[7662509]

2250: AF411850
Homo sapiens C-type lectin-like receptor CLEC-6 mRNA, complete cds
gi|17226267|gb|AF411850.1|AF411850[17226267]

2251: AF325460
Homo sapiens dendritic lectin b isoform (CLECSF11) mRNA, complete cds, alternatively spliced
gi|17225338|gb|AF325460.1|AF325460[17225338]

2252: AF325459
Homo sapiens dendritic lectin (CLECSF11) mRNA, complete cds, alternatively spliced
gi|17225336|gb|AF325459.1|AF325459[17225336]

2253: AF293357
Homo sapiens AT2 receptor-interacting protein 1 mRNA, complete cds
gi|17224595|gb|AF293357.1|AF293357[17224595]

2254: AF283988
Homo sapiens leukocyte immunoglobulin-like receptor-5 (LILRB5) mRNA, LILRB5-v1 allele, complete cds
gi|17224473|gb|AF283988.1|AF283988[17224473]

2255: AF283987

Homo sapiens leukocyte immunoglobulin-like receptor-2 (LILRB2) mRNA, LILRB2-v2 allele, complete cds
gi|17224471|gb|AF283987.1|AF283987[17224471]

2256: AF283986
Homo sapiens leukocyte immunoglobulin-like receptor-2 (LILRB2) mRNA, LILRB2-v1 allele, complete cds
gi|17224469|gb|AF283986.1|AF283986[17224469]

2257: AF283985
Homo sapiens leukocyte immunoglobulin-like receptor-1 (LILRB1) mRNA, LILRB1-v2 allele, complete cds
gi|17224467|gb|AF283985.1|AF283985[17224467]

2258: AF283984
Homo sapiens leukocyte immunoglobulin-like receptor-1 (LILRB1) mRNA, LILRB1-v1 allele, complete cds
gi|17224465|gb|AF283984.1|AF283984[17224465]

2259: NM_057170
Homo sapiens G protein-coupled receptor kinase-interactor 2 (GIT2), transcript variant 2, mRNA
gi|17149831|ref|NM_057170.1|[17149831]

2260: NM_057169
Homo sapiens G protein-coupled receptor kinase-interactor 2 (GIT2), transcript variant 1, mRNA
gi|17149829|ref|NM_057169.1|[17149829]

2261: AJ417151
Homo sapiens partial mRNA for T cell receptor beta chain (TCRB gene), clone 25
gi|17148488|emb|AJ417151.1|HSA417151[17148488]

2262: AJ417150
Homo sapiens partial mRNA for T cell receptor beta chain (TCRB gene), clone 27
gi|17148486|emb|AJ417150.1|HSA417150[17148486]

2263: NM_014776

Homo sapiens G protein-coupled receptor kinase-interactor 2 (GIT2), transcript variant 3, mRNA
gi|7661943|ref|NM_014776.1|[7661943]

2264: AJ239326
Homo sapiens chromosome 21 clone cosmid LLNLc116 32E2 map 21q22.3, * SEQUENCING IN PROGRESS *, 4 ordered pieces
gi|6982097|emb|AJ239326.3|HSS171M[6982097]

2265: NM_000675
Homo sapiens adenosine A2a receptor (ADORA2A), mRNA
gi|17136146|ref|NM_000675.3|[17136146]

2266: AF035374
Homo sapiens Cys-rich protein (RAMP) mRNA, complete cds
gi|2665702|gb|AF035374.1|AF035374[2665702]

2267: AF282269
Homo sapiens G protein-coupled receptor kinase 7 mRNA, complete cds
gi|17026317|gb|AF282269.1|AF282269[17026317]

2268: AF437510
Homo sapiens T-cell receptor beta-chain mRNA, partial cds
gi|16974744|gb|AF437510.1|AF437510[16974744]

2269: AX286800
Sequence 35 from Patent WO0178796
gi|17048833|emb|AX286800.1|AX286800[17048833]

2270: AX286799
Sequence 34 from Patent WO0178796
gi|17048832|emb|AX286799.1|AX286799[17048832]

2271: AB005145
Homo sapiens CL-P1 mRNA for collectin placenta 1, complete cds
gi|17026100|dbj|AB005145.1|AB005145[17026100]

2272: SEG_HUMIL3RA
Homo sapiens gene for interleukin 3 receptor alpha subunit
gi|1345401|dbj||SEG_HUMIL3RA[1345401]

2273: L34720
Homo sapiens T-cell receptor beta (TCRB) mRNA, partial cds
gi|1100194|gb|L34720.1|HUMTCRBP[1100194]

2274: L34734
Homo sapiens T-cell receptor beta (TCRB) mRNA, complete cds
gi|1100181|gb|L34734.1|HUMTCRBAL[1100181]

2275: L34729
Homo sapiens T-cell receptor beta (TCRB) mRNA, partial cds
gi|1100171|gb|L34729.1|HUMTCRBAG[1100171]

2276: D49412
Homo sapiens gene for interleukin 3 receptor alpha subunit, exon 11
gi|684969|dbj|D49412.1|HUMIL3RA11[684969]

2277: D49410
Homo sapiens gene for interleukin 3 receptor alpha subunit, exon 12 and partial cds
gi|684968|dbj|D49410.1|HUMIL3RA12[684968]

2278: D49408
Homo sapiens gene for interleukin 3 receptor alpha subunit, exon 10
gi|684967|dbj|D49408.1|HUMIL3RA10[684967]

2279: D49409
Homo sapiens gene for interleukin 3 receptor alpha subunit, exon 6
gi|684966|dbj|D49409.1|HUMIL3RA06[684966]

2280: D49407
Homo sapiens gene for interleukin 3 receptor alpha subunit, exon 4
gi|684965|dbj|D49407.1|HUMIL3RA04[684965]

2281: D49406
Homo sapiens gene for interleukin 3 receptor alpha subunit, exon 2
gi|684964|dbj|D49406.1|HUMIL3RA02[684964]

2282: D49404
Homo sapiens gene for interleukin 3 receptor alpha subunit, exon 7
gi|684963|dbj|D49404.1|HUMIL3RA07[684963]

2283: D49403
Homo sapiens gene for interleukin 3 receptor alpha subunit, exon 5
gi|684962|dbj|D49403.1|HUMIL3RA05[684962]

2284: D49402
Homo sapiens gene for interleukin 3 receptor alpha subunit, exon 3
gi|684961|dbj|D49402.1|HUMIL3RA03[684961]

2285: D49401
Homo sapiens gene for interleukin 3 receptor alpha subunit, exon 1
gi|684960|dbj|D49401.1|HUMIL3RA01[684960]

2286: D49411
Homo sapiens gene for interleukin 3 receptor alpha subunit, exon 9
gi|684959|dbj|D49411.1|HUMIL3RA09[684959]

2287: D49405
Homo sapiens gene for interleukin 3 receptor alpha subunit, exon 8
gi|684958|dbj|D49405.1|HUMIL3RA08[684958]

2288: SEG_HUMGRAS
Homo sapiens gene for granulocyte-macrophage colony stimulating factor (GM-CSF) receptor alpha subunit
gi|522101|dbj||SEG_HUMGRAS[522101]

2289: D26625
Homo sapiens gene for granulocyte-macrophage colony stimulating factor (GM-CSF) receptor alpha subunit, exon 10
gi|467508|dbj|D26625.1|HUMGRAS10[467508]

2290: D26624
Homo sapiens gene for granulocyte-macrophage colony stimulating factor (GM-CSF) receptor alpha subunit, exon 9
gi|467507|dbj|D26624.1|HUMGRAS09[467507]

2291: D26623
Homo sapiens gene for granulocyte-macrophage colony stimulating factor (GM-CSF) receptor alpha subunit, exon 8
gi|467506|dbj|D26623.1|HUMGRAS08[467506]

2292: D26622
Homo sapiens gene for granulocyte-macrophage colony stimulating factor (GM-CSF) receptor alpha subunit, exon 7
gi|467505|dbj|D26622.1|HUMGRAS07[467505]

2293: D26621
Homo sapiens gene for granulocyte-macrophage colony stimulating factor (GM-CSF) receptor alpha subunit, exon 6
gi|467504|dbj|D26621.1|HUMGRAS06[467504]

2294: D26628
Homo sapiens gene for granulocyte-macrophage colony stimulating factor (GM-CSF) receptor alpha subunit, exon 13 and partial cds
gi|456594|dbj|D26628.1|HUMGRAS13[456594]

2295: D26627
Homo sapiens gene for granulocyte-macrophage colony stimulating factor (GM-CSF) receptor alpha subunit, exon 12
gi|456593|dbj|D26627.1|HUMGRAS12[456593]

2296: D26626
Homo sapiens gene for granulocyte-macrophage colony stimulating factor (GM-CSF) receptor alpha subunit, exon 11
gi|456592|dbj|D26626.1|HUMGRAS11[456592]

2297: D26620
Homo sapiens gene for granulocyte-macrophage colony stimulating factor (GM-CSF) receptor alpha subunit, exon 5 gi|456591|dbj|D26620.1|HUMGRAS05[456591]

2298: D26619
Homo sapiens gene for granulocyte-macrophage colony stimulating factor (GM-CSF) receptor alpha subunit, exon 4
gi|456590|dbj|D26619.1|HUMGRAS04[456590]

2299: D26618
Homo sapiens gene for granulocyte-macrophage colony stimulating factor (GM-CSF) receptor alpha subunit, exon 3
gi|456589|dbj|D26618.1|HUMGRAS03[456589]

2300: D26617
Homo sapiens gene for granulocyte-macrophage colony stimulating factor (GM-CSF) receptor alpha subunit, exon 2
gi|456588|dbj|D26617.1|HUMGRAS02[456588]

2301: D26616
Homo sapiens gene for granulocyte-macrophage colony stimulating factor (GM-CSF) receptor alpha subunit, exon 1
gi|456587|dbj|D26616.1|HUMGRAS01[456587]

2307: AF324499
Homo sapiens olfactory-like receptor mRNA, complete cds
gi|17016397|gb|AF324499.1|AF324499[17016397]

2308: AF308814
Homo sapiens olfactory receptor-like protein (JCG10) mRNA, partial cds
gi|17016395|gb|AF308814.1|AF308814[17016395]

2309: AF238488
Homo sapiens olfactory-like receptor JCG8 (JCG8) mRNA, complete cds
gi|17016318|gb|AF238488.1|AF238488[17016318]

2310: AF238487
Homo sapiens olfactory-like receptor PJCG2 (PJCG2) mRNA, partial cds
gi|17016316|gb|AF238487.1|AF238487[17016316]

2311: AF220494
Homo sapiens olfactory receptor-like protein JCG4 (JCG4) mRNA, partial cds
gi|17016314|gb|AF220494.1|AF220494[17016314]

2312: AF220493
Homo sapiens olfactory receptor-like protein PJCG1 (PJCG1) mRNA, partial cds
gi|17016312|gb|AF220493.1|AF220493[17016312]

2313: AF209507
Homo sapiens olfactory receptor-like protein mRNA, complete sequence
gi|17016311|gb|AF209507.1|AF209507[17016311]

2314: AF403014
Homo sapiens type II gonadotropin-releasing hormone receptor gene, partial cds
gi|16589055|gb|AF403014.1|AF403014[16589055]

2316: AF403012
Homo sapiens ribonucleoprotein RBM8 gene, complete cds
gi|16589051|gb|AF403012.1|AF403012[16589051]

2317: AY011601
Homo sapiens cannabinoid receptor 1 (CNR1) gene, partial cds
gi|12699807|gb|AY011601.1|[12699807]

2318: AY011231
Homo sapiens adenosine A3 receptor (ADORA3) gene, partial cds
gi|12699245|gb|AY011231.1|[12699245]

2319: AF400602
Homo sapiens beta-glucan receptor isoform H (BGR) mRNA, complete cds, alternatively spliced
gi|15986713|gb|AF400602.1|AF400602[15986713]

2320: AF400601
Homo sapiens beta-glucan receptor isoform G (BGR) mRNA, complete cds, alternatively spliced
gi|15986711|gb|AF400601.1|AF400601[15986711]

2321: AF400600
Homo sapiens beta-glucan receptor isoform F (BGR) mRNA, complete cds, alternatively spliced
gi|15986709|gb|AF400600.1|AF400600[15986709]

2322: AF400599
Homo sapiens beta-glucan receptor isoform E (BGR) mRNA, complete cds, alternatively spliced
gi|15986707|gb|AF400599.1|AF400599[15986707]

2323: AF400598
Homo sapiens beta-glucan receptor isoform D (BGR) mRNA, complete cds, alternatively spliced
gi|15986705|gb|AF400598.1|AF400598[15986705]

2324: AF400597
Homo sapiens beta-glucan receptor isoform C (BGR) mRNA, complete cds, alternatively spliced
gi|15986703|gb|AF400597.1|AF400597[15986703]

2325: AF400596
Homo sapiens beta-glucan receptor isoform B (BGR) mRNA, complete cds, alternatively spliced
gi|15986701|gb|AF400596.1|AF400596[15986701]

2326: AF400595
Homo sapiens beta-glucan receptor isoform A (BGR) mRNA, complete cds, alternatively spliced
gi|15986699|gb|AF400595.1|AF400595[15986699]

2329: AF162669
Homo sapiens olfactory receptor-like protein JCG2 (JCG2) gene, complete cds
gi|12002783|gb|AF162669.1|AF162669[12002783]

2330: NM_004895
Homo sapiens cold autoinflammatory syndrome 1 (CIAS1), mRNA
gi|4757727|ref|NM_004895.1|[4757727]

2331: AF409103
Homo sapiens T-cell receptor VB3 CDR3 region mRNA, partial cds
gi|15425973|gb|AF409103.1|AF409103[15425973]

2332: NM_033181
Homo sapiens cannabinoid receptor 1 (brain) (CNR1), transcript variant 3, mRNA
gi|15208647|ref|NM_033181.1|[15208647]

2333: AF373846
Homo sapiens BAFF receptor mRNA, complete cds
gi|15208474|gb|AF373846.1|AF373846[15208474]

2334: AF361108
Homo sapiens CRHF2 receptor beta-isoform mRNA, partial sequence, aberrantly spliced
gi|14586959|gb|AF361108.1|AF361108[14586959]

2335: NM_005755
Homo sapiens Epstein-Barr virus induced gene 3 (EBI3), mRNA
gi|14577916|ref|NM_005755.2|[14577916]

2336: AF369794
Homo sapiens B cell crosslinked IgM-activating sequence protein (BXMAS1) mRNA, complete cds
gi|14278718|gb|AF369794.2|AF369794[14278718]

2337: AF376725
Homo sapiens lung seven transmembrane receptor 1 (LUSTR1) mRNA, complete cds
gi|14248996|gb|AF376725.1|AF376725[14248996]

2343: AF352324
Homo sapiens killer cell Ig-like receptor KIR3DL7 (KIRC1) mRNA, complete cds
gi|13560903|gb|AF352324.1|AF352324[13560903]

2344: AJ249131
Homo sapiens partiel mPR gene for progesterone membrane binding protein gi|6688178|emb|AJ249131.1|HSA249131[6688178]

2345: S73474
Homo sapiens folate receptor alpha isoform mRNA, partial cds
gi|688233|gb|S73474.1|S73490S2[688233]

2346: S73490
Homo sapiens folate receptor alpha isoform mRNA, partial cds
gi|688232|gb|S73490.1|S73490S1[688232]

2347: S69142
Homo sapiens T-cell receptor alpha-chain (TcR V alpha) mRNA, partial cds
gi|545977|gb|S69142.1|S69142[545977]

2348: S67401
Homo sapiens T-cell receptor beta chain VDJ region (TCR Vbeta 7.1 Jbeta 2.3) mRNA, partial cds
gi|455870|gb|S67401.1|S67401[455870]

2349: S62797
Homo sapiens T cell receptor beta chain VDJ region (TcrVbeta 6) mRNA, TcrVbeta 6.7a allele, partial cds
gi|385951|gb|S62797.1|S62797[385951]

2350: AF310685
Homo sapiens ADP-glucose receptor gene, complete cds
gi|16973448|gb|AF310685.1|AF310685[16973448]

2351: NM_057160
Homo sapiens artemin (ARTN), transcript variant 3, mRNA
gi|16950644|ref|NM_057160.1|[16950644]

2352: NM_057091
Homo sapiens artemin (ARTN), transcript variant 2, mRNA
gi|16950642|ref|NM_057091.1|[16950642]

2353: NM_057090

Homo sapiens artemin (ARTN), transcript variant 4, mRNA
gi|16950640|ref|NM_057090.1|[16950640]

2354: NM_003976
Homo sapiens artemin (ARTN), transcript variant 1, mRNA
gi|16950639|ref|NM_003976.2|[16950639]

2355: NM_053032
Homo sapiens myosin, light polypeptide kinase (MYLK), transcript variant 8, mRNA
gi|16950624|ref|NM_053032.1|[16950624]

2356: NM_053031
Homo sapiens myosin, light polypeptide kinase (MYLK), transcript variant 7, mRNA
gi|16950622|ref|NM_053031.1|[16950622]

2357: NM_053030
Homo sapiens myosin, light polypeptide kinase (MYLK), transcript variant 5, mRNA
gi|16950620|ref|NM_053030.1|[16950620]

2358: NM_053029
Homo sapiens myosin, light polypeptide kinase (MYLK), transcript variant 4, mRNA
gi|16950618|ref|NM_053029.1|[16950618]

2359: NM_053028
Homo sapiens myosin, light polypeptide kinase (MYLK), transcript variant 3B, mRNA
gi|16950616|ref|NM_053028.1|[16950616]

2360: NM_053027
Homo sapiens myosin, light polypeptide kinase (MYLK), transcript variant 3A, mRNA
gi|16950614|ref|NM_053027.1|[16950614]

2361: NM_053026
Homo sapiens myosin, light polypeptide kinase (MYLK), transcript variant 2, mRNA
gi|16950612|ref|NM_053026.1|[16950612]

2362: NM_053025
Homo sapiens myosin, light polypeptide kinase (MYLK), transcript variant 1, mRNA
gi|16950610|ref|NM_053025.1|[16950610]

2363: NM_005965
Homo sapiens myosin, light polypeptide kinase (MYLK), transcript variant 6, mRNA
gi|16950600|ref|NM_005965.2|[16950600]

2364: AF106202
Homo sapiens endothelial cell protein C receptor precursor (EPCR) gene, promoter region and complete cds
gi|16950557|gb|AF106202.2|AF106202[16950557]

2365: AY033942
Homo sapiens prostate-specific G protein-coupled receptor (PSGR) mRNA, complete cds
gi|16943640|gb|AY033942.1|[16943640]

2366: AF369708
Homo sapiens prostate-specific G-protein coupled receptor mRNA, complete cds
gi|13752563|gb|AF369708.1|AF369708[13752563]

2368: AJ276204
Homo sapiens partial mRNA for T-cell receptor beta-chain (TCRB gene) Plasmid-C-8
gi|9968287|emb|AJ276204.1|HSA276204[9968287]

2369: AJ276203
Homo sapiens partial mRNA for T-cell receptor beta-chain (TCRB gene) Plasmid-C-7
gi|9968285|emb|AJ276203.1|HSA276203[9968285]

2370: AJ276202
Homo sapiens partial mRNA for T-cell receptor beta-chain (TCRB gene) Plasmid-C-6
gi|9968266|emb|AJ276202.1|HSA276202[9968266]

2371: AJ276201
Homo sapiens partial mRNA for T-cell receptor beta-chain (TCRB gene) Plasmid-C-5
gi|9968264|emb|AJ276201.1|HSA276201[9968264]

2372: AJ276200
Homo sapiens partial mRNA for T-cell receptor beta-chain (TCRB gene) Plasmid-C-4
gi|9968262|emb|AJ276200.1|HSA276200[9968262]

2373: AJ276199
Homo sapiens partial mRNA for T-cell receptor beta-chain (TCRB gene) Plasmid-C-3
gi|9968260|emb|AJ276199.1|HSA276199[9968260]

2374: AJ276198
Homo sapiens partial mRNA for T-cell receptor beta-chain (TCRB gene) Plasmid-C-2
gi|9968258|emb|AJ276198.1|HSA276198[9968258]

2375: AJ276197
Homo sapiens partial mRNA for T-cell receptor beta-chain (TCRB gene) Plasmid-C-1
gi|9968256|emb|AJ276197.1|HSA276197[9968256]

2376: AJ276196
Homo sapiens partial mRNA for T-cell receptor beta-chain (TCRB gene) Gel-C
gi|9968254|emb|AJ276196.1|HSA276196[9968254]

2377: AJ276195
Homo sapiens partial mRNA for T-cell receptor beta-chain (TCRB gene)
Plasmid-B-11
gi|9968252|emb|AJ276195.1|HSA276195[9968252]

2378: AJ276194
Homo sapiens partial mRNA for T-cell receptor beta-chain (TCRB gene)
Plasmid-B-10
gi|9968250|emb|AJ276194.1|HSA276194[9968250]

2379: AJ276193
Homo sapiens partial mRNA for T-cell receptor beta-chain (TCRB gene) Plasmid-B-9
gi|9968248|emb|AJ276193.1|HSA276193[9968248]

2380: AJ276192
Homo sapiens partial mRNA for T-cell receptor beta-chain (TCRB gene) Plasmid-B-8
gi|9968246|emb|AJ276192.1|HSA276192[9968246]

2381: AJ276191
Homo sapiens partial mRNA for T-cell receptor beta-chain (TCRB gene) Plasmid-B-7
gi|9968244|emb|AJ276191.1|HSA276191[9968244]

2382: AJ276190
Homo sapiens partial mRNA for T-cell receptor beta-chain (TCRB gene) Plasmid-B-6
gi|9968242|emb|AJ276190.1|HSA276190[9968242]

2383: AJ276189
Homo sapiens partial mRNA for T-cell receptor beta-chain (TCRB gene) Plasmid-B-5
gi|9968240|emb|AJ276189.1|HSA276189[9968240]

2384: AJ276188
Homo sapiens partial mRNA for T-cell receptor beta-chain (TCRB gene) Plasmid-B-4
gi|9968238|emb|AJ276188.1|HSA276188[9968238]

2385: AJ276187
Homo sapiens partial mRNA for T-cell receptor beta-chain (TCRB gene) Plasmid-B-3
gi|9968236|emb|AJ276187.1|HSA276187[9968236]

2386: AJ276186
Homo sapiens partial mRNA for T-cell receptor beta-chain (TCRB gene) Plasmid-B-2
gi|9968234|emb|AJ276186.1|HSA276186[9968234]

2387: AJ276185
Homo sapiens partial mRNA for T-cell receptor beta-chain (TCRB gene) Plasmid-B-1
gi|9968232|emb|AJ276185.1|HSA276185[9968232]

2388: AJ276184
Homo sapiens partial mRNA for T-cell receptor beta-chain (TCRB gene) Gel-A2
gi|9968230|emb|AJ276184.1|HSA276184[9968230]

2389: AJ276183
Homo sapiens partial mRNA for T-cell receptor beta-chain (TCRB gene) Gel-A1
gi|9968228|emb|AJ276183.1|HSA276183[9968228]

2390: NM_005086
Homo sapiens sarcospan (Kras oncogene-associated gene) (SSPN), mRNA
gi|16933560|ref|NM_005086.3|[16933560]

2391: NM_018153
Homo sapiens tumor endothelial marker 8 (TEM8), transcript variant 3, mRNA
gi|16933552|ref|NM_018153.2|[16933552]

2392: NM_053034
Homo sapiens tumor endothelial marker 8 (TEM8), transcript variant 2, mRNA
gi|16933550|ref|NM_053034.1|[16933550]

2393: NM_005929
Homo sapiens antigen p97 (melanoma associated) identified by monoclonal antibodies 133.2 and 96.5 (MFI2), transcript variant 1, mRNA
gi|16933549|ref|NM_005929.3|[16933549]

2394: NM_033316
Homo sapiens antigen p97 (melanoma associated) identified by monoclonal antibodies 133.2 and 96.5 (MFI2), transcript variant 2, mRNA
gi|16933548|ref|NM_033316.2|[16933548]

2395: AF361473
Homo sapiens magic roundabout mRNA, complete cds
gi|16930357|gb|AF361473.1|AF361473[16930357]

2396: NM_032208
Homo sapiens tumor endothelial marker 8 (TEM8), transcript variant 1, mRNA
gi|14149903|ref|NM_032208.1|[14149903]

2397: NM_007346
Homo sapiens opioid growth factor receptor (OGFR), mRNA
gi|6671492|ref|NM_007346.1|[6671492]

2398: BC017412
Homo sapiens, leukocyte immunoglobulin-like receptor, subfamily A (with TM domain), member 2, clone MGC:27265 IMAGE:4618777, mRNA, complete cds gi|16924270|gb|BC017412.1|BC017412[16924270]

2401: AF435588
Homo sapiens melatonin receptor Mel1a (MTNR1A) mRNA, partial cds
gi|16904202|gb|AF435588.1|AF435588[16904202]

2402: AF421380
Homo sapiens anthrax toxin receptor mRNA, complete cds
gi|16566412|gb|AF421380.1|AF421380[16566412]

2403: AF291815
Homo sapiens NK cell receptor (CS1) mRNA, complete cds
gi|13021809|gb|AF291815.1|AF291815[13021809]

2404: AF117899
Homo sapiens LDLR-FUT fusion protein (LDLR-FUT) mRNA, complete cds
gi|6739499|gb|AF117899.1|AF117899[6739499]

2405: AF054013
Homo sapiens lipoxin A4 receptor mRNA, complete cds
gi|3047268|gb|AF054013.1|AF054013[3047268]

2406: AF013250
Homo sapiens leukocyte-associated Ig-like receptor-2 (LAIR-2) mRNA, complete cds
gi|2352942|gb|AF013250.1|AF013250[2352942]

2407: AF013249
Homo sapiens leukocyte-associated Ig-like receptor-1 (LAIR-1) mRNA, complete cds
gi|2352940|gb|AF013249.1|AF013249[2352940]

2409: AF326353
Homo sapiens Src-like adapter protein-2 mRNA, complete cds
gi|16797891|gb|AF326353.1|AF326353[16797891]

2411: BC017065
Homo sapiens, tumor necrosis factor receptor superfamily, member 6b, decoy, clone MGC:9587 IMAGE:3886635, mRNA, complete cds gi|16877637|gb|BC017065.1|BC017065[16877637]

2412: BC016938
Homo sapiens, neuromedin U receptor 2, clone MGC:21396 IMAGE:3852151, mRNA, complete cds
gi|16877376|gb|BC016938.1|BC016938[16877376]

2413: BC016860
Homo sapiens, G protein-coupled receptor, family C, group 5, member C, clone MGC:17384 IMAGE:3904655, mRNA, complete cds
gi|16877192|gb|BC016860.1|BC016860[16877192]

2414: BC016692
Homo sapiens, progesterone receptor membrane component 2, clone MGC:22407 IMAGE:4067832, mRNA, complete cds
gi|16876813|gb|BC016692.1|BC016692[16876813]

2415: AY026949
Homo sapiens stresscopin mRNA, complete cds
gi|15026913|gb|AY026949.1|[15026913]

2416: AF285092
Homo sapiens Bcl-2-like protein 10 mRNA, complete cds
gi|9837265|gb|AF285092.1|AF285092[9837265]

2417: D78579
Homo sapiens NOR-1 mRNA for neuron derived orphan receptor, complete cds
gi|1651190|dbj|D78579.1|D78579[1651190]

2418: D38044
Homo sapiens gene for Ah-receptor, partial cds, exons 7-9
gi|532672|dbj|D38044.1|HUMAHRA[532672]

2419: NM_053278
Homo sapiens G protein-coupled receptor 102 (GPR102), mRNA
gi|16751916|ref|NM_053278.1|[16751916]

2420: NM_030916
Homo sapiens Ig superfamily receptor LNIR (LNIR), mRNA
gi|16716338|ref|NM_030916.1|[16716338]

2421: AF403479
Homo sapiens EWS/FLI1 activated transcript 2 protein mRNA, complete cds
gi|16611777|gb|AF403479.1|AF403479[16611777]

2422: NM_053036
Homo sapiens G protein-coupled receptor 74 (GPR74), mRNA
gi|16604257|ref|NM_053036.1|[16604257]

2431: BC016004
Homo sapiens, macrophage receptor with collagenous structure, clone MGC:27263 IMAGE:4618447, mRNA, complete cds
gi|16359078|gb|BC016004.1|BC016004[16359078]

2432: BC013827
Homo sapiens, laminin receptor 1 (67kD, ribosomal protein SA), clone MGC:17122 IMAGE:3446816, mRNA, complete cds
gi|16307601|gb|BC013827.1|BC013827[16307601]

2433: BC001590
Homo sapiens, cargo selection protein (mannose 6 phosphate receptor binding protein), clone MGC:2012 IMAGE:2987965, mRNA, complete cds
gi|16306788|gb|BC001590.1|BC001590[16306788]

2434: BC001492
Homo sapiens, ciliary neurotrophic factor receptor, clone MGC:1774 IMAGE:3510004, mRNA, complete cds
gi|16306633|gb|BC001492.1|BC001492[16306633]

2435: BC015768
Homo sapiens, interleukin 13 receptor, alpha 1, clone MGC:23204 IMAGE:4868206, mRNA, complete cds
gi|16041774|gb|BC015768.1|BC015768[16041774]

2436: BC015731

Homo sapiens, leukocyte immunoglobulin-like receptor, subfamily B (with TM and ITIM domains), member 1, clone MGC:22968 IMAGE:4878915, mRNA, complete cds
gi|16041710|gb|BC015731.1|BC015731[16041710]

2437: BC015542
Homo sapiens, poliovirus receptor, clone MGC:9603 IMAGE:3902226, mRNA, complete cds
gi|15930222|gb|BC015542.1|BC015542[15930222]

2439: BC015195
Homo sapiens, Fc fragment of IgE, high affinity I, receptor for; alpha polypeptide, clone MGC:14717 IMAGE:4251469, mRNA, complete cds
gi|15929529|gb|BC015195.1|BC015195[15929529]

2440: BC014972
Homo sapiens, interleukin 2 receptor, gamma (severe combined immunodeficiency), clone MGC:23116 IMAGE:4878734, mRNA, complete cds
gi|15929027|gb|BC014972.1|BC014972[15929027]

2441: BC014962
Homo sapiens, GDNF family receptor alpha 1, clone MGC:23045 IMAGE:4874042, mRNA, complete cds
gi|15929001|gb|BC014962.1|BC014962[15929001]

2442: BC014960
Homo sapiens, low density lipoprotein receptor defect C complementing, clone MGC:23019 IMAGE:4876271, mRNA, complete cds
gi|15928995|gb|BC014960.1|BC014960[15928995]

2443: BC013816
Homo sapiens, platelet-activating factor receptor, clone MGC:17210 IMAGE:4343214, mRNA, complete cds
gi|15489458|gb|BC013816.1|BC013816[15489458]

2444: BC013780
Homo sapiens, adenosine A2a receptor, clone MGC:21342 IMAGE:4385637, mRNA, complete cds
gi|15489369|gb|BC013780.1|BC013780[15489369]

2445: NM_032551
Homo sapiens G protein-coupled receptor 54 (GPR54), mRNA
gi|14211846|ref|NM_032551.1|[14211846]

2446: AF329490
Homo sapiens IFGP2 mRNA, complete cds
gi|16506260|gb|AF329490.1|AF329490[16506260]

2447: AF329488
Homo sapiens IFGP1 mRNA, complete cds
gi|16506256|gb|AF329488.1|AF329488[16506256]

2448: NM_000798
Homo sapiens dopamine receptor D5 (DRD5), mRNA
gi|16445405|ref|NM_000798.2|[16445405]

2449: NM_000794
Homo sapiens dopamine receptor D1 (DRD1), mRNA
gi|16445404|ref|NM_000794.2|[16445404]

2450: NM_000796
Homo sapiens dopamine receptor D3 (DRD3), transcript variant a, mRNA
gi|16445403|ref|NM_000796.2|[16445403]

2451: NM_033663
Homo sapiens dopamine receptor D3 (DRD3), transcript variant e, mRNA
gi|16445401|ref|NM_033663.1|[16445401]

2452: NM_033660
Homo sapiens dopamine receptor D3 (DRD3), transcript variant d, mRNA
gi|16445399|ref|NM_033660.1|[16445399]

2453: NM_033659
Homo sapiens dopamine receptor D3 (DRD3), transcript variant c, mRNA
gi|16445397|ref|NM_033659.1|[16445397]

2454: NM_033658
Homo sapiens dopamine receptor D3 (DRD3), transcript variant b, mRNA
gi|16445395|ref|NM_033658.1|[16445395]

2455: AJ298918
Homo sapiens t(8;22)(p11;q11) translocation breakpoint, BCR/FGFR gene
gi|16444915|emb|AJ298918.1|HSA298918[16444915]

2456: AJ298917
Homo sapiens partial mRNA for FGFR1/BCR chimaeric fusion peptide
gi|16444913|emb|AJ298917.1|HSA298917[16444913]

2457: AJ298916
Homo sapiens partial mRNA for BCR/FGFR1 chimaeric fusion protein
gi|16444911|emb|AJ298916.1|HSA298916[16444911]

2458: AF325925
Homo sapiens tandem motif downstream of INSRR gene, allele 2
gi|13374363|gb|AF325925.1|AF325925[13374363]

2459: AF325924
Homo sapiens tandem motif downstream of INSRR gene, allele 1
gi|13374362|gb|AF325924.1|AF325924[13374362]

2460: NM_014879
Homo sapiens G protein-coupled receptor 105 (GPR105), mRNA
gi|7661847|ref|NM_014879.1|[7661847]

2461: NM_000797
Homo sapiens dopamine receptor D4 (DRD4), mRNA
gi|4503388|ref|NM_000797.1|[4503388]

2462: NM_052962
Homo sapiens class II cytokine receptor (IL22RA2), mRNA
gi|16418458|ref|NM_052962.1|[16418458]

2463: NM_052932

Homo sapiens pro-oncosis receptor inducing membrane injury gene (PORIMIN), mRNA
gi|16418408|ref|NM_052932.1|[16418408]

2464: NM_052887
Homo sapiens Toll-interleukin 1 receptor (TIR) domain-containing adapter protein (TIRAP), mRNA
gi|16418398|ref|NM_052887.1|[16418398]

2465: NM_018835
Homo sapiens olfactory receptor, family 1, subfamily K, member 1 (OR1K1), mRNA
gi|9256536|ref|NM_018835.1|[9256536]

2466: BC016141
Homo sapiens, interleukin 1 receptor accessory protein, clone IMAGE:3920152, mRNA
gi|16359373|gb|BC016141.1|BC016141[16359373]

2467: AF177765
Homo sapiens toll-like receptor 4 (TLR4) gene, TLR4A allele, complete cds
gi|6175872|gb|AF177765.1|AF177765[6175872]

2468: U11813
Homo sapiens hepatocyte growth factor receptor precursor, mRNA, partial cds; alternatively spliced
gi|530799|gb|U11813.1|HSU11813[530799]

2469: BC009540
Homo sapiens, G protein-coupled receptor 87, clone MGC:10065 IMAGE:3894333, mRNA, complete cds
gi|16306940|gb|BC009540.1|BC009540[16306940]

2474: AJ313162
Homo sapiens mRNA for soluble cytokine class II receptor, long isoform (CRF2-S1 gene)
gi|16304592|emb|AJ313162.1|HSA313162[16304592]

2475: AJ313161

Homo sapiens mRNA for soluble cytokine class II receptor, short isoform (CRF2-S1 gene)
gi|16304590|emb|AJ313161.1|HSA313161[16304590]

2476: AY048757
Homo sapiens ATP-binding cassette transporter G1 (ABCG1) mRNA, complete cds, alternatively spliced
gi|16304310|gb|AY048757.1|[16304310]

2501: AJ313161
Homo sapiens mRNA for soluble cytokine class II receptor, short isoform (CRF2-S1 gene)
gi|16304590|emb|AJ313161.1|HSA313161[16304590]

2502: AY048757
Homo sapiens ATP-binding cassette transporter G1 (ABCG1) mRNA, complete cds, alternatively spliced
gi|16304310|gb|AY048757.1|[16304310]

2626: NM_012068
Homo sapiens activating transcription factor 5 (ATF5), mRNA
gi|12597624|ref|NM_012068.2|[12597624]

2627: AF055084
Homo sapiens very large G-protein coupled receptor-1 (VLGR1) mRNA, complete cds
gi|5902965|gb|AF055084.1|AF055084[5902965]

2629: AJ414821
Homo sapiens partial IGVKL12 gene for immunoglobulin kappa chain variable region, donor TG, cell84
gi|16215495|emb|AJ414821.2|HSA414821[16215495]

2630: AY056048
Homo sapiens receptor protein tyrosine kinase variant EphB4v1 (EPHB4) mRNA, complete cds, alternatively spliced
gi|16209619|gb|AY056048.1|[16209619]

2631: AY056047
Homo sapiens receptor protein tyrosine kinase EphB4 (EPHB4) gene, complete cds, alternatively spliced
gi|16209617|gb|AY056047.1|[16209617]

2632: AY052498
Homo sapiens NK cell receptor (KIR2DL4) mRNA, KIR2DL4-10A allele, partial cds
gi|16209550|gb|AY052498.1|[16209550]

2633: AY052497
Homo sapiens NK cell receptor (KIR2DL4) mRNA, KIR2DL4-9A allele, partial cds
gi|16209510|gb|AY052497.1|[16209510]

2634: AY052496
Homo sapiens truncated NK cell receptor (KIR2DL4) mRNA, KIR2DL4-9A allele, partial cds
gi|16209507|gb|AY052496.1|[16209507]

2635: AF267245
Homo sapiens killer cell lectin-like receptor KLRF1-S3 (KLRF1) mRNA, complete cds., alternatively spliced
gi|16151842|gb|AF267245.1|AF267245[16151842]

2636: AF267244
Homo sapiens killer cell lectin-like receptor KLRF1-S2 (KLRF1) mRNA, complete cds., alternatively spliced
gi|16151840|gb|AF267244.1|AF267244[16151840]

2637: NM_033637
Homo sapiens beta-transducin repeat containing (BTRC), transcript variant 1, mRNA
gi|16117782|ref|NM_033637.1|[16117782]

3563: NM_033050
Homo sapiens G protein-coupled receptor 91 (GPR91), mRNA
gi|14780893|ref|NM_033050.1|[14780893]

3564: NM_023914

Homo sapiens G protein-coupled receptor 86 (GPR86), mRNA
gi|13194202|ref|NM_023914.1|[13194202]

3565: NM_020402
Homo sapiens cholinergic receptor, nicotinic, alpha polypeptide 10 (CHRNA10), mRNA
gi|11138122|ref|NM_020402.2|[11138122]

3566: NM_020370
Homo sapiens G protein-coupled receptor 84 (GPR84), mRNA
gi|9966838|ref|NM_020370.1|[9966838]

3567: NM_012301
Homo sapiens atrophin-1 interacting protein 1; activin receptor interacting protein 1 (KIAA0705), mRNA
gi|6912461|ref|NM_012301.1|[6912461]

3568: AF208541
Homo sapiens V1-vascular vasopressin receptor AVPR1A gene, promoter region and partial cds
gi|6581121|gb|AF208541.1|AF208541[6581121]

3569: NM_005756
Homo sapiens G protein-coupled receptor 64 (GPR64), mRNA
gi|5031732|ref|NM_005756.1|[5031732]

3570: NM_003939
Homo sapiens beta-transducin repeat containing (BTRC), transcript variant 2, mRNA
gi|4502476|ref|NM_003939.1|[4502476]

3571: AH003597
Homo sapiens A3 adenosine receptor (ADORA3) gene
gi|1387984|gb|AH003597.1|SEG_HUMADOR0[1387984]

3572: L77730
Homo sapiens A3 adenosine receptor (ADORA3) gene, exon 2
gi|1387983|gb|L77730.1|HUMADOR02[1387983]

3573: L77729
Homo sapiens A3 adenosine receptor (ADORA3) gene, exon 1
gi|1387982|gb|L77729.1|HUMADOR01[1387982]

3574: AF000381
Homo sapiens folate binding protein mRNA, partial cds
gi|16041647|gb|AF000381.2|AF000381[16041647]

3583: AY054974
Homo sapiens RAE-1-like transcript 4 mRNA, complete cds
gi|15990603|gb|AY054974.1|[15990603]

3584: AF421855
Homo sapiens interleukin 4 receptor (IL4R) gene, complete cds
gi|15987825|gb|AF421855.1|AF421855[15987825]

3585: AF359241
Homo sapiens soluble truncated fibroblast growth factor receptor 4 (FGFR4) mRNA, complete cds
gi|13877134|gb|AF359241.1|AF359241[13877134]

3586: NM_022148
Homo sapiens cytokine receptor-like factor 2 (CRLF2), mRNA
gi|13375623|ref|NM_022148.1|[13375623]

3587: AF179770
Homo sapiens olfactory receptor (HSA8) gene, partial cds
gi|7211542|gb|AF179770.1|AF179770[7211542]

3590: AF179767
Homo sapiens olfactory receptor (HSA5) gene, partial cds
gi|7211538|gb|AF179767.1|AF179767[7211538]

3591: AF179766
Homo sapiens olfactory receptor (HSA3) gene, partial cds
gi|7211536|gb|AF179766.1|AF179766[7211536]

3596: AF179761
Homo sapiens olfactory receptor (HSA12) gene, partial cds
gi|7211530|gb|AF179761.1|AF179761[7211530]

3597: AF179760
Homo sapiens olfactory receptor (HSA10) gene, partial cds
gi|7211528|gb|AF179760.1|AF179760[7211528]

3598: AF179759
Homo sapiens olfactory receptor (HSA1) gene, partial cds
gi|7211526|gb|AF179759.1|AF179759[7211526]

3599: D86962
Human mRNA for KIAA0207 gene, complete cds
gi|1503997|dbj|D86962.1|D86962[1503997]

3600: D13626
Human mRNA for KIAA0001 gene, complete cds
gi|285994|dbj|D13626.1|HUMRSC338[285994]

3601: AY026770
Homo sapiens lectin-like receptor 1B (DECTIN1) mRNA, complete cds, alternatively spliced
gi|15967098|gb|AY026770.2|[15967098]

3602: AY026769
Homo sapiens lectin-like receptor 1 (DECTIN1) mRNA, complete cds
gi|15967096|gb|AY026769.2|[15967096]

3605: AJ344142
Homo sapiens mRNA for putative MCP-1 chemokine receptor (CCR11 gene)
gi|15919090|cmb|AJ344142.1|HSA344142[15919090]

3606: AY029770
Homo sapiens CCK-B/gastrin receptor variant mRNA, complete cds, alternatively spliced gi|15911832|gb|AY029770.1|[15911832]

3607: NM_002821

Homo sapiens PTK7 protein tyrosine kinase 7 (PTK7), mRNA
gi|15826839|ref|NM_002821.2|[15826839]

3608: AF303576

Homo sapiens G protein-coupled receptor 75 (GPR75) gene, exon 1
gi|15824419|gb|AF303576.1|AF303576[15824419]

3609: AB032427

Homo sapiens VRL-2 mRNA for vanilloid receptor like channel-2, complete cds
gi|15822824|dbj|AB032427.1|AB032427[15822824]

3610: AY008280

Homo sapiens histamine receptor H4 (H4) mRNA, complete cds
gi|15822540|gb|AY008280.1|[15822540]

3611: U40271

Homo sapiens transmembrane receptor precursor (PTK7) mRNA, complete cds
gi|15808058|gb|U40271.2|HSU40271[15808058]

3612: NM_000575

Homo sapiens interleukin 1, alpha (IL1A), mRNA
gi|13236493|ref|NM_000575.1|[13236493]

3615: NM_014312

Homo sapiens cortical thymocyte receptor (X. laevis CTX) like (CTXL), mRNA
gi|7657000|ref|NM_014312.1|[7657000]

3616: AB032738

Homo sapiens gene for chemokine receptor CXCR3, partial cds
gi|7209698|dbj|AB032738.1|AB032738[7209698]

3617: AB032737

Homo sapiens gene for chemokine receptor CXCR3, partial cds
gi|7209696|dbj|AB032737.1|AB032737[7209696]

3618: AB032736
Homo sapiens gene for chemokine receptor CXCR3, partial cds
gi|7209694|dbj|AB032736.1|AB032736[7209694]

3619: AB032735
Homo sapiens gene for chemokine receptor CXCR3, partial cds
gi|7209692|dbj|AB032735.1|AB032735[7209692]

3620: AB032734
Homo sapiens CXCR2 gene for IL-8 receptor type B, partial cds
gi|7209690|dbj|AB032734.1|AB032734[7209690]

3621: AB032733
Homo sapiens CXCR2 gene for IL-8 receptor type B, partial cds
gi|7209688|dbj|AB032733.1|AB032733[7209688]

3622: AB032732
Homo sapiens CXCR1 gene for IL-8 receptor type A, partial cds
gi|7209686|dbj|AB032732.1|AB032732[7209686]

3623: AB032731
Homo sapiens CXCR1 gene for IL-8 receptor type A, partial cds
gi|7209684|dbj|AB032731.1|AB032731[7209684]

3624: AB032730
Homo sapiens CXCR1 gene for IL-8 receptor type A, partial cds
gi|7209682|dbj|AB032730.1|AB032730[7209682]

3625: AB032729
Homo sapiens CXCR1 gene for IL-8 receptor type A, partial cds
gi|7209680|dbj|AB032729.1|AB032729[7209680]

3626: AB032728
Homo sapiens CXCR1 gene for IL-8 receptor type A, partial cds
gi|7209678|dbj|AB032728.1|AB032728[7209678]

3628: AB030952
Homo sapiens TNFR2 gene for tumor necrosis factor receptor 2, partial cds
gi|6683135|dbj|AB030952.1|AB030952[6683135]

3629: AB030951
Homo sapiens TNFR2 gene for tumor necrosis factor receptor 2, partial cds
gi|6683133|dbj|AB030951.1|AB030951[6683133]

3630: AB030950
Homo sapiens TNFR2 gene for tumor necrosis factor receptor 2, partial cds
gi|6683131|dbj|AB030950.1|AB030950[6683131]

3631: AB030949
Homo sapiens TNFR2 gene for tumor necrosis factor receptor 2, partial cds
gi|6683129|dbj|AB030949.1|AB030949[6683129]

3632: AB023892
Homo sapiens gene for b-chemokine receptor CCR4, complete cds
gi|6467142|dbj|AB023892.1|AB023892[6467142]

3633: AB023891
Homo sapiens gene for b-chemokine receptor CCR4, complete cds
gi|6467140|dbj|AB023891.1|AB023891[6467140]

3634: AB023890
Homo sapiens gene for b-chemokine receptor CCR4, complete cds
gi|6467138|dbj|AB023890.1|AB023890[6467138]

3635: AB023889
Homo sapiens gene for b-chemokine receptor CCR4, complete cds
gi|6467136|dbj|AB023889.1|AB023889[6467136]

3636: AB023888
Homo sapiens gene for b-chemokine receptor CCR4, complete cds
gi|6467134|dbj|AB023888.1|AB023888[6467134]

3637: AB023887
Homo sapiens gene for b-chemokine receptor CCR3, complete cds
gi|6467132|dbj|AB023887.1|AB023887[6467132]

3638: AH008153
Homo sapiens IL-1RI gene, complete sequence
gi|5823144|gb|AH008153.1|SEG_HSAIL1R[5823144]

3639: AF146427
Homo sapiens interleukin-1 receptor type I (IL1R1) gene, exon 1c
gi|5823143|gb|AF146427.1|HSAIL1R2[5823143]

3640: AF146426
Homo sapiens interleukin-1 receptor type I (IL1R1) gene, exon 1b and intron 1b
gi|5823142|gb|AF146426.1|HSAIL1R1[5823142]

3641: NM_006691
Homo sapiens extracellular link domain-containing 1 (XLKD1), mRNA
gi|5729910|ref|NM_006691.1|[5729910]

3642: Z99761
Homo sapiens gonadotrophin-releasing hormone receptor gene exon 2
gi|5514748|emb|Z99761.2|HSGRHRX2[5514748]

3643: Z99760
Homo sapiens gonadotropin-releasing hormone receptor gene exon 1 variant 1
gi|5514747|emb|Z99760.2|HSGRHRX1[5514747]

3644: NM_001250
Homo sapiens tumor necrosis factor receptor superfamily, member 5 (TNFRSF5), mRNA
gi|4507580|ref|NM_001250.1|[4507580]

3645: NM_000406
Homo sapiens gonadotropin-releasing hormone receptor (GNRHR), mRNA
gi|4504058|ref|NM_000406.1|[4504058]

3646: Z99995
Homo sapiens partial gonadotropin releasing hormone receptor gene
gi|3334762|cmb|Z99995.1|HSZ99995[3334762]

3647: G16069
928H1R CEPH YAC and mega-YAC libraries (DBThompson) Homo sapiens STS genomic clone 928H1 right arm, sequence tagged site
gi|1825444|gb|G16069.1|G16069[1825444]

3648: G16077
817D6L CEPH YAC and mega-YAC libraries (DBThompson) Homo sapiens STS genomic clone 817D6 left arm, sequence tagged site
gi|1592357|gb|G16077.1|G16077[1592357]

3649: G16076
807B6L CEPH YAC and mega-YAC libraries (DBThompson) Homo sapiens STS genomic clone 807B6 left arm, sequence tagged site
gi|1592356|gb|G16076.1|G16076[1592356]

3650: G16075
940H12L CEPH YAC and mega-YAC libraries (DBThompson) Homo sapiens STS genomic clone 940H12 left arm, sequence tagged site
gi|1592355|gb|G16075.1|G16075[1592355]

3651: G16074
706A2L CEPH YAC and mega-YAC libraries (DBThompson) Homo sapiens STS genomic clone 706A2 left arm, sequence tagged site
gi|1592354|gb|G16074.1|G16074[1592354]

3652: G16073
967A10L CEPH YAC and mega-YAC libraries (DBThompson) Homo sapiens STS genomic clone 967A10 left arm, sequence tagged site
gi|1592353|gb|G16073.1|G16073[1592353]

3653: G16072
816C10L CEPH YAC and mega-YAC libraries (DBThompson) Homo sapiens STS genomic clone 816C10 left arm, sequence tagged site
gi|1592352|gb|G16072.1|G16072[1592352]

3654: G16071
765B8R CEPH YAC and mega-YAC libraries (DBThompson) Homo sapiens STS genomic clone 765B8 right arm, sequence tagged site
gi|1592351|gb|G16071.1|G16071[1592351]

3655: G16070
622F2R CEPH YAC and mega-YAC libraries (DBThompson) Homo sapiens STS genomic clone 622F2 right arm, sequence tagged site
gi|1592350|gb|G16070.1|G16070[1592350]

3656: G16068
868H11L CEPH YAC and mega-YAC libraries (DBThompson) Homo sapiens STS genomic clone 868H11 left arm, sequence tagged site
gi|1592349|gb|G16068.1|G16068[1592349]

3657: G16067
662F2L CEPH YAC and mega-YAC libraries (DBThompson) Homo sapiens STS genomic clone 662F2 left arm, sequence tagged site
gi|1592348|gb|G16067.1|G16067[1592348]

3658: G16066
918D7R CEPH YAC and mega-YAC libraries (DBThompson) Homo sapiens STS genomic clone 918D7 right arm, sequence tagged site
gi|1592347|gb|G16066.1|G16066[1592347]

3659: G16065
758C4R CEPH YAC and mega-YAC libraries (DBThompson) Homo sapiens STS genomic clone 758C4 right arm, sequence tagged site
gi|1592346|gb|G16065.1|G16065[1592346]

3660: G16064
677D7L CEPH YAC and mega-YAC libraries (DBThompson) Homo sapiens STS genomic clone 677D7 left arm, sequence tagged site
gi|1592345|gb|G16064.1|G16064[1592345]

3663: L11238
Homo sapiens platelet membrane glycoprotein V mRNA, complete cds
gi|388759|gb|L11238.1|HUMGLYCOPR[388759]

3665: AF406652
Homo sapiens MyD88 adapter-like protein mRNA, complete cds
gi|15528826|gb|AF406652.1|AF406652[15528826]

4053: NM_022059
Homo sapiens chemokine (C-X-C motif) ligand 16 (CXCL16), mRNA
gi|11545764|ref|NM_022059.1|[11545764]

4054: NM_030956
Homo sapiens toll-like receptor 10 (TLR10), mRNA
gi|13569929|ref|NM_030956.1|[13569929]

4055: NM_033358
Homo sapiens caspase 8, apoptosis-related cysteine protease (CASP8), transcript variant E, mRNA
gi|15718711|ref|NM_033358.1|[15718711]

4056: NM_033357
Homo sapiens caspase 8, apoptosis-related cysteine protease (CASP8), transcript variant D, mRNA
gi|15718709|ref|NM_033357.1|[15718709]

4057: NM_033356
Homo sapiens caspase 8, apoptosis-related cysteine protease (CASP8), transcript variant C, mRNA
gi|15718707|ref|NM_033356.1|[15718707]

4058: NM_033355
Homo sapiens caspase 8, apoptosis-related cysteine protease (CASP8), transcript variant B, mRNA
gi|15718705|ref|NM_033355.1|[15718705]

4059: NM_001228
Homo sapiens caspase 8, apoptosis-related cysteine protease (CASP8), transcript variant A, mRNA
gi|15718703|ref|NM_001228.2|[15718703]

4061: NM_000024
Homo sapiens adrenergic, beta-2-, receptor, surface (ADRB2), mRNA
gi|15718673|ref|NM_000024.3|[15718673]

4062: NM_000683
Homo sapiens adrenergic, alpha-2C-, receptor (ADRA2C), mRNA
gi|15718672|ref|NM_000683.2|[15718672]

4063: NM_000682
Homo sapiens adrenergic, alpha-2B-, receptor (ADRA2B), mRNA
gi|15718671|ref|NM_000682.2|[15718671]

4064: NM_000681
Homo sapiens adrenergic, alpha-2A-, receptor (ADRA2A), mRNA
gi|15718669|ref|NM_000681.2|[15718669]

4065: NM_006179
Homo sapiens neurotrophin 5 (neurotrophin 4/5) (NTF5), mRNA
gi|15718666|ref|NM_006179.2|[15718666]

4066: L26458
Homo sapiens T-cell receptor mRNA, partial sequence
gi|432477|gb|L26458.1|HUMEBSH[432477]

4067: L26457
Homo sapiens T-cell receptor mRNA, partial sequence
gi|432476|gb|L26457.1|HUMEBSG[432476]

4068: L26456
Homo sapiens T-cell receptor mRNA, partial sequence
gi|432475|gb|L26456.1|HUMEBSF[432475]

4069: L26455
Homo sapiens T-cell receptor mRNA, partial sequence
gi|432474|gb|L26455.1|HUMEBSE[432474]

4070: L26454
Homo sapiens T-cell receptor mRNA, partial sequence
gi|432473|gb|L26454.1|HUMEBSD[432473]

4071: L26453
Homo sapiens T-cell receptor mRNA, partial sequence
gi|432472|gb|L26453.1|HUMEBSC[432472]

4072: L26452
Homo sapiens T-cell receptor mRNA, partial sequence
gi|432471|gb|L26452.1|HUMEBSB[432471]

4073: L26451
Homo sapiens T-cell receptor mRNA, partial sequence
gi|432470|gb|L26451.1|HUMEBSA[432470]

4074: AH009839
Homo sapiens HVEC cell-cell adhesion molecule/herpesvirus receptor (HVEC) gene, partial cds, alternatively spliced
gi|15706245|gb|AH009839.2|[15706245]

4075: AJ301610
Homo sapiens mRNA for GluR6 kainate receptor (GRIK2 gene), isoform-b
gi|15485591|emb|AJ301610.1|HSA301610[15485591]

4076: AJ301609
Homo sapiens partial mRNA for GluR6 kainate receptor (GRIK2 gene), exons 10, 11 and 13
gi|15485589|emb|AJ301609.1|HSA301609[15485589]

4077: AJ301608
Homo sapiens partial mRNA for GluR6 kainate receptor (GRIK2 gene), exons 11, 13 and 14
gi|15485587|emb|AJ301608.1|HSA301608[15485587]

4078: AF196774
Homo sapiens HVEC cell-cell adhesion molecule/herpesvirus receptor (HVEC) gene, exon 8 and partial cds, alternatively spliced gi|10312084|gb|AF196774.1|AH009839S8[10312084]

4079: AF196773
Homo sapiens HVEC cell-cell adhesion molecule/herpesvirus receptor (HVEC) gene, exon 7
gi|10312083|gb|AF196773.1|AH009839S7[10312083]

4080: AF196772
Homo sapiens HVEC cell-cell adhesion molecule/herpesvirus receptor (HVEC) gene, exon 6
gi|10312082|gb|AF196772.1|AH009839S6[10312082]

4081: AF252867
Homo sapiens HVEC cell-cell adhesion molecule/herpesvirus receptor (HVEC) gene, exon 6A and partial cds, alternatively spliced
gi|10312081|gb|AF252867.1|AH009839S5[10312081]

4082: AF196771
Homo sapiens HVEC cell-cell adhesion molecule/herpesvirus receptor (HVEC) gene, exon 5
gi|10312080|gb|AF196771.1|AH009839S4[10312080]

4083: AF196770
Homo sapiens HVEC cell-cell adhesion molecule/herpesvirus receptor (HVEC) gene, exon 4
gi|10312079|gb|AF196770.1|AH009839S3[10312079]

4084: AF196769
Homo sapiens HVEC cell-cell adhesion molecule/herpesvirus receptor (HVEC) gene, exon 3
gi|10312078|gb|AF196769.1|AH009839S2[10312078]

4085: AF196768
Homo sapiens HVEC cell-cell adhesion molecule/herpesvirus receptor (HVEC) gene, exon 2
gi|10312077|gb|AF196768.1|AH009839S1[10312077]

4086: AF399937

Homo sapiens melanin-concentrating hormone receptor MCH-R2 mRNA, complete cds
gi|15667842|gb|AF399937.1|AF399937[15667842]

4087: NM_032405
Homo sapiens transmembrane protease, serine 3 (TMPRSS3), transcript variant D, mRNA
gi|14602456|ref|NM_032405.1|[14602456]

4088: NM_032404
Homo sapiens transmembrane protease, serine 3 (TMPRSS3), transcript variant C, mRNA
gi|14602454|ref|NM_032404.1|[14602454]

4089: NM_032401
Homo sapiens transmembrane protease, serine 3 (TMPRSS3), transcript variant B, mRNA
gi|14602452|ref|NM_032401.1|[14602452]

4090: NM_024022
Homo sapiens transmembrane protease, serine 3 (TMPRSS3), transcript variant A, mRNA
gi|13173470|ref|NM_024022.1|[13173470]

4091: AY046418
Homo sapiens brain immunoglobulin receptor precursor, mRNA, complete cds
gi|15636797|gb|AY046418.1|[15636797]

4092: AF069333
Homo sapiens insulin-like growth factor II receptor (IGF2R) gene, partial cds
gi|15628184|gb|AF069333.2|AF069333[15628184]

4093: AY029541
Homo sapiens putative G protein-coupled receptor mRNA, complete cds
gi|15626067|gb|AY029541.1|[15626067]

4094: AF117819
Homo sapiens bradykinin B1 receptor mRNA, partial cds and 3'-untranslated region
gi|4325046|gb|AF117819.1|AF117819[4325046]

4095: NM_004624
Homo sapiens vasoactive intestinal peptide receptor 1 (VIPR1), mRNA
gi|15619005|ref|NM_004624.2|[15619005]

4096: AY042216
Homo sapiens G protein-coupled receptor (MRGX4) gene, complete cds
gi|15546067|gb|AY042216.1|[15546067]

4097: AY042215
Homo sapiens G protein-coupled receptor (MRGX3) gene, complete cds
gi|15546065|gb|AY042215.1|[15546065]

4098: AY042214
Homo sapiens G protein-coupled receptor (MRGX2) gene, complete cds
gi|15546063|gb|AY042214.1|[15546063]

4099: AY042213
Homo sapiens G protein-coupled receptor (MRGX1) gene, complete cds
gi|15546061|gb|AY042213.1|[15546061]

4100: Y11395
Homo sapiens mRNA for lanthionine synthetase C-like protein 1 (LANCL1 gene)
gi|2894085|emb|Y11395.1|HSRNAP40[2894085]

4101: BC014108
Homo sapiens, Fc fragment of IgE, low affinity II, receptor for (CD23A), clone
MGC:20696 IMAGE:4309266, mRNA, complete cds
gi|15559484|gb|BC014108.1|BC014108[15559484]

4102: AF306329
Homo sapiens neuronal nicotinic acetylcholine receptor beta 4 subunit (CHRNB4)
gene, exon 6 and complete cds
gi|15558964|gb|AF306329.1|AF306325S5[15558964]

4103: AF306328
Homo sapiens neuronal nicotinic acetylcholine receptor beta 4 subunit (CHRNB4)

gene, exon 5
gi|15558963|gb|AF306328.1|AF306325S4[15558963]

4104: AF306327
Homo sapiens neuronal nicotinic acetylcholine receptor beta 4 subunit (CHRNB4) gene, exons 3, 4, and 4a, alternatively spliced
gi|15558962|gb|AF306327.1|AF306325S3[15558962]

4105: AF306326
Homo sapiens neuronal nicotinic acetylcholine receptor beta 4 subunit (CHRNB4) gene, exon 2
gi|15558961|gb|AF306326.1|AF306325S2[15558961]

4106: AF306325
Homo sapiens neuronal nicotinic acetylcholine receptor beta 4 subunit (CHRNB4) gene, exon 1
gi|15558960|gb|AF306325.1|AF306325S1[15558960]

4107: AH011061
Homo sapiens neuronal nicotinic acetylcholine receptor beta 4 subunit (CHRNB4) gene, complete cds
gi|15558959|gb|AH011061.1|SEG_AF306325S[15558959]

4108: AJ316282
Homo sapiens partial TCRB gene for T cell receptor beta chain, allele TCRBV1J2S3, isolate P15SF, clone 9
gi|15558855|emb|AJ316282.1|HSA316282[15558855]

4109: AJ316281
Homo sapiens partial TCRB gene for T cell receptor beta chain, allele TCRBV1J2S3, patient P22SF, clone 3
gi|15558853|emb|AJ316281.1|HSA316281[15558853]

4110: AJ316280
Homo sapiens partial TCRB gene for T cell receptor beta chain, allele TCRBV1J2S3, patient P14SF, clone 1
gi|15558851|emb|AJ316280.1|HSA316280[15558851]

4111: NM_001954
Homo sapiens discoidin domain receptor family, member 1 (DDR1), transcript variant 2, mRNA
gi|7669486|ref|NM_001954.2|[7669486]

4112: NM_013994
Homo sapiens discoidin domain receptor family, member 1 (DDR1), transcript variant 3, mRNA
gi|7669484|ref|NM_013994.1|[7669484]

4113: NM_013993
Homo sapiens discoidin domain receptor family, member 1 (DDR1), transcript variant 1, mRNA
gi|7669482|ref|NM_013993.1|[7669482]

4114: AF325356
Homo sapiens histamine receptor H4 (AXOR35) mRNA, complete cds
gi|15553202|gb|AF325356.1|AF325356[15553202]

4115: AF349574
Homo sapiens interleukin 12 receptor beta 2 (IL12RB2) gene, partial sequence
gi|15088551|gb|AF349574.1|AF349574[15088551]

4116: NM_014395
Homo sapiens dual adaptor of phosphotyrosine and 3-phosphoinositides (DAPP1), mRNA
gi|7657006|ref|NM_014395.1|[7657006]

4117: AY043466
Homo sapiens Fc receptor-like protein 3 (FCRH3) mRNA, complete cds
gi|15528834|gb|AY043466.1|[15528834]

4118: AY043465
Homo sapiens Fc receptor-like protein 2 (FCRH2) mRNA, complete cds
gi|15528832|gb|AY043465.1|[15528832]

4119: AY043464
Homo sapiens Fc receptor-like protein 1 (FCRH1) mRNA, complete cds 4120: AJ344350
Homo sapiens partial IGDH3-9 gene segment, isolate case6-cell520
gi|15528515|emb|AJ344350.1|HSA344350[15528515]

4121: AJ344349
Homo sapiens partial IGDH3-9 gene segment, isolate case5-cell49
gi|15528514|emb|AJ344349.1|HSA344349[15528514]

4122: AJ344348
Homo sapiens partial IGDH6-25 gene segment, isolate case4-cell89
gi|15528513|emb|AJ344348.1|HSA344348[15528513]

4125: NM_033135
Homo sapiens spinal cord-derived growth factor-B (SCDGF-B), transcript variant 2, mRNA
gi|15451920|ref|NM_033135.1|[15451920]

4126: NM_025208
Homo sapiens spinal cord-derived growth factor-B (SCDGF-B), transcript variant 1, mRNA
gi|15451919|ref|NM_025208.2|[15451919]

4127: NM_033346
Homo sapiens bone morphogenetic protein receptor, type II (serine/threonine kinase) (BMPR2), transcript variant 2, mRNA
gi|15451917|ref|NM_033346.1|[15451917]

4128: NM_001204
Homo sapiens bone morphogenetic protein receptor, type II (serine/threonine kinase) (BMPR2), transcript variant 1, mRNA
gi|15451915|ref|NM_001204.3|[15451915]

4129: NM_003933
Homo sapiens BAI1-associated protein 3 (BAIAP3), mRNA
gi|15451913|ref|NM_003933.3|[15451913]

4130: NM_002006
Homo sapiens fibroblast growth factor 2 (basic) (FGF2), mRNA
gi|15451897|ref|NM_002006.2|[15451897]

4131: NM_000647
Homo sapiens chemokine (C-C motif) receptor 2 (CCR2), transcript variant A, mRNA
gi|15451896|ref|NM_000647.3|[15451896]

4132: NM_004631
Homo sapiens low density lipoprotein receptor-related protein 8, apolipoprotein e receptor (LRP8), transcript variant 1, mRNA
gi|15451869|ref|NM_004631.2|[15451869]

4133: NM_033300
Homo sapiens low density lipoprotein receptor-related protein 8, apolipoprotein e receptor (LRP8), transcript variant 2, mRNA
gi|15451867|ref|NM_033300.1|[15451867]

4134: NM_017522
Homo sapiens low density lipoprotein receptor-related protein 8, apolipoprotein e receptor (LRP8), transcript variant 3, mRNA
gi|15451865|ref|NM_017522.2|[15451865]

4135: NM_033337
Homo sapiens caveolin 3 (CAV3), transcript variant 1, mRNA
gi|15451859|ref|NM_033337.1|[15451859]

4136: NM_001234
Homo sapiens caveolin 3 (CAV3), transcript variant 2, mRNA
gi|15451858|ref|NM_001234.3|[15451858]

4137: NM_002609
Homo sapiens platelet-derived growth factor receptor, beta polypeptide (PDGFRB), mRNA
gi|15451788|ref|NM_002609.2|[15451788]

4138: NM_006206

Homo sapiens platelet-derived growth factor receptor, alpha polypeptide (PDGFRA), mRNA
gi|15451787|ref|NM_006206.2|[15451787]

4139: NM_000679
Homo sapiens adrenergic, alpha-1B-, receptor (ADRA1B), mRNA
gi|15451783|ref|NM_000679.2|[15451783]

4140: AY026771
Homo sapiens lectin-like receptor 1C (DECTIN1) mRNA, complete cds, alternatively spliced
gi|14278822|gb|AY026771.1|[14278822]

4142: NM_000648
Homo sapiens chemokine (C-C motif) receptor 2 (CCR2), transcript variant B, mRNA
gi|4757937|ref|NM_000648.1|[4757937]

4143: AB041403
Homo sapiens HTR1A gene for serotonin receptor 1A, complete cds
gi|7592996|dbj|AB041403.1|AB041403[7592996]

4144: NM_015722
Homo sapiens calcyon; D1 dopamine receptor-interacting protein (CALCYON), mRNA
gi|9257200|ref|NM_015722.2|[9257200]

4145: AY044429
Homo sapiens class II cytokine receptor (IL22RA2) mRNA, complete cds
gi|15419022|gb|AY044429.1|[15419022]

4148: AJ306388
Homo sapiens mRNA for NTB-A receptor (KALI b gene)
gi|15384842|emb|AJ306388.1|HSA306388[15384842]

4149: AJ277141
Homo sapiens mRNA for activating NK receptor (KALI gene)
gi|15384840|emb|AJ277141.1|HSA277141[15384840]

4150: NM_033199
Homo sapiens stresscopin-related peptide (SRP), mRNA
gi|15082239|ref|NM_033199.1|[15082239]

4151: AB052684
Homo sapiens mRNA for Gi-coupled ADP receptor HORK3, complete cds
gi|14422409|dbj|AB052684.1|AB052684[14422409]

4152: AF227732
Homo sapiens nicotinic acetylcholine receptor alpha 9 subunit mRNA, partial cds
gi|7407124|gb|AF227732.1|AF227732[7407124]

4153: NM_005849
Homo sapiens immunoglobulin superfamily, member 6 (IGSF6), mRNA
gi|5031672|ref|NM_005849.1|[5031672]

4154: AF317654
Homo sapiens G protein-coupled receptor (GPR63) gene, complete cds
gi|15321723|gb|AF317654.2|AF317654[15321723]

4155: AF399637
Homo sapiens clone OR5B16 olfactory receptor gene, partial cds
gi|15293858|gb|AF399637.1|AF399637[15293858]

4156: AF399636
Homo sapiens clone OR5B2 olfactory receptor gene, partial cds
gi|15293856|gb|AF399636.1|AF399636[15293856]

4157: AF399635
Homo sapiens clone OR5AU1 olfactory receptor gene, partial cds
gi|15293854|gb|AF399635.1|AF399635[15293854]

4158: AF399634
Homo sapiens clone OR10A3 olfactory receptor gene, partial cds
gi|15293852|gb|AF399634.1|AF399634[15293852]

4159: AF399633

Homo sapiens clone OR13H1 olfactory receptor gene, partial cds
gi|15293850|gb|AF399633.1|AF399633[15293850]

4160: AF399632
Homo sapiens clone OR2B3 olfactory receptor gene, partial cds
gi|15293848|gb|AF399632.1|AF399632[15293848]

4161: AF399631
Homo sapiens clone OR2H2 olfactory receptor gene, partial cds
gi|15293846|gb|AF399631.1|AF399631[15293846]

4162: AF399630
Homo sapiens clone OR2J3 olfactory receptor gene, partial cds
gi|15293844|gb|AF399630.1|AF399630[15293844]

4163: AF399629
Homo sapiens clone OR2Y1 olfactory receptor gene, partial cds
gi|15293842|gb|AF399629.1|AF399629[15293842]

4164: AF399628
Homo sapiens clone OR2W1 olfactory receptor gene, partial cds
gi|15293840|gb|AF399628.1|AF399628[15293840]

4165: AF399627
Homo sapiens clone OR10C2 olfactory receptor gene, partial cds
gi|15293838|gb|AF399627.1|AF399627[15293838]

4166: AF399626
Homo sapiens clone OR10A7 olfactory receptor gene, partial cds
gi|15293836|gb|AF399626.1|AF399626[15293836]

4167: AF399625
Homo sapiens clone OR10A4 olfactory receptor gene, partial cds
gi|15293834|gb|AF399625.1|AF399625[15293834]

4168: AF399624
Homo sapiens clone OR10A1 olfactory receptor gene, partial cds gi|15293832|gb|AF399624.1|AF399624[15293832]

4169: AF399623
Homo sapiens clone OR10A5 olfactory receptor gene, partial cds
gi|15293830|gb|AF399623.1|AF399623[15293830]

4170: AF399622
Homo sapiens clone OR1K1 olfactory receptor gene, partial cds
gi|15293828|gb|AF399622.1|AF399622[15293828]

4171: AF399621
Homo sapiens clone OR3A4 olfactory receptor gene, partial cds
gi|15293826|gb|AF399621.1|AF399621[15293826]

4172: AF399620
Homo sapiens clone OR3A3 olfactory receptor gene, partial cds
gi|15293824|gb|AF399620.1|AF399620[15293824]

4173: AF399619
Homo sapiens clone OR2Z2 olfactory receptor gene, partial cds
gi|15293822|gb|AF399619.1|AF399619[15293822]

4174: AF399618
Homo sapiens clone OR2AG1 olfactory receptor gene, partial cds
gi|15293820|gb|AF399618.1|AF399618[15293820]

4175: AF399617
Homo sapiens clone OR2M4 olfactory receptor gene, partial cds
gi|15293818|gb|AF399617.1|AF399617[15293818]

4176: AF399616
Homo sapiens clone OR2M2 olfactory receptor gene, partial cds
gi|15293816|gb|AF399616.1|AF399616[15293816]

4177: AF399615
Homo sapiens clone OR2M1 olfactory receptor gene, partial cds
gi|15293814|gb|AF399615.1|AF399615[15293814]

4178: AF399614
Homo sapiens clone OR2V2 olfactory receptor gene, partial cds
gi|15293812|gb|AF399614.1|AF399614[15293812]

4179: AF399613
Homo sapiens clone OR2T1 olfactory receptor gene, partial cds
gi|15293810|gb|AF399613.1|AF399613[15293810]

4180: AF399612
Homo sapiens clone OR2T3 olfactory receptor gene, partial cds
gi|15293808|gb|AF399612.1|AF399612[15293808]

4181: AF399611
Homo sapiens clone OR11H1 olfactory receptor gene, partial cds
gi|15293806|gb|AF399611.1|AF399611[15293806]

4182: AF399610
Homo sapiens clone OR11G2 olfactory receptor gene, partial cds
gi|15293804|gb|AF399610.1|AF399610[15293804]

4183: AF399609
Homo sapiens clone OR6Q1 olfactory receptor gene, partial cds
gi|15293802|gb|AF399609.1|AF399609[15293802]

4184: AF399608
Homo sapiens clone OR6N1 olfactory receptor gene, partial cds
gi|15293800|gb|AF399608.1|AF399608[15293800]

4185: AF399607
Homo sapiens clone OR6W1 olfactory receptor gene, partial cds
gi|15293798|gb|AF399607.1|AF399607[15293798]

4186: AF399606
Homo sapiens clone OR6M1 olfactory receptor gene, partial cds
gi|15293796|gb|AF399606.1|AF399606[15293796]

4187: AF399605
Homo sapiens clone OR6B1 olfactory receptor gene, partial cds
gi|15293794|gb|AF399605.1|AF399605[15293794]

4188: AF399604
Homo sapiens clone OR6F1 olfactory receptor gene, partial cds
gi|15293792|gb|AF399604.1|AF399604[15293792]

4189: AF399603
Homo sapiens clone OR13J1 olfactory receptor gene, partial cds
gi|15293790|gb|AF399603.1|AF399603[15293790]

4190: AF399602
Homo sapiens clone OR13C4 olfactory receptor gene, partial cds
gi|15293788|gb|AF399602.1|AF399602[15293788]

4191: AF399601
Homo sapiens clone OR2S2 olfactory receptor gene, partial cds
gi|15293786|gb|AF399601.1|AF399601[15293786]

4192: AF399600
Homo sapiens clone OR13C7 olfactory receptor gene, partial cds
gi|15293784|gb|AF399600.1|AF399600[15293784]

4193: AF399599
Homo sapiens clone OR13C8 olfactory receptor gene, partial cds
gi|15293782|gb|AF399599.1|AF399599[15293782]

4194: AF399598
Homo sapiens clone OR2A7 olfactory receptor gene, partial cds
gi|15293780|gb|AF399598.1|AF399598[15293780]

4195: AF399597
Homo sapiens clone OR2A1 olfactory receptor gene, partial cds
gi|15293778|gb|AF399597.1|AF399597[15293778]

4196: AF399596
Homo sapiens clone OR2A6 olfactory receptor gene, partial cds
gi|15293776|gb|AF399596.1|AF399596[15293776]

4197: AF399595
Homo sapiens clone OR2A5 olfactory receptor gene, partial cds
gi|15293774|gb|AF399595.1|AF399595[15293774]

4198: AF399594
Homo sapiens clone OR2F1 olfactory receptor gene, partial cds
gi|15293772|gb|AF399594.1|AF399594[15293772]

4199: AF399593
Homo sapiens clone OR10V1 olfactory receptor gene, partial cds
gi|15293770|gb|AF399593.1|AF399593[15293770]

4200: AF399592
Homo sapiens clone OR2D3 olfactory receptor gene, partial cds
gi|15293768|gb|AF399592.1|AF399592[15293768]

4201: AF399591
Homo sapiens clone OR2D2 olfactory receptor gene, partial cds
gi|15293766|gb|AF399591.1|AF399591[15293766]

4202: AF399590
Homo sapiens clone OR5AY1 olfactory receptor gene, partial cds
gi|15293764|gb|AF399590.1|AF399590[15293764]

4203: AF399589
Homo sapiens clone OR5AX1 olfactory receptor gene, partial cds
gi|15293762|gb|AF399589.1|AF399589[15293762]

4204: AF399588
Homo sapiens clone OR10J6 olfactory receptor gene, partial cds
gi|15293760|gb|AF399588.1|AF399588[15293760]

4205: AF399587

Homo sapiens clone OR10J1 olfactory receptor gene, partial cds
gi|15293758|gb|AF399587.1|AF399587[15293758]

4206: AF399586
Homo sapiens clone OR10H4 olfactory receptor gene, partial cds
gi|15293756|gb|AF399586.1|AF399586[15293756]

4207: AF399585
Homo sapiens clone OR10H2 olfactory receptor gene, partial cds
gi|15293754|gb|AF399585.1|AF399585[15293754]

4208: AF399584
Homo sapiens clone OR10H1 olfactory receptor gene, partial cds
gi|15293752|gb|AF399584.1|AF399584[15293752]

4209: AF399583
Homo sapiens clone OR10H5 olfactory receptor gene, partial cds
gi|15293750|gb|AF399583.1|AF399583[15293750]

4210: AF399582
Homo sapiens clone OR10R2 olfactory receptor gene, partial cds
gi|15293748|gb|AF399582.1|AF399582[15293748]

4211: AF399581
Homo sapiens clone OR4E2 olfactory receptor gene, partial cds
gi|15293746|gb|AF399581.1|AF399581[15293746]

4212: AF399580
Homo sapiens clone OR4X2 olfactory receptor gene, partial cds
gi|15293744|gb|AF399580.1|AF399580[15293744]

4213: AF399579
Homo sapiens clone OR4B1 olfactory receptor gene, partial cds
gi|15293742|gb|AF399579.1|AF399579[15293742]

4214: AF399578
Homo sapiens clone OR4A15 olfactory receptor gene, partial cds gi|15293740|gb|AF399578.1|AF399578[15293740]

4215: AF399577
Homo sapiens clone OR4A4 olfactory receptor gene, partial cds
gi|15293738|gb|AF399577.1|AF399577[15293738]

4216: AF399576
Homo sapiens clone OR4C12 olfactory receptor gene, partial cds
gi|15293736|gb|AF399576.1|AF399576[15293736]

4217: AF399575
Homo sapiens clone OR4C13 olfactory receptor gene, partial cds
gi|15293734|gb|AF399575.1|AF399575[15293734]

4218: AF399574
Homo sapiens clone OR4F4 olfactory receptor gene, partial cds
gi|15293732|gb|AF399574.1|AF399574[15293732]

4219: AF399573
Homo sapiens clone OR4F15 olfactory receptor gene, partial cds
gi|15293730|gb|AF399573.1|AF399573[15293730]

4220: AF399572
Homo sapiens clone OR4K14 olfactory receptor gene, partial cds
gi|15293728|gb|AF399572.1|AF399572[15293728]

4221: AF399571
Homo sapiens clone OR4K3 olfactory receptor gene, partial cds
gi|15293726|gb|AF399571.1|AF399571[15293726]

4222: AF399570
Homo sapiens clone OR4K1 olfactory receptor gene, partial cds
gi|15293724|gb|AF399570.1|AF399570[15293724]

4223: AF399569
Homo sapiens clone OR4D6 olfactory receptor gene, partial cds
gi|15293722|gb|AF399569.1|AF399569[15293722]

4224: AF399568
Homo sapiens clone OR4D2 olfactory receptor gene, partial cds
gi|15293720|gb|AF399568.1|AF399568[15293720]

4225: AF399567
Homo sapiens clone OR4D1 olfactory receptor gene, partial cds
gi|15293718|gb|AF399567.1|AF399567[15293718]

4226: AF399566
Homo sapiens clone OR10G3 olfactory receptor gene, partial cds
gi|15293716|gb|AF399566.1|AF399566[15293716]

4227: AF399565
Homo sapiens clone OR10S1 olfactory receptor gene, partial cds
gi|15293714|gb|AF399565.1|AF399565[15293714]

4228: AF399564
Homo sapiens clone OR1L8 olfactory receptor gene, partial cds
gi|15293712|gb|AF399564.1|AF399564[15293712]

4229: AF399563
Homo sapiens clone OR1L6 olfactory receptor gene, partial cds
gi|15293710|gb|AF399563.1|AF399563[15293710]

4230: AF399562
Homo sapiens clone OR1L4 olfactory receptor gene, partial cds
gi|15293708|gb|AF399562.1|AF399562[15293708]

4231: AF399561
Homo sapiens clone OR1Q1 olfactory receptor gene, partial cds
gi|15293706|gb|AF399561.1|AF399561[15293706]

4232: AF399560
Homo sapiens clone OR1C1 olfactory receptor gene, partial cds
gi|15293704|gb|AF399560.1|AF399560[15293704]

4233: AF399559
Homo sapiens clone OR1F1 olfactory receptor gene, partial cds
gi|15293702|gb|AF399559.1|AF399559[15293702]

4234: AF399558
Homo sapiens clone OR1F2 olfactory receptor gene, partial cds
gi|15293700|gb|AF399558.1|AF399558[15293700]

4235: AF399557
Homo sapiens clone OR1S2 olfactory receptor gene, partial cds
gi|15293698|gb|AF399557.1|AF399557[15293698]

4236: AF399556
Homo sapiens clone OR1A2 olfactory receptor gene, partial cds
gi|15293696|gb|AF399556.1|AF399556[15293696]

4237: AF399555
Homo sapiens clone OR1A1 olfactory receptor gene, partial cds
gi|15293694|gb|AF399555.1|AF399555[15293694]

4238: AF399554
Homo sapiens clone OR1J1 olfactory receptor gene, partial cds
gi|15293692|gb|AF399554.1|AF399554[15293692]

4239: AF399553
Homo sapiens clone OR1J4 olfactory receptor gene, partial cds
gi|15293690|gb|AF399553.1|AF399553[15293690]

4240: AF399552
Homo sapiens clone OR1J2 olfactory receptor gene, partial cds
gi|15293688|gb|AF399552.1|AF399552[15293688]

4241: AF399551
Homo sapiens clone OR1E2 olfactory receptor gene, partial cds
gi|15293686|gb|AF399551.1|AF399551[15293686]

4242: AF399550

Homo sapiens clone OR1E1 olfactory receptor gene, partial cds
gi|15293684|gb|AF399550.1|AF399550[15293684]

4243: AF399549

Homo sapiens clone OR1M1 olfactory receptor gene, partial cds
gi|15293682|gb|AF399549.1|AF399549[15293682]

4244: AF399548

Homo sapiens clone OR1I1 olfactory receptor gene, partial cds
gi|15293680|gb|AF399548.1|AF399548[15293680]

4245: AF399547

Homo sapiens clone OR1N3 olfactory receptor gene, partial cds
gi|15293678|gb|AF399547.1|AF399547[15293678]

4246: AF399546

Homo sapiens clone OR7C1 olfactory receptor gene, partial cds
gi|15293676|gb|AF399546.1|AF399546[15293676]

4247: AF399545

Homo sapiens clone OR7C2 olfactory receptor gene, partial cds
gi|15293674|gb|AF399545.1|AF399545[15293674]

4248: AF399544

Homo sapiens clone OR7A2 olfactory receptor gene, partial cds
gi|15293672|gb|AF399544.1|AF399544[15293672]

4249: AF399543

Homo sapiens clone OR7A5 olfactory receptor gene, partial cds
gi|15293670|gb|AF399543.1|AF399543[15293670]

4250: AF399542

Homo sapiens clone OR7A10 olfactory receptor gene, partial cds
gi|15293668|gb|AF399542.1|AF399542[15293668]

4251: AF399541

Homo sapiens clone OR7A17 olfactory receptor gene, partial cds
gi|15293666|gb|AF399541.1|AF399541[15293666]

4252: AF399540
Homo sapiens clone OR7G3 olfactory receptor gene, partial cds
gi|15293664|gb|AF399540.1|AF399540[15293664]

4253: AF399539
Homo sapiens clone OR7G2 olfactory receptor gene, partial cds
gi|15293662|gb|AF399539.1|AF399539[15293662]

4254: AF399538
Homo sapiens clone OR7G1 olfactory receptor gene, partial cds
gi|15293660|gb|AF399538.1|AF399538[15293660]

4255: AF399537
Homo sapiens clone OR7D2 olfactory receptor gene, partial cds
gi|15293658|gb|AF399537.1|AF399537[15293658]

4256: AF399536
Homo sapiens clone OR1N2 olfactory receptor gene, partial cds
gi|15293656|gb|AF399536.1|AF399536[15293656]

4257: AF399535
Homo sapiens clone OR1D2 olfactory receptor gene, partial cds
gi|15293654|gb|AF399535.1|AF399535[15293654]

4258: AF399534
Homo sapiens clone OR1D4 olfactory receptor gene, partial cds
gi|15293652|gb|AF399534.1|AF399534[15293652]

4259: AF399533
Homo sapiens clone OR1D5 olfactory receptor gene, partial cds
gi|15293650|gb|AF399533.1|AF399533[15293650]

4260: AF399532
Homo sapiens clone OR9Q1 olfactory receptor gene, partial cds gi|15293648|gb|AF399532.1|AF399532[15293648]

4261: AF399531
Homo sapiens clone OR9I1 olfactory receptor gene, partial cds
gi|15293646|gb|AF399531.1|AF399531[15293646]

4262: AF399530
Homo sapiens clone OR9G4 olfactory receptor gene, partial cds
gi|15293644|gb|AF399530.1|AF399530[15293644]

4263: AF399529
Homo sapiens clone OR5A2 olfactory receptor gene, partial cds
gi|15293642|gb|AF399529.1|AF399529[15293642]

4264: AF399528
Homo sapiens clone OR5A1 olfactory receptor gene, partial cds
gi|15293640|gb|AF399528.1|AF399528[15293640]

4265: AF399527
Homo sapiens clone OR5F1 olfactory receptor gene, partial cds
gi|15293638|gb|AF399527.1|AF399527[15293638]

4266: AF399526
Homo sapiens clone OR5L2 olfactory receptor gene, partial cds
gi|15293636|gb|AF399526.1|AF399526[15293636]

4267: AF399525
Homo sapiens clone OR5D18 olfactory receptor gene, partial cds
gi|15293634|gb|AF399525.1|AF399525[15293634]

4268: AF399524
Homo sapiens clone OR5D16 olfactory receptor gene, partial cds
gi|15293632|gb|AF399524.1|AF399524[15293632]

4269: AF399523
Homo sapiens clone OR5D14 olfactory receptor gene, partial cds
gi|15293630|gb|AF399523.1|AF399523[15293630]

4270: AF399522
Homo sapiens clone OR5M1 olfactory receptor gene, partial cds
gi|15293628|gb|AF399522.1|AF399522[15293628]

4271: AF399521
Homo sapiens clone OR5M11 olfactory receptor gene, partial cds
gi|15293626|gb|AF399521.1|AF399521[15293626]

4272: AF399520
Homo sapiens clone OR5M8 olfactory receptor gene, partial cds
gi|15293624|gb|AF399520.1|AF399520[15293624]

4273: AF399519
Homo sapiens clone OR5M9 olfactory receptor gene, partial cds
gi|15293622|gb|AF399519.1|AF399519[15293622]

4274: AF399518
Homo sapiens clone OR5M3 olfactory receptor gene, partial cds
gi|15293620|gb|AF399518.1|AF399518[15293620]

4275: AF399517
Homo sapiens clone OR8K1 olfactory receptor gene, partial cds
gi|15293618|gb|AF399517.1|AF399517[15293618]

4276: AF399516
Homo sapiens clone OR8J3 olfactory receptor gene, partial cds
gi|15293616|gb|AF399516.1|AF399516[15293616]

4277: AF399515
Homo sapiens clone OR8J1 olfactory receptor gene, partial cds
gi|15293614|gb|AF399515.1|AF399515[15293614]

4278: AF399514
Homo sapiens clone OR5C1 olfactory receptor gene, partial cds
gi|15293612|gb|AF399514.1|AF399514[15293612]

4279: AF399513
Homo sapiens clone OR8I2 olfactory receptor gene, partial cds
gi|15293610|gb|AF399513.1|AF399513[15293610]

4280: AF399512
Homo sapiens clone OR8A1 olfactory receptor gene, partial cds
gi|15293608|gb|AF399512.1|AF399512[15293608]

4281: AF399511
Homo sapiens clone OR8B12 olfactory receptor gene, partial cds
gi|15293606|gb|AF399511.1|AF399511[15293606]

4282: AF399510
Homo sapiens clone OR8B8 olfactory receptor gene, partial cds
gi|15293604|gb|AF399510.1|AF399510[15293604]

4283: AF399509
Homo sapiens clone OR8B4 olfactory receptor gene, partial cds
gi|15293602|gb|AF399509.1|AF399509[15293602]

4284: AF399508
Homo sapiens clone OR8B2 olfactory receptor gene, partial cds
gi|15293600|gb|AF399508.1|AF399508[15293600]

4285: AF399507
Homo sapiens clone OR8G1 olfactory receptor gene, partial cds
gi|15293598|gb|AF399507.1|AF399507[15293598]

4286: AF399506
Homo sapiens clone OR6C1 olfactory receptor gene, partial cds
gi|15293596|gb|AF399506.1|AF399506[15293596]

4287: AF399505
Homo sapiens clone OR52B2 olfactory receptor gene, partial cds
gi|15293594|gb|AF399505.1|AF399505[15293594]

4288: AF399504
Homo sapiens clone OR52E6 olfactory receptor gene, partial cds
gi|15293592|gb|AF399504.1|AF399504[15293592]

4289: AF399503
Homo sapiens clone OR51B2 olfactory receptor gene, partial cds
gi|15293590|gb|AF399503.1|AF399503[15293590]

4290: AF244813
Homo sapiens platelet-derived growth factor C mRNA, complete cds
gi|8886883|gb|AF244813.1|AF244813[8886883]

4291: AF169650
Homo sapiens high mobility group 1 protein (HMG1) gene, exon 5
gi|14522864|gb|AF169650.1|AF169650[14522864]

4451: AF330055
Homo sapiens neuropeptide NPVF receptor mRNA, complete cds
gi|15281399|gb|AF330055.1|AF330055[15281399]

4452: AF330053
Homo sapiens neuropeptide NPFF receptor mRNA, complete cds
gi|15281395|gb|AF330053.1|AF330053[15281395]

4453: AF402318
Homo sapiens differentiation-related DIF14 long form (DIF14) mRNA, complete cds, alternatively spliced
gi|15278166|gb|AF402318.1|AF402318[15278166]

4454: AF397453
Homo sapiens Fc receptor-like protein 5 (FCRH5) mRNA, complete cds
gi|15277745|gb|AF397453.1|AF397453[15277745]

4455: AF397452
Homo sapiens Fc receptor-like protein 4 (FCRH4) mRNA, complete cds
gi|15277740|gb|AF397452.1|AF397452[15277740]

4456: AF400441
Homo sapiens neurotrophic tyrosine kinase receptor type 2 (NTRK2) mRNA, complete cds
gi|15217076|gb|AF400441.1|AF400441[15217076]

4462: NM_020535
Homo sapiens killer cell immunoglobulin-like receptor, two domains, long cytoplasmic tail, 5 (KIR2DL5), mRNA
gi|11968153|ref|NM_020535.1|[11968153]

4463: AP000511
Homo sapiens genomic DNA, chromosome 6p21.3, HLA Class I region, section 10/20
gi|5926698|dbj|AP000511.1|AP000511[5926698]

4465: L20295
Homo sapiens vasoactive intestinal peptide receptor mRNA, partial cds
gi|403461|gb|L20295.1|HUMVAIPR[403461]

4466: AY040568
Homo sapiens interleukin 22-binding protein CRF2-10S (IL22BP) mRNA, complete cds, alternatively spliced
gi|15212829|gb|AY040568.1|[15212829]

4467: AY040567
Homo sapiens interleukin 22-binding protein CRF2-10L (IL22BP) mRNA, complete cds, alternatively spliced
gi|15212827|gb|AY040567.1|[15212827]

4468: AY040566
Homo sapiens interleukin 22-binding protein CRF2-10 (IL22BP) mRNA, complete cds
gi|15212825|gb|AY040566.1|[15212825]

4471: AX193708
Sequence 30 from Patent WO0136467
gi|15211557|emb|AX193708.1|AX193708[15211557]

4472: AX193705
Sequence 27 from Patent WO0136467 gi|15211554|emb|AX193705.1|AX193705[15211554]

4473: AX193702
Sequence 24 from Patent WO0136467
gi|15211551|emb|AX193702.1|AX193702[15211551]

4474: AX193682
Sequence 4 from Patent WO0136467
gi|15211548|emb|AX193682.1|AX193682[15211548]

4475: AX193679
Sequence 1 from Patent WO0136467
gi|15211545|emb|AX193679.1|AX193679[15211545]

4476: NM_005675
Homo sapiens DiGeorge syndrome critical region gene 6 (DGCR6), mRNA
gi|15208653|ref|NM_005675.2|[15208653]

4477: NM_016083
Homo sapiens cannabinoid receptor 1 (brain) (CNR1), transcript variant 2, mRNA
gi|15208646|ref|NM_016083.2|[15208646]

4478: NM_016205
Homo sapiens platelet derived growth factor C (PDGFC), mRNA
gi|9994186|ref|NM_016205.1|[9994186]

4479: AF159056
Homo sapiens T-cell gamma receptor locus, complete sequence
gi|5566238|gb|AF159056.1|AF159056[5566238]

4480: NM_006207
Homo sapiens platelet-derived growth factor receptor-like (PDGFRL), mRNA
gi|5453871|ref|NM_006207.1|[5453871]

4481: NM_004986
Homo sapiens kinectin 1 (kinesin receptor) (KTN1), mRNA
gi|4826813|ref|NM_004986.1|[4826813]

4482: NM_001840
Homo sapiens cannabinoid receptor 1 (brain) (CNR1), transcript variant 1, mRNA
gi|4502926|ref|NM_001840.1|[4502926]

4483: NM_033223
Homo sapiens gamma-aminobutyric acid (GABA) A receptor, gamma 3 (GABRG3), mRNA
gi|15193297|ref|NM_033223.1|[15193297]

4484: AY008283
Homo sapiens porimin mRNA, complete cds
gi|15192138|gb|AY008283.1|[15192138]

4485: NM_015906
Homo sapiens tripartite motif-containing 33 (TRIM33), transcript variant alpha, mRNA
gi|14971412|ref|NM_015906.2|[14971412]

4486: NM_033020
Homo sapiens tripartite motif-containing 33 (TRIM33), transcript variant beta, mRNA
gi|14971410|ref|NM_033020.1|[14971410]

4487: AH006431
Homo sapiens glycine receptor alpha 2 subunit, complete cds
gi|3598700|gb|AH006431.1|SEG_HSGLRA2G[3598700]

4488: AF053495
Homo sapiens glycine receptor alpha 2 subunit (GLRA2) gene, exon 9 and complete cds
gi|3598699|gb|AF053495.1|HSGLRA2G9[3598699]

4489: AF053494
Homo sapiens glycine receptor alpha 2 subunit (GLRA2) gene, exon 8
gi|3598698|gb|AF053494.1|HSGLRA2G8[3598698]

4490: AF053493

Homo sapiens glycine receptor alpha 2 subunit (GLRA2) gene, exon 7
gi|3598697|gb|AF053493.1|HSGLRA2G7[3598697]

4491: AF053492
Homo sapiens glycine receptor alpha 2 subunit (GLRA2) gene, exon 6
gi|3598696|gb|AF053492.1|HSGLRA2G6[3598696]

4492: AF053491
Homo sapiens glycine receptor alpha 2 subunit (GLRA2) gene, exon 5
gi|3598695|gb|AF053491.1|HSGLRA2G5[3598695]

4493: AF053490
Homo sapiens glycine receptor alpha 2 subunit (GLRA2) gene, exon 4
gi|3598694|gb|AF053490.1|HSGLRA2G4[3598694]

4494: AF053489
Homo sapiens glycine receptor alpha 2 subunit (GLRA2) gene, exons 3a and 3b
gi|3598693|gb|AF053489.1|HSGLRA2G3[3598693]

4495: AF053488
Homo sapiens glycine receptor alpha 2 subunit (GLRA2) gene, exon 2
gi|3598692|gb|AF053488.1|HSGLRA2G2[3598692]

4496: AF053487
Homo sapiens glycine receptor alpha 2 subunit (GLRA2) gene, exon 1
gi|3598691|gb|AF053487.1|HSGLRA2G1[3598691]

4499: AF344654
Homo sapiens growth hormone receptor variant gene, partial cds
gi|15186845|gb|AF344654.1|[15186845]

4501: AF179680
Homo sapiens apelin gene, complete cds
gi|6708145|gb|AF179680.1|AF179680[6708145]

4502: AJ296652
Homo sapiens HRH3 gene for histamine h3 receptor, exons 1-3
gi|15149878|emb|AJ296652.1|HSA296652[15149878]

4503: NM_006707
Homo sapiens butyrophilin-like 3 (BTNL3), mRNA
gi|5729747|ref|NM_006707.1|[5729747]

4504: NM_002009
Homo sapiens fibroblast growth factor 7 (keratinocyte growth factor) (FGF7), mRNA
gi|15147344|ref|NM_002009.2|[15147344]

4505: AF190501
Homo sapiens leucine-rich repeat-containing G protein-coupled receptor 6 (LGR6) mRNA, partial cds
gi|10441731|gb|AF190501.1|AF190501[10441731]

4506: AF190500
Homo sapiens leucine-rich repeat-containing G protein-coupled receptor 7 (LGR7) mRNA, complete cds
gi|10441729|gb|AF190500.1|AF190500[10441729]

4507: NM_016543
Homo sapiens sialic acid binding Ig-like lectin 7 (SIGLEC7), mRNA
gi|7706570|ref|NM_016543.1|[7706570]

4508: NM_014385
Homo sapiens sialic acid binding Ig-like lectin 7 (SIGLEC7), mRNA
gi|7657569|ref|NM_014385.1|[7657569]

4509: AC005153
Homo sapiens PAC clone RP4-537P9 from 7p11.2-p12, complete sequence
gi|3242766|gb|AC005153.1|AC005153[3242766]

4528: AJ309020
Homo sapiens mRNA for G protein-coupled receptor (AXOR12 gene)
gi|14330412|emb|AJ309020.1|HSA309020[14330412]

4529: AJ243297

Homo sapiens partial RET gene, exons 2 to 20
gi|5419752|emb|AJ243297.1|HSA243297[5419752]

4530: X57019
H.sapiens mRNA for tyrosine kinase receptor
gi|37592|emb|X57019.1|HSUF025[37592]

4585: AF166361
Homo sapiens GABA receptor subunit alpha 3 (GABRA3) gene, exon 9 and complete cds
gi|10086249|gb|AF166361.1|AF165901S9[10086249]

4586: AF166360
Homo sapiens GABA receptor subunit alpha 3 (GABRA3) gene, exon 8
gi|10086248|gb|AF166360.1|AF165901S8[10086248]

4587: AF166359
Homo sapiens GABA receptor subunit alpha 3 (GABRA3) gene, exon 7
gi|10086247|gb|AF166359.1|AF165901S7[10086247]

4588: AF165906
Homo sapiens GABA receptor subunit alpha 3 (GABRA3) gene, exon 6
gi|10086246|gb|AF165906.1|AF165901S6[10086246]

4589: AF165905
Homo sapiens GABA receptor subunit alpha 3 (GABRA3) gene, exon 5
gi|10086245|gb|AF165905.1|AF165901S5[10086245]

4590: AF165904
Homo sapiens GABA receptor subunit alpha 3 (GABRA3) gene, exon 4
gi|10086244|gb|AF165904.1|AF165901S4[10086244]

4591: AF165903
Homo sapiens GABA receptor subunit alpha 3 (GABRA3) gene, exon 3
gi|10086243|gb|AF165903.1|AF165901S3[10086243]

4592: AF165902
Homo sapiens GABA receptor subunit alpha 3 (GABRA3) gene, exon 2 gi|10086242|gb|AF165902.1|AF165901S2[10086242]

4593: AF165901
Homo sapiens GABA receptor subunit alpha 3 (GABRA3) gene, exon 1
gi|10086241|gb|AF165901.1|AF165901S1[10086241]

4594: AH009803
Homo sapiens GABA receptor subunit alpha 3 (GABRA3) gene, complete cds
gi|10086240|gb|AH009803.1|SEG_AF165901S[10086240]

4595: AF167332
Homo sapiens glutamate receptor subunit 3 flip and flop isoforms (GRIA3) gene, exon 16 and partial cds, alternatively spliced
gi|9738978|gb|AF167332.1|F166362S15[9738978]

4596: AF166375
Homo sapiens glutamate receptor subunit 3 (GRIA3) gene, exon 15
gi|9738977|gb|AF166375.1|F166362S14[9738977]

4597: AF166374
Homo sapiens glutamate receptor subunit 3 (GRIA3) gene, exon 14
gi|9738976|gb|AF166374.1|F166362S13[9738976]

4598: AF166373
Homo sapiens glutamate receptor subunit 3 (GRIA3) gene, exon 13
gi|9738975|gb|AF166373.1|F166362S12[9738975]

4599: AF166372
Homo sapiens glutamate receptor subunit 3 (GRIA3) gene, exon 12
gi|9738974|gb|AF166372.1|F166362S11[9738974]

4600: AF166371
Homo sapiens glutamate receptor subunit 3 (GRIA3) gene, exon 11
gi|9738973|gb|AF166371.1|F166362S10[9738973]

4601: AF166370
Homo sapiens glutamate receptor subunit 3 (GRIA3) gene, exon 10 gi|9738972|gb|AF166370.1|F166362S09[9738972]

4602: AF166369
Homo sapiens glutamate receptor subunit 3 (GRIA3) gene, exon 9
gi|9738971|gb|AF166369.1|F166362S08[9738971]

4603: AF166368
Homo sapiens glutamate receptor subunit 3 (GRIA3) gene, exon 8
gi|9738970|gb|AF166368.1|F166362S07[9738970]

4604: AF166367
Homo sapiens glutamate receptor subunit 3 (GRIA3) gene, exon 7
gi|9738969|gb|AF166367.1|F166362S06[9738969]

4605: AF166366
Homo sapiens glutamate receptor subunit 3 (GRIA3) gene, exon 6
gi|9738968|gb|AF166366.1|F166362S05[9738968]

4606: AF166365
Homo sapiens glutamate receptor subunit 3 flip and flop isoforms (GRIA3) gene, exon 4 and partial cds
gi|9738967|gb|AF166365.1|F166362S04[9738967]

4607: AF166364
Homo sapiens glutamate receptor subunit 3 (GRIA3) gene, exon 3
gi|9738966|gb|AF166364.1|F166362S03[9738966]

4608: AF166363
Homo sapiens glutamate receptor subunit 3 (GRIA3) gene, exon 2
gi|9738965|gb|AF166363.1|F166362S02[9738965]

4609: AF166362
Homo sapiens glutamate receptor subunit 3 (GRIA3) gene, exon 1
gi|9738964|gb|AF166362.1|F166362S01[9738964]

4610: AH009704
Homo sapiens glutamate receptor subunit 3 (GRIA3) gene, partial cds; and glutamate receptor subunit 3 (GRIA3) gene, partial cds, alternatively spliced
gi|9738963|gb|AH009704.1|SEG_F166362S[9738963]

4611: AF272389
Homo sapiens natural killer cell immunoglobulin-like receptor (KIR2DS5) mRNA, partial cds
gi|15080894|gb|AF272389.1|AF272389[15080894]

4612: BC011847
Homo sapiens, fibroblast growth factor receptor 4, clone MGC:20292 IMAGE:4121396, mRNA, complete cds
gi|15080147|gb|BC011847.1|BC011847[15080147]

4613: BC011787
Homo sapiens, nogo receptor, clone MGC:19831 IMAGE:4040540, mRNA, complete cds
gi|15080004|gb|BC011787.1|BC011787[15080004]

4614: AF353942
Homo sapiens lantibiotic synthetase C-like protein 2 (LANCL2) mRNA, complete cds
gi|15077638|gb|AF353942.1|AF353942[15077638]

4615: AF343725
Homo sapiens G-protein-coupled receptor GPR54 (GPR54) mRNA, complete cds
gi|15077535|gb|AF343725.1|AF343725[15077535]

4617: AJ272063
Homo sapiens mRNA for vanilloid receptor 1 (VR1 gene)
gi|15028818|emb|AJ272063.2|HSA272063[15028818]

4618: AF133266
Homo sapiens cysteinyl leukotriene receptor mRNA, complete cds
gi|5359717|gb|AF133266.1|AF133266[5359717]

4619: NM_033130
Homo sapiens sialic acid binding Ig-like lectin 10 (SIGLEC10), mRNA
gi|15055512|ref|NM_033130.1|[15055512]

4620: NM_033180
Homo sapiens olfactory receptor, family 51, subfamily B, member 2 (OR51B2), mRNA
gi|15042966|ref|NM_033180.1|[15042966]

4621: NM_033179
Homo sapiens olfactory receptor, family 51, subfamily B, member 4 (OR51B4), mRNA
gi|15042964|ref|NM_033179.1|[15042964]

4622: AF380193
Homo sapiens trace amine receptor 5 (TA5) gene, complete cds
gi|14600089|gb|AF380193.1|AF380193[14600089]

4623: AF380192
Homo sapiens trace amine receptor 4 (TA4) gene, complete cds
gi|14600087|gb|AF380192.1|AF380192[14600087]

4624: AF380189
Homo sapiens trace amine receptor 3 (TA3) gene, complete cds
gi|14600081|gb|AF380189.1|AF380189[14600081]

4625: AF380185
Homo sapiens trace amine receptor 1 (TA1) gene, complete cds
gi|14600073|gb|AF380185.1|AF380185[14600073]

4626: AF313468
Homo sapiens dendritic cell-associated C-type lectin-1 mRNA, complete cds
gi|13649707|gb|AF313468.1|AF313468[13649707]

4627: NM_007096
Homo sapiens clathrin, light polypeptide (Lca) (CLTA), transcript variant brain-specific, mRNA
gi|6005992|ref|NM_007096.1|[6005992]

4628: NM_001833
Homo sapiens clathrin, light polypeptide (Lca) (CLTA), transcript variant nonbrain, mRNA
gi|4502898|ref|NM_001833.1|[4502898]

4629: NM_005292
Homo sapiens G protein-coupled receptor 18 (GPR18), mRNA
gi|15029527|ref|NM_005292.1|[15029527]

4630: NM_012276
Homo sapiens leukocyte immunoglobulin-like receptor, subfamily A (without TM domain), member 4 (ILT7), mRNA
gi|15029521|ref|NM_012276.1|[15029521]

4631: AJ299451
Homo sapiens mRNA for glutamate receptor 7 (GRIK3 gene)
gi|15028906|emb|AJ299451.1|HSA299451[15028906]

4632: AY033606
Homo sapiens fused in glioblastoma mRNA, complete cds
gi|14289128|gb|AY033606.1|[14289128]

4633: AF190696
Homo sapiens bile salt export pump (ABCB11) gene, promoter region and partial sequence
gi|14280234|gb|AF190696.1|AF190696[14280234]

4634: NM_018558
Homo sapiens gamma-aminobutyric acid (GABA) receptor, theta (GABRQ), mRNA
gi|8924257|ref|NM_018558.1|[8924257]

4635: NM_014452
Homo sapiens tumor necrosis factor receptor superfamily, member 21 (TNFRSF21), mRNA
gi|7657038|ref|NM_014452.1|[7657038]

4637: AF320560
Homo sapiens stresscopin-related protein mRNA, complete cds
gi|14029393|gb|AF320560.1|AF320560[14029393]

4638: NM_007368
Homo sapiens RAS p21 protein activator (GTPase activating protein) 3

(Ins(1,3,4,5)P4-binding protein) (GAP1IP4BP), mRNA
gi|12545409|ref|NM_007368.1|[12545409]

4639: NM_016109
Homo sapiens angiopoietin-like 4 (ANGPTL4), mRNA
gi|7705828|ref|NM_016109.1|[7705828]

4640: NM_006667
Homo sapiens progesterone receptor membrane component 1 (PGRMC1), mRNA
gi|6857798|ref|NM_006667.2|[6857798]

4641: NM_006320
Homo sapiens progesterone receptor membrane component 2 (PGRMC2), mRNA
gi|5453915|ref|NM_006320.1|[5453915]

4662: AF319553
Homo sapiens TNFRSF19L mRNA, complete cds
gi|15011026|gb|AF319553.1|AF319553[15011026]

4663: AF395806
Homo sapiens adrenergic receptor alpha-1a (ADRA1A) mRNA, complete cds
gi|15004693|gb|AF395806.1|AF395806[15004693]

4664: AF388194
Homo sapiens PML/RARA fusion mRNA, partial sequence
gi|15004544|gb|AF388194.1|AF388194[15004544]

4665: AF388193
Homo sapiens PML/RARA fusion mRNA, partial sequence
gi|15004543|gb|AF388193.1|AF388193[15004543]

4666: AF334818
Homo sapiens sodium-dependent neutral amino acid transporter type 2 truncated isoform (ASCT2) mRNA, partial cds
gi|15004316|gb|AF334818.1|AF334818[15004316]

4667: NM_022788
Homo sapiens Purinergic receptor P2Y, G protein-coupled, 12 (P2RY12), mRNA
gi|12232482|ref|NM_022788.1|[12232482]

4668: NM_016523
Homo sapiens killer cell lectin-like receptor subfamily F, member 1 (KLRF1), mRNA
gi|7705573|ref|NM_016523.1|[7705573]

4669: NM_002558
Homo sapiens purinergic receptor P2X, ligand-gated ion channel, 1 (P2RX1), mRNA
gi|4505544|ref|NM_002558.1|[4505544]

4670: AF391809
Homo sapiens coagulation factor II (thrombin) receptor (F2R) gene, complete cds
gi|14971463|gb|AF391809.2|AF391809[14971463]

4671: NM_016930
Homo sapiens syntaxin 18 (STX18), mRNA
gi|8394375|ref|NM_016930.1|[8394375]

4672: NM_032957
Homo sapiens tumor necrosis factor receptor superfamily, member 6b, decoy (TNFRSF6B), transcript variant 1, mRNA
gi|14790173|ref|NM_032957.1|[14790173]

4673: NM_032945
Homo sapiens tumor necrosis factor receptor superfamily, member 6b, decoy (TNFRSF6B), transcript variant M68C, mRNA
gi|14790169|ref|NM_032945.1|[14790169]

4674: NM_015647
Homo sapiens tumor necrosis factor receptor superfamily, member 6b, decoy (TNFRSF6B), transcript variant 3, mRNA
gi|14790156|ref|NM_015647.2|[14790156]

4675: NM_005409
Homo sapiens small inducible cytokine subfamily B (Cys-X-Cys), member 11

(SCYB11), mRNA
gi|14790145|ref|NM_005409.3|[14790145]

4676: NM_001305
Homo sapiens claudin 4 (CLDN4), mRNA
gi|14790131|ref|NM_001305.2|[14790131]

4677: NM_004346
Homo sapiens caspase 3, apoptosis-related cysteine protease (CASP3), transcript variant alpha, mRNA
gi|14790118|ref|NM_004346.2|[14790118]

4678: NM_032991
Homo sapiens caspase 3, apoptosis-related cysteine protease (CASP3), transcript variant beta, mRNA
gi|14790114|ref|NM_032991.1|[14790114]

4679: NM_033057
Homo sapiens olfactory receptor, family 2, subfamily B, member 2 (OR2B2), mRNA
gi|14780899|ref|NM_033057.1|[14780899]

4680: NM_020137
Homo sapiens GRIP-associated protein 1 (GRASP1), mRNA
gi|14719405|ref|NM_020137.1|[14719405]

4681: NM_032503
Homo sapiens G protein-coupled receptor slt (SLT), mRNA
gi|14210483|ref|NM_032503.1|[14210483]

4682: AF260738
Homo sapiens platelet-derived growth factor C (PDGFC) mRNA, complete cds
gi|14009503|gb|AF260738.1|AF260738[14009503]

4683: AF326275
Homo sapiens melanocortin 1 receptor (MC1R) gene, complete cds
gi|12658397|gb|AF326275.1|AF326275[12658397]

4684: NM_016434
Homo sapiens tumor necrosis factor receptor superfamily, member 6b, decoy (TNFRSF6B), transcript variant 2, mRNA
gi|7706540|ref|NM_016434.1|[7706540]

4685: NM_013314
Homo sapiens B-cell linker (BLNK), mRNA
gi|7019534|ref|NM_013314.1|[7019534]

4686: NM_005817
Homo sapiens cargo selection protein (mannose 6 phosphate receptor binding protein) (TIP47), mRNA
gi|5032182|ref|NM_005817.1|[5032182]

4687: NM_003110
Homo sapiens Sp2 transcription factor (SP2), mRNA
gi|4507166|ref|NM_003110.1|[4507166]

4688: NM_002704
Homo sapiens pro-platelet basic protein (includes platelet basic protein, beta-thromboglobulin, connective tissue-activating peptide III, neutrophil-activating peptide-2) (PPBP), mRNA
gi|4505980|ref|NM_002704.1|[4505980]

4689: AF064083
Homo sapiens T-cell receptor beta chain variable region (TCRBV28) mRNA, TCRBV28*S2 allele, partial cds
gi|3859856|gb|AF064083.1|AF064083[3859856]

4690: BC010641
Homo sapiens, gamma-aminobutyric acid (GABA) A receptor, beta 3, clone MGC:9051 IMAGE:3871111, mRNA, complete cds
gi|14714964|gb|BC010641.1|BC010641[14714964]

4691: BC010574
Homo sapiens, glutamate receptor, ionotropic, AMPA2 (alpha 2), clone MGC:17079 IMAGE:4215347, mRNA, complete cds
gi|14714845|gb|BC010574.1|BC010574[14714845]

4692: BC010536
Homo sapiens, coxsackie virus and adenovirus receptor, clone MGC:17118 IMAGE:3456544, mRNA, complete cds
gi|14714774|gb|BC010536.1|BC010536[14714774]

4693: BC010423
Homo sapiens, Ig superfamily receptor LNIR, clone MGC:15117 IMAGE:3610849, mRNA, complete cds
gi|14714573|gb|BC010423.1|BC010423[14714573]

4694: BC010418
Homo sapiens, laminin receptor 1 (67kD, ribosomal protein SA), clone MGC:16557 IMAGE:4079845, mRNA, complete cds
gi|14714563|gb|BC010418.1|BC010418[14714563]

4695: NM_020168
Homo sapiens p21(CDKN1A)-activated kinase 6 (PAK6), mRNA
gi|14670348|ref|NM_020168.2|[14670348]

4696: BC010140
Homo sapiens, tumor necrosis factor receptor superfamily, member 1A, clone MGC:19588 IMAGE:4131360, mRNA, complete cds
gi|14603367|gb|BC010140.1|BC010140[14603367]

4697: BC010054
Homo sapiens, laminin receptor 1 (67kD, ribosomal protein SA), clone MGC:19795 IMAGE:3845335, mRNA, complete cds
gi|14603183|gb|BC010054.1|BC010054[14603183]

4698: BC009974
Homo sapiens, laminin receptor 1 (67kD, ribosomal protein SA), clone MGC:16607 IMAGE:4110990, mRNA, complete cds
gi|14602973|gb|BC009974.1|BC009974[14602973]

4699: BC009960
Homo sapiens, interleukin 13 receptor, alpha 1, clone MGC:15228 IMAGE:4300487, mRNA, complete cds
gi|14602931|gb|BC009960.1|BC009960[14602931]

4701: BC009877
Homo sapiens, purinergic receptor P2Y, G-protein coupled, 11, clone MGC:16468 IMAGE:3953307, mRNA, complete cds
gi|14602717|gb|BC009877.1|BC009877[14602717]

4702: BC009861
Homo sapiens, super conserved receptor expressed in brain 3, clone MGC:16375 IMAGE:3936037, mRNA, complete cds
gi|14602675|gb|BC009861.1|BC009861[14602675]

4703: BC009748
Homo sapiens, dopamine receptor D5, clone MGC:10601 IMAGE:3928370, mRNA, complete cds
gi|14602484|gb|BC009748.1|BC009748[14602484]

4705: BC009391
Homo sapiens, pyrimidinergic receptor P2Y, G-protein coupled, 6, clone MGC:15335 IMAGE:4128941, mRNA, complete cds
gi|14424757|gb|BC009391.1|BC009391[14424757]

4707: BC009237
Homo sapiens, thyroid stimulating hormone receptor, clone MGC:2216 IMAGE:2989823, mRNA, complete cds
gi|14328043|gb|BC009237.1|BC009237[14328043]

4708: BC008982
Homo sapiens, complement component 5 receptor 1 (C5a ligand), clone MGC:17119 IMAGE:4177114, mRNA, complete cds
gi|14290435|gb|BC008982.1|BC008982[14290435]

4709: BC008867
Homo sapiens, laminin receptor 1 (67kD, ribosomal protein SA), clone MGC:16750 IMAGE:4130936, mRNA, complete cds
gi|14250793|gb|BC008867.1|BC008867[14250793]

4710: BC008786
Homo sapiens, integrin, alpha 5 (fibronectin receptor, alpha polypeptide), clone MGC:3697 IMAGE:3629647, mRNA, complete cds gi|14250643|gb|BC008786.1|BC008786[14250643]

4711: BC008770
Homo sapiens, G protein-coupled receptor 56, clone MGC:1409 IMAGE:3139174, mRNA, complete cds
gi|14250619|gb|BC008770.1|BC008770[14250619]

4712: BC008734
Homo sapiens, Fc fragment of IgG, receptor, transporter, alpha, clone MGC:1506 IMAGE:3163446, mRNA, complete cds
gi|14250560|gb|BC008734.1|BC008734[14250560]

4714: BC008716
Homo sapiens, discoidin domain receptor family, member 1, clone MGC:8681 IMAGE:2964574, mRNA, complete cds
gi|14250529|gb|BC008716.1|BC008716[14250529]

4715: BC008406
Homo sapiens, CD36 antigen (collagen type I receptor, thrombospondin receptor), clone MGC:14530 IMAGE:4244251, mRNA, complete cds
gi|14250019|gb|BC008406.1|BC008406[14250019]

4716: NM_032571
Homo sapiens EGF-like module-containing mucin-like receptor EMR3 (EMR3), mRNA
gi|14211882|ref|NM_032571.1|[14211882]

4717: AF345568
Homo sapiens putative chemokine receptor (FKSG80) mRNA, complete cds
gi|13517963|gb|AF345568.1|AF345568[13517963]

4718: AF345567
Homo sapiens putative purinergic receptor (FKSG79) mRNA, complete cds
gi|13517961|gb|AF345567.1|AF345567[13517961]

4719: AF345566
Homo sapiens putative G-protein-coupled receptor FKSG78 (FKSG78) mRNA, complete cds
gi|13517959|gb|AF345566.1|AF345566[13517959]

4720: AF345565
Homo sapiens putative G-protein-coupled receptor FKSG77 (FKSG77) mRNA, complete cds
gi|13517957|gb|AF345565.1|AF345565[13517957]

4722: NM_013447
Homo sapiens egf-like module containing, mucin-like, hormone receptor-like sequence 2 (EMR2), mRNA
gi|7305024|ref|NM_013447.1|[7305024]

4724: BC007720
Homo sapiens, 5-hydroxytryptamine (serotonin) receptor 1D, clone MGC:12645 IMAGE:4299633, mRNA, complete cds
gi|14043458|gb|BC007720.1|BC007720[14043458]

4725: BC007713
Homo sapiens, protein tyrosine phosphatase, receptor type, N, clone MGC:12646 IMAGE:4130827, mRNA, complete cds
gi|14043446|gb|BC007713.1|BC007713[14043446]

4727: BC007566
Homo sapiens, cargo selection protein (mannose 6 phosphate receptor binding protein), clone MGC:15516 IMAGE:3028104, mRNA, complete cds
gi|14043156|gb|BC007566.1|BC007566[14043156]

4728: BC007408
Homo sapiens, low density lipoprotein receptor-related protein 3, clone MGC:2428 IMAGE:3009711, mRNA, complete cds
gi|13938518|gb|BC007408.1|BC007408[13938518]

4729: BC006196
Homo sapiens, tumor necrosis factor receptor superfamily, member 9, clone MGC:2172 IMAGE:2924109, mRNA, complete cds
gi|13623200|gb|BC006196.1|BC006196[13623200]

4730: BC005912
Homo sapiens, Fc fragment of IgE, high affinity I, receptor for; alpha polypeptide, clone MGC:14507 IMAGE:4294467, mRNA, complete cds
gi|13543505|gb|BC005912.1|BC005912[13543505]

4731: BC005818
Homo sapiens, cargo selection protein (mannose 6 phosphate receptor binding protein), clone MGC:11117 IMAGE:3833411, mRNA, complete cds
gi|13543306|gb|BC005818.1|BC005818[13543306]

4732: BC005391
Homo sapiens, laminin receptor 1 (67kD, ribosomal protein SA), clone MGC:12521 IMAGE:3997019, mRNA, complete cds
gi|13529268|gb|BC005391.1|BC005391[13529268]

4733: BC005333
Homo sapiens, interferon gamma receptor 1, clone MGC:12420 IMAGE:3950528, mRNA, complete cds
gi|13529118|gb|BC005333.1|BC005333[13529118]

4734: BC005315
Homo sapiens, formyl peptide receptor 1, clone MGC:12392 IMAGE:3829614, mRNA, complete cds
gi|13529064|gb|BC005315.1|BC005315[13529064]

4735: BC005268
Homo sapiens, putative receptor protein, clone MGC:12310 IMAGE:4051155, mRNA, complete cds
gi|13528953|gb|BC005268.1|BC005268[13528953]

4737: BC004555
Homo sapiens, G protein-coupled receptor, clone MGC:10314 IMAGE:4054377, mRNA, complete cds
gi|13528716|gb|BC004555.1|BC004555[13528716]

4738: BC004553
Homo sapiens, receptor-interacting serine-threonine kinase 2, clone MGC:10684 IMAGE:4026156, mRNA, complete cds
gi|13528713|gb|BC004553.1|BC004553[13528713]

4739: BC004545
Homo sapiens, leukotriene b4 receptor (chemokine receptor-like 1), clone
MGC:10388 IMAGE:3946189, mRNA, complete cds
gi|13528695|gb|BC004545.1|BC004545[13528695]

4740: BC004899
Homo sapiens, sigma receptor (SR31747 binding protein 1), clone MGC:3851
IMAGE:3529352, mRNA, complete cds
gi|13436169|gb|BC004899.1|BC004899[13436169]

4741: BC004348
Homo sapiens, interleukin 21 receptor, clone MGC:10967 IMAGE:3634520, mRNA,
complete cds
gi|13279298|gb|BC004348.1|BC004348[13279298]

4742: BC003684
Homo sapiens, coxsackie virus and adenovirus receptor, clone MGC:5086
IMAGE:3463613, mRNA, complete cds
gi|13277551|gb|BC003684.1|BC003684[13277551]

4743: BC003624
Homo sapiens, interferon gamma receptor 2 (interferon gamma transducer 1), clone
MGC:2193 IMAGE:2967074, mRNA, complete cds
gi|13177681|gb|BC003624.1|BC003624[13177681]

4744: BC003187
Homo sapiens, putative G-protein coupled receptor, clone MGC:688 IMAGE:3537949,
mRNA, complete cds
gi|13112026|gb|BC003187.1|BC003187[13112026]

4745: BC003142
Homo sapiens, vesicle-associated soluble NSF attachment protein receptor
(v-SNARE; homolog of S. cerevisiae VTI1), clone MGC:3767 IMAGE:2958320, mRNA,
complete cds
gi|13111940|gb|BC003142.1|BC003142[13111940]

4746: BC003110
Homo sapiens, interleukin 11 receptor, alpha, clone MGC:2146 IMAGE:3502059,
mRNA, complete cds gi|13111884|gb|BC003110.1|BC003110[13111884]

4747: BC003091
Homo sapiens, poliovirus receptor-related 2 (herpesvirus entry mediator B),
clone MGC:1349 IMAGE:3503222, mRNA, complete cds
gi|13111848|gb|BC003091.1|BC003091[13111848]

4748: BC000181
Homo sapiens, putative G protein-coupled receptor, clone MGC:5003 IMAGE:3048193,
mRNA, complete cds
gi|13111815|gb|BC000181.2|BC000181[13111815]

4751: BC003005
Homo sapiens, unactive progesterone receptor, 23 kD, clone MGC:4004
IMAGE:2821965, mRNA, complete cds
gi|12804292|gb|BC003005.1|BC003005[12804292]

4752: BC002996
Homo sapiens, cholinergic receptor, nicotinic, alpha polypeptide 3, clone
MGC:3862 IMAGE:2822768, mRNA, complete cds
gi|12804274|gb|BC002996.1|BC002996[12804274]

4753: BC002947
Homo sapiens, folate receptor 1 (adult), clone MGC:10473 IMAGE:3956659, mRNA,
complete cds
gi|12804178|gb|BC002947.1|BC002947[12804178]

4754: BC002819
Homo sapiens, putative receptor protein, clone MGC:3676 IMAGE:3636199, mRNA,
complete cds
gi|12803944|gb|BC002819.1|BC002819[12803944]

4755: BC002794
Homo sapiens, tumor necrosis factor receptor superfamily, member 14 (herpesvirus
entry mediator), clone MGC:3753 IMAGE:3614650, mRNA, complete cds
gi|12803894|gb|BC002794.1|BC002794[12803894]

4756: BC002793

Homo sapiens, interferon (alpha, beta and omega) receptor 2, clone MGC:3873 IMAGE:3626374, mRNA, complete cds
gi|12803892|gb|BC002793.1|BC002793[12803892]

4757: BC002788
Homo sapiens, plasminogen activator, urokinase receptor, clone MGC:3905 IMAGE:3617894, mRNA, complete cds
gi|12803884|gb|BC002788.1|BC002788[12803884]

4758: BC002635
Homo sapiens, colony stimulating factor 2 receptor, alpha, low-affinity (granulocyte-macrophage), clone MGC:3848 IMAGE:3606186, mRNA, complete cds
gi|12803600|gb|BC002635.1|BC002635[12803600]

4759: BC002537
Homo sapiens, fibroblast growth factor receptor-like 1, clone IMAGE:3140874, mRNA
gi|12803426|gb|BC002537.1|BC002537[12803426]

4760: BC002464
Homo sapiens, coagulation factor II (thrombin) receptor, clone MGC:1197 IMAGE:3343051, mRNA, complete cds
gi|12803296|gb|BC002464.1|BC002464[12803296]

4761: BC002443
Homo sapiens, putative T1/ST2 receptor binding protein, clone MGC:1270 IMAGE:3346273, mRNA, complete cds
gi|12803256|gb|BC002443.1|BC002443[12803256]

4762: BC002354
Homo sapiens, 5-hydroxytryptamine (serotonin) receptor 3A, clone MGC:8469 IMAGE:2821710, mRNA, complete cds
gi|12803100|gb|BC002354.1|BC002354[12803100]

4763: BC001379
Homo sapiens, G protein-coupled receptor kinase-interactor 2, clone MGC:760 IMAGE:3051069, mRNA, complete cds
gi|12655058|gb|BC001379.1|BC001379[12655058]

4764: BC001281
Homo sapiens, tumor necrosis factor receptor superfamily, member 10b, clone MGC:5144 IMAGE:3458466, mRNA, complete cds
gi|12654874|gb|BC001281.1|BC001281[12654874]

4766: BC001188
Homo sapiens, transferrin receptor (p90, CD71), clone MGC:3151 IMAGE:3354176, mRNA, complete cds
gi|12654696|gb|BC001188.1|BC001188[12654696]

4769: BC001110
Homo sapiens, benzodiazapine receptor (peripheral), clone MGC:1184 IMAGE:2989070, mRNA, complete cds
gi|12654552|gb|BC001110.1|BC001110[12654552]

4770: BC000740
Homo sapiens, cholecystokinin B receptor, clone MGC:2199 IMAGE:3504160, mRNA, complete cds
gi|12653894|gb|BC000740.1|BC000740[12653894]

4772: BC000571
Homo sapiens, pyrimidinergic receptor P2Y, G-protein coupled, 6, clone MGC:2067 IMAGE:3162734, mRNA, complete cds
gi|12653590|gb|BC000571.1|BC000571[12653590]

4773: BC000548
Homo sapiens, receptor (calcitonin) activity modifying protein 1, clone MGC:1996 IMAGE:3163522, mRNA, complete cds
gi|12653550|gb|BC000548.1|BC000548[12653550]

4774: BC000513
Homo sapiens, cholinergic receptor, nicotinic, alpha polypeptide 3, clone MGC:8545 IMAGE:2822768, mRNA, complete cds
gi|12653482|gb|BC000513.1|BC000513[12653482]

4776: BC000254
Homo sapiens, activin A receptor, type IB, clone MGC:2177 IMAGE:3352720, mRNA, complete cds gi|12652986|gb|BC000254.1|BC000254[12652986]

4780: AF037351
Homo sapiens macrophage scavenger receptor type III (SR-A) mRNA, complete cds
gi|3004959|gb|AF037351.1|AF037351[3004959]

4781: BC009277
Homo sapiens, G protein-coupled receptor kinase 6, clone IMAGE:4053197, mRNA
gi|14627273|gb|BC009277.1|BC009277[14627273]

4782: AF369786
Homo sapiens growth hormone secretagogue receptor gene, complete cds, alternatively spliced
gi|14625865|gb|AF369786.1|AF369786[14625865]

4784: U35877
Homo sapiens (-) genotype B2 bradykinin receptor gene, exon 1
gi|1353393|gb|U35877.1|HSU35877[1353393]

4785: U35876
Homo sapiens (+) genotype B2 bradykinin receptor gene, exon 1
gi|1353392|gb|U35876.1|HSU35876[1353392]

4786: NM_005656
Homo sapiens transmembrane protease, serine 2 (TMPRSS2), mRNA
gi|14602458|ref|NM_005656.2|[14602458]

4787: NM_004167
Homo sapiens small inducible cytokine subfamily A (Cys-Cys), member 15 (SCYA15), transcript variant 2, mRNA
gi|14602450|ref|NM_004167.2|[14602450]

4788: NM_032965
Homo sapiens small inducible cytokine subfamily A (Cys-Cys), member 15 (SCYA15), transcript variant 3, mRNA
gi|14602448|ref|NM_032965.1|[14602448]

4789: NM_032964
Homo sapiens small inducible cytokine subfamily A (Cys-Cys), member 15 (SCYA15), transcript variant 1, mRNA
gi|14602446|ref|NM_032964.1|[14602446]

4790: AJ312373
Homo sapiens mRNA for DECTIN-1 receptor, splice variant 2
gi|14599395|emb|AJ312373.1|HSA312373[14599395]

4791: AJ312372
Homo sapiens mRNA for DECTIN-1 receptor, splice variant 1
gi|14599393|emb|AJ312372.1|HSA312372[14599393]

4792: AJ307885
Homo sapiens mRNA for T-cell receptor beta chain, clone 83
gi|14595016|emb|AJ307885.1|HSA307885[14595016]

4793: NM_001987
Homo sapiens ets variant gene 6 (TEL oncogene) (ETV6), mRNA
gi|14589947|ref|NM_001987.2|[14589947]

4794: NM_020403
Homo sapiens protocadherin 9 (PCDH9), mRNA
gi|14589940|ref|NM_020403.2|[14589940]

4795: NM_022843
Homo sapiens protocadherin 20 (PCDH20), mRNA
gi|14589938|ref|NM_022843.1|[14589938]

4797: NM_020164
Homo sapiens aspartate beta-hydroxylase (ASPH), transcript variant 5, mRNA
gi|14589858|ref|NM_020164.2|[14589858]

4798: AF361107
Homo sapiens CRHF2 receptor beta-isoform mRNA, partial sequence, aberrantly spliced
gi|14586958|gb|AF361107.1|AF361107[14586958]

4799: AF361106
Homo sapiens CRHF2 receptor beta-isoform mRNA, partial sequence, aberrantly spliced
gi|14586957|gb|AF361106.1|AF361106[14586957]

4800: AF284768
Homo sapiens laminin receptor-like protein LAMRL5 mRNA, complete cds
gi|14583013|gb|AF284768.1|AF284768[14583013]

4801: AF343090
Homo sapiens HSF-27 protein mRNA, complete cds
gi|14582809|gb|AF343090.1|AF343090[14582809]

4802: AF286696
Homo sapiens olfactory receptor sdolf mRNA, complete cds
gi|14582606|gb|AF286696.1|AF286696[14582606]

4803: AF279673
Homo sapiens vanilloid receptor-like protein 2 (VRL2) mRNA, complete cds
gi|14582397|gb|AF279673.1|AF279673[14582397]

4804: AF279611
Homo sapiens cysteinyl leukotriene receptor type 2 (CYSLT2) gene, complete cds
gi|14582393|gb|AF279611.1|AF279611[14582393]

4806: NM_005111
Homo sapiens crystallin, zeta (quinone reductase)-like 1 (CRYZL1), mRNA
gi|14577924|ref|NM_005111.2|[14577924]

4807: NM_000592
Homo sapiens complement component 4B (C4B), mRNA
gi|14577920|ref|NM_000592.3|[14577920]

4809: NM_016557
Homo sapiens orphan seven-transmembrane receptor, chemokine related (VSHK1), mRNA
gi|7706768|ref|NM_016557.1|[7706768]

4810: NM_006850
Homo sapiens interleukin 24 (IL24), mRNA
gi|5803085|ref|NM_006850.1|[5803085]

4811: NM_000029
Homo sapiens angiotensinogen (serine (or cysteine) proteinase inhibitor, clade A (alpha-1 antiproteinase, antitrypsin), member 8) (AGT), mRNA
gi|4557286|ref|NM_000029.1|[4557286]

4812: AF385591
Homo sapiens m5 muscarinic cholinergic receptor (CHRM5) mRNA, complete cds
gi|14573544|gb|AF385591.1|AF385591[14573544]

4813: AF385590
Homo sapiens m4 muscarinic cholinergic receptor (CHRM4) mRNA, complete cds
gi|14573542|gb|AF385590.1|AF385590[14573542]

4814: AF385589
Homo sapiens m3 muscarinic cholinergic receptor (CHRM3) mRNA, partial cds
gi|14573540|gb|AF385589.1|AF385589[14573540]

4815: AF385588
Homo sapiens m2 muscarinic cholinergic receptor (CHRM2) mRNA, complete cds
gi|14573538|gb|AF385588.1|AF385588[14573538]

4816: AF385587
Homo sapiens m1 muscarinic cholinergic receptor (CHRM1) mRNA, complete cds
gi|14573536|gb|AF385587.1|AF385587[14573536]

4817: AF385585
Homo sapiens nicotinic cholinergic receptor alpha 7 (CHRNA7) mRNA, complete cds
gi|14573533|gb|AF385585.1|AF385585[14573533]

4818: AF385584
Homo sapiens nicotinic cholinergic receptor alpha 3 (CHRNA3) mRNA, partial cds
gi|14573531|gb|AF385584.1|AF385584[14573531]

4819: AF361943
Homo sapiens urocortin III (UCNIII) gene, complete cds
gi|14571921|gb|AF361943.1|AF361943[14571921]

4825: NM_031282
Homo sapiens immunoglobulin superfamily receptor translocation associated 1 (IRTA1), mRNA
gi|14550415|ref|NM_031282.1|[14550415]

4826: NM_031281
Homo sapiens immunoglobulin superfamily receptor translocation associated 2 (IRTA2), mRNA
gi|14550413|ref|NM_031281.1|[14550413]

4827: NM_020404
Homo sapiens tumor endothelial marker 1 precursor (TEM1), mRNA
gi|9966884|ref|NM_020404.1|[9966884]

4830: AF338733
Homo sapiens thymic stromal lymphopoietin protein receptor TSLPR mRNA, complete cds
gi|14335439|gb|AF338733.1|AF338733[14335439]

4831: AF338732
Homo sapiens thymic stromal lymphopoietin protein TSLP mRNA, complete cds
gi|14335437|gb|AF338732.1|AF338732[14335437]

4832: AJ272324
Homo sapiens mRNA for PRAM-1 protein
gi|11558108|emb|AJ272324.1|HSA272324[11558108]

4833: AF281043
Homo sapiens high mobility group 1 protein (HMG1) gene, promoter and partial cds
gi|14522873|gb|AF281043.1|AF281043[14522873]

4834: NM_024298

Homo sapiens malignant cell expression-enhanced gene/tumor progression-enhanc (LENG4), mRNA
gi|13236521|ref|NM_024298.1|[13236521]

4835: AB051580
Homo sapiens gene for IgG receptor IIIB, complete cds
gi|11344590|dbj|AB051580.1|AB051580[11344590]

4836: NM_006134
Homo sapiens chromosome 21 open reading frame 4 (C21orf4), mRNA
gi|8659558|ref|NM_006134.2|[8659558]

4837: NM_015927
Homo sapiens transforming growth factor beta 1 induced transcript 1 (TGFB1I1), mRNA
gi|7706249|ref|NM_015927.1|[7706249]

4838: NM_000956
Homo sapiens prostaglandin E receptor 2 (subtype EP2), 53kD (PTGER2), mRNA
gi|4506254|ref|NM_000956.1|[4506254]

4839: AF019381
Homo sapiens corticotropin releasing hormone receptor type 2 gamma isoform (CRH2R) mRNA, complete cds
gi|2738888|gb|AF019381.1|AF019381[2738888]

4840: AB043702
Homo sapiens FZD5 mRNA for seven-transmembrane receptor Frizzled-5, complete cds
gi|14495150|dbj|AB043702.1|AB043702[14495150]

4841: AF384819
Homo sapiens coagulation factor II receptor-like 3 (F2RL3) gene, complete cds
gi|14488403|gb|AF384819.2|AF384819[14488403]

4842: AF343666
Homo sapiens translocation associated fusion protein IRTA1/IGA1 (IRTA1/IGHA1) mRNA, complete cds
gi|13591717|gb|AF343666.1|AF343666[13591717]

4843: AF343665
Homo sapiens immunoglobulin superfamily receptor translocation associated protein 2d (IRTA2) mRNA, partial cds, alternatively spliced
gi|13591715|gb|AF343665.1|AF343665[13591715]

4844: AF343664
Homo sapiens immunoglobulin superfamily receptor translocation associated protein 2c (IRTA2) mRNA, complete cds, alternatively spliced
gi|13591713|gb|AF343664.1|AF343664[13591713]

4845: AF343663
Homo sapiens immunoglobulin superfamily receptor translocation associated protein 2b (IRTA2) mRNA, complete cds, alternatively spliced
gi|13591711|gb|AF343663.1|AF343663[13591711]

4846: AF343662
Homo sapiens immunoglobulin superfamily receptor translocation associated protein 2a (IRTA2) mRNA, complete cds, alternatively spliced
gi|13591709|gb|AF343662.1|AF343662[13591709]

4847: AF343661
Homo sapiens immunoglobulin superfamily receptor translocation associated protein 1a (IRTA1) mRNA, complete cds, alternatively spliced
gi|13591707|gb|AF343661.1|AF343661[13591707]

4848: AF343660
Homo sapiens immunoglobulin superfamily receptor translocation associated protein 1b (IRTA1) mRNA, complete cds, alternatively spliced
gi|13591705|gb|AF343660.1|AF343660[13591705]

4849: AF343659
Homo sapiens immunoglobulin superfamily receptor translocation associated protein 1c (IRTA1) mRNA, complete cds, alternatively spliced
gi|13591703|gb|AF343659.1|AF343659[13591703]

4850: AF321237
Homo sapiens chromosome 11p15.4 clone RPC11-610i20 P2-containing olfactory receptor gene cluster, complete sequence
gi|12007433|gb|AF321237.1|AF321237[12007433]

4851: NM_005567
Homo sapiens lectin, galactoside-binding, soluble, 3 binding protein (LGALS3BP), mRNA
gi|6006016|ref|NM_005567.2|[6006016]

4852: AF351620
Homo sapiens lipocalin-1 interacting membrane receptor (LIMR) gene, complete cds
gi|14485746|gb|AF351620.1|AF351620[14485746]

4853: AF366519

4890: AB063174
Homo sapiens SLC-1 mRNA for somatostatin receptor-like protein, complete cds
gi|14475646|dbj|AB063174.1|AB063174[14475646]

4891: AF238470
Homo sapiens natural killer cell receptor NKG2F gene, partial cds
gi|11023178|gb|AF238470.1|AF238470[11023178]

4892: AF238469
Homo sapiens natural killer cell receptor NKG2E gene, partial cds
gi|11023176|gb|AF238469.1|AF238469[11023176]

4893: AF238468
Homo sapiens natural killer cell receptor NKG2C gene, partial cds
gi|11023174|gb|AF238468.1|AF238468[11023174]

4894: AE000662
Homo sapiens T-cell receptor alpha delta locus from bases 1000498 to 1071650 (section 5 of 5) of the Complete Nucleotide Sequence
gi|2358068|gb|AE000662.1|HUAE000662[2358068]

4895: AE000661
Homo sapiens T-cell receptor alpha delta locus from bases 752679 to 1000555

(section 4 of 5) of the Complete Nucleotide Sequence
gi|2358060|gb|AE000661.1|HUAE000661[2358060]

4896: AE000660
Homo sapiens T-cell receptor alpha delta locus from bases 501613 to 752736 (section 3 of 5) of the Complete Nucleotide Sequence
gi|2358042|gb|AE000660.1|HUAE000660[2358042]

4897: AE000659
Homo sapiens T-cell receptor alpha delta locus from bases 250472 to 501670 (section 2 of 5) of the Complete Nucleotide Sequence
gi|2358025|gb|AE000659.1|HUAE000659[2358025]

4898: AE000658
Homo sapiens T-cell receptor alpha delta locus from bases 1 to 250529 (section 1 of 5) of the Complete Nucleotide Sequence
gi|2358019|gb|AE000658.1|HUAE000658[2358019]

4899: AF364129
Homo sapiens tandem repeat region 76.3 kb upstream of BMPR1A exon 1
gi|14423333|gb|AF364129.1|AF364129[14423333]

4900: AF364128
Homo sapiens tandem repeat region 49.4 kb upsteam of BMPR1A exon 1
gi|14423332|gb|AF364128.1|AF364128[14423332]

4901: AF261083
Homo sapiens polymeric immunoglobulin receptor (PIGR) gene, partial cds
gi|8099662|gb|AF261083.1|AF261083[8099662]

4902: AF243129
Homo sapiens intrinsic factor-vitamin B12 receptor (CUBN) gene, exon 67 and partial cds
gi|14388671|gb|AF243129.1|F243081S49[14388671]

4903: AF243128
Homo sapiens intrinsic factor-vitamin B12 receptor (CUBN) gene, exon 66
gi|14388670|gb|AF243128.1|F243081S48[14388670]

4904: AF243127
Homo sapiens intrinsic factor-vitamin B12 receptor (CUBN) gene, exon 65
gi|14388669|gb|AF243127.1|F243081S47[14388669]

4905: AF243126
Homo sapiens intrinsic factor-vitamin B12 receptor (CUBN) gene, exons 63 and 64
gi|14388668|gb|AF243126.1|F243081S46[14388668]

4906: AF243125
Homo sapiens intrinsic factor-vitamin B12 receptor (CUBN) gene, exons 61 and 62
gi|14388667|gb|AF243125.1|F243081S45[14388667]

4907: AF243124
Homo sapiens intrinsic factor-vitamin B12 receptor (CUBN) gene, exon 60
gi|14388666|gb|AF243124.1|F243081S44[14388666]

4908: AF243123
Homo sapiens intrinsic factor-vitamin B12 receptor (CUBN) gene, exon 59
gi|14388665|gb|AF243123.1|F243081S43[14388665]

4909: AF243122
Homo sapiens intrinsic factor-vitamin B12 receptor (CUBN) gene, exon 58
gi|14388664|gb|AF243122.1|F243081S42[14388664]

4910: AF243121
Homo sapiens intrinsic factor-vitamin B12 receptor (CUBN) gene, exon 57
gi|14388663|gb|AF243121.1|F243081S41[14388663]

4911: AF243120
Homo sapiens intrinsic factor-vitamin B12 receptor (CUBN) gene, exon 56
gi|14388662|gb|AF243120.1|F243081S40[14388662]

4912: AF243119
Homo sapiens intrinsic factor-vitamin B12 receptor (CUBN) gene, exon 55
gi|14388661|gb|AF243119.1|F243081S39[14388661]

4913: AF243118
Homo sapiens intrinsic factor-vitamin B12 receptor (CUBN) gene, exon 54
gi|14388660|gb|AF243118.1|F243081S38[14388660]

4914: AF243117
Homo sapiens intrinsic factor-vitamin B12 receptor (CUBN) gene, exons 52 and 53
gi|14388659|gb|AF243117.1|F243081S37[14388659]

4915: AF243116
Homo sapiens intrinsic factor-vitamin B12 receptor (CUBN) gene, exon 51
gi|14388658|gb|AF243116.1|F243081S36[14388658]

4916: AF243115
Homo sapiens intrinsic factor-vitamin B12 receptor (CUBN) gene, exons 49 and 50
gi|14388657|gb|AF243115.1|F243081S35[14388657]

4917: AF243114
Homo sapiens intrinsic factor-vitamin B12 receptor (CUBN) gene, exon 48
gi|14388656|gb|AF243114.1|F243081S34[14388656]

4918: AF243113
Homo sapiens intrinsic factor-vitamin B12 receptor (CUBN) gene, exon 47
gi|14388655|gb|AF243113.1|F243081S33[14388655]

4919: AF243112
Homo sapiens intrinsic factor-vitamin B12 receptor (CUBN) gene, exon 46
gi|14388654|gb|AF243112.1|F243081S32[14388654]

4920: AF243111
Homo sapiens intrinsic factor-vitamin B12 receptor (CUBN) gene, exon 45
gi|14388653|gb|AF243111.1|F243081S31[14388653]

4921: AF243110
Homo sapiens intrinsic factor-vitamin B12 receptor (CUBN) gene, exon 44
gi|14388652|gb|AF243110.1|F243081S30[14388652]

4922: AF243109
Homo sapiens intrinsic factor-vitamin B12 receptor (CUBN) gene, exons 42 and 43
gi|14388651|gb|AF243109.1|F243081S29[14388651]

4923: AF243108
Homo sapiens intrinsic factor-vitamin B12 receptor (CUBN) gene, exon 41
gi|14388650|gb|AF243108.1|F243081S28[14388650]

4924: AF243107
Homo sapiens intrinsic factor-vitamin B12 receptor (CUBN) gene, exon 40
gi|14388649|gb|AF243107.1|F243081S27[14388649]

4925: AF243106
Homo sapiens intrinsic factor-vitamin B12 receptor (CUBN) gene, exon 39
gi|14388648|gb|AF243106.1|F243081S26[14388648]

4926: AF243105
Homo sapiens intrinsic factor-vitamin B12 receptor (CUBN) gene, exons 37 and 38
gi|14388647|gb|AF243105.1|F243081S25[14388647]

4927: AF243104
Homo sapiens intrinsic factor-vitamin B12 receptor (CUBN) gene, exons 35 and 36
gi|14388646|gb|AF243104.1|F243081S24[14388646]

4928: AF243103
Homo sapiens intrinsic factor-vitamin B12 receptor (CUBN) gene, exon 34
gi|14388645|gb|AF243103.1|F243081S23[14388645]

4929: AF243102
Homo sapiens intrinsic factor-vitamin B12 receptor (CUBN) gene, exon 33
gi|14388644|gb|AF243102.1|F243081S22[14388644]

4930: AF243101
Homo sapiens intrinsic factor-vitamin B12 receptor (CUBN) gene, exon 32
gi|14388643|gb|AF243101.1|F243081S21[14388643]

4931: AF243100

Homo sapiens intrinsic factor-vitamin B12 receptor (CUBN) gene, exon 31
gi|14388642|gb|AF243100.1|F243081S20[14388642]

4932: AF243099
Homo sapiens intrinsic factor-vitamin B12 receptor (CUBN) gene, exon 30
gi|14388641|gb|AF243099.1|F243081S19[14388641]

4933: AF243098
Homo sapiens intrinsic factor-vitamin B12 receptor (CUBN) gene, exon 29
gi|14388640|gb|AF243098.1|F243081S18[14388640]

4934: AF243097
Homo sapiens intrinsic factor-vitamin B12 receptor (CUBN) gene, exon 28
gi|14388639|gb|AF243097.1|F243081S17[14388639]

4935: AF243096
Homo sapiens intrinsic factor-vitamin B12 receptor (CUBN) gene, exon 27
gi|14388638|gb|AF243096.1|F243081S16[14388638]

4936: AF243095
Homo sapiens intrinsic factor-vitamin B12 receptor (CUBN) gene, exon 26
gi|14388637|gb|AF243095.1|F243081S15[14388637]

4937: AF243094
Homo sapiens intrinsic factor-vitamin B12 receptor (CUBN) gene, exons 23, 24, and 25
gi|14388636|gb|AF243094.1|F243081S14[14388636]

4938: AF243093
Homo sapiens intrinsic factor-vitamin B12 receptor (CUBN) gene, exon 22
gi|14388635|gb|AF243093.1|F243081S13[14388635]

4939: AF243092
Homo sapiens intrinsic factor-vitamin B12 receptor (CUBN) gene, exons 20 and 21
gi|14388634|gb|AF243092.1|F243081S12[14388634]

4940: AF243091

Homo sapiens intrinsic factor-vitamin B12 receptor (CUBN) gene, exons 18 and 19
gi|14388633|gb|AF243091.1|F243081S11[14388633]

4941: AF243090
Homo sapiens intrinsic factor-vitamin B12 receptor (CUBN) gene, exons 16 and 17
gi|14388632|gb|AF243090.1|F243081S10[14388632]

4942: AF243089
Homo sapiens intrinsic factor-vitamin B12 receptor (CUBN) gene, exon 15
gi|14388631|gb|AF243089.1|F243081S09[14388631]

4943: AF243088
Homo sapiens intrinsic factor-vitamin B12 receptor (CUBN) gene, exon 14
gi|14388630|gb|AF243088.1|F243081S08[14388630]

4944: AF243087
Homo sapiens intrinsic factor-vitamin B12 receptor (CUBN) gene, exons 11, 12, and 13
gi|14388629|gb|AF243087.1|F243081S07[14388629]

4945: AF243086
Homo sapiens intrinsic factor-vitamin B12 receptor (CUBN) gene, exons 9 and 10
gi|14388628|gb|AF243086.1|F243081S06[14388628]

4946: AF243085
Homo sapiens intrinsic factor-vitamin B12 receptor (CUBN) gene, exon 8
gi|14388627|gb|AF243085.1|F243081S05[14388627]

4947: AF243084
Homo sapiens intrinsic factor-vitamin B12 receptor (CUBN) gene, exon 7
gi|14388626|gb|AF243084.1|F243081S04[14388626]

4948: AF243083
Homo sapiens intrinsic factor-vitamin B12 receptor (CUBN) gene, exons 5 and 6
gi|14388625|gb|AF243083.1|F243081S03[14388625]

4949: AF243082

Homo sapiens intrinsic factor-vitamin B12 receptor (CUBN) gene, exon 3 and partial cds
gi|14388624|gb|AF243082.1|F243081S02[14388624]

4950: AF243081
Homo sapiens intrinsic factor-vitamin B12 receptor (CUBN) gene, exons 1 and 2
gi|14388623|gb|AF243081.1|F243081S01[14388623]

4951: AH010855
Homo sapiens intrinsic factor-vitamin B12 receptor (CUBN) and intrinsic factor-vitamin B12 receptor (CUBN) genes, partial cds
gi|14388622|gb|AH010855.1|SEG_F243081S[14388622]

4952: AY029596
Homo sapiens melanin-concentrating hormone 2 receptor mRNA, complete cds
gi|14388165|gb|AY029596.1|[14388165]

4953: AF233349
Homo sapiens neuronal phosphoprotein DARPP-32 mRNA, partial cds
gi|7243754|gb|AF233349.1|AF233349[7243754]

4954: AF208690
Homo sapiens clone 24 p70 killer cell inhibitory receptor mRNA, partial cds
gi|6851353|gb|AF208690.1|AF208690[6851353]

4955: AF208689
Homo sapiens clone 22 p70 killer cell inhibitory receptor mRNA, partial cds
gi|6851351|gb|AF208689.1|AF208689[6851351]

4956: AF208688
Homo sapiens clone 3 p70 killer cell inhibitory receptor mRNA, partial cds
gi|6851349|gb|AF208688.1|AF208688[6851349]

4957: AF208687
Homo sapiens clone 25 p70 killer cell inhibitory receptor mRNA, partial cds
gi|6851347|gb|AF208687.1|AF208687[6851347]

4958: AF208686
Homo sapiens clone 23 p70 killer cell inhibitory receptor mRNA, partial cds
gi|6851345|gb|AF208686.1|AF208686[6851345]

4959: AF208685
Homo sapiens clone 21 p70 killer cell inhibitory receptor mRNA, partial cds
gi|6851343|gb|AF208685.1|AF208685[6851343]

4960: AF208684
Homo sapiens clone 6 p70 killer cell inhibitory receptor mRNA, partial cds
gi|6851341|gb|AF208684.1|AF208684[6851341]

4961: AF208683
Homo sapiens clone 1 p70 killer cell inhibitory receptor mRNA, partial cds
gi|6851339|gb|AF208683.1|AF208683[6851339]

4962: AB052639
Homo sapiens mRNA for IL-XR, complete cds
gi|14349288|dbj|AB052639.1|AB052639[14349288]

4963: AF366364
Homo sapiens interleukin-1 receptor type 1 (IL1R1) gene, exon 1A, partial sequence
gi|14348871|gb|AF366364.1|AF366364[14348871]

4967: AF260728
Homo sapiens lipocalin-interacting protein mRNA, complete cds
gi|14335227|gb|AF260728.1|AF260728[14335227]

4968: AJ308526
Homo sapiens partial GRIK3 gene for glutamate receptor 7, exon 18
gi|14329723|emb|AJ308526.1|HSA308526[14329723]

4969: AJ308525
Homo sapiens partial GRIK3 gene for glutamate receptor 7, exon 16
gi|14329720|emb|AJ308525.1|HSA308525[14329720]

4970: AF165124
Homo sapiens chromosome 5q31.1-q33.1 clone BAC djn082c10 containing GABRG2 gene, complete sequence
gi|5738137|gb|AF165124.1|AF165124[5738137]

4971: AF353733
Homo sapiens leukocyte immunoglobulin-like receptor A3 (LILRA3) gene, exon 3 and partial cds
gi|14280086|gb|AF353733.1|AF353733[14280086]

4972: AF236083
Homo sapiens G-protein-coupled receptor 74 (GPR74) mRNA, complete cds
gi|14279164|gb|AF236083.1|AF236083[14279164]

4973: AF375468
Homo sapiens endothelial protein C receptor (PROCR) gene, complete cds
gi|14278711|gb|AF375468.2|AF375468[14278711]

4974: AF374726
Homo sapiens coagulation factor II receptor-like 2 (F2RL2) gene, complete cds
gi|14278710|gb|AF374726.2|AF374726[14278710]

4975: AF378542
Homo sapiens bradykinin receptor B2 (BDKRB2) gene, complete cds
gi|14278705|gb|AF378542.2|AF378542[14278705]

4976: AB051065
Homo sapiens hot7t175 mRNA for G protein-coupled receptor, complete cds
gi|14041797|dbj|AB051065.1|AB051065[14041797]

4977: AF347063
Homo sapiens G protein-coupled receptor MCH2 mRNA, complete cds
gi|13604341|gb|AF347063.1|AF347063[13604341]

4978: AJ278250
Homo sapiens HRH3 gene for histamine H3 receptor, exons 1-3
gi|14270360|emb|AJ278250.1|HSA278250[14270360]

4979: AF297616
Homo sapiens natural killer cell receptor 2B4 gene, partial cds
gi|14268841|gb|AF297616.1|AF297616[14268841]

4980: AJ271068
Homo sapiens mRNA for transient receptor potential channel 6, variant delta377-431 (TRP6 gene)
gi|9716912|emb|AJ271068.1|HSA271068[9716912]

4981: AJ271067
Homo sapiens mRNA for transient receptor potential channel 6, variant delta316-431 (TRP6 gene)
gi|9716910|emb|AJ271067.1|HSA271067[9716910]

4982: AJ271066
Homo sapiens mRNA for transient receptor potential channel 6 (TRP6 gene)
gi|9716908|emb|AJ271066.1|HSA271066[9716908]

4983: X91852
H.sapiens P2Y4 gene
gi|1124904|emb|X91852.1|HSP2Y4[1124904]

4984: NM_032565
Homo sapiens emopamil binding related protein, delta8-delta7 sterol isomerase related protein (EBRP), mRNA
gi|14211872|ref|NM_032565.1|[14211872]

4986: AY029539
Homo sapiens soluble nectin1 gamma mRNA, complete cds
gi|14196221|gb|AY029539.1|[14196221]

4987: NM_006986
Homo sapiens melanoma antigen, family D, 1 (MAGED1), mRNA
gi|14195633|ref|NM_006986.2|[14195633]

4988: AF351784
Homo sapiens dopamine receptor interacting protein mRNA, partial cds gi|14194056|gb|AF351784.1|AF351784[14194056]

4989: AF336376
Homo sapiens platelet-derived growth factor D (PDGFD) mRNA, complete cds
gi|14193795|gb|AF336376.1|AF336376[14193795]

4992: AH010778
Homo sapiens CHRNA3 gene, partial sequence
gi|14190789|gb|AH010778.1|SEG_AY027913S[14190789]

4995: AH010779
Homo sapiens CHRNB4 gene, partial sequence
gi|14190786|gb|AH010779.1|SEG_AY027915S[14190786]

4996: AF310234
Homo sapiens sialic acid binding immunoglobulin-like lectin 8 (SIGLEC8) mRNA, complete cds, alternatively spliced
gi|14164614|gb|AF310234.1|AF310234[14164614]

4997: AF310233
Homo sapiens sialic acid binding immunoglobulin-like lectin 10 (SIGLEC10) mRNA, complete cds
gi|14164612|gb|AF310233.1|AF310233[14164612]

4998: AB060151
Homo sapiens slt mRNA for G protein-coupled receptor, complete cds
gi|14164382|dbj|AB060151.1|AB060151[14164382]

4999: AF239764
Homo sapiens EGF-like module-containing mucin-like receptor EMR3 mRNA, complete cds
gi|13183148|gb|AF239764.1|AF239764[13183148]

5000: AF199235
Homo sapiens nicotinic acetylcholine receptor subunit alpha 10 mRNA, complete cds
gi|11128455|gb|AF199235.2|AF199235[11128455]

5001: AF054176
Homo sapiens angiotensin/vasopressin receptor AII/AVP mRNA, complete cds
gi|3341995|gb|AF054176.1|AF054176[3341995]

5002: AF369213
Homo sapiens fibroblast growth factor receptor 3 IIIc isoform (FGFR3) mRNA, partial cds
gi|14161391|gb|AF369213.1|AF369213[14161391]

5003: AF369212
Homo sapiens fibroblast growth factor receptor 3 IIIc isoform (FGFR3) mRNA, partial cds
gi|14161389|gb|AF369212.1|AF369212[14161389]

5004: AF369211
Homo sapiens fibroblast growth factor receptor 3 IIIc isoform (FGFR3) mRNA, partial cds
gi|14161387|gb|AF369211.1|AF369211[14161387]

5005: AF274714
Homo sapiens oxysterol-binding protein-related protein (ORP1) mRNA, complete cds
gi|13183326|gb|AF274714.1|AF274714[13183326]

5034: NM_005959
Homo sapiens melatonin receptor 1B (MTNR1B), mRNA
gi|14141172|ref|NM_005959.2|[14141172]

5035: NM_005958
Homo sapiens melatonin receptor 1A (MTNR1A), mRNA
gi|14141171|ref|NM_005958.2|[14141171]

5036: AF366903
Homo sapiens MER receptor tyrosine kinase gene, exon 1 and partial cds
gi|14133725|gb|AF366903.1|AF366903[14133725]

5037: NM_002226
Homo sapiens jagged 2 (JAG2), mRNA gi|4504800|ref|NM_002226.1|[4504800]

5039: NM_009585
Homo sapiens angiotensin receptor 1 (AGTR1), transcript variant 2, mRNA
gi|14043067|ref|NM_009585.2|[14043067]

5040: NM_032049
Homo sapiens angiotensin receptor 1 (AGTR1), transcript variant 5, mRNA
gi|14043065|ref|NM_032049.1|[14043065]

5041: NM_031850
Homo sapiens angiotensin receptor 1 (AGTR1), transcript variant 4, mRNA
gi|14043063|ref|NM_031850.1|[14043063]

5042: NM_004835
Homo sapiens angiotensin receptor 1 (AGTR1), transcript variant 3, mRNA
gi|14043061|ref|NM_004835.2|[14043061]

5043: NM_000685
Homo sapiens angiotensin receptor 1 (AGTR1), transcript variant 1, mRNA
gi|14043060|ref|NM_000685.3|[14043060]

5044: NM_003965
Homo sapiens chemokine (C-C motif) receptor-like 2 (CCRL2), mRNA
gi|14043058|ref|NM_003965.2|[14043058]

5045: AJ298334
Homo sapiens mRNA for P2Y11 receptor (P2Y11 gene)
gi|12964589|emb|AJ298334.1|HSA298334[12964589]

5046: NM_000323
Homo sapiens ret proto-oncogene (multiple endocrine neoplasia and medullary thyroid carcinoma 1, Hirschsprung disease) (RET), transcript variant 1, mRNA
gi|10862704|ref|NM_000323.1|[10862704]

5047: NM_020975
Homo sapiens ret proto-oncogene (multiple endocrine neoplasia and medullary thyroid carcinoma 1, Hirschsprung disease) (RET), transcript variant 2, mRNA
gi|10862702|ref|NM_020975.1|[10862702]

5048: NM_020630
Homo sapiens ret proto-oncogene (multiple endocrine neoplasia and medullary thyroid carcinoma 1, Hirschsprung disease) (RET), transcript variant 4, mRNA
gi|10862700|ref|NM_020630.1|[10862700]

5049: NM_020629
Homo sapiens ret proto-oncogene (multiple endocrine neoplasia and medullary thyroid carcinoma 1, Hirschsprung disease) (RET), transcript variant 3, mRNA
gi|10862698|ref|NM_020629.1|[10862698]

5050: NM_002342
Homo sapiens lymphotoxin beta receptor (TNFR superfamily, member 3) (LTBR), mRNA
gi|4505038|ref|NM_002342.1|[4505038]

5051: AY032736
Homo sapiens alpha-2A adrenergic receptor (ADR2AR) gene, complete cds
gi|14029162|gb|AY032736.1|[14029162]

5052: AF322014
Homo sapiens growth hormone receptor gene, partial sequence
gi|14028657|gb|AF322014.1|AF322014S1[14028657]

5053: AF283321
Homo sapiens low density lipoprotein receptor-related protein 5 (LRP5) gene, exons 10 through 23 and complete cds
gi|14028617|gb|AF283321.1|AF283320S2[14028617]

5054: AF283320
Homo sapiens low density lipoprotein receptor-related protein 5 (LRP5) gene, exons 1 through 9
gi|14028616|gb|AF283320.1|AF283320S1[14028616]

5055: AH010745
Homo sapiens low density lipoprotein receptor-related protein 5 (LRP5) gene, complete cds gi|14028615|gb|AH010745.1|SEG_AF283320S[14028615]

5056: NM_017934
Homo sapiens pleckstrin homology domain interacting protein (PHIP), mRNA
gi|8923633|ref|NM_017934.1|[8923633]

5057: AF203386
Homo sapiens beta-2 adrenergic receptor (ADRB2) gene, complete cds
gi|6636495|gb|AF203386.1|AF203386[6636495]

5058: AF202305
Homo sapiens beta-2 andrenergic receptor gene, complete cds
gi|6573152|gb|AF202305.1|AF202305[6573152]

5059: AF169225
Homo sapiens beta-2-adrenergic receptor gene, complete cds
gi|5714687|gb|AF169225.1|AF169225[5714687]

5060: AF063657
Homo sapiens vascular endothelial growth factor receptor (FLT1) mRNA, complete cds
gi|3132830|gb|AF063657.1|AF063657[3132830]

5061: AF022049
Homo sapiens natural killer cell inhibitory receptor KIR3DL1 variant mRNA, complete cds
gi|2760898|gb|AF022049.1|AF022049[2760898]

5062: AF022048
Homo sapiens natural killer cell inhibitory receptor KIR2DL3 variant mRNA, complete cds
gi|2760896|gb|AF022048.1|AF022048[2760896]

5066: AF361880
Homo sapiens neurokinin-2 receptor gene, partial cds
gi|14010294|gb|AF361880.1|AF361880[14010294]

5068: AF209923
Homo sapiens orphan G-protein coupled receptor (GPRC5D) mRNA, complete cds
gi|8118039|gb|AF209923.1|AF209923[8118039]

5069: AF207989
Homo sapiens orphan G-protein coupled receptor (GPRC5C) mRNA, complete cds
gi|8118031|gb|AF207989.1|AF207989[8118031]

5070: AB018076
Homo sapiens hedgehog gene, exon 3 and complete cds
gi|13990993|dbj|AB018076.2|AB010092S3[13990993]

5071: SEG_AB010092S
Homo sapiens hedgehog gene
gi|13990992|dbj||SEG_AB010092S[13990992]

5072: NM_018980
Homo sapiens taste receptor, type 2, member 5 (TAS2R5), mRNA
gi|9507172|ref|NM_018980.1|[9507172]

5073: NM_016945
Homo sapiens taste receptor, type 2, member 16 (TAS2R16), mRNA
gi|8394394|ref|NM_016945.1|[8394394]

5074: AB018075
Homo sapiens hedgehog gene, exon 2
gi|3702725|dbj|AB018075.1|AB010092S2[3702725]

5075: AB010092
Homo sapiens hedgehog gene, exon 1
gi|2810977|dbj|AB010092.1|AB010092S1[2810977]

5076: AF130867
Homo sapiens smoothened mRNA, partial cds
gi|4732138|gb|AF130867.1|AF130867[4732138]

5077: AF363791

Homo sapiens histamine receptor H3S (HRH3) mRNA, complete cds
gi|13937081|gb|AF363791.1|AF363791[13937081]

5078: AF363452
Homo sapiens NK cell type I receptor protein 2B4 (CD244) mRNA, partial cds, alternatively spliced
gi|13937022|gb|AF363452.1|AF363452[13937022]

5079: AY029486
Homo sapiens G protein gamma subunit 13 mRNA, complete cds
gi|13936268|gb|AY029486.1|[13936268]

5080: AF224497
Homo sapiens CC chemokine receptor 3 (CCR3) gene, exon 2 and partial cds
gi|13924486|gb|AF224497.1|AF224496S2[13924486]

5081: AF224496
Homo sapiens CC chemokine receptor 3 (CCR3) gene, exon 1
gi|13924485|gb|AF224496.1|AF224496S1[13924485]

5082: AH010691
Homo sapiens CC chemokine receptor 3 (CCR3) gene, partial cds
gi|13924484|gb|AH010691.1|SEG_AF224496S[13924484]

5083: AF224495
Homo sapiens CC chemokine receptor 3 (CCR3) mRNA, partial cds
gi|13924481|gb|AF224495.1|AF224495[13924481]

5084: AF251120
Homo sapiens interleukin-1-related protein short isoform mRNA, complete cds; alternatively spliced
gi|10185739|gb|AF251120.1|AF251120[10185739]

5085: AF251119
Homo sapiens interleukin-1-related protein long isoform mRNA, complete cds; alternatively spliced
gi|10185737|gb|AF251119.1|AF251119[10185737]

5086: AF251118
Homo sapiens interleukin-1-related protein long isoform a mRNA, complete cds; alternatively spliced
gi|10185735|gb|AF251118.1|AF251118[10185735]

5087: AF103013
Homo sapiens JME clone 4 KIR3DL1-like natural killer cell receptor mRNA, complete cds
gi|3983423|gb|AF103013.1|AF103013[3983423]

5088: AF103012
Homo sapiens JME clone 3 KIR3DL1-like natural killer cell receptor mRNA, complete cds
gi|3983421|gb|AF103012.1|AF103012[3983421]

5089: AF103011
Homo sapiens JME clone 2 KIR3DL1-like natural killer cell receptor mRNA, complete cds
gi|3983419|gb|AF103011.1|AF103011[3983419]

5090: AF103010
Homo sapiens JME clone 1 KIR3DL1-like natural killer cell receptor mRNA, complete cds
gi|3983417|gb|AF103010.1|AF103010[3983417]

5091: AF353183
Homo sapiens discoidin domain receptor DDR1e (DDR1) mRNA, partial cds, alternatively spliced
gi|13898644|gb|AF353183.1|AF353183[13898644]

5092: AF353182
Homo sapiens discoidin domain receptor DDR1d (DDR1) mRNA, partial cds, alternatively spliced
gi|13898642|gb|AF353182.1|AF353182[13898642]

5096: AF014112
Homo sapiens phenol UDP-glucuronosyltransferase (UGT1A6) gene, partial cds gi|2645490|gb|AF014112.1|AF014112[2645490]

5097: AJ293654
Homo sapiens partial IL4RA gene for interleukin-4 receptor alfa chain, exon 11, ARSPRV allele
gi|12054061|emb|AJ293654.1|HSA293654[12054061]

5098: AJ293653
Homo sapiens partial IL4RA gene for interleukin-4 receptor alfa chain, exon 11, ACSPRV allele
gi|12054059|emb|AJ293653.1|HSA293653[12054059]

5099: AJ293652
Homo sapiens partial IL4RA gene for interleukin-4 receptor alfa chain, exon 11, ACSSRI allele
gi|12054057|emb|AJ293652.1|HSA293652[12054057]

5100: AJ293651
Homo sapiens partial IL4RA gene for interleukin-4 receptor alfa chain, exon 11, ECLPRV allele
gi|12054055|emb|AJ293651.1|HSA293651[12054055]

5101: AJ293650
Homo sapiens partial IL4RA gene for interleukin-4 receptor alfa chain, exon 11, ECSPRV allele
gi|12054053|emb|AJ293650.1|HSA293650[12054053]

5102: AJ293649
Homo sapiens partial IL4RA gene for interleukin-4 receptor alfa chain, exon 11, ECSSRV allele
gi|12054051|emb|AJ293649.1|HSA293649[12054051]

5103: AJ293648
Homo sapiens partial IL4RA gene for interleukin-4 receptor alfa chain, exon 11, ECSPQV allele
gi|12054049|emb|AJ293648.1|HSA293648[12054049]

5104: AJ293647

Homo sapiens partial IL4RA gene for interleukin-4 receptor alfa chain, exon 11, ECSSQV allele
gi|12054047|emb|AJ293647.1|HSA293647[12054047]

5105: AF329449
Homo sapiens histamine receptor H4 mRNA, complete cds
gi|13876643|gb|AF329449.1|AF329449[13876643]

5106: AF276893
Homo sapiens p21-activated protein kinase 6 (PAK6) mRNA, complete cds
gi|9082305|gb|AF276893.1|AF276893[9082305]

5107: AY029324
Homo sapiens mRNA sequence
gi|13752242|gb|AY029324.1|[13752242]

5108: AF307337
Homo sapiens ALPP, ALPPL2, ALPI, XCE, CHRND, and CHRNG genes, complete sequence
gi|10732831|gb|AF307337.1|AF307337[10732831]

5109: Z75190
H.sapiens mRNA for apolipoprotein E receptor 2
gi|1834533|emb|Z75190.1|HSZ75190[1834533]

5110: NM_004523
Homo sapiens kinesin-like 1 (KNSL1), mRNA
gi|13699823|ref|NM_004523.2|[13699823]

5111: NM_006646
Homo sapiens WAS protein family, member 3 (WASF3), mRNA
gi|13699802|ref|NM_006646.2|[13699802]

5112: NM_030667
Homo sapiens protein tyrosine phosphatase, receptor type, O (PTPRO), transcript variant 1, mRNA
gi|13677213|ref|NM_030667.1|[13677213]

5113: NM_002848
Homo sapiens protein tyrosine phosphatase, receptor type, O (PTPRO), transcript variant 2, mRNA
gi|13677212|ref|NM_002848.2|[13677212]

5114: NM_006990
Homo sapiens WAS protein family, member 2 (WASF2), mRNA
gi|11386182|ref|NM_006990.1|[11386182]

5115: AF250309
Homo sapiens putative cytokine receptor CRL4 precusor mRNA, complete cds
gi|13649476|gb|AF250309.1|AF250309[13649476]

5116: AY029180
Homo sapiens soluble urokinase plasminogen activator receptor precursor (SUPAR) mRNA, complete cds
gi|13641308|gb|AY029180.1|[13641308]

5117: AF346711
Homo sapiens G-protein couple receptor (GPR48) gene, exons 3 through 18, and complete cds
gi|13569576|gb|AF346711.1|AF346709S3[13569576]

5118: AF346710
Homo sapiens G-protein couple receptor (GPR48) gene, exon 2
gi|13569575|gb|AF346710.1|AF346709S2[13569575]

5119: AF346709
Homo sapiens G-protein couple receptor (GPR48) gene, exon 1
gi|13569574|gb|AF346709.1|AF346709S1[13569574]

5120: AH010608
Homo sapiens G-protein couple receptor (GPR48) gene, complete cds
gi|13569573|gb|AH010608.1|SEG_AF346709S[13569573]

5121: AF251059
Homo sapiens FGF receptor 4b mRNA, complete cds
gi|13625179|gb|AF251059.1|AF251059[13625179]

5122: AF251055
Homo sapiens 5-HT receptor mRNA, complete cds
gi|13625171|gb|AF251055.1|AF251055[13625171]

5123: NM_030905
Homo sapiens olfactory receptor, family 2, subfamily J, member 2 (OR2J2), mRNA
gi|13624330|ref|NM_030905.1|[13624330]

5124: NM_012377
Homo sapiens olfactory receptor, family 7, subfamily C, member 2 (OR7C2), mRNA
gi|13624324|ref|NM_012377.1|[13624324]

5125: AB043703
Homo sapiens FZD8 mRNA for seven-transmembrane receptor Frizzled-8, complete cds
gi|13623798|dbj|AB043703.1|AB043703[13623798]

5126: AB051851
Homo sapiens DR3 gene for death receptor 3, complete cds, mutant DR3 sequnce
gi|13537362|dbj|AB051851.1|AB051851[13537362]

5127: AB051850
Homo sapiens DR3 gene for death receptor 3, complete cds
gi|13537360|dbj|AB051850.1|AB051850[13537360]

5128: AF349939
Homo sapiens prolactin receptor isoform delta S1 precursor, mRNA, complete cds
gi|13605397|gb|AF349939.1|AF349939[13605397]

5130: AF346629
Homo sapiens channel-kinase 1 (CHAK1) mRNA, complete cds
gi|13562152|gb|AF346629.2|AF346629[13562152]

5131: NM_012373
Homo sapiens olfactory receptor, family 3, subfamily A, member 3 (OR3A3), mRNA
gi|13562103|ref|NM_012373.1|[13562103]

5132: AF056979
Homo sapiens clone YAN1 interferon-gamma receptor mRNA, complete cds
gi|13562048|gb|AF056979.1|AF056979[13562048]

5133: NM_017506
Homo sapiens olfactory receptor, family 7, subfamily C, member 1 (OR7C1), mRNA
gi|9506798|ref|NM_017506.1|[9506798]

5134: AF222689
Homo sapiens protein arginine N-methyltransferase 1 (HRMT1L2) gene, complete cds, alternatively spliced
gi|7453574|gb|AF222689.1|AF222689[7453574]

5135: NM_005137
Homo sapiens DiGeorge syndrome critical region gene 2 (DGCR2), mRNA
gi|4826693|ref|NM_005137.1|[4826693]

5136: AC002533
Homo sapiens clone SCb-24C13 from 7q31.3, complete sequence
gi|2388587|gb|AC002533.1|AC002533[2388587]

5139: AF263617
Homo sapiens killer cell immunoglobulin-like receptor 3DL2 (KIR3DL2) mRNA, KIR3DL2*00901 allele, complete cds
gi|13560454|gb|AF263617.1|AF263617[13560454]

5140: AF262974
Homo sapiens killer cell immunoglobulin-like receptor 3DL1 (KIR3DL1) mRNA, KIR3DL1*00801 allele, complete cds
gi|13560452|gb|AF262974.1|AF262974[13560452]

5141: AF262973
Homo sapiens killer cell immunoglobulin-like receptor 3DL1 (KIR3DL1) mRNA, KIR3DL1*00701 allele, complete cds
gi|13560450|gb|AF262973.1|AF262973[13560450]

5142: AF262972

Homo sapiens killer cell immunoglobulin-like receptor 3DL1 (KIR3DL1) mRNA, KIR3DL1*00601 allele, partial cds
gi|13560448|gb|AF262972.1|AF262972[13560448]

5143: AF262971
Homo sapiens killer cell immunoglobulin-like receptor 3DL1 (KIR3DL1) mRNA, KIR3DL1*00501 allele, partial cds
gi|13560446|gb|AF262971.1|AF262971[13560446]

5144: AF262970
Homo sapiens killer cell immunoglobulin-like receptor 3DL1 (KIR3DL1) mRNA, KIR3DL1*00402 allele, partial cds
gi|13560444|gb|AF262970.1|AF262970[13560444]

5145: AF262969
Homo sapiens killer cell immunoglobulin-like receptor 3DL1 (KIR3DL1) mRNA, KIR3DL1*00401 allele, partial cds
gi|13560442|gb|AF262969.1|AF262969[13560442]

5146: AF262968
Homo sapiens killer cell immunoglobulin-like receptor 3DL1 (KIR3DL1) mRNA, KIR3DL1*00102 allele, partial cds
gi|13560440|gb|AF262968.1|AF262968[13560440]

5147: AF262967
Homo sapiens killer cell immunoglobulin-like receptor 3DL2 (KIR3DL2) mRNA, KIR3DL2*00801 allele, complete cds
gi|13560438|gb|AF262967.1|AF262967[13560438]

5148: AF262966
Homo sapiens killer cell immunoglobulin-like receptor 3DL2 (KIR3DL2) mRNA, KIR3DL2*00601 allele, partial cds
gi|13560436|gb|AF262966.1|AF262966[13560436]

5149: AF262965
Homo sapiens killer cell immunoglobulin-like receptor 3DL2 (KIR3DL2) mRNA, KIR3DL2*00701 allele, partial cds
gi|13560434|gb|AF262965.1|AF262965[13560434]

5150: AF348491
Homo sapiens chemokine receptor CXCR4 mRNA, complete cds
gi|13549089|gb|AF348491.1|AF348491[13549089]

5151: AF295368
Homo sapiens G-protein coupled receptor GPR86 (GPR86) mRNA, complete cds
gi|12711484|gb|AF295368.1|AF295368[12711484]

5152: AF237763
Homo sapiens orphan G protein-coupled receptor 87 (GPR87) mRNA, complete cds
gi|12711472|gb|AF237763.1|AF237763[12711472]

5153: AF237762
Homo sapiens orphan G protein-coupled receptor 84 (GPR84) mRNA, complete cds
gi|12711470|gb|AF237762.1|AF237762[12711470]

5154: NM_004248
Homo sapiens G protein-coupled receptor 10 (GPR10), mRNA
gi|4758473|ref|NM_004248.1|[4758473]

5155: AC000099
Homo sapiens chromosome 7 map 7q31.3 cosmid g0771a003, complete sequence
gi|1764159|gb|AC000099.1|HSAC000099[1764159]

5156: NM_030784
Homo sapiens brain expressed G-protein-coupled receptor PSP24 beta (PSP24B), mRNA
gi|13540556|ref|NM_030784.1|[13540556]

5157: NM_030774
Homo sapiens prostate specific G-protein coupled receptor (PSGR), mRNA
gi|13540538|ref|NM_030774.1|[13540538]

5158: NM_030764
Homo sapiens SH2 domain-containing phosphatase anchor protein 1 (SPAP1), mRNA
gi|13540524|ref|NM_030764.1|[13540524]

5160: AJ249921
Homo sapiens intergenic region between apoE and apoCI genes
gi|6006507|emb|AJ249921.1|HSA249921[6006507]

5161: AF050737
Homo sapiens dopamine D2 receptor (DRD2) gene, complete cds
gi|3820491|gb|AF050737.1|AF050737[3820491]

5162: NM_004987
Homo sapiens LIM and senescent cell antigen-like domains 1 (LIMS1), mRNA
gi|13518025|ref|NM_004987.2|[13518025]

5163: AF348078
Homo sapiens G-protein coupled receptor 91 (GPR91) mRNA, complete cds
gi|13517982|gb|AF348078.1|AF348078[13517982]

5164: AJ276125
Homo sapiens mRNA for inhibitory NK receptor (kir3d gene)
gi|13516222|emb|AJ276125.1|HSA276125[13516222]

5165: AF246999
Homo sapiens TRADEbeta mRNA, complete cds
gi|13506909|gb|AF246999.1|AF246999[13506909]

5166: AF246998
Homo sapiens TRADEalpha mRNA, complete cds
gi|13506907|gb|AF246998.1|AF246998[13506907]

5167: AF263450
Homo sapiens dopamine D3 receptor (DRD3) gene, exon 2 and partial cds
gi|13506728|gb|AF263450.1|AF148807S2[13506728]

5168: AF148807
Homo sapiens dopamine D3 receptor (DRD3) gene, exon 1
gi|13506727|gb|AF148807.1|AF148807S1[13506727]

5169: AH010591
Homo sapiens dopamine D3 receptor (DRD3) gene, partial cds
gi|13506726|gb|AH010591.1|SEG_AF148807S[13506726]

5170: Y18388
Homo sapiens CD163 gene, exon 1 and joined CDS
gi|5107944|emb|Y18388.1|HSA118388[5107944]

5171: NM_002183
Homo sapiens interleukin 3 receptor, alpha (low affinity) (IL3RA), mRNA
gi|13324709|ref|NM_002183.1|[13324709]

5172: AF142570
Homo sapiens cytokine receptor CRL2 precusor (CRL2) mRNA, complete cds
gi|11055018|gb|AF142570.1|AF142570[11055018]

5173: NM_006140
Homo sapiens colony stimulating factor 2 receptor, alpha, low-affinity (granulocyte-macrophage) (CSF2RA), mRNA
gi|5453626|ref|NM_006140.1|[5453626]

5174: NM_002186
Homo sapiens interleukin 9 receptor (IL9R), mRNA
gi|4504684|ref|NM_002186.1|[4504684]

5175: AF296673
Homo sapiens toll-like receptor 10 mRNA, complete cds
gi|13447752|gb|AF296673.1|AF296673[13447752]

5176: AF284095
Homo sapiens alpha-2A adrenergic receptor mRNA, complete cds
gi|13447750|gb|AF284095.1|AF284095[13447750]

5177: AF279689
Homo sapiens fibroblast growth factor receptor 5 (FGFR5) mRNA, complete cds
gi|13447748|gb|AF279689.1|AF279689[13447748]

5178: NM_000861
Homo sapiens histamine receptor H1 (HRH1), mRNA
gi|13435403|ref|NM_000861.2|[13435403]

5179: NM_001514
Homo sapiens general transcription factor IIB (GTF2B), mRNA
gi|13435384|ref|NM_001514.2|[13435384]

5180: NM_022845
Homo sapiens core-binding factor, beta subunit (CBFB), transcript variant 1, mRNA
gi|13124880|ref|NM_022845.1|[13124880]

5181: AF213460
Homo sapiens ephrin receptor EPHA3 secreted form (EPHA3) mRNA, complete cds
gi|12003436|gb|AF213460.1|AF213460[12003436]

5182: AF213459
Homo sapiens ephrin receptor EPHA3 complete form (EPHA3) mRNA, complete cds
gi|12003434|gb|AF213459.1|AF213459[12003434]

5183: NM_019599
Homo sapiens taste receptor, type 2, member 1 (TAS2R1), mRNA
gi|9625042|ref|NM_019599.1|[9625042]

5184: NM_017579
Homo sapiens deleted in malignant brain tumors 1 (DMBT1), transcript variant 3, mRNA
gi|8923739|ref|NM_017579.1|[8923739]

5185: AJ306481
Homo sapiens partial CHRNA5 gene for neuronal nicotinic acetylcholine receptor alpha-5 subunit, exon 1 and joined CDS
gi|13400975|emb|AJ306481.1|HSA306481[13400975]

5186: AJ306454
Homo sapiens partial CHRNB4 gene for neuronal nicotinic acetylcholine receptor beta-4 subunit, exon 1 and joined CDS gi|13400963|emb|AJ306454.1|HSA306454[13400963]

5187: NM_024317
Homo sapiens immunoglobulin-like transcript 10 (ILT10), mRNA
gi|13399319|ref|NM_024317.1|[13399319]

5188: NM_020070
Homo sapiens immunoglobulin lambda-like polypeptide 1 (IGLL1), mRNA
gi|13399297|ref|NM_020070.1|[13399297]

5189: NM_002383
Homo sapiens MYC-associated zinc finger protein (purine-binding transcription factor) (MAZ), mRNA
gi|13399295|ref|NM_002383.1|[13399295]

5190: AJ306486
Homo sapiens partial CHRNA5 gene for neuronal nicotinic acetylcholine receptor alpha-5 subunit, exon 6
gi|13399189|emb|AJ306486.1|HSA306486[13399189]

5191: AJ306485
Homo sapiens partial CHRNA5 gene for neuronal nicotinic acetylcholine receptor alpha-5 subunit, exon 5
gi|13399188|emb|AJ306485.1|HSA306485[13399188]

5192: AJ306484
Homo sapiens partial CHRNA5 gene for neuronal nicotinic acetylcholine receptor alpha-5 subunit, exon 4
gi|13399187|emb|AJ306484.1|HSA306484[13399187]

5193: AJ306483
Homo sapiens partial CHRNA5 gene for neuronal nicotinic acetylcholine receptor alpha-5 subunit, exon 3
gi|13399186|emb|AJ306483.1|HSA306483[13399186]

5194: AJ306482
Homo sapiens partial CHRNA5 gene for neuronal nicotinic acetylcholine receptor alpha-5 subunit, exon 2

5195: AJ306459
Homo sapiens partial CHRNB4 gene for neuronal nicotinic acetylcholine receptor beta-4 subunit, exon 6
gi|13399184|emb|AJ306459.1|HSA306459[13399184]

5196: AJ306458
Homo sapiens partial CHRNB4 gene for neuronal nicotinic acetylcholine receptor beta-4 subunit, exon 5
gi|13399183|emb|AJ306458.1|HSA306458[13399183]

5197: AJ306457
Homo sapiens partial CHRNB4 gene for neuronal nicotinic acetylcholine receptor beta-4 subunit, exon 4
gi|13399182|emb|AJ306457.1|HSA306457[13399182]

5198: AJ306456
Homo sapiens partial CHRNB4 gene for neuronal nicotinic acetylcholine receptor beta-4 subunit, exon 3
gi|13399181|emb|AJ306456.1|HSA306456[13399181]

5199: AJ306455
Homo sapiens partial CHRNB4 gene for neuronal nicotinic acetylcholine receptor beta-4 subunit, exon 2
gi|13399180|emb|AJ306455.1|HSA306455[13399180]

5200: AJ291675
Homo sapiens mRNA for putative GDNF family receptor alpha 4, secreted isoform c (GFRA4 gene)
gi|12038960|emb|AJ291675.1|HSA291675[12038960]

5201: AJ291674
Homo sapiens mRNA for putative GDNF family receptor alpha 4, GPI anchored isoform b (GFRA4 gene)
gi|12038958|emb|AJ291674.1|HSA291674[12038958]

5202: AJ291673

Homo sapiens mRNA for GDNF family receptor alpha 4, GPI anchored isoform (GFRA4 gene)
gi|12038956|emb|AJ291673.1|HSA291673[12038956]

5203: AF245704
Homo sapiens toll-like receptor 9 (TLR9) mRNA, complete cds
gi|8575528|gb|AF245704.1|AF245704[8575528]

5204: AF245703
Homo sapiens toll-like receptor 8 (TLR8) mRNA, complete cds
gi|8575526|gb|AF245703.1|AF245703[8575526]

5205: AF245702
Homo sapiens toll-like receptor 7 (TLR7) mRNA, complete cds
gi|8575524|gb|AF245702.1|AF245702[8575524]

5206: NM_016944
Homo sapiens taste receptor, type 2, member 4 (TAS2R4), mRNA
gi|8394401|ref|NM_016944.1|[8394401]

5207: NM_016943
Homo sapiens taste receptor, type 2, member 3 (TAS2R3), mRNA
gi|8394397|ref|NM_016943.1|[8394397]

5209: AF307776
Homo sapiens beta-1 adrenergic receptor gene, 5' UTR and partial cds
gi|11837864|gb|AF307776.1|AF307776[11837864]

5210: AB026043
Homo sapiens mRNA for MS4A7, complete cds
gi|11559249|dbj|AB026043.1|AB026043[11559249]

5211: AB013104
Homo sapiens mRNA for MS4A6, complete cds
gi|11559215|dbj|AB013104.1|AB013104[11559215]

5212: AB013103

Homo sapiens mRNA for MS4A5, complete cds
gi|11559213|dbj|AB013103.1|AB013103[11559213]

5213: AB013102
Homo sapiens mRNA for MS4A4, complete cds
gi|11559211|dbj|AB013102.1|AB013102[11559211]

5215: NM_003789
Homo sapiens TNFRSF1A-associated via death domain (TRADD), mRNA
gi|13378136|ref|NM_003789.1|[13378136]

5216: NM_025218
Homo sapiens UL16-binding protein 1 (ULBP1), mRNA
gi|13376825|ref|NM_025218.1|[13376825]

5217: NM_025217
Homo sapiens UL16-binding protein 2 (ULBP2), mRNA
gi|13376823|ref|NM_025217.1|[13376823]

5218: NM_024518
Homo sapiens UL16-binding protein 3 (ULBP3), mRNA
gi|13375655|ref|NM_024518.1|[13375655]

5220: AB052103
Homo sapiens SRCL mRNA for scavenger receptor with C-type lectin type II, complete cds
gi|13365552|dbj|AB052103.1|AB052103[13365552]

5221: AB038518
Homo sapiens SRCL mRNA for scavenger receptor with C-type lectin type I, complete cds
gi|13365514|dbj|AB038518.1|AB038518[13365514]

5222: NM_021708
Homo sapiens leukocyte-associated Ig-like receptor 1 (LAIR1), transcript variant d, mRNA
gi|11231178|ref|NM_021708.1|[11231178]

5223: NM_021706
Homo sapiens leukocyte-associated Ig-like receptor 1 (LAIR1), transcript variant b, mRNA
gi|11231176|ref|NM_021706.1|[11231176]

5224: NM_002287
Homo sapiens leukocyte-associated Ig-like receptor 1 (LAIR1), transcript variant a, mRNA
gi|11231175|ref|NM_002287.2|[11231175]

5225: AB038237
Homo sapiens mRNA for G protein-coupled receptor C5L2, complete cds
gi|7707800|dbj|AB038237.1|AB038237[7707800]

5226: S82756
Homo sapiens T cell receptor (Vbeta8.2-N1DbetaN2-Jbeta1.6) mRNA, partial cds
gi|1835847|gb|S82756.1|S82756[1835847]

5227: S82754
Homo sapiens T cell receptor mRNA, partial cds
gi|1835843|gb|S82754.1|S82754[1835843]

5233: NM_024318
Homo sapiens immunoglobulin-like transcript 8 (ILT8), mRNA
gi|13324689|ref|NM_024318.1|[13324689]

5234: AF178982
Homo sapiens putative G protein-coupled receptor GPCR1 precursor, mRNA, complete cds
gi|13324450|gb|AF178982.1|AF178982[13324450]

5236: NM_021956
Homo sapiens glutamate receptor, ionotropic, kainate 2 (GRIK2), mRNA
gi|11386136|ref|NM_021956.1|[11386136]

5237: NM_018724
Homo sapiens interleukin 20 (IL20), mRNA
gi|11036633|ref|NM_018724.1|[11036633]

5238: AJ295846
Homo sapiens mRNA for endosialin protein
gi|13277300|emb|AJ295846.1|HSA295846[13277300]

5242: AF310249
Homo sapiens peroxisome proliferator activated receptor gamma 2 gene, upstream sequence
gi|13274397|gb|AF310249.1|AF310249[13274397]

5243: AF321815
Homo sapiens G-protein coupled receptor SP1999 mRNA, complete cds
gi|12656597|gb|AF321815.1|AF321815[12656597]

5244: AL136818
Homo sapiens mRNA; cDNA DKFZp434F1726 (from clone DKFZp434F1726)
gi|12053146|emb|AL136818.1|HSM801786[12053146]

5245: AF285440
Homo sapiens clone KIR2DS4v1 killer-cell Ig-like receptor mRNA, complete cds
gi|11385699|gb|AF285440.1|AF285440[11385699]

5246: AF285439
Homo sapiens clone KIR2DS2v2 killer-cell Ig-like receptor mRNA, complete cds
gi|11385697|gb|AF285439.1|AF285439[11385697]

5247: AF285438
Homo sapiens clone KIR2DS2v1 killer-cell Ig-like receptor mRNA, partial cds
gi|11385695|gb|AF285438.1|AF285438[11385695]

5248: AF285437
Homo sapiens clone KIR2DS1v2 killer-cell Ig-like receptor mRNA, partial cds
gi|11385693|gb|AF285437.1|AF285437[11385693]

5249: AF285436
Homo sapiens clone KIR2DL4v4 killer-cell Ig-like receptor mRNA, complete cds
gi|11385691|gb|AF285436.1|AF285436[11385691]

5250: AF285435
Homo sapiens clone KIR2DL3v2 killer-cell Ig-like receptor mRNA, partial cds
gi|11385689|gb|AF285435.1|AF285435[11385689]

5251: AF285434
Homo sapiens clone KIR2DL2v2 killer-cell Ig-like receptor mRNA, partial cds
gi|11385687|gb|AF285434.1|AF285434[11385687]

5252: AF285433
Homo sapiens clone KIR2DL2v1 killer-cell Ig-like receptor mRNA, partial cds
gi|11385685|gb|AF285433.1|AF285433[11385685]

5253: AF285432
Homo sapiens clone KIR2DL1v3 killer-cell Ig-like receptor mRNA, partial cds
gi|11385683|gb|AF285432.1|AF285432[11385683]

5254: AF285431
Homo sapiens clone KIR2DL1v2 killer-cell Ig-like receptor mRNA, complete cds
gi|11385681|gb|AF285431.1|AF285431[11385681]

5255: AJ245872
Homo sapiens mRNA for putative truncated metabotropic glutamatereceptor 6 form
b, partial (tr-mGluR6 b)
gi|6688173|emb|AJ245872.1|HSA245872[6688173]

5256: AJ245871
Homo sapiens mRNA for putative truncated metabotropic glutamatereceptor 6 form
a, partial (tr-mGluR6 a)
gi|6688171|emb|AJ245871.1|HSA245871[6688171]

5258: AL050262
Homo sapiens mRNA; cDNA DKFZp564I0682 (from clone DKFZp564I0682); complete cds
gi|4886482|emb|AL050262.1|HSM800268[4886482]

5259: AF308820
Homo sapiens adrenocorticotropin receptor gene, upstream sequence gi|13272368|gb|AF308820.1|AF308820[13272368]

5260: NM_014432
Homo sapiens interleukin 20 receptor, alpha (IL20RA), mRNA
gi|7657690|ref|NM_014432.1|[7657690]

5261: NM_004967
Homo sapiens integrin-binding sialoprotein (bone sialoprotein, bone sialoprotein II) (IBSP), mRNA
gi|13259536|ref|NM_004967.2|[13259536]

5270: AF348323
Homo sapiens nociceptin receptor (ORL1) mRNA, complete cds
gi|13022242|gb|AF348323.1|AF348323[13022242]

5272: S79217
Homo sapiens Ca(2+)-sensing receptor mRNA, partial cds
gi|1050985|gb|S79217.1|S79217[1050985]

5273: S78723
Homo sapiens serotonin 5-HT2A receptor (5-HT2A R) gene, partial cds
gi|1042173|gb|S78723.1|S78723[1042173]

5274: S78505
Homo sapiens prolactin receptor mRNA, partial cds
gi|999114|gb|S78505.1|S78505[999114]

5277: S77555
Homo sapiens corticotropin receptor/ACTH receptor gene, partial cds
gi|957294|gb|S77555.1|S77555[957294]

5278: NM_024012
Homo sapiens 5-hydroxytryptamine (serotonin) receptor 5A (HTR5A), mRNA
gi|13236496|ref|NM_024012.1|[13236496]

5279: NM_021904
Homo sapiens gamma-aminobutyric acid (GABA) B receptor, 1 (GABBR1), transcript variant 3, mRNA
gi|11497613|ref|NM_021904.1|[11497613]

5280: NM_021903
Homo sapiens gamma-aminobutyric acid (GABA) B receptor, 1 (GABBR1), transcript variant 2, mRNA
gi|11497611|ref|NM_021903.1|[11497611]

5281: NM_001470
Homo sapiens gamma-aminobutyric acid (GABA) B receptor, 1 (GABBR1), transcript variant 1, mRNA
gi|10835014|ref|NM_001470.1|[10835014]

5282: NM_007329
Homo sapiens deleted in malignant brain tumors 1 (DMBT1), transcript variant 2, mRNA
gi|6633800|ref|NM_007329.1|[6633800]

5283: S71404
Homo sapiens interleukin-9 receptor mRNA, partial cds
gi|551356|gb|S71404.1|S71404[551356]

5356: NM_023031
Homo sapiens fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) (FGFR2), transcript variant 13, mRNA
gi|13186272|ref|NM_023031.1|[13186272]

5357: NM_023030
Homo sapiens fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) (FGFR2), transcript variant 12, mRNA
gi|13186270|ref|NM_023030.1|[13186270]

5358: NM_023028
Homo sapiens fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) (FGFR2), transcript variant 10, mRNA
gi|13186268|ref|NM_023028.1|[13186268]

5359: NM_022976
Homo sapiens fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) (FGFR2), transcript variant 9, mRNA
gi|13186266|ref|NM_022976.1|[13186266]

5360: NM_022975
Homo sapiens fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) (FGFR2), transcript variant 8, mRNA
gi|13186264|ref|NM_022975.1|[13186264]

5361: NM_022974
Homo sapiens fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) (FGFR2), transcript variant 7, mRNA
gi|13186262|ref|NM_022974.1|[13186262]

5362: NM_022973
Homo sapiens fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) (FGFR2), transcript variant 6, mRNA
gi|13186260|ref|NM_022973.1|[13186260]

5363: NM_022972
Homo sapiens fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) (FGFR2), transcript variant 5, mRNA
gi|13186258|ref|NM_022972.1|[13186258]

5364: NM_022971

Homo sapiens fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) (FGFR2), transcript variant 4, mRNA
gi|13186256|ref|NM_022971.1|[13186256]

5365: NM_022970
Homo sapiens fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) (FGFR2), transcript variant 3, mRNA
gi|13186254|ref|NM_022970.1|[13186254]

5366: NM_022969
Homo sapiens fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) (FGFR2), transcript variant 2, mRNA
gi|13186252|ref|NM_022969.1|[13186252]

5367: NM_023029
Homo sapiens fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) (FGFR2), transcript variant 11, mRNA
gi|13186242|ref|NM_023029.1|[13186242]

5368: NM_000141
Homo sapiens fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) (FGFR2), transcript variant 1, mRNA
gi|13186239|ref|NM_000141.2|[13186239]

5369: AF312678
Homo sapiens FGF homologous factor receptor (FHFR) mRNA, complete cds
gi|13183617|gb|AF312678.1|AF312678[13183617]

5370: AF243385
Homo sapiens beta-2 syntrophin mRNA, complete cds, alternatively spliced gi|13183299|gb|AF243385.1|AF243385[13183299]

5371: M97191
Homo sapiens Sp3 protein mRNA, partial cds
gi|13162672|gb|M97191.2|HUMSP3A[13162672]

5474: NM_024075
Homo sapiens LENG5 protein (LENG5), mRNA
gi|13129061|ref|NM_024075.1|[13129061]

5475: AF304379
Homo sapiens ULBP3 protein mRNA, complete cds
gi|13128926|gb|AF304379.1|AF304379[13128926]

5476: AF304378
Homo sapiens ULBP2 protein mRNA, complete cds
gi|13128924|gb|AF304378.1|AF304378[13128924]

5477: AF304377
Homo sapiens ULBP1 protein mRNA, complete cds
gi|13128922|gb|AF304377.1|AF304377[13128922]

5481: AF000549
AF000549 Human Homo sapiens genomic clone P1 clone DMPC-HFF#1-1075-D9, genomic survey sequence
gi|2232072|gb|AF000549.1|AF000549[2232072]

5482: NM_001755
Homo sapiens core-binding factor, beta subunit (CBFB), transcript variant 2, mRNA
gi|13124872|ref|NM_001755.1|[13124872]

5483: AF172398
Homo sapiens junctional adhesion molecule-1 mRNA, complete cds
gi|13124448|gb|AF172398.2|AF172398[13124448]

5484: AF317655

Homo sapiens G protein-coupled receptor (GPR77) gene, complete cds
gi|13122466|gb|AF317655.1|AF317655[13122466]

5485: AF317653
Homo sapiens G protein-coupled receptor (GPR62) gene, complete cds
gi|13122462|gb|AF317653.1|AF317653[13122462]

5486: AF317652
Homo sapiens G protein-coupled receptor (GPR61) mRNA, complete cds
gi|13122460|gb|AF317652.1|AF317652[13122460]

5487: NM_022036
Homo sapiens G protein-coupled receptor, family C, group 5, member C (GPRC5C), transcript variant 1, mRNA
gi|13112058|ref|NM_022036.1|[13112058]

5488: NM_018653
Homo sapiens G protein-coupled receptor, family C, group 5, member C (GPRC5C), transcript variant 2, mRNA
gi|13112056|ref|NM_018653.2|[13112056]

5489: NM_000707
Homo sapiens arginine vasopressin receptor 1B (AVPR1B), mRNA
gi|13112055|ref|NM_000707.2|[13112055]

5490: NM_000706
Homo sapiens arginine vasopressin receptor 1A (AVPR1A), mRNA
gi|13112054|ref|NM_000706.2|[13112054]

5491: NM_021923
Homo sapiens fibroblast growth factor receptor-like 1 (FGFRL1), mRNA
gi|13112053|ref|NM_021923.2|[13112053]

5492: NM_002011
Homo sapiens fibroblast growth factor receptor 4 (FGFR4), transcript variant 1, mRNA
gi|13112051|ref|NM_002011.2|[13112051]

5493: NM_022963
Homo sapiens fibroblast growth factor receptor 4 (FGFR4), transcript variant 2, mRNA
gi|13112049|ref|NM_022963.1|[13112049]

5494: NM_022965
Homo sapiens fibroblast growth factor receptor 3 (achondroplasia, thanatophoric dwarfism) (FGFR3), transcript variant 2, mRNA
gi|13112047|ref|NM_022965.1|[13112047]

5495: NM_000142
Homo sapiens fibroblast growth factor receptor 3 (achondroplasia, thanatophoric dwarfism) (FGFR3), transcript variant 1, mRNA
gi|13112046|ref|NM_000142.2|[13112046]

5496: NM_022336
Homo sapiens ectodysplasin 1, anhidrotic receptor (EDAR), mRNA
gi|11641230|ref|NM_022336.1|[11641230]

5497: NM_018654
Homo sapiens G protein-coupled receptor, family C, group 5, member D (GPRC5D), mRNA
gi|8923704|ref|NM_018654.1|[8923704]

5498: AF312230
Homo sapiens histamine receptor H4 subtype mRNA, complete cds
gi|13094918|gb|AF312230.1|AF312230[13094918]

5504: AY016370
Homo sapiens hnRNPA1 pseudogene, complete sequence; and CC chemokine receptor 8 (CCR8) and CX3C chemokine receptor 1 (CX3CR1) genes, complete cds
gi|13027668|gb|AY016370.1|[13027668]

5505: E32517
Scavenger receptor-like protein
gi|13026764|dbj|E32517.1|E32517[13026764]

5506: E32511
Scavenger receptor-like protein
gi|13026758|dbj|E32511.1|E32511[13026758]

5507: E32510
Scavenger receptor-like protein
gi|13026757|dbj|E32510.1|E32510[13026757]

5508: E32509
Scavenger receptor-like protein
gi|13026756|dbj|E32509.1|E32509[13026756]

5509: E32504
Scavenger receptor-like protein
gi|13026751|dbj|E32504.1|E32504[13026751]

5510: E32503
Scavenger receptor-like protein
gi|13026750|dbj|E32503.1|E32503[13026750]

5511: E60222
Melatonin receptor expressing cell and utilization thereof
gi|13025812|dbj|E60222.1|E60222[13025812]

5512: E36078
cDNA clone HNEAA81 encoding human seven-pass transmembrane receptor
gi|13022480|dbj|E36078.1|E36078[13022480]

5522: AJ309545
Homo sapiens mRNA for T-cell receptor alpha chain, clone 57LSK10 (Va2, Ja45)
gi|13016702|emb|AJ309545.1|HSA309545[13016702]

5523: AF323176
Homo sapiens death receptor-interacting protein mRNA, complete cds
gi|12964787|gb|AF323176.1|AF323176[12964787]

5524: AF329496

Homo sapiens immunoglobulin kappa light chain gene, partial cds
gi|12963392|gb|AF329496.1|AF329496[12963392]

5529: NM_015717
Homo sapiens Langerhans cell specific c-type lectin (LANGERIN), mRNA
gi|7657290|ref|NM_015717.1|[7657290]

5530: NM_012329
Homo sapiens monocyte to macrophage differentiation-associated (MMD), mRNA
gi|6912507|ref|NM_012329.1|[6912507]

5571: AH009956
Homo sapiens chromosome 12 clone pacHRARg map 12q13
gi|12746591|gb|AH009956.2|SEG_AF311283S[12746591]

5573: AF230330
Homo sapiens angiopoietin-related protein 5 (ARP5) mRNA, complete cds
gi|12743935|gb|AF230330.1|AF230330[12743935]

5574: AF316895
Homo sapiens alpha 2B adrenergic receptor (ADRA2B) gene, complete cds
gi|12698669|gb|AF316895.1|AF316895[12698669]

5575: NM_021905
Homo sapiens gamma-aminobutyric acid (GABA) B receptor, 1 (GABBR1), transcript variant 4, mRNA
gi|11497615|ref|NM_021905.1|[11497615]

5578: NM_016730
Homo sapiens folate receptor 1 (adult) (FOLR1), transcript variant 3, mRNA
gi|9257214|ref|NM_016730.1|[9257214]

5579: NM_016729
Homo sapiens folate receptor 1 (adult) (FOLR1), transcript variant 4, mRNA
gi|9257212|ref|NM_016729.1|[9257212]

5580: NM_016725
Homo sapiens folate receptor 1 (adult) (FOLR1), transcript variant 1, mRNA gi|9257206|ref|NM_016725.1|[9257206]

5581: NM_016724
Homo sapiens folate receptor 1 (adult) (FOLR1), transcript variant 7, mRNA
gi|9257204|ref|NM_016724.1|[9257204]

5582: NM_004406
Homo sapiens deleted in malignant brain tumors 1 (DMBT1), transcript variant 1, mRNA
gi|4758169|ref|NM_004406.1|[4758169]

5583: L27609
Homo sapiens T-cell receptor beta gene, partial cds
gi|457265|gb|L27609.1|HUMTCRBD[457265]

5584: U65905
U65905 Human Homo sapiens genomic, genomic survey sequence
gi|1743863|gb|U65905.1|U65905[1743863]

5585: U65904
U65904 Human Homo sapiens genomic, genomic survey sequence
gi|1743862|gb|U65904.1|U65904[1743862]

5586: U65903
U65903 Human Homo sapiens genomic, genomic survey sequence
gi|1743861|gb|U65903.1|U65903[1743861]

5587: NM_016731
Homo sapiens folate receptor 1 (adult) (FOLR1), transcript variant 8, mRNA
gi|12719454|ref|NM_016731.2|[12719454]

5588: AF316870
Homo sapiens T cell receptor beta chain variable region mRNA, partial cds
gi|12711595|gb|AF316870.1|AF316870[12711595]

5589: AX074315
Sequence 29 from Patent WO0104310 gi|12710501|emb|AX074315.1|AX074315[12710501]

5590: AX074314
Sequence 28 from Patent WO0104310
gi|12710500|emb|AX074314.1|AX074314[12710500]

5591: NM_022113
Homo sapiens kinesin family member 13A (KIF13A), mRNA
gi|11545828|ref|NM_022113.1|[11545828]

5592: AF283296
Homo sapiens interleukin-15 receptor alpha gene, 5' regulatory region and exon 1, partial sequence
gi|9965299|gb|AF283296.1|AF283296[9965299]

5593: NM_014688
Homo sapiens related to the N terminus of tre (RNTRE), mRNA
gi|7661863|ref|NM_014688.1|[7661863]

5594: NM_000916
Homo sapiens oxytocin receptor (OXTR), mRNA
gi|12707575|ref|NM_000916.2|[12707575]

5595: NM_000915
Homo sapiens oxytocin, prepro- (neurophysin I) (OXT), mRNA
gi|12707574|ref|NM_000915.2|[12707574]

5596: NM_004961
Homo sapiens gamma-aminobutyric acid (GABA) A receptor, epsilon (GABRE), transcript variant 1, mRNA
gi|12707559|ref|NM_004961.2|[12707559]

5597: NM_021990
Homo sapiens gamma-aminobutyric acid (GABA) A receptor, epsilon (GABRE), transcript variant 4, mRNA
gi|12707557|ref|NM_021990.1|[12707557]

5598: NM_021987
Homo sapiens gamma-aminobutyric acid (GABA) A receptor, epsilon (GABRE), transcript variant 3, mRNA
gi|12707555|ref|NM_021987.1|[12707555]

5599: NM_021984
Homo sapiens gamma-aminobutyric acid (GABA) A receptor, epsilon (GABRE), transcript variant 2, mRNA
gi|12707553|ref|NM_021984.1|[12707553]

5600: AY011291
Homo sapiens beta-2 adrenergic receptor (ADRB2) gene, partial cds
gi|12699005|gb|AY011291.1|[12699005]

5601: AF316894
Homo sapiens alpha 2A adrenergic receptor (ADRA2A) gene, complete cds
gi|12698667|gb|AF316894.1|AF316894[12698667]

5602: AJ300340
Homo sapiens partial RYR2 gene for ryanodine receptor 2, exon 1 and joined complete CDS
gi|11878410|emb|AJ300340.1|HSA300340[11878410]

5603: AF063605
Homo sapiens brain my047 protein mRNA, complete cds
gi|4071360|gb|AF063605.1|AF063605[4071360]

5604: AF319440
Homo sapiens SH2 domain-containing phosphatase anchor protein 1c (SPAP1) mRNA, complete cds, alternatively spliced
gi|12667355|gb|AF319440.1|AF319440[12667355]

5605: AF319439
Homo sapiens SH2 domain-containing phosphatase anchor protein 1b (SPAP1) mRNA, complete cds, alternatively spliced
gi|12667353|gb|AF319439.1|AF319439[12667353]

5606: AF319438

Homo sapiens SH2 domain-containing phosphatase anchor protein 1a (SPAP1) mRNA, complete cds, alternatively spliced
gi|12667351|gb|AF319438.1|AF319438[12667351]

5607: NM_021912
Homo sapiens gamma-aminobutyric acid (GABA) A receptor, beta 3 (GABRB3), transcript variant 2, mRNA
gi|12548787|ref|NM_021912.1|[12548787]

5608: NM_021911
Homo sapiens gamma-aminobutyric acid (GABA) A receptor, beta 2 (GABRB2), transcript variant 1, mRNA
gi|12548784|ref|NM_021911.1|[12548784]

5609: NM_000814
Homo sapiens gamma-aminobutyric acid (GABA) A receptor, beta 3 (GABRB3), transcript variant 1, mRNA
gi|12548782|ref|NM_000814.2|[12548782]

5610: NM_000812
Homo sapiens gamma-aminobutyric acid (GABA) A receptor, beta 1 (GABRB1), mRNA
gi|12548775|ref|NM_000812.2|[12548775]

5611: NM_006786
Homo sapiens urotensin 2 (UTS2), transcript variant 2, mRNA
gi|12056480|ref|NM_006786.2|[12056480]

5612: NM_021995
Homo sapiens urotensin 2 (UTS2), transcript variant 1, mRNA
gi|12056478|ref|NM_021995.1|[12056478]

5613: AJ300444
Homo sapiens partial RYR2 gene for ryanodine receptor 2, exon 105
gi|11863669|emb|AJ300444.1|HSA300444[11863669]

5614: AJ300443
Homo sapiens partial RYR2 gene for ryanodine receptor 2, exon 104
gi|11863668|emb|AJ300443.1|HSA300443[11863668]

5615: AJ300442
Homo sapiens partial RYR2 gene for ryanodine receptor 2, exon 103
gi|11863667|emb|AJ300442.1|HSA300442[11863667]

5616: AJ300441
Homo sapiens partial RYR2 gene for ryanodine receptor 2, exon 102
gi|11863666|emb|AJ300441.1|HSA300441[11863666]

5617: AJ300440
Homo sapiens partial RYR2 gene for ryanodine receptor 2, exon 101
gi|11863665|emb|AJ300440.1|HSA300440[11863665]

5618: AJ300439
Homo sapiens partial RYR2 gene for ryanodine receptor 2, exon 100
gi|11863664|emb|AJ300439.1|HSA300439[11863664]

5619: AJ300438
Homo sapiens partial RYR2 gene for ryanodine receptor 2, exon 99
gi|11863663|emb|AJ300438.1|HSA300438[11863663]

5620: AJ300437
Homo sapiens partial RYR2 gene for ryanodine receptor 2, exon 98
gi|11863662|emb|AJ300437.1|HSA300437[11863662]

5621: AJ300436
Homo sapiens partial RYR2 gene for ryanodine receptor 2, exon 97
gi|11863661|emb|AJ300436.1|HSA300436[11863661]

5622: AJ300435
Homo sapiens partial RYR2 gene for ryanodine receptor 2, exon 96
gi|11863660|emb|AJ300435.1|HSA300435[11863660]

5623: AJ300434
Homo sapiens partial RYR2 gene for ryanodine receptor 2, exon 95
gi|11863659|emb|AJ300434.1|HSA300434[11863659]

5624: AJ300433

Homo sapiens partial RYR2 gene for ryanodine receptor 2, exon 94
gi|11863658|emb|AJ300433.1|HSA300433[11863658]

5625: AJ300432

Homo sapiens partial RYR2 gene for ryanodine receptor 2, exon 93
gi|11863657|emb|AJ300432.1|HSA300432[11863657]

5626: AJ300431

Homo sapiens partial RYR2 gene for ryanodine receptor 2, exon 92
gi|11863656|emb|AJ300431.1|HSA300431[11863656]

5627: AJ300430

Homo sapiens partial RYR2 gene for ryanodine receptor 2, exon 91
gi|11863655|emb|AJ300430.1|HSA300430[11863655]

5628: AJ300429

Homo sapiens partial RYR2 gene for ryanodine receptor 2, exon 90
gi|11863654|emb|AJ300429.1|HSA300429[11863654]

5629: AJ300428

Homo sapiens partial RYR2 gene for ryanodine receptor 2, exon 89
gi|11863653|emb|AJ300428.1|HSA300428[11863653]

5630: AJ300427

Homo sapiens partial RYR2 gene for ryanodine receptor 2, exon 88
gi|11863652|emb|AJ300427.1|HSA300427[11863652]

5631: AJ300426

Homo sapiens partial RYR2 gene for ryanodine receptor 2, exon 87
gi|11863651|emb|AJ300426.1|HSA300426[11863651]

5632: AJ300425

Homo sapiens partial RYR2 gene for ryanodine receptor 2, exon 86
gi|11863650|emb|AJ300425.1|HSA300425[11863650]

5633: AJ300424
Homo sapiens partial RYR2 gene for ryanodine receptor 2, exon 85
gi|11863649|emb|AJ300424.1|HSA300424[11863649]

5634: AJ300423
Homo sapiens partial RYR2 gene for ryanodine receptor 2, exon 84
gi|11863648|emb|AJ300423.1|HSA300423[11863648]

5635: AJ300422
Homo sapiens partial RYR2 gene for ryanodine receptor 2, exon 83
gi|11863647|emb|AJ300422.1|HSA300422[11863647]

5636: AJ300421
Homo sapiens partial RYR2 gene for ryanodine receptor 2, exon 82
gi|11863646|emb|AJ300421.1|HSA300421[11863646]

5637: AJ300420
Homo sapiens partial RYR2 gene for ryanodine receptor 2, exon 81
gi|11863645|emb|AJ300420.1|HSA300420[11863645]

5638: AJ300419
Homo sapiens partial RYR2 gene for ryanodine receptor 2, exon 80
gi|11863644|emb|AJ300419.1|HSA300419[11863644]

5639: AJ300418
Homo sapiens partial RYR2 gene for ryanodine receptor 2, exon 79
gi|11863643|emb|AJ300418.1|HSA300418[11863643]

5640: AJ300417
Homo sapiens partial RYR2 gene for ryanodine receptor 2, exon 78
gi|11863642|emb|AJ300417.1|HSA300417[11863642]

5641: AJ300416
Homo sapiens partial RYR2 gene for ryanodine receptor 2, exon 77
gi|11863641|emb|AJ300416.1|HSA300416[11863641]

5642: AJ300415

Homo sapiens partial RYR2 gene for ryanodine receptor 2, exon 76
gi|11863640|emb|AJ300415.1|HSA300415[11863640]

5643: AJ300414
Homo sapiens partial RYR2 gene for ryanodine receptor 2, exon 75
gi|11863639|emb|AJ300414.1|HSA300414[11863639]

5644: AJ300413
Homo sapiens partial RYR2 gene for ryanodine receptor 2, exon 74
gi|11863638|emb|AJ300413.1|HSA300413[11863638]

5645: AJ300412
Homo sapiens partial RYR2 gene for ryanodine receptor 2, exon 73
gi|11863637|emb|AJ300412.1|HSA300412[11863637]

5646: AJ300411
Homo sapiens partial RYR2 gene for ryanodine receptor 2, exon 72
gi|11863636|emb|AJ300411.1|HSA300411[11863636]

5647: AJ300410
Homo sapiens partial RYR2 gene for ryanodine receptor 2, exon 71
gi|11863635|emb|AJ300410.1|HSA300410[11863635]

5648: AJ300409
Homo sapiens partial RYR2 gene for ryanodine receptor 2, exon 70
gi|11863634|emb|AJ300409.1|HSA300409[11863634]

5649: AJ300408
Homo sapiens partial RYR2 gene for ryanodine receptor 2, exon 69
gi|11863633|emb|AJ300408.1|HSA300408[11863633]

5650: AJ300407
Homo sapiens partial RYR2 gene for ryanodine receptor 2, exon 68
gi|11863632|emb|AJ300407.1|HSA300407[11863632]

5651: AJ300406
Homo sapiens partial RYR2 gene for ryanodine receptor 2, exon 67 gi|11863631|emb|AJ300406.1|HSA300406[11863631]

5652: AJ300405
Homo sapiens partial RYR2 gene for ryanodine receptor 2, exon 66
gi|11863630|emb|AJ300405.1|HSA300405[11863630]

5653: AJ300404
Homo sapiens partial RYR2 gene for ryanodine receptor 2, exon 65
gi|11863629|emb|AJ300404.1|HSA300404[11863629]

5654: AJ300403
Homo sapiens partial RYR2 gene for ryanodine receptor 2, exon 64
gi|11863628|emb|AJ300403.1|HSA300403[11863628]

5655: AJ300402
Homo sapiens partial RYR2 gene for ryanodine receptor 2, exon 63
gi|11863627|emb|AJ300402.1|HSA300402[11863627]

5656: AJ300401
Homo sapiens partial RYR2 gene for ryanodine receptor 2, exon 62
gi|11863626|emb|AJ300401.1|HSA300401[11863626]

5657: AJ300400
Homo sapiens partial RYR2 gene for ryanodine receptor 2, exon 61
gi|11863625|emb|AJ300400.1|HSA300400[11863625]

5658: AJ300399
Homo sapiens partial RYR2 gene for ryanodine receptor 2, exon 60
gi|11863624|emb|AJ300399.1|HSA300399[11863624]

5659: AJ300398
Homo sapiens partial RYR2 gene for ryanodine receptor 2, exon 59
gi|11863623|emb|AJ300398.1|HSA300398[11863623]

5660: AJ300397
Homo sapiens partial RYR2 gene for ryanodine receptor 2, exon 58
gi|11863622|emb|AJ300397.1|HSA300397[11863622]

5661: AJ300396
Homo sapiens partial RYR2 gene for ryanodine receptor 2, exon 57
gi|11863621|emb|AJ300396.1|HSA300396[11863621]

5662: AJ300395
Homo sapiens partial RYR2 gene for ryanodine receptor 2, exon 56
gi|11863620|emb|AJ300395.1|HSA300395[11863620]

5663: AJ300394
Homo sapiens partial RYR2 gene for ryanodine receptor 2, exon 55
gi|11863619|emb|AJ300394.1|HSA300394[11863619]

5664: AJ300393
Homo sapiens partial RYR2 gene for ryanodine receptor 2, exon 54
gi|11863618|emb|AJ300393.1|HSA300393[11863618]

5665: AJ300392
Homo sapiens partial RYR2 gene for ryanodine receptor 2, exon 53
gi|11863617|emb|AJ300392.1|HSA300392[11863617]

5666: AJ300391
Homo sapiens partial RYR2 gene for ryanodine receptor 2, exon 52
gi|11863616|emb|AJ300391.1|HSA300391[11863616]

5667: AJ300390
Homo sapiens partial RYR2 gene for ryanodine receptor 2, exon 51
gi|11863615|emb|AJ300390.1|HSA300390[11863615]

5668: AJ300389
Homo sapiens partial RYR2 gene for ryanodine receptor 2, exon 50
gi|11863614|emb|AJ300389.1|HSA300389[11863614].

5669: AJ300388
Homo sapiens partial RYR2 gene for ryanodine receptor 2, exon 49
gi|11863613|emb|AJ300388.1|HSA300388[11863613]

5670: AJ300387
Homo sapiens partial RYR2 gene for ryanodine receptor 2, exon 48
gi|11863612|emb|AJ300387.1|HSA300387[11863612]

5671: AJ300386
Homo sapiens partial RYR2 gene for ryanodine receptor 2, exon 47
gi|11863611|emb|AJ300386.1|HSA300386[11863611]

5672: AJ300385
Homo sapiens partial RYR2 gene for ryanodine receptor 2, exon 46
gi|11863610|emb|AJ300385.1|HSA300385[11863610]

5673: AJ300384
Homo sapiens partial RYR2 gene for ryanodine receptor 2, exon 45
gi|11863609|emb|AJ300384.1|HSA300384[11863609]

5674: AJ300383
Homo sapiens partial RYR2 gene for ryanodine receptor 2, exon 44
gi|11863608|emb|AJ300383.1|HSA300383[11863608]

5675: AJ300382
Homo sapiens partial RYR2 gene for ryanodine receptor 2, exon 43
gi|11863607|emb|AJ300382.1|HSA300382[11863607]

5676: AJ300381
Homo sapiens partial RYR2 gene for ryanodine receptor 2, exon 42
gi|11863606|emb|AJ300381.1|HSA300381[11863606]

5677: AJ300380
Homo sapiens partial RYR2 gene for ryanodine receptor 2, exon 41
gi|11863605|emb|AJ300380.1|HSA300380[11863605]

5678: AJ300379
Homo sapiens partial RYR2 gene for ryanodine receptor 2, exon 40
gi|11863604|emb|AJ300379.1|HSA300379[11863604]

5679: AJ300378
Homo sapiens partial RYR2 gene for ryanodine receptor 2, exon 39
gi|11863603|emb|AJ300378.1|HSA300378[11863603]

5680: AJ300377
Homo sapiens partial RYR2 gene for ryanodine receptor 2, exon 38
gi|11863602|emb|AJ300377.1|HSA300377[11863602]

5681: AJ300376
Homo sapiens partial RYR2 gene for ryanodine receptor 2, exon 37
gi|11863601|emb|AJ300376.1|HSA300376[11863601]

5682: AJ300375
Homo sapiens partial RYR2 gene for ryanodine receptor 2, exon 36
gi|11863600|emb|AJ300375.1|HSA300375[11863600]

5683: AJ300374
Homo sapiens partial RYR2 gene for ryanodine receptor 2, exon 35
gi|11863599|emb|AJ300374.1|HSA300374[11863599]

5684: AJ300373
Homo sapiens partial RYR2 gene for ryanodine receptor 2, exon 34
gi|11863598|emb|AJ300373.1|HSA300373[11863598]

5685: AJ300372
Homo sapiens partial RYR2 gene for ryanodine receptor 2, exon 33
gi|11863597|emb|AJ300372.1|HSA300372[11863597]

5686: AJ300371
Homo sapiens partial RYR2 gene for ryanodine receptor 2, exon 32
gi|11863596|emb|AJ300371.1|HSA300371[11863596]

5687: AJ300370
Homo sapiens partial RYR2 gene for ryanodine receptor 2, exon 31
gi|11863595|emb|AJ300370.1|HSA300370[11863595]

5688: AJ300369

Homo sapiens partial RYR2 gene for ryanodine receptor 2, exon 30
gi|11863594|emb|AJ300369.1|HSA300369[11863594]

5689: AJ300368
Homo sapiens partial RYR2 gene for ryanodine receptor 2, exon 29
gi|11863593|emb|AJ300368.1|HSA300368[11863593]

5690: AJ300367
Homo sapiens partial RYR2 gene for ryanodine receptor 2, exon 28
gi|11863592|emb|AJ300367.1|HSA300367[11863592]

5691: AJ300366
Homo sapiens partial RYR2 gene for ryanodine receptor 2, exon 27
gi|11863591|emb|AJ300366.1|HSA300366[11863591]

5692: AJ300365
Homo sapiens partial RYR2 gene for ryanodine receptor 2, exon 26
gi|11863590|emb|AJ300365.1|HSA300365[11863590]

5693: AJ300364
Homo sapiens partial RYR2 gene for ryanodine receptor 2, exon 25
gi|11863589|emb|AJ300364.1|HSA300364[11863589]

5694: AJ300363
Homo sapiens partial RYR2 gene for ryanodine receptor 2, exon 24
gi|11863588|emb|AJ300363.1|HSA300363[11863588]

5695: AJ300362
Homo sapiens partial RYR2 gene for ryanodine receptor 2, exon 23
gi|11863587|emb|AJ300362.1|HSA300362[11863587]

5696: AJ300361
Homo sapiens partial RYR2 gene for ryanodine receptor 2, exon 22
gi|11863586|emb|AJ300361.1|HSA300361[11863586]

5697: AJ300360
Homo sapiens partial RYR2 gene for ryanodine receptor 2, exon 21 gi|11863585|emb|AJ300360.1|HSA300360[11863585]

5698: AJ300359
Homo sapiens partial RYR2 gene for ryanodine receptor 2, exon 20
gi|11863584|emb|AJ300359.1|HSA300359[11863584]

5699: AJ300358
Homo sapiens partial RYR2 gene for ryanodine receptor 2, exon 19
gi|11863583|emb|AJ300358.1|HSA300358[11863583]

5700: AJ300357
Homo sapiens partial RYR2 gene for ryanodine receptor 2, exon 18
gi|11863582|emb|AJ300357.1|HSA300357[11863582]

5701: AJ300356
Homo sapiens partial RYR2 gene for ryanodine receptor 2, exon 17
gi|11863581|emb|AJ300356.1|HSA300356[11863581]

5702: AJ300355
Homo sapiens partial RYR2 gene for ryanodine receptor 2, exon 16
gi|11863580|emb|AJ300355.1|HSA300355[11863580]

5703: AJ300354
Homo sapiens partial RYR2 gene for ryanodine receptor 2, exon 15
gi|11863579|emb|AJ300354.1|HSA300354[11863579]

5704: AJ300353
Homo sapiens partial RYR2 gene for ryanodine receptor 2, exon 14
gi|11863578|emb|AJ300353.1|HSA300353[11863578]

5705: AJ300352
Homo sapiens partial RYR2 gene for ryanodine receptor 2, exon 13
gi|11863577|emb|AJ300352.1|HSA300352[11863577]

5706: AJ300351
Homo sapiens partial RYR2 gene for ryanodine receptor 2, exon 12
gi|11863576|emb|AJ300351.1|HSA300351[11863576]

5707: AJ300350
Homo sapiens partial RYR2 gene for ryanodine receptor 2, exon 11
gi|11863575|emb|AJ300350.1|HSA300350[11863575]

5708: AJ300349
Homo sapiens partial RYR2 gene for ryanodine receptor 2, exon 10
gi|11863574|emb|AJ300349.1|HSA300349[11863574]

5709: AJ300348
Homo sapiens partial RYR2 gene for ryanodine receptor 2, exon 9
gi|11863573|emb|AJ300348.1|HSA300348[11863573]

5710: AJ300347
Homo sapiens partial RYR2 gene for ryanodine receptor 2, exon 8
gi|11863572|emb|AJ300347.1|HSA300347[11863572]

5711: AJ300346
Homo sapiens partial RYR2 gene for ryanodine receptor 2, exon 7
gi|11863571|emb|AJ300346.1|HSA300346[11863571]

5712: AJ300345
Homo sapiens partial RYR2 gene for ryanodine receptor 2, exon 6
gi|11863570|emb|AJ300345.1|HSA300345[11863570]

5713: AJ300344
Homo sapiens partial RYR2 gene for ryanodine receptor 2, exon 5
gi|11863569|emb|AJ300344.1|HSA300344[11863569]

5714: AJ300343
Homo sapiens partial RYR2 gene for ryanodine receptor 2, exon 4
gi|11863568|emb|AJ300343.1|HSA300343[11863568]

5715: AJ300342
Homo sapiens partial RYR2 gene for ryanodine receptor 2, exon 3
gi|11863567|emb|AJ300342.1|HSA300342[11863567]

5716: AJ300341
Homo sapiens partial RYR2 gene for ryanodine receptor 2, exon 2
gi|11863566|emb|AJ300341.1|HSA300341[11863566]

5717: NM_000832
Homo sapiens glutamate receptor, ionotropic, N-methyl D-aspartate 1 (GRIN1), transcript variant NR1-1, mRNA
gi|11496970|ref|NM_000832.4|[11496970]

5718: NM_021709
Homo sapiens CD27-binding (Siva) protein (SIVA), transcript variant 2, mRNA
gi|11277469|ref|NM_021709.1|[11277469]

5719: NM_006427
Homo sapiens CD27-binding (Siva) protein (SIVA), transcript variant 1, mRNA
gi|11277467|ref|NM_006427.2|[11277467]

5720: NM_016232
Homo sapiens interleukin 1 receptor-like 1 (IL1RL1), mRNA
gi|11136631|ref|NM_016232.2|[11136631]

5721: AF202091
Homo sapiens hypocretin receptor-2 (HCRTR2) gene, exon 7 and complete cds
gi|11055242|gb|AF202091.1|F202078S14[11055242]

5722: AF202090
Homo sapiens hypocretin receptor-2 (HCRTR2) gene, exon 6
gi|11055241|gb|AF202090.1|F202078S13[11055241]

5723: AF202089
Homo sapiens hypocretin receptor-2 (HCRTR2) gene, exon 5
gi|11055240|gb|AF202089.1|F202078S12[11055240]

5724: AF202088
Homo sapiens hypocretin receptor-2 (HCRTR2) gene, exon 4
gi|11055239|gb|AF202088.1|F202078S11[11055239]

5725: AF202087
Homo sapiens hypocretin receptor-2 (HCRTR2) gene, exon 3
gi|11055238|gb|AF202087.1|F202078S10[11055238]

5726: AF202086
Homo sapiens hypocretin receptor-2 (HCRTR2) gene, exon 2
gi|11055237|gb|AF202086.1|F202078S09[11055237]

5727: AF202085
Homo sapiens hypocretin receptor-2 (HCRTR2) gene, exon 1
gi|11055236|gb|AF202085.1|F202078S08[11055236]

5728: AF202084
Homo sapiens hypocretin receptor-1 (HCRTR1) gene, exon 7 and complete cds
gi|11055235|gb|AF202084.1|F202078S07[11055235]

5729: AF202083
Homo sapiens hypocretin receptor-1 (HCRTR1) gene, exon 6
gi|11055234|gb|AF202083.1|F202078S06[11055234]

5730: AF202082
Homo sapiens hypocretin receptor-1 (HCRTR1) gene, exon 5
gi|11055233|gb|AF202082.1|F202078S05[11055233]

5731: AF202081
Homo sapiens hypocretin receptor-1 (HCRTR1) gene, exon 4
gi|11055232|gb|AF202081.1|F202078S04[11055232]

5732: AF202080
Homo sapiens hypocretin receptor-1 (HCRTR1) gene, exon 3
gi|11055231|gb|AF202080.1|F202078S03[11055231]

5733: AF202079
Homo sapiens hypocretin receptor-1 (HCRTR1) gene, exon 2
gi|11055230|gb|AF202079.1|F202078S02[11055230]

5734: AF202078
Homo sapiens hypocretin receptor-1 (HCRTR1) gene, exon 1
gi|11055229|gb|AF202078.1|F202078S01[11055229]

5735: AH009943
Homo sapiens hypocretin receptor-1 (HCRTR1) and hypocretin receptor-2 (HCRTR2) genes, complete cds
gi|11055228|gb|AH009943.1|SEG_F202078S[11055228]

5736: NM_021602
Homo sapiens CD79B antigen (immunoglobulin-associated beta) (CD79B), transcript variant 2, mRNA
gi|11038675|ref|NM_021602.1|[11038675]

5737: NM_000626
Homo sapiens CD79B antigen (immunoglobulin-associated beta) (CD79B), transcript variant 1, mRNA
gi|11038673|ref|NM_000626.1|[11038673]

5738: NM_021601
Homo sapiens CD79A antigen (immunoglobulin-associated alpha) (CD79A), transcript variant 2, mRNA
gi|11038671|ref|NM_021601.1|[11038671]

5739: NM_007327
Homo sapiens glutamate receptor, ionotropic, N-methyl D-aspartate 1 (GRIN1), transcript variant NR1-3, mRNA
gi|11038636|ref|NM_007327.1|[11038636]

5740: NM_021569
Homo sapiens glutamate receptor, ionotropic, N-methyl D-aspartate 1 (GRIN1), transcript variant NR1-2, mRNA
gi|11038634|ref|NM_021569.1|[11038634]

5743: NM_021270
Homo sapiens leukocyte-associated Ig-like receptor 2 (LAIR2), transcript variant 2, mRNA
gi|10947102|ref|NM_021270.1|[10947102]

5744: NM_002288
Homo sapiens leukocyte-associated Ig-like receptor 2 (LAIR2), transcript variant 1, mRNA
gi|10947100|ref|NM_002288.2|[10947100]

5745: NM_004041
Homo sapiens arrestin, beta 1 (ARRB1), transcript variant 1, mRNA
gi|10880135|ref|NM_004041.2|[10880135]

5746: NM_020251
Homo sapiens arrestin, beta 1 (ARRB1), transcript variant 2, mRNA
gi|10880133|ref|NM_020251.1|[10880133]

5747: NM_000872
Homo sapiens 5-hydroxytryptamine (serotonin) receptor 7 (adenylate cyclase-coupled) (HTR7), transcript variant a, mRNA
gi|10880132|ref|NM_000872.2|[10880132]

5748: NM_019860
Homo sapiens 5-hydroxytryptamine (serotonin) receptor 7 (adenylate cyclase-coupled) (HTR7), transcript variant b, mRNA
gi|10880130|ref|NM_019860.1|[10880130]

5749: NM_019859
Homo sapiens 5-hydroxytryptamine (serotonin) receptor 7 (adenylate cyclase-coupled) (HTR7), transcript variant d, mRNA
gi|10880128|ref|NM_019859.1|[10880128]

5750: NM_004302
Homo sapiens activin A receptor, type IB (ACVR1B), transcript variant 1, mRNA
gi|10862695|ref|NM_004302.2|[10862695]

5751: NM_020328
Homo sapiens activin A receptor, type IB (ACVR1B), transcript variant 3, mRNA
gi|10862693|ref|NM_020328.1|[10862693]

5752: NM_020327

Homo sapiens activin A receptor, type IB (ACVR1B), transcript variant 2, mRNA
gi|10862691|ref|NM_020327.1|[10862691]

5753: NM_020525
Homo sapiens interleukin 22 (IL22), mRNA
gi|10092624|ref|NM_020525.1|[10092624]

5754: NM_000407
Homo sapiens glycoprotein Ib (platelet), beta polypeptide (GP1BB), mRNA
gi|9945387|ref|NM_000407.3|[9945387]

5755: NM_018971
Homo sapiens G protein-coupled receptor 27 (GPR27), mRNA
gi|9506746|ref|NM_018971.1|[9506746]

5756: NM_017455
Homo sapiens stromal cell derived factor receptor 1 (SDFR1), transcript variant alpha, mRNA
gi|9257239|ref|NM_017455.1|[9257239]

5757: NM_002197
Homo sapiens aconitase 1, soluble (ACO1), mRNA
gi|8659554|ref|NM_002197.1|[8659554]

5758: NM_005242
Homo sapiens coagulation factor II (thrombin) receptor-like 1 (F2RL1), mRNA
gi|8051581|ref|NM_005242.2|[8051581]

5759: NM_016388
Homo sapiens T-cell receptor interacting molecule (TRIM), mRNA
gi|7706744|ref|NM_016388.1|[7706744]

5760: NM_016334
Homo sapiens putative G-protein coupled receptor (SH120), mRNA
gi|7706703|ref|NM_016334.1|[7706703]

5761: NM_016318

Homo sapiens purinergic receptor P2X, ligand-gated ion channel, 2 (P2RX2), mRNA
gi|7706628|ref|NM_016318.1|[7706628]

5762: NM_016602
Homo sapiens G protein-coupled receptor 2 (GPR2), mRNA
gi|7705315|ref|NM_016602.1|[7705315]

5763: NM_013964
Homo sapiens neuregulin 1 (NRG1), transcript variant HRG-alpha, mRNA
gi|7669525|ref|NM_013964.1|[7669525]

5764: NM_013962
Homo sapiens neuregulin 1 (NRG1), transcript variant GGF2, mRNA
gi|7669523|ref|NM_013962.1|[7669523]

5765: NM_013961
Homo sapiens neuregulin 1 (NRG1), transcript variant GGF, mRNA
gi|7669521|ref|NM_013961.1|[7669521]

5766: NM_013960
Homo sapiens neuregulin 1 (NRG1), transcript variant ndf43, mRNA
gi|7669519|ref|NM_013960.1|[7669519]

5767: NM_013959
Homo sapiens neuregulin 1 (NRG1), transcript variant SMDF, mRNA
gi|7669517|ref|NM_013959.1|[7669517]

5768: NM_013958
Homo sapiens neuregulin 1 (NRG1), transcript variant HRG-beta3, mRNA
gi|7669515|ref|NM_013958.1|[7669515]

5769: NM_013957
Homo sapiens neuregulin 1 (NRG1), transcript variant HRG-beta2, mRNA
gi|7669513|ref|NM_013957.1|[7669513]

5770: NM_013956
Homo sapiens neuregulin 1 (NRG1), transcript variant HRG-beta1, mRNA gi|7669511|ref|NM_013956.1|[7669511]

5771: NM_007334
Homo sapiens killer cell lectin-like receptor subfamily D, member 1 (KLRD1), transcript variant 2, mRNA
gi|7669498|ref|NM_007334.1|[7669498]

5772: NM_002262
Homo sapiens killer cell lectin-like receptor subfamily D, member 1 (KLRD1), transcript variant 1, mRNA
gi|7669497|ref|NM_002262.2|[7669497]

5773: NM_007319
Homo sapiens presenilin 1 (Alzheimer disease 3) (PSEN1), transcript variant I-374., mRNA
gi|7549814|ref|NM_007319.1|[7549814]

5774: NM_007318
Homo sapiens presenilin 1 (Alzheimer disease 3) (PSEN1), transcript variant I-463, mRNA
gi|7549812|ref|NM_007318.1|[7549812]

5775: NM_007333
Homo sapiens killer cell lectin-like receptor subfamily C, member 3 (KLRC3), transcript variant NKG2-H, mRNA
gi|7262385|ref|NM_007333.1|[7262385]

5776: NM_007328
Homo sapiens killer cell lectin-like receptor subfamily C, member 1 (KLRC1), transcript variant NKG2-B, mRNA
gi|7262383|ref|NM_007328.1|[7262383]

5777: NM_002259
Homo sapiens killer cell lectin-like receptor subfamily C, member 1 (KLRC1), transcript variant NKG2-A, mRNA
gi|7262382|ref|NM_002259.2|[7262382]

5778: NM_006350

Homo sapiens follistatin (FST), transcript variant FST317, mRNA
gi|7242223|ref|NM_006350.2|[7242223]

5779: NM_013409
Homo sapiens follistatin (FST), transcript variant FST344, mRNA
gi|7242221|ref|NM_013409.1|[7242221]

5780: NM_012486
Homo sapiens presenilin 2 (Alzheimer disease 4) (PSEN2), transcript variant 2, mRNA
gi|7108359|ref|NM_012486.1|[7108359]

5781: NM_012485
Homo sapiens hyaluronan-mediated motility receptor (RHAMM) (HMMR), transcript variant 2, mRNA
gi|7108350|ref|NM_012485.1|[7108350]

5782: NM_012484
Homo sapiens hyaluronan-mediated motility receptor (RHAMM) (HMMR), transcript variant 1, mRNA
gi|7108348|ref|NM_012484.1|[7108348]

5783: NM_012428
Homo sapiens stromal cell derived factor receptor 1 (SDFR1), transcript variant beta, mRNA
gi|6912645|ref|NM_012428.1|[6912645]

5784: NM_012226
Homo sapiens purinergic receptor P2X, ligand-gated ion channel, 2 (P2RX2), mRNA
gi|6912565|ref|NM_012226.1|[6912565]

5785: NM_012369
Homo sapiens olfactory receptor, family 2, subfamily F, member 1 (OR2F1), mRNA
gi|6912557|ref|NM_012369.1|[6912557]

5786: NM_007325
Homo sapiens glutamate receptor, ionotrophic, AMPA 3 (GRIA3), transcript variant flip, mRNA gi|6598324|ref|NM_007325.1|[6598324]

5787: NM_000632
Homo sapiens integrin, alpha M (complement component receptor 3, alpha; also known as CD11b (p170), macrophage antigen alpha polypeptide) (ITGAM), mRNA
gi|6006013|ref|NM_000632.2|[6006013]

5788: NM_007097
Homo sapiens clathrin, light polypeptide (Lcb) (CLTB), mRNA
gi|6005994|ref|NM_007097.1|[6005994]

5789: NM_000655
Homo sapiens selectin L (lymphocyte adhesion molecule 1) (SELL), mRNA
gi|5713320|ref|NM_000655.2|[5713320]

5790: NM_005751
Homo sapiens A kinase (PRKA) anchor protein (yotiao) 9 (AKAP9), mRNA
gi|5032230|ref|NM_005751.1|[5032230]

5791: NM_005691
Homo sapiens ATP-binding cassette, sub-family C (CFTR/MRP), member 9 (ABCC9), transcript variant SUR2A, mRNA
gi|5032134|ref|NM_005691.1|[5032134]

5792: NM_005534
Homo sapiens interferon gamma receptor 2 (interferon gamma transducer 1) (IFNGR2), mRNA
gi|5031782|ref|NM_005534.1|[5031782]

5793: NM_005682
Homo sapiens G protein-coupled receptor 56 (GPR56), mRNA
gi|5031724|ref|NM_005682.1|[5031724]

5794: NM_005446
Homo sapiens purinergic receptor P2X-like 1, orphan receptor (P2RXL1), mRNA
gi|4885534|ref|NM_005446.1|[4885534]

5795: NM_004958
Homo sapiens FK506 binding protein 12-rapamycin associated protein 1 (FRAP1), mRNA
gi|4826729|ref|NM_004958.1|[4826729]

5796: NM_004495
Homo sapiens neuregulin 1 (NRG1), transcript variant HRG-gamma, mRNA
gi|4758525|ref|NM_004495.1|[4758525]

5797: NM_003995
Homo sapiens natriuretic peptide receptor B/guanylate cyclase B (atrionatriuretic peptide receptor B) (NPR2), mRNA
gi|4580421|ref|NM_003995.2|[4580421]

5798: NM_003994
Homo sapiens KIT ligand (KITLG), mRNA
gi|4580419|ref|NM_003994.2|[4580419]

5799: NM_000115
Homo sapiens endothelin receptor type B (EDNRB), transcript variant 1, mRNA
gi|4557546|ref|NM_000115.1|[4557546]

5800: NM_000734
Homo sapiens CD3Z antigen, zeta polypeptide (TiT3 complex) (CD3Z), mRNA
gi|4557430|ref|NM_000734.1|[4557430]

5801: NM_003856
Homo sapiens interleukin 1 receptor-like 1 (IL1RL1), mRNA
gi|4507244|ref|NM_003856.1|[4507244]

5802: NM_002980
Homo sapiens secretin receptor (SCTR), mRNA
gi|4506824|ref|NM_002980.1|[4506824]

5803: NM_000447
Homo sapiens presenilin 2 (Alzheimer disease 4) (PSEN2), transcript variant 1, mRNA
gi|4506164|ref|NM_000447.1|[4506164]

5804: NM_000021
Homo sapiens presenilin 1 (Alzheimer disease 3) (PSEN1), transcript variant I-467, mRNA
gi|4506162|ref|NM_000021.1|[4506162]

5805: NM_000907
Homo sapiens natriuretic peptide receptor B/guanylate cyclase B (atrionatriuretic peptide receptor B) (NPR2), mRNA
gi|4505436|ref|NM_000907.1|[4505436]

5806: NM_000899
Homo sapiens KIT ligand (KITLG), mRNA
gi|4505174|ref|NM_000899.1|[4505174]

5807: NM_002353
Homo sapiens tumor-associated calcium signal transducer 2 (TACSTD2), mRNA
gi|4505056|ref|NM_002353.1|[4505056]

5808: NM_002261
Homo sapiens killer cell lectin-like receptor subfamily C, member 3 (KLRC3), transcript variant NKG2-E, mRNA
gi|4504884|ref|NM_002261.1|[4504884]

5809: NM_000836
Homo sapiens glutamate receptor, ionotropic, N-methyl D-aspartate 2D (GRIN2D), mRNA
gi|4504130|ref|NM_000836.1|[4504130]

5810: NM_000828
Homo sapiens glutamate receptor, ionotrophic, AMPA 3 (GRIA3), transcript variant flop, mRNA
gi|4504114|ref|NM_000828.1|[4504114]

5811: NM_000813
Homo sapiens gamma-aminobutyric acid (GABA) A receptor, beta 2 (GABRB2), transcript variant 2, mRNA
gi|4503864|ref|NM_000813.1|[4503864]

5812: NM_003991
Homo sapiens endothelin receptor type B (EDNRB), transcript variant 2, mRNA
gi|4503466|ref|NM_003991.1|[4503466]

5813: NM_001337
Homo sapiens chemokine (C-X3-C) receptor 1 (CX3CR1), mRNA
gi|4503170|ref|NM_001337.1|[4503170]

5814: NM_001834
Homo sapiens clathrin, light polypeptide (Lcb) (CLTB), transcript variant nonbrain, mRNA
gi|4502900|ref|NM_001834.1|[4502900]

5815: NM_001783
Homo sapiens CD79A antigen (immunoglobulin-associated alpha) (CD79A), transcript variant 1, mRNA
gi|4502684|ref|NM_001783.1|[4502684]

5816: AF277897
Homo sapiens truncated epidermal growth factor receptor (EGFR) mRNA, partial cds; alternatively spliced
gi|12658300|gb|AF277897.1|AF277897[12658300]

5817: AF192403
Homo sapiens ETL protein (ETL) mRNA, complete cds
gi|11225482|gb|AF192403.1|AF192403[11225482]

5818: AF259263
Homo sapiens toll-like receptor 9 form B (TLR9) mRNA, complete cds; alternatively spliced
gi|8099653|gb|AF259263.1|AF259263[8099653]

5819: AF259262
Homo sapiens toll-like receptor 9 form A (TLR9) mRNA, complete cds; alternatively spliced
gi|8099651|gb|AF259262.1|AF259262[8099651]

5820: AF246971
Homo sapiens Toll-like receptor 8 (TLR8) mRNA, complete cds
gi|7576932|gb|AF246971.1|AF246971[7576932]

5821: AF240467
Homo sapiens toll-like receptor 7 (TLR7) mRNA, complete cds
gi|7330280|gb|AF240467.1|AF240467[7330280]

5822: AF230073
Homo sapiens sialoadhesin mRNA, complete cds
gi|12656129|gb|AF230073.1|AF230073[12656129]

5823: BC000783
Homo sapiens, calcitonin gene-related peptide-receptor component protein, clone
MGC:804, mRNA, complete cds
gi|12653974|gb|BC000783.1|BC000783[12653974]

5824: NM_016184
Homo sapiens C-type (calcium dependent, carbohydrate-recognition domain) lectin,
superfamily member 6 (CLECSF6), mRNA
gi|7705337|ref|NM_016184.1|[7705337]

5825: AF242540
Homo sapiens NK cell type I receptor protein 2B4 (2B4) mRNA, complete cds,
alternatively spliced
gi|12642415|gb|AF242540.1|AF242540[12642415]

5826: NM_020979
Homo sapiens adaptor protein with pleckstrin homology and src homology 2 domains
(APS), mRNA
gi|10280625|ref|NM_020979.1|[10280625]

5827: NM_018557
Homo sapiens low density lipoprotein-related protein 1B (deleted in tumors)
(LRP1B), mRNA
gi|9055269|ref|NM_018557.1|[9055269]

5828: NM_012452
Homo sapiens transmembrane activator and CAML interactor (TACI), mRNA
gi|6912693|ref|NM_012452.1|[6912693]

5829: NM_005338
Homo sapiens huntingtin interacting protein 1 (HIP1), mRNA
gi|12545385|ref|NM_005338.3|[12545385]

5830: AF321238
Homo sapiens T-cell receptor variable beta-chain 15 mRNA, partial cds
gi|12484115|gb|AF321238.1|AF321238[12484115]

5831: AF125253
Homo sapiens truncated epidermal growth factor receptor precursor (EGFR) mRNA, complete cds
gi|12002211|gb|AF125253.1|AF125253[12002211]

5832: NM_014211
Homo sapiens gamma-aminobutyric acid (GABA) A receptor, pi (GABRP), mRNA
gi|7657105|ref|NM_014211.1|[7657105]

5833: AF283463
Homo sapiens Nogo receptor mRNA, complete cds
gi|12407652|gb|AF283463.1|AF283463[12407652]

5834: AF224266
Homo sapiens four alpha helix cytokine (ZCYTO10) mRNA, ZCYTO10-1 allele, complete cds
gi|7109206|gb|AF224266.1|AF224266[7109206]

5837: AB045370
Homo sapiens mRNA for histamine H4 receptor HH4R, complete cds
gi|12248411|dbj|AB045370.1|AB045370[12248411]

5838: AB045369
Homo sapiens mRNA for histamine H3 receptor HH3R, complete cds
gi|12248409|dbj|AB045369.1|AB045369[12248409]

5840: NM_016363
Homo sapiens glycoprotein VI (platelet) (GP6), mRNA
gi|7705956|ref|NM_016363.1|[7705956]

5841: NM_022139
Homo sapiens GDNF family receptor alpha 4 (GFRA4), mRNA
gi|11545874|ref|NM_022139.1|[11545874]

5842: NM_004403
Homo sapiens deafness, autosomal dominant 5 (DFNA5), mRNA
gi|4758153|ref|NM_004403.1|[4758153]

5847: AF308156
Homo sapiens HERV-E LTR/leader long terminal repeat, complete sequence; and endothelin B receptor mRNA, partial cds
gi|12239519|gb|AF308156.1|AF308156[12239519]

5850: NM_022789
Homo sapiens interleukin 17E (IL17E), mRNA
gi|12232484|ref|NM_022789.1|[12232484]

5851: AX054991
Sequence 3 from Patent WO0073451
gi|12228357|emb|AX054991.1|AX054991[12228357]

5852: AX054989
Sequence 1 from Patent WO0073451
gi|12228355|emb|AX054989.1|AX054989[12228355]

5853: AJ278581
Homo sapiens DREV gene and IGSF6 gene for immunoglobulin superfamily 6 protein
gi|12053852|emb|AJ278581.1|HSA278581[12053852]

5854: AJ302556
Homo sapiens 6M1-3*02 gene for olfactory receptor, cell line OLGA olfactory receptor
gi|12140483|emb|AJ302556.1|HSA302556[12140483]

5855: AJ302555
Homo sapiens 6M1-3*02 gene for olfactory receptor, cell line SA olfactory receptor
gi|12140479|emb|AJ302555.1|HSA302555[12140479]

5856: AJ302554
Homo sapiens 6M1-3*02 gene for olfactory receptor, cell line KR3598 olfactory receptor
gi|12140476|emb|AJ302554.1|HSA302554[12140476]

5857: AJ302553
Homo sapiens 6M1-3*02 gene for olfactory receptor, cell line BM19.7 olfactory receptor
gi|12140472|emb|AJ302553.1|HSA302553[12140472]

5858: AJ302552
Homo sapiens 6M1-3*02 gene for olfactory receptor, cell line BM28.7 olfactory receptor
gi|12140468|emb|AJ302552.1|HSA302552[12140468]

5859: AF209481
Homo sapiens probable mannose binding C-type lectin DC-SIGNR gene, exons 3-8, and complete cds
gi|12084794|gb|AF209481.2|AF209480S2[12084794]

5860: AH009824
Homo sapiens chromosome 19 probable mannose binding C-type lectin DC-SIGNR (abc) gene, complete cds
gi|12084793|gb|AH009824.2|SEG_AF209480S[12084793]

5861: AF313449
Homo sapiens P2Y12 platelet ADP receptor mRNA, complete cds
gi|12083901|gb|AF313449.1|AF313449[12083901]

5884: AH009659
Homo sapiens RON gene, partial sequence
gi|9621821|gb|AH009659.1|SEG_HSRONPO[9621821]

5885: NM_002351
Homo sapiens SH2 domain protein 1A, Duncan's disease (lymphoproliferative syndrome) (SH2D1A), mRNA
gi|4506922|ref|NM_002351.1|[4506922]

5886: NM_000171
Homo sapiens glycine receptor, alpha 1 (startle disease/hyperekplexia, stiff man syndrome) (GLRA1), mRNA
gi|4504018|ref|NM_000171.1|[4504018]

5887: NM_000569
Homo sapiens Fc fragment of IgG, low affinity IIIa, receptor for (CD16) (FCGR3A), mRNA
gi|12056966|ref|NM_000569.2|[12056966]

5888: NM_000802
Homo sapiens folate receptor 1 (adult) (FOLR1), transcript variant 2, mRNA
gi|12056965|ref|NM_000802.2|[12056965]

5889: NM_003979
Homo sapiens retinoic acid induced 3 (RAI3), mRNA
gi|12056470|ref|NM_003979.2|[12056470]

5900: AJ302633
Homo sapiens 6M1-02P*02 gene for olfactory receptor, cell line BM28.7
gi|12054481|emb|AJ302633.1|HSA302633[12054481]

5910: AJ302623
Homo sapiens 6M1-18*02 gene for olfactory receptor, cell line KR3598
gi|12054470|emb|AJ302623.1|HSA302623[12054470]

5911: AJ302622
Homo sapiens 6M1-18*01 gene for olfactory receptor, cell line AMAI
gi|12054468|emb|AJ302622.1|HSA302622[12054468]

5912: AJ302621
Homo sapiens 6M1-18*01 gene for olfactory receptor, cell line OLGA
gi|12054466|emb|AJ302621.1|HSA302621[12054466]

5913: AJ302620
Homo sapiens 6M1-18*01 gene for olfactory receptor, cell line YAR
gi|12054464|emb|AJ302620.1|HSA302620[12054464]

5914: AJ302619
Homo sapiens 6M1-18*01 gene for olfactory receptor, cell line SA
gi|12054462|emb|AJ302619.1|HSA302619[12054462]

5915: AJ302618
Homo sapiens 6M1-18*01 gene for olfactory receptor, cell line WT51
gi|12054460|emb|AJ302618.1|HSA302618[12054460]

5916: AJ302617
Homo sapiens 6M1-18*01 gene for olfactory receptor, cell line H2LCL
gi|12054458|emb|AJ302617.1|HSA302617[12054458]

5917: AJ302616
Homo sapiens 6M1-18*01 gene for olfactory receptor, cell line LG2
gi|12054456|emb|AJ302616.1|HSA302616[12054456]

5918: AJ302615
Homo sapiens 6M1-18*01 gene for olfactory receptor, cell line BM19.7
gi|12054454|emb|AJ302615.1|HSA302615[12054454]

5919: AJ302614
Homo sapiens 6M1-18*01 gene for olfactory receptor, cell line BM28.7
gi|12054452|emb|AJ302614.1|HSA302614[12054452]

5920: AJ302613
Homo sapiens 6M1-16*03 gene for olfactory receptor, cell line AMAI
gi|12054450|emb|AJ302613.1|HSA302613[12054450]

5921: AJ302612

Homo sapiens 6M1-16*03 gene for olfactory receptor, cell line BM19.7
gi|12054448|emb|AJ302612.1|HSA302612[12054448]

5922: AJ302611
Homo sapiens 6M1-16*02 gene for olfactory receptor, cell line BM28.7
gi|12054446|emb|AJ302611.1|HSA302611[12054446]

5923: AJ302610
Homo sapiens 6M1-16*01 gene for olfactory receptor, cell line OLGA
gi|12054444|emb|AJ302610.1|HSA302610[12054444]

5924: AJ302609
Homo sapiens 6M1-16*01 gene for olfactory receptor, cell line YAR
gi|12054442|emb|AJ302609.1|HSA302609[12054442]

5925: AJ302608
Homo sapiens 6M1-16*01 gene for olfactory receptor, cell line SA
gi|12054440|emb|AJ302608.1|HSA302608[12054440]

5926: AJ302607
Homo sapiens 6M1-16*01 gene for olfactory receptor, cell line WT51
gi|12054438|emb|AJ302607.1|HSA302607[12054438]

5927: AJ302606
Homo sapiens 6M1-16*01 gene for olfactory receptor, cell line H2LCL
gi|12054436|emb|AJ302606.1|HSA302606[12054436]

5928: AJ302605
Homo sapiens 6M1-16*01 gene for olfactory receptor, cell line KR3598
gi|12054434|emb|AJ302605.1|HSA302605[12054434]

5929: AJ302604
Homo sapiens 6M1-16*01 gene for olfactory receptor, cell line LG2
gi|12054432|emb|AJ302604.1|HSA302604[12054432]

5930: AJ302603
Homo sapiens 6M1-15*03 gene for olfactory receptor, cell line AMAI gi|12054430|emb|AJ302603.1|HSA302603[12054430]

5931: AJ302602

Homo sapiens 6M1-15*02 gene for olfactory receptor, cell line WT51
gi|12054428|emb|AJ302602.1|HSA302602[12054428]

5932: AJ302601

Homo sapiens 6M1-15*01 gene for olfactory receptor, cell line OLGA
gi|12054426|emb|AJ302601.1|HSA302601[12054426]

5933: AJ302600

Homo sapiens 6M1-15*01 gene for olfactory receptor, cell line YAR
gi|12054424|emb|AJ302600.1|HSA302600[12054424]

5934: AJ302599

Homo sapiens 6M1-15*01 gene for olfactory receptor, cell line SA
gi|12054422|emb|AJ302599.1|HSA302599[12054422]

5935: AJ302598

Homo sapiens 6M1-15*01 gene for olfactory receptor, cell line H2LCL
gi|12054420|emb|AJ302598.1|HSA302598[12054420]

5936: AJ302597

Homo sapiens 6M1-15*01 gene for olfactory receptor, cell line KR3598
gi|12054418|emb|AJ302597.1|HSA302597[12054418]

5937: AJ302596

Homo sapiens 6M1-15*01 gene for olfactory receptor, cell line LG2
gi|12054416|emb|AJ302596.1|HSA302596[12054416]

5938: AJ302595

Homo sapiens 6M1-15*01 gene for olfactory receptor, cell line BM19.7
gi|12054414|emb|AJ302595.1|HSA302595[12054414]

5939: AJ302594

Homo sapiens 6M1-15*01 gene for olfactory receptor, cell line BM28.7
gi|12054412|emb|AJ302594.1|HSA302594[12054412]

5940: AJ302593

Homo sapiens 6M1-10*02 gene for olfactory receptor, cell line KR3598
gi|12054410|emb|AJ302593.1|HSA302593[12054410]

5941: AJ302592

Homo sapiens 6M1-10*01 gene for olfactory receptor, cell line AMAI
gi|12054408|emb|AJ302592.1|HSA302592[12054408]

5942: AJ302591

Homo sapiens 6M1-10*01 gene for olfactory receptor, cell line OLGA
gi|12054406|emb|AJ302591.1|HSA302591[12054406]

5943: AJ302590

Homo sapiens 6M1-10*01 gene for olfactory receptor, cell line YAR
gi|12054404|emb|AJ302590.1|HSA302590[12054404]

5944: AJ302589

Homo sapiens 6M1-10*01 gene for olfactory receptor, cell line SA
gi|12054402|emb|AJ302589.1|HSA302589[12054402]

5945: AJ302588

Homo sapiens 6M1-10*01 gene for olfactory receptor, cell line WT51
gi|12054400|emb|AJ302588.1|HSA302588[12054400]

5946: AJ302587

Homo sapiens 6M1-10*01 gene for olfactory receptor, cell line H2LCL
gi|12054398|emb|AJ302587.1|HSA302587[12054398]

5947: AJ302586

Homo sapiens 6M1-10*01 gene for olfactory receptor, cell line LG2
gi|12054396|emb|AJ302586.1|HSA302586[12054396]

5948: AJ302585

Homo sapiens 6M1-10*01 gene for olfactory receptor, cell line BM19.7
gi|12054394|emb|AJ302585.1|HSA302585[12054394]

5949: AJ302584

Homo sapiens 6M1-10*01 gene for olfactory receptor, cell line BM28.7
gi|12054392|emb|AJ302584.1|HSA302584[12054392]

5950: AJ302583

Homo sapiens 6M1-6*03 gene for olfactory receptor, cell line WT51
gi|12054390|emb|AJ302583.1|HSA302583[12054390]

5951: AJ302582

Homo sapiens 6M1-6*02 gene for olfactory receptor, cell line OLGA
gi|12054388|emb|AJ302582.1|HSA302582[12054388]

5952: AJ302581

Homo sapiens 6M1-6*02 gene for olfactory receptor, cell line KR3598
gi|12054386|emb|AJ302581.1|HSA302581[12054386]

5953: AJ302580

Homo sapiens 6M1-6*02 gene for olfactory receptor, cell line SA
gi|12054384|emb|AJ302580.1|HSA302580[12054384]

5954: AJ302579

Homo sapiens 6M1-6*02 gene for olfactory receptor, cell line AMAI
gi|12054382|emb|AJ302579.1|HSA302579[12054382]

5955: AJ302578

Homo sapiens 6M1-6*02 gene for olfactory receptor, cell line BM28.7
gi|12054380|emb|AJ302578.1|HSA302578[12054380]

5956: AJ302577

Homo sapiens 6M1-6*02 gene for olfactory receptor, cell line BM19.7
gi|12054378|emb|AJ302577.1|HSA302577[12054378]

5957: AJ302576

Homo sapiens 6M1-6*01 gene for olfactory receptor, cell line OLGA
gi|12054376|emb|AJ302576.1|HSA302576[12054376]

5958: AJ302575
Homo sapiens 6M1-6*01 gene for olfactory receptor, cell line YAR
gi|12054374|emb|AJ302575.1|HSA302575[12054374]

5959: AJ302574
Homo sapiens 6M1-6*01 gene for olfactory receptor, cell line SA
gi|12054372|emb|AJ302574.1|HSA302574[12054372]

5960: AJ302573
Homo sapiens 6M1-6*01 gene for olfactory receptor, cell line H2LCL
gi|12054370|emb|AJ302573.1|HSA302573[12054370]

5961: AJ302572
Homo sapiens 6M1-6*01 gene for olfactory receptor, cell line KR3598
gi|12054368|emb|AJ302572.1|HSA302572[12054368]

5962: AJ302571
Homo sapiens 6M1-6*01 gene for olfactory receptor, cell line LG2
gi|12054366|emb|AJ302571.1|HSA302571[12054366]

5963: AJ302570
Homo sapiens 6M1-4P*05 gene for olfactory receptor, cell line BM19.7
gi|12054364|emb|AJ302570.1|HSA302570[12054364]

5964: AJ302569
Homo sapiens 6M1-4P*05 gene for olfactory receptor, cell line BM28.7
gi|12054362|emb|AJ302569.1|HSA302569[12054362]

5965: AJ302568
Homo sapiens 6M1-4P*04 gene for olfactory receptor, cell line AMAI
gi|12054360|emb|AJ302568.1|HSA302568[12054360]

5966: AJ302567
Homo sapiens 6M1-4P*03 gene for olfactory receptor, cell line WT51
gi|12054358|emb|AJ302567.1|HSA302567[12054358]

5967: AJ302566

Homo sapiens 6M1-4P*02 gene for olfactory receptor, cell line OLGA
gi|12054356|emb|AJ302566.1|HSA302566[12054356]

5968: AJ302565
Homo sapiens 6M1-4P*02 gene for olfactory receptor, cell line KR3598
gi|12054354|emb|AJ302565.1|HSA302565[12054354]

5975: AJ302558
Homo sapiens 6M1-3*04 gene for olfactory receptor, cell line AMAI
gi|12054346|emb|AJ302558.1|HSA302558[12054346]

5976: AJ302557
Homo sapiens 6M1-3*03 gene for olfactory receptor, cell line WT51
gi|12054344|emb|AJ302557.1|HSA302557[12054344]

5977: AJ302551
Homo sapiens 6M1-3*01 gene for olfactory receptor, cell line OLGA
gi|12054342|emb|AJ302551.1|HSA302551[12054342]

5978: AJ302550
Homo sapiens 6M1-3*01 gene for olfactory receptor, cell line YAR
gi|12054340|emb|AJ302550.1|HSA302550[12054340]

5979: AJ302549
Homo sapiens 6M1-3*01 gene for olfactory receptor, cell line SA
gi|12054338|emb|AJ302549.1|HSA302549[12054338]

5980: AJ302548
Homo sapiens 6M1-3*01 gene for olfactory receptor, cell line H2LCL
gi|12054336|emb|AJ302548.1|HSA302548[12054336]

5981: AJ302547
Homo sapiens 6M1-3*01 gene for olfactory receptor, cell line LG2
gi|12054334|emb|AJ302547.1|HSA302547[12054334]

5982: AJ302546
Homo sapiens 6M1-1*02 gene for olfactory receptor, cell line BM19.7 gi|12054332|emb|AJ302546.1|HSA302546[12054332]

5983: AJ302545
Homo sapiens 6M1-1*01 gene for olfactory receptor, cell line KR3598
gi|12054330|emb|AJ302545.1|HSA302545[12054330]

5984: AJ302544
Homo sapiens 6M1-1*01 gene for olfactory receptor, cell line YAR
gi|12054328|emb|AJ302544.1|HSA302544[12054328]

5985: AJ302543
Homo sapiens 6M1-1*01 gene for olfactory receptor, cell line OLGA
gi|12054326|emb|AJ302543.1|HSA302543[12054326]

5986: AJ302542
Homo sapiens 6M1-1*01 gene for olfactory receptor, cell line SA
gi|12054324|emb|AJ302542.1|HSA302542[12054324]

5987: AJ302541
Homo sapiens 6M1-1*01 gene for olfactory receptor, cell line AMAI
gi|12054322|emb|AJ302541.1|HSA302541[12054322]

5988: AJ302540
Homo sapiens 6M1-1*01 gene for olfactory receptor, cell line WT51
gi|12054320|emb|AJ302540.1|HSA302540[12054320]

5989: AJ302539
Homo sapiens 6M1-1*01 gene for olfactory receptor, cell line H2LCL
gi|12054318|emb|AJ302539.1|HSA302539[12054318]

5990: AJ302538
Homo sapiens 6M1-1*01 gene for olfactory receptor, cell line BM28.7
gi|12054316|emb|AJ302538.1|HSA302538[12054316]

5991: AJ302537
Homo sapiens 6M1-1*01 gene for olfactory receptor, cell line LG2
gi|12054314|emb|AJ302537.1|HSA302537[12054314]

5993: AJ131724
Homo sapiens mRNA for serotonin receptor 5-HT4 (splice variant h5-HT4(b))
gi|12053629|emb|AJ131724.1|HSA131724[12053629]

5994: AF305200
Homo sapiens interleukin 17E (IL17E) mRNA, complete cds
gi|11878209|gb|AF305200.1|AF305200[11878209]

5995: AH003378
Homo sapiens ciliary neurotrophic factor alpha receptor gene
gi|608655|gb|AH003378.1|SEG_HUMCNFAR0[608655]

5996: L38025
Homo sapiens ciliary neurotrophic factor alpha receptor gene, exons 8-10, complete cds
gi|608654|gb|L38025.1|HUMCNFAR06[608654]

5997: L38024
Homo sapiens ciliary neurotrophic factor alpha receptor gene, exons 5-7
gi|608653|gb|L38024.1|HUMCNFAR05[608653]

5998: L38023
Homo sapiens ciliary neurotrophic factor alpha receptor gene, exon 4
gi|608652|gb|L38023.1|HUMCNFAR04[608652]

5999: L38022
Homo sapiens ciliary neurotrophic factor alpha receptor gene, exon 3
gi|608651|gb|L38022.1|HUMCNFAR03[608651]

6000: L38021
Homo Sapiens ciliary neurutrophic factor alpha receptor gene, exon 2
gi|608650|gb|L38021.1|HUMCNFAR02[608650]

6001: L38020
Homo sapiens ciliary neurotrophic factor alpha receptor gene, exon 1
gi|608649|gb|L38020.1|HUMCNFAR01[608649]

6050: NM_012152
Homo sapiens endothelial differentiation, lysophosphatidic acid
G-protein-coupled receptor, 7 (EDG7), mRNA
gi|6912347|ref|NM_012152.1|[6912347]

6051: NM_007360
Homo sapiens DNA segment on chromosome 12 (unique) 2489 expressed sequence
(D12S2489E), mRNA
gi|6679051|ref|NM_007360.1|[6679051]

6054: AF263029
Homo sapiens protein tyrosine phosphatase receptor type R (PTPRR) gene, exon 14
and complete cds
gi|12043771|gb|AF263029.1|F263016S14[12043771]

6055: AF263028
Homo sapiens protein tyrosine phosphatase receptor type R (PTPRR) gene, exon 13
gi|12043770|gb|AF263028.1|F263016S13[12043770]

6056: AF263027
Homo sapiens protein tyrosine phosphatase receptor type R (PTPRR) gene, exon 12
gi|12043769|gb|AF263027.1|F263016S12[12043769]

6057: AF263026
Homo sapiens protein tyrosine phosphatase receptor type R (PTPRR) gene, exon
11
gi|12043768|gb|AF263026.1|F263016S11[12043768]

6058: AF263025
Homo sapiens protein tyrosine phosphatase receptor type R (PTPRR) gene, exon 10
gi|12043767|gb|AF263025.1|F263016S10[12043767]

6059: AF263024
Homo sapiens protein tyrosine phosphatase receptor type R (PTPRR) gene, exon 9
gi|12043766|gb|AF263024.1|F263016S09[12043766]

6060: AF263023
Homo sapiens protein tyrosine phosphatase receptor type R (PTPRR) gene, exon 8
gi|12043765|gb|AF263023.1|F263016S08[12043765]

6061: AF263022
Homo sapiens protein tyrosine phosphatase receptor type R (PTPRR) gene, exon 7
gi|12043764|gb|AF263022.1|F263016S07[12043764]

6062: AF263021
Homo sapiens protein tyrosine phosphatase receptor type R (PTPRR) gene, exon 6
gi|12043763|gb|AF263021.1|F263016S06[12043763]

6063: AF263020
Homo sapiens protein tyrosine phosphatase receptor type R (PTPRR) gene, exon 5
gi|12043762|gb|AF263020.1|F263016S05[12043762]

6064: AF263019
Homo sapiens protein tyrosine phosphatase receptor type R (PTPRR) gene, exon 4
gi|12043761|gb|AF263019.1|F263016S04[12043761]

6065: AF263018
Homo sapiens protein tyrosine phosphatase receptor type R (PTPRR) gene, exon 3
gi|12043760|gb|AF263018.1|F263016S03[12043760]

6066: AF263017
Homo sapiens protein tyrosine phosphatase receptor type R (PTPRR) gene, exon 2
gi|12043759|gb|AF263017.1|F263016S02[12043759]

6067: AF263016
Homo sapiens protein tyrosine phosphatase receptor type R (PTPRR) gene, exon 1
gi|12043758|gb|AF263016.1|F263016S01[12043758]

6068: AH010208
Homo sapiens chromosome 12 map 12q15
gi|12043757|gb|AH010208.1|SEG_F263016S[12043757]

6069: AF310676

Homo sapiens E3 ubiquitin ligase SMURF2 mRNA, complete cds
gi|12018150|gb|AF310676.1|AF310676[12018150]

6070: AF310250
Homo sapiens IRS-1 PH domain binding protein PHIP mRNA, complete cds
gi|12007333|gb|AF310250.1|AF310250[12007333]

6071: AF276292
Homo sapiens killer cell immunoglobulin-like receptor KIR2DL4 mRNA, complete cds
gi|12006296|gb|AF276292.1|AF276292[12006296]

6072: AF272157
Homo sapiens killer cell immunoglobulin-like receptor precursor (KIR2DLX) gene, complete cds
gi|12006228|gb|AF272157.1|AF272157[12006228]

6073: AF271608
Homo sapiens clone 3 killer cell immunoglobulin-like receptor KIR2DLX (KIR2DLX) mRNA, complete cds
gi|12006190|gb|AF271608.1|AF271608[12006190]

6074: AF271607
Homo sapiens clone 13 killer cell immunoglobulin-like receptor KIR2DLX (KIR2DLX) mRNA, complete cds
gi|12006188|gb|AF271607.1|AF271607[12006188]

6075: AF223941
Homo sapiens complement receptor 2 (CR2) gene, promoter region and partial sequence
gi|12004993|gb|AF223941.1|AF223941[12004993]

6076: AF196176
Homo sapiens capsaicin receptor variant mRNA, complete cds
gi|12003147|gb|AF196176.1|AF196176[12003147]

6077: AF196175
Homo sapiens capsaicin receptor mRNA, complete cds
gi|12003145|gb|AF196175.1|AF196175[12003145]

6078: AF125539
Homo sapiens epidermal growth factor receptor (EGFR) gene, alternative exons, exons 16 and 17 and partial cds, alternatively spliced
gi|12002219|gb|AF125539.1|AF125538S2[12002219]

6079: AF125538
Homo sapiens epidermal growth factor receptor (EGFR) gene, exon 15
gi|12002218|gb|AF125538.1|AF125538S1[12002218]

6080: AH010139
Homo sapiens epidermal growth factor receptor (EGFR) gene, partial cds, alternatively spliced
gi|12002217|gb|AH010139.1|SEG_AF125538S[12002217]

6081: AF308571
Homo sapiens hepatointestinal leukotriene B4 receptor mRNA, complete cds
gi|11878227|gb|AF308571.1|AF308571[11878227]

6082: AF275260
Homo sapiens SRPSOX (SRPSOX) mRNA, complete cds
gi|11139543|gb|AF275260.1|AF275260[11139543]

6083: NM_007161
Homo sapiens DNA segment on chromosome 6 (unique) 49 expressed sequence, NK cell triggering receptor, p30 (D6S49E), mRNA
gi|6005740|ref|NM_007161.1|[6005740]

6090: AF289204
Homo sapiens odorant receptor HOR3'beta4 and odorant receptor HOR3'beta5 genes, complete cds
gi|11991862|gb|AF289204.1|AF289203S2[11991862]

6091: AF289203
Homo sapiens odorant receptor HOR3'beta1, odorant receptor HOR3'beta2, and odorant receptor HOR3'beta3 genes, complete cds
gi|11991861|gb|AF289203.1|AF289203S1[11991861]

6092: AH010109
Homo sapiens odorant receptor HOR3'beta1, odorant receptor HOR3'beta4, odorant receptor HOR3'beta2, odorant receptor HOR3'beta5, and odorant receptor HOR3'beta3 genes, complete cds
gi|11991860|gb|AH010109.1|SEG_AF289203S[11991860]

6093: AF217689
Homo sapiens nociceptin receptor ORL1 (ORL1) gene, exons 1b and 2, and partial cds, alternatively spliced
gi|11991833|gb|AF217689.1|AF217688S2[11991833]

6094: AF217688
Homo sapiens G alpha interacting protein (GAIP) gene, partial cds, alternatively spliced; and nociceptin receptor ORL1 (ORL1) gene, exon 1a
gi|11991832|gb|AF217688.1|AF217688S1[11991832]

6095: AH010108
Homo sapiens G alpha interacting protein (GAIP) and nociceptin receptor ORL1 (ORL1) genes, partial cds
gi|11991831|gb|AH010108.1|SEG_AF217688S[11991831]

6096: AB045011
Homo sapiens hmGluR2 gene for metabotropic glutamate receptor type 2, complete cds
gi|11990938|dbj|AB045011.1|AB045011[11990938]

6097: AF281074
Homo sapiens neuropilin 2 (NRP2) gene, complete cds, alternatively spliced
gi|11934947|gb|AF281074.1|AF281074[11934947]

6098: AJ400846
Homo sapiens mRNA for immunoglobulin-like cell surface receptor FDFACT1, activating counterpart allele 1
gi|11932154|emb|AJ400846.1|HSA400846[11932154]

6099: AJ400845
Homo sapiens mRNA for immunoglobulin-like cell surface receptor FDFACT2, activating counterpart allele 2 gi|11932151|emb|AJ400845.1|HSA400845[11932151]

6100: AB024327
Homo sapiens pt-wd mRNA for WD-40 repeat protein, complete cds
gi|4519416|dbj|AB024327.1|AB024327[4519416]

6102: AF280547
Homo sapiens neuropilin-1 soluble isoform 11 (NRP1) mRNA, complete cds, alternatively spliced
gi|11907931|gb|AF280547.1|AF280547[11907931]

6103: AF280546
Homo sapiens neuropilin-2 soluble isoform 9 (NRP2) mRNA, complete cds, alternatively spliced
gi|11907929|gb|AF280546.1|AF280546[11907929]

6104: AF280545
Homo sapiens neuropilin-2b(5) (NRP2) mRNA, complete cds, alternatively spliced
gi|11907927|gb|AF280545.1|AF280545[11907927]

6105: AF280544
Homo sapiens neuropilin-2b(O) (NRP2) mRNA, complete cds, alternatively spliced
gi|11907925|gb|AF280544.1|AF280544[11907925]

6106: AF268899
Homo sapiens neuropeptide FF receptor 2 (NPFF2) mRNA, complete cds
gi|11907914|gb|AF268899.1|AF268899[11907914]

6107: AF268898
Homo sapiens neuropeptide FF receptor 1 (NPFF1) mRNA, complete cds
gi|11907912|gb|AF268898.1|AF268898[11907912]

6111: Y19228
Homo sapiens partial GIR gene for glucocorticoid induced receptor, exons and joined CDS
gi|11878425|emb|Y19228.1|HSY19228[11878425]

6118: Y19231

Homo sapiens partial GIR gene for glucocorticoid induced receptor, exon 4
gi|11877264|emb|Y19231.1|HSY19231[11877264]

6119: Y19230
Homo sapiens partial GIR gene for glucocorticoid induced receptor, exon 3
gi|11877263|emb|Y19230.1|HSY19230[11877263]

6120: Y19229
Homo sapiens partial GIR gene for glucocorticoid induced receptor, exon 2
gi|11877262|emb|Y19229.1|HSY19229[11877262]

6121: AX047952
Sequence 19 from Patent WO0070045
gi|11876875|emb|AX047952.1|AX047952[11876875]

6122: AX047940
Sequence 7 from Patent WO0070045
gi|11876863|emb|AX047940.1|AX047940[11876863]

6123: AX047936
Sequence 3 from Patent WO0070045
gi|11876859|emb|AX047936.1|AX047936[11876859]

6124: AJ272207
Homo sapiens mRNA for putative G protein-coupled receptor 92 (GPR92 gene)
gi|9843745|emb|AJ272207.1|HSA272207[9843745]

6125: AF311306
Homo sapiens prostate specific G-protein coupled receptor gene, complete cds
gi|11875777|gb|AF311306.1|AF311306[11875777]

6126: NM_022146
Homo sapiens neuropeptide FF 1; RFamide-related peptide receptor (OT7T022), mRNA
gi|11545886|ref|NM_022146.1|[11545886]

6127: NM_004885
Homo sapiens neuropeptide G protein-coupled receptor; neuropeptide FF 2 (NPGPR), mRNA
gi|4758819|ref|NM_004885.1|[4758819]

6128: NM_002958
Homo sapiens RYK receptor-like tyrosine kinase (RYK), mRNA
gi|11863158|ref|NM_002958.1|[11863158]

6129: AF217485
Homo sapiens KIR3DS1 gene, partial sequence; and killer cell Ig-like receptor KIR2DL5.1 (KIR2DL5.1) gene, complete cds
gi|11761705|gb|AF217485.1|AF217485[11761705]

6130: NM_005856
Homo sapiens receptor (calcitonin) activity modifying protein 3 (RAMP3), mRNA
gi|5032022|ref|NM_005856.1|[5032022]

6131: NM_005854
Homo sapiens receptor (calcitonin) activity modifying protein 2 (RAMP2), mRNA
gi|5032020|ref|NM_005854.1|[5032020]

6132: NM_005855
Homo sapiens receptor (calcitonin) activity modifying protein 1 (RAMP1), mRNA
gi|5032018|ref|NM_005855.1|[5032018]

6133: NM_000025
Homo sapiens adrenergic, beta-3-, receptor (ADRB3), mRNA
gi|4557266|ref|NM_000025.1|[4557266]

6134: AF245390
Homo sapiens GREB1c (GREB1) mRNA, complete cds, alternatively spliced
gi|11611737|gb|AF245390.1|AF245390[11611737]

6135: AF245389
Homo sapiens GREB1b (GREB1) mRNA, complete cds, alternatively spliced
gi|11611735|gb|AF245389.1|AF245389[11611735]

6136: AF245388

Homo sapiens GREB1a (GREB1) mRNA, partial cds, alternatively spliced
gi|11611733|gb|AF245388.1|AF245388[11611733]

6137: AF292402
Homo sapiens neuromedin U receptor-type 2 mRNA, complete cds
gi|9944989|gb|AF292402.1|AF292402[9944989]

6138: NM_002855
Homo sapiens poliovirus receptor-related 1 (herpesvirus entry mediator C;
nectin) (PVRL1), mRNA
gi|11602905|ref|NM_002855.2|[11602905]

6143: AH010043
Homo sapiens
gi|11559571|gb|AH010043.1|SEG_AF260138S[11559571]

6144: AF260137
Homo sapiens killer-cell immunoglobulin-like receptor KIR2DL5.3 (KIR2DL5) gene,
exon 1 and partial cds
gi|11559569|gb|AF260137.1|AF260137[11559569]

6145: X76400
Homo sapiens mRNA for nectin 1 (PRR1 gene)
gi|11558774|emb|X76400.2|HSPRR[11558774]

6147: NM_022159
Homo sapiens ETL protein (ETL), mRNA
gi|11545907|ref|NM_022159.1|[11545907]

6148: NM_022150
Homo sapiens RFamide-related peptide precursor (RFRP), mRNA
gi|11545893|ref|NM_022150.1|[11545893]

6149: NM_022049
Homo sapiens G-protein coupled receptor 88 (GPR88), mRNA
gi|11545752|ref|NM_022049.1|[11545752]

6219: AF281308
Homo sapiens alpha 2A adrenergic receptor (ADRA2A) gene, complete cds
gi|9652209|gb|AF281308.1|AF281308[9652209]

6241: AF217487
Homo sapiens killer cell Ig-like receptor KIR2DL5.3 (KIR2DL5.3) mRNA, complete cds
gi|11528059|gb|AF217487.1|AF217487[11528059]

6242: NM_003553
Homo sapiens olfactory receptor, family 1, subfamily E, member 1 (OR1E1), mRNA
gi|11496274|ref|NM_003553.1|[11496274]

6243: AF208054
Homo sapiens non-inhibitory killer-cell Ig-like receptor KIR (KIR2DS5) mRNA, complete cds
gi|11493968|gb|AF208054.1|AF208054[11493968]

6244: NM_018690
Homo sapiens apolipoprotein B48 receptor (APOB48R), mRNA
gi|8922078|ref|NM_018690.1|[8922078]

6245: AB044934
Homo sapiens H4R mRNA for histamine H4 receptor, complete cds
gi|10241846|dbj|AB044934.1|AB044934[10241846]

6246: NM_003555
Homo sapiens olfactory receptor, family 1, subfamily G, member 1 (OR1G1), mRNA
gi|11415033|ref|NM_003555.1|[11415033]

6247: NM_003552
Homo sapiens olfactory receptor, family 1, subfamily D, member 4 (OR1D4), mRNA
gi|11415031|ref|NM_003552.1|[11415031]

6248: NM_003554
Homo sapiens olfactory receptor, family 1, subfamily E, member 2 (OR1E2), mRNA
gi|11386152|ref|NM_003554.1|[11386152]

6390: AF264014
Homo sapiens scavenger receptor cysteine-rich type 1 protein M160 precursor, mRNA, complete cds, alternatively spliced
gi|9652086|gb|AF264014.1|AF264014[9652086]

6391: AF169007
Homo sapiens beta-1-adrenergic receptor (ADRB1) gene, complete cds
gi|5833816|gb|AF169007.1|AF169007[5833816]

6392: AF169006
Homo sapiens beta-1-adrenergic receptor (ADRB1) gene, complete cds
gi|5833814|gb|AF169006.1|AF169006[5833814]

6393: AF159854
Homo sapiens cytokine signaling suppressor (SOCS3) mRNA, complete cds
gi|5353755|gb|AF159854.1|AF159854[5353755]

6394: AF032124
Homo sapiens RET proto-oncogene (RET) gene, 5' flanking region and partial cds
gi|2795879|gb|AF032124.1|AF032124[2795879]

6395: NM_002644
Homo sapiens polymeric immunoglobulin receptor (PIGR), mRNA
gi|11342673|ref|NM_002644.1|[11342673]

6396: AJ249248
Homo sapiens mRNA for putative G protein-coupled Receptor
gi|5834594|emb|AJ249248.1|HSA249248[5834594]

6397: AJ277028
Homo sapiens mRNA for vanilloid receptor 1 (VR1 gene)
gi|8977865|emb|AJ277028.1|HSA277028[8977865]

6398: AF072872
Homo sapiens frizzled 1 mRNA, complete cds
gi|5305406|gb|AF072872.1|AF072872[5305406]

6399: AF073727
Homo sapiens EH domain-binding mitotic phosphoprotein (EPSIN) mRNA, complete cds
gi|5051635|gb|AF073727.1|AF073727[5051635]

6400: NM_002551
Homo sapiens olfactory receptor, family 3, subfamily A, member 2 (OR3A2), mRNA
gi|11321568|ref|NM_002551.1|[11321568]

6401: NM_000870
Homo sapiens 5-hydroxytryptamine (serotonin) receptor 4 (HTR4), mRNA
gi|11321562|ref|NM_000870.1|[11321562]

6419: AB042411
Homo sapiens strg gene for striatum-specific G potein-coupled receptor, complete cds
gi|11275369|dbj|AB042411.1|AB042411[11275369]

6420: AB042410
Homo sapiens strg mRNA for striatum-specific G protein-coupled receptor, complete cds
gi|11275367|dbj|AB042410.1|AB042410[11275367]

6434: AJ289159
Homo sapiens CD30 gene for cytokine receptor CD30, exons 1-8
gi|11230634|emb|AJ289159.1|HSA289159[11230634]

6435: AF279762
Homo sapiens ROR2 (ROR2) gene, exon 9 and partial cds
gi|11228720|gb|AF279762.1|AF279755S8[11228720]

6436: AF279761
Homo sapiens ROR2 (ROR2) gene, exon 8
gi|11228719|gb|AF279761.1|AF279755S7[11228719]

6437: AF279760
Homo sapiens ROR2 (ROR2) gene, exon 7
gi|11228718|gb|AF279760.1|AF279755S6[11228718]

6438: AF279759
Homo sapiens ROR2 (ROR2) gene, exon 6
gi|11228717|gb|AF279759.1|AF279755S5[11228717]

6439: AF279758
Homo sapiens ROR2 (ROR2) gene, exon 5
gi|11228716|gb|AF279758.1|AF279755S4[11228716]

6440: AF279757
Homo sapiens ROR2 (ROR2) gene, exon 4
gi|11228715|gb|AF279757.1|AF279755S3[11228715]

6441: AF279756
Homo sapiens ROR2 (ROR2) gene, exon 3
gi|11228714|gb|AF279756.1|AF279755S2[11228714]

6442: AF279755
Homo sapiens ROR2 (ROR2) gene, exon 2
gi|11228713|gb|AF279755.1|AF279755S1[11228713]

6443: AH010002
Homo sapiens ROR2 (ROR2) gene, partial cds
gi|11228712|gb|AH010002.1|SEG_AF279755S[11228712]

6444: AF260529
Homo sapiens MER receptor tyrosine kinase (MERTK) gene, exon 19 and partial cds
gi|11228705|gb|AF260529.1|F260514S16[11228705]

6445: AF260528
Homo sapiens MER receptor tyrosine kinase (MERTK) gene, exons 17 and 18
gi|11228704|gb|AF260528.1|F260514S15[11228704]

6446: AF260527
Homo sapiens MER receptor tyrosine kinase (MERTK) gene, exon 16
gi|11228703|gb|AF260527.1|F260514S14[11228703]

6447: AF260526
Homo sapiens MER receptor tyrosine kinase (MERTK) gene, exon 15
gi|11228702|gb|AF260526.1|F260514S13[11228702]

6448: AF260525
Homo sapiens MER receptor tyrosine kinase (MERTK) gene, exon 14
gi|11228701|gb|AF260525.1|F260514S12[11228701]

6449: AF260524
Homo sapiens MER receptor tyrosine kinase (MERTK) gene, exons 12 and 13
gi|11228700|gb|AF260524.1|F260514S11[11228700]

6450: AF260523
Homo sapiens MER receptor tyrosine kinase (MERTK) gene, exon 11
gi|11228699|gb|AF260523.1|F260514S10[11228699]

6451: AF260522
Homo sapiens MER receptor tyrosine kinase (MERTK) gene, exon 10
gi|11228698|gb|AF260522.1|F260514S09[11228698]

6452: AF260521
Homo sapiens MER receptor tyrosine kinase (MERTK) gene, exon 9
gi|11228697|gb|AF260521.1|F260514S08[11228697]

6453: AF260520
Homo sapiens MER receptor tyrosine kinase (MERTK) gene, exon 8
gi|11228696|gb|AF260520.1|F260514S07[11228696]

6454: AF260519
Homo sapiens MER receptor tyrosine kinase (MERTK) gene, exon 7
gi|11228695|gb|AF260519.1|F260514S06[11228695]

6455: AF260518
Homo sapiens MER receptor tyrosine kinase (MERTK) gene, exon 6
gi|11228694|gb|AF260518.1|F260514S05[11228694]

6456: AF260517
Homo sapiens MER receptor tyrosine kinase (MERTK) gene, exon 5
gi|11228693|gb|AF260517.1|F260514S04[11228693]

6457: AF260516
Homo sapiens MER receptor tyrosine kinase (MERTK) gene, exon 4
gi|11228692|gb|AF260516.1|F260514S03[11228692]

6458: AF260515
Homo sapiens MER receptor tyrosine kinase (MERTK) gene, exon 3
gi|11228691|gb|AF260515.1|F260514S02[11228691]

6459: AF260514
Homo sapiens MER receptor tyrosine kinase (MERTK) gene, exon 2
gi|11228690|gb|AF260514.1|F260514S01[11228690]

6460: AH010001
Homo sapiens MER receptor tyrosine kinase (MERTK) gene, partial cds
gi|11228689|gb|AH010001.1|SEG_F260514S[11228689]

6461: AF175406
Homo sapiens transient receptor potential 4 (TRP4) mRNA, complete cds
gi|5802614|gb|AF175406.1|AF175406[5802614]

6462: NM_017416
Homo sapiens interleukin 1 receptor accessory protein-like 2 (IL1RAPL2), mRNA
gi|11225606|ref|NM_017416.1|[11225606]

6463: AJ295237
Homo sapiens mRNA for neuronal nicotinic acetylcholine receptor subunit alpha 10
(NACHR alpha 10 gene)
gi|11182127|emb|AJ295237.1|HSA295237[11182127]

6464: NM_004720
Homo sapiens endothelial differentiation, lysophosphatidic acid
G-protein-coupled receptor, 4 (EDG4), mRNA
gi|11038657|ref|NM_004720.3|[11038657]

6465: AF298770
Homo sapiens Smac/DIABLO-S protein mRNA, complete cds
gi|10719653|gb|AF298770.1|AF298770[10719653]

6562: NM_005226
Homo sapiens endothelial differentiation, sphingolipid G-protein-coupled receptor, 3 (EDG3), mRNA
gi|4885194|ref|NM_005226.1|[4885194]

6563: NM_021803
Homo sapiens interleukin 21 (IL21), mRNA
gi|11141874|ref|NM_021803.1|[11141874]

6564: NM_021798
Homo sapiens interleukin 21 receptor (IL21R), mRNA
gi|11141868|ref|NM_021798.1|[11141868]

6565: AF307973
Homo sapiens histamine H4 receptor mRNA, complete cds
gi|11141732|gb|AF307973.1|AF307973[11141732]

6566: X06026
Homo sapiens partial CD3G gene, exon 1 (and joined CDS)
gi|36809|emb|X06026.1|HSTCR3G1[36809]

6567: AF200220
Homo sapiens FcRn alpha chain (FCGRT) gene, exons 5, 6, 7, and complete cds
gi|11138512|gb|AF200220.1|AF200219S2[11138512]

6568: AF200219
Homo sapiens FcRn alpha chain (FCGRT) gene, exons 1 through 4
gi|11138511|gb|AF200219.1|AF200219S1[11138511]

6569: AH009974
Homo sapiens FcRn alpha chain (FCGRT) gene, exons 1 through 4
gi|11138510|gb|AH009974.1|SEG_AF200219S[11138510]

6570: NM_017581
Homo sapiens cholinergic receptor, nicotinic, alpha polypeptide 9 (CHRNA9), mRNA
gi|8923741|ref|NM_017581.1|[8923741]

6571: AB040290
Homo sapiens RFRP mRNA for RFamide-related peptide precursor, complete cds
gi|11125707|dbj|AB040290.1|AB040290[11125707]

6572: AB040104
Homo sapiens OT7T022 mRNA for RFamide-related peptide receptor, complete cds
gi|11125701|dbj|AB040104.1|AB040104[11125701]

6598: AF308542
Homo sapiens clone ST1L_G11 immunoglobulin heavy chain mRNA, partial cds
gi|11119124|gb|AF308542.1|AF308542[11119124]

6599: AJ271338
Homo sapiens IL1L1 gene for interleukin-1 like protein 1, exons 1-6
gi|6729586|emb|AJ271338.1|HSA271338[6729586]

6600: AJ242738
Homo sapiens mRNA for interleukin-1-like protein 1 (IL1L1 gene) transcript 2
gi|6165335|emb|AJ242738.1|HSA242738[6165335]

6601: AJ242737
Homo sapiens mRNA for interleukin-1-like protein-1 (IL1L1 gene), transcript 1
gi|6165333|emb|AJ242737.1|HSA242737[6165333]

6602: NM_005508
Homo sapiens chemokine (C-C motif) receptor 4 (CCR4), mRNA
gi|5031626|ref|NM_005508.1|[5031626]

6603: NM_005283
Homo sapiens chemokine (C motif) XC receptor 1 (CCXCR1), mRNA
gi|4885338|ref|NM_005283.1|[4885338]

6604: AJ238419
Homo sapiens mRNA for HIV-specific T-cell receptor beta chain, clone RI, partial
gi|4691321|emb|AJ238419.1|HSA238419[4691321]

6605: AJ238418
Homo sapiens mRNA for HIV-specific T-cell receptor beta chain, clone MA, partial
gi|4691319|emb|AJ238418.1|HSA238418[4691319]

6606: AJ238417
Homo sapiens mRNA for HIV-specific T-cell receptor beta chain, clone HA, partial
gi|4691317|emb|AJ238417.1|HSA238417[4691317]

6607: AJ238416
Homo sapiens mRNA for HIV-specific T-cell receptor alpha chain, clone RI, partial
gi|4691315|emb|AJ238416.1|HSA238416[4691315]

6608: AJ238415
Homo sapiens mRNA for HIV-specific T-cell receptor alpha chain, clone MA, partial
gi|4691313|emb|AJ238415.1|HSA238415[4691313]

6609: AJ238414
Homo sapiens mRNA for HIV-specific T-cell receptor alpha chain, clone HA, partial
gi|4691311|emb|AJ238414.1|HSA238414[4691311]

6610: AF074042
AF074042 Human Homo sapiens genomic clone pTWB15.69 T7, genomic survey sequence
gi|3342086|gb|AF074042.1|AF074042[3342086]

6611: AF074041
AF074041 Human Homo sapiens genomic clone pTWB15.69 SP6, genomic survey sequence
gi|3342085|gb|AF074041.1|AF074041[3342085]

6612: AF074040
AF074040 Human Homo sapiens genomic clone pTWB15.53 T7, genomic survey sequence gi|3342084|gb|AF074040.1|AF074040[3342084]

6613: AF074039
AF074039 Human Homo sapiens genomic clone pTWB15.53 SP6, genomic survey sequence
gi|3342083|gb|AF074039.1|AF074039[3342083]

6614: AF074038
AF074038 Human Homo sapiens genomic clone pTWB15.43 T7, genomic survey sequence
gi|3342082|gb|AF074038.1|AF074038[3342082]

6615: AF074037
AF074037 Human Homo sapiens genomic clone pTWB15.43 SP6, genomic survey sequence
gi|3342081|gb|AF074037.1|AF074037[3342081]

6616: AF074036
AF074036 Human Homo sapiens genomic clone pTWB15.42, genomic survey sequence
gi|3342080|gb|AF074036.1|AF074036[3342080]

6617: AF074034
AF074034 Human Homo sapiens genomic clone pTWB15.32 T7, genomic survey sequence
gi|3342079|gb|AF074034.1|AF074034[3342079]

6618: AF074033
AF074033 Human Homo sapiens genomic clone pTWB15.32 SP6, genomic survey sequence
gi|3342078|gb|AF074033.1|AF074033[3342078]

6619: AF074032
AF074032 Human Homo sapiens genomic clone pTWB15.31 T7, genomic survey sequence
gi|3342077|gb|AF074032.1|AF074032[3342077]

6620: AF074031
AF074031 Human Homo sapiens genomic clone pTWB15.31 SP6, genomic survey sequence
gi|3342076|gb|AF074031.1|AF074031[3342076]

6621: AF074030
AF074030 Human Homo sapiens genomic clone pTWB15.28 T7, genomic survey sequence
gi|3342075|gb|AF074030.1|AF074030[3342075]

6622: AF074028
AF074028 Human Homo sapiens genomic clone pTWB15.21, genomic survey sequence
gi|3342074|gb|AF074028.1|AF074028[3342074]

6623: AF074027
AF074027 Human Homo sapiens genomic clone pTWB15.12, genomic survey sequence
gi|3342073|gb|AF074027.1|AF074027[3342073]

6624: AF074026
AF074026 Human Homo sapiens genomic clone pTWB15.09, genomic survey sequence
gi|3342072|gb|AF074026.1|AF074026[3342072]

6625: AF074025
AF074025 Human Homo sapiens genomic clone pTWB15.08, genomic survey sequence
gi|3342071|gb|AF074025.1|AF074025[3342071]

6626: AF074024
AF074024 Human Homo sapiens genomic clone pTWB15.07, genomic survey sequence
gi|3342070|gb|AF074024.1|AF074024[3342070]

6627: AF074023
AF074023 Human Homo sapiens genomic clone pTWB15.04, genomic survey sequence
gi|3342069|gb|AF074023.1|AF074023[3342069]

6628: AF074022
AF074022 Human Homo sapiens genomic clone pTWB15.04 SP6, genomic survey sequence
gi|3342068|gb|AF074022.1|AF074022[3342068]

6629: NM_000450
Homo sapiens selectin E (endothelial adhesion molecule 1) (SELE), mRNA
gi|4506870|ref|NM_000450.1|[4506870]

6630: AF254069
Homo sapiens interleukin 21 (IL21) mRNA, complete cds
gi|11093535|gb|AF254069.1|AF254069[11093535]

6631: AF254067
Homo sapiens interleukin 21 receptor (IL21R) mRNA, complete cds
gi|11093531|gb|AF254067.1|AF254067[11093531]

6632: AF251510
Homo sapiens leukocyte-associated Ig-like receptor 1D isoform mRNA, complete cds
gi|11090865|gb|AF251510.2|AF251510[11090865]

6633: AF251509
Homo sapiens leukocyte-associated Ig-like receptor 1C isoform mRNA, complete cds
gi|11090859|gb|AF251509.2|AF251509[11090859]

6634: AB043943
Homo sapiens GPVI gene for platelet glycoprotein VI, partial cds
gi|9955915|dbj|AB043943.1|AB043943[9955915]

6635: AB043821
Homo sapiens GPVI mRNA for platelet glycoprotein VI-3, complete cds
gi|9955913|dbj|AB043821.1|AB043821[9955913]

6636: AB043820
Homo sapiens GPVI mRNA for platelet glycoprotein VI-2, complete cds
gi|9955911|dbj|AB043820.1|AB043820[9955911]

6637: AB043819
Homo sapiens GPVI mRNA for platelet glycoprotein VI-1, complete cds
gi|9955909|dbj|AB043819.1|AB043819[9955909]

6638: NM_000527
Homo sapiens low density lipoprotein receptor (familial hypercholesterolemia) (LDLR), mRNA
gi|8051613|ref|NM_000527.2|[8051613]

6639: NM_012407
Homo sapiens protein kinase C, alpha binding protein (PRKCABP), mRNA
gi|7110696|ref|NM_012407.1|[7110696]

6640: NM_005232
Homo sapiens EphA1 (EPHA1), mRNA
gi|4885208|ref|NM_005232.1|[4885208]

6641: NM_000214
Homo sapiens jagged 1 (Alagille syndrome) (JAG1), mRNA
gi|4557678|ref|NM_000214.1|[4557678]

6642: NM_000875
Homo sapiens insulin-like growth factor 1 receptor (IGF1R), mRNA
gi|11068002|ref|NM_000875.2|[11068002]

6643: AF298812
Homo sapiens X-linked ectodysplasin-A2 receptor (XEDAR) mRNA, complete cds
gi|11066914|gb|AF298812.1|AF298812[11066914]

6644: AF197929
Homo sapiens short form lysophosphatidic acid receptor EDG4 (EDG4) mRNA, complete cds
gi|11066253|gb|AF197929.1|AF197929[11066253]

6645: NM_021642
Homo sapiens Fc fragment of IgG, low affinity IIa, receptor for (CD32) (FCGR2A), mRNA
gi|11056051|ref|NM_021642.1|[11056051]

6646: AF280400
Homo sapiens alpha 2C adrenergic receptor variant (ADRA2C) gene, complete cds
gi|11055420|gb|AF280400.1|AF280400[11055420]

6647: AF280399
Homo sapiens alpha 2C adrenergic receptor (ADRA2C) gene, complete cds
gi|11055418|gb|AF280399.1|AF280399[11055418]

6648: AF263523
Homo sapiens vanilloid receptor-related osmotically activated channel (VROAC) mRNA, complete cds gi|11055321|gb|AF263523.1|AF263523[11055321]

6649: NM_001117
Homo sapiens adenylate cyclase activating polypeptide 1 (pituitary) (ADCYAP1), mRNA
gi|10947062|ref|NM_001117.2|[10947062]

6650: NM_002355
Homo sapiens mannose-6-phosphate receptor (cation dependent) (M6PR), mRNA
gi|10947032|ref|NM_002355.2|[10947032]

6651: NM_000541
Homo sapiens S-antigen; retina and pineal gland (arrestin) (SAG), mRNA
gi|10880124|ref|NM_000541.2|[10880124]

6652: NM_021130
Homo sapiens peptidylprolyl isomerase A (cyclophilin A) (PPIA), mRNA
gi|10863926|ref|NM_021130.1|[10863926]

6653: NM_001106
Homo sapiens activin A receptor, type IIB (ACVR2B), mRNA
gi|10862697|ref|NM_001106.2|[10862697]

6654: NM_001616
Homo sapiens activin A receptor, type II (ACVR2), mRNA
gi|10862696|ref|NM_001616.2|[10862696]

6655: NM_001105
Homo sapiens activin A receptor, type I (ACVR1), mRNA
gi|10862690|ref|NM_001105.2|[10862690]

6656: NM_001136
Homo sapiens advanced glycosylation end product-specific receptor (AGER), mRNA
gi|10835202|ref|NM_001136.1|[10835202]

6657: NM_000866
Homo sapiens 5-hydroxytryptamine (serotonin) receptor 1F (HTR1F), mRNA gi|10835196|ref|NM_000866.1|[10835196]

6658: NM_000629
Homo sapiens interferon (alpha, beta and omega) receptor 1 (IFNAR1), mRNA
gi|10835182|ref|NM_000629.1|[10835182]

6659: NM_000621
Homo sapiens 5-hydroxytryptamine (serotonin) receptor 2A (HTR2A), mRNA
gi|10835174|ref|NM_000621.1|[10835174]

6660: NM_000610
Homo sapiens CD44 antigen (homing function and Indian blood group system) (CD44), mRNA
gi|10835162|ref|NM_000610.1|[10835162]

6661: NM_000585
Homo sapiens interleukin 15 (IL15), mRNA
gi|10835152|ref|NM_000585.1|[10835152]

6662: NM_000586
Homo sapiens interleukin 2 (IL2), mRNA
gi|10835148|ref|NM_000586.1|[10835148]

6663: NM_000577
Homo sapiens interleukin 1 receptor antagonist (IL1RN), mRNA
gi|10835146|ref|NM_000577.1|[10835146]

6664: NM_000576
Homo sapiens interleukin 1, beta (IL1B), mRNA
gi|10835144|ref|NM_000576.1|[10835144]

6665: NM_000570
Homo sapiens Fc fragment of IgG, low affinity IIIb, receptor for (CD16) (FCGR3B), mRNA
gi|10835138|ref|NM_000570.1|[10835138]

6666: NM_000566

Homo sapiens Fc fragment of IgG, high affinity Ia, receptor for (CD64) (FCGR1A), mRNA
gi|10835132|ref|NM_000566.1|[10835132]

6667: NM_000564
Homo sapiens interleukin 5 receptor, alpha (IL5RA), mRNA
gi|10835130|ref|NM_000564.1|[10835130]

6668: NM_000525
Homo sapiens potassium inwardly-rectifying channel, subfamily J, member 11 (KCNJ11), mRNA
gi|10835116|ref|NM_000525.1|[10835116]

6669: NM_003841
Homo sapiens tumor necrosis factor receptor superfamily, member 10c, decoy without an intracellular domain (TNFRSF10C), mRNA
gi|10835042|ref|NM_003841.1|[10835042]

6672: NM_001307
Homo sapiens claudin 7 (CLDN7), mRNA
gi|10835007|ref|NM_001307.1|[10835007]

6673: NM_000640
Homo sapiens interleukin 13 receptor, alpha 2 (IL13RA2), mRNA
gi|10834991|ref|NM_000640.1|[10834991]

6674: NM_001993
Homo sapiens coagulation factor III (thromboplastin, tissue factor) (F3), mRNA
gi|10518499|ref|NM_001993.2|[10518499]

6675: NM_013252
Homo sapiens C-type (calcium dependent, carbohydrate-recognition domain) lectin, superfamily member 5 (CLECSF5), mRNA
gi|10281668|ref|NM_013252.1|[10281668]

6676: NM_020547
Homo sapiens anti-Mullerian hormone receptor, type II (AMHR2), mRNA
gi|10198655|ref|NM_020547.1|[10198655]

6677: NM_018970
Homo sapiens G protein-coupled receptor 85 (GPR85), mRNA
gi|10190654|ref|NM_018970.2|[10190654]

6678: NM_014292
Homo sapiens chromobox homolog 6 (CBX6), mRNA
gi|10140848|ref|NM_014292.1|[10140848]

6679: NM_019897
Homo sapiens olfactory receptor, family 2, subfamily S, member 2 (OR2S2), mRNA
gi|10092668|ref|NM_019897.1|[10092668]

6680: NM_014499
Homo sapiens putative purinergic receptor (P2Y10), mRNA
gi|10092632|ref|NM_014499.1|[10092632]

6681: NM_017572
Homo sapiens G protein-coupled receptor kinase 7 (GPRK7), mRNA
gi|9994196|ref|NM_017572.1|[9994196]

6682: NM_020406
Homo sapiens polycythemia rubra vera 1; cell surface receptor (PRV1), mRNA
gi|9966888|ref|NM_020406.1|[9966888]

6683: NM_020377
Homo sapiens cysteinyl leukotriene CysLT2 receptor; cDNA: PSEC0146 from clone PLACE1006979 (LOC57105), mRNA
gi|9966850|ref|NM_020377.1|[9966850]

6686: NM_002295
Homo sapiens laminin receptor 1 (67kD, ribosomal protein SA) (LAMR1), mRNA
gi|9845501|ref|NM_002295.2|[9845501]

6687: NM_019839
Homo sapiens seven transmembrane receptor BLTR2; leukotriene B4 receptor BLT2 (BLTR2), mRNA
gi|9789896|ref|NM_019839.1|[9789896]

6688: NM_018969
Homo sapiens super conserved receptor expressed in brain 3 (SREB3), mRNA
gi|9507142|ref|NM_018969.1|[9507142]

6689: NM_018949
Homo sapiens G protein-coupled receptor 14 (GPR14), mRNA
gi|9506744|ref|NM_018949.1|[9506744]

6690: NM_000804
Homo sapiens folate receptor 3 (gamma) (FOLR3), mRNA
gi|9257219|ref|NM_000804.2|[9257219]

6691: NM_000803
Homo sapiens folate receptor 2 (fetal) (FOLR2), mRNA
gi|9257218|ref|NM_000803.2|[9257218]

6692: NM_017526
Homo sapiens leptin receptor gene-related protein (HSOBRGRP), mRNA
gi|8923784|ref|NM_017526.1|[8923784]

6693: NM_017532
Homo sapiens p65 protein (HSAJ2425), mRNA
gi|8923776|ref|NM_017532.1|[8923776]

6694: NM_017442
Homo sapiens toll-like receptor 9 (TLR9), mRNA
gi|8394455|ref|NM_017442.1|[8394455]

6695: NM_016946
Homo sapiens junctional adhesion molecule (JAM), mRNA
gi|8393637|ref|NM_016946.1|[8393637]

6697: NM_013280
Homo sapiens fibronectin leucine rich transmembrane protein 1 (FLRT1), mRNA
gi|8051591|ref|NM_013280.2|[8051591]

6698: NM_013431
Homo sapiens killer cell lectin-like receptor subfamily C, member 4 (KLRC4), mRNA
gi|7710123|ref|NM_013431.1|[7710123]

6699: NM_016568
Homo sapiens G-protein coupled receptor SALPR; somatostatin and angiotensin-like peptide receptor (LOC51289), mRNA
gi|7706102|ref|NM_016568.1|[7706102]

6700: NM_015863
Homo sapiens surfactant protein B (LOC51041), mRNA
gi|7705659|ref|NM_015863.1|[7705659]

6702: NM_015868
Homo sapiens NK-receptor (KIR-023GB), mRNA
gi|7705567|ref|NM_015868.1|[7705567]

6703: NM_016540
Homo sapiens G protein-coupled receptor 72 (GPR72), mRNA
gi|7705384|ref|NM_016540.1|[7705384]

6704: NM_001059
Homo sapiens tachykinin receptor 3 (TACR3), mRNA
gi|7669547|ref|NM_001059.1|[7669547]

6705: NM_014030
Homo sapiens G protein-coupled receptor kinase-interactor 1 (GIT1), mRNA
gi|7661711|ref|NM_014030.1|[7661711]

6706: NM_014521
Homo sapiens SH3-domain binding protein 4 (SH3BP4), mRNA
gi|7657561|ref|NM_014521.1|[7657561]

6707: NM_014285
Homo sapiens homolog of Yeast RRP4 (ribosomal RNA processing 4), 3'-5'-exoribonuclease (RRP4), mRNA
gi|7657527|ref|NM_014285.1|[7657527]

6708: NM_014566
Homo sapiens olfactory receptor, family 1, subfamily D, member 5 (OR1D5), mRNA
gi|7657422|ref|NM_014566.1|[7657422]

6709: NM_014565
Homo sapiens olfactory receptor, family 1, subfamily A, member 1 (OR1A1), mRNA
gi|7657420|ref|NM_014565.1|[7657420]

6710: NM_014221
Homo sapiens mature T-cell proliferation 1 (MTCP1), mRNA
gi|7657348|ref|NM_014221.1|[7657348]

6711: NM_014387
Homo sapiens linker for activation of T cells (LAT), mRNA
gi|7657292|ref|NM_014387.1|[7657292]

6712: NM_014514
Homo sapiens killer cell immunoglobulin-like receptor, three domains, short cytoplasmic tail, 1 (KIR3DS1), mRNA
gi|7657280|ref|NM_014514.1|[7657280]

6713: NM_014513
Homo sapiens killer cell immunoglobulin-like receptor, two domains, short cytoplasmic tail, 5 (KIR2DS5), mRNA
gi|7657278|ref|NM_014513.1|[7657278]

6714: NM_014512
Homo sapiens killer cell immunoglobulin-like receptor, two domains, short cytoplasmic tail, 1 (KIR2DS1), mRNA
gi|7657276|ref|NM_014512.1|[7657276]

6715: NM_014511
Homo sapiens killer cell immunoglobulin-like receptor, two domains, long cytoplasmic tail, 3 (KIR2DL3), mRNA
gi|7657274|ref|NM_014511.1|[7657274]

6716: NM_014219
Homo sapiens killer cell immunoglobulin-like receptor, two domains, long cytoplasmic tail, 2 (KIR2DL2), mRNA
gi|7657272|ref|NM_014219.1|[7657272]

6717: NM_014218
Homo sapiens killer cell immunoglobulin-like receptor, two domains, long cytoplasmic tail, 1 (KIR2DL1), mRNA
gi|7657270|ref|NM_014218.1|[7657270]

6718: NM_014271
Homo sapiens interleukin 1 receptor accessory protein-like 1 (IL1RAPL1), mRNA
gi|7657231|ref|NM_014271.1|[7657231]

6719: NM_014339
Homo sapiens interleukin 17 receptor (IL17R), mRNA
gi|7657229|ref|NM_014339.1|[7657229]

6720: NM_014619
Homo sapiens glutamate receptor, ionotropic, kainate 4 (GRIK4), mRNA
gi|7657143|ref|NM_014619.1|[7657143]

6721: NM_014626
Homo sapiens G protein-coupled receptor 58 (GPR58), mRNA
gi|7657141|ref|NM_014626.1|[7657141]

6722: NM_014627
Homo sapiens G protein-coupled receptor 57 (GPR57), mRNA
gi|7657139|ref|NM_014627.1|[7657139]

6723: NM_014373
Homo sapiens putative G protein-coupled receptor (GPCR150), mRNA
gi|7657135|ref|NM_014373.1|[7657135]

6724: NM_005529
Homo sapiens heparan sulfate proteoglycan 2 (perlecan) (HSPG2), mRNA
gi|7427516|ref|NM_005529.2|[7427516]

6727: NM_005415
Homo sapiens solute carrier family 20 (phosphate transporter), member 1 (SLC20A1), mRNA
gi|7382462|ref|NM_005415.2|[7382462]

6728: NM_005199
Homo sapiens cholinergic receptor, nicotinic, gamma polypeptide (CHRNG), mRNA
gi|7382453|ref|NM_005199.3|[7382453]

6729: NM_013940
Homo sapiens olfactory receptor, family 10, subfamily H, member 1 (OR10H1), mRNA
gi|7363438|ref|NM_013940.1|[7363438]

6730: NM_013440
Homo sapiens paired immunoglobulin-like receptor beta (PILR(BETA)), mRNA
gi|7305386|ref|NM_013440.1|[7305386]

6731: NM_013439
Homo sapiens paired immunoglobulin-like receptor alpha (PILR(ALPHA)), mRNA
gi|7305384|ref|NM_013439.1|[7305384]

6732: NM_002260
Homo sapiens killer cell lectin-like receptor subfamily C, member 2 (KLRC2), mRNA
gi|7108353|ref|NM_002260.2|[7108353]

6733: NM_012125
Homo sapiens cholinergic receptor, muscarinic 5 (CHRM5), mRNA
gi|7108335|ref|NM_012125.1|[7108335]

6734: NM_013378
Homo sapiens pre-B lymphocyte gene 3 (VPREB3), mRNA
gi|7019566|ref|NM_013378.1|[7019566]

6735: NM_013261
Homo sapiens peroxisome proliferative activated receptor, gamma, coactivator 1 (PPARGC1), mRNA gi|7019498|ref|NM_013261.1|[7019498]

6736: NM_013269
Homo sapiens lectin-like NK cell receptor (LLT1), mRNA
gi|7019446|ref|NM_013269.1|[7019446]

6737: NM_013289
Homo sapiens killer cell immunoglobulin-like receptor, three domains, long cytoplasmic tail, 1 (KIR3DL1), mRNA
gi|7019440|ref|NM_013289.1|[7019440]

6738: NM_013281
Homo sapiens fibronectin leucine rich transmembrane protein 3 (FLRT3), mRNA
gi|7019382|ref|NM_013281.1|[7019382]

6739: NM_013231
Homo sapiens fibronectin leucine rich transmembrane protein 2 (FLRT2), mRNA
gi|7019380|ref|NM_013231.1|[7019380]

6740: NM_012410
Homo sapiens type I transmembrane receptor (seizure-related protein) (PSK-1), mRNA
gi|6912611|ref|NM_012410.1|[6912611]

6741: NM_012391
Homo sapiens prostate epithelium-specific Ets transcription factor (PDEF), mRNA
gi|6912579|ref|NM_012391.1|[6912579]

6742: NM_012375
Homo sapiens olfactory receptor, family 52, subfamily A, member 1 (OR52A1), mRNA
gi|6912559|ref|NM_012375.1|[6912559]

6743: NM_012368
Homo sapiens olfactory receptor, family 2, subfamily C, member 1 (OR2C1), mRNA
gi|6912555|ref|NM_012368.1|[6912555]

6744: NM_012360

Homo sapiens olfactory receptor, family 1, subfamily F, member 8 (OR1F8), mRNA
gi|6912553|ref|NM_012360.1|[6912553]

6745: NM_012352
Homo sapiens olfactory receptor, family 1, subfamily A, member 2 (OR1A2), mRNA
gi|6912551|ref|NM_012352.1|[6912551]

6746: NM_012351
Homo sapiens olfactory receptor, family 10, subfamily J, member 1 (OR10J1), mRNA
gi|6912549|ref|NM_012351.1|[6912549]

6747: NM_012344
Homo sapiens neurotensin receptor 2 (NTSR2), mRNA
gi|6912537|ref|NM_012344.1|[6912537]

6748: NM_012314
Homo sapiens killer cell immunoglobulin-like receptor, two domains, short cytoplasmic tail, 4 (KIR2DS4), mRNA
gi|6912475|ref|NM_012314.1|[6912475]

6749: NM_012313
Homo sapiens killer cell immunoglobulin-like receptor, two domains, short cytoplasmic tail, 3 (KIR2DS3), mRNA
gi|6912473|ref|NM_012313.1|[6912473]

6750: NM_012312
Homo sapiens killer cell immunoglobulin-like receptor, two domains, short cytoplasmic tail, 2 (KIR2DS2), mRNA
gi|6912471|ref|NM_012312.1|[6912471]

6751: NM_012211
Homo sapiens integrin, alpha 11 (ITGA11), mRNA
gi|6912435|ref|NM_012211.1|[6912435]

6752: NM_012275
Homo sapiens interleukin-1 receptor antagonist homolog 1 (IL1HY1), mRNA
gi|6912431|ref|NM_012275.1|[6912431]

6753: NM_004525
Homo sapiens low density lipoprotein-related protein 2 (LRP2), mRNA
gi|6806918|ref|NM_004525.1|[6806918]

6754: NM_004304
Homo sapiens anaplastic lymphoma kinase (Ki-1) (ALK), mRNA
gi|6715586|ref|NM_004304.2|[6715586]

6755: NM_000686
Homo sapiens angiotensin receptor 2 (AGTR2), mRNA
gi|6715584|ref|NM_000686.2|[6715584]

6756: NM_007366
Homo sapiens phospholipase A2 receptor 1, 180kD (PLA2R1), mRNA
gi|6679370|ref|NM_007366.1|[6679370]

6757: NM_005385
Homo sapiens natural killer-tumor recognition sequence (NKTR), mRNA
gi|6631099|ref|NM_005385.2|[6631099]

6758: NM_005266
Homo sapiens gap junction protein, alpha 5, 40kD (connexin 40) (GJA5), mRNA
gi|6631082|ref|NM_005266.2|[6631082]

6759: NM_000827
Homo sapiens glutamate receptor, ionotropic, AMPA 1 (GRIA1), mRNA
gi|6552333|ref|NM_000827.2|[6552333]

6760: NM_001619
Homo sapiens adrenergic, beta, receptor kinase 1 (ADRBK1), mRNA
gi|6138971|ref|NM_001619.2|[6138971]

6761: NM_000810
Homo sapiens gamma-aminobutyric acid (GABA) A receptor, alpha 5 (GABRA5), mRNA
gi|6031207|ref|NM_000810.2|[6031207]

6762: NM_003006
Homo sapiens selectin P ligand (SELPLG), mRNA
gi|6031197|ref|NM_003006.2|[6031197]

6763: NM_001480
Homo sapiens galanin receptor 1 (GALR1), mRNA
gi|6031165|ref|NM_001480.2|[6031165]

6764: NM_001992
Homo sapiens coagulation factor II (thrombin) receptor (F2R), mRNA
gi|6031164|ref|NM_001992.2|[6031164]

6765: NM_000677
Homo sapiens adenosine A3 receptor (ADORA3), mRNA
gi|6031156|ref|NM_000677.2|[6031156]

6766: NM_001526
Homo sapiens hypocretin (orexin) receptor 2 (HCRTR2), mRNA
gi|6006037|ref|NM_001526.2|[6006037]

6767: NM_000885
Homo sapiens integrin, alpha 4 (antigen CD49D, alpha 4 subunit of VLA-4 receptor) (ITGA4), mRNA
gi|6006032|ref|NM_000885.2|[6006032]

6768: NM_002377
Homo sapiens MAS1 oncogene (MAS1), mRNA
gi|6006022|ref|NM_002377.2|[6006022]

6769: NM_000887
Homo sapiens integrin, alpha X (antigen CD11C (p150), alpha polypeptide) (ITGAX), mRNA
gi|6006014|ref|NM_000887.2|[6006014]

6770: NM_000419
Homo sapiens integrin, alpha 2b (platelet glycoprotein IIb of IIb/IIIa complex, antigen CD41B) (ITGA2B), mRNA
gi|6006009|ref|NM_000419.2|[6006009]

6771: NM_002203
Homo sapiens integrin, alpha 2 (CD49B, alpha 2 subunit of VLA-2 receptor) (ITGA2), mRNA
gi|6006008|ref|NM_002203.2|[6006008]

6772: NM_000843
Homo sapiens glutamate receptor, metabotropic 6 (GRM6), mRNA
gi|6006006|ref|NM_000843.2|[6006006]

6773: NM_000838
Homo sapiens glutamate receptor, metabotropic 1 (GRM1), mRNA
gi|6006005|ref|NM_000838.2|[6006005]

6774: NM_000835
Homo sapiens glutamate receptor, ionotropic, N-methyl D-aspartate 2C (GRIN2C), mRNA
gi|6006004|ref|NM_000835.2|[6006004]

6775: NM_000834
Homo sapiens glutamate receptor, ionotropic, N-methyl D-aspartate 2B (GRIN2B), mRNA
gi|6006003|ref|NM_000834.2|[6006003]

6776: NM_000833
Homo sapiens glutamate receptor, ionotropic, N-methyl D-aspartate 2A (GRIN2A), mRNA
gi|6006002|ref|NM_000833.2|[6006002]

6777: NM_007155
Homo sapiens zona pellucida glycoprotein 3A (sperm receptor) (ZP3A), mRNA
gi|6005983|ref|NM_007155.1|[6005983]

6778: NM_007124
Homo sapiens utrophin (homologous to dystrophin) (UTRN), mRNA
gi|6005937|ref|NM_007124.1|[6005937]

6779: NM_007114
Homo sapiens TATA element modulatory factor 1 (TMF1), mRNA
gi|6005903|ref|NM_007114.1|[6005903]

6780: NM_007273
Homo sapiens B-cell associated protein (REA), mRNA
gi|6005853|ref|NM_007273.1|[6005853]

6781: NM_007160
Homo sapiens olfactory receptor, family 2, subfamily H, member 3 (OR2H3), mRNA
gi|6005821|ref|NM_007160.1|[6005821]

6782: NM_007227
Homo sapiens G protein-coupled receptor 45 (GPR45), mRNA
gi|6005769|ref|NM_007227.1|[6005769]

6783: NM_006934
Homo sapiens solute carrier family 6 (neurotransmitter transporter, glycine), member 9 (SLC6A9), mRNA
gi|5902093|ref|NM_006934.1|[5902093]

6785: NM_007011
Homo sapiens putative transmembrane protein (HS1-2), mRNA
gi|5901977|ref|NM_007011.1|[5901977]

6786: NM_007045
Homo sapiens FGFR1 oncogene partner (FOP), mRNA
gi|5901953|ref|NM_007045.1|[5901953]

6787: NM_006889
Homo sapiens CD86 antigen (CD28 antigen ligand 2, B7-2 antigen) (CD86), mRNA
gi|5901919|ref|NM_006889.1|[5901919]

6788: NM_006749
Homo sapiens solute carrier family 20 (phosphate transporter), member 2 (SLC20A2), mRNA
gi|5803172|ref|NM_006749.1|[5803172]

6789: NM_006770
Homo sapiens macrophage receptor with collagenous structure (MARCO), mRNA
gi|5803079|ref|NM_006770.1|[5803079]

6790: NM_006840
Homo sapiens leukocyte immunoglobulin-like receptor, subfamily B (with TM and ITIM domains), member 5 (LILRB5), mRNA
gi|5803069|ref|NM_006840.1|[5803069]

6791: NM_006866
Homo sapiens leukocyte immunoglobulin-like receptor, subfamily A (with TM domain), member 2 (LILRA2), mRNA
gi|5803067|ref|NM_006866.1|[5803067]

6792: NM_006863
Homo sapiens leukocyte immunoglobulin-like receptor, subfamily A (with TM domain), member 1 (LILRA1), mRNA
gi|5803065|ref|NM_006863.1|[5803065]

6793: NM_006847
Homo sapiens leukocyte immunoglobulin-like receptor, subfamily B (with TM and ITIM domains), member 4 (LILRB4), mRNA
gi|5803063|ref|NM_006847.1|[5803063]

6794: NM_006865
Homo sapiens leukocyte immunoglobulin-like receptor, subfamily A (without TM domain), member 3 (LILRA3), mRNA
gi|5803061|ref|NM_006865.1|[5803061]

6795: NM_006864
Homo sapiens leukocyte immunoglobulin-like receptor, subfamily B (with TM and ITIM domains), member 3 (LILRB3), mRNA
gi|5803059|ref|NM_006864.1|[5803059]

6796: NM_006738
Homo sapiens lymphoid blast crisis oncogene (LBC), mRNA
gi|5803057|ref|NM_006738.1|[5803057]

6797: NM_006737
Homo sapiens killer cell immunoglobulin-like receptor, three domains, long cytoplasmic tail, 2 (KIR3DL2), mRNA
gi|5803051|ref|NM_006737.1|[5803051]

6799: NM_006564
Homo sapiens G protein-coupled receptor (TYMSTR), mRNA
gi|5730105|ref|NM_006564.1|[5730105]

6800: NM_001561
Homo sapiens tumor necrosis factor receptor superfamily, member 9 (TNFRSF9), mRNA
gi|5730094|ref|NM_001561.2|[5730094]

6801: NM_006664
Homo sapiens small inducible cytokine subfamily A (Cys-Cys), member 27 (SCYA27), mRNA
gi|5730034|ref|NM_006664.1|[5730034]

6802: NM_006583
Homo sapiens retinal pigment epithelium-derived rhodopsin homolog (RRH), mRNA
gi|5730018|ref|NM_006583.1|[5730018]

6803: NM_006505
Homo sapiens poliovirus receptor (PVR), mRNA
gi|5729994|ref|NM_006505.1|[5729994]

6804: NM_006637
Homo sapiens olfactory receptor, family 5, subfamily I, member 1 (OR5I1), mRNA
gi|5729959|ref|NM_006637.1|[5729959]

6805: NM_006669
Homo sapiens leukocyte immunoglobulin-like receptor, subfamily B (with TM and ITIM domains), member 1 (LILRB1), mRNA
gi|5729926|ref|NM_006669.1|[5729926]

6806: NM_006611

Homo sapiens killer cell lectin-like receptor subfamily A, member 1 (KLRA1), mRNA
gi|5729898|ref|NM_006611.1|[5729898]

6807: NM_006496
Homo sapiens guanine nucleotide binding protein (G protein), alpha inhibiting activity polypeptide 3 (GNAI3), mRNA
gi|5729849|ref|NM_006496.1|[5729849]

6808: NM_006529
Homo sapiens glycine receptor, alpha 3 (GLRA3), mRNA
gi|5729843|ref|NM_006529.1|[5729843]

6809: NM_006639
Homo sapiens cysteinyl leukotriene receptor 1 (CYSLT1), mRNA
gi|5729797|ref|NM_006639.1|[5729797]

6810: NM_006293
Homo sapiens TYRO3 protein tyrosine kinase (TYRO3), mRNA
gi|5454141|ref|NM_006293.1|[5454141]

6813: NM_006238
Homo sapiens peroxisome proliferative activated receptor, delta (PPARD), mRNA
gi|5453939|ref|NM_006238.1|[5453939]

6814: NM_006189
Homo sapiens olfactory marker protein (OMP), mRNA
gi|5453827|ref|NM_006189.1|[5453827]

6815: NM_006182
Homo sapiens discoidin domain receptor family, member 2 (DDR2), mRNA
gi|5453813|ref|NM_006182.1|[5453813]

6816: NM_006180
Homo sapiens neurotrophic tyrosine kinase, receptor, type 2 (NTRK2), mRNA
gi|5453811|ref|NM_006180.1|[5453811]

6817: NM_006403
Homo sapiens enhancer of filamentation 1 (cas-like docking; Crk-associated substrate related) (HEF1), mRNA
gi|5453679|ref|NM_006403.1|[5453679]

6818: NM_006143
Homo sapiens G protein-coupled receptor 19 (GPR19), mRNA
gi|5453665|ref|NM_006143.1|[5453665]

6819: NM_006404
Homo sapiens protein C receptor, endothelial (EPCR) (PROCR), mRNA
gi|5453645|ref|NM_006404.1|[5453645]

6820: NM_006419
Homo sapiens small inducible cytokine B subfamily (Cys-X-Cys motif), member 13 (B-cell chemoattractant) (SCYB13), mRNA
gi|5453576|ref|NM_006419.1|[5453576]

6821: NM_005954
Homo sapiens metallothionein 3 (growth inhibitory factor (neurotrophic)) (MT3), mRNA
gi|5174761|ref|NM_005954.1|[5174761]

6822: NM_006006
Homo sapiens zinc finger protein 145 (Kruppel-like, expressed in promyelocytic leukemia) (ZNF145), mRNA
gi|5174752|ref|NM_006006.1|[5174752]

6823: NM_006072
Homo sapiens small inducible cytokine subfamily A (Cys-Cys), member 26 (SCYA26), mRNA
gi|5174670|ref|NM_006072.1|[5174670]

6824: NM_005972
Homo sapiens pancreatic polypeptide receptor 1 (PPYR1), mRNA
gi|5174638|ref|NM_005972.1|[5174638]

6825: NM_005913

Homo sapiens melanocortin 5 receptor (MC5R), mRNA
gi|5174534|ref|NM_005913.1|[5174534]

6826: NM_005912

Homo sapiens melanocortin 4 receptor (MC4R), mRNA
gi|5174532|ref|NM_005912.1|[5174532]

6827: NM_006028

Homo sapiens 5-hydroxytryptamine (serotonin) receptor 3B (HTR3B), mRNA
gi|5174468|ref|NM_006028.1|[5174468]

6828: NM_005628

Homo sapiens solute carrier family 1 (neutral amino acid transporter), member 5 (SLC1A5), mRNA
gi|5032092|ref|NM_005628.1|[5032092]

6829: NM_005767

Homo sapiens purinergic receptor (family A group 5) (P2Y5), mRNA
gi|5031968|ref|NM_005767.1|[5031968]

6830: NM_005592

Homo sapiens muscle, skeletal, receptor tyrosine kinase (MUSK), mRNA
gi|5031926|ref|NM_005592.1|[5031926]

6831: NM_005874

Homo sapiens leukocyte immunoglobulin-like receptor, subfamily B (with TM and ITIM domains), member 2 (LILRB2), mRNA
gi|5031910|ref|NM_005874.1|[5031910]

6832: NM_005810

Homo sapiens killer cell lectin-like receptor subfamily G, member 1 (KLRG1), mRNA
gi|5031900|ref|NM_005810.1|[5031900]

6833: NM_005544

Homo sapiens insulin receptor substrate 1 (IRS1), mRNA
gi|5031804|ref|NM_005544.1|[5031804]

6834: NM_005535
Homo sapiens interleukin 12 receptor, beta 1 (IL12RB1), mRNA
gi|5031784|ref|NM_005535.1|[5031784]

6835: NM_005683
Homo sapiens G protein-coupled receptor 55 (GPR55), mRNA
gi|5031722|ref|NM_005683.1|[5031722]

6836: NM_005684
Homo sapiens G protein-coupled receptor 52 (GPR52), mRNA
gi|5031720|ref|NM_005684.1|[5031720]

6837: NM_001621
Homo sapiens aryl hydrocarbon receptor (AHR), mRNA
gi|5016091|ref|NM_001621.2|[5016091]

6838: NM_005429
Homo sapiens vascular endothelial growth factor C (VEGFC), mRNA
gi|4885652|ref|NM_005429.1|[4885652]

6839: NM_005424
Homo sapiens tyrosine kinase with immunoglobulin and epidermal growth factor homology domains (TIE), mRNA
gi|4885630|ref|NM_005424.1|[4885630]

6840: NM_005408
Homo sapiens small inducible cytokine subfamily A (Cys-Cys), member 13 (SCYA13), mRNA
gi|4885586|ref|NM_005408.1|[4885586]

6841: NM_005328
Homo sapiens hyaluronan synthase 2 (HAS2), mRNA
gi|4885390|ref|NM_005328.1|[4885390]

6842: NM_005314
Homo sapiens gastrin-releasing peptide receptor (GRPR), mRNA
gi|4885360|ref|NM_005314.1|[4885360]

6843: NM_005311
Homo sapiens growth factor receptor-bound protein 10 (GRB10), mRNA
gi|4885352|ref|NM_005311.1|[4885352]

6844: NM_005308
Homo sapiens G protein-coupled receptor kinase 5 (GPRK5), mRNA
gi|4885348|ref|NM_005308.1|[4885348]

6845: NM_005286
Homo sapiens G protein-coupled receptor 8 (GPR8), mRNA
gi|4885344|ref|NM_005286.1|[4885344]

6846: NM_005285
Homo sapiens G protein-coupled receptor 7 (GPR7), mRNA
gi|4885342|ref|NM_005285.1|[4885342]

6847: NM_005284
Homo sapiens G protein-coupled receptor 6 (GPR6), mRNA
gi|4885340|ref|NM_005284.1|[4885340]

6848: NM_005458
Homo sapiens G protein-coupled receptor 51 (GPR51), mRNA
gi|4885336|ref|NM_005458.1|[4885336]

6849: NM_005282
Homo sapiens G protein-coupled receptor 4 (GPR4), mRNA
gi|4885334|ref|NM_005282.1|[4885334]

6850: NM_005306
Homo sapiens G protein-coupled receptor 43 (GPR43), mRNA
gi|4885332|ref|NM_005306.1|[4885332]

6851: NM_005305
Homo sapiens G protein-coupled receptor 42 (GPR42), mRNA
gi|4885330|ref|NM_005305.1|[4885330]

6852: NM_005304
Homo sapiens G protein-coupled receptor 41 (GPR41), mRNA
gi|4885328|ref|NM_005304.1|[4885328]

6853: NM_005303
Homo sapiens G protein-coupled receptor 40 (GPR40), mRNA
gi|4885326|ref|NM_005303.1|[4885326]

6854: NM_005281
Homo sapiens G protein-coupled receptor 3 (GPR3), mRNA
gi|4885324|ref|NM_005281.1|[4885324]

6855: NM_005302
Homo sapiens G protein-coupled receptor 37 (endothelin receptor type B-like) (GPR37), mRNA
gi|4885322|ref|NM_005302.1|[4885322]

6856: NM_005301
Homo sapiens G protein-coupled receptor 35 (GPR35), mRNA
gi|4885320|ref|NM_005301.1|[4885320]

6857: NM_005300
Homo sapiens G protein-coupled receptor 34 (GPR34), mRNA
gi|4885318|ref|NM_005300.1|[4885318]

6858: NM_005299
Homo sapiens G protein-coupled receptor 31 (GPR31), mRNA
gi|4885316|ref|NM_005299.1|[4885316]

6859: NM_005298
Homo sapiens G protein-coupled receptor 25 (GPR25), mRNA
gi|4885314|ref|NM_005298.1|[4885314]

6860: NM_005297
Homo sapiens G protein-coupled receptor 24 (GPR24), mRNA
gi|4885312|ref|NM_005297.1|[4885312]

6861: NM_005296
Homo sapiens G protein-coupled receptor 23 (GPR23), mRNA
gi|4885310|ref|NM_005296.1|[4885310]

6862: NM_005295
Homo sapiens G protein-coupled receptor 22 (GPR22), mRNA
gi|4885308|ref|NM_005295.1|[4885308]

6863: NM_005294
Homo sapiens G protein-coupled receptor 21 (GPR21), mRNA
gi|4885306|ref|NM_005294.1|[4885306]

6864: NM_005293
Homo sapiens G protein-coupled receptor 20 (GPR20), mRNA
gi|4885304|ref|NM_005293.1|[4885304]

6865: NM_005279
Homo sapiens G protein-coupled receptor 1 (GPR1), mRNA
gi|4885302|ref|NM_005279.1|[4885302]

6866: NM_005291
Homo sapiens G protein-coupled receptor 17 (GPR17), mRNA
gi|4885300|ref|NM_005291.1|[4885300]

6867: NM_005290
Homo sapiens G protein-coupled receptor 15 (GPR15), mRNA
gi|4885298|ref|NM_005290.1|[4885298]

6868: NM_005288
Homo sapiens G protein-coupled receptor 12 (GPR12), mRNA
gi|4885294|ref|NM_005288.1|[4885294]

6869: NM_005264
Homo sapiens GDNF family receptor alpha 1 (GFRA1), mRNA
gi|4885268|ref|NM_005264.1|[4885268]

6870: NM_005246
Homo sapiens fer (fps/fes related) tyrosine kinase (phosphoprotein NCP94) (FER), mRNA
gi|4885230|ref|NM_005246.1|[4885230]

6871: NM_005233
Homo sapiens EphA3 (EPHA3), mRNA
gi|4885210|ref|NM_005233.1|[4885210]

6872: NM_005227
Homo sapiens ephrin-A4 (EFNA4), mRNA
gi|4885196|ref|NM_005227.1|[4885196]

6873: NM_005211
Homo sapiens colony stimulating factor 1 receptor, formerly McDonough feline sarcoma viral (v-fms) oncogene homolog (CSF1R), mRNA
gi|4885158|ref|NM_005211.1|[4885158]

6875: NM_005161
Homo sapiens angiotensin receptor-like 1 (AGTRL1), mRNA
gi|4885056|ref|NM_005161.1|[4885056]

6876: NM_005092
Homo sapiens tumor necrosis factor (ligand) superfamily, member 18 (TNFSF18), mRNA
gi|4827033|ref|NM_005092.1|[4827033]

6877: NM_005118
Homo sapiens tumor necrosis factor (ligand) superfamily, member 15 (TNFSF15), mRNA
gi|4827031|ref|NM_005118.1|[4827031]

6878: NM_005048
Homo sapiens parathyroid hormone receptor 2 (PTHR2), mRNA
gi|4826953|ref|NM_005048.1|[4826953]

6879: NM_004963
Homo sapiens guanylate cyclase 2C (heat stable enterotoxin receptor) (GUCY2C), mRNA
gi|4826751|ref|NM_004963.1|[4826751]

6880: NM_005145
Homo sapiens guanine nucleotide binding protein (G protein), gamma 7 (GNG7), mRNA
gi|4826745|ref|NM_005145.1|[4826745]

6881: NM_004952
Homo sapiens ephrin-A3 (EFNA3), mRNA
gi|4826707|ref|NM_004952.1|[4826707]

6882: NM_004736
Homo sapiens xenotropic and polytropic retrovirus receptor (XPR1), mRNA
gi|4759333|ref|NM_004736.1|[4759333]

6883: NM_004664
Homo sapiens Vertebrate LIN7 homolog 1, Tax interaction protein 33 (VELI1), mRNA
gi|4759305|ref|NM_004664.1|[4759305]

6884: NM_004195
Homo sapiens tumor necrosis factor receptor superfamily, member 18 (TNFRSF18), mRNA
gi|4759245|ref|NM_004195.1|[4759245]

6885: NM_004612
Homo sapiens transforming growth factor, beta receptor I (activin A receptor type II-like kinase, 53kD) (TGFBR1), mRNA
gi|4759225|ref|NM_004612.1|[4759225]

6887: NM_004154
Homo sapiens pyrimidinergic receptor P2Y, G-protein coupled, 6 (P2RY6), mRNA
gi|4758863|ref|NM_004154.1|[4758863]

6888: NM_004244
Homo sapiens CD163 antigen (CD163), mRNA
gi|4758721|ref|NM_004244.1|[4758721]

6889: NM_002332
Homo sapiens low density lipoprotein-related protein 1 (alpha-2-macroglobulin receptor) (LRP1), mRNA
gi|4758685|ref|NM_002332.1|[4758685]

6890: NM_004514
Homo sapiens interleukin enhancer binding factor 1 (ILF1), mRNA
gi|4758599|ref|NM_004514.1|[4758599]

6891: NM_004633
Homo sapiens interleukin 1 receptor, type II (IL1R2), mRNA
gi|4758597|ref|NM_004633.1|[4758597]

6892: NM_004512
Homo sapiens interleukin 11 receptor, alpha (IL11RA), mRNA
gi|4758593|ref|NM_004512.1|[4758593]

6894: NM_000826
Homo sapiens glutamate receptor, ionotropic, AMPA 2 (GRIA2), mRNA
gi|4758479|ref|NM_000826.1|[4758479]

6896: NM_004224
Homo sapiens G protein-coupled receptor 50 (GPR50), mRNA
gi|4758467|ref|NM_004224.1|[4758467]

6898: NM_004246
Homo sapiens glucagon-like peptide 2 receptor (GLP2R), mRNA
gi|4758437|ref|NM_004246.1|[4758437]

6899: NM_004293
Homo sapiens guanine deaminase (GDA), mRNA
gi|4758425|ref|NM_004293.1|[4758425]

6900: NM_002030
Homo sapiens formyl peptide receptor-like 2 (FPRL2), mRNA
gi|4758401|ref|NM_002030.2|[4758401]

6901: NM_004469
Homo sapiens c-fos induced growth factor (vascular endothelial growth factor D) (FIGF), mRNA
gi|4758377|ref|NM_004469.1|[4758377]

6902: NM_004107
Homo sapiens Fc fragment of IgG, receptor, transporter, alpha (FCGRT), mRNA
gi|4758345|ref|NM_004107.1|[4758345]

6903: NM_004101
Homo sapiens coagulation factor II (thrombin) receptor-like 2 (F2RL2), mRNA
gi|4758325|ref|NM_004101.1|[4758325]

6904: NM_004447
Homo sapiens epidermal growth factor receptor pathway substrate 8 (EPS8), mRNA
gi|4758295|ref|NM_004447.1|[4758295]

6905: NM_004431
Homo sapiens EphA2 (EPHA2), mRNA
gi|4758277|ref|NM_004431.1|[4758277]

6906: NM_004093
Homo sapiens ephrin-B2 (EFNB2), mRNA
gi|4758249|ref|NM_004093.1|[4758249]

6907: NM_004429
Homo sapiens ephrin-B1 (EFNB1), mRNA
gi|4758247|ref|NM_004429.1|[4758247]

6908: NM_004428
Homo sapiens ephrin-A1 (EFNA1), mRNA
gi|4758245|ref|NM_004428.1|[4758245]

6909: NM_004393
Homo sapiens dystroglycan 1 (dystrophin-associated glycoprotein 1) (DAG1), mRNA
gi|4758115|ref|NM_004393.1|[4758115]

6910: NM_004383
Homo sapiens c-src tyrosine kinase (CSK), mRNA
gi|4758077|ref|NM_004383.1|[4758077]

6911: NM_004778
Homo sapiens G protein-coupled receptor 44 (GPR44), mRNA
gi|4758069|ref|NM_004778.1|[4758069]

6912: NM_004382
Homo sapiens corticotropin releasing hormone receptor 1 (CRHR1), mRNA
gi|4758059|ref|NM_004382.1|[4758059]

6913: NM_004072
Homo sapiens chemokine-like receptor 1 (CMKLR1), mRNA
gi|4758013|ref|NM_004072.1|[4758013]

6914: NM_004329
Homo sapiens bone morphogenetic protein receptor, type IA (BMPR1A), mRNA
gi|4757853|ref|NM_004329.1|[4757853]

6915: NM_004313
Homo sapiens arrestin, beta 2 (ARRB2), mRNA
gi|4757779|ref|NM_004313.1|[4757779]

6916: NM_004039
Homo sapiens annexin A2 (ANXA2), mRNA
gi|4757755|ref|NM_004039.1|[4757755]

6917: NM_000806
Homo sapiens gamma-aminobutyric acid (GABA) A receptor, alpha 1 (GABRA1), mRNA
gi|4585862|ref|NM_000806.2|[4585862]

6918: NM_002529
Homo sapiens neurotrophic tyrosine kinase, receptor, type 1 (NTRK1), mRNA
gi|4585711|ref|NM_002529.2|[4585711]

6919: NM_000395
Homo sapiens colony stimulating factor 2 receptor, beta, low-affinity (granulocyte-macrophage) (CSF2RB), mRNA
gi|4559407|ref|NM_000395.1|[4559407]

6920: NM_000211
Homo sapiens integrin, beta 2 (antigen CD18 (p95), lymphocyte function-associated antigen 1; macrophage antigen 1 (mac-1) beta subunit) (ITGB2), mRNA
gi|4557885|ref|NM_000211.1|[4557885]

6921: NM_000208
Homo sapiens insulin receptor (INSR), mRNA
gi|4557883|ref|NM_000208.1|[4557883]

6922: NM_000206
Homo sapiens interleukin 2 receptor, gamma (severe combined immunodeficiency) (IL2RG), mRNA
gi|4557881|ref|NM_000206.1|[4557881]

6923: NM_000416
Homo sapiens interferon gamma receptor 1 (IFNGR1), mRNA
gi|4557879|ref|NM_000416.1|[4557879]

6924: NM_000201
Homo sapiens intercellular adhesion molecule 1 (CD54), human rhinovirus receptor (ICAM1), mRNA
gi|4557877|ref|NM_000201.1|[4557877]

6925: NM_000459
Homo sapiens TEK tyrosine kinase, endothelial (venous malformations, multiple cutaneous and mucosal) (TEK), mRNA
gi|4557868|ref|NM_000459.1|[4557868]

6926: NM_001053
Homo sapiens somatostatin receptor 5 (SSTR5), mRNA
gi|4557864|ref|NM_001053.1|[4557864]

6927: NM_001052
Homo sapiens somatostatin receptor 4 (SSTR4), mRNA
gi|4557862|ref|NM_001052.1|[4557862]

6928: NM_001051
Homo sapiens somatostatin receptor 3 (SSTR3), mRNA
gi|4557860|ref|NM_001051.1|[4557860]

6929: NM_001050
Homo sapiens somatostatin receptor 2 (SSTR2), mRNA
gi|4557858|ref|NM_001050.1|[4557858]

6930: NM_001049
Homo sapiens somatostatin receptor 1 (SSTR1), mRNA
gi|4557856|ref|NM_001049.1|[4557856]

6931: NM_000245
Homo sapiens met proto-oncogene (hepatocyte growth factor receptor) (MET), mRNA
gi|4557746|ref|NM_000245.1|[4557746]

6932: NM_000242
Homo sapiens mannose-binding lectin (protein C) 2, soluble (opsonic defect) (MBL2), mRNA
gi|4557738|ref|NM_000242.1|[4557738]

6933: NM_000237
Homo sapiens lipoprotein lipase (LPL), mRNA
gi|4557726|ref|NM_000237.1|[4557726]

6934: NM_000236
Homo sapiens lipase, hepatic (LIPC), mRNA
gi|4557722|ref|NM_000236.1|[4557722]

6935: NM_000233
Homo sapiens luteinizing hormone/choriogonadotropin receptor (LHCGR), mRNA
gi|4557716|ref|NM_000233.1|[4557716]

6936: NM_000222
Homo sapiens v-kit Hardy-Zuckerman 4 feline sarcoma viral oncogene homolog (KIT), mRNA
gi|4557694|ref|NM_000222.1|[4557694]

6937: NM_000212
Homo sapiens integrin, beta 3 (platelet glycoprotein IIIa, antigen CD61) (ITGB3), mRNA
gi|4557676|ref|NM_000212.1|[4557676]

6939: NM_000418
Homo sapiens interleukin 4 receptor (IL4R), mRNA
gi|4557668|ref|NM_000418.1|[4557668]

6940: NM_000417
Homo sapiens interleukin 2 receptor, alpha (IL2RA), mRNA
gi|4557666|ref|NM_000417.1|[4557666]

6941: NM_001551
Homo sapiens immunoglobulin (CD79A) binding protein 1 (IGBP1), mRNA
gi|4557662|ref|NM_001551.1|[4557662]

6942: NM_000859
Homo sapiens 3-hydroxy-3-methylglutaryl-Coenzyme A reductase (HMGCR), mRNA
gi|4557642|ref|NM_000859.1|[4557642]

6943: NM_001525
Homo sapiens hypocretin (orexin) receptor 1 (HCRTR1), mRNA
gi|4557636|ref|NM_001525.1|[4557636]

6944: NM_001510
Homo sapiens glutamate receptor, ionotropic, delta 2 (GRID2), mRNA
gi|4557632|ref|NM_001510.1|[4557632]

6945: NM_000829
Homo sapiens glutamate receptor, ionotrophic, AMPA 4 (GRIA4), mRNA
gi|4557630|ref|NM_000829.1|[4557630]

6946: NM_001496
Homo sapiens GDNF family receptor alpha 3 (GFRA3), mRNA
gi|4557622|ref|NM_001496.1|[4557622]

6947: NM_000820
Homo sapiens growth arrest-specific 6 (GAS6), mRNA
gi|4557616|ref|NM_000820.1|[4557616]

6948: NM_000155
Homo sapiens galactose-1-phosphate uridylyltransferase (GALT), mRNA
gi|4557614|ref|NM_000155.1|[4557614]

6949: NM_000816
Homo sapiens gamma-aminobutyric acid (GABA) A receptor, gamma 2 (GABRG2), mRNA
gi|4557610|ref|NM_000816.1|[4557610]

6950: NM_000815
Homo sapiens gamma-aminobutyric acid (GABA) A receptor, delta (GABRD), mRNA
gi|4557608|ref|NM_000815.1|[4557608]

6951: NM_000811
Homo sapiens gamma-aminobutyric acid (GABA) A receptor, alpha 6 (GABRA6), mRNA
gi|4557606|ref|NM_000811.1|[4557606]

6952: NM_000809
Homo sapiens gamma-aminobutyric acid (GABA) A receptor, alpha 4 (GABRA4), mRNA
gi|4557604|ref|NM_000809.1|[4557604]

6953: NM_000808
Homo sapiens gamma-aminobutyric acid (GABA) A receptor, alpha 3 (GABRA3), mRNA
gi|4557602|ref|NM_000808.1|[4557602]

6954: NM_000807
Homo sapiens gamma-aminobutyric acid (GABA) A receptor, alpha 2 (GABRA2), mRNA
gi|4557600|ref|NM_000807.1|[4557600]

6955: NM_000121
Homo sapiens erythropoietin receptor (EPOR), mRNA
gi|4557561|ref|NM_000121.2|[4557561]

6956: NM_000118
Homo sapiens endoglin (Osler-Rendu-Weber syndrome 1) (ENG), mRNA
gi|4557554|ref|NM_000118.1|[4557554]

6957: NM_000114
Homo sapiens endothelin 3 (EDN3), mRNA
gi|4557544|ref|NM_000114.1|[4557544]

6958: NM_001365
Homo sapiens discs, large (Drosophila) homolog 4 (DLG4), mRNA
gi|4557528|ref|NM_001365.1|[4557528]

6959: NM_000080
Homo sapiens cholinergic receptor, nicotinic, epsilon polypeptide (CHRNE), mRNA
gi|4557462|ref|NM_000080.1|[4557462]

6960: NM_000751
Homo sapiens cholinergic receptor, nicotinic, delta polypeptide (CHRND), mRNA
gi|4557460|ref|NM_000751.1|[4557460]

6961: NM_000747
Homo sapiens cholinergic receptor, nicotinic, beta polypeptide 1 (muscle) (CHRNB1), mRNA
gi|4557458|ref|NM_000747.1|[4557458]

6962: NM_000079
Homo sapiens cholinergic receptor, nicotinic, alpha polypeptide 1 (muscle) (CHRNA1), mRNA
gi|4557456|ref|NM_000079.1|[4557456]

6963: NM_000074
Homo sapiens tumor necrosis factor (ligand) superfamily, member 5 (hyper-IgM syndrome) (TNFSF5), mRNA
gi|4557432|ref|NM_000074.1|[4557432]

6964: NM_000073
Homo sapiens CD3G antigen, gamma polypeptide (TiT3 complex) (CD3G), mRNA
gi|4557428|ref|NM_000073.1|[4557428]

6965: NM_000072
Homo sapiens CD36 antigen (collagen type I receptor, thrombospondin receptor) (CD36), mRNA
gi|4557418|ref|NM_000072.1|[4557418]

6966: NM_000388
Homo sapiens calcium-sensing receptor (hypocalciuric hypercalcemia 1, severe neonatal hyperparathyroidism) (CASR), mRNA
gi|4557410|ref|NM_000388.1|[4557410]

6967: NM_000069
Homo sapiens calcium channel, voltage-dependent, L type, alpha 1S subunit (CACNA1S), mRNA
gi|4557400|ref|NM_000069.1|[4557400]

6968: NM_000041
Homo sapiens apolipoprotein E (APOE), mRNA
gi|4557324|ref|NM_000041.1|[4557324]

6969: NM_000684
Homo sapiens adrenergic, beta-1-, receptor (ADRB1), mRNA
gi|4557264|ref|NM_000684.1|[4557264]

6970: NM_001116
Homo sapiens adenylate cyclase 9 (ADCY9), mRNA
gi|4557258|ref|NM_001116.1|[4557258]

6971: NM_001115
Homo sapiens adenylate cyclase 8 (brain) (ADCY8), mRNA
gi|4557256|ref|NM_001115.1|[4557256]

6972: NM_004001

Homo sapiens Fc fragment of IgG, low affinity IIb, receptor for (CD32) (FCGR2B), mRNA
gi|4557021|ref|NM_004001.1|[4557021]

6975: NM_003931
Homo sapiens WAS protein family, member 1 (WASF1), mRNA
gi|4507912|ref|NM_003931.1|[4507912]

6976: NM_003383
Homo sapiens very low density lipoprotein receptor (VLDLR), mRNA
gi|4507900|ref|NM_003383.1|[4507900]

6977: NM_003382
Homo sapiens vasoactive intestinal peptide receptor 2 (VIPR2), mRNA
gi|4507898|ref|NM_003382.1|[4507898]

6978: NM_000376
Homo sapiens vitamin D (1,25- dihydroxyvitamin D3) receptor (VDR), mRNA
gi|4507882|ref|NM_000376.1|[4507882]

6979: NM_003329
Homo sapiens thioredoxin (TXN), mRNA
gi|4507744|ref|NM_003329.1|[4507744]

6980: NM_000369
Homo sapiens thyroid stimulating hormone receptor (TSHR), mRNA
gi|4507700|ref|NM_000369.1|[4507700]

6981: NM_003301
Homo sapiens thyrotropin-releasing hormone receptor (TRHR), mRNA
gi|4507680|ref|NM_003301.1|[4507680]

6982: NM_001244
Homo sapiens tumor necrosis factor (ligand) superfamily, member 8 (TNFSF8), mRNA
gi|4507606|ref|NM_001244.1|[4507606]

6983: NM_003809

Homo sapiens tumor necrosis factor (ligand) superfamily, member 12 (TNFSF12), mRNA
gi|4507596|ref|NM_003809.1|[4507596]

6984: NM_001243
Homo sapiens tumor necrosis factor receptor superfamily, member 8 (TNFRSF8), mRNA
gi|4507588|ref|NM_001243.1|[4507588]

6985: NM_001242
Homo sapiens tumor necrosis factor receptor superfamily, member 7 (TNFRSF7), mRNA
gi|4507586|ref|NM_001242.1|[4507586]

6986: NM_000043
Homo sapiens tumor necrosis factor receptor superfamily, member 6 (TNFRSF6), mRNA
gi|4507582|ref|NM_000043.1|[4507582]

6987: NM_003327
Homo sapiens tumor necrosis factor receptor superfamily, member 4 (TNFRSF4), mRNA
gi|4507578|ref|NM_003327.1|[4507578]

6988: NM_001065
Homo sapiens tumor necrosis factor receptor superfamily, member 1A (TNFRSF1A), mRNA
gi|4507574|ref|NM_001065.1|[4507574]

6989: NM_001192
Homo sapiens tumor necrosis factor receptor superfamily, member 17 (TNFRSF17), mRNA
gi|4507572|ref|NM_001192.1|[4507572]

6990: NM_003820
Homo sapiens tumor necrosis factor receptor superfamily, member 14 (herpesvirus entry mediator) (TNFRSF14), mRNA
gi|4507570|ref|NM_003820.1|[4507570]

6991: NM_003790
Homo sapiens tumor necrosis factor receptor superfamily, member 12
(translocating chain-association membrane protein) (TNFRSF12), mRNA
gi|4507568|ref|NM_003790.1|[4507568]

6992: NM_002546
Homo sapiens tumor necrosis factor receptor superfamily, member 11b
(osteoprotegerin) (TNFRSF11B), mRNA
gi|4507566|ref|NM_002546.1|[4507566]

6993: NM_003839
Homo sapiens tumor necrosis factor receptor superfamily, member 11a, activator
of NFKB (TNFRSF11A), mRNA
gi|4507564|ref|NM_003839.1|[4507564]

6994: NM_003840
Homo sapiens tumor necrosis factor receptor superfamily, member 10d, decoy with
truncated death domain (TNFRSF10D), mRNA
gi|4507562|ref|NM_003840.1|[4507562]

6995: NM_003842
Homo sapiens tumor necrosis factor receptor superfamily, member 10b (TNFRSF10B),
mRNA
gi|4507560|ref|NM_003842.1|[4507560]

6996: NM_003844
Homo sapiens tumor necrosis factor receptor superfamily, member 10a (TNFRSF10A),
mRNA
gi|4507558|ref|NM_003844.1|[4507558]

6997: NM_003692
Homo sapiens transmembrane protein with EGF-like and two follistatin-like
domains 1 (TMEFF1), mRNA
gi|4507548|ref|NM_003692.1|[4507548]

6998: NM_003273
Homo sapiens transmembrane 7 superfamily member 2 (TM7SF2), mRNA
gi|4507546|ref|NM_003273.1|[4507546]

6999: NM_003272
Homo sapiens transmembrane 7 superfamily member 1 (upregulated in kidney) (TM7SF1), mRNA
gi|4507544|ref|NM_003272.1|[4507544]

7000: NM_000460
Homo sapiens thrombopoietin (myeloproliferative leukemia virus oncogene ligand, megakaryocyte growth and development factor) (THPO), mRNA
gi|4507492|ref|NM_000460.1|[4507492]

7001: NM_003844
Homo sapiens tumor necrosis factor receptor superfamily, member 10a (TNFRSF10A), mRNA
gi|4507558|ref|NM_003844.1|[4507558]

7002: NM_003692
Homo sapiens transmembrane protein with EGF-like and two follistatin-like domains 1 (TMEFF1), mRNA
gi|4507548|ref|NM_003692.1|[4507548]

7003: NM_003273
Homo sapiens transmembrane 7 superfamily member 2 (TM7SF2), mRNA
gi|4507546|ref|NM_003273.1|[4507546]

7004: NM_003272
Homo sapiens transmembrane 7 superfamily member 1 (upregulated in kidney) (TM7SF1), mRNA
gi|4507544|ref|NM_003272.1|[4507544]

7005: NM_000460
Homo sapiens thrombopoietin (myeloproliferative leukemia virus oncogene ligand, megakaryocyte growth and development factor) (THPO), mRNA
gi|4507492|ref|NM_000460.1|[4507492]

7006: NM_000361
Homo sapiens thrombomodulin (THBD), mRNA
gi|4507482|ref|NM_000361.1|[4507482]

7007: NM_003243
Homo sapiens transforming growth factor, beta receptor III (betaglycan, 300kD) (TGFBR3), mRNA
gi|4507470|ref|NM_003243.1|[4507470]

7008: NM_003234
Homo sapiens transferrin receptor (p90, CD71) (TFRC), mRNA
gi|4507456|ref|NM_003234.1|[4507456]

7009: NM_003608
Homo sapiens G protein-coupled receptor 65 (GPR65), mRNA
gi|4507420|ref|NM_003608.1|[4507420]

7010: NM_001060
Homo sapiens thromboxane A2 receptor (TBXA2R), mRNA
gi|4507380|ref|NM_001060.1|[4507380]

7012: NM_001057
Homo sapiens tachykinin receptor 2 (TACR2), mRNA
gi|4507344|ref|NM_001057.1|[4507344]

7013: NM_003177
Homo sapiens spleen tyrosine kinase (SYK), mRNA
gi|4507328|ref|NM_003177.1|[4507328]

7015: NM_003070
Homo sapiens SWI/SNF related, matrix associated, actin dependent regulator of chromatin, subfamily a, member 2 (SMARCA2), mRNA
gi|4507068|ref|NM_003070.1|[4507068]

7016: NM_003045
Homo sapiens solute carrier family 7 (cationic amino acid transporter, y+ system), member 1 (SLC7A1), mRNA
gi|4507046|ref|NM_003045.1|[4507046]

7017: NM_003037

Homo sapiens signaling lymphocytic activation molecule (SLAM), mRNA
gi|4506968|ref|NM_003037.1|[4506968]

7019: NM_001036
Homo sapiens ryanodine receptor 3 (RYR3), mRNA
gi|4506758|ref|NM_001036.1|[4506758]

7020: NM_001035
Homo sapiens ryanodine receptor 2 (cardiac) (RYR2), mRNA
gi|4506756|ref|NM_001035.1|[4506756]

7023: NM_002921
Homo sapiens retinal G protein coupled receptor (RGR), mRNA
gi|4506502|ref|NM_002921.1|[4506502]

7026: NM_002852
Homo sapiens pentaxin-related gene, rapidly induced by IL-1 beta (PTX3), mRNA
gi|4506332|ref|NM_002852.1|[4506332]

7027: NM_002851
Homo sapiens protein tyrosine phosphatase, receptor-type, Z polypeptide 1 (PTPRZ1), mRNA
gi|4506328|ref|NM_002851.1|[4506328]

7028: NM_000316
Homo sapiens parathyroid hormone receptor 1 (PTHR1), mRNA
gi|4506270|ref|NM_000316.1|[4506270]

7029: NM_000960
Homo sapiens prostaglandin I2 (prostacyclin) receptor (IP) (PTGIR), mRNA
gi|4506262|ref|NM_000960.1|[4506262]

7030: NM_000959
Homo sapiens prostaglandin F receptor (FP) (PTGFR), mRNA
gi|4506260|ref|NM_000959.1|[4506260]

7031: NM_000958

Homo sapiens prostaglandin E receptor 4 (subtype EP4) (PTGER4), mRNA
gi|4506258|ref|NM_000958.1|[4506258]

7032: NM_000957
Homo sapiens prostaglandin E receptor 3 (subtype EP3) (PTGER3), mRNA
gi|4506256|ref|NM_000957.1|[4506256]

7033: NM_000955
Homo sapiens prostaglandin E receptor 1 (subtype EP1), 42kD (PTGER1), mRNA
gi|4506252|ref|NM_000955.1|[4506252]

7034: NM_000952
Homo sapiens platelet-activating factor receptor (PTAFR), mRNA
gi|4506240|ref|NM_000952.1|[4506240]

7035: NM_002769
Homo sapiens protease, serine, 1 (trypsin 1) (PRSS1), mRNA
gi|4506144|ref|NM_002769.1|[4506144]

7036: NM_000949
Homo sapiens prolactin receptor (PRLR), mRNA
gi|4506106|ref|NM_000949.1|[4506106]

7037: NM_002745
Homo sapiens mitogen-activated protein kinase 1 (MAPK1), mRNA
gi|4506086|ref|NM_002745.1|[4506086]

7038: NM_002702
Homo sapiens POU domain, class 6, transcription factor 1 (POU6F1), mRNA
gi|4505968|ref|NM_002702.1|[4505968]

7039: NM_003967
Homo sapiens putative neurotransmitter receptor (PNR), mRNA
gi|4505924|ref|NM_003967.1|[4505924]

7040: NM_002659
Homo sapiens plasminogen activator, urokinase receptor (PLAUR), mRNA gi|4505864|ref|NM_002659.1|[4505864]

7041: NM_000926
Homo sapiens progesterone receptor (PGR), mRNA
gi|4505766|ref|NM_000926.1|[4505766]

7042: NM_000288
Homo sapiens peroxisomal biogenesis factor 7 (PEX7), mRNA
gi|4505730|ref|NM_000288.1|[4505730]

7043: NM_000287
Homo sapiens peroxisomal biogenesis factor 6 (PEX6), mRNA
gi|4505728|ref|NM_000287.1|[4505728]

7044: NM_002618
Homo sapiens peroxisome biogenesis factor 13 (PEX13), mRNA
gi|4505722|ref|NM_002618.1|[4505722]

7045: NM_002591
Homo sapiens phosphoenolpyruvate carboxykinase 1 (soluble) (PCK1), mRNA
gi|4505638|ref|NM_002591.1|[4505638]

7046: NM_002586
Homo sapiens pre-B-cell leukemia transcription factor 2 (PBX2), mRNA
gi|4505624|ref|NM_002586.1|[4505624]

7047: NM_002569
Homo sapiens paired basic amino acid cleaving enzyme (furin, membrane associated receptor protein) (PACE), mRNA
gi|4505578|ref|NM_002569.1|[4505578]

7048: NM_002565
Homo sapiens pyrimidinergic receptor P2Y, G-protein coupled, 4 (P2RY4), mRNA
gi|4505560|ref|NM_002565.1|[4505560]

7049: NM_002566
Homo sapiens purinergic receptor P2Y, G-protein coupled, 11 (P2RY11), mRNA gi|4505554|ref|NM_002566.1|[4505554]

7050: NM_002562
Homo sapiens purinergic receptor P2X, ligand-gated ion channel, 7 (P2RX7), mRNA
gi|4505552|ref|NM_002562.1|[4505552]

7051: NM_002561
Homo sapiens purinergic receptor P2X, ligand-gated ion channel, 5 (P2RX5), mRNA
gi|4505550|ref|NM_002561.1|[4505550]

7052: NM_002560
Homo sapiens purinergic receptor P2X, ligand-gated ion channel, 4 (P2RX4), mRNA
gi|4505548|ref|NM_002560.1|[4505548]

7053: NM_002559
Homo sapiens purinergic receptor P2X, ligand-gated ion channel, 3 (P2RX3), mRNA
gi|4505546|ref|NM_002559.1|[4505546]

7054: NM_002556
Homo sapiens oxysterol binding protein (OSBP), mRNA
gi|4505530|ref|NM_002556.1|[4505530]

7055: NM_003696
Homo sapiens olfactory receptor, family 6, subfamily A, member 1 (OR6A1), mRNA
gi|4505520|ref|NM_003696.1|[4505520]

7056: NM_002550
Homo sapiens olfactory receptor, family 3, subfamily A, member 1 (OR3A1), mRNA
gi|4505518|ref|NM_002550.1|[4505518]

7057: NM_002548
Homo sapiens olfactory receptor, family 1, subfamily D, member 2 (OR1D2), mRNA
gi|4505516|ref|NM_002548.1|[4505516]

7058: NM_000914
Homo sapiens opioid receptor, mu 1 (OPRM1), mRNA
gi|4505514|ref|NM_000914.1|[4505514]

7059: NM_000912
Homo sapiens opioid receptor, kappa 1 (OPRK1), mRNA
gi|4505510|ref|NM_000912.1|[4505510]

7060: NM_000911
Homo sapiens opioid receptor, delta 1 (OPRD1), mRNA
gi|4505508|ref|NM_000911.1|[4505508]

7061: NM_002543
Homo sapiens oxidised low density lipoprotein (lectin-like) receptor 1 (OLR1), mRNA
gi|4505500|ref|NM_002543.1|[4505500]

7062: NM_003485
Homo sapiens G protein-coupled receptor 68 (GPR68), mRNA
gi|4505496|ref|NM_003485.1|[4505496]

7063: NM_002531
Homo sapiens neurotensin receptor 1 (high affinity) (NTSR1), mRNA
gi|4505476|ref|NM_002531.1|[4505476]

7064: NM_002530
Homo sapiens neurotrophic tyrosine kinase, receptor, type 3 (NTRK3), mRNA
gi|4505474|ref|NM_002530.1|[4505474]

7065: NM_003580
Homo sapiens neutral sphingomyelinase (N-SMase) activation associated factor (NSMAF), mRNA
gi|4505464|ref|NM_003580.1|[4505464]

7066: NM_003872
Homo sapiens neuropilin 2 (NRP2), mRNA
gi|4505458|ref|NM_003872.1|[4505458]

7067: NM_003873
Homo sapiens neuropilin 1 (NRP1), mRNA gi|4505456|ref|NM_003873.1|[4505456]

7068: NM_000910
Homo sapiens neuropeptide Y receptor Y2 (NPY2R), mRNA
gi|4505446|ref|NM_000910.1|[4505446]

7069: NM_000909
Homo sapiens neuropeptide Y receptor Y1 (NPY1R), mRNA
gi|4505444|ref|NM_000909.1|[4505444]

7070: NM_000908
Homo sapiens natriuretic peptide receptor C/guanylate cyclase C
(atrionatriuretic peptide receptor C) (NPR3), mRNA
gi|4505440|ref|NM_000908.1|[4505440]

7071: NM_000906
Homo sapiens natriuretic peptide receptor A/guanylate cyclase A
(atrionatriuretic peptide receptor A) (NPR1), mRNA
gi|4505434|ref|NM_000906.1|[4505434]

7072: NM_002511
Homo sapiens neuromedin B receptor (NMBR), mRNA
gi|4505406|ref|NM_002511.1|[4505406]

7073: NM_003954
Homo sapiens mitogen-activated protein kinase kinase kinase 14 (MAP3K14), mRNA
gi|4505396|ref|NM_003954.1|[4505396]

7074: NM_002507
Homo sapiens nerve growth factor receptor (TNFR superfamily, member 16) (NGFR), mRNA
gi|4505392|ref|NM_002507.1|[4505392]

7075: NM_002447
Homo sapiens macrophage stimulating 1 receptor (c-met-related tyrosine kinase) (MST1R), mRNA
gi|4505264|ref|NM_002447.1|[4505264]

7076: NM_002445
Homo sapiens macrophage scavenger receptor 1 (MSR1), mRNA
gi|4505258|ref|NM_002445.1|[4505258]

7077: NM_000529
Homo sapiens melanocortin 2 receptor (adrenocorticotropic hormone) (MC2R), mRNA
gi|4505126|ref|NM_000529.1|[4505126]

7078: NM_002386
Homo sapiens melanocortin 1 receptor (alpha melanocyte stimulating hormone receptor) (MC1R), mRNA
gi|4505124|ref|NM_002386.1|[4505124]

7079: NM_002349
Homo sapiens lymphocyte antigen 75 (LY75), mRNA
gi|4505052|ref|NM_002349.1|[4505052]

7080: NM_002344
Homo sapiens leukocyte tyrosine kinase (LTK), mRNA
gi|4505044|ref|NM_002344.1|[4505044]

7081: NM_000752
Homo sapiens leukotriene b4 receptor (chemokine receptor-like 1) (LTB4R), mRNA
gi|4505032|ref|NM_000752.1|[4505032]

7082: NM_002336
Homo sapiens low density lipoprotein receptor-related protein 6 (LRP6), mRNA
gi|4505016|ref|NM_002336.1|[4505016]

7083: NM_002319
Homo sapiens leucine-rich neuronal protein (LRN), mRNA
gi|4505012|ref|NM_002319.1|[4505012]

7084: NM_002303
Homo sapiens leptin receptor (LEPR), mRNA
gi|4504978|ref|NM_002303.1|[4504978]

7085: NM_002291
Homo sapiens laminin, beta 1 (LAMB1), mRNA
gi|4504950|ref|NM_002291.1|[4504950]

7086: NM_002258
Homo sapiens killer cell lectin-like receptor subfamily B, member 1 (KLRB1), mRNA
gi|4504878|ref|NM_002258.1|[4504878]

7087: NM_002255
Homo sapiens killer cell immunoglobulin-like receptor, two domains, long cytoplasmic tail, 4 (KIR2DL4), mRNA
gi|4504870|ref|NM_002255.1|[4504870]

7088: NM_002227
Homo sapiens Janus kinase 1 (a protein tyrosine kinase) (JAK1), mRNA
gi|4504802|ref|NM_002227.1|[4504802]

7091: NM_002210
Homo sapiens integrin, alpha V (vitronectin receptor, alpha polypeptide, antigen CD51) (ITGAV), mRNA
gi|4504762|ref|NM_002210.1|[4504762]

7092: NM_002205
Homo sapiens integrin, alpha 5 (fibronectin receptor, alpha polypeptide) (ITGA5), mRNA
gi|4504750|ref|NM_002205.1|[4504750]

7094: NM_001565
Homo sapiens small inducible cytokine subfamily B (Cys-X-Cys), member 10 (SCYB10), mRNA
gi|4504700|ref|NM_001565.1|[4504700]

7095: NM_001557
Homo sapiens interleukin 8 receptor, beta (IL8RB), mRNA
gi|4504682|ref|NM_001557.1|[4504682]

7096: NM_000634
Homo sapiens interleukin 8 receptor, alpha (IL8RA), mRNA
gi|4504680|ref|NM_000634.1|[4504680]

7097: NM_002185
Homo sapiens interleukin 7 receptor (IL7R), mRNA
gi|4504678|ref|NM_002185.1|[4504678]

7098: NM_002184
Homo sapiens interleukin 6 signal transducer (gp130, oncostatin M receptor) (IL6ST), mRNA
gi|4504674|ref|NM_002184.1|[4504674]

7099: NM_000565
Homo sapiens interleukin 6 receptor (IL6R), mRNA
gi|4504672|ref|NM_000565.1|[4504672]

7100: NM_000878
Homo sapiens interleukin 2 receptor, beta (IL2RB), mRNA
gi|4504664|ref|NM_000878.1|[4504664]

7101: NM_003854
Homo sapiens interleukin 1 receptor-like 2 (IL1RL2), mRNA
gi|4504662|ref|NM_003854.1|[4504662]

7102: NM_000877
Homo sapiens interleukin 1 receptor, type I (IL1R1), mRNA
gi|4504658|ref|NM_000877.1|[4504658]

7103: NM_003853
Homo sapiens interleukin 18 receptor accessory protein (IL18RAP), mRNA
gi|4504656|ref|NM_003853.1|[4504656]

7104: NM_002189
Homo sapiens interleukin 15 receptor, alpha (IL15RA), mRNA
gi|4504648|ref|NM_002189.1|[4504648]

7105: NM_001559
Homo sapiens interleukin 12 receptor, beta 2 (IL12RB2), mRNA
gi|4504642|ref|NM_001559.1|[4504642]

7106: NM_001558
Homo sapiens interleukin 10 receptor, alpha (IL10RA), mRNA
gi|4504632|ref|NM_001558.1|[4504632]

7107: NM_000876
Homo sapiens insulin-like growth factor 2 receptor (IGF2R), mRNA
gi|4504610|ref|NM_000876.1|[4504610]

7108: NM_000871
Homo sapiens 5-hydroxytryptamine (serotonin) receptor 6 (HTR6), mRNA
gi|4504544|ref|NM_000871.1|[4504544]

7109: NM_000869
Homo sapiens 5-hydroxytryptamine (serotonin) receptor 3A (HTR3A), mRNA
gi|4504542|ref|NM_000869.1|[4504542]

7110: NM_000868
Homo sapiens 5-hydroxytryptamine (serotonin) receptor 2C (HTR2C), mRNA
gi|4504540|ref|NM_000868.1|[4504540]

7111: NM_000867
Homo sapiens 5-hydroxytryptamine (serotonin) receptor 2B (HTR2B), mRNA
gi|4504538|ref|NM_000867.1|[4504538]

7112: NM_000865
Homo sapiens 5-hydroxytryptamine (serotonin) receptor 1E (HTR1E), mRNA
gi|4504536|ref|NM_000865.1|[4504536]

7113: NM_000863
Homo sapiens 5-hydroxytryptamine (serotonin) receptor 1B (HTR1B), mRNA
gi|4504532|ref|NM_000863.1|[4504532]

7114: NM_000524

Homo sapiens 5-hydroxytryptamine (serotonin) receptor 1A (HTR1A), mRNA
gi|4504530|ref|NM_000524.1|[4504530]

7115: NM_000186
Homo sapiens H factor 1 (complement) (HF1), mRNA
gi|4504374|ref|NM_000186.1|[4504374]

7116: NM_001523
Homo sapiens hyaluronan synthase 1 (HAS1), mRNA
gi|4504338|ref|NM_001523.1|[4504338]

7117: NM_000845
Homo sapiens glutamate receptor, metabotropic 8 (GRM8), mRNA
gi|4504148|ref|NM_000845.1|[4504148]

7118: NM_000844
Homo sapiens glutamate receptor, metabotropic 7 (GRM7), mRNA
gi|4504146|ref|NM_000844.1|[4504146]

7119: NM_000841
Homo sapiens glutamate receptor, metabotropic 4 (GRM4), mRNA
gi|4504140|ref|NM_000841.1|[4504140]

7120: NM_000840
Homo sapiens glutamate receptor, metabotropic 3 (GRM3), mRNA
gi|4504138|ref|NM_000840.1|[4504138]

7121: NM_000831
Homo sapiens glutamate receptor, ionotropic, kainate 3 (GRIK3), mRNA
gi|4504118|ref|NM_000831.1|[4504118]

7122: NM_000830
Homo sapiens glutamate receptor, ionotropic, kainate 1 (GRIK1), mRNA
gi|4504116|ref|NM_000830.1|[4504116]

7123: NM_002086
Homo sapiens growth factor receptor-bound protein 2 (GRB2), mRNA gi|4504110|ref|NM_002086.1|[4504110]

7124: NM_002082
Homo sapiens G protein-coupled receptor kinase 6 (GPRK6), mRNA
gi|4504100|ref|NM_002082.1|[4504100]

7125: NM_001504
Homo sapiens G protein-coupled receptor 9 (GPR9), mRNA
gi|4504098|ref|NM_001504.1|[4504098]

7126: NM_001508
Homo sapiens G protein-coupled receptor 39 (GPR39), mRNA
gi|4504096|ref|NM_001508.1|[4504096]

7127: NM_001507
Homo sapiens G protein-coupled receptor 38 (GPR38), mRNA
gi|4504094|ref|NM_001507.1|[4504094]

7128: NM_001506
Homo sapiens G protein-coupled receptor 32 (GPR32), mRNA
gi|4504092|ref|NM_001506.1|[4504092]

7129: NM_001505
Homo sapiens G protein-coupled receptor 30 (GPR30), mRNA
gi|4504090|ref|NM_001505.1|[4504090]

7130: NM_000173
Homo sapiens glycoprotein Ib (platelet), alpha polypeptide (GP1BA), mRNA
gi|4504070|ref|NM_000173.1|[4504070]

7131: NM_000824
Homo sapiens glycine receptor, beta (GLRB), mRNA
gi|4504022|ref|NM_000824.1|[4504022]

7132: NM_002063
Homo sapiens glycine receptor, alpha 2 (GLRA2), mRNA
gi|4504020|ref|NM_002063.1|[4504020]

7133: NM_000164
Homo sapiens gastric inhibitory polypeptide receptor (GIPR), mRNA
gi|4503998|ref|NM_000164.1|[4503998]

7134: NM_000823
Homo sapiens growth hormone releasing hormone receptor (GHRHR), mRNA
gi|4503996|ref|NM_000823.1|[4503996]

7135: NM_000163
Homo sapiens growth hormone receptor (GHR), mRNA
gi|4503992|ref|NM_000163.1|[4503992]

7136: NM_000160
Homo sapiens glucagon receptor (GCGR), mRNA
gi|4503946|ref|NM_000160.1|[4503946]

7137: NM_003614
Homo sapiens galanin receptor 3 (GALR3), mRNA
gi|4503906|ref|NM_003614.1|[4503906]

7138: NM_002043
Homo sapiens gamma-aminobutyric acid (GABA) receptor, rho 2 (GABRR2), mRNA
gi|4503870|ref|NM_002043.1|[4503870]

7139: NM_002042
Homo sapiens gamma-aminobutyric acid (GABA) receptor, rho 1 (GABRR1), mRNA
gi|4503868|ref|NM_002042.1|[4503868]

7140: NM_002036
Homo sapiens Duffy blood group (FY), mRNA
gi|4503818|ref|NM_002036.1|[4503818]

7141: NM_001462
Homo sapiens formyl peptide receptor-like 1 (FPRL1), mRNA
gi|4503780|ref|NM_001462.1|[4503780]

7142: NM_002029
Homo sapiens formyl peptide receptor 1 (FPR1), mRNA
gi|4503778|ref|NM_002029.1|[4503778]

7143: NM_001461
Homo sapiens flavin containing monooxygenase 5 (FMO5), mRNA
gi|4503760|ref|NM_001461.1|[4503760]

7144: NM_002020
Homo sapiens fms-related tyrosine kinase 4 (FLT4), mRNA
gi|4503752|ref|NM_002020.1|[4503752]

7145: NM_001459
Homo sapiens fms-related tyrosine kinase 3 ligand (FLT3LG), mRNA
gi|4503750|ref|NM_001459.1|[4503750]

7146: NM_002019
Homo sapiens fms-related tyrosine kinase 1 (vascular endothelial growth
factor/vascular permeability factor receptor) (FLT1), mRNA
gi|4503748|ref|NM_002019.1|[4503748]

7147: NM_002002
Homo sapiens Fc fragment of IgE, low affinity II, receptor for (CD23A) (FCER2),
mRNA
gi|4503678|ref|NM_002002.1|[4503678]

7148: NM_002001
Homo sapiens Fc fragment of IgE, high affinity I, receptor for; alpha
polypeptide (FCER1A), mRNA
gi|4503674|ref|NM_002001.1|[4503674]

7149: NM_003950
Homo sapiens coagulation factor II (thrombin) receptor-like 3 (F2RL3), mRNA
gi|4503638|ref|NM_003950.1|[4503638]

7150: NM_001981
Homo sapiens epidermal growth factor receptor pathway substrate 15 (EPS15), mRNA gi|4503592|ref|NM_001981.1|[4503592]

7151: NM_001974
Homo sapiens egf-like module containing, mucin-like, hormone receptor-like sequence 1 (EMR1), mRNA
gi|4503564|ref|NM_001974.1|[4503564]

7152: NM_001423
Homo sapiens epithelial membrane protein 1 (EMP1), mRNA
gi|4503558|ref|NM_001423.1|[4503558]

7153: NM_003757
Homo sapiens eukaryotic translation initiation factor 3, subunit 2 (beta, 36kD) (EIF3S2), mRNA
gi|4503512|ref|NM_003757.1|[4503512]

7154: NM_001406
Homo sapiens ephrin-B3 (EFNB3), mRNA
gi|4503488|ref|NM_001406.1|[4503488]

7155: NM_001962
Homo sapiens ephrin-A5 (EFNA5), mRNA
gi|4503486|ref|NM_001962.1|[4503486]

7156: NM_001405
Homo sapiens ephrin-A2 (EFNA2), mRNA
gi|4503484|ref|NM_001405.1|[4503484]

7157: NM_003775
Homo sapiens endothelial differentiation, G-protein-coupled receptor 6 (EDG6), mRNA
gi|4503458|ref|NM_003775.1|[4503458]

7158: NM_001945
Homo sapiens diphtheria toxin receptor (heparin-binding epidermal growth factor-like growth factor) (DTR), mRNA
gi|4503412|ref|NM_001945.1|[4503412]

7159: NM_001360
Homo sapiens 7-dehydrocholesterol reductase (DHCR7), mRNA
gi|4503320|ref|NM_001360.1|[4503320]

7160: NM_003467
Homo sapiens chemokine (C-X-C motif), receptor 4 (fusin) (CXCR4), mRNA
gi|4503174|ref|NM_003467.1|[4503174]

7161: NM_001338
Homo sapiens coxsackie virus and adenovirus receptor (CXADR), mRNA
gi|4503172|ref|NM_001338.1|[4503172]

7162: NM_003478
Homo sapiens cullin 5 (CUL5), mRNA
gi|4503166|ref|NM_003478.1|[4503166]

7163: NM_001330
Homo sapiens cardiotrophin 1 (CTF1), mRNA
gi|4503120|ref|NM_001330.1|[4503120]

7164: NM_000760
Homo sapiens colony stimulating factor 3 receptor (granulocyte) (CSF3R), mRNA
gi|4503080|ref|NM_000760.1|[4503080]

7165: NM_003805
Homo sapiens CASP2 and RIPK1 domain containing adaptor with death domain (CRADD), mRNA
gi|4503030|ref|NM_003805.1|[4503030]

7166: NM_001877
Homo sapiens complement component (3d/Epstein Barr virus) receptor 2 (CR2), mRNA
gi|4503026|ref|NM_001877.1|[4503026]

7167: NM_001842
Homo sapiens ciliary neurotrophic factor receptor (CNTFR), mRNA
gi|4502930|ref|NM_001842.1|[4502930]

7168: NM_001281
Homo sapiens cytoskeleton-associated protein 1 (CKAP1), mRNA
gi|4502848|ref|NM_001281.1|[4502848]

7169: NM_000750
Homo sapiens cholinergic receptor, nicotinic, beta polypeptide 4 (CHRNB4), mRNA
gi|4502836|ref|NM_000750.1|[4502836]

7170: NM_000749
Homo sapiens cholinergic receptor, nicotinic, beta polypeptide 3 (CHRNB3), mRNA
gi|4502834|ref|NM_000749.1|[4502834]

7171: NM_000748
Homo sapiens cholinergic receptor, nicotinic, beta polypeptide 2 (neuronal) (CHRNB2), mRNA
gi|4502832|ref|NM_000748.1|[4502832]

7172: NM_000746
Homo sapiens cholinergic receptor, nicotinic, alpha polypeptide 7 (CHRNA7), mRNA
gi|4502830|ref|NM_000746.1|[4502830]

7173: NM_000745
Homo sapiens cholinergic receptor, nicotinic, alpha polypeptide 5 (CHRNA5), mRNA
gi|4502828|ref|NM_000745.1|[4502828]

7174: NM_000744
Homo sapiens cholinergic receptor, nicotinic, alpha polypeptide 4 (CHRNA4), mRNA
gi|4502826|ref|NM_000744.1|[4502826]

7175: NM_000742
Homo sapiens cholinergic receptor, nicotinic, alpha polypeptide 2 (neuronal) (CHRNA2), mRNA
gi|4502822|ref|NM_000742.1|[4502822]

7176: NM_000741
Homo sapiens cholinergic receptor, muscarinic 4 (CHRM4), mRNA
gi|4502820|ref|NM_000741.1|[4502820]

7177: NM_000740
Homo sapiens cholinergic receptor, muscarinic 3 (CHRM3), mRNA
gi|4502818|ref|NM_000740.1|[4502818]

7178: NM_000739
Homo sapiens cholinergic receptor, muscarinic 2 (CHRM2), mRNA
gi|4502816|ref|NM_000739.1|[4502816]

7179: NM_000738
Homo sapiens cholinergic receptor, muscarinic 1 (CHRM1), mRNA
gi|4502814|ref|NM_000738.1|[4502814]

7181: NM_001768
Homo sapiens CD8 antigen, alpha polypeptide (p32) (CD8A), mRNA
gi|4502688|ref|NM_001768.1|[4502688]

7182: NM_001781
Homo sapiens CD69 antigen (p60, early T-cell activation antigen) (CD69), mRNA
gi|4502680|ref|NM_001781.1|[4502680]

7183: NM_001779
Homo sapiens CD58 antigen, (lymphocyte function-associated antigen 3) (CD58), mRNA
gi|4502676|ref|NM_001779.1|[4502676]

7184: NM_000733
Homo sapiens CD3E antigen, epsilon polypeptide (TiT3 complex) (CD3E), mRNA
gi|4502670|ref|NM_000733.1|[4502670]

7185: NM_000732
Homo sapiens CD3D antigen, delta polypeptide (TiT3 complex) (CD3D), mRNA
gi|4502668|ref|NM_000732.1|[4502668]

7186: NM_001775
Homo sapiens CD38 antigen (p45) (CD38), mRNA
gi|4502664|ref|NM_001775.1|[4502664]

7187: NM_001767
Homo sapiens CD2 antigen (p50), sheep red blood cell receptor (CD2), mRNA
gi|4502652|ref|NM_001767.1|[4502652]

7188: NM_001837
Homo sapiens chemokine (C-C motif) receptor 3 (CCR3), mRNA
gi|4502636|ref|NM_001837.1|[4502636]

7189: NM_000731
Homo sapiens cholecystokinin B receptor (CCKBR), mRNA
gi|4502608|ref|NM_000731.1|[4502608]

7190: NM_000730
Homo sapiens cholecystokinin A receptor (CCKAR), mRNA
gi|4502606|ref|NM_000730.1|[4502606]

7191: NM_001742
Homo sapiens calcitonin receptor (CALCR), mRNA
gi|4502546|ref|NM_001742.1|[4502546]

7192: NM_001737
Homo sapiens complement component 9 (C9), mRNA
gi|4502510|ref|NM_001737.1|[4502510]

7193: NM_001736
Homo sapiens complement component 5 receptor 1 (C5a ligand) (C5R1), mRNA
gi|4502508|ref|NM_001736.1|[4502508]

7194: NM_001732
Homo sapiens butyrophilin, subfamily 1, member A1 (BTN1A1), mRNA
gi|4502474|ref|NM_001732.1|[4502474]

7195: NM_001729
Homo sapiens betacellulin (BTC), mRNA
gi|4502460|ref|NM_001729.1|[4502460]

7196: NM_001727
Homo sapiens bombesin-like receptor 3 (BRS3), mRNA
gi|4502454|ref|NM_001727.1|[4502454]

7197: NM_001203
Homo sapiens bone morphogenetic protein receptor, type IB (BMPR1B), mRNA
gi|4502430|ref|NM_001203.1|[4502430]

7198: NM_000710
Homo sapiens bradykinin receptor B1 (BDKRB1), mRNA
gi|4502390|ref|NM_000710.1|[4502390]

7199: NM_003921
Homo sapiens B-cell CLL/lymphoma 10 (BCL10), mRNA
gi|4502378|ref|NM_003921.1|[4502378]

7200: NM_001168
Homo sapiens baculoviral IAP repeat-containing 5 (survivin) (BIRC5), mRNA
gi|4502144|ref|NM_001168.1|[4502144]

7201: NM_001150
Homo sapiens alanyl (membrane) aminopeptidase (aminopeptidase N, aminopeptidase M, microsomal aminopeptidase, CD13, p150) (ANPEP), mRNA
gi|4502094|ref|NM_001150.1|[4502094]

7202: NM_001146
Homo sapiens angiopoietin 1 (ANGPT1), mRNA
gi|4502086|ref|NM_001146.1|[4502086]

7203: NM_000676
Homo sapiens adenosine A2b receptor (ADORA2B), mRNA
gi|4501950|ref|NM_000676.1|[4501950]

7204: NM_000674
Homo sapiens adenosine A1 receptor (ADORA1), mRNA
gi|4501946|ref|NM_000674.1|[4501946]

7205: NM_001118
Homo sapiens adenylate cyclase activating polypeptide 1 (pituitary) receptor type I (ADCYAP1R1), mRNA
gi|4501922|ref|NM_001118.1|[4501922]

7206: AF287270
Homo sapiens mucolipin (MCOLN1) gene, complete cds
gi|9844925|gb|AF287270.1|AF287270[9844925]

7207: AF287269
Homo sapiens mucolipin (MCOLN1) mRNA, complete cds
gi|9844923|gb|AF287269.1|AF287269[9844923]

7208: AF307080
Homo sapiens lectomedin-3 (LEC3) mRNA, complete cds
gi|11037015|gb|AF307080.1|AF307080[11037015]

7209: AF307079
Homo sapiens lectomedin-2 (LEC2) mRNA, complete cds
gi|11037013|gb|AF307079.1|AF307079[11037013]

7216: AF265242
Homo sapiens type-I T cell cytokine receptor mRNA, complete cds
gi|11036791|gb|AF265242.1|AF265242[11036791]

7217: AF018284
Homo sapiens P2Y1 receptor (P2YR1) mRNA, partial cds
gi|2738815|gb|AF018284.1|AF018284[2738815]

7218: AF017307
Homo sapiens Ets-related transcription factor (ERT) mRNA, complete cds
gi|2338755|gb|AF017307.1|AF017307[2338755]

7219: AF106912
Homo sapiens CRL1 protein (CRL1) mRNA, complete cds
gi|11022746|gb|AF106912.1|AF106912[11022746]

7220: AB042033
Homo sapiens FCER1B gene for high affinity IgE receptor beta subunit, 5' flanking sequence and partial cds
gi|11022658|dbj|AB042033.1|AB042033[11022658]

7221: AB019000
Homo sapiens mRNA for G-protein coupled receptor, complete cds
gi|11022652|dbj|AB019000.1|AB019000[11022652]

7222: AH007076
Homo sapiens chromosome 13 map 13q34
gi|3955190|gb|AH007076.1|SEG_HSGRKIN[3955190]

7223: AF019765
Homo sapiens G protein-coupled receptor kinase 1 and G protein-coupled receptor kinase 1b (GRK1) gene, alternatively spliced, alternative exon 6, exon 7, and partial cds
gi|3955189|gb|AF019765.1|HSGRKIN2[3955189]

7224: AF019764
Homo sapiens G protein-coupled receptor kinase 1 and G protein-coupled receptor kinase 1b (GRK1) gene, alternatively spliced, exon 6, alternative exon 6, and partial cds
gi|3955188|gb|AF019764.1|HSGRKIN1[3955188]

7225: AF035819
Homo sapiens macrophage receptor MARCO mRNA, complete cds
gi|3002790|gb|AF035819.1|AF035819[3002790]

7227: AF253318
Homo sapiens GFR receptor alpha 4 protein (GFRA4) mRNA, complete cds
gi|10998399|gb|AF253318.1|AF253318[10998399]

7228: AF077186
Homo sapiens neuronal nicotinic acetylcholine receptor beta 2 (CHRNB2) gene, complete cds
gi|10947140|gb|AF077186.2|[10947140]

7229: AF272363
Homo sapiens neuromedin U receptor 2 (NMUR2) mRNA, complete cds
gi|10946202|gb|AF272363.1|AF272363[10946202]

7230: AF272362
Homo sapiens neuromedin U receptor 1 (NMUR1) mRNA, complete cds
gi|10946200|gb|AF272362.1|AF272362[10946200]

7231: AJ277437
Homo sapiens mRNA for fibroblast growth factor receptor-like protein 1, (FGFRL1 gene)
gi|10944886|emb|AJ277437.1|HSA277437[10944886]

7232: G64264
Alk4/3' Human Chromosome 12 Homo sapiens STS genomic, sequence tagged site
gi|9802476|gb|G64264.1|G64264[9802476]

7233: G64261
AMHR2/ex1-2 Human Chromosome 12 Homo sapiens STS genomic, sequence tagged site
gi|9802473|gb|G64261.1|G64261[9802473]

7234: G64251
Alk4/ex1 Human Chromosome 12 Homo sapiens STS genomic, sequence tagged site
gi|9802463|gb|G64251.1|G64251[9802463]

7235: G64250
Alk1/ex10 Human Chromosome 12 Homo sapiens STS genomic, sequence tagged site
gi|9802462|gb|G64250.1|G64250[9802462]

7236: G64249
Alk1/ex2 Human Chromosome 12 Homo sapiens STS genomic, sequence tagged site
gi|9802461|gb|G64249.1|G64249[9802461]

7237: AF301005
Homo sapiens gamma-aminobutyric acid receptor GABA-B1e mRNA, complete cds
gi|10863757|gb|AF301005.1|AF301005[10863757]

7238: AF269133
Homo sapiens novel interleukin receptor (NILR) mRNA, complete cds
gi|10801190|gb|AF269133.1|AF269133[10801190]

7239: AF127670
Homo sapiens hyaluronic acid receptor (HAR) mRNA, complete cds
gi|10800121|gb|AF127670.2|AF127670[10800121]

7241: AF284436
Homo sapiens TIGIRR-1 mRNA, complete cds
gi|10644689|gb|AF284436.1|AF284436[10644689]

7242: AF284435
Homo sapiens TIGIRR-2 mRNA, complete cds
gi|10644687|gb|AF284435.1|AF284435[10644687]

7243: AF284434
Homo sapiens IL-1Rrp2 mRNA, complete cds
gi|10644685|gb|AF284434.1|AF284434[10644685]

7244: M35198
Homo sapiens integrin beta-subunit mRNA, complete cds
gi|9961228|gb|M35198.3|HUMINTB6A[9961228]

7245: AF302903
Homo sapiens vomeronasal receptor 1 (VNR19I1) mRNA, complete cds
gi|10732801|gb|AF302903.1|AF302903[10732801]

7246: AF286095
Homo sapiens IL-22 receptor (IL22R) mRNA, complete cds
gi|10719607|gb|AF286095.1|AF286095[10719607]

7248: AF239668
Homo sapiens CCK-B/gastrin receptor mRNA, complete cds; alternatively spliced
gi|7677459|gb|AF239668.1|AF239668[7677459]

7249: AF029759
Homo sapiens mutant G protein-coupled receptor STRL33 (STRL33) gene, STRL33-3K allele, complete cds
gi|10716827|gb|AF029759.1|AF029759[10716827]

7250: AB041644
Homo sapiens gene for cysteinyl leukotriene receptor like receptor, complete cds
gi|10716135|dbj|AB041644.1|AB041644[10716135]

7251: AF237381
Homo sapiens CCR3 gene and exon 3
gi|10643653|gb|AF237381.1|AF237380S2[10643653]

7252: AF237380
Homo sapiens CCR3 gene, promotor and exon 1
gi|10643652|gb|AF237380.1|AF237380S1[10643652]

7253: AH009867
Homo sapiens
gi|10643651|gb|AH009867.1|SEG_AF237380S[10643651]

7254: AF233516
Homo sapiens PD-1-ligand precursor, mRNA, complete cds
gi|10567621|gb|AF233516.1|AF233516[10567621]

7255: AJ297688
Homo sapiens partial IL-12RB1 gene for IL-12 receptor beta1 chain, exon 1 and joined CDS
gi|10445329|emb|AJ297688.1|HSA297688[10445329]

7256: AJ297701
Homo sapiens partial IL-12RB1 gene for IL-12 receptor beta1 chain, exons 16-17
gi|10443220|emb|AJ297701.1|HSA297701[10443220]

7257: AJ297700
Homo sapiens partial IL-12RB1 gene for IL-12 receptor beta1 chain, exon 15
gi|10443219|emb|AJ297700.1|HSA297700[10443219]

7258: AJ297699

Homo sapiens partial IL-12RB1 gene for IL-12 receptor beta1 chain, exon 14
gi|10443218|emb|AJ297699.1|HSA297699[10443218]

7259: AJ297698
Homo sapiens partial IL-12RB1 gene for IL-12 receptor beta1 chain, exon 13
gi|10443217|emb|AJ297698.1|HSA297698[10443217]

7260: AJ297697
Homo sapiens partial IL-12RB1 gene for IL-12 receptor beta1 chain, exon 12
gi|10443216|emb|AJ297697.1|HSA297697[10443216]

7261: AJ297696
Homo sapiens partial IL-12RB1 gene for IL-12 receptor beta1 chain, exon 11
gi|10443215|emb|AJ297696.1|HSA297696[10443215]

7262: AJ297695
Homo sapiens partial IL-12RB1 gene for IL-12 receptor beta1 chain, exon 10
gi|10443214|emb|AJ297695.1|HSA297695[10443214]

7263: AJ297694
Homo sapiens partial IL-12RB1 gene for IL-12 receptor beta1 chain, exon 9
gi|10443213|emb|AJ297694.1|HSA297694[10443213]

7264: AJ297693
Homo sapiens partial IL-12RB1 gene for IL-12 receptor beta1 chain, exon 8
gi|10443212|emb|AJ297693.1|HSA297693[10443212]

7265: AJ297692
Homo sapiens partial IL-12RB1 gene for IL-12 receptor beta1 chain, exons 6-7
gi|10443211|emb|AJ297692.1|HSA297692[10443211]

7266: AJ297691
Homo sapiens partial IL-12RB1 gene for IL-12 receptor beta1 chain, exon 5
gi|10443210|emb|AJ297691.1|HSA297691[10443210]

7267: AJ297690
Homo sapiens partial IL-12RB1 gene for IL-12 receptor beta1 chain, exon 4

7268: AJ297689
Homo sapiens partial IL-12RB1 gene for IL-12 receptor beta1 chain, exons 2-3
gi|10443208|emb|AJ297689.1|HSA297689[10443208]

7269: AJ276452
Homo sapiens partial pIgR gene for polymeric immunoglobulin receptor, partial intron 1 and partial exon 2
gi|10303247|emb|AJ276452.1|HSA276452[10303247]

7271: AF254664
Homo sapiens cysteinyl leukotriene receptor CYSLT2 gene, complete cds
gi|10442007|gb|AF254664.1|AF254664[10442007]

7273: AC005330
Homo sapiens chromosome 19, cosmid R34047 and overlapping PCR product, complete sequence
gi|10305189|gb|AC005330.2|AC005330[10305189]

7517: AF176039
Homo sapiens high mobility group protein-R mRNA, complete cds
gi|5834272|gb|AF176039.1|AF176039[5834272]

7518: AB041228
Homo sapiens mRNA for G protein-coupled receptor TGR-1, complete cds
gi|10257380|dbj|AB041228.1|AB041228[10257380]

7519: AF282262
Homo sapiens GHRH receptor splice variant 4 mRNA, complete cds
gi|10242297|gb|AF282262.1|AF282262[10242297]

7520: AF282261
Homo sapiens GHRH receptor splice variant 3 mRNA, complete cds
gi|10242295|gb|AF282261.1|AF282261[10242295]

7521: AF282260 gi|10443209|emb|AJ297690.1|HSA297690[10443209]

Homo sapiens GHRH receptor splice variant 2 mRNA, complete cds
gi|10242293|gb|AF282260.1|AF282260[10242293]

7522: AF282259

Homo sapiens GHRH receptor splice variant 1 mRNA, complete cds
gi|10242291|gb|AF282259.1|AF282259[10242291]

7523: X80389

H.sapiens platelet-derived growth factor alpha receptor DNA
gi|10241726|emb|X80389.2|HSPDGFAD[10241726]

7524: AF177761

Homo sapiens herstatin (HER-2) mRNA, alternatively spliced, complete cds
gi|10181232|gb|AF177761.2|AF177761[10181232]

7525: AF005058

Homo sapiens chemokine receptor (CXCR-4) gene, complete cds
gi|2735718|gb|AF005058.1|AF005058[2735718]

7526: AF264716

Homo sapiens complement receptor type 1 (CR1) gene, CR1*SCR25-HUM1 allele, partial cds
gi|10185787|gb|AF264716.1|AF264716[10185787]

7527: AF264715

Homo sapiens complement receptor type 1 (CR1) gene, CR1*SCR25-HUM2 allele, partial cds
gi|10185785|gb|AF264715.1|AF264715[10185785]

7528: AF250237

Homo sapiens orphan G protein-coupled receptor 85 (GPR85) mRNA, complete cds
gi|10181092|gb|AF250237.2|AF250237[10181092]

7533: AF189277

Homo sapiens leukocyte immunoglobulin-like receptor 1 (LIR1) gene, complete cds
gi|9954209|gb|AF189277.1|AF189277[9954209]

7534: AB010994
Homo sapiens hedgehog gene, exon 3 and complete cds
gi|10047225|dbj|AB010994.2|AB010581S3[10047225]

7535: AB010993
Homo sapiens hedgehog gene, exon 2
gi|10047224|dbj|AB010993.2|AB010581S2[10047224]

7536: AB010581
Homo sapiens hedgehog gene, exon 1
gi|10047223|dbj|AB010581.2|AB010581S1[10047223]

7537: SEG_AB010581S
Homo sapiens hedgehog gene
gi|10047222|dbj||SEG_AB010581S[10047222]

7538: AX015117
Sequence 8 from Patent WO9952943
gi|10041220|emb|AX015117.1|AX015117[10041220]

7539: AX015116
Sequence 7 from Patent WO9952943
gi|10041219|emb|AX015116.1|AX015116[10041219]

7540: AX015115
Sequence 6 from Patent WO9952943
gi|10041218|emb|AX015115.1|AX015115[10041218]

7541: AX015114
Sequence 5 from Patent WO9952943
gi|10041217|emb|AX015114.1|AX015114[10041217]

7542: AX015113
Sequence 4 from Patent WO9952943
gi|10041216|emb|AX015113.1|AX015113[10041216]

7543: AX015112

Sequence 3 from Patent WO9952943
gi|10041215|emb|AX015112.1|AX015112[10041215]

7544: AX015111
Sequence 2 from Patent WO9952943
gi|10041214|emb|AX015111.1|AX015111[10041214]

7545: AX015110
Sequence 1 from Patent WO9952943
gi|10041213|emb|AX015110.1|AX015110[10041213]

7546: AF042080
Homo sapiens glial cell line-derived neurotrophic factor receptor alpha (GFRA1) mRNA, complete cds
gi|2801556|gb|AF042080.1|AF042080[2801556]

7547: AF255342
Homo sapiens putative pheromone receptor V1RL1 long form (V1RL1) mRNA, complete cds
gi|9988584|gb|AF255342.1|AF255342[9988584]

7548: AF254747
Homo sapiens ROR2 protein (ROR2) gene, exon 2
gi|9664303|gb|AF254747.1|AF254747S1[9664303]

7550: AJ295613
Homo sapiens partial GHR gene for growth hormone receptor, exon 2
gi|9968301|emb|AJ295613.1|HSA295613[9968301]

7551: AJ278681
Homo sapiens partial GHR gene for growth hormone receptor, exons 8-10
gi|9968297|emb|AJ278681.1|HSA278681[9968297]

7553: AF217963
Homo sapiens NRAGE mRNA, complete cds
gi|9963809|gb|AF217963.1|AF217963[9963809]

7554: AF169970
Homo sapiens complement receptor 1 (CR1) gene, CR1*SCR25-HUM5 allele, exon 29 and partial cds
gi|9956947|gb|AF169970.1|AF169970[9956947]

7555: AF169969
Homo sapiens complement receptor 1 (CR1) gene, CR1*SCR25-HUM4 allele, exon 29 and partial cds
gi|9956945|gb|AF169969.1|AF169969[9956945]

7556: AB044402
Homo sapiens mRNA for LTB4 receptor JULF2, complete cds
gi|9081802|dbj|AB044402.1|AB044402[9081802]

7557: U96190
Homo sapiens p58 NK cell inhibitory receptor NKR-K7 mRNA, partial cds
gi|2088618|gb|U96190.1|HSU96190[2088618]

7558: U96189
Homo sapiens p58 NK cell inhibitory receptor NKR-K6 mRNA, partial cds
gi|2088616|gb|U96189.1|HSU96189[2088616]

7559: U96188
Homo sapiens p50 cell activatory receptor NKR-K1 mRNA, partial cds
gi|2088614|gb|U96188.1|HSU96188[2088614]

7560: AF251841
Homo sapiens vitronectin receptor alpha polypeptide (ITGAV) gene, exons 29, 30, and complete cds
gi|9944844|gb|AF251841.1|F251818S24[9944844]

7561: AF251840
Homo sapiens vitronectin receptor alpha polypeptide (ITGAV) gene, exons 27 and 28
gi|9944843|gb|AF251840.1|F251818S23[9944843]

7562: AF251839

Homo sapiens vitronectin receptor alpha polypeptide (ITGAV) gene, exon 26
gi|9944842|gb|AF251839.1|F251818S22[9944842]

7563: AF251838
Homo sapiens vitronectin receptor alpha polypeptide (ITGAV) gene, exon 25
gi|9944841|gb|AF251838.1|F251818S21[9944841]

7564: AF251837
Homo sapiens vitronectin receptor alpha polypeptide (ITGAV) gene, exons 23 and 24
gi|9944840|gb|AF251837.1|F251818S20[9944840]

7565: AF251836
Homo sapiens vitronectin receptor alpha polypeptide (ITGAV) gene, exon 22
gi|9944839|gb|AF251836.1|F251818S19[9944839]

7566: AF251835
Homo sapiens vitronectin receptor alpha polypeptide (ITGAV) gene, exons 20 and 21
gi|9944838|gb|AF251835.1|F251818S18[9944838]

7567: AF251834
Homo sapiens vitronectin receptor alpha polypeptide (ITGAV) gene, exon 19
gi|9944837|gb|AF251834.1|F251818S17[9944837]

7568: AF251833
Homo sapiens vitronectin receptor alpha polypeptide (ITGAV) gene, exon 18
gi|9944836|gb|AF251833.1|F251818S16[9944836]

7569: AF251832
Homo sapiens vitronectin receptor alpha polypeptide (ITGAV) gene, exon 17
gi|9944835|gb|AF251832.1|F251818S15[9944835]

7570: AF251831
Homo sapiens vitronectin receptor alpha polypeptide (ITGAV) gene, exon 16
gi|9944834|gb|AF251831.1|F251818S14[9944834]

7571: AF251830
Homo sapiens vitronectin receptor alpha polypeptide (ITGAV) gene, exon 15
gi|9944833|gb|AF251830.1|F251818S13[9944833]

7572: AF251829
Homo sapiens vitronectin receptor alpha polypeptide (ITGAV) gene, exon 14
gi|9944832|gb|AF251829.1|F251818S12[9944832]

7573: AF251828
Homo sapiens vitronectin receptor alpha polypeptide (ITGAV) gene, exon 13
gi|9944831|gb|AF251828.1|F251818S11[9944831]

7574: AF251827
Homo sapiens vitronectin receptor alpha polypeptide (ITGAV) gene, exons 11 and 12
gi|9944830|gb|AF251827.1|F251818S10[9944830]

7575: AF251826
Homo sapiens vitronectin receptor alpha polypeptide (ITGAV) gene, exons 9 and 10
gi|9944829|gb|AF251826.1|F251818S09[9944829]

7576: AF251825
Homo sapiens vitronectin receptor alpha polypeptide (ITGAV) gene, exon 8
gi|9944828|gb|AF251825.1|F251818S08[9944828]

7577: AF251824
Homo sapiens vitronectin receptor alpha polypeptide (ITGAV) gene, exon 7
gi|9944827|gb|AF251824.1|F251818S07[9944827]

7578: AF251823
Homo sapiens vitronectin receptor alpha polypeptide (ITGAV) gene, exon 6
gi|9944826|gb|AF251823.1|F251818S06[9944826]

7579: AF251822
Homo sapiens vitronectin receptor alpha polypeptide (ITGAV) gene, exon 5
gi|9944825|gb|AF251822.1|F251818S05[9944825]

7580: AF251821
Homo sapiens vitronectin receptor alpha polypeptide (ITGAV) gene, exon 4
gi|9944824|gb|AF251821.1|F251818S04[9944824]

7581: AF251820
Homo sapiens vitronectin receptor alpha polypeptide (ITGAV) gene, exon 3
gi|9944823|gb|AF251820.1|F251818S03[9944823]

7582: AF251819
Homo sapiens vitronectin receptor alpha polypeptide (ITGAV) gene, exon 2
gi|9944822|gb|AF251819.1|F251818S02[9944822]

7583: AF251818
Homo sapiens vitronectin receptor alpha polypeptide (ITGAV) gene, promoter region and exon 1
gi|9944821|gb|AF251818.1|F251818S01[9944821]

7584: AH009773
Homo sapiens vitronectin receptor alpha polypeptide (ITGAV) gene, complete cds
gi|9944820|gb|AH009773.1|SEG_F251818S[9944820]

7585: AF189768
Homo sapiens leukocyte immunoglobulin-like receptor 5 (LIR5) gene, complete cds
gi|9930102|gb|AF189768.1|AF189768[9930102]

7600: AJ245377
Homo sapiens mRNA for 2B4 NK receptor homologue (h2B4 gene)
gi|9621661|emb|AJ245377.1|HSA245377[9621661]

7601: X07206
H.sapiens TRGV10 gene, allele V10*A1
gi|1848182|emb|X07206.1|HSTRGV10[1848182]

7603: AF246974
Homo sapiens toll-like receptor 9 (TLR9) mRNA, partial cds, alternatively spliced
gi|9887086|gb|AF246974.1|AF246974[9887086]

7604: AF246973
Homo sapiens toll-like receptor 9 (TLR9) mRNA, partial cds, alternatively spliced
gi|9887084|gb|AF246973.1|AF246973[9887084]

7605: AF246972
Homo sapiens toll-like receptor 9 (TLR9) mRNA, partial cds
gi|9887082|gb|AF246972.1|AF246972[9887082]

7606: AF215826
Homo sapiens killer-cell Ig-like receptor KIR2DL4v1 (KIR2DL4) gene, KIR2DL4v1 allele, exon 3 and partial cds
gi|9886965|gb|AF215826.1|AF215826[9886965]

7607: AF215825
Homo sapiens killer-cell Ig-like receptor KIR3DL1v (KIR3DL1) gene, KIR3DL1v allele, exon 3 and partial cds
gi|9886963|gb|AF215825.1|AF215825[9886963]

7608: AB008193
Homo sapiens genes for leukotriene B4 receptor BLT2, leukotriene B4 receptor BLT1, complete cds
gi|9229835|dbj|AB008193.1|AB008193[9229835]

7609: AB029892
Homo sapiens hBLT2 mRNA for Leukotriene B4 receptor BLT2, complete cds
gi|9186899|dbj|AB029892.1|AB029892[9186899]

7610: AF211978
Homo sapiens LENG11 mRNA, partial sequence
gi|9885308|gb|AF211978.1|AF211978[9885308]

7611: AF211977
Homo sapiens LENG10 mRNA, partial sequence
gi|9885307|gb|AF211977.1|AF211977[9885307]

7612: AF211976
Homo sapiens LENG9 mRNA, partial sequence
gi|9885306|gb|AF211976.1|AF211976[9885306]

7613: AF211975
Homo sapiens LENG8 mRNA, variant C, partial sequence
gi|9885305|gb|AF211975.1|AF211975[9885305]

7614: AF211974
Homo sapiens LENG8 mRNA, variant B, partial sequence
gi|9885304|gb|AF211974.1|AF211974[9885304]

7615: AF211973
Homo sapiens LENG8 mRNA, variant A, partial sequence
gi|9885303|gb|AF211973.1|AF211973[9885303]

7616: AF211972
Homo sapiens LENG7 mRNA, partial sequence
gi|9885302|gb|AF211972.1|AF211972[9885302]

7617: AF211971
Homo sapiens LENG6 mRNA, partial sequence
gi|9885301|gb|AF211971.1|AF211971[9885301]

7618: AF211970
Homo sapiens LENG5 mRNA, partial sequence
gi|9885300|gb|AF211970.1|AF211970[9885300]

7619: AF211969
Homo sapiens LENG4 mRNA, partial sequence
gi|9885299|gb|AF211969.1|AF211969[9885299]

7620: AF211968
Homo sapiens LENG3 mRNA, partial sequence
gi|9885298|gb|AF211968.1|AF211968[9885298]

7621: AF211967

Homo sapiens LENG2 mRNA, partial sequence
gi|9885297|gb|AF211967.1|AF211967[9885297]

7622: AF211966
Homo sapiens LENG1 protein (LENG1) mRNA, partial cds
gi|9885295|gb|AF211966.1|AF211966[9885295]

7624: AF262016
Homo sapiens adrenergic receptor alpha-2A gene, complete cds
gi|9864781|gb|AF262016.2|AF262016[9864781]

7626: AF242865
Homo sapiens coxsackie virus and adenovirus receptor (CXADR) gene, exon 7 and complete cds
gi|9858570|gb|AF242865.1|AF242862S4[9858570]

7627: AF242864
Homo sapiens coxsackie virus and adenovirus receptor (CXADR) gene, exons 2 through 6
gi|9858569|gb|AF242864.1|AF242862S3[9858569]

7629: AF242862
Homo sapiens coxsackie virus and adenovirus receptor (CXADR) gene, exon 1
gi|9858567|gb|AF242862.1|AF242862S1[9858567]

7630: AH009718
Homo sapiens coxsackie virus and adenovirus receptor (CXADR) gene, complete cds
gi|9858566|gb|AH009718.1|SEG_AF242862S[9858566]

7631: AF257210
Homo sapiens G-protein coupled receptor HLWAR77 mRNA, complete cds
gi|9309468|gb|AF257210.1|AF257210[9309468]

7632: AF292403
Homo sapiens type B natriuretic peptide receptor gene, promoter region and partial cds
gi|9858187|gb|AF292403.1|AF292403[9858187]

7633: AF288571
Homo sapiens lymphoid enhancer factor-1 (LEF1) mRNA, complete cds
gi|9858157|gb|AF288571.1|AF288571[9858157]

7634: AF146747
Homo sapiens cell surface receptor (PRV1) mRNA, complete cds
gi|9857660|gb|AF146747.1|AF146747[9857660]

7862: AF233092
Homo sapiens lysophosphatidic acid G protein-coupled receptor 4 (EDG4) mRNA, complete cds
gi|7243675|gb|AF233092.1|AF233092[7243675]

7863: AF269144
Homo sapiens GABAA receptor gamma 3 subunit (GABRG3) gene, exon 10 and complete cds
gi|9802369|gb|AF269144.1|F269135S10[9802369]

7864: AF269143
Homo sapiens GABAA receptor gamma 3 subunit (GABRG3) gene, exon 9
gi|9802368|gb|AF269143.1|F269135S09[9802368]

7865: AF269142
Homo sapiens GABAA receptor gamma 3 subunit (GABRG3) gene, exon 8
gi|9802367|gb|AF269142.1|F269135S08[9802367]

7866: AF269141
Homo sapiens GABAA receptor gamma 3 subunit (GABRG3) gene, exon 7
gi|9802366|gb|AF269141.1|F269135S07[9802366]

7867: AF269140
Homo sapiens GABAA receptor gamma 3 subunit (GABRG3) gene, exon 6
gi|9802365|gb|AF269140.1|F269135S06[9802365]

7868: AF269139
Homo sapiens GABAA receptor gamma 3 subunit (GABRG3) gene, exon 5 gi|9802364|gb|AF269139.1|F269135S05[9802364]

7869: AF269138
Homo sapiens GABAA receptor gamma 3 subunit (GABRG3) gene, exon 4
gi|9802363|gb|AF269138.1|F269135S04[9802363]

7870: AF269137
Homo sapiens GABAA receptor gamma 3 subunit (GABRG3) gene, exon 3
gi|9802362|gb|AF269137.1|F269135S03[9802362]

7871: AF269136
Homo sapiens GABAA receptor gamma 3 subunit (GABRG3) gene, exon 2
gi|9802361|gb|AF269136.1|F269135S02[9802361]

7872: AF269135
Homo sapiens GABAA receptor gamma 3 subunit (GABRG3) gene, exon 1
gi|9802360|gb|AF269135.1|F269135S01[9802360]

7873: AH009710
Homo sapiens GABAA receptor gamma 3 subunit (GABRG3) gene, complete cds
gi|9802359|gb|AH009710.1|SEG_F269135S[9802359]

7874: AF211942
Homo sapiens haplotype 1089 olfactory receptor (OR2H3) gene, partial cds
gi|9798923|gb|AF211942.1|AF211942[9798923]

7875: AF211941
Homo sapiens haplotype 1037 olfactory receptor (OR2H3) gene, partial cds
gi|9798921|gb|AF211941.1|AF211941[9798921]

7876: AF211940
Homo sapiens haplotype 1012 olfactory receptor (OR2H3) gene, partial cds
gi|9798919|gb|AF211940.1|AF211940[9798919]

7877: AF211939
Homo sapiens haplotype 1013 olfactory receptor (OR2H3) gene, partial cds
gi|9798917|gb|AF211939.1|AF211939[9798917]

7878: AJ272029
Homo sapiens partial CD30 gene for cytokine receptor CD30 and promoter region
gi|9798449|emb|AJ272029.1|HSA272029[9798449]

7880: AF101726
Homo sapiens vasopressin receptor subtype 1b mRNA, complete cds
gi|4336681|gb|AF101726.1|AF101726[4336681]

7881: AF101725
Homo sapiens vasopressin receptor subtype 1a mRNA, complete cds
gi|4336679|gb|AF101725.1|AF101725[4336679]

7882: AF101728
Homo sapiens truncated vasopressin receptor type 2 mRNA, complete cds
gi|4323606|gb|AF101728.1|AF101728[4323606]

7883: AF101727
Homo sapiens vasopressin receptor type 2 mRNA, complete cds
gi|4323604|gb|AF101727.1|AF101727[4323604]

7884: AF064078
Homo sapiens insulin receptor-related receptor (INSRR) mRNA, partial cds
gi|3152883|gb|AF064078.1|AF064078[3152883]

7885: S82307
Homo sapiens p65 mRNA, partial cds
gi|1839613|gb|S82307.1|S82307[1839613]

7886: S83176
Homo sapiens calcium-sensing receptor long isoform (CASR) mRNA, partial cds
gi|1836093|gb|S83176.1|S83176[1836093]

7887: S82755
Homo sapiens T cell receptor mRNA, partial cds
gi|1835845|gb|S82755.1|S82755[1835845]

7888: S82612
Homo sapiens 5-hydroxytryptamine type 3AS receptor subunit mRNA, complete cds
gi|1699437|gb|S82612.1|S82612[1699437]

7891: AF238374
Homo sapiens mutant fibroblast growth factor receptor 3 (FGFR3) mRNA, partial cds
gi|9719331|gb|AF238374.1|AF238374[9719331]

7894: AJ400843
Homo sapiens partial mRNA for immunoglobulin-like cell surface receptor FDF03-M14, soluble alternative form
gi|9715838|emb|AJ400843.1|HSA400843[9715838]

7895: AJ400842
Homo sapiens partial mRNA for immunoglobulin-like cell surface receptor FDF03-dtm, soluble form
gi|9715835|emb|AJ400842.1|HSA400842[9715835]

7896: AJ400841
Homo sapiens mRNA for immunoglobulin-like cell surface receptor FDF03
gi|9715833|emb|AJ400841.1|HSA400841[9715833]

8061: AJ005205
Homo sapiens 5HT3 gene for serotonin 3 receptor
gi|7019744|emb|AJ005205.2|HSA005205[7019744]

8062: AB038269
Homo sapiens mRNA for cysteinyl leukotriene CysLT2 receptor, complete cds; cDNA: PSEC0146 from clone PLACE1006979
gi|9663957|dbj|AB038269.1|AB038269[9663957]

8063: AJ278476
Homo sapiens partial mRNA for transport-secretion protein 2.2, (TTS-2.2 gene)
gi|9663152|emb|AJ278476.1|HSA278476[9663152]

8064: AJ278475

Homo sapiens partial mRNA for transport-secretion protein 2.1 (TTS-2.1 gene)
gi|9663150|emb|AJ278475.1|HSA278475[9663150]

8065: AF282693
Homo sapiens inflammation-related G protein-coupled receptor EX33 (EX33) mRNA, complete cds
gi|9652260|gb|AF282693.1|AF282693[9652260]

8066: AF254409
Homo sapiens scavenger receptor class B type III SR-BIII mRNA, partial cds
gi|9651987|gb|AF254409.1|AF254409[9651987]

8067: AF236117
Homo sapiens G-protein coupled receptor EDG-7 mRNA, complete cds
gi|9651838|gb|AF236117.1|AF236117[9651838]

8068: AF287008
Homo sapiens triggering receptor expressed on monocytes 1 (TREM1) mRNA, complete cds
gi|9624485|gb|AF287008.1|AF287008[9624485]

8069: AF172171
Homo sapiens toll-like receptor 4 (TLR4) gene, exon 4 and complete cds
gi|9622356|gb|AF172171.1|HSTLR3[9622356]

8070: AF172170
Homo sapiens toll-like receptor 4 (TLR4) gene, exons 2 and 3
gi|9622355|gb|AF172170.1|HSTLR2[9622355]

8071: AF172169
Homo sapiens toll-like receptor 4 (TLR4) gene, exon 1
gi|9622354|gb|AF172169.1|HSTLR1[9622354]

8072: AH009665
Homo sapiens toll-like receptor 4 (TLR4) gene, complete cds
gi|9622353|gb|AH009665.1|SEG_HSTLR[9622353]

8073: AF165312
Homo sapiens pre-T-cell receptor alpha chain (PTA) mRNA, alternatively spliced, complete cds
gi|9621867|gb|AF165312.1|AF165312[9621867]

8074: AJ245375
Homo sapiens mRNA for PP35 act (h2B4 gene)
gi|9621657|emb|AJ245375.1|HSA245375[9621657]

8075: AF277230
Homo sapiens seven transmembrane receptor BLTR2 (BLTR2) mRNA, complete cds
gi|8896158|gb|AF277230.1|AF277230[8896158]

8076: AF114491
Homo sapiens EGF-like module EMR2 (EMR2) mRNA, complete cds
gi|6650688|gb|AF114491.1|AF114491[6650688]

8077: AF107259
Homo sapiens chromosome 21q22.1 cosmid clone ICRFcA0552D2, complete sequence, containing part of the glutamate receptor gene GLUR5
gi|4154320|gb|AF107259.1|AF107259[4154320]

8078: AF107257
Homo sapiens chromosome 21q22.1 PAC L12209, complete sequence
gi|4106881|gb|AF107257.1|AF107257[4106881]

8079: AZ081535
p133B6#4 RPCI-6 Homo sapiens genomic, genomic survey sequence
gi|9587541|gb|AZ081535.1|AZ081535[9587541]

8081: AF285168
Homo sapiens GABA-A receptor beta 1 subunit (GABRB1) gene, promoter and partial cds
gi|9502261|gb|AF285168.1|AF285168[9502261]

8126: AC018755
Homo sapiens chromosome 19, BAC BC330783 (CIT-HSPC_470E3), complete sequence
gi|9454515|gb|AC018755.3|AC018755[9454515]

8159: AF246303
Homo sapiens peroxisome proliferative activated receptor delta (PPARD) gene, exon 9 and complete cds
gi|7417394|gb|AF246303.1|AF246296S8[7417394]

8160: AF246302
Homo sapiens peroxisome proliferative activated receptor delta (PPARD) gene, exons 7 and 8
gi|7417393|gb|AF246302.1|AF246296S7[7417393]

8161: AF246301
Homo sapiens peroxisome proliferative activated receptor delta (PPARD) gene, exon 6
gi|7417392|gb|AF246301.1|AF246296S6[7417392]

8162: AF246300
Homo sapiens peroxisome proliferative activated receptor delta (PPARD) gene, exon 5
gi|7417391|gb|AF246300.1|AF246296S5[7417391]

8163: AF246299
Homo sapiens peroxisome proliferative activated receptor delta (PPARD) gene, exon 4
gi|7417390|gb|AF246299.1|AF246296S4[7417390]

8164: AF246298
Homo sapiens peroxisome proliferative activated receptor delta (PPARD) gene, exon 3
gi|7417389|gb|AF246298.1|AF246296S3[7417389]

8165: AF246297
Homo sapiens peroxisome proliferative activated receptor delta (PPARD) gene, exon 2
gi|7417388|gb|AF246297.1|AF246296S2[7417388]

8166: AF246296
Homo sapiens peroxisome proliferative activated receptor delta (PPARD) gene, promoter and exon 1
gi|7417387|gb|AF246296.1|AF246296S1[7417387]

8167: AH009223
Homo sapiens peroxisome proliferative activated receptor delta (PPARD) gene, complete cds
gi|7417386|gb|AH009223.1|SEG_AF246296S[7417386]

8168: U94888
Homo sapiens CC-chemokine-binding receptor JAB61 mRNA, complete cds
gi|2213808|gb|U94888.1|HSU94888[2213808]

8169: AB040434
Homo sapiens mRNA for hTROY, complete cds
gi|9392329|dbj|AB040434.1|AB040434[9392329]

8170: AJ272427
Homo sapiens mRNA for frizzled homolog 3 (FZD3 gene)
gi|7649448|emb|AJ272427.1|HSA272427[7649448]

8173: U88356
Homo sapiens receptor tyrosine kinase ErbB-3 (c-erbB-3) gene, exons 12, 13, 14, and partial cds
gi|9294704|gb|U88356.1|HSCERBR3[9294704]

8174: U88355
Homo sapiens receptor tyrosine kinase ErbB-3 (c-erbB-3) gene, exon 10 and partial cds
gi|9294703|gb|U88355.1|HSCERBR2[9294703]

8175: U88354
Homo sapiens receptor tyrosine kinase ErbB-3 (c-erbB-3) gene, exons 8 and 9
gi|9294702|gb|U88354.1|HSCERBR1[9294702]

8176: AB037533
Homo sapiens HTR1F gene for 5-hydroxytryptamine (serotonin) receptor 1F, partial cds
gi|6815236|dbj|AB037533.1|AB037533[6815236]

8177: AB037513
Homo sapiens HTR2A gene for 5-hydroxytryptamine (serotonin) receptor 2A, partial cds
gi|6815196|dbj|AB037513.1|AB037513[6815196]

8178: AF180301
Homo sapiens corticotropin-releasing factor receptor variant 1d (CRHR1) mRNA, alternative splice product, complete cds
gi|5815472|gb|AF180301.1|AF180301[5815472]

8181: AF208111
Homo sapiens truncated IL-17 receptor homolog precursor (EVI27) mRNA, complete cds
gi|9246434|gb|AF208111.1|AF208111[9246434]

8182: AF208110
Homo sapiens IL-17 receptor homolog precursor (EVI27) mRNA, complete cds
gi|9246432|gb|AF208110.1|AF208110[9246432]

8183: M15222
Homo sapiens T-cell receptor (TCRB) mRNA, partial cds
gi|338893|gb|M15222.1|HUMTCBVO[338893]

8189: AF263279
Homo sapiens CD164 mRNA, complete cds
gi|9230740|gb|AF263279.1|AF263279[9230740]

8192: AF242874
Homo sapiens neuromedin U receptor 2 (NMU2R) mRNA, complete cds
gi|9082155|gb|AF242874.1|AF242874[9082155]

8193: AF160477
Homo sapiens Ig superfamily receptor LNIR precursor, mRNA, complete cds
gi|9049507|gb|AF160477.1|AF160477[9049507]

8194: AF058290
Homo sapiens imidazoline receptor antisera-selected protein mRNA, partial cds
gi|3493224|gb|AF058290.1|AF058290[3493224]

8195: AF082516
Homo sapiens I-1 receptor candidate protein mRNA, complete cds
gi|3462806|gb|AF082516.1|AF082516[3462806]

8211: X06031
Homo sapiens partial T-cell receptor CD3-gamma gene, exon 6
gi|36818|emb|X06031.1|HSTCR3G6[36818]

8212: X06030
Homo sapiens partial T-cell receptor CD3-gamma gene, exon 5
gi|36816|emb|X06030.1|HSTCR3G5[36816]

8213: X06029
Homo sapiens partial T-cell receptor CD3-gamma gene exon 4
gi|36814|emb|X06029.1|HSTCR3G4[36814]

8214: X06027
Homo sapiens partial CD3G gene, exon 2 (and joined mature peptide)
gi|36811|emb|X06027.1|HSTCR3G2[36811]

8216: Z30426
H.sapiens gene for early lymphocyte activation antigen CD69, exon 1
gi|525242|emb|Z30426.1|HSLACD691[525242]

8302: AJ278605
Homo sapiens BLT-2R gene for leukotriene B4 receptor 2
gi|8919627|emb|AJ278605.1|HSA278605[8919627]

8444: AF246925
Homo sapiens haplotype 28 CC chemokine receptor 5 (CCR5) gene, partial sequence
gi|8809841|gb|AF246925.1|AF246925[8809841]

8445: AF246924
Homo sapiens haplotype 27 CC chemokine receptor 5 (CCR5) gene, partial sequence
gi|8809840|gb|AF246924.1|AF246924[8809840]

8446: AF246923
Homo sapiens haplotype 26 CC chemokine receptor 5 (CCR5) gene, partial sequence
gi|8809839|gb|AF246923.1|AF246923[8809839]

8447: AF246922
Homo sapiens haplotype 24 CC chemokine receptor 5 (CCR5) gene, partial sequence
gi|8809838|gb|AF246922.1|AF246922[8809838]

8448: AF246921
Homo sapiens haplotype 23 CC chemokine receptor 5 (CCR5) gene, partial sequence
gi|8809837|gb|AF246921.1|AF246921[8809837]

8449: AF246920
Homo sapiens haplotype 22 CC chemokine receptor 5 (CCR5) gene, partial sequence
gi|8809836|gb|AF246920.1|AF246920[8809836]

8450: AF246919
Homo sapiens haplotype 21 CC chemokine receptor 5 (CCR5) gene, partial sequence
gi|8809835|gb|AF246919.1|AF246919[8809835]

8451: AF246918
Homo sapiens haplotype 20 CC chemokine receptor 5 (CCR5) gene, partial sequence
gi|8809834|gb|AF246918.1|AF246918[8809834]

8452: AF246917
Homo sapiens haplotype 19 CC chemokine receptor 5 (CCR5) gene, partial sequence
gi|8809833|gb|AF246917.1|AF246917[8809833]

8453: AF246916
Homo sapiens haplotype 18 CC chemokine receptor 5 (CCR5) gene, partial sequence
gi|8809832|gb|AF246916.1|AF246916[8809832]

8454: AF246915

Homo sapiens haplotype 17 CC chemokine receptor 5 (CCR5) gene, partial sequence
gi|8809831|gb|AF246915.1|AF246915[8809831]

8455: AF246914

Homo sapiens haplotype 16 CC chemokine receptor 5 (CCR5) gene, partial sequence
gi|8809830|gb|AF246914.1|AF246914[8809830]

8456: AF246913

Homo sapiens haplotype 15 CC chemokine receptor 5 (CCR5) gene, partial sequence
gi|8809829|gb|AF246913.1|AF246913[8809829]

8457: AF246912

Homo sapiens haplotype 14 CC chemokine receptor 5 (CCR5) gene, partial sequence
gi|8809828|gb|AF246912.1|AF246912[8809828]

8458: AF246911

Homo sapiens haplotype 13 CC chemokine receptor 5 (CCR5) gene, partial sequence
gi|8809827|gb|AF246911.1|AF246911[8809827]

8459: AF246910

Homo sapiens haplotype 12 CC chemokine receptor 5 (CCR5) gene, partial sequence
gi|8809826|gb|AF246910.1|AF246910[8809826]

8460: AF246909

Homo sapiens haplotype 11 CC chemokine receptor 5 (CCR5) gene, partial sequence
gi|8809825|gb|AF246909.1|AF246909[8809825]

8461: AF246908

Homo sapiens haplotype 10 CC chemokine receptor 5 (CCR5) gene, partial sequence
gi|8809824|gb|AF246908.1|AF246908[8809824]

8462: AF246907

Homo sapiens haplotype 9 CC chemokine receptor 5 (CCR5) gene, partial sequence
gi|8809823|gb|AF246907.1|AF246907[8809823]

8463: AF246906

Homo sapiens haplotype 8 CC chemokine receptor 5 (CCR5) gene, partial sequence gi|8809822|gb|AF246906.1|AF246906[8809822]

8464: AF246905
Homo sapiens haplotype 7 CC chemokine receptor 5 (CCR5) gene, partial sequence
gi|8809821|gb|AF246905.1|AF246905[8809821]

8465: AF246904
Homo sapiens haplotype 6 CC chemokine receptor 5 (CCR5) gene, partial sequence
gi|8809820|gb|AF246904.1|AF246904[8809820]

8466: AF246903
Homo sapiens haplotype 5 CC chemokine receptor 5 (CCR5) gene, partial sequence
gi|8809819|gb|AF246903.1|AF246903[8809819]

8467: AF246902
Homo sapiens haplotype 4 CC chemokine receptor 5 (CCR5) gene, partial sequence
gi|8809818|gb|AF246902.1|AF246902[8809818]

8468: AF246901
Homo sapiens haplotype 1 CC chemokine receptor 5 (CCR5) gene, partial sequence
gi|8809817|gb|AF246901.1|AF246901[8809817]

8469: AF246900
Homo sapiens haplotype 2 CC chemokine receptor 5 (CCR5) gene, partial sequence
gi|8809816|gb|AF246900.1|AF246900[8809816]

8470: AF246899
Homo sapiens haplotype 3 CC chemokine receptor 5 (CCR5) gene, partial sequence
gi|8809815|gb|AF246899.1|AF246899[8809815]

8471: AF210633
Homo sapiens growth hormone receptor (GHR) gene, GHR-d3 allele, partial sequence
gi|8809760|gb|AF210633.1|AF210633[8809760]

8472: M22057
Homo sapiens T-cell receptor epsilon (CD3E) gene, exon 5 and partial cds
gi|339220|gb|M22057.1|HUMTCR3E[339220]

8476: AF212311
Homo sapiens interleukin 20 (IL20) mRNA, complete cds
gi|8705219|gb|AF212311.1|AF212311[8705219]

8477: AF141334
Homo sapiens placenta apolipoprotein B48 receptor type 2 (APOB48R) mRNA, complete cds
gi|8699629|gb|AF141334.1|AF141334[8699629]

8478: AF277379
Homo sapiens vitamin D receptor-interacting protein complex component DRIP100 (DRIP100) mRNA, complete cds
gi|8699627|gb|AF277379.1|AF277379[8699627]

8480: AJ251962
Homo sapiens partial TGF-beta III receptor gene
gi|6634455|emb|AJ251962.1|HSA251962[6634455]

8481: AJ251961
Homo sapiens partial mRNA for betaglycan (TBR III gene)
gi|6634453|emb|AJ251961.1|HSA251961[6634453]

8483: AF062039
Homo sapiens integrin alpha-2 subunit (ITGA2) gene, ITGA2-1 allele, partial cds
gi|8574452|gb|AF062039.1|AF062039[8574452]

8485: AF141333
Homo sapiens apolipoprotein B48 receptor (APOB48R) gene, complete cds
gi|8547065|gb|AF141333.1|AF141333[8547065]

8486: AF141332
Homo sapiens apolipoprotein B48 receptor (APOB48R) mRNA, complete cds
gi|8547063|gb|AF141332.1|AF141332[8547063]

8488: X56253

Homo sapiens partial MPR46 gene for 46kd mannose 6-phosphate receptor, exon 1 and join mRNA
gi|34727|emb|X56253.1|HSMPR461[34727]

8489: AF155912
Homo sapiens growth hormone receptor (GHR) gene, exon 3 and partial cds
gi|8037572|gb|AF155912.1|AF155912[8037572]

8490: AF263744
Homo sapiens erbb2-interacting protein ERBIN mRNA, complete cds
gi|8572220|gb|AF263744.1|AF263744[8572220]

8501: X56254
Homo sapiens partial MPR46 gene for 46kd mannose 6-phosphate receptor, exon 2 join CDS
gi|34729|emb|X56254.1|HSMPR462[34729]

8503: AB040801
Homo sapiens mRNA for SREB3, complete cds
gi|8467969|dbj|AB040801.1|AB040801[8467969]

8504: AB040800
Homo sapiens mRNA for SREB2, complete cds
gi|8467967|dbj|AB040800.1|AB040800[8467967]

8505: AB040799
Homo sapiens mRNA for SREB1, complete cds
gi|8467965|dbj|AB040799.1|AB040799[8467965]

8506: AF187064
Homo sapiens p75NTR-associated cell death executor (NADE) mRNA, complete cds
gi|8452893|gb|AF187064.1|AF187064[8452893]

8507: AF045606
Homo sapiens C21orf4 mRNA, complete cds
gi|8277249|gb|AF045606.2|AF045606[8277249]

8508: AF204920

Homo sapiens killer cell Ig-like receptor (KIR48) gene, KIR48b variant, exon 5
gi|8248132|gb|AF204920.1|AF204918S3[8248132]

8509: AF204919
Homo sapiens killer cell Ig-like receptor (KIR48) gene, KIR48b variant, exon 4
gi|8248131|gb|AF204919.1|AF204918S2[8248131]

8510: AF204918
Homo sapiens killer cell Ig-like receptor (KIR48) gene, KIR48b variant, exons 2 and 3
gi|8248130|gb|AF204918.1|AF204918S1[8248130]

8511: AH009422
Homo sapiens
gi|8248129|gb|AH009422.1|SEG_AF204918S[8248129]

8512: AF204917
Homo sapiens killer cell Ig-like receptor (KIR48) gene, KIR48a variant, exon 5
gi|8248128|gb|AF204917.1|AF204915S3[8248128]

8513: AF204916
Homo sapiens killer cell Ig-like receptor (KIR48) gene, KIR48a variant, exon 4
gi|8248127|gb|AF204916.1|AF204915S2[8248127]

8514: AF204915
Homo sapiens killer cell Ig-like receptor (KIR48) gene, KIR48a variant, exons 2 and 3
gi|8248126|gb|AF204915.1|AF204915S1[8248126]

8515: AH009421
Homo sapiens
gi|8248125|gb|AH009421.1|SEG_AF204915S[8248125]

8516: AF204914
Homo sapiens killer cell Ig-like receptor (KIR44) gene, KIR44b variant, exon 5
gi|8248124|gb|AF204914.1|AF204912S3[8248124]

8517: AF204913
Homo sapiens killer cell Ig-like receptor (KIR44) gene, KIR44b variant, exon 4
gi|8248123|gb|AF204913.1|AF204912S2[8248123]

8518: AF204912
Homo sapiens killer cell Ig-like receptor (KIR44) gene, KIR44b variant, exons 2 and 3
gi|8248122|gb|AF204912.1|AF204912S1[8248122]

8519: AH009420
Homo sapiens
gi|8248121|gb|AH009420.1|SEG_AF204912S[8248121]

8520: AF204911
Homo sapiens killer cell Ig-like receptor (KIR44) gene, KIR44a variant, exon 5
gi|8248120|gb|AF204911.1|AF204909S3[8248120]

8521: AF204910
Homo sapiens killer cell Ig-like receptor (KIR44) gene, KIR44a variant, exon 4
gi|8248119|gb|AF204910.1|AF204909S2[8248119]

8522: AF204909
Homo sapiens killer cell Ig-like receptor (KIR44) gene, KIR44a variant, exons 2 and 3
gi|8248118|gb|AF204909.1|AF204909S1[8248118]

8523: AH009419
Homo sapiens
gi|8248117|gb|AH009419.1|SEG_AF204909S[8248117]

8524: AF204905
Homo sapiens killer cell Ig-like receptor (KIR2DL5) gene, KIR2DL5.2 variant, partial sequence
gi|8248112|gb|AF204905.1|AF204905[8248112]

8525: AF204904
Homo sapiens killer cell Ig-like receptor (KIR2DL5) gene, KIR2DL5.1 variant, partial cds gi|8248110|gb|AF204904.1|AF204904[8248110]

8607: AF212842
Homo sapiens immunoglobulin-like transcript 11 protein (ILT11) mRNA, partial cds
gi|8163785|gb|AF212842.1|AF212842[8163785]

8608: AF208237
Homo sapiens 7-transmembrane G-protein coupled receptor 2 (GPR2) mRNA, complete cds
gi|8118034|gb|AF208237.1|AF208237[8118034]

8609: AF204903
Homo sapiens killer-cell immunoglobulin-like receptor KIR2DL5.1 (KIR2DL5) mRNA, complete cds
gi|8117976|gb|AF204903.1|AF204903[8117976]

8610: AP001716
Homo sapiens genomic DNA, chromosome 21q, section 60/105
gi|7768717|dbj|AP001716.1|AP001716[7768717]

8611: AP001705
Homo sapiens genomic DNA, chromosome 21q, section 49/105
gi|7768711|dbj|AP001705.1|AP001705[7768711]

8612: AP001670
Homo sapiens genomic DNA, chromosome 21q, section 14/105
gi|7768690|dbj|AP001670.1|AP001670[7768690]

8613: AP001717
Homo sapiens genomic DNA, chromosome 21q, section 61/105
gi|7768678|dbj|AP001717.1|AP001717[7768678]

8616: AJ012074
Homo sapiens VPAC1 receptor gene, 5' end and promoter region
gi|3758828|emb|AJ012074.1|HSA012074[3758828]

8617: AF039906

Homo sapiens cosmid D16B8, chromosome 21 3' of IFNGR2
gi|2914756|gb|AF039906.1|AF039906[2914756]

8619: S77335
Homo sapiens growth hormone receptor gene, partial cds
gi|999143|gb|S77335.1|S77335[999143]

8621: S75765
Homo sapiens delta CCK-B gene, partial cds
gi|913754|gb|S75765.1|S75765[913754]

8624: S78717
Homo sapiens ryanodine receptor (RYR1) gene, partial cds
gi|244183|gb|S78717.1|S78717[244183]

8625: X15266
Homo sapiens gene for muscarinic acetylcholine receptor HM3
gi|32323|emb|X15266.1|HSACM3[32323]

8626: X15265
Homo sapiens gene for muscarinic acetylcholine receptor M4
gi|32321|emb|X15265.1|HSACM4[32321]

8627: AF220542
Homo sapiens FcRN protein gene, complete cds
gi|8101614|gb|AF220542.1|AF220542[8101614]

8629: AF073924
Homo sapiens putative taste receptor HTR2 mRNA, partial cds
gi|8100088|gb|AF073924.1|AF073924[8100088]

8630: D88437
Homo sapiens mRNA for G-protein coupled receptor SALPR, complete cds
gi|7340885|dbj|D88437.1|D88437[7340885]

8631: AB032369
Homo sapiens MIST mRNA, partial cds gi|8099156|dbj|AB032369.1|AB032369[8099156]

8632: AF167555
Homo sapiens TAJ-alpha mRNA, complete cds
gi|8071643|gb|AF167555.1|AF167555[8071643]

8633: AF002982
Homo sapiens killer cell receptor (KIR103) mRNA, allele ASD2, complete cds
gi|2443483|gb|AF002982.1|AF002982[2443483]

8634: AF002981
Homo sapiens killer cell receptor (KIR103) mRNA, allele ASD1, complete cds
gi|2443481|gb|AF002981.1|AF002981[2443481]

8635: AF002980
Homo sapiens killer cell receptor (KIR103) mRNA, allele AS, complete cds
gi|2443479|gb|AF002980.1|AF002980[2443479]

8636: AF002979
Homo sapiens killer cell receptor (KIR103) mRNA, allele LP, complete cds
gi|2443477|gb|AF002979.1|AF002979[2443477]

8637: AH005453
Homo sapiens chromosome 19 clone 4 map 19q13.4
gi|2228790|gb|AH005453.1|SEG_HSKIR[2228790]

8638: AF003123
Homo sapiens killer cell inhibitory receptor (KIR-103AS) gene, exon 8 and complete cds
gi|2228789|gb|AF003123.1|HSKIR8[2228789]

8639: AF003122
Homo sapiens killer cell inhibitory receptor (KIR-103AS) gene, exon 7
gi|2228788|gb|AF003122.1|HSKIR7[2228788]

8640: AF003121
Homo sapiens killer cell inhibitory receptor (KIR-103AS) gene, exon 6 gi|2228787|gb|AF003121.1|HSKIR6[2228787]

8641: AF003120
Homo sapiens killer cell inhibitory receptor (KIR-103AS) gene, exon 5
gi|2228786|gb|AF003120.1|HSKIR5[2228786]

8642: AF003119
Homo sapiens killer cell inhibitory receptor (KIR-103AS) gene, exon 4
gi|2228785|gb|AF003119.1|HSKIR4[2228785]

8643: AF003118
Homo sapiens killer cell inhibitory receptor (KIR-103AS) gene, exon 3
gi|2228784|gb|AF003118.1|HSKIR3[2228784]

8644: AF003117
Homo sapiens killer cell inhibitory receptor (KIR-103AS) gene, exon 2
gi|2228783|gb|AF003117.1|HSKIR2[2228783]

8645: AF003116
Homo sapiens killer cell inhibitory receptor (KIR-103AS) gene, exon 1
gi|2228782|gb|AF003116.1|HSKIR1[2228782]

8646: AF196329
Homo sapiens triggering receptor expressed on monocytes 1 mRNA, complete cds
gi|8050526|gb|AF196329.1|AF196329[8050526]

8647: AF167342
Homo sapiens membrane interleukin 1 receptor accessory protein (IL1RAP) gene, exon 12 and complete cds, alternatively spliced
gi|8050498|gb|AF167342.1|F167333S10[8050498]

8648: AF167341
Homo sapiens membrane interleukin 1 receptor accessory protein (IL1RAP) gene, exons 10 and 11
gi|8050497|gb|AF167341.1|F167333S09[8050497]

8649: AF167340

Homo sapiens soluble interleukin 1 receptor accessory protein (IL1RAP) gene, exon 8, alternative exons 9 and complete cds, alternatively spliced
gi|8050496|gb|AF167340.1|F167333S08[8050496]

8650: AF167339
Homo sapiens interleukin 1 receptor accessory protein (IL1RAP) gene, exon 7
gi|8050495|gb|AF167339.1|F167333S07[8050495]

8651: AF167338
Homo sapiens interleukin 1 receptor accessory protein (IL1RAP) gene, exon 6
gi|8050494|gb|AF167338.1|F167333S06[8050494]

8652: AF167337
Homo sapiens interleukin 1 receptor accessory protein (IL1RAP) gene, exon 5
gi|8050493|gb|AF167337.1|F167333S05[8050493]

8653: AF167336
Homo sapiens interleukin 1 receptor accessory protein (IL1RAP) gene, exon 4
gi|8050492|gb|AF167336.1|F167333S04[8050492]

8654: AF167335
Homo sapiens interleukin 1 receptor accessory protein (IL1RAP) gene, exon 3
gi|8050491|gb|AF167335.1|F167333S03[8050491]

8655: AF167334
Homo sapiens interleukin 1 receptor accessory protein (IL1RAP) gene, exon 2
gi|8050490|gb|AF167334.1|F167333S02[8050490]

8656: AF167333
Homo sapiens interleukin 1 receptor accessory protein (IL1RAP) gene, exon 1
gi|8050489|gb|AF167333.1|F167333S01[8050489]

8657: AH009309
Homo sapiens interleukin 1 receptor accessory protein (IL1RAP) gene, complete cds, alternatively spliced
gi|8050488|gb|AH009309.1|SEG_F167333S[8050488]

8658: AF167343
Homo sapiens soluble interleukin-1 receptor accessory protein (IL1RAP) mRNA, complete cds
gi|8050486|gb|AF167343.1|AF167343[8050486]

8659: AF213457
Homo sapiens triggering receptor expressed on myeloid cells 2 mRNA, complete cds
gi|7800156|gb|AF213457.1|AF213457[7800156]

8661: AF233281
Homo sapiens CC chemokine receptor (CCBP2) gene, complete cds
gi|7274391|gb|AF233281.1|AF233281[7274391]

8662: AF189259
Homo sapiens GABA-A receptor theta subunit (THETA) mRNA, complete cds
gi|7861735|gb|AF189259.1|AF189259[7861735]

8663: AF176832
Homo sapiens low density lipoprotein receptor related protein-deleted in tumor (LRPDIT) mRNA, complete cds
gi|7861732|gb|AF176832.1|AF176832[7861732]

8664: AH001455
Homo sapiens protooncogene protein (c-erb-2) gene, partial cds
gi|182164|gb|AH001455.1|SEG_HUMERB2[182164]

8665: M11767
Homo sapiens protooncogene protein (c-erb-2) gene, exon 7 and partial cds
gi|182163|gb|M11767.1|HUMERB27[182163]

8666: M11766
Homo sapiens protooncogene protein (c-erb-2) gene, exon 6
gi|182162|gb|M11766.1|HUMERB26[182162]

8667: M11765
Homo sapiens protooncogene protein (c-erb-2) gene, exon 5
gi|182161|gb|M11765.1|HUMERB25[182161]

8668: M11764
Homo sapiens protooncogene protein (c-erb-2) gene, exon 4
gi|182160|gb|M11764.1|HUMERB24[182160]

8669: M11763
Homo sapiens protooncogene protein (c-erb-2) gene, exon 3
gi|182159|gb|M11763.1|HUMERB23[182159]

8670: M11762
Homo sapiens protooncogene protein (c-erb-2) gene, exon 2
gi|182158|gb|M11762.1|HUMERB22[182158]

8671: M11761
Homo sapiens protooncogene protein (c-erb-2) gene, exon 1
gi|182157|gb|M11761.1|HUMERB21[182157]

8674: AC068948
Homo sapiens chromosome 19, cosmid R28371 (LLNL-R_244D7), complete sequence
gi|7798735|gb|AC068948.1|AC068948[7798735]

8675: AF060231
Homo sapiens herpesvirus entry protein C (HVEC) mRNA, complete cds
gi|3242792|gb|AF060231.1|AF060231[3242792]

8676: Z24459
H.sapiens MTCP1 gene, exons 2A to 7 (and joined mRNA)
gi|2252491|emb|Z24459.1|HSMTCP12A[2252491]

8677: AB006200
Homo sapiens gene for parathyroid hormone/parathyroid hormone-related protein
receptor, exon1, partial sequence
gi|7770088|dbj|AB006200.1|AB006200[7770088]

8693: AB023493
Homo sapiens mRNA for preproapelin, complete cds
gi|6009585|dbj|AB023493.1|AB023493[6009585]

8697: M55336
Homo sapiens oncogene tyrosine protein kinase receptor (trk2) mRNA, partial cds
gi|339913|gb|M55336.1|HUMTRK2[339913]

8701: AB028741
Homo sapiens mRNA for syntaxin 18, complete cds
gi|7707423|dbj|AB028741.1|AB028741[7707423]

8702: U27478
Homo sapiens angiotensin II type 2 receptor (AT2) gene, partial cds
gi|1143833|gb|U27478.1|HSU27478[1143833]

8707: M81774
Homo sapiens T-cell receptor alpha (TCRB) mRNA, partial cds
gi|186224|gb|M81774.1|HUMIGTCACA[186224]

8708: S70782
Homo sapiens alpha adrenergic receptor subtype alpha 1a mRNA, complete cds
gi|547219|gb|S70782.1|S70782[547219]

8709: S70057
Homo sapiens cholecystokinin B receptor mRNA, complete cds
gi|546748|gb|S70057.1|S70057[546748]

8711: S70123
Homo sapiens low density lipoprotein receptor mRNA, partial cds
gi|546107|gb|S70123.1|S70123[546107]

8712: S56143
Homo sapiens A1 adenosine receptor mRNA, complete cds
gi|298327|gb|S56143.1|S56143[298327]

8715: S57793
Homo sapiens luteinizing hormone receptor mRNA, complete cds
gi|236050|gb|S57793.1|S57793[236050]

8722: AF202640
Homo sapiens orphan G-protein coupled receptor (GPRC5B) mRNA, complete cds
gi|7682556|gb|AF202640.1|AF202640[7682556]

8723: AF211154
AF211154 Clontech HL1008b Homo sapiens cDNA, mRNA sequence
gi|7677996|gb|AF211154.1|AF211154[7677996]

8724: AF211153
AF211153 Clontech HL1008b Homo sapiens cDNA, mRNA sequence
gi|7677995|gb|AF211153.1|AF211153[7677995]

8729: AF145440
Homo sapiens CC chemokine receptor 9B (CCR9) mRNA, alternatively spliced, complete cds
gi|7673010|gb|AF145440.1|AF145440[7673010]

8730: AF145439
Homo sapiens CC chemokine receptor 9A (CCR9) mRNA, alternatively spliced, complete cds
gi|7673008|gb|AF145439.1|AF145439[7673008]

8731: AF129170
Homo sapiens apolipoprotein E receptor 2 gene, exon 6b and partial cds, alternatively spliced
gi|7672339|gb|AF129170.1|AF129169S2[7672339]

8732: AF129169
Homo sapiens apolipoprotein E receptor 2 gene, exon 6a and partial cds, alternatively spliced
gi|7672338|gb|AF129169.1|AF129169S1[7672338]

8733: AH009264
Homo sapiens apolipoprotein E receptor 2 and apolipoprotein E receptor 2 genes, partial cds
gi|7672337|gb|AH009264.1|SEG_AF129169S[7672337]

8812: AB039723
Homo sapiens FZD3 mRNA for WNT receptor frizzled-3, complete cds
gi|7670051|dbj|AB039723.1|AB039723[7670051]

8813: AL353940
Homo sapiens mRNA; cDNA DKFZp761P1010 (from clone DKFZp761P1010)
gi|7669978|emb|AL353940.1|HSM802647[7669978]

8814: AC067969
Homo sapiens chromosome 19, cosmid R26839 (LLNL-R_228D1), complete sequence
gi|7656699|gb|AC067969.1|AC067969[7656699]

8815: AF236081
Homo sapiens orphan G-protein coupled receptor GPR72 (GPR72) mRNA, complete cds
gi|7248881|gb|AF236081.1|AF236081[7248881]

8819: AC004416
Homo sapiens BAC clone CTB-13N12 from 7q31.2, complete sequence
gi|2979585|gb|AC004416.1|AC004416[2979585]

8820: AF056020
Homo sapiens chemokine receptor CCR5 (CCR5) gene, CCR5-delta32 allele, partial cds
gi|7648496|gb|AF056020.1|AF056020[7648496]

8821: AF056019
Homo sapiens mutant chemokine receptor CCR5 (CCR5) gene, CCR5-delta32 allele, partial cds
gi|7648494|gb|AF056019.1|AF056019[7648494]

8822: AF052244
Homo sapiens mutant chemokine receptor CCR5 (CCR5) gene, CCR5-delta32 allele, partial cds
gi|7648492|gb|AF052244.1|AF052244[7648492]

8824: AF068288
Homo sapiens HDCME31P mRNA, complete cds
gi|7643783|gb|AF068288.1|AF068288[7643783]

8825: AF186022
Homo sapiens B lymphocyte adapter protein BAM32 (BAM32) mRNA, complete cds
gi|6503077|gb|AF186022.1|AF186022[6503077]

8826: AB002168
Homo sapiens gene for vitamin D receptor, exon 9 and complete cds
gi|5736651|dbj|AB002168.1|AB00215S12[5736651]

8827: AB002167
Homo sapiens gene for vitamin D receptor, exon 8
gi|5736591|dbj|AB002167.1|AB00215S11[5736591]

8828: AB002166
Homo sapiens gene for vitamin D receptor, exon 7
gi|5736588|dbj|AB002166.1|AB00215S10[5736588]

8829: AB002165
Homo sapiens gene for vitamin D receptor, exon 6
gi|5736585|dbj|AB002165.1|AB00215S09[5736585]

8830: AB002164
Homo sapiens gene for vitamin D receptor, exon 5
gi|5736582|dbj|AB002164.1|AB00215S08[5736582]

8831: AB002163
Homo sapiens gene for vitamin D receptor, exon 4
gi|5736579|dbj|AB002163.1|AB00215S07[5736579]

8832: AB002162
Homo sapiens gene for vitamin D receptor, exon 3
gi|5736575|dbj|AB002162.1|AB00215S06[5736575]

8833: AB002161
Homo sapiens gene for vitamin D receptor, exon 2
gi|5736571|dbj|AB002161.1|AB00215S05[5736571]

8834: AB002160
Homo sapiens gene for vitamin D receptor, exon 1c, 5' non-coding region
gi|5736566|dbj|AB002160.1|AB00215S04[5736566]

8835: AB002159
Homo sapiens gene for vitamin D receptor, exon 1b, 5' non-coding region
gi|5736562|dbj|AB002159.1|AB00215S03[5736562]

8839: AB005647
Homo sapiens gene for atrial natriuretic peptide Btype receptor, exon 22 and complete cds
gi|5139788|dbj|AB005647.1|AB00562S23[5139788]

8840: AB005646
Homo sapiens gene for atrial natriuretic peptide Btype receptor, exon 21
gi|5139787|dbj|AB005646.1|AB00562S22[5139787]

8841: AB005645
Homo sapiens gene for atrial natriuretic peptide Btype receptor, exon 20
gi|5139786|dbj|AB005645.1|AB00562S21[5139786]

8842: AB005644
Homo sapiens gene for atrial natriuretic peptide Btype receptor, exon 19
gi|5139785|dbj|AB005644.1|AB00562S20[5139785]

8843: AB005643
Homo sapiens gene for atrial natriuretic peptide Btype receptor, exon 18
gi|5139784|dbj|AB005643.1|AB00562S19[5139784]

8844: AB005642
Homo sapiens gene for atrial natriuretic peptide Btype receptor, exon 17
gi|5139783|dbj|AB005642.1|AB00562S18[5139783]

8845: AB005641
Homo sapiens gene for atrial natriuretic peptide Btype receptor, exon 16
gi|5139782|dbj|AB005641.1|AB00562S17[5139782]

8846: AB005640
Homo sapiens gene for atrial natriuretic peptide Btype receptor, exon 15
gi|5139781|dbj|AB005640.1|AB00562S16[5139781]

8847: AB005639
Homo sapiens gene for atrial natriuretic peptide Btype receptor, exon 14
gi|5139780|dbj|AB005639.1|AB00562S15[5139780]

8848: AB005638
Homo sapiens gene for atrial natriuretic peptide Btype receptor, exon 13
gi|5139779|dbj|AB005638.1|AB00562S14[5139779]

8849: AB005637
Homo sapiens gene for atrial natriuretic peptide Btype receptor, exon 12
gi|5139778|dbj|AB005637.1|AB00562S13[5139778]

8850: AB005636
Homo sapiens gene for atrial natriuretic peptide Btype receptor, exon 11
gi|5139777|dbj|AB005636.1|AB00562S12[5139777]

8851: AB005635
Homo sapiens gene for atrial natriuretic peptide Btype receptor, exon 10
gi|5139776|dbj|AB005635.1|AB00562S11[5139776]

8852: AB005634
Homo sapiens gene for atrial natriuretic peptide Btype receptor, exon 9
gi|5139775|dbj|AB005634.1|AB00562S10[5139775]

8853: AB005633
Homo sapiens gene for atrial natriuretic peptide Btype receptor, exon 8
gi|5139774|dbj|AB005633.1|AB00562S09[5139774]

8854: AB005632
Homo sapiens gene for atrial natriuretic peptide Btype receptor, exon 7
gi|5139773|dbj|AB005632.1|AB00562S08[5139773]

8855: AB005631
Homo sapiens gene for atrial natriuretic peptide Btype receptor, exon 6
gi|5139772|dbj|AB005631.1|AB00562S07[5139772]

8856: AB005630
Homo sapiens gene for atrial natriuretic peptide Btype receptor, exon 5
gi|5139771|dbj|AB005630.1|AB00562S06[5139771]

8857: AB005629
Homo sapiens gene for atrial natriuretic peptide Btype receptor, exon 4
gi|5139770|dbj|AB005629.1|AB00562S05[5139770]

8858: AB005628
Homo sapiens gene for atrial natriuretic peptide Btype receptor, exon 3
gi|5139769|dbj|AB005628.1|AB00562S04[5139769]

8859: AB005627
Homo sapiens gene for atrial natriuretic peptide Btype receptor, exon 2
gi|5139768|dbj|AB005627.1|AB00562S03[5139768]

8860: AB005626
Homo sapiens gene for atrial natriuretic peptide Btype receptor, exon 1
gi|5139767|dbj|AB005626.1|AB00562S02[5139767]

8862: AF030335
Homo sapiens purinergic P2Y11 receptor (P2Y11) mRNA, complete cds
gi|2674119|gb|AF030335.1|AF030335[2674119]

8863: AF003522
Homo sapiens Delta mRNA, complete cds
gi|2197068|gb|AF003522.1|AF003522[2197068]

8864: AF003521
Homo sapiens Jagged 2 mRNA, complete cds
gi|2197066|gb|AF003521.1|AF003521[2197066]

8865: AF068292

Homo sapiens HDCMA39P mRNA, partial cds
gi|7634778|gb|AF068292.1|AF068292[7634778]

8868: AH007819
Homo sapiens 5-hydroxytryptamine 2B receptor (HTR2B) gene, complete cds
gi|5442455|gb|AH007819.2|SEG_HSHTR2B[5442455]

8869: AF156158
Homo sapiens 5-hydroxytryptamine 2B receptor (HTR2B) gene, exon 1
gi|5442454|gb|AF156158.2|HSHTR2B1[5442454]

8870: AF156160
Homo sapiens 5-hydroxytryptamine 2B receptor (HTR2B) gene, exon 3 and complete cds
gi|5070703|gb|AF156160.1|HSHTR2B3[5070703]

8871: AF156159
Homo sapiens 5-hydroxytryptamine 2B receptor (HTR2B) gene, exon 2
gi|5070702|gb|AF156159.1|HSHTR2B2[5070702]

8872: AB041713
Homo sapiens fp gene for prostaglandin F2alpha receptor, exon 1 and 2, partial cds
gi|7619988|dbj|AB041713.1|AB041713[7619988]

8873: AF041811
Homo sapiens ETS related protein-growth factor receptor tyrosine kinase fusion proteins (ETV6-NTRK3 fusion) mRNA, partial cds
gi|6274523|gb|AF041811.2|AF041811[6274523]

8874: AF172453
Homo sapiens opioid growth factor receptor mRNA, complete cds
gi|7595306|gb|AF172453.1|AF172453[7595306]

8875: AF172452
Homo sapiens opioid growth factor receptor mRNA, complete cds
gi|7595304|gb|AF172452.1|AF172452[7595304]

8876: AF172451

Homo sapiens opioid growth factor receptor mRNA, complete cds
gi|7595302|gb|AF172451.1|AF172451[7595302]

8877: AF172450

Homo sapiens opioid growth factor receptor mRNA, complete cds
gi|7595300|gb|AF172450.1|AF172450[7595300]

8878: AF172449

Homo sapiens clone 127 opioid growth factor receptor mRNA, complete cds
gi|7595298|gb|AF172449.1|AF172449[7595298]

8879: D49394

Homo sapiens mRNA for serotonin 5-HT3 receptor, complete cds
gi|681913|dbj|D49394.1|HUMS5HT3RA[681913]

8880: AB041395

Homo sapiens CHRM3 gene for muscarinic acetylcholine receptor m3, complete cds
gi|7592980|dbj|AB041395.1|AB041395[7592980]

8881: AB041391

Homo sapiens CHRM2 gene for muscarinic acetylcholine receptor m2, partial cds
gi|7592971|dbj|AB041391.1|AB041391[7592971]

8882: AB041384

Homo sapiens gene for histamine H2 receptor, complete cds
gi|7592957|dbj|AB041384.1|AB041384[7592957]

8883: AB041380

Homo sapiens gene for histamine H1 receptor, complete cds
gi|7592949|dbj|AB041380.1|AB041380[7592949]

8884: AB041373

Homo sapiens HTR1E gene for 5-hydroxytryptamine (serotonin) receptor 1E, partial cds
gi|7592934|dbj|AB041373.1|AB041373[7592934]

8885: AB041370
Homo sapiens HTR1B gene for 5-hydroxytryptamine (serotonin) receptor 1B, complete cds
gi|7592928|dbj|AB041370.1|AB041370[7592928]

8887: AB033598
Homo sapiens gene for melatonin 1b receptor, exon 2 and complete cds
gi|7209599|dbj|AB033598.1|AB033597S2[7209599]

8888: AB033597
Homo sapiens gene for melatonin 1b receptor, exon 1
gi|7209598|dbj|AB033597.1|AB033597S1[7209598]

8889: SEG_AB033597S
Homo sapiens gene for melatonin 1b receptor
gi|7209597|dbj||SEG_AB033597S[7209597]

8890: D85606
Homo sapiens gene for cholecystokinin type-A receptor, complete cds
gi|7008026|dbj|D85606.1|D85606[7008026]

8891: SEG_AB019480S
Homo sapiens NTRK1 gene for TRKA
gi|6492387|dbj||SEG_AB019480S[6492387]

8892: AB019485
Homo sapiens NTRK1 gene for TRKA, exon 8-14
gi|6492386|dbj|AB019485.2|AB019480S6[6492386]

8893: SEG_AB029932S
Homo sapiens hMel1a gene for melatonin 1a receptor
gi|6045084|dbj||SEG_AB029932S[6045084]

8894: AB029933
Homo sapiens hMel1a gene for melatonin 1a receptor, exon 2 and complete cds
gi|6045083|dbj|AB029933.1|AB029932S2[6045083]

8895: AB029932

Homo sapiens hMel1a gene for melatonin 1a receptor, exon 1
gi|6045082|dbj|AB029932.1|AB029932S1[6045082]

8896: AB026584

Homo sapiens gene for endothelial protein C receptor, complete cds
gi|5837963|dbj|AB026584.2|AB026584[5837963]

8897: AB017444

Homo sapiens gene for lectin-like oxidized LDL receptor, exon 6
gi|5821166|dbj|AB017444.1|AB017444[5821166]

8898: AB017443

Homo sapiens gene for lectin-like oxidized LDL receptor, exon 5
gi|5821165|dbj|AB017443.1|AB017443[5821165]

8899: AB017442

Homo sapiens gene for lectin-like oxidized LDL receptor, exon 4
gi|5821164|dbj|AB017442.1|AB017442[5821164]

8900: AB017441

Homo sapiens gene for lectin-like oxidized LDL receptor, exon 3
gi|5821163|dbj|AB017441.1|AB017441[5821163]

8901: AB017440

Homo sapiens gene for lectin-like oxidized LDL receptor, exon 2
gi|5821162|dbj|AB017440.1|AB017440[5821162]

8902: AB017439

Homo sapiens gene for lectin-like oxidized LDL receptor, exon 1
gi|5821161|dbj|AB017439.1|AB017439[5821161]

8903: AB019488

Homo sapiens NTRK1 gene for TRKA, exon 17 and complete cds
gi|3869111|dbj|AB019488.1|AB019480S9[3869111]

8904: AB019487
Homo sapiens NTRK1 gene for TRKA, exon 16
gi|3869110|dbj|AB019487.1|AB019480S8[3869110]

8905: AB019486
Homo sapiens NTRK1 gene for TRKA, exon 15
gi|3869109|dbj|AB019486.1|AB019480S7[3869109]

8906: AB019484
Homo sapiens NTRK1 gene for TRKA, exon 7
gi|3869107|dbj|AB019484.1|AB019480S5[3869107]

8907: AB019483
Homo sapiens NTRK1 gene for TRKA, exon 5 and 6
gi|3869106|dbj|AB019483.1|AB019480S4[3869106]

8908: AB019482
Homo sapiens NTRK1 gene for TRKA, exon 4
gi|3869105|dbj|AB019482.1|AB019480S3[3869105]

8909: AB019481
Homo sapiens NTRK1 gene for TRKA, exon 2,3
gi|3869104|dbj|AB019481.1|AB019480S2[3869104]

8910: AB019480
Homo sapiens NTRK1 gene for TRKA, exon 1
gi|3869103|dbj|AB019480.1|AB019480S1[3869103]

8911: SEG_AB01471S
Homo sapiens DR5 gene
gi|3721877|dbj||SEG_AB01471S[3721877]

8912: AB014718
Homo sapiens DR5 gene, exon 9 and complete cds
gi|3721876|dbj|AB014718.1|AB01471S9[3721876]

8913: AB014717
Homo sapiens DR5 gene, exon 8
gi|3721875|dbj|AB014717.1|AB01471S8[3721875]

8914: AB014716
Homo sapiens DR5 gene, exon 7
gi|3721874|dbj|AB014716.1|AB01471S7[3721874]

8915: AB014715
Homo sapiens DR5 gene, exon 6
gi|3721873|dbj|AB014715.1|AB01471S6[3721873]

8916: AB014714
Homo sapiens DR5 gene, exon 5
gi|3721872|dbj|AB014714.1|AB01471S5[3721872]

8917: AB014713
Homo sapiens DR5 gene, exon 4
gi|3721871|dbj|AB014713.1|AB01471S4[3721871]

8918: AB014712
Homo sapiens DR5 gene, exon 3
gi|3721870|dbj|AB014712.1|AB01471S3[3721870]

8919: AB014711
Homo sapiens DR5 gene, exon 2
gi|3721869|dbj|AB014711.1|AB01471S2[3721869]

8920: AB014710
Homo sapiens DR5 gene, exon 1, partial sequence
gi|3721868|dbj|AB014710.1|AB01471S1[3721868]

8921: SEG_AB01047S
Homo sapiens gene for natriuretic peptide A type receptor
gi|3297985|dbj||SEG_AB01047S[3297985]

8922: AB010491

Homo sapiens gene for natriuretic peptide A type receptor,exon 22 and complete cds
gi|3297984|dbj|AB010491.1|AB01047S22[3297984]

8923: AB010490
Homo sapiens gene for natriuretic peptide A type receptor, exon 21
gi|3297983|dbj|AB010490.1|AB01047S21[3297983]

8924: AB010489
Homo sapiens gene for natriuretic peptide A type receptor, exon 20
gi|3297982|dbj|AB010489.1|AB01047S20[3297982]

8925: AB010488
Homo sapiens gene for natriuretic peptide A type receptor, exon 19
gi|3297981|dbj|AB010488.1|AB01047S19[3297981]

8926: AB010487
Homo sapiens gene for natriuretic peptide A type receptor, exon 18
gi|3297980|dbj|AB010487.1|AB01047S18[3297980]

8927: AB010486
Homo sapiens gene for natriuretic peptide A type receptor, exon 17
gi|3297979|dbj|AB010486.1|AB01047S17[3297979]

8928: AB010485
Homo sapiens gene for natriuretic peptide A type receptor, exon 16
gi|3297978|dbj|AB010485.1|AB01047S16[3297978]

8929: AB010484
Homo sapiens gene for natriuretic peptide A type receptor, exon 15
gi|3297977|dbj|AB010484.1|AB01047S15[3297977]

8930: AB010483
Homo sapiens gene for natriuretic peptide A type receptor, exon 14
gi|3297976|dbj|AB010483.1|AB01047S14[3297976]

8931: AB010482

Homo sapiens gene for natriuretic peptide A type receptor, exon 13
gi|3297975|dbj|AB010482.1|AB01047S13[3297975]

8932: AB010481
Homo sapiens gene for natriuretic peptide A type receptor, exon 12
gi|3297974|dbj|AB010481.1|AB01047S12[3297974]

8933: AB010480
Homo sapiens gene for natriuretic peptide A type receptor, exon 11
gi|3297973|dbj|AB010480.1|AB01047S11[3297973]

8934: AB010479
Homo sapiens gene for natriuretic peptide A type receptor, exon 10
gi|3297972|dbj|AB010479.1|AB01047S10[3297972]

8935: AB010478
Homo sapiens gene for natriuretic peptide A type receptor, exon 9
gi|3297971|dbj|AB010478.1|AB01047S09[3297971]

8936: AB010477
Homo sapiens gene for natriuretic peptide A type receptor, exon 8
gi|3297970|dbj|AB010477.1|AB01047S08[3297970]

8937: AB010476
Homo sapiens gene for natriuretic peptide A type receptor, exon 7
gi|3297969|dbj|AB010476.1|AB01047S07[3297969]

8938: AB010475
Homo sapiens gene for natriuretic peptide A type receptor, exon 6
gi|3297968|dbj|AB010475.1|AB01047S06[3297968]

8939: AB010474
Homo sapiens gene for natriuretic peptide A type receptor, exon 5
gi|3297967|dbj|AB010474.1|AB01047S05[3297967]

8940: AB010473
Homo sapiens gene for natriuretic peptide A type receptor, exon 4 gi|3297966|dbj|AB010473.1|AB01047S04[3297966]

8941: AB010472
Homo sapiens gene for natriuretic peptide A type receptor, exon 3
gi|3297965|dbj|AB010472.1|AB01047S03[3297965]

8942: AB010471
Homo sapiens gene for natriuretic peptide A type receptor, exon 2
gi|3297964|dbj|AB010471.1|AB01047S02[3297964]

8943: AB010470
Homo sapiens gene for natriuretic peptide A type receptor, exon 1, partial sequence
gi|3297963|dbj|AB010470.1|AB01047S01[3297963]

8944: AB008681
Homo sapiens gene for activin receptor type IIB, complete cds
gi|2760152|dbj|AB008681.1|AB008681[2760152]

8945: SEG_AB005521S
Homo sapiens ppar gamma gene for peroxisome proliferator activated-receptor gamma
gi|2605496|dbj||SEG_AB005521S[2605496]

8946: AB005526
Homo sapiens ppar gamma gene for peroxisome proliferator activated-receptor gamma, eoxn 6 and complete cds
gi|2605495|dbj|AB005526.1|AB005521S6[2605495]

8947: AB005525
Homo sapiens ppar gamma gene for peroxisome proliferator activated-receptor gamma, exon 5
gi|2605494|dbj|AB005525.1|AB005521S5[2605494]

8948: AB005524
Homo sapiens ppar gamma gene for peroxisome proliferator activated-receptor gamma, exon 4
gi|2605493|dbj|AB005524.1|AB005521S4[2605493]

8949: AB005523
Homo sapiens ppar gamma gene for peroxisome proliferator activated-receptor gamma, exon 3
gi|2605492|dbj|AB005523.1|AB005521S3[2605492]

8950: AB005522
Homo sapiens ppar gamma gene for peroxisome proliferator activated-receptor gamma, exon 2
gi|2605491|dbj|AB005522.1|AB005521S2[2605491]

8951: AB005521
Homo sapiens ppar gamma gene for peroxisome proliferator activated-receptor gamma, exon 1
gi|2605490|dbj|AB005521.1|AB005521S1[2605490]

8954: AB002059
Homo sapiens DNA for Human P2XM, complete cds
gi|2350848|dbj|AB002059.1|AB002059[2350848]

8955: SEG_D86389S
Homo sapiens DNA for apoER2
gi|2344801|dbj||SEG_D86389S[2344801]

8956: D86407
Homo sapiens DNA for apoER2, complete cds, and exon 19
gi|2344800|dbj|D86407.1|D86389S19[2344800]

8957: D86406
Homo sapiens DNA for apoER2, exon 18
gi|2344799|dbj|D86406.1|D86389S18[2344799]

8958: D86405
Homo sapiens DNA for apoER2, exon 17
gi|2344798|dbj|D86405.1|D86389S17[2344798]

8959: D86404

Homo sapiens DNA for apoER2, exon 16
gi|2344797|dbj|D86404.1|D86389S16[2344797]

8960: D86403
Homo sapiens DNA for apoER2, exon 15
gi|2344796|dbj|D86403.1|D86389S15[2344796]

8961: D86402
Homo sapiens DNA for apoER2, exon 14
gi|2344795|dbj|D86402.1|D86389S14[2344795]

8962: D86401
Homo sapiens DNA for apoER2, exon 13
gi|2344794|dbj|D86401.1|D86389S13[2344794]

8963: D86400
Homo sapiens DNA apoER2, exon 12
gi|2344793|dbj|D86400.1|D86389S12[2344793]

8964: D86399
Homo sapiens DNA for apoER2, exon 11
gi|2344792|dbj|D86399.1|D86389S11[2344792]

8965: D86398
Homo sapiens DNA for apoER2, exon 10
gi|2344791|dbj|D86398.1|D86389S10[2344791]

8966: D86397
Homo sapiens DNA for apoER2, exon 9
gi|2344790|dbj|D86397.1|D86389S09[2344790]

8967: D86396
Homo sapiens DNA for apoER2, exon 8
gi|2344789|dbj|D86396.1|D86389S08[2344789]

8968: D86395
Homo sapiens DNA for apoER2, exon 7 gi|2344788|dbj|D86395.1|D86389S07[2344788]

8969: D86394
Homo sapiens DNA for apoER2, exon 6
gi|2344787|dbj|D86394.1|D86389S06[2344787]

8970: D86393
Homo sapiens DNA for apoER2, exon 5
gi|2344786|dbj|D86393.1|D86389S05[2344786]

8971: D86392
Homo sapiens DNA for apoER2, exon 4
gi|2344785|dbj|D86392.1|D86389S04[2344785]

8972: D86391
Homo sapiens DNA for apoER2, exon 3
gi|2344784|dbj|D86391.1|D86389S03[2344784]

8973: D86390
Homo sapiens DNA for apoER2, exon 2
gi|2344783|dbj|D86390.1|D86389S02[2344783]

8974: D86389
Homo sapiens DNA for apoER2, exon 1
gi|2344782|dbj|D86389.1|D86389S01[2344782]

8975: D86096
Human DNA for prostaglandin EP3 receptor subtype, complete cds
gi|2114186|dbj|D86096.1|D86087S10[2114186]

8976: D86095
Human DNA for prostaglandin E receptor EP3 subtype, exon 9
gi|2114185|dbj|D86095.1|D86087S09[2114185]

8977: D86094
Human DNA for prostaglandin E receptor EP3 subtype, exon 8
gi|2114184|dbj|D86094.1|D86087S08[2114184]

8978: D86093
Human DNA for prostaglandin E receptor EP3 subtype, exon 7
gi|2114183|dbj|D86093.1|D86087S07[2114183]

8979: D86092
Human DNA for prostaglandin E receptor EP3 subtype, exon 6
gi|2114182|dbj|D86092.1|D86087S06[2114182]

8980: D86091
Human DNA for prostaglandin E receptor EP3 subtype, exon 5
gi|2114181|dbj|D86091.1|D86087S05[2114181]

8981: D86090
Human DNA for prostaglandin E receptor EP3 subtype, exon 4
gi|2114180|dbj|D86090.1|D86087S04[2114180]

8982: D86089
Human DNA for prostaglandin E receptor EP3 subtype, exon 3
gi|2114179|dbj|D86089.1|D86087S03[2114179]

8983: D86088
Human DNA for prostaglandin E receptor EP3 subtype, exon 2
gi|2114178|dbj|D86088.1|D86087S02[2114178]

8984: D86087
Human DNA for prostaglandin E receptor EP3 subtype, exon 1
gi|2114177|dbj|D86087.1|D86087S01[2114177]

8985: SEG_D49555S
Homo sapiens DNA for gastric inhibitory polypeptide receptor
gi|1805368|dbj||SEG_D49555S[1805368]

8986: D85376
Human DNA for thyrotropin-releasing hormone receptor, exon 3 and copmplete cds
gi|1616933|dbj|D85376.1|D85375S2[1616933]

8987: D85375
Human DNA for thyrotropin-releasing hormon receptor, exon 1, 2
gi|1616932|dbj|D85375.1|D85375S1[1616932]

8988: D49559
Human DNA for gastric inhibitory polypeptide receptor, exon 13 and 14, complete cds
gi|1088442|dbj|D49559.1|D49555S5[1088442]

8989: D49558
Human DNA for gastric inhibitory polypeptide receptor, exon 5, 6, 7, 8, 9, 10, 11 and 12
gi|1088441|dbj|D49558.1|D49555S4[1088441]

8990: D49557
Human DNA for gastric inhibitory polypeptide receptor, exon 3 and 4
gi|1088440|dbj|D49557.1|D49555S3[1088440]

8991: D49556
Homo sapiens DNA for gastric inhibitory polypeptide receptor, exon 2
gi|1088439|dbj|D49556.1|D49555S2[1088439]

8992: D49555
Homo sapiens DNA for gastric inhibitory polypeptide receptor, exon 1
gi|1088438|dbj|D49555.1|D49555S1[1088438]

8993: D64016
Human gene for vascular endothelial growth factor receptor, promoter and exon 1
gi|1088437|dbj|D64016.1|HUMES[1088437]

8994: D38128
Homo sapiens IP gene for prostacyclin receptor, exon 3
gi|1019364|dbj|D38128.1|HUMIP2[1019364]

8995: D38127
Human IP gene for prostacyclin receptor, exon 1 and exon 2
gi|1019362|dbj|D38127.1|HUMIP1[1019362]

8996: D37965
Human mRNA for PDGF receptor beta-like tumor suppressor (PRLTS), complete cds
gi|807818|dbj|D37965.1|HUMPRLTS[807818]

8997: D50017
Human DNA for alpha-platelet-derived growth factor receptor, exon 23
gi|767797|dbj|D50017.1|D50001S17[767797]

8998: D50016
Human DNA for alpha-platelet-derived growth factor receptor, exon 22
gi|767796|dbj|D50016.1|D50001S16[767796]

8999: D50015
Human DNA for alpha-platelet-derived growth factor receptor, exon 20 and 21
gi|767795|dbj|D50015.1|D50001S15[767795]

9000: D50014
Human DNA for alpha-platelet-derived growth factor receptor, exon 19
gi|767794|dbj|D50014.1|D50001S14[767794]

9001: D50013
Human DNA for alpha-platelet-derived growth factor receptor, exon 18
gi|767793|dbj|D50013.1|D50001S13[767793]

9002: D50012
Human DNA for alpha-platelet-derived growth factor receptor, exon 17
gi|767792|dbj|D50012.1|D50001S12[767792]

9003: D50011
Human DNA for alpha-platelet-derived growth factor receptor, exon 16
gi|767791|dbj|D50011.1|D50001S11[767791]

9004: D50010
Human DNA for alpha-platelet-derived growth factor receptor, exon 15
gi|767790|dbj|D50010.1|D50001S10[767790]

9005: D50009

Human DNA for alpha-platelet-derived growth factor receptor, exon 14
gi|767789|dbj|D50009.1|D50001S09[767789]

9006: D50008

Human DNA for alpha-platelet-derived growth factor receptor, exon 13
gi|767788|dbj|D50008.1|D50001S08[767788]

9007: D50007

Human DNA for alpha-platelet-derived growth factor receptor, exon 11 and 12
gi|767787|dbj|D50007.1|D50001S07[767787]

9008: D50006

Human DNA for alpha-platelet-derived growth factor receptor, exon 6-10
gi|767786|dbj|D50006.1|D50001S06[767786]

9009: D50005

Human DNA for alpha-platelet-derived growth factor receptor, exon 5
gi|767785|dbj|D50005.1|D50001S05[767785]

9010: D50004

Human DNA for alpha-platelet-derived growth factor receptor, exon 4
gi|767784|dbj|D50004.1|D50001S04[767784]

9011: D50003

Human DNA for alpha-platelet-derived growth factor receptor, exon 3
gi|767783|dbj|D50003.1|D50001S03[767783]

9012: D50002

Human DNA for alpha-platelet-derived growth factor receptor, exon 2
gi|767781|dbj|D50002.1|D50001S02[767781]

9013: D50001

Human DNA for alpha-platelet-derived growth factor receptor, exon 1
gi|767780|dbj|D50001.1|D50001S01[767780]

9014: D31793
Human CD40 ligand (CD40L) gene, 5' flanking region and exon 1
gi|662386|dbj|D31793.1|HUMCD40L1[662386]

9015: D28768
Homo sapiens leukocyte DNA for Ah receptor, exon 1
gi|567941|dbj|D28768.1|HUMAHRP[567941]

9016: D28769
Human HOX12 and RAGE genes, complete cds
gi|561657|dbj|D28769.1|HUMHOXRAGE[561657]

9017: D31708
Human DNA for Ah-receptor, exon 1
gi|538228|dbj|D31708.1|HUMAHR[538228]

9019: D26535
Human gene for dihydrolipoamide succinyltransferase, complete cds (exon 1-15)
gi|537349|dbj|D26535.1|HUMDS[537349]

9020: SEG_HUMTA2R
Homo sapiens gene for thromboxane A2 receptor
gi|488600|dbj||SEG_HUMTA2R[488600]

9021: D15056
Homo sapiens gene for thromboxane A2 receptor, exon 3
gi|441173|dbj|D15056.1|HUMTA2R4[441173]

9022: D15055
Homo sapiens gene for thromboxane A2 receptor, exon 2
gi|441172|dbj|D15055.1|HUMTA2R3[441172]

9023: D15054
Homo sapiens gene for thromboxane A2 receptor, exon 1b (promoter region II)
gi|441171|dbj|D15054.1|HUMTA2R2[441171]

9024: D15053

Homo sapiens gene for thromboxane A2 receptor, exon 1 (promoter region I)
gi|441170|dbj|D15053.1|HUMTA2R1[441170]

9025: D21219
Human CCKBR gene for cholecystokinin-B receptor/gastrin receptor, exon 2-5, partial cds
gi|416225|dbj|D21219.1|HUMCCKBR2[416225]

9026: D21218
Human CCKBR gene for cholecystokinin-B receptor/gastrin receptor, exon 1
gi|416224|dbj|D21218.1|HUMCCKBR1[416224]

9027: D16532
Human gene for very low density lipoprotein receptor, exon 19
gi|407219|dbj|D16532.1|HUMVLDLR19[407219]

9028: D16531
Human gene for very low density lipoprotein receptor, exon 18
gi|407218|dbj|D16531.1|HUMVLDLR18[407218]

9029: D16530
Huma gene for very low density lipoprotein receptor, exon 17
gi|407217|dbj|D16530.1|HUMVLDLR17[407217]

9030: D16529
Human gene for very low density lipoprotein receptor, exon 16
gi|407216|dbj|D16529.1|HUMVLDLR16[407216]

9031: D16528
Human gene for very low density lipoprotein receptor, exon 15
gi|407215|dbj|D16528.1|HUMVLDLR15[407215]

9032: D16527
Human gene for very low density lipoprotein receptor, exon 14
gi|407214|dbj|D16527.1|HUMVLDLR14[407214]

9033: D16526

Human gene for very low density lipoprotein receptor, exon 13
gi|407213|dbj|D16526.1|HUMVLDLR13[407213]

9034: D16525
Human gene for very low density lipoprotein receptor, exon 12
gi|407212|dbj|D16525.1|HUMVLDLR12[407212]

9035: D16524
Human gene for very low density lipoprotein receptor, exon 11
gi|407211|dbj|D16524.1|HUMVLDLR11[407211]

9036: D16523
Human gene for very low density lipoprotein receptor, exon 10
gi|407210|dbj|D16523.1|HUMVLDLR10[407210]

9037: D16522
Human gene for very low density lipoprotein receptor, exon 9
gi|407209|dbj|D16522.1|HUMVLDLR09[407209]

9038: D16520
Human gene for very low density lipoprotein receptor, exon 8
gi|407208|dbj|D16520.1|HUMVLDLR08[407208]

9039: D16518
Human gene for very low density lipoprotein receptor, exon 7
gi|407207|dbj|D16518.1|HUMVLDLR07[407207]

9040: D16516
Human gene for very low density lipoprotein receptor, exon 6
gi|407206|dbj|D16516.1|HUMVLDLR06[407206]

9041: D16514
Human gene for very low density lipoprotein receptor, exon 5
gi|407205|dbj|D16514.1|HUMVLDLR05[407205]

9042: D16512
Human gene for very low density lipoprotein receptor, exon 4 gi|407204|dbj|D16512.1|HUMVLDLR04[407204]

9043: D16510
Human gene for very low density lipoprotein receptor, exon 3
gi|407203|dbj|D16510.1|HUMVLDLR03[407203]

9044: D16508
Human gene for very low density lipoprotein receptor, exon 2
gi|407202|dbj|D16508.1|HUMVLDLR02[407202]

9045: D16495
Human gene for very low density lipoprotein receptor, 5'flanking and exon 1
gi|407201|dbj|D16495.1|HUMVLDLR01[407201]

9046: D13168
Human gene for endothelin-B receptor (hET-BR), exon 7
gi|285924|dbj|D13168.1|HUMHETBR7[285924]

9047: D13167
Human gene for endothelin-B receptor (hET-BR), exon 6
gi|285923|dbj|D13167.1|HUMHETBR6[285923]

9048: D13166
Human gene for endothelin-B receptor (hET-BR), exon 5
gi|285922|dbj|D13166.1|HUMHETBR5[285922]

9049: D13165
Human gene for endothelin-B receptor (hET-BR), exon 4
gi|285921|dbj|D13165.1|HUMHETBR4[285921]

9050: D13164
Human gene for endothelin-B receptor (hET-BR), exon 3
gi|285920|dbj|D13164.1|HUMHETBR3[285920]

9051: D13163
Human gene for endothelin-B receptor (hET-BR), exon 2
gi|285919|dbj|D13163.1|HUMHETBR2[285919]

9052: D13162
Human gene for endothelin-B receptor (hET-BR), exon 1
gi|285918|dbj|D13162.1|HUMHETBR1[285918]

9053: D10604
Human midkine gene, complete cds
gi|219928|dbj|D10604.1|HUMMK[219928]

9054: D11151
Human DNA for endothelin-A receptor, exon 8 and 3' flanking region
gi|219628|dbj|D11151.1|HUMETAR8[219628]

9055: D11150
Human DNA for endothelin-A receptor, exon 7
gi|219627|dbj|D11150.1|HUMETAR7[219627]

9056: D11149
Human DNA for endothelin-A receptor, exon 6
gi|219626|dbj|D11149.1|HUMETAR6[219626]

9057: D11148
Human DNA for endothelin-A receptor, exon 5
gi|219625|dbj|D11148.1|HUMETAR5[219625]

9058: D11147
Human DNA for endothelin-A receptor, exon 4
gi|219624|dbj|D11147.1|HUMETAR4[219624]

9059: D11146
Human DNA for endothelin-A receptor, exon 3
gi|219623|dbj|D11146.1|HUMETAR3[219623]

9060: D11145
Human DNA for endothelin-A receptor, exon 2
gi|219622|dbj|D11145.1|HUMETAR2[219622]

9061: D11144
Human DNA for endothelin-A receptor, 5' flanking region and exon 1
gi|219621|dbj|D11144.1|HUMETAR1[219621]

9063: AF215981
Homo sapiens CC chemokine receptor 10 (CCR10) mRNA, complete cds
gi|7546844|gb|AF215981.1|AF215981[7546844]

9066: AF065440
Homo sapiens low density lipoprotein receptor-related protein II (LRP2) gene, exon 1 and partial cds
gi|7534311|gb|AF065440.2|AF065440[7534311]

9068: AF228458
Homo sapiens GABAA receptor gamma 3 subunit (GABRG3) gene, exon 10 and partial cds
gi|7530451|gb|AF228458.1|AF228450S9[7530451]

9069: AF228457
Homo sapiens GABAA receptor gamma 3 subunit (GABRG3) gene, exon 9
gi|7530450|gb|AF228457.1|AF228450S8[7530450]

9070: AF228456
Homo sapiens GABAA receptor gamma 3 subunit (GABRG3) gene, exon 8
gi|7530449|gb|AF228456.1|AF228450S7[7530449]

9071: AF228455
Homo sapiens GABAA receptor gamma 3 subunit (GABRG3) gene, exon 7
gi|7530448|gb|AF228455.1|AF228450S6[7530448]

9072: AF228454
Homo sapiens GABAA receptor gamma 3 subunit (GABRG3) gene, exon 6
gi|7530447|gb|AF228454.1|AF228450S5[7530447]

9073: AF228453
Homo sapiens GABAA receptor gamma 3 subunit (GABRG3) gene, exon 5
gi|7530446|gb|AF228453.1|AF228450S4[7530446]

9074: AF228452
Homo sapiens GABAA receptor gamma 3 subunit (GABRG3) gene, exon 4
gi|7530445|gb|AF228452.1|AF228450S3[7530445]

9075: AF228451
Homo sapiens GABAA receptor gamma 3 subunit (GABRG3) gene, exon 3
gi|7530444|gb|AF228451.1|AF228450S2[7530444]

9076: AF228450
Homo sapiens GABAA receptor gamma 3 subunit (GABRG3) gene, exon 2
gi|7530443|gb|AF228450.1|AF228450S1[7530443]

9077: AH009226
Homo sapiens GABAA receptor gamma 3 subunit (GABRG3) gene, partial cds
gi|7530442|gb|AH009226.1|SEG_AF228450S[7530442]

9078: AJ272208
Homo sapiens mRNA for IL-1 receptor accessory protein-like 2 (IL1RAPL-2 gene)
gi|7530096|emb|AJ272208.1|HSA272208[7530096]

9081: AF056085
Homo sapiens GABA-B receptor mRNA, complete cds
gi|3719225|gb|AF056085.1|AF056085[3719225]

9083: AF161081
Homo sapiens activating receptor PILRbeta mRNA, complete cds
gi|5817856|gb|AF161081.1|AF161081[5817856]

9084: AF161080
Homo sapiens inhibitory receptor PILRalpha mRNA, complete cds
gi|5817854|gb|AF161080.1|AF161080[5817854]

9085: AF228449
Homo sapiens gamma-aminobutyric acid receptor alpha 5 subunit (GABRA5) gene, exon 10 and partial cds gi|7417243|gb|AF228449.1|AF228447S3[7417243]

9086: AF228448
Homo sapiens gamma-aminobutyric acid receptor alpha 5 subunit (GABRA5) gene, exon 8 and partial cds
gi|7417242|gb|AF228448.1|AF228447S2[7417242]

9087: AF228447
Homo sapiens gamma-aminobutyric acid receptor alpha 5 subunit (GABRA5) gene, exons 5, 6, and partial cds
gi|7417241|gb|AF228447.1|AF228447S1[7417241]

9088: AH009221
Homo sapiens gamma-aminobutyric acid receptor alpha 5 subunit (GABRA5), gamma-aminobutyric acid receptor alpha 5 subunit (GABRA5), and gamma-aminobutyric acid receptor alpha 5 subunit (GABRA5) genes, partial cds
gi|7417240|gb|AH009221.1|SEG_AF228447S[7417240]

9089: AF198052
Homo sapiens EVH1 domain binding protein mRNA, complete cds
gi|7416992|gb|AF198052.1|AF198052[7416992]

9091: AF159278
Homo sapiens glutamate receptor subunit 3 (GRIA3) gene, exon 17
gi|7406946|gb|AF159278.1|F159262S17[7406946]

9092: AF159277
Homo sapiens glutamate receptor subunit 3 (GRIA3) gene, exon 16 and complete cds, alternatively spliced
gi|7406945|gb|AF159277.1|F159262S16[7406945]

9093: AF159276
Homo sapiens glutamate receptor subunit 3 (GRIA3) gene, exon 15
gi|7406944|gb|AF159276.1|F159262S15[7406944]

9094: AF159275
Homo sapiens glutamate receptor subunit 3 (GRIA3) gene, exon 14
gi|7406943|gb|AF159275.1|F159262S14[7406943]

9095: AF159274
Homo sapiens glutamate receptor subunit 3 (GRIA3) gene, exon 13
gi|7406942|gb|AF159274.1|F159262S13[7406942]

9096: AF159273
Homo sapiens glutamate receptor subunit 3 (GRIA3) gene, exon 12
gi|7406941|gb|AF159273.1|F159262S12[7406941]

9097: AF159272
Homo sapiens glutamate receptor subunit 3 (GRIA3) gene, exon 11
gi|7406940|gb|AF159272.1|F159262S11[7406940]

9098: AF159271
Homo sapiens glutamate receptor subunit 3 (GRIA3) gene, exon 10
gi|7406939|gb|AF159271.1|F159262S10[7406939]

9099: AF159270
Homo sapiens glutamate receptor subunit 3 (GRIA3) gene, exon 9
gi|7406938|gb|AF159270.1|F159262S09[7406938]

9100: AF159269
Homo sapiens glutamate receptor subunit 3 (GRIA3) gene, exon 8
gi|7406937|gb|AF159269.1|F159262S08[7406937]

9101: AF159268
Homo sapiens glutamate receptor subunit 3 (GRIA3) gene, exon 7
gi|7406936|gb|AF159268.1|F159262S07[7406936]

9102: AF159267
Homo sapiens glutamate receptor subunit 3 (GRIA3) gene, exon 6
gi|7406935|gb|AF159267.1|F159262S06[7406935]

9103: AF159266
Homo sapiens glutamate receptor subunit 3 (GRIA3) gene, exon 5
gi|7406934|gb|AF159266.1|F159262S05[7406934]

9104: AF159265
Homo sapiens glutamate receptor subunit 3 (GRIA3) gene, exon 4
gi|7406933|gb|AF159265.1|F159262S04[7406933]

9105: AF159264
Homo sapiens glutamate receptor subunit 3 (GRIA3) gene, exon 3
gi|7406932|gb|AF159264.1|F159262S03[7406932]

9106: AF159263
Homo sapiens glutamate receptor subunit 3 (GRIA3) gene, exon 2
gi|7406931|gb|AF159263.1|F159262S02[7406931]

9107: AF159262
Homo sapiens glutamate receptor subunit 3 (GRIA3) gene, exon 1
gi|7406930|gb|AF159262.1|F159262S01[7406930]

9108: AH009217
Homo sapiens glutamate receptor subunit 3 (GRIA3) gene, complete cds, alternatively spliced
gi|7406929|gb|AH009217.1|SEG_F159262S[7406929]

9109: AF176812
Homo sapiens dopamine receptor D2longer mRNA, complete cds
gi|7381415|gb|AF176812.1|AF176812[7381415]

9112: AF193507
Homo sapiens chemokine receptor (CCR11) gene, complete cds
gi|7363341|gb|AF193507.1|AF193507[7363341]

9113: AF105239
Homo sapiens killer cell immunoglobulin receptor variant (KIR3DL) gene, exon 9 and complete cds
gi|7363319|gb|AF105239.1|KIR3DL9[7363319]

9114: AF105238
Homo sapiens killer cell immunoglobulin receptor variant (KIR3DL) gene, exon 8
gi|7363318|gb|AF105238.1|KIR3DL8[7363318]

9115: AF105237
Homo sapiens killer cell immunoglobulin receptor variant (KIR3DL) gene, exon 7
gi|7363317|gb|AF105237.1|KIR3DL7[7363317]

9116: AF105236
Homo sapiens killer cell immunoglobulin receptor variant (KIR3DL) gene, exon 6
gi|7363316|gb|AF105236.1|KIR3DL6[7363316]

9117: AF105235
Homo sapiens killer cell immunoglobulin receptor variant (KIR3DL) gene, exon 5
gi|7363315|gb|AF105235.1|KIR3DL5[7363315]

9118: AF105234
Homo sapiens killer cell immunoglobulin receptor variant (KIR3DL) gene, exon 4
gi|7363314|gb|AF105234.1|KIR3DL4[7363314]

9119: AF105233
Homo sapiens killer cell immunoglobulin receptor variant (KIR3DL) gene, exon 3
gi|7363313|gb|AF105233.1|KIR3DL3[7363313]

9120: AF105232
Homo sapiens killer cell immunoglobulin receptor variant (KIR3DL) gene, exon 2
gi|7363312|gb|AF105232.1|KIR3DL2[7363312]

9121: AF105231
Homo sapiens killer cell immunoglobulin receptor variant (KIR3DL) gene, exon 1
gi|7363311|gb|AF105231.1|KIR3DL1[7363311]

9122: AH009212
Homo sapiens killer cell immunoglobulin receptor variant (KIR3DL) gene, complete cds
gi|7363310|gb|AH009212.1|SEG_KIR3DL[7363310]

9123: AF104856
Homo sapiens killer cell immunoglobulin receptor variant (KIR3DL1) gene, exon 9 and complete cds gi|7363308|gb|AF104856.1|HSKCIRV9[7363308]

9124: AF104855
Homo sapiens killer cell immunoglobulin receptor variant (KIR3DL1) gene, exon 8
gi|7363307|gb|AF104855.1|HSKCIRV8[7363307]

9125: AF104854
Homo sapiens killer cell immunoglobulin receptor variant (KIR3DL1) gene, exon 7
gi|7363306|gb|AF104854.1|HSKCIRV7[7363306]

9126: AF104853
Homo sapiens killer cell immunoglobulin receptor variant (KIR3DL1) gene, exon 6
gi|7363305|gb|AF104853.1|HSKCIRV6[7363305]

9127: AF104852
Homo sapiens killer cell immunoglobulin receptor variant (KIR3DL1) gene, exon 5
gi|7363304|gb|AF104852.1|HSKCIRV5[7363304]

9128: AF104851
Homo sapiens killer cell immunoglobulin receptor variant (KIR3DL1) gene, exon 4
gi|7363303|gb|AF104851.1|HSKCIRV4[7363303]

9129: AF104850
Homo sapiens killer cell immunoglobulin receptor variant (KIR3DL1) gene, exon 3
gi|7363302|gb|AF104850.1|HSKCIRV3[7363302]

9130: AF104849
Homo sapiens killer cell immunoglobulin receptor variant (KIR3DL1) gene, exon 2
gi|7363301|gb|AF104849.1|HSKCIRV2[7363301]

9131: AF104848
Homo sapiens killer cell immunoglobulin receptor variant (KIR3DL1) gene, exon 1
gi|7363300|gb|AF104848.1|HSKCIRV1[7363300]

9132: AH009211
Homo sapiens killer cell immunoglobulin receptor variant (KIR3DL1) gene, complete cds gi|7363299|gb|AH009211.1|SEG_HSKCIRV[7363299]

9136: AF130742
AF130742 Homo sapiens LNCaP prostate cancer Homo sapiens cDNA, mRNA sequence
gi|7330628|gb|AF130742.1|AF130742[7330628]

9137: AF130741
AF130741 Homo sapiens LNCaP prostate cancer Homo sapiens cDNA, mRNA sequence
gi|7330627|gb|AF130741.1|AF130741[7330627]

9138: AF130740
AF130740 Homo sapiens LNCaP prostate cancer Homo sapiens cDNA, mRNA sequence
gi|7330626|gb|AF130740.1|AF130740[7330626]

9139: AF130739
AF130739 Homo sapiens LNCaP prostate cancer Homo sapiens cDNA, mRNA sequence
gi|7330625|gb|AF130739.1|AF130739[7330625]

9140: AF130738
AF130738 Homo sapiens LNCaP prostate cancer Homo sapiens cDNA, mRNA sequence
gi|7330624|gb|AF130738.1|AF130738[7330624]

9141: AF130737
AF130737 Homo sapiens LNCaP prostate cancer Homo sapiens cDNA, mRNA sequence
gi|7330623|gb|AF130737.1|AF130737[7330623]

9142: AF130743
AF130743 Homo sapiens LNCaP prostate cancer Homo sapiens cDNA, mRNA sequence
gi|7330622|gb|AF130743.1|AF130743[7330622]

9143: AB032593
Homo sapiens mRNA for PXR2b, complete cds
gi|7328930|dbj|AB032593.1|AB032593[7328930]

9144: AB032592
Homo sapiens mRNA for PXR2a, complete cds
gi|7328928|dbj|AB032592.1|AB032592[7328928]

9145: AF110640
Homo sapiens orphan seven-transmembrane receptor (VSHK1) mRNA, complete cds
gi|7328551|gb|AF110640.1|AF110640[7328551]

9147: AF181286
Homo sapiens mutant dystrophin mRNA, partial cds
gi|7321332|gb|AF181286.1|AF181286[7321332]

9148: AF181285
Homo sapiens X-linked interleukin-1 receptor accessory protein-like 2 (IL1RAPL2) mRNA, partial cds
gi|7321330|gb|AF181285.1|AF181285[7321330]

9149: AF181284
Homo sapiens X-linked interleukin-1 receptor accessory protein-like 1 (IL1RAPL1) mRNA, complete cds
gi|7321328|gb|AF181284.1|AF181284[7321328]

9150: G64286
34 Human Homo sapiens STS cDNA, sequence tagged site
gi|7274484|gb|G64286.1|G64286[7274484]

9151: AF145712
Homo sapiens soluble neuropilin-1 mRNA, complete cds
gi|7271464|gb|AF145712.1|AF145712[7271464]

9180: AB031325
Homo sapiens gene for calcium-sensing receptor, exons, promoter region
gi|7023984|dbj|AB031325.1|AB031325[7023984]

9183: AF112461
Homo sapiens G protein-coupled receptor 57 (GPR57) gene, complete cds
gi|6739495|gb|AF112461.1|AF112461[6739495]

9184: AF112460
Homo sapiens G protein-coupled receptor 58 (GPR58) gene, complete cds gi|6739493|gb|AF112460.1|AF112460[6739493]

9185: AF184174
Homo sapiens somatostatin receptor 2 (SSTR2) gene, complete cds, alternatively spliced
gi|7229402|gb|AF184174.1|AF184174[7229402]

9227: AF175207
Homo sapiens lectin-like receptor F1, splice variant 1 KLRF1-s1 (KLRF1) mRNA, complete cds
gi|7188568|gb|AF175207.1|AF175207[7188568]

9228: AF175206
Homo sapiens lectin-like receptor F1 (KLRF1) mRNA, complete cds
gi|7188566|gb|AF175206.1|AF175206[7188566]

9229: AJ271348
Homo sapiens partial DRD3 gene for dopamine D3 receptor, exon 1
gi|7159738|emb|AJ271348.2|HSA271348[7159738]

9236: AF180814
Homo sapiens peroxisomal PTS2 receptor (PEX7) gene, exon 10 and complete cds
gi|7157949|gb|AF180814.1|HSPEX7NB9[7157949]

9237: AF180813
Homo sapiens peroxisomal PTS2 receptor (PEX7) gene, exon 9
gi|7157948|gb|AF180813.1|HSPEX7NB8[7157948]

9238: AF180812
Homo sapiens peroxisomal PTS2 receptor (PEX7) gene, exon 8
gi|7157947|gb|AF180812.1|HSPEX7NB7[7157947]

9239: AF180811
Homo sapiens peroxisomal PTS2 receptor (PEX7) gene, exon 7
gi|7157946|gb|AF180811.1|HSPEX7NB6[7157946]

9240: AF180810
Homo sapiens peroxisomal PTS2 receptor (PEX7) gene, exon 6 gi|7157945|gb|AF180810.1|HSPEX7NB5[7157945]

9241: AF180809
Homo sapiens peroxisomal PTS2 receptor (PEX7) gene, exons 4 and 5
gi|7157944|gb|AF180809.1|HSPEX7NB4[7157944]

9242: AF180808
Homo sapiens peroxisomal PTS2 receptor (PEX7) gene, exon 3
gi|7157943|gb|AF180808.1|HSPEX7NB3[7157943]

9243: AF180807
Homo sapiens peroxisomal PTS2 receptor (PEX7) gene, exon 2
gi|7157942|gb|AF180807.1|HSPEX7NB2[7157942]

9244: AF180806
Homo sapiens peroxisomal PTS2 receptor (PEX7) gene, 5' region and exon 1
gi|7157941|gb|AF180806.1|HSPEX7NB1[7157941]

9245: AH009157
Homo sapiens peroxisomal PTS2 receptor (PEX7) gene, complete cds
gi|7157940|gb|AH009157.1|SEG_HSPEX7NB[7157940]

9246: AF087930
Homo sapiens olfactory receptor 17-228 (OR3A2) gene, complete cds
gi|7144641|gb|AF087930.1|AF087930[7144641]

9248: AF087928
Homo sapiens olfactory receptor 17-209 (OR1G1) gene, complete cds
gi|7144638|gb|AF087928.1|AF087928[7144638]

9250: AF087926
Homo sapiens olfactory receptor 17-201 (OR3A3) gene, complete cds
gi|7144635|gb|AF087926.1|AF087926[7144635]

9251: AF087925
Homo sapiens olfactory receptor 17-93 (OR1E2) gene, complete cds
gi|7144633|gb|AF087925.1|AF087925[7144633]

9252: AF087924
Homo sapiens olfactory receptor 17-40 (OR3A1) gene, complete cds
gi|7144631|gb|AF087924.1|AF087924[7144631]

9253: AF087923
Homo sapiens olfactory receptor 17-31 (OR1D5) gene, complete cds
gi|7144629|gb|AF087923.1|AF087923[7144629]

9254: AF087922
Homo sapiens olfactory receptor 17-30 (OR1D4) gene, complete cds
gi|7144627|gb|AF087922.1|AF087922[7144627]

9258: AF087918
Homo sapiens olfactory receptor 17-7 (OR1A1) gene, complete cds
gi|7144622|gb|AF087918.1|AF087918[7144622]

9259: AF087917
Homo sapiens olfactory receptor 17-4 (OR1D2) gene, complete cds
gi|7144620|gb|AF087917.1|AF087917[7144620]

9260: AF087916
Homo sapiens olfactory receptor 17-2 (OR1E1) gene, complete cds
gi|7144618|gb|AF087916.1|AF087916[7144618]

9262: AC010582
Homo sapiens chromosome 14 clone CTD-2547F10, complete sequence
gi|6721135|gb|AC010582.6|AC010582[6721135]

9263: AC010072
Homo sapiens chromosome 14q31 clone CTD-2173I4 containing TSHR gene, partial cds; and unknown gene, complete sequence
gi|6453843|gb|AC010072.5|AC010072[6453843]

9264: AF155225
Homo sapiens olfactory receptor 17-6 (OR1A2) gene, complete cds
gi|5081803|gb|AF155225.1|AF155225[5081803]

9265: AC007262
Homo sapiens chromosome 14 clone containing gene for thyroid stimulating hormone receptor, partial CDS, complete sequence
gi|4883585|gb|AC007262.4|AC007262[4883585]

9266: AC002085
Homo sapiens Chromosome 17p13 Cosmid Clone cos26, complete sequence
gi|4835805|gb|AC002085.2|AC002085[4835805]

9267: AC006531
Homo sapiens chromosome 16 clone 113K5, complete sequence
gi|4235137|gb|AC006531.1|AC006531[4235137]

9268: AC004164
Homo sapiens chromosome 19, cosmid R26450, complete sequence
gi|2905827|gb|AC004164.1|AC004164[2905827]

9269: AF200949
Homo sapiens C-type lectin-like receptor-1 mRNA, complete cds
gi|7110215|gb|AF200949.1|AF200949[7110215]

9277: AF124841
Homo sapiens C-type lectin-like receptor-2 mRNA, complete cds
gi|7109730|gb|AF124841.1|AF124841[7109730]

9278: AF210818
Homo sapiens SWAP-70 mRNA, complete cds
gi|6691098|gb|AF210818.1|AF210818[6691098]

9281: AF134838
Homo sapiens endocytic receptor Endo180 (ENDO180) mRNA, complete cds
gi|4835877|gb|AF134838.1|AF134838[4835877]

9282: U89326
Homo sapiens bone morphogenetic protein receptor type I ALK-6 mRNA, complete cds
gi|3377788|gb|U89326.1|HSU89326[3377788]

9283: AJ003080
Homo sapiens mRNA for serotonin receptor (short isoform)
gi|3115225|emb|AJ003080.1|HSAJ3080[3115225]

9284: AJ003079
Homo sapiens mRNA for 5-hydroxytryptamine3 receptor
gi|3115223|emb|AJ003079.1|HSAJ3079[3115223]

9285: AJ003078
Homo sapiens mRNA for 5-HT3 serotonin receptor (long isoform)
gi|3115221|emb|AJ003078.1|HSAJ3078[3115221]

9286: AC024126
Homo sapiens chromosome 11 clone cosmid f-o-8180 map 11q13, * SEQUENCING IN PROGRESS *, 2 ordered pieces
gi|7025812|gb|AC024126.1|AC024126[7025812]

9287: AC024124
Homo sapiens chromosome 11 clone cosmid b-o-7185 map 11q13, * SEQUENCING IN PROGRESS *, 4 ordered pieces
gi|7025810|gb|AC024124.1|AC024124[7025810]

9288: AC024123
Homo sapiens chromosome 11 clone bac67-m-5 map 11q13, * SEQUENCING IN PROGRESS *, 3 ordered pieces
gi|7025809|gb|AC024123.1|AC024123[7025809]

9289: AF226728
Homo sapiens somatostatin receptor-interacting protein splice variant b (SSTRIP) mRNA, complete cds
gi|7025450|gb|AF226728.1|AF226728[7025450]

9290: AL157442
Homo sapiens mRNA; cDNA DKFZp586P1424 (from clone DKFZp586P1424); partial cds
gi|7018558|emb|AL157442.1|HSM802508[7018558]

9291: AF217796
Homo sapiens SCG10 like-protein, helicase-like protein NHL, M68, and ADP-ribosylation factor related protein 1 (ARFRP1) genes, complete cds
gi|7012928|gb|AF217796.1|AF217796[7012928]

9293: AL137719
Homo sapiens mRNA; cDNA DKFZp434K1831 (from clone DKFZp434K1831); partial cds
gi|6808155|emb|AL137719.1|HSM802224[6808155]

9294: AL137432
Homo sapiens mRNA; cDNA DKFZp761E1824 (from clone DKFZp761E1824); partial cds
gi|6807990|emb|AL137432.1|HSM802135[6807990]

9295: AL137375
Homo sapiens mRNA; cDNA DKFZp434I1926 (from clone DKFZp434I1926); partial cds
gi|6807903|emb|AL137375.1|HSM802063[6807903]

9296: AL137288
Homo sapiens mRNA; cDNA DKFZp434F1516 (from clone DKFZp434F1516); partial cds
gi|6807745|emb|AL137288.1|HSM801953[6807745]

9297: AL137651
Homo sapiens mRNA; cDNA DKFZp434O0213 (from clone DKFZp434O0213); partial cds
gi|6807717|emb|AL137651.1|HSM801924[6807717]

9298: AL133666
Homo sapiens mRNA; cDNA DKFZp434C1418 (from clone DKFZp434C1418); partial cds
gi|6599298|emb|AL133666.1|HSM801500[6599298]

9299: AL133097
Homo sapiens mRNA; cDNA DKFZp434N1928 (from clone DKFZp434N1928)
gi|6453551|emb|AL133097.1|HSM801374[6453551]

9300: AL133058
Homo sapiens mRNA; cDNA DKFZp434K0615 (from clone DKFZp434K0615); partial cds
gi|6453479|emb|AL133058.1|HSM801329[6453479]

9301: AL133030
Homo sapiens mRNA; cDNA DKFZp434H177 (from clone DKFZp434H177); partial cds
gi|6453431|emb|AL133030.1|HSM801297[6453431]

9304: AL117432
Homo sapiens mRNA; cDNA DKFZp434E066 (from clone DKFZp434E066); partial cds
gi|5911868|emb|AL117432.1|HSM800941[5911868]

9305: AL096753
Homo sapiens mRNA; cDNA DKFZp434C192 (from clone DKFZp434C192); partial cds
gi|5419889|emb|AL096753.1|HSM800719[5419889]

9306: AL080164
Homo sapiens mRNA; cDNA DKFZp564C1940 (from clone DKFZp564C1940); partial cds
gi|5262628|emb|AL080164.1|HSM800683[5262628]

9307: AL050071
Homo sapiens mRNA; cDNA DKFZp566B0846 (from clone DKFZp566B0846); partial cds
gi|4884302|emb|AL050071.1|HSM800396[4884302]

9308: AL049924
Homo sapiens mRNA; cDNA DKFZp564G1182 (from clone DKFZp564G1182); partial cds
gi|4884170|emb|AL049924.1|HSM800265[4884170]

9309: X68559
Homo sapiens partial FGFR-4 gene for acidic fibroblast growth factor
gi|556841|emb|X68559.1|HSFGRF[556841]

9310: AF228312
Homo sapiens T-cell receptor zeta chain precursor, mRNA, partial cds
gi|6984206|gb|AF228312.1|AF228312[6984206]

9311: AF199028
Homo sapiens B7-like protein (GL50) mRNA, complete cds
gi|6983943|gb|AF199028.1|AF199028[6983943]

9315: AF225903

Homo sapiens D1 dopamine receptor interacting protein calcyon mRNA, complete cds
gi|6980075|gb|AF225903.1|AF225903[6980075]

9316: AF222340
Homo sapiens type 1 tumor necrosis factor receptor shedding aminopeptidase
regulator mRNA, complete cds
gi|6979942|gb|AF222340.1|AF222340[6979942]

9317: AF201349
Homo sapiens glutamate receptor C gene, partial cds
gi|6690029|gb|AF201349.1|AF201349[6690029]

9318: AF201343
Homo sapiens glutamate receptor B flop isoform and glutamate receptor B flip
isoform genes, partial cds
gi|6690023|gb|AF201343.1|AF201343[6690023]

9319: AJ271729
Homo sapiens mRNA for glucose-regulated protein (HSPA5 gene)
gi|6900103|emb|AJ271729.1|HSA271729[6900103]

9320: AF217794
Homo sapiens M68E mRNA, alternatively spliced, complete cds
gi|6969262|gb|AF217794.1|AF217794[6969262]

9321: AF217793
Homo sapiens M68C mRNA, alternatively spliced, complete cds
gi|6969260|gb|AF217793.1|AF217793[6969260]

9322: AF152238
Homo sapiens V1b vasopressin receptor (VPR3) gene, complete cds
gi|6969252|gb|AF152238.1|AF152238[6969252]

9325: X89271
H.sapiens mRNA for HG11 orphan receptor
gi|6911643|emb|X89271.1|HSHG11ORP[6911643]

9328: AJ240085
Homo sapiens mRNA for T-cell receptor interacting molecule protein, splice variant (TRIM gene)
gi|6911580|emb|AJ240085.1|HSA240085[6911580]

9330: AJ271684
Homo sapiens mRNA for myeloid DAP12-associating lectin (MDL-1 gene)
gi|6900101|emb|AJ271684.1|HSA271684[6900101]

9331: AJ243213
Homo sapiens partial 5-HT4 receptor gene, exons 2 to 5
gi|6900061|emb|AJ243213.1|HSA243213[6900061]

9332: AC003075
Human PAC clone RP4-658N5 from 7p21, complete sequence
gi|2588637|gb|AC003075.1|AC003075[2588637]

9333: AC003078
Human BAC clone GS1-117O10 from 7q21-q22, complete sequence
gi|2588631|gb|AC003078.1|AC003078[2588631]

9334: AC002381
Human BAC clone CTB-20D2 from 7q22, complete sequence
gi|2275186|gb|AC002381.1|AC002381[2275186]

9335: AC005155
Homo sapiens PAC clone RP5-877J2 from 7p14-p15, complete sequence
gi|3242760|gb|AC005155.1|AC005155[3242760]

9338: D50678
Human mRNA for apolipoprotein E receptor 2, complete cds
gi|1321643|dbj|D50678.1|D50678[1321643]

9339: D31770
Human osteosarcoma mRNA for activin typeII A receptor, complete cds
gi|1321631|dbj|D31770.1|HUMACTRIIA[1321631]

9340: D50516
Human mRNA for type II receptor for bone morphogenetic protein-4, complete cds
gi|807712|dbj|D50516.1|HUMBMP4A[807712]

9341: D31661
Human mRNA for tyrosine kinase, complete cds
gi|495677|dbj|D31661.1|HUMERKA[495677]

9342: D17516
Homo sapiens mRNA for PACAP receptor, complete cds
gi|457562|dbj|D17516.1|HUMPACAPR[457562]

9343: D16105
Human mRNA for leukocyte tyrosine kinase, complete cds
gi|440854|dbj|D16105.1|HUMLTKLP2[440854]

9344: D16494
Human mRNA for very low density lipoprotein receptor, complete cds
gi|391735|dbj|D16494.1|HUMVLDLRB[391735]

9345: D16493
Human mRNA for very low density lipoprotein receptor, complete cds
gi|391733|dbj|D16493.1|HUMVLDLRA[391733]

9346: G63891
GRM7 Human Homo sapiens STS genomic 3', sequence tagged site
gi|6842052|gb|G63891.1|G63891[6842052]

9347: G63890
GRM4 Human Homo sapiens STS genomic 5', sequence tagged site
gi|6842051|gb|G63890.1|G63890[6842051]

9471: AF148806
Homo sapiens dopamine receptor D2 (DRD2) gene, 5'-flanking region and exon 1
gi|6759904|gb|AF148806.1|AF148806[6759904]

9473: AF189251

Homo sapiens cytomegalovirus partial fusion receptor mRNA, partial cds
gi|6760349|gb|AF189251.1|AF189251[6760349]

9474: AF202063
Homo sapiens fibroblast growth factor receptor 4, soluble-form splice variant (FGFR4) mRNA, complete cds
gi|6739817|gb|AF202063.1|AF202063[6739817]

9475: AF201951
Homo sapiens high affinity immunoglobulin epsilon receptor beta subunit mRNA, complete cds
gi|6563299|gb|AF201951.1|AF201951[6563299]

9476: AB037108
Homo sapiens mRNA for seven transmembrane domain orphan receptor, complete cds
gi|6729335|dbj|AB037108.1|AB037108[6729335]

9478: AF209721
Homo sapiens IgG Fc receptor locus, partial sequence
gi|6715394|gb|AF209721.1|AF209721[6715394]

9480: AJ238323
Homo sapiens mRNA for NK inhibitory receptor (IRC2)
gi|6707798|emb|AJ238323.1|HSA238323[6707798]

9481: AB036432
Homo sapiens RAGE mRNA for advanced glycation endproducts receptor, complete cds
gi|6691625|dbj|AB036432.1|AB036432[6691625]

9482: AF192548
Homo sapiens tumor necrosis factor receptor-like protein ZTNFR9 (ZTNFR9) mRNA, complete cds
gi|6319129|gb|AF192548.1|AF192548[6319129]

9483: AF184971
Homo sapiens class II cytokine receptor ZCYTOR7 (ZCYTOR7) mRNA, complete cds
gi|6013324|gb|AF184971.1|AF184971[6013324]

9484: AJ012288
Homo sapiens mRNA for GABA-BR1
gi|4186035|emb|AJ012288.1|HSA012288[4186035]

9485: AB035073
Homo sapiens mRNA for platelet glycoprotein VI, complete cds
gi|6691622|dbj|AB035073.1|AB035073[6691622]

9486: AF217403
Homo sapiens low density lipoprotein receptor (LDLR) gene, partial cds
gi|6691160|gb|AF217403.1|AF217403[6691160]

9487: AF200465
Homo sapiens coxsackievirus and adenovirus receptor (CXADR) gene, complete cds;
and ANA gene, partial cds
gi|6690789|gb|AF200465.1|AF200465[6690789]

9509: AJ243342
Homo sapiens mRNA for nicotinic acetylcholine receptor alpha 9 subunit (NACHRA9
gene)
gi|6688135|emb|AJ243342.1|HSA243342[6688135]

9510: AJ223183
Homo sapiens mRNA for DORA protein
gi|3925598|emb|AJ223183.1|HSAJ3183[3925598]

9512: AF006265
Homo sapiens cancer associated surface antigen (RCAS1) mRNA, complete cds
gi|2213933|gb|AF006265.1|AF006265[2213933]

9513: AF159570
Homo sapiens regulator of G-protein signalling 5 (RGS5) mRNA, complete cds
gi|5230675|gb|AF159570.1|AF159570[5230675]

9515: D29952
Human DNA for alpha1A/D adrenergic receptor, complete cds
gi|914933|dbj|D29952.1|HUMA1ADAR[914933]

9516: NM_004441
Homo sapiens EphB1 (EPHB1) mRNA
gi|4758283|ref|NM_004441.1|[4758283]

9532: AF133299
Homo sapiens lectin-like NK cell receptor LLT1 (LLT1) mRNA, complete cds
gi|6651064|gb|AF133299.1|AF133299[6651064]

9533: AF110265
Homo sapiens epidermal growth factor receptor substrate EPS15R mRNA, complete cds
gi|6650598|gb|AF110265.1|AF110265[6650598]

9535: AF061779
Homo sapiens cosmid 25, complete sequence
gi|6650204|gb|AF061779.1|AF061779[6650204]

9537: AF118224
Homo sapiens matriptase mRNA, complete cds
gi|6647301|gb|AF118224.2|AF118224[6647301]

9538: AF125809
Homo sapiens neurotrophic receptor tyrosine kinase-ETS related protein fusion protein (NTRK3-ETV6 fusion) mRNA, partial cds
gi|6635288|gb|AF125809.1|AF125809[6635288]

9539: AF125808
Homo sapiens ETS related protein-neurotrophic receptor tyrosine kinase fusion protein (ETV6-NTRK3 fusion) mRNA, partial cds
gi|6635286|gb|AF125808.1|AF125808[6635286]

9540: AJ000542
Homo sapiens partial p58 gene for NK receptor
gi|6624934|emb|AJ000542.2|HSP58NKRC[6624934]

9541: AF190826

Homo sapiens P2X2A receptor (P2X2) gene, complete cds
gi|6606329|gb|AF190826.1|AF190826[6606329]

9542: AF190825
Homo sapiens P2X2D receptor (P2X2) mRNA, complete cds
gi|6606327|gb|AF190825.1|AF190825[6606327]

9543: AF190824
Homo sapiens P2X2C receptor (P2X2) mRNA, complete cds
gi|6606325|gb|AF190824.1|AF190824[6606325]

9544: AF190823
Homo sapiens P2X2B receptor (P2X2) mRNA, complete cds
gi|6606323|gb|AF190823.1|AF190823[6606323]

9545: AF190822
Homo sapiens P2X2A receptor (P2X2) mRNA, complete cds
gi|6606321|gb|AF190822.1|AF190822[6606321]

9546: AH008809
Homo sapiens FGF receptor activating protein 1 (FRAG1) gene, complete cds
gi|6606289|gb|AH008809.1|SEG_AF159616S[6606289]

9547: AF159621
Homo sapiens FGF receptor activating protein 1 (FRAG1) gene, exon 6 and complete cds
gi|6606288|gb|AF159621.1|AF159616S6[6606288]

9548: AF159620
Homo sapiens FGF receptor activating protein 1 (FRAG1) gene, exon 5
gi|6606287|gb|AF159620.1|AF159616S5[6606287]

9549: AF159619
Homo sapiens FGF receptor activating protein 1 (FRAG1) gene, exon 4
gi|6606286|gb|AF159619.1|AF159616S4[6606286]

9550: AF159618

Homo sapiens FGF receptor activating protein 1 (FRAG1) gene, exon 3
gi|6606285|gb|AF159618.1|AF159616S3[6606285]

9551: AF159617
Homo sapiens FGF receptor activating protein 1 (FRAG1) gene, exon 2
gi|6606284|gb|AF159617.1|AF159616S2[6606284]

9552: AF159616
Homo sapiens FGF receptor activating protein 1 (FRAG1) gene, exon 1
gi|6606283|gb|AF159616.1|AF159616S1[6606283]

9553: AH008808
Homo sapiens PPAR gamma coactivator (PPAR gamma coactivator) gene, complete cds
gi|6606153|gb|AH008808.1|SEG_F108193S[6606153]

9554: AF108205
Homo sapiens PPAR gamma coactivator-1 (PPARGC1) gene, exon 13 and complete cds
gi|6606152|gb|AF108205.1|F108193S13[6606152]

9555: AF108204
Homo sapiens PPAR gamma coactivator-1 (PPARGC1) gene, exon 12
gi|6606151|gb|AF108204.1|F108193S12[6606151]

9556: AF108203
Homo sapiens PPAR gamma coactivator-1 (PPARGC1) gene, exon 11
gi|6606150|gb|AF108203.1|F108193S11[6606150]

9557: AF108202
Homo sapiens PPAR gamma coactivator-1 (PPARGC1) gene, exon 10
gi|6606149|gb|AF108202.1|F108193S10[6606149]

9558: AF108201
Homo sapiens PPAR gamma coactivator-1 (PPARGC1) gene, exon 9
gi|6606148|gb|AF108201.1|F108193S09[6606148]

9559: AF108200
Homo sapiens PPAR gamma coactivator-1 (PPARGC1) gene, exon 8 gi|6606147|gb|AF108200.1|F108193S08[6606147]

9560: AF108199
Homo sapiens PPAR gamma coactivator-1 (PPARGC1) gene, exon 7
gi|6606146|gb|AF108199.1|F108193S07[6606146]

9561: AF108198
Homo sapiens PPAR gamma coactivator-1 (PPARGC1) gene, exon 6
gi|6606145|gb|AF108198.1|F108193S06[6606145]

9562: AF108197
Homo sapiens PPAR gamma coactivator-1 (PPARGC1) gene, exon 5
gi|6606144|gb|AF108197.1|F108193S05[6606144]

9563: AF108196
Homo sapiens PPAR gamma coactivator-1 (PPARGC1) gene, exon 4
gi|6606143|gb|AF108196.1|F108193S04[6606143]

9564: AF108195
Homo sapiens PPAR gamma coactivator-1 (PPARGC1) gene, exon 3
gi|6606142|gb|AF108195.1|F108193S03[6606142]

9565: AF108194
Homo sapiens PPAR gamma coactivator-1 (PPARGC1) gene, exon 2
gi|6606141|gb|AF108194.1|F108193S02[6606141]

9566: AF108193
Homo sapiens PPAR gamma coactivator-1 (PPARGC1) gene, exon 1
gi|6606140|gb|AF108193.1|F108193S01[6606140]

9567: AC005009
Homo sapiens BAC clone GS1-67A24 from 7q21.q21.2, complete sequence
gi|4156150|gb|AC005009.1|AC005009[4156150]

9568: AF047487
Homo sapiens Nck-2 (NCK2) mRNA, complete cds
gi|3930216|gb|AF047487.1|AF047487[3930216]

9569: AC004822
Homo sapiens PAC clone RP1-170D19 from Xq23, complete sequence
gi|3845420|gb|AC004822.1|AC004822[3845420]

9570: AC002543
Homo sapiens BAC clone CTA-300C3 from 7q31.2, complete sequence
gi|3645947|gb|AC002543.1|AC002543[3645947]

9571: AC002081
Homo sapiens BAC clone CTA-331C24 from 7q21, complete sequence
gi|2078453|gb|AC002081.1|AC002081[2078453]

9572: AF106698
Homo sapiens PPAR gamma coactivator-1 (PPARGC1) mRNA, complete cds
gi|6594644|gb|AF106698.1|AF106698[6594644]

9574: AH002552
Homo sapiens CHRNG gene, complete sequence; and acetylcholine receptor gamma-subunit (ACHR) gene, partial cds
gi|6579185|gb|AH002552.2|SEG_HUMACHRG[6579185]

9575: L29197
Homo sapiens acetylcholine receptor gamma-subunit (ACHR) gene, exons 10 and 11
gi|457433|gb|L29197.1|HUMACHRG7[457433]

9576: M11811
Homo sapiens acetylcholine receptor gamma-subunit (ACHR) gene, exon 12 and partial cds
gi|177984|gb|M11811.1|HUMACHRG8[177984]

9580: AF119666
Homo sapiens insulin receptor tyrosine kinase substrate mRNA, complete cds
gi|6563257|gb|AF119666.1|AF119666[6563257]

9581: AF109683
Homo sapiens leukocyte-associated Ig-like receptor 1b mRNA, complete cds gi|6563041|gb|AF109683.1|AF109683[6563041]

9582: AH008758
Homo sapiens insulin-like growth factor 2 receptor (IGF2R) gene, complete cds
gi|6561205|gb|AH008758.1|SEG_HSILGFR[6561205]

9583: AF109291
Homo sapiens insulin-like growth factor 2 receptor (IGF2R) gene, exon 48 and complete cds
gi|6561204|gb|AF109291.1|HSILGFR48[6561204]

9584: AF109290
Homo sapiens insulin-like growth factor 2 receptor (IGF2R) gene, exon 47
gi|6561203|gb|AF109290.1|HSILGFR47[6561203]

9585: AF109289
Homo sapiens insulin-like growth factor 2 receptor (IGF2R) gene, exon 46
gi|6561202|gb|AF109289.1|HSILGFR46[6561202]

9586: AF109288
Homo sapiens insulin-like growth factor 2 receptor (IGF2R) gene, exon 45
gi|6561201|gb|AF109288.1|HSILGFR45[6561201]

9587: AF109287
Homo sapiens insulin-like growth factor 2 receptor (IGF2R) gene, exon 44
gi|6561200|gb|AF109287.1|HSILGFR44[6561200]

9588: AF109286
Homo sapiens insulin-like growth factor 2 receptor (IGF2R) gene, exon 43
gi|6561199|gb|AF109286.1|HSILGFR43[6561199]

9589: AF109285
Homo sapiens insulin-like growth factor 2 receptor (IGF2R) gene, exon 42
gi|6561198|gb|AF109285.1|HSILGFR42[6561198]

9590: AF109284
Homo sapiens insulin-like growth factor 2 receptor (IGF2R) gene, exon 41 gi|6561197|gb|AF109284.1|HSILGFR41[6561197]

9591: AF109283
Homo sapiens insulin-like growth factor 2 receptor (IGF2R) gene, exon 40
gi|6561196|gb|AF109283.1|HSILGFR40[6561196]

9592: AF109282
Homo sapiens insulin-like growth factor 2 receptor (IGF2R) gene, exon 39
gi|6561195|gb|AF109282.1|HSILGFR39[6561195]

9593: AF109281
Homo sapiens insulin-like growth factor 2 receptor (IGF2R) gene, exon 38
gi|6561194|gb|AF109281.1|HSILGFR38[6561194]

9594: AF109280
Homo sapiens insulin-like growth factor 2 receptor (IGF2R) gene, exon 37
gi|6561193|gb|AF109280.1|HSILGFR37[6561193]

9595: AF109279
Homo sapiens insulin-like growth factor 2 receptor (IGF2R) gene, exon 36
gi|6561192|gb|AF109279.1|HSILGFR36[6561192]

9596: AF109278
Homo sapiens insulin-like growth factor 2 receptor (IGF2R) gene, exon 35
gi|6561191|gb|AF109278.1|HSILGFR35[6561191]

9597: AF109277
Homo sapiens insulin-like growth factor 2 receptor (IGF2R) gene, exon 34
gi|6561190|gb|AF109277.1|HSILGFR34[6561190]

9598: AF109276
Homo sapiens insulin-like growth factor 2 receptor (IGF2R) gene, exon 33
gi|6561189|gb|AF109276.1|HSILGFR33[6561189]

9599: AF109275
Homo sapiens insulin-like growth factor 2 receptor (IGF2R) gene, exon 32
gi|6561188|gb|AF109275.1|HSILGFR32[6561188]

9600: AF109274
Homo sapiens insulin-like growth factor 2 receptor (IGF2R) gene, exon 31
gi|6561187|gb|AF109274.1|HSILGFR31[6561187]

9601: AF109273
Homo sapiens insulin-like growth factor 2 receptor (IGF2R) gene, exon 30
gi|6561186|gb|AF109273.1|HSILGFR30[6561186]

9602: AF109272
Homo sapiens insulin-like growth factor 2 receptor (IGF2R) gene, exon 29
gi|6561185|gb|AF109272.1|HSILGFR29[6561185]

9603: AF109271
Homo sapiens insulin-like growth factor 2 receptor (IGF2R) gene, exon 28
gi|6561184|gb|AF109271.1|HSILGFR28[6561184]

9604: AF109270
Homo sapiens insulin-like growth factor 2 receptor (IGF2R) gene, exon 27
gi|6561183|gb|AF109270.1|HSILGFR27[6561183]

9605: AF109269
Homo sapiens insulin-like growth factor 2 receptor (IGF2R) gene, exon 26
gi|6561182|gb|AF109269.1|HSILGFR26[6561182]

9606: AF109268
Homo sapiens insulin-like growth factor 2 receptor (IGF2R) gene, exon 25
gi|6561181|gb|AF109268.1|HSILGFR25[6561181]

9607: AF109267
Homo sapiens insulin-like growth factor 2 receptor (IGF2R) gene, exon 24
gi|6561180|gb|AF109267.1|HSILGFR24[6561180]

9608: AF109266
Homo sapiens insulin-like growth factor 2 receptor (IGF2R) gene, exon 23
gi|6561179|gb|AF109266.1|HSILGFR23[6561179]

9609: AF109265

Homo sapiens insulin-like growth factor 2 receptor (IGF2R) gene, exon 22
gi|6561178|gb|AF109265.1|HSILGFR22[6561178]

9610: AF109264

Homo sapiens insulin-like growth factor 2 receptor (IGF2R) gene, exon 21
gi|6561177|gb|AF109264.1|HSILGFR21[6561177]

9611: AF109263

Homo sapiens insulin-like growth factor 2 receptor (IGF2R) gene, exon 20
gi|6561176|gb|AF109263.1|HSILGFR20[6561176]

9612: AF109262

Homo sapiens insulin-like growth factor 2 receptor (IGF2R) gene, exon 19
gi|6561175|gb|AF109262.1|HSILGFR19[6561175]

9613: AF109261

Homo sapiens insulin-like growth factor 2 receptor (IGF2R) gene, exon 18
gi|6561174|gb|AF109261.1|HSILGFR18[6561174]

9614: AF109260

Homo sapiens insulin-like growth factor 2 receptor (IGF2R) gene, exon 17
gi|6561173|gb|AF109260.1|HSILGFR17[6561173]

9615: AF109259

Homo sapiens insulin-like growth factor 2 receptor (IGF2R) gene, exon 16
gi|6561172|gb|AF109259.1|HSILGFR16[6561172]

9616: AF109258

Homo sapiens insulin-like growth factor 2 receptor (IGF2R) gene, exon 15
gi|6561171|gb|AF109258.1|HSILGFR15[6561171]

9617: AF109257

Homo sapiens insulin-like growth factor 2 receptor (IGF2R) gene, exon 14
gi|6561170|gb|AF109257.1|HSILGFR14[6561170]

9618: AF109256
Homo sapiens insulin-like growth factor 2 receptor (IGF2R) gene, exon 13
gi|6561169|gb|AF109256.1|HSILGFR13[6561169]

9619: AF109255
Homo sapiens insulin-like growth factor 2 receptor (IGF2R) gene, exon 12
gi|6561168|gb|AF109255.1|HSILGFR12[6561168]

9620: AF109254
Homo sapiens insulin-like growth factor 2 receptor (IGF2R) gene, exon 11
gi|6561167|gb|AF109254.1|HSILGFR11[6561167]

9621: AF109253
Homo sapiens insulin-like growth factor 2 receptor (IGF2R) gene, exon 10
gi|6561166|gb|AF109253.1|HSILGFR10[6561166]

9622: AF109252
Homo sapiens insulin-like growth factor 2 receptor (IGF2R) gene, exon 9
gi|6561165|gb|AF109252.1|HSILGFR09[6561165]

9623: AF109251
Homo sapiens insulin-like growth factor 2 receptor (IGF2R) gene, exon 8
gi|6561164|gb|AF109251.1|HSILGFR08[6561164]

9624: AF109250
Homo sapiens insulin-like growth factor 2 receptor (IGF2R) gene, exon 7
gi|6561163|gb|AF109250.1|HSILGFR07[6561163]

9625: AF109249
Homo sapiens insulin-like growth factor 2 receptor (IGF2R) gene, exon 6
gi|6561162|gb|AF109249.1|HSILGFR06[6561162]

9626: AF109248
Homo sapiens insulin-like growth factor 2 receptor (IGF2R) gene, exon 5
gi|6561161|gb|AF109248.1|HSILGFR05[6561161]

9627: AF109247

Homo sapiens insulin-like growth factor 2 receptor (IGF2R) gene, exon 4
gi|6561160|gb|AF109247.1|HSILGFR04[6561160]

9628: AF109246
Homo sapiens insulin-like growth factor 2 receptor (IGF2R) gene, exon 3
gi|6561159|gb|AF109246.1|HSILGFR03[6561159]

9629: AF109245
Homo sapiens insulin-like growth factor 2 receptor (IGF2R) gene, exon 2
gi|6561158|gb|AF109245.1|HSILGFR02[6561158]

9630: AF109244
Homo sapiens insulin-like growth factor 2 receptor (IGF2R) gene, exon 1
gi|6561157|gb|AF109244.1|HSILGFR01[6561157]

9631: AF178684
Homo sapiens class I cytokine receptor (zcytor5) mRNA, complete cds
gi|5853247|gb|AF178684.1|AF178684[5853247]

9632: AQ917583
hxa18 Bac Human I Homo sapiens genomic, genomic survey sequence
gi|6552294|gb|AQ917583.1|AQ917583[6552294]

9633: AQ917582
hxa17 Bac Human I Homo sapiens genomic, genomic survey sequence
gi|6552293|gb|AQ917582.1|AQ917582[6552293]

9634: AQ917581
hxa16 Bac Human I Homo sapiens genomic, genomic survey sequence
gi|6552292|gb|AQ917581.1|AQ917581[6552292]

9635: AQ917580
hxa15 Bac Human I Homo sapiens genomic, genomic survey sequence
gi|6552291|gb|AQ917580.1|AQ917580[6552291]

9636: AQ917579
hxa14 Bac Human I Homo sapiens genomic, genomic survey sequence gi|6552290|gb|AQ917579.1|AQ917579[6552290]

9637: AQ917578
hxa13 Bac Human I Homo sapiens genomic, genomic survey sequence
gi|6552289|gb|AQ917578.1|AQ917578[6552289]

9638: AQ917577
hxa12 Bac Human I Homo sapiens genomic, genomic survey sequence
gi|6552288|gb|AQ917577.1|AQ917577[6552288]

9639: AQ917576
Hxa11 Bac Human I Homo sapiens genomic, genomic survey sequence
gi|6552287|gb|AQ917576.1|AQ917576[6552287]

9640: AQ917575
hxa10 Bac Human I Homo sapiens genomic, genomic survey sequence
gi|6552286|gb|AQ917575.1|AQ917575[6552286]

9641: AQ917574
hxa9 Bac Human I Homo sapiens genomic, genomic survey sequence
gi|6552285|gb|AQ917574.1|AQ917574[6552285]

9642: AQ917573
hxa8 Bac Human I Homo sapiens genomic, genomic survey sequence
gi|6552284|gb|AQ917573.1|AQ917573[6552284]

9643: AQ917572
hxa7 Bac Human I Homo sapiens genomic, genomic survey sequence
gi|6552283|gb|AQ917572.1|AQ917572[6552283]

9644: AQ917571
hxa6 Bac Human I Homo sapiens genomic, genomic survey sequence
gi|6552282|gb|AQ917571.1|AQ917571[6552282]

9645: AQ917570
hxa5 Bac Human I Homo sapiens genomic, genomic survey sequence
gi|6552281|gb|AQ917570.1|AQ917570[6552281]

9646: AQ917569
hxa4 Bac Human I Homo sapiens genomic, genomic survey sequence
gi|6552280|gb|AQ917569.1|AQ917569[6552280]

9647: AQ917568
hxa3 Bac Human I Homo sapiens genomic, genomic survey sequence
gi|6552279|gb|AQ917568.1|AQ917568[6552279]

9648: AQ917567
hxa2 Bac Human I Homo sapiens genomic, genomic survey sequence
gi|6552278|gb|AQ917567.1|AQ917567[6552278]

9649: AQ917566
hxa1 Bac Human I Homo sapiens genomic, genomic survey sequence
gi|6552277|gb|AQ917566.1|AQ917566[6552277]

9650: AH008470
Homo sapiens somatostatin receptor subtype 2 gene, partial cds
gi|6531649|gb|AH008470.1|SEG_AF182397S[6531649]

9652: AF182397
Homo sapiens somatostatin receptor subtype 2 gene, promoter region and partial cds
gi|6531647|gb|AF182397.1|AF182397S1[6531647]

9654: AF068757
Homo sapiens somatostatin receptor subtype 3 (SSTR3) gene, 5' flanking region and partial cds
gi|6523784|gb|AF068757.1|AF068757[6523784]

9656: AF166329
Homo sapiens intermediate prolactin receptor isoform mRNA, complete cds
gi|5734139|gb|AF166329.1|AF166329[5734139]

9658: AJ251595
Homo sapiens mRNA for transmembrane glycoprotein (CD44 gene)

gi|6491738|emb|AJ251595.1|HSA251595[6491738]

9659: AF100772
Homo sapiens tenascin-M1 (TNM1) mRNA, complete cds
gi|6165844|gb|AF100772.1|AF100772[6165844]

9660: AF100634
Homo sapiens Duffy antigen/Receptor for chemokines (DARC) gene, DARC-Fya allele, partial cds
gi|6048958|gb|AF100634.1|AF100634[6048958]

9661: AH008438
Homo sapiens outer membrane receptor Tom20 (TOM20) gene, complete cds
gi|6469611|gb|AH008438.1|SEG_HS20TOM[6469611]

9662: AF019638
Homo sapiens nedasin s-form mRNA, complete cds
gi|6469319|gb|AF019638.1|AF019638[6469319]

9663: AB010445
Homo sapiens mRNA for CC chemokine ILC, complete cds
gi|6469037|dbj|AB010445.1|AB010445[6469037]

9664: AF119330
Synthetic construct from Homo sapiens dopamine receptor D4-7 mRNA, partial cds
gi|4325159|gb|AF119330.1|AF119330[4325159]

9665: AF119329
Synthetic construct from Homo sapiens dopamine receptor D4-4 mRNA, partial cds
gi|4325157|gb|AF119329.1|AF119329[4325157]

9666: AF119328
Synthetic construct from Homo sapiens dopamine receptor D4-2 mRNA, partial cds
gi|4325155|gb|AF119328.1|AF119328[4325155]

9667: AL021940
Homo sapiens DNA sequence from PAC 117P20 on chromosome 1q24. Contains the LNHR (SELL) gene coding for Lymph Node Homing Receptor (L-Selectin precursor, LAM-1 Leukocyte Adhesion Molecule, Leukocyte surface antigen Leu-8, TQ1, GP90-MEL, LECAM1 Leukocyte-Endothelial Cell Adhesion Molecule 1, CD62L). Contains the SELE gene coding for E-Selectin precursor (CD62E, ELAM-1 Endothelial Leukocyte Adhesion Molecule 1, LECAM-2 Leukocyte-Endothelial Cell Adhesion Molecule 2). Contains an unknown gene with homology to predicted yeast. plant and worm proteins. Contains ESTs and STSs, complete sequence
gi|3115962|emb|AL021940.1|HS117P20[3115962]

9668: AF152113
Homo sapiens perforin gene, IL-2 responsive enhancer sequence
gi|6467393|gb|AF152113.1|AF152113[6467393]

9669: AB022178
Homo sapiens mRNA for calcitonin receptor, complete cds, isolate from bone marrow osteoclast
gi|6456431|dbj|AB022178.1|AB022178[6456431]

9670: AB022177
Homo sapiens mRNA for calcitonin receptor, complete cds, isolate from breast carcinoma
gi|6456429|dbj|AB022177.1|AB022177[6456429]

9671: AJ251004
Homo sapiens ITGB4 gene for integrin beta 4, exons 1-2 and joined CDS
gi|6453379|emb|AJ251004.1|HSA251004[6453379]

9672: AJ133822
Homo sapiens mRNA for receptor for Advanced Glycation End Product, secreted isoform (RAGEsec gene)
gi|4877290|emb|AJ133822.1|HSA133822[4877290]

9673: Y18994
Homo sapiens GABRR3 gene, partial
gi|6434194|emb|Y18994.1|HSP18994[6434194]

9676: AF177766
Homo sapiens human toll-like receptor 4 (TLR4) gene, TLR4B allele, partial cds
gi|6403466|gb|AF177766.1|AF177766[6403466]

9677: AH008297
Homo sapiens dihydropyridine receptor alpha 2 subunit (CACNA2D1) gene, complete cds
gi|6090614|gb|AH008297.1|SEG_HSDRA2S[6090614]

9678: AF083854
Homo sapiens dihydropyridine receptor alpha 2 subunit (CACNA2D1) gene, exon 40 and complete cds
gi|6090613|gb|AF083854.1|HSDRA2S38[6090613]

9679: AF083853
Homo sapiens dihydropyridine receptor alpha 2 subunit (CACNA2D1) gene, exon 39
gi|6090612|gb|AF083853.1|HSDRA2S37[6090612]

9680: AF083852
Homo sapiens dihydropyridine receptor alpha 2 subunit (CACNA2D1) gene, exon 38
gi|6090611|gb|AF083852.1|HSDRA2S36[6090611]

9681: AF083851
Homo sapiens dihydropyridine receptor alpha 2 subunit (CACNA2D1) gene, exon 37
gi|6090610|gb|AF083851.1|HSDRA2S35[6090610]

9682: AF083850
Homo sapiens dihydropyridine receptor alpha 2 subunit (CACNA2D1) gene, exon 36
gi|6090609|gb|AF083850.1|HSDRA2S34[6090609]

9683: AF083849
Homo sapiens dihydropyridine receptor alpha 2 subunit (CACNA2D1) gene, exons 34 and 35
gi|6090608|gb|AF083849.1|HSDRA2S33[6090608]

9684: AF083848
Homo sapiens dihydropyridine receptor alpha 2 subunit (CACNA2D1) gene, exon 33
gi|6090607|gb|AF083848.1|HSDRA2S32[6090607]

9685: AF083847

Homo sapiens dihydropyridine receptor alpha 2 subunit (CACNA2D1) gene, exon 32
gi|6090606|gb|AF083847.1|HSDRA2S31[6090606]

9686: AF083846
Homo sapiens dihydropyridine receptor alpha 2 subunit (CACNA2D1) gene, exon 31
gi|6090605|gb|AF083846.1|HSDRA2S30[6090605]

9687: AF083845
Homo sapiens dihydropyridine receptor alpha 2 subunit (CACNA2D1) gene, exon 30
gi|6090604|gb|AF083845.1|HSDRA2S29[6090604]

9688: AF083844
Homo sapiens dihydropyridine receptor alpha 2 subunit (CACNA2D1) gene, exon 29
gi|6090603|gb|AF083844.1|HSDRA2S28[6090603]

9689: AF083843
Homo sapiens dihydropyridine receptor alpha 2 subunit (CACNA2D1) gene, exon 28
gi|6090602|gb|AF083843.1|HSDRA2S27[6090602]

9690: AF083842
Homo sapiens dihydropyridine receptor alpha 2 subunit (CACNA2D1) gene, exon 27
gi|6090601|gb|AF083842.1|HSDRA2S26[6090601]

9691: AF083841
Homo sapiens dihydropyridine receptor alpha 2 subunit (CACNA2D1) gene, exon 26
gi|6090600|gb|AF083841.1|HSDRA2S25[6090600]

9692: AF083840
Homo sapiens dihydropyridine receptor alpha 2 subunit (CACNA2D1) gene, exon 25
gi|6090599|gb|AF083840.1|HSDRA2S24[6090599]

9693: AF083839
Homo sapiens dihydropyridine receptor alpha 2 subunit (CACNA2D1) gene, exon 24
gi|6090598|gb|AF083839.1|HSDRA2S23[6090598]

9694: AF083838
Homo sapiens dihydropyridine receptor alpha 2 subunit (CACNA2D1) gene, exon 23 gi|6090597|gb|AF083838.1|HSDRA2S22[6090597]

9695: AF083837
Homo sapiens dihydropyridine receptor alpha 2 subunit (CACNA2D1) gene, exon 22
gi|6090596|gb|AF083837.1|HSDRA2S21[6090596]

9696: AF083836
Homo sapiens dihydropyridine receptor alpha 2 subunit (CACNA2D1) gene, exon 21
gi|6090595|gb|AF083836.1|HSDRA2S20[6090595]

9697: AF083835
Homo sapiens dihydropyridine receptor alpha 2 subunit (CACNA2D1) gene, exon 20
gi|6090594|gb|AF083835.1|HSDRA2S19[6090594]

9698: AF083834
Homo sapiens dihydropyridine receptor alpha 2 subunit (CACNA2D1) gene, exon 19
gi|6090593|gb|AF083834.1|HSDRA2S18[6090593]

9699: AF083833
Homo sapiens dihydropyridine receptor alpha 2 subunit (CACNA2D1) gene, exons 17 and 18
gi|6090592|gb|AF083833.1|HSDRA2S17[6090592]

9700: AF083832
Homo sapiens dihydropyridine receptor alpha 2 subunit (CACNA2D1) gene, exon 16
gi|6090591|gb|AF083832.1|HSDRA2S16[6090591]

9701: AF083831
Homo sapiens dihydropyridine receptor alpha 2 subunit (CACNA2D1) gene, exon 15
gi|6090590|gb|AF083831.1|HSDRA2S15[6090590]

9702: AF083830
Homo sapiens dihydropyridine receptor alpha 2 subunit (CACNA2D1) gene, exon 14
gi|6090589|gb|AF083830.1|HSDRA2S14[6090589]

9703: AF083829
Homo sapiens dihydropyridine receptor alpha 2 subunit (CACNA2D1) gene, exon 13 gi|6090588|gb|AF083829.1|HSDRA2S13[6090588]

9704: AF083828
Homo sapiens dihydropyridine receptor alpha 2 subunit (CACNA2D1) gene, exon 12
gi|6090587|gb|AF083828.1|HSDRA2S12[6090587]

9705: AF083827
Homo sapiens dihydropyridine receptor alpha 2 subunit (CACNA2D1) gene, exon 11
gi|6090586|gb|AF083827.1|HSDRA2S11[6090586]

9706: AF083826
Homo sapiens dihydropyridine receptor alpha 2 subunit (CACNA2D1) gene, exon 10
gi|6090585|gb|AF083826.1|HSDRA2S10[6090585]

9707: AF083825
Homo sapiens dihydropyridine receptor alpha 2 subunit (CACNA2D1) gene, exon 9
gi|6090584|gb|AF083825.1|HSDRA2S09[6090584]

9708: AF083824
Homo sapiens dihydropyridine receptor alpha 2 subunit (CACNA2D1) gene, exon 8
gi|6090583|gb|AF083824.1|HSDRA2S08[6090583]

9709: AF083823
Homo sapiens dihydropyridine receptor alpha 2 subunit (CACNA2D1) gene, exon 7
gi|6090582|gb|AF083823.1|HSDRA2S07[6090582]

9710: AF083822
Homo sapiens dihydropyridine receptor alpha 2 subunit (CACNA2D1) gene, exon 6
gi|6090581|gb|AF083822.1|HSDRA2S06[6090581]

9711: AF083821
Homo sapiens dihydropyridine receptor alpha 2 subunit (CACNA2D1) gene, exon 5
gi|6090580|gb|AF083821.1|HSDRA2S05[6090580]

9712: AF083820
Homo sapiens dihydropyridine receptor alpha 2 subunit (CACNA2D1) gene, exon 4
gi|6090579|gb|AF083820.1|HSDRA2S04[6090579]

9713: AF083819
Homo sapiens dihydropyridine receptor alpha 2 subunit (CACNA2D1) gene, exon 3
gi|6090578|gb|AF083819.1|HSDRA2S03[6090578]

9714: AF083818
Homo sapiens dihydropyridine receptor alpha 2 subunit (CACNA2D1) gene, exon 2
gi|6090577|gb|AF083818.1|HSDRA2S02[6090577]

9715: AF083817
Homo sapiens dihydropyridine receptor alpha 2 subunit (CACNA2D1) gene, exon 1
gi|6090576|gb|AF083817.1|HSDRA2S01[6090576]

9716: U68492
Homo sapiens 5-hydroxytryptamine 7 receptor isoform B gene, alternatively spliced, partial cds
gi|1857150|gb|U68492.1|HS5HTSEV01[1857150]

9717: AB032417
Homo sapiens FZD4 mRNA for WNT receptor Frizzled-4, complete cds
gi|6277265|dbj|AB032417.1|AB032417[6277265]

9718: AF191093
Homo sapiens P2X4 purinoceptor gene, complete cds
gi|6274470|gb|AF191093.1|AF191093[6274470]

9719: AJ130713
Homo sapiens mRNA for QA79 membrane protein, splice product airm-1
gi|5541875|emb|AJ130713.1|HSA130713[5541875]

9720: AJ130712
Homo sapiens mRNA for QA79 membrane protein, splice product airm-3
gi|5541873|emb|AJ130712.1|HSA130712[5541873]

9721: AJ130711
Homo sapiens mRNA for QA79 membrane protein, splice product airm-2
gi|5541871|emb|AJ130711.1|HSA130711[5541871]

9722: AJ130710
Homo sapiens mRNA for QA79 membrane protein, allelic variant airm-1b
gi|5541869|emb|AJ130710.1|HSA130710[5541869]

9723: AJ007395
Homo sapiens mRNA for QA79 membrane protein
gi|5295849|emb|AJ007395.1|HSA7395[5295849]

9724: X95097
Homo sapiens mRNA for VIP receptor 2
gi|4837717|emb|X95097.2|HSVIP2R[4837717]

9725: Y18423
Homo sapiens VIP2R gene, exons 1-2 (and joined CDS)
gi|4753150|emb|Y18423.1|HA18423[4753150]

9726: Y18431
Homo sapiens VIP2R gene, exon 13
gi|4741409|emb|Y18431.1|HA18431[4741409]

9727: Y18430
Homo sapiens VIP2R gene, exons 9-12
gi|4741408|emb|Y18430.1|HA18430[4741408]

9728: Y18429
Homo sapiens VIP2R gene, exon 8
gi|4741407|emb|Y18429.1|HA18429[4741407]

9729: Y18428
Homo sapiens VIP2R gene, exon 7
gi|4741406|emb|Y18428.1|HA18428[4741406]

9730: Y18427
Homo sapiens VIP2R gene, exon 6
gi|4741405|emb|Y18427.1|HA18427[4741405]

9731: Y18426
Homo sapiens VIPR2 gene exon 5
gi|4741404|emb|Y18426.1|HA18426[4741404]

9732: Y18425
Homo sapiens VIPR2 gene exon 4
gi|4741403|emb|Y18425.1|HA18425[4741403]

9733: Y18424
Homo sapiens VIPR2 gene exon 3
gi|4741402|emb|Y18424.1|HA18424[4741402]

9734: X57250
H.sapiens C5aR mRNA for C5 anaphylatoxin receptor
gi|29569|emb|X57250.1|HSC5AR[29569]

9735: AF200348
Homo sapiens melanoma-associated antigen MG50 mRNA, partial cds
gi|6273398|gb|AF200348.1|AF200348[6273398]

9736: AH008357
Homo sapiens coxsackievirus B-adenovirus receptor (CAR) gene, exon 1
gi|6224699|gb|AH008357.1|SEG_HSCXADR[6224699]

9737: AF169366
Homo sapiens coxsackievirus B-adenovirus receptor (CAR) gene, exon 7 and complete cds
gi|6224698|gb|AF169366.1|HSCXADR7[6224698]

9738: AF169365
Homo sapiens coxsackievirus B-adenovirus receptor (CAR) gene, exon 6
gi|6224697|gb|AF169365.1|HSCXADR6[6224697]

9739: AF169364
Homo sapiens coxsackievirus B-adenovirus receptor (CAR) gene, exon 5
gi|6224696|gb|AF169364.1|HSCXADR5[6224696]

9740: AF169363
Homo sapiens coxsackievirus B-adenovirus receptor (CAR) gene, exon 4
gi|6224695|gb|AF169363.1|HSCXADR4[6224695]

9741: AF169362
Homo sapiens coxsackievirus B-adenovirus receptor (CAR) gene, exon 3
gi|6224694|gb|AF169362.1|HSCXADR3[6224694]

9742: AF169361
Homo sapiens coxsackievirus B-adenovirus receptor (CAR) gene, exon 2
gi|6224693|gb|AF169361.1|HSCXADR2[6224693]

9743: AF169360
Homo sapiens coxsackievirus B-adenovirus receptor (CAR) gene, exon 1
gi|6224692|gb|AF169360.1|HSCXADR1[6224692]

9744: AF181862
Homo sapiens G protein-coupled receptor mRNA, complete cds
gi|6175912|gb|AF181862.1|AF181862[6175912]

9745: AF178632
Homo sapiens FEM-1-like death receptor binding protein mRNA, complete cds
gi|6175868|gb|AF178632.1|AF178632[6175868]

9755: X80763
Homo sapiens gene for 5-hydroxytrptamine 2C receptor, exons 1 to 4
gi|602872|emb|X80763.1|HS5HT2C[602872]

9756: X68149
Homo sapiens BLR1 gene for Burkitt's lymphoma receptor 1
gi|29459|emb|X68149.1|HSBLR1A[29459]

9757: AF187320
Homo sapiens transferrin receptor (TFRC) gene, complete cds
gi|6164847|gb|AF187320.1|AF187320[6164847]

9758: AF154673
Homo sapiens olfactory receptor HPFH1OR (HPFH1OR) gene, complete cds
gi|5764388|gb|AF154673.1|AF154673[5764388]

9760: AF169255
Homo sapiens 5-hydroxytryptamine 3 receptor B subunit (5-HTR3B) mRNA, complete cds
gi|6103620|gb|AF169255.1|AF169255[6103620]

9762: AJ133107
Homo sapiens CD163 gene, exon 17
gi|5102659|emb|AJ133107.1|HSA133107[5102659]

9763: Y18403
Homo sapiens CD163 gene, exon 16
gi|5102656|emb|Y18403.1|HSA118403[5102656]

9764: Y18402
Homo sapiens CD163 gene, exon 15
gi|5102655|emb|Y18402.1|HSA118402[5102655]

9765: Y18401
Homo sapiens CD163 gene, exon 14
gi|5102654|emb|Y18401.1|HSA118401[5102654]

9766: Y18400
Homo sapiens CD163 gene, exon 13
gi|5102653|emb|Y18400.1|HSA118400[5102653]

9767: Y18399
Homo sapiens CD163 gene, exon 12
gi|5102652|emb|Y18399.1|HSA118399[5102652]

9768: Y18398
Homo sapiens CD163 gene, exon 11
gi|5102651|emb|Y18398.1|HSA118398[5102651]

9769: Y18397
Homo sapiens CD163 gene, exon 10
gi|5102650|emb|Y18397.1|HSA118397[5102650]

9770: Y18396
Homo sapiens CD163 gene, exon 9
gi|5102649|emb|Y18396.1|HSA118396[5102649]

9771: Y18395
Homo sapiens CD163 gene, exon 8
gi|5102648|emb|Y18395.1|HSA118395[5102648]

9772: Y18394
Homo sapiens CD163 gene, exon 7
gi|5102647|emb|Y18394.1|HSA118394[5102647]

9773: Y18393
Homo sapiens CD163 gene, exon 6
gi|5102646|emb|Y18393.1|HSA118393[5102646]

9774: Y18392
Homo sapiens CD163 gene, exon 5
gi|5102645|emb|Y18392.1|HSA118392[5102645]

9775: Y18391
Homo sapiens CD163 gene, exon 4
gi|5102644|emb|Y18391.1|HSA118391[5102644]

9776: Y18390
Homo sapiens CD163 gene, exon 3
gi|5102643|emb|Y18390.1|HSA118390[5102643]

9777: Y18389
Homo sapiens CD163 gene, exon 2
gi|5102642|emb|Y18389.1|HSA118389[5102642]

9791: AF095725
Homo sapiens PAC LLNLP704E02527Q3 olfactory receptor 17-1 (OR17-1), olfactory receptor 17-2 (OR17-2), olfactory receptor 17-201 (OR17-201), and olfactory receptor 17-93 (OR17-93) genes, complete cds
gi|6090622|gb|AF095725.1|AF095725[6090622]

9792: AH007997
Homo sapiens prostaglandin E2 receptor EP2 subtype (PTGER2) gene, complete cds
gi|5524234|gb|AH007997.1|SEG_HSPTGER2G[5524234]

9793: AF134202
Homo sapiens prostaglandin E2 receptor EP2 subtype (PTGER2) gene, alternatively spliced exons and complete cds
gi|5524233|gb|AF134202.1|HSPTGER2G2[5524233]

9794: AF134201
Homo sapiens prostaglandin E2 receptor EP2 subtype (PTGER2) gene, exon 1
gi|5524232|gb|AF134201.1|HSPTGER2G1[5524232]

9797: AF139768
Homo sapiens type II transmembrane protein MDL-1 (MDL1) mRNA, complete cds
gi|6049175|gb|AF139768.1|AF139768[6049175]

9799: X75318
H.sapiens ITIH1 gene (exon 22) and ITIH3 gene (exon 1 and joining features)
gi|575256|emb|X75318.1|HSITIH[575256]

9800: AJ245822
Homo sapiens mRNA for type I transmembrane receptor (psk-3 gene)
gi|6018463|emb|AJ245822.1|HSA245822[6018463]

9801: AJ245820
Homo sapiens mRNA for type I transmembrane receptor (psk-1 gene)
gi|6018459|emb|AJ245820.1|HSA245820[6018459]

9802: L46722
Homo sapiens BTG1 binding factor 1 (CAF1) mRNA, complete cds
gi|6016011|gb|L46722.1|L46722[6016011]

9803: X87831
Homo sapiens mRNA for partial OCT/plexin-A2 protein
gi|6010214|emb|X87831.2|HSOCTPROT[6010214]

9804: AJ000994
Homo sapiens DNA for p58 NK receptor gene
gi|2764562|emb|AJ000994.1|HSP58NK[2764562]

9805: X84761
H.sapiens LHCGR gene, exon 9
gi|1225992|emb|X84761.1|HSLHCGRX9[1225992]

9806: X84760
H.sapiens LHCGR gene, exon 8
gi|1225991|emb|X84760.1|HSLHCGRX8[1225991]

9807: X84759
H.sapiens LHCGR gene, exon 7
gi|1225990|emb|X84759.1|HSLHCGRX7[1225990]

9808: X84758
H.sapiens LHCGR gene, exon 6
gi|1225989|emb|X84758.1|HSLHCGRX6[1225989]

9809: X84757
H.sapiens LHCGR gene, exon 5
gi|1225988|emb|X84757.1|HSLHCGRX5[1225988]

9810: X84756
H.sapiens LHCGR gene, exon 4
gi|1225987|emb|X84756.1|HSLHCGRX4[1225987]

9811: X84754
H.sapiens LHCGR gene, exon 2
gi|1225985|emb|X84754.1|HSLHCGRX2[1225985]

9812: X84753
H.sapiens LHCGR gene, exon 1
gi|1225983|emb|X84753.1|HSLHCGRX1[1225983]

9813: X84763
H.sapiens LHCGR gene, exon 11
gi|1225982|emb|X84763.1|HSLHCGR11[1225982]

9814: X84762
H.sapiens LHCGR gene, exon 10
gi|1225981|emb|X84762.1|HSLHCGR10[1225981]

9815: AF140631
Homo sapiens G-protein coupled receptor 14 (GPR14) gene, complete cds
gi|5902615|gb|AF140631.1|AF140631[5902615]

9816: AF140630
Homo sapiens urotensin-II mRNA, complete cds
gi|5902613|gb|AF140630.1|AF140630[5902613]

9817: AF040752
Homo sapiens G protein-coupled receptor kinase 6, splice variant C (GRK6) mRNA, complete cds
gi|3005017|gb|AF040752.1|AF040752[3005017]

9818: AF040751
Homo sapiens G protein-coupled receptor kinase 6, splice variant B (GRK6) mRNA, complete cds
gi|3005015|gb|AF040751.1|AF040751[3005015]

9819: AF040753
Homo sapiens G protein-coupled receptor kinase 6 (GRK6) gene, partial cds
gi|3004990|gb|AF040753.1|AF040753[3004990]

9820: X87832
Homo sapiens mRNA for partial NOV/plexin-A1 protein
gi|6010216|emb|X87832.2|HSNOVPROT[6010216]

9821: X87904
Homo sapiens mRNA for semaphorin receptor (plexin-B1/SEP gene)
gi|6010210|emb|X87904.2|HSRNASEP[6010210]

9822: AJ011415
Homo sapiens mRNA for plexin-B1 plasma membrane receptor, splice variant R (plexin-B1/SEP gene)
gi|5918166|emb|AJ011415.1|HSA011415[5918166]

9823: AJ011414
Homo sapiens mRNA for plexin-B1 plasma membrane receptor, truncated splice variant (plexin-B1/SEP gene)
gi|5918164|emb|AJ011414.1|HSA011414[5918164]

9824: X07019
Homo sapiens partial TRDC gene for T-cell receptor delta chain, exon 1
gi|29766|emb|X07019.1|HSCD1G[29766]

9825: X54559
Homo sapiens mRNA for met proto-oncogene
gi|34557|emb|X54559.1|HSMETPRO[34557]

9826: AF186380
Homo sapiens calcium-mobilizing lysophosphatidic acid receptor LP-A3/Edg-7 mRNA, complete cds
gi|6003655|gb|AF186380.1|AF186380[6003655]

9827: AF147204
Homo sapiens chemokine receptor CXCR4-Lo (CXCR4) mRNA, alternatively spliced, complete cds
gi|6002763|gb|AF147204.1|AF147204[6002763]

9828: AF029213
Homo sapiens IL-1 receptor accessory protein mRNA, complete cds
gi|2599126|gb|AF029213.1|AF029213[2599126]

9829: Z24462
H.sapiens MTCP-1 gene
gi|406858|emb|Z24462.1|HSMTCP1B[406858]

9830: Z24455
H.sapiens MTCP-1 gene
gi|406857|emb|Z24455.1|HSMTCP1A[406857]

9832: AF124598
Homo sapiens coxsackie and adenovirus receptor protein (HCAR2) mRNA, partial cds
gi|4884701|gb|AF124598.1|AF124598[4884701]

9833: AF124145
Homo sapiens autocrine motility factor receptor (AMFR) mRNA, complete cds
gi|5931954|gb|AF124145.1|AF124145[5931954]

9835: AF118637
Homo sapiens feline leukemia virus subgroup C receptor FLVCR (C10) mRNA, complete cds
gi|5565871|gb|AF118637.1|AF118637[5565871]

9836: AF127138
Homo sapiens lysophosphatidic acid G protein-coupled receptor (EDG7) mRNA, complete cds
gi|5922724|gb|AF127138.1|AF127138[5922724]

9837: AF104939
Homo sapiens lectomedin-1 gamma (LEC1) mRNA, complete cds
gi|5880493|gb|AF104939.1|AF104939[5880493]

9838: AF104266
Homo sapiens lectomedin-1 alpha (LEC1) mRNA, complete cds
gi|5880489|gb|AF104266.1|AF104266[5880489]

9839: X51646
Homo sapiens DRD2 gene for dopamine receptor D2
gi|30868|emb|X51646.1|HSDOPD2GE[30868]

9840: X51645
Homo sapiens mRNA for dopamine receptor D2 (DRD2 gene)
gi|30867|emb|X51645.1|HSDOPD2[30867]

9841: AB010447
Homo sapiens mRNA for CC chemokine eotaxin3, complete cds
gi|5921130|dbj|AB010447.1|AB010447[5921130]

9844: AF137378
Homo sapiens integrin alpha 11 subunit precursor (ITGA11) mRNA, complete cds
gi|5915661|gb|AF137378.2|AF137378[5915661]

9845: AJ243212
Homo sapiens mRNA for DMBT1 protein 8kb transcript variant 2 (DMBT1/8kb.2)
gi|5912463|emb|AJ243212.1|HSA243212[5912463]

9846: AJ243874
Homo sapiens mRNA for oligophrenin-4 (OPHN4 gene)
gi|5911829|emb|AJ243874.1|HSA243874[5911829]

9847: AF091352
Homo sapiens vascular permeability factor 148 mRNA, complete cds
gi|5901560|gb|AF091352.1|AF091352[5901560]

9848: AF159456
Homo sapiens gp-340 variant protein (DMBT1) mRNA, complete cds
gi|5733597|gb|AF159456.1|AF159456[5733597]

9948: AB023486
Homo sapiens gene for histamine H2 receptor, promoter region and complete cds
gi|5881575|dbj|AB023486.1|AB023486[5881575]

9949: AF104938
Homo sapiens lectomedin-1 beta (LEC1) mRNA, complete cds
gi|5880491|gb|AF104938.1|AF104938[5880491]

9950: U81379
Homo sapiens interleukin-13 receptor mRNA, complete cds
gi|5870850|gb|U81379.3|HSU81379[5870850]

9951: AH008056
Homo sapiens galanin receptor (GALR3) gene, complete cds
gi|5870844|gb|AH008056.2|SEG_HSGALR3S[5870844]

9952: AF129514
Homo sapiens galanin receptor (GALR3) gene, exon 2 and complete cds
gi|5870843|gb|AF129514.2|HSGALR3S2[5870843]

9953: AF129513
Homo sapiens galanin receptor (GALR3) gene, exon 1
gi|5870842|gb|AF129513.2|HSGALR3S1[5870842]

9954: AF101472
Homo sapiens G protein-coupled receptor 75 (GPR75) gene, complete cds
gi|4558866|gb|AF101472.1|AF101472[4558866]

9955: AF072693
Homo sapiens G protein-coupled receptor 75 (GPR75) mRNA, complete cds
gi|4406084|gb|AF072693.1|AF072693[4406084]

9957: AJ246000
Homo sapiens mRNA for leucocyte adhesion receptor, L-selectin
gi|5852071|emb|AJ246000.1|HSA246000[5852071]

9959: AJ224864
Homo sapiens mRNA for IRC1 protein
gi|5834585|emb|AJ224864.1|HSA224864[5834585]

9960: AJ132948
Homo sapiens mRNA for rfg7 protein, partial
gi|5834581|emb|AJ132948.1|HSA132948[5834581]

9961: AB027464

Homo sapiens FZD10 mRNA for Frizzled-10, complete cds
gi|5834487|dbj|AB027464.1|AB027464[5834487]

9963: AJ133532
Homo sapiens mRNA for dendritic cell immunoreceptor
gi|5823973|emb|AJ133532.1|HSA133532[5823973]

9964: AJ223153
Homo sapiens mRNA for activating NK-A1 receptor
gi|5823969|emb|AJ223153.1|HSAJ3153[5823969]

9965: AB025257
Homo sapiens FCER1B gene for high affinity IgE receptor beta chain, promoter region, partial sequence
gi|5821396|dbj|AB025257.1|AB025257[5821396]

9970: Y16434
Homo sapiens mRNA for T-cell receptor beta, clone PPN82
gi|2879843|emb|Y16434.1|HSTCRB82[2879843]

9971: Y16433
Homo sapiens mRNA for T-cell receptor alpha, clone PPN82
gi|2879842|emb|Y16433.1|HSTCRA82[2879842]

9972: AF144648
Homo sapiens GABA-A receptor theta (theta) mRNA, complete cds
gi|5764186|gb|AF144648.1|AF144648[5764186]

9973: AF151104
Homo sapiens T-cell receptor gamma gene sequence
gi|5758137|gb|AF151104.1|AF151104[5758137]

9974: AF039686
Homo sapiens G-protein coupled receptor GPR34 (GPR34) mRNA, complete cds
gi|5757633|gb|AF039686.1|AF039686[5757633]

9975: AF000548

Homo sapiens P1 clone DMPC-HFF#1-1075-D9, repeat region
gi|2232071|gb|AF000548.1|HSAF000548[2232071]

9976: X83701
Homo sapiens IGF2R gene (subclone pE3UP)
gi|929648|emb|X83701.1|HSIGF2RX3[929648]

9977: X83700
Home sapiens IGF2R gene (subclone pEX2)
gi|929646|emb|X83700.1|HSIGF2RX2[929646]

9978: X83702
Homo sapiens IGF2R gene (subclone pEX3)
gi|929644|emb|X83702.1|HSIGF2RI3[929644]

9979: G16210
967A10R CEPH YAC and mega-YAC libraries (DBThompson) Homo sapiens STS genomic clone 967A10, sequence tagged site
gi|1592382|gb|G16210.1|G16210[1592382]

9980: AH008077
Homo sapiens ectodysplasin-A receptor protein (EDAR) gene, complete cds
gi|5737745|gb|AH008077.1|SEG_HSEDAR[5737745]

9981: AF130996
Homo sapiens ectodysplasin-A receptor protein (EDAR) gene, exon 12 and complete cds
gi|5737744|gb|AF130996.1|HSEDAR8[5737744]

9982: AF130995
Homo sapiens ectodysplasin-A receptor protein (EDAR) gene, exon 11
gi|5737743|gb|AF130995.1|HSEDAR7[5737743]

9983: AF130994
Homo sapiens ectodysplasin-A receptor protein (EDAR) gene, exon 10
gi|5737742|gb|AF130994.1|HSEDAR6[5737742]

9984: AF130993
Homo sapiens ectodysplasin-A receptor protein (EDAR) gene, exons 7, 8, and 9
gi|5737741|gb|AF130993.1|HSEDAR5[5737741]

9985: AF130992
Homo sapiens ectodysplasin-A receptor protein (EDAR) gene, exon 6
gi|5737740|gb|AF130992.1|HSEDAR4[5737740]

9986: AF130991
Homo sapiens ectodysplasin-A receptor protein (EDAR) gene, exon 5
gi|5737739|gb|AF130991.1|HSEDAR3[5737739]

9987: AF130990
Homo sapiens ectodysplasin-A receptor protein (EDAR) gene, exons 2, 3, and 4
gi|5737738|gb|AF130990.1|HSEDAR2[5737738]

9988: AF130989
Homo sapiens ectodysplasin-A receptor protein (EDAR) gene, exon 1
gi|5737737|gb|AF130989.1|HSEDAR1[5737737]

9989: AF130988
Homo sapiens ectodysplasin-A receptor protein (EDAR) mRNA, complete cds
gi|5737735|gb|AF130988.1|AF130988[5737735]

9990: AF033111
Homo sapiens Siva-2 mRNA, complete cds
gi|5737690|gb|AF033111.1|AF033111[5737690]

9992: AJ238044
Homo sapiens mRNA for bradykinin B1 receptor (B1BKR gene)
gi|5139485|emb|AJ238044.1|HSA238044[5139485]

9993: X95425
H.sapiens mRNA for EHK-1 receptor tyrosine kinase
gi|1177465|emb|X95425.1|HSEHK1[1177465]

9995: AF135562

Homo sapiens p58 killer cell inhibitory receptor KIR-K78 (KIR-K78) mRNA, partial cds
gi|5730925|gb|AF135562.1|AF135562[5730925]

9996: AF135561
Homo sapiens p58 killer cell inhibitory receptor KIR-K65 (KIR-K65) mRNA, partial cds
gi|5730923|gb|AF135561.1|AF135561[5730923]

9997: AF135560
Homo sapiens p58 killer cell inhibitory receptor KIR-K64 (KIR-K64) mRNA, partial cds
gi|5730921|gb|AF135560.1|AF135560[5730921]

9998: AF135559
Homo sapiens p58 killer cell inhibitory receptor KIR-K61 (KIR-K61) mRNA, partial cds
gi|5730919|gb|AF135559.1|AF135559[5730919]

9999: AF135558
Homo sapiens p58 killer cell inhibitory receptor KIR-K39 (KIR-K39) mRNA, partial cds
gi|5730917|gb|AF135558.1|AF135558[5730917]

10000: AF135557
Homo sapiens p58 killer cell inhibitory receptor KIR-K36 (KIR-K36) mRNA, partial cds
gi|5730915|gb|AF135557.1|AF135557[5730915]

10001: AF135556
Homo sapiens p58 killer cell inhibitory receptor KIR-K15 (KIR-K15) mRNA, partial cds
gi|5730913|gb|AF135556.1|AF135556[5730913]

10002: AF135555
Homo sapiens p58 killer cell inhibitory receptor KIR-K9 (KIR-K9) mRNA, partial cds
gi|5730911|gb|AF135555.1|AF135555[5730911]

10003: AF135554
Homo sapiens p58 killer cell inhibitory receptor KIR-K3 (KIR-K3) mRNA, partial cds
gi|5730909|gb|AF135554.1|AF135554[5730909]

10004: AF135567
Homo sapiens p58 killer cell inhibitory receptor KIR-K7c mRNA, alternatively spliced, partial cds
gi|5730907|gb|AF135567.1|AF135567[5730907]

10005: AF135566
Homo sapiens p58 killer cell inhibitory receptor KIR-K7b mRNA, alternatively spliced, partial cds
gi|5730905|gb|AF135566.1|AF135566[5730905]

10006: AF135565
Homo sapiens p58 killer cell inhibitory receptor KIR-K7a mRNA, alternatively spliced, partial cds
gi|5730903|gb|AF135565.1|AF135565[5730903]

10007: AF135564
Homo sapiens p50 killer cell activating receptor KAR-K1d mRNA, alternatively spliced, partial cds
gi|5730901|gb|AF135564.1|AF135564[5730901]

10008: AF135563
Homo sapiens p50 killer cell activating receptor KAR-K1a mRNA, alternatively spliced, partial cds
gi|5730899|gb|AF135563.1|AF135563[5730899]

10009: AF172932
Homo sapiens MIS type II receptor (MISRII) mRNA, complete cds
gi|5726642|gb|AF172932.1|AF172932[5726642]

10010: AF162790
Homo sapiens Fc gamma receptor III-A gene, partial cds
gi|5726469|gb|AF162790.1|AF162790[5726469]

10012: AF161921
Homo sapiens clone G7 C-C chemokine receptor 5 (CCR5) mRNA, partial cds
gi|5712813|gb|AF161921.1|[5712813]

10013: AF161920
Homo sapiens clone G6 C-C chemokine receptor 5 (CCR5) mRNA, partial cds
gi|5712812|gb|AF161920.1|[5712812]

10014: AF161919
Homo sapiens clone F4 C-C chemokine receptor 5 (CCR5) mRNA, partial cds
gi|5712811|gb|AF161919.1|[5712811]

10015: AF161918
Homo sapiens clone F3 C-C chemokine receptor 5 (CCR5) mRNA, partial cds
gi|5712810|gb|AF161918.1|[5712810]

10016: AF161917
Homo sapiens clone F1.1 C-C chemokine receptor 5 (CCR5) mRNA, partial cds
gi|5712809|gb|AF161917.1|[5712809]

10017: AF161916
Homo sapiens clone H-JM-2 C-C chemokine receptor 5 (CCR5) mRNA, partial cds
gi|5712808|gb|AF161916.1|[5712808]

10018: AF161915
Homo sapiens clone JM-1 C-C chemokine receptor 5 (CCR5) mRNA, partial cds
gi|5712807|gb|AF161915.1|[5712807]

10019: AF161914
Homo sapiens clone 9/8.2 C-C chemokine receptor 5 (CCR5) mRNA, partial cds
gi|5712806|gb|AF161914.1|[5712806]

10020: AF161913
Homo sapiens clone 6-53 C-C chemokine receptor 5 (CCR5) mRNA, partial cds
gi|5712805|gb|AF161913.1|[5712805]

10021: AF161912
Homo sapiens clone 5-53 C-C chemokine receptor 5 (CCR5) mRNA, partial cds
gi|5712804|gb|AF161912.1|[5712804]

10022: AF161911
Homo sapiens clone 4-55 C-C chemokine receptor 5 (CCR5) mRNA, partial cds
gi|5712803|gb|AF161911.1|[5712803]

10023: AF161910
Homo sapiens clone 4-53 C-C chemokine receptor 5 (CCR5) mRNA, partial cds
gi|5712802|gb|AF161910.1|[5712802]

10024: AF161909
Homo sapiens clone 3-55 C-C chemokine receptor 5 (CCR5) mRNA, partial cds
gi|5712801|gb|AF161909.1|[5712801]

10025: E17202
Human cDNA for JEG18 complete cds
gi|5711885|dbj|E17202.1|E17202[5711885]

10026: E17201
Human mRNA for JEG18 complete cds
gi|5711884|dbj|E17201.1|E17201[5711884]

10027: E16188
cDNA encoding G protein-coupled receptor
gi|5710871|dbj|E16188.1|E16188[5710871]

10028: E16187
Partial sequence of cDNA encoding G protein-coupled receptor
gi|5710870|dbj|E16187.1|E16187[5710870]

10029: E16186
Partial sequence of cDNA encoding G protein-coupled receptor
gi|5710869|dbj|E16186.1|E16186[5710869]

10030: E16000

EST sequence containing human G protein-coupling receptor gene
gi|5710683|dbj|E16000.1|E16000[5710683]

10031: E15999
EST sequence containing human G protein-coupling receptor gene
gi|5710682|dbj|E15999.1|E15999[5710682]

10032: E15998
cDNA encoding G protein-coupling receptor protein
gi|5710681|dbj|E15998.1|E15998[5710681]

10033: E15997
cDNA encoding human G protein-coupling receptor protein
gi|5710680|dbj|E15997.1|E15997[5710680]

10034: E15919
cDNA encoding prostaglandin EP3-6 receptor
gi|5710602|dbj|E15919.1|E15919[5710602]

10035: E15918
cDNA encoding prostaglandin EP3-5 receptor
gi|5710601|dbj|E15918.1|E15918[5710601]

10037: E15242
Human mRNA for endothelin B receptor, complete cds
gi|5709925|dbj|E15242.1|E15242[5709925]

10038: E14946
Human mRNA for adrenaline beta 3 receptor
gi|5709629|dbj|E14946.1|E14946[5709629]

10039: E14587
Human mRNA isoform fragment for Vitamin D receptor
gi|5709270|dbj|E14587.1|E14587[5709270]

10040: E14586
Human mRNA isoform fragment for Vitamin D receptor gi|5709269|dbj|E14586.1|E14586[5709269]

10041: E14585
Human mRNA isoform for Vitamin D receptor
gi|5709268|dbj|E14585.1|E14585[5709268]

10042: E14219
Partial sequence of human cDNA encoding a G protein-coupled receptor, 63A2full
gi|5708902|dbj|E14219.1|E14219[5708902]

10043: E14218
Partial sequence of human cDNA encoding a G protein-coupled receptor, 63A2full
gi|5708901|dbj|E14218.1|E14218[5708901]

10044: E14217
Human mRNA for a G protein-coupled receptor, 63A2full, complete cds
gi|5708900|dbj|E14217.1|E14217[5708900]

10046: X83699
Homo sapiens IGF2R gene (subclone pEX1-P)
gi|1006660|emb|X83699.1|HSIGF2RX1[1006660]

10048: AF007790
Homo sapiens ICERE-1 mRNA, complete cds
gi|5670325|gb|AF007790.2|AF007790[5670325]

10054: AF036718
Homo sapiens FGFR signalling adaptor SNT-2 mRNA, complete cds
gi|2708629|gb|AF036718.1|AF036718[2708629]

10056: AF099033
Homo sapiens gamma-aminobutyric acid type B receptor 2 (GABABR2) mRNA, complete cds
gi|5639666|gb|AF099033.1|AF099033[5639666]

10057: AF009221
Homo sapiens leucocyte immunoglobulin-like receptor-1 mRNA, complete cds gi|2267169|gb|AF009221.1|AF009221[2267169]

10058: AF009220
Homo sapiens leucocyte immunoglobulin-like receptor-1 mRNA, complete cds
gi|2267167|gb|AF009220.1|AF009220[2267167]

10059: AF067864
Homo sapiens transferrin receptor 2 alpha (TFR2) mRNA, complete cds
gi|5596369|gb|AF067864.1|AF067864[5596369]

10061: AF040257
Homo sapiens TNF receptor homolog mRNA, partial cds
gi|3170220|gb|AF040257.1|AF040257[3170220]

10062: AF026245
Homo sapiens yotiao mRNA, complete cds
gi|2623067|gb|AF026245.1|AF026245[2623067]

10064: AF163302
Homo sapiens somatostatin receptor interacting protein splice variant a (SSTRIP) mRNA, complete cds
gi|5533304|gb|AF163302.1|AF163302[5533304]

10065: AF153500
Homo sapiens mu opioid receptor (MOR1) gene, partial cds
gi|5524612|gb|AF153500.1|AF153500[5524612]

10066: AH007996
Homo sapiens NK receptor Ly-49L gene, complete cds
gi|5524171|gb|AH007996.1|SEG_HSLY49L[5524171]

10067: AF126038
Homo sapiens NK receptor Ly-49L gene, pseudoexon 7
gi|5524170|gb|AF126038.1|HSLY49L3[5524170]

10068: AF126037
Homo sapiens NK receptor Ly-49L gene, exon 5, pseudoexon 6, and complete cds gi|5524169|gb|AF126037.1|HSLY49L2[5524169]

10069: AF126036
Homo sapiens NK receptor Ly-49L gene, exons 1 through 4
gi|5524168|gb|AF126036.1|HSLY49L1[5524168]

10070: AF081675
Homo sapiens ITIM-containing receptor MAFA-L mRNA, complete cds
gi|3421400|gb|AF081675.1|AF081675[3421400]

10071: AF145782
Homo sapiens 2B4 type I transmembrane protein mRNA, complete cds
gi|5059179|gb|AF145782.1|AF145782[5059179]

10072: AH007960
Homo sapiens receptor tyrosine kinase (EPHA1) gene, complete cds
gi|5453121|gb|AH007960.1|SEG_HSEPHAI[5453121]

10073: AF101171
Homo sapiens receptor tyrosine kinase (EPHA1) gene, exon 18 and complete cds
gi|5453120|gb|AF101171.1|HSEPHAI7[5453120]

10074: AF101170
Homo sapiens receptor tyrosine kinase (EPHA1) gene, exon 17
gi|5453119|gb|AF101170.1|HSEPHAI6[5453119]

10075: AF101169
Homo sapiens receptor tyrosine kinase (EPHA1) gene, exons 12 through 16
gi|5453118|gb|AF101169.1|HSEPHAI5[5453118]

10076: AF101168
Homo sapiens receptor tyrosine kinase (EPHA1) gene, exons 4 through 11
gi|5453117|gb|AF101168.1|HSEPHAI4[5453117]

10077: AF101167
Homo sapiens receptor tyrosine kinase (EPHA1) gene, exon 3
gi|5453116|gb|AF101167.1|HSEPHAI3[5453116]

10078: AF101166
Homo sapiens receptor tyrosine kinase (EPHA1) gene, exon 2
gi|5453115|gb|AF101166.1|HSEPHAI2[5453115]

10079: AF101165
Homo sapiens receptor tyrosine kinase (EPHA1) gene, exon 1
gi|5453114|gb|AF101165.1|HSEPHAI1[5453114]

10080: AF107761
Homo sapiens NK cell receptor (2B4) mRNA, complete cds
gi|5442467|gb|AF107761.2|AF107761[5442467]

10081: AF109127
Homo sapiens stromal cell-derived receptor-1 alpha mRNA, complete cds
gi|5442037|gb|AF109127.1|AF109127[5442037]

10082: AF109126
Homo sapiens stromal cell-derived receptor-1 beta mRNA, complete cds
gi|5442035|gb|AF109126.1|AF109126[5442035]

10084: Y17131
Homo sapiens FGFR2 gene, exon 7 and exon 8 (partial)
gi|3077606|emb|Y17131.1|HSY17131[3077606]

10085: X57829
H.sapiens serotonin 5-HT1a receptor gene
gi|36428|emb|X57829.1|HSSERR51[36428]

10086: AF100762
Homo sapiens thyroid receptor interactor trip15 mRNA, complete cds
gi|5410309|gb|AF100762.1|TRIP15[5410309]

10087: AF109388
Homo sapiens P2X2B receptor mRNA, complete cds
gi|5381338|gb|AF109388.1|AF109388[5381338]

10088: AF109387
Homo sapiens P2X2A receptor mRNA, complete cds
gi|5381336|gb|AF109387.1|AF109387[5381336]

10089: AF118108
Homo sapiens lymphatic endothelium-specific hyaluronan receptor LYVE-1 mRNA, complete cds
gi|5359672|gb|AF118108.1|AF118108[5359672]

10090: AF119711
Homo sapiens cysLT1 LTD4 receptor (CYSLT1) mRNA, complete cds
gi|5353886|gb|AF119711.1|AF119711[5353886]

10091: X72861
H.sapiens gene for beta-3-adrenergic receptor
gi|298094|emb|X72861.1|HSB3A[298094]

10092: AF103906
Homo sapiens vanilloid receptor-like protein (VRL) mRNA, complete cds
gi|5305597|gb|AF103906.1|AF103906[5305597]

10093: AF072873
Homo sapiens frizzled 6 mRNA, complete cds
gi|5305408|gb|AF072873.1|AF072873[5305408]

10095: AF153437
Homo sapiens haplotype val92met/A942G melanocortin 1 receptor (MC1R) gene, complete cds
gi|5257473|gb|AF153437.1|AF153437[5257473]

10096: AF153436
Homo sapiens haplotype A942G melanocortin 1 receptor (MC1R) gene, complete cds
gi|5257472|gb|AF153436.1|AF153436[5257472]

10097: AF153435
Homo sapiens haplotype arg67gln/arg163gln melanocortin 1 receptor (MC1R) gene, complete cds gi|5257471|gb|AF153435.1|AF153435[5257471]

10098: AF153434
Homo sapiens haplotype arg163gln melanocortin 1 receptor (MC1R) gene, complete cds
gi|5257470|gb|AF153434.1|AF153434[5257470]

10099: AF153433
Homo sapiens haplotype arg151cys melanocortin 1 receptor (MC1R) gene, complete cds
gi|5257469|gb|AF153433.1|AF153433[5257469]

10100: AF153432
Homo sapiens haplotype asp84glu melanocortin 1 receptor (MC1R) gene, complete cds
gi|5257468|gb|AF153432.1|AF153432[5257468]

10101: AF153431
Homo sapiens melanocortin 1 receptor (MC1R) gene, complete cds
gi|5257467|gb|AF153431.1|AF153431[5257467]

10103: AH007879
Homo sapiens macrophage receptor (MARCO) gene, complete cds
gi|5231091|gb|AH007879.1|SEG_HSMARCO[5231091]

10104: AF128186
Homo sapiens macrophage receptor (MARCO) gene, exon 17 and complete cds
gi|5231090|gb|AF128186.1|HSMARCO15[5231090]

10105: AF128185
Homo sapiens macrophage receptor (MARCO) gene, exon 16
gi|5231089|gb|AF128185.1|HSMARCO14[5231089]

10106: AF128184
Homo sapiens macrophage receptor (MARCO) gene, exon 15
gi|5231088|gb|AF128184.1|HSMARCO13[5231088]

10107: AF128183
Homo sapiens macrophage receptor (MARCO) gene, exon 14
gi|5231087|gb|AF128183.1|HSMARCO12[5231087]

10108: AF128182
Homo sapiens macrophage receptor (MARCO) gene, exon 13
gi|5231086|gb|AF128182.1|HSMARCO11[5231086]

10109: AF128181
Homo sapiens macrophage receptor (MARCO) gene, exons 11 and 12
gi|5231085|gb|AF128181.1|HSMARCO10[5231085]

10110: AF128180
Homo sapiens macrophage receptor (MARCO) gene, exons 9 and 10
gi|5231084|gb|AF128180.1|HSMARCO09[5231084]

10111: AF128179
Homo sapiens macrophage receptor (MARCO) gene, exon 8
gi|5231083|gb|AF128179.1|HSMARCO08[5231083]

10112: AF128178
Homo sapiens macrophage receptor (MARCO) gene, exon 7
gi|5231082|gb|AF128178.1|HSMARCO07[5231082]

10113: AF128177
Homo sapiens macrophage receptor (MARCO) gene, exon 6
gi|5231081|gb|AF128177.1|HSMARCO06[5231081]

10114: AF128176
Homo sapiens macrophage receptor (MARCO) gene, exon 5
gi|5231080|gb|AF128176.1|HSMARCO05[5231080]

10115: AF128175
Homo sapiens macrophage receptor (MARCO) gene, exon 4
gi|5231079|gb|AF128175.1|HSMARCO04[5231079]

10116: AF128174

Homo sapiens macrophage receptor (MARCO) gene, exon 3
gi|5231078|gb|AF128174.1|HSMARCO03[5231078]

10117: AF128173
Homo sapiens macrophage receptor (MARCO) gene, exon 2
gi|5231077|gb|AF128173.1|HSMARCO02[5231077]

10118: AF128172
Homo sapiens macrophage receptor (MARCO) gene, exon 1
gi|5231076|gb|AF128172.1|HSMARCO01[5231076]

10140: D50855
Human mRNA for Ca-sensing receptor, complete cds
gi|904209|dbj|D50855.1|HUMCASR[904209]

10141: D49783
Human gene for histamine H2 receptor, complete cds
gi|728495|dbj|D49783.1|HUMHH2R[728495]

10142: D16826
Human gene for fourth somatostatin receptor subtype
gi|693907|dbj|D16826.1|HUMSSTR4[693907]

10143: D29984
Human mRNA for monocyte chemoattractant protein 1 receptor (MCP-1 receptor), complete cds
gi|531246|dbj|D29984.1|HUMMCP1R[531246]

10144: D14436
Human gene for histamine H1-receptor, complete cds
gi|506335|dbj|D14436.1|HUMHH1RE[506335]

10145: D16827
Human gene for fifth somatostatin receptor subtype
gi|487683|dbj|D16827.1|HUMSSTR5[487683]

10146: D14717

Human mRNA for large erk kinase
gi|285916|dbj|D14717.1|HUMERK[285916]

10147: AF073515
Homo sapiens cytokine type 1 receptor CRLP-1 precursor, mRNA, complete cds
gi|5106394|gb|AF073515.1|AF073515[5106394]

10148: AH007696
Homo sapiens fibroblast growth factor receptor 2 (FGFR2) gene, partial cds; fibroblast growth factor receptor 2 Ksam IV secreted isoform (FGFR2) gene, complete cds; fibroblast growth factor receptor (FGFR2) gene, alternative splice products, partial cds; and fibroblast growth factor receptor 2 (FGFR2) gene, partial cds
gi|4808621|gb|AH007696.1|SEG_HSFGFR2A[4808621]

10149: AF097354
Homo sapiens fibroblast growth factor receptor 2 (FGFR2) gene, exon 20, alternative splice products and partial cds
gi|4808620|gb|AF097354.1|HSFGFR2A19[4808620]

10150: AF097353
Homo sapiens fibroblast growth factor receptor 2 (FGFR2) gene, exon 19, alternative splice products and partial cds
gi|4808619|gb|AF097353.1|HSFGFR2A18[4808619]

10151: AF097352
Homo sapiens fibroblast growth factor receptor 2 (FGFR2) gene, exon 18
gi|4808618|gb|AF097352.1|HSFGFR2A17[4808618]

10152: AF097351
Homo sapiens fibroblast growth factor receptor 2 (FGFR2) gene, exon 17
gi|4808617|gb|AF097351.1|HSFGFR2A16[4808617]

10153: AF097350
Homo sapiens fibroblast growth factor receptor 2 (FGFR2) gene, exon 16
gi|4808616|gb|AF097350.1|HSFGFR2A15[4808616]

10154: AF097349

Homo sapiens fibroblast growth factor receptor 2 (FGFR2) gene, exon 15
gi|4808615|gb|AF097349.1|HSFGFR2A14[4808615]

10155: AF097348
Homo sapiens fibroblast growth factor receptor 2 (FGFR2) gene, exon 14
gi|4808614|gb|AF097348.1|HSFGFR2A13[4808614]

10156: AF097347
Homo sapiens fibroblast growth factor receptor 2 (FGFR2) gene, exon 13
gi|4808613|gb|AF097347.1|HSFGFR2A12[4808613]

10157: AF097346
Homo sapiens fibroblast growth factor receptor 2 (FGFR2) gene, exon 12
gi|4808612|gb|AF097346.1|HSFGFR2A11[4808612]

10158: AF097345
Homo sapiens fibroblast growth factor receptor 2 (FGFR2) gene, exons 11 and 11'
gi|4808611|gb|AF097345.1|HSFGFR2A10[4808611]

10159: AF097344
Homo sapiens fibroblast growth factor receptor 2 (FGFR2) gene, exon 10
gi|4808610|gb|AF097344.1|HSFGFR2A09[4808610]

10160: AF097343
Homo sapiens fibroblast growth factor receptor 2 (FGFR2) gene, exon 9
gi|4808609|gb|AF097343.1|HSFGFR2A08[4808609]

10161: AF097342
Homo sapiens fibroblast growth factor receptor 2 (FGFR2) gene, exon 8
gi|4808608|gb|AF097342.1|HSFGFR2A07[4808608]

10162: AF097341
Homo sapiens fibroblast growth factor receptor 2 (FGFR2) gene, exons 6 and 7, alternative splice products and partial cds
gi|4808607|gb|AF097341.1|HSFGFR2A06[4808607]

10163: AF097340

Homo sapiens fibroblast growth factor receptor 2 (FGFR2) gene, exon 5, alternative splice products and partial cds
gi|4808606|gb|AF097340.1|HSFGFR2A05[4808606]

10164: AF097339
Homo sapiens fibroblast growth factor receptor 2 (FGFR2) gene, exon 4
gi|4808605|gb|AF097339.1|HSFGFR2A04[4808605]

10165: AF097338
Homo sapiens fibroblast growth factor receptor 2 (FGFR2) gene, exon 3
gi|4808604|gb|AF097338.1|HSFGFR2A03[4808604]

10166: AF097337
Homo sapiens fibroblast growth factor receptor 2 (FGFR2) gene, exon 2
gi|4808603|gb|AF097337.1|HSFGFR2A02[4808603]

10167: AF097336
Homo sapiens fibroblast growth factor receptor 2 (FGFR2) gene, exon 1
gi|4808602|gb|AF097336.1|HSFGFR2A01[4808602]

10168: U58146
Homo sapiens alternatively spliced interleukin-6 receptor beta chain mRNA, partial cds
gi|2253597|gb|U58146.1|HSU58146[2253597]

10169: AF134395
Homo sapiens CARD-like apoptotic protein (CLAP) mRNA, complete cds
gi|5070371|gb|AF134395.1|AF134395[5070371]

10170: AF015044
Homo sapiens EH-binding protein mRNA, partial cds
gi|4102712|gb|AF015044.1|AF015044[4102712]

10171: AF015043
Homo sapiens EH-binding protein mRNA, partial cds
gi|4102710|gb|AF015043.1|AF015043[4102710]

10172: AF145207
Homo sapiens CCR9 chemokine receptor (CCR9) mRNA, partial cds
gi|5052417|gb|AF145207.1|AF145207[5052417]

10173: AB018549
Homo sapiens MD-2 mRNA, complete cds
gi|5051739|dbj|AB018549.1|AB018549[5051739]

10174: AH007443
Homo sapiens chromosome 19 clone cosmid R31931 map 19q13.4
gi|4322573|gb|AH007443.1|SEG_HSCD89S[4322573]

10175: AF091544
Homo sapiens myeloid FcalphaRI (CD89) gene, 3' sequence
gi|4322572|gb|AF091544.1|HSCD89S2[4322572]

10177: AF152962
Homo sapiens somatostatin receptor type 5 (SSTR5) gene, promoter region and partial cds
gi|5031446|gb|AF152962.1|AF152962[5031446]

10178: AF140538
Homo sapiens histamine H3 receptor mRNA, complete cds
gi|5031290|gb|AF140538.1|AF140538[5031290]

10179: AJ238896
Homo sapiens partial RAGE gene, exons 9 to 11
gi|4867820|emb|AJ238896.1|HSA238896[4867820]

10180: AF039904
Homo sapiens cosmid D66B10, chromosome 21 5' of IFNAR1
gi|2853622|gb|AF039904.1|AF039904[2853622]

10181: AF039905
Homo sapiens cosmid Q95D4, chromosome 21 5' of IFNAR2
gi|2766549|gb|AF039905.1|AF039905[2766549]

10182: AF039907
Homo sapiens cosmid Q50G2, chromosome 21 3' of IFNAR1
gi|2754858|gb|AF039907.1|AF039907[2754858]

10183: AB020807
Homo sapiens mRNA for TLR6, complete cds
gi|5006247|dbj|AB020807.1|AB020807[5006247]

10184: AF144308
Homo sapiens putative G protein-coupled receptor (DL1R) mRNA, complete cds
gi|4959876|gb|AF144308.1|AF144308[4959876]

10185: AF107262
Homo sapiens central cannabinoid receptor (CB1K5) mRNA, complete cds
gi|4959366|gb|AF107262.1|AF107262[4959366]

10263: AH007742
Homo sapiens neuronal acetylcholine receptor beta-3 subunit precursor (CHRNB3) gene, complete cds
gi|4927249|gb|AH007742.1|SEG_HSCHRNB[4927249]

10264: AF140765
Homo sapiens neuronal acetylcholine receptor beta-3 subunit precursor (CHRNB3) gene, exon 6 and complete cds
gi|4927248|gb|AF140765.1|HSCHRNB6[4927248]

10265: AF140764
Homo sapiens neuronal acetylcholine receptor beta-3 subunit precursor (CHRNB3) gene, exon 5
gi|4927247|gb|AF140764.1|HSCHRNB5[4927247]

10266: AF140763
Homo sapiens neuronal acetylcholine receptor beta-3 subunit precursor (CHRNB3) gene, exon 4
gi|4927246|gb|AF140763.1|HSCHRNB4[4927246]

10267: AF140762
Homo sapiens neuronal acetylcholine receptor beta-3 subunit precursor (CHRNB3)

gene, exon 3
gi|4927245|gb|AF140762.1|HSCHRNB3[4927245]

10268: AF140761
Homo sapiens neuronal acetylcholine receptor beta-3 subunit precursor (CHRNB3) gene, exon 2
gi|4927244|gb|AF140761.1|HSCHRNB2[4927244]

10269: AF140760
Homo sapiens neuronal acetylcholine receptor beta-3 subunit precursor (CHRNB3) gene, exon 1
gi|4927243|gb|AF140760.1|HSCHRNB1[4927243]

10270: U19261
Homo sapiens Epstein-Barr virus-induced protein mRNA, complete cds
gi|675461|gb|U19261.1|HSU19261[675461]

10272: AF105261
Homo sapiens natural killer cell receptor 2B4 mRNA, complete cds
gi|4894519|gb|AF105261.1|AF105261[4894519]

10273: AH007727
Homo sapiens prolactin receptor gene, complete cds
gi|4886767|gb|AH007727.1|SEG_HSPLR[4886767]

10274: AF091870
Homo sapiens prolactin receptor gene, alternatively spliced, exon 10 and complete cds
gi|4886766|gb|AF091870.1|HSPLR12[4886766]

10275: AF091869
Homo sapiens prolactin receptor gene, exon 9
gi|4886765|gb|AF091869.1|HSPLR11[4886765]

10276: AF091868
Homo sapiens prolactin receptor gene, exon 8
gi|4886764|gb|AF091868.1|HSPLR10[4886764]

10277: AF091867
Homo sapiens prolactin receptor gene, exon 7
gi|4886763|gb|AF091867.1|HSPLR09[4886763]

10278: AF091866
Homo sapiens prolactin receptor gene, exon 6
gi|4886762|gb|AF091866.1|HSPLR08[4886762]

10279: AF091865
Homo sapiens prolactin receptor gene, exon 5
gi|4886761|gb|AF091865.1|HSPLR07[4886761]

10280: AF091864
Homo sapiens prolactin receptor gene, exon 4
gi|4886760|gb|AF091864.1|HSPLR06[4886760]

10281: AF091863
Homo sapiens prolactin receptor gene, exon 3
gi|4886759|gb|AF091863.1|HSPLR05[4886759]

10282: AF091862
Homo sapiens prolactin receptor gene, exon 2
gi|4886758|gb|AF091862.1|HSPLR04[4886758]

10283: AF091859
Homo sapiens prolactin receptor gene, promoter region and alternative exons 1
gi|4886757|gb|AF091859.1|HSPLR01[4886757]

10284: AJ132337
Homo sapiens mRNA for chemokine receptor CCR9
gi|4886431|emb|AJ132337.1|HSA132337[4886431]

10285: AF120152
Mus musculus cytokine receptor-like molecule 9 (Creme9) mRNA, complete cds
gi|4884628|gb|AF120152.1|AF120152[4884628]

10286: AF120151
Homo sapiens cytokine receptor-like molecule 9 (CREME9) mRNA, complete cds
gi|4884626|gb|AF120151.1|AF120151[4884626]

10287: D13814
Homo sapiens mRNA for angiotensin II type 1b receptor, complete cds
gi|471120|dbj|D13814.1|HUMAGRT1B[471120]

10288: AJ236922
Homo sapiens mRNA for metabotropic glutamate receptor 8c
gi|4456479|emb|AJ236922.1|HSA236922[4456479]

10289: AJ236921
Homo sapiens mRNA for metabotropic glutamate receptor 8b
gi|4456477|emb|AJ236921.1|HSA236921[4456477]

10478: AF106858
Homo sapiens G-protein-coupled receptor (GPR56) mRNA, complete cds
gi|4836764|gb|AF106858.1|AF106858[4836764]

10479: AF095784
Homo sapiens GABA-B receptor R2 (GABBR2) mRNA, complete cds
gi|4836217|gb|AF095784.1|AF095784[4836217]

10500: AJ006520
Homo sapiens mRNA for m1 muscarinic acetylcholine receptor protein, partial
gi|3292964|emb|AJ006520.1|HSA6520[3292964]

10693: AF110907
Homo sapiens TNF-receptor associated factor-3 (TRAF-3) gene, exons 1a and 1b, complete sequence
gi|4761208|gb|AF110907.1|AF110907[4761208]

10694: AJ002425
Homo sapiens mRNA for p65 protein
gi|4753767|emb|AJ002425.2|HSAJ2425[4753767]

10697: Y15220
Homo sapiens mRNA for chemokine IP-9
gi|4225953|emb|Y15220.1|HSCHIP9RN[4225953]

10698: AJ005282
Homo sapiens mRNA for NPR-Bi
gi|3059110|emb|AJ005282.1|HSAJ5282[3059110]

10699: AJ012188
Homo sapiens mRNA for GABAB receptor, subunit 2
gi|3776097|emb|AJ012188.1|HSA012188[3776097]

10700: AJ012187
Homo sapiens mRNA for GABAB receptor, subunit 1c,
gi|3776095|emb|AJ012187.1|HSA012187[3776095]

10701: AJ012186
Homo sapiens mRNA for GABAB receptor, subunit 1b
gi|3776093|emb|AJ012186.1|HSA012186[3776093]

10702: AJ012185
Homo sapiens mRNA for GABAB-receptor, subunit 1a
gi|3776072|emb|AJ012185.1|HSA012185[3776072]

10704: AF129112
Homo sapiens vanilloid receptor-like protein 1 (VRL-1) mRNA, complete cds
gi|4589140|gb|AF129112.1|AF129112[4589140]

10705: AF068265
Homo sapiens monocyte chemoattractant protein 1 receptor (CCR2) gene promoter and mRNA, partial sequence
gi|4587865|gb|AF068265.1|AF068265[4587865]

10706: AB020625
Homo sapiens mRNA for butyrophilin like receptor, complete cds
gi|4587208|dbj|AB020625.1|AB020625[4587208]

10709: AH007576

Homo sapiens killer cell inhibitory receptor G9P gene, complete cds
gi|4581764|gb|AH007576.1|SEG_HSKIRG9P[4581764]

10710: AF110035
Homo sapiens killer cell inhibitory receptor G9P gene, complete cds
gi|4581763|gb|AF110035.1|HSKIRG9P4[4581763]

10711: AF110034
Homo sapiens killer cell inhibitory receptor G9P gene, partial sequence
gi|4581762|gb|AF110034.1|HSKIRG9P3[4581762]

10712: AF110033
Homo sapiens killer cell inhibitory receptor G9P gene, partial sequence
gi|4581761|gb|AF110033.1|HSKIRG9P2[4581761]

10713: AF110032
Homo sapiens killer cell inhibitory receptor G9P gene, partial sequence
gi|4581760|gb|AF110032.1|HSKIRG9P1[4581760]

10714: AF114165
Homo sapiens endothelin receptor B delta 3 mRNA, complete cds
gi|4580923|gb|AF114165.1|AF114165[4580923]

10717: AF105999
Homo sapiens acetylcholine receptor epsilon subunit (CHRNE) gene, complete cds
gi|4580858|gb|AF105999.1|AF105999[4580858]

10718: AH007573
Homo sapiens killer inhibitory receptor 1 (KIR1) gene, complete cds; and kill inhibitory receptor 2 (KIR2) gene, partial cds
gi|4580703|gb|AH007573.1|SEG_HS2KIR[4580703]

10720: AF134316
Homo sapiens killer inhibitory receptor 4-1-2 (KIR412) gene, exon 5 and partial cds
gi|4580701|gb|AF134316.1|SEG_HS2KIR7[4580701]

10721: AF134315
Homo sapiens killer inhibitory receptor 4-1-2 (KIR412) gene, exon 4
gi|4580700|gb|AF134315.1|SEG_HS2KIR6[4580700]

10723: AF134313
Homo sapiens killer inhibitory receptor 4-1-2 (KIR412) gene, exon 2 and
pseudoexon 3
gi|4580698|gb|AF134313.1|SEG_HS2KIR4[4580698]

10724: AF134312
Homo sapiens killer inhibitory receptor 4-1-1 (KIR411) gene, exons 7, 8 and 9
and partial cds; killer inhibitory receptor 4-1-2 (KIR412) gene, exon 1
gi|4580697|gb|AF134312.1|SEG_HS2KIR3[4580697]

10725: AF134311
Homo sapiens killer inhibitory receptor 4-1-1 (KIR411) gene, exon 6
gi|4580696|gb|AF134311.1|SEG_HS2KIR2[4580696]

10727: AH007572
Homo sapiens killer inhibitory receptor (KIR) gene, partial cds
gi|4580693|gb|AH007572.1|SEG_HSKIRP[4580693]

10728: AF133900
Homo sapiens killer inhibitory receptor cl 2-3 (KIRCL23) gene, exons 7, 8, and 9
and partial cds
gi|4580692|gb|AF133900.1|HSKIRP5[4580692]

10729: AF133899
Homo sapiens killer inhibitory receptor cl 2-3 (KIRCL23) gene, exon 6
gi|4580691|gb|AF133899.1|HSKIRP4[4580691]

10730: AF133898
Homo sapiens killer inhibitory receptor cl 2-3 (KIRCL23) gene, exon 5
gi|4580690|gb|AF133898.1|HSKIRP3[4580690]

10731: AF133897

Homo sapiens killer inhibitory receptor cl 2-3 (KIRCL23) gene, exon 4
gi|4580689|gb|AF133897.1|HSKIRP2[4580689]

10732: AF133896
Homo sapiens killer inhibitory receptor cl 2-3 (KIRCL23) gene, pseudoexon 3
gi|4580688|gb|AF133896.1|HSKIRP1[4580688]

10733: AF133901
Homo sapiens killer inhibitory receptor 2-2-1 (KIR221) and killer inhibitory
receptor 2-2-2 (KIR222) genes, partial cds
gi|4580682|gb|AF133901.1|AF133901[4580682]

10736: AF069755
Homo sapiens orphan G protein-coupled receptor HG20 (HG20) mRNA, complete cds
gi|4091932|gb|AF069755.1|AF069755[4091932]

10738: AC007229
Homo sapiens chromosome 19, cosmid R34187, complete sequence
gi|4567173|gb|AC007229.1|AC007229[4567173]

10740: AF125303
Homo sapiens glucocorticoid-induced TNFR-related protein ligand (TNFSF18) mRNA,
complete cds
gi|4558500|gb|AF125303.1|AF125303[4558500]

10742: AF058762
Homo sapiens galanin receptor subtype 2 (GALNR2) gene, complete cds
gi|3170598|gb|AF058762.1|AF058762[3170598]

10743: AF096786
Homo sapiens chromosome 2 G protein-coupled receptor (GPR55) gene, complete cds
gi|4545136|gb|AF096786.1|AF096786[4545136]

10745: AF096784
Homo sapiens chromosome 1 G protein-coupled receptor (GPR52) gene, complete cds
gi|4545133|gb|AF096784.1|AF096784[4545133]

10746: AF119815

Homo sapiens G-protein coupled receptor (NPGPR) mRNA, complete cds
gi|4530468|gb|AF119815.1|AF119815[4530468]

10749: AF098664
Homo sapiens olfactory receptor-like protein (OR2C1) gene, complete cds
gi|3982606|gb|AF098664.1|AF098664[3982606]

10752: AF090131
Homo sapiens clone b312C2EN9 LDL receptor-related protein 6 gene, partial cds, and CpG island sequence
gi|4494988|gb|AF090131.1|AF090131[4494988]

10778: X95583
H.sapiens mRNA for monocyte chemotactic protein-1 (MCP-1) receptor
gi|4468944|emb|X95583.1|HSMCP1REC[4468944]

10791: AJ131757
Homo sapiens olr1 gene
gi|4468343|emb|AJ131757.1|HSA131757[4468343]

10792: X58674
H.sapiens RNA for receptor for C5a anaphylatoxin
gi|29568|emb|X58674.1|HSC5ANAPL[29568]

10793: U51134
Homo sapiens calcitonin gene-related peptide receptor component protein mRNA, complete cds
gi|4097252|gb|U51134.1|HSU51134[4097252]

10794: Y13464
Homo sapiens mRNA for cholecystokinin B receptor
gi|3287189|emb|Y13464.1|HSY13464[3287189]

10795: Z66558
H.sapiens FAS/Apo1 gene (Del B1 mutation; partial)
gi|1150414|emb|Z66558.1|HSFASAPOC[1150414]

10796: Z66557
H.sapiens of FAS/Apo1 gene (partial)
gi|1150413|emb|Z66557.1|HSFASAPOB[1150413]

10797: Z66556
H.sapiens FASExo8Del mRNA
gi|1150412|emb|Z66556.1|HSFASAPOA[1150412]

10825: AF118266
Homo sapiens orphan G protein-coupled receptor GPR45 (GPR45) gene, complete cds
gi|4455062|gb|AF118266.1|AF118266[4455062]

10826: AF118265
Homo sapiens orphan G protein-coupled receptor GPR44 (GPR44) gene, complete cds
gi|4455060|gb|AF118265.1|AF118265[4455060]

10827: Y18046
Homo sapiens mRNA for FOP (FGFR1 oncogene partner)
gi|4454262|emb|Y18046.1|HSAY18046[4454262]

10828: AJ006276
Homo sapiens mRNA for transient receptor potential protein TRP6
gi|4454260|emb|AJ006276.1|HSAJ6276[4454260]

10829: M13918
Homo sapiens fibronectin receptor alpha-subunit precursor (ITGA5) mRNA, partial cds
gi|4464190|gb|M13918.2|HUMFNRAS[4464190]

10831: D13515
Homo sapiens mRNA for key subunit of N-methyl-D-aspartate receptor, complete cds
gi|219919|dbj|D13515.1|HUMMARR[219919]

10832: D10583
Homo sapiens mRNA for IgE receptor beta subunit, complete cds
gi|219881|dbj|D10583.1|HUMIGERB[219881]

10834: AH007490
Homo sapiens gibbon ape leukemia virus receptor 1 (SLC20A1) gene, partial cds
gi|4416260|gb|AH007490.1|SEG_HSGLVR1G[4416260]

10835: AF102063
Homo sapiens gibbon ape leukemia virus receptor 1 (SLC20A1) gene, exon 11 and complete cds
gi|4416259|gb|AF102063.1|HSGLVR1G5[4416259]

10836: AF102062
Homo sapiens gibbon ape leukemia virus receptor 1 (SLC20A1) gene, exons 7 through 10
gi|4416258|gb|AF102062.1|HSGLVR1G4[4416258]

10837: AF102061
Homo sapiens gibbon ape leukemia virus receptor 1 (SLC20A1) gene, exon 6
gi|4416257|gb|AF102061.1|HSGLVR1G3[4416257]

10838: AF102060
Homo sapiens gibbon ape leukemia virus receptor 1 (SLC20A1) gene, exon 5
gi|4416256|gb|AF102060.1|HSGLVR1G2[4416256]

10839: AF102059
Homo sapiens gibbon ape leukemia virus receptor 1 (SLC20A1) gene, exons 1 through 4
gi|4416255|gb|AF102059.1|HSGLVR1G1[4416255]

10840: AF098798
Homo sapiens unknown mRNA
gi|4416073|gb|AF098798.1|AF098798[4416073]

10841: AF118670
Homo sapiens orphan G protein-coupled receptor (GPR34) gene, complete cds
gi|4325085|gb|AF118670.1|AF118670[4325085]

10842: AF053072
Homo sapiens GABA subunit A receptor alpha 6 precursor, gene, partial cds
gi|4405812|gb|AF053072.1|AF053072[4405812]

10843: AF052539
Homo sapiens chemokine receptor 5 (CCR5) gene, CCR5-CYS allele, complete cds
gi|4337455|gb|AF052539.1|AF052539[4337455]

10844: AF117713
Homo sapiens AITR ligand (TL6) mRNA, complete cds
gi|4378801|gb|AF117713.1|AF117713[4378801]

10845: AF117297
Homo sapiens TNF receptor superfamily activation-inducible protein mRNA, complete cds
gi|4378799|gb|AF117297.1|AF117297[4378799]

10974: Z29585
H.sapiens gene for high affinity IgE receptor alpha chain
gi|452350|emb|Z29585.1|HSHAIGER[452350]

10975: AF050154
Homo sapiens clone F19374 APO E-C2 gene cluster, complete sequence
gi|4105701|gb|AF050154.1|AF050154[4105701]

10981: X97881
H.sapiens mRNA for G protein coupled receptor kinase, GRK4D
gi|1770427|emb|X97881.1|HSGRK4D[1770427]

10982: X97880
H.sapiens mRNA for G protein coupled receptor kinase, GRK4C
gi|1770425|emb|X97880.1|HSGRK4C[1770425]

10983: X97879
H.sapiens mRNA for G protein coupled receptor kinase, GRK4B
gi|1770423|emb|X97879.1|HSGRK4B[1770423]

10984: AJ007787
Homo sapiens CHRNA3 gene, exon 6, partial
gi|4164387|emb|AJ007787.1|HSA7787[4164387]

10985: AJ007786
Homo sapiens CHRNA3 gene, exon 5
gi|4164386|emb|AJ007786.1|HSA7786[4164386]

10986: AJ007785
Homo sapiens CHRNA3 gene, exon 4
gi|4164383|emb|AJ007785.1|HSA7785[4164383]

10987: AJ007784
Homo sapiens CHRNA3 gene, exons 2 to 3
gi|4164382|emb|AJ007784.1|HSA7784[4164382]

10988: AJ007783
Homo sapiens CHRNA3 gene, exon 1 and joined CDS
gi|4164380|emb|AJ007783.1|HSA7783[4164380]

10989: AJ001939
Homo sapiens CHRNB2 gene, exon 6
gi|3766463|emb|AJ001939.1|HSAJ1939[3766463]

10990: AJ001938
Homo sapiens CHRNB2 gene, exon 5
gi|3766454|emb|AJ001938.1|HSAJ1938[3766454]

10991: AJ001937
Homo sapiens CHRNB2 gene, exon 4
gi|3766453|emb|AJ001937.1|HSAJ1937[3766453]

10992: AJ001936
Homo sapiens CHRNB2 gene, exon 2 and exon 3
gi|3766452|emb|AJ001936.1|HSAJ1936[3766452]

10993: AJ001935
Homo sapiens CHRNB2 gene, exon 1 (and joined CDS)
gi|3766450|emb|AJ001935.1|HSAJ1935[3766450]

10998: AJ003147
Homo sapiens complete genomic sequence between D16S3070 and D16S3275, containing Familial Mediterranean Fever gene disease
gi|2808656|emb|AJ003147.1|HSAJ03147[2808656]

11000: AJ225029
Homo sapiens mRNA for GABA-B R1b receptor
gi|3892873|emb|AJ225029.1|HSA225029[3892873]

11004: AJ003147
Homo sapiens complete genomic sequence between D16S3070 and D16S3275, containing Familial Mediterranean Fever gene disease
gi|2808656|emb|AJ003147.1|HSAJ03147[2808656]

11006: AJ225029
Homo sapiens mRNA for GABA-B R1b receptor
gi|3892873|emb|AJ225029.1|HSA225029[3892873]

11007: AJ225028
Homo sapiens mRNA for GABA-B R1a receptor
gi|3892593|emb|AJ225028.1|HSA225028[3892593]

11092: AJ132194
Homo sapiens olfr89 gene
gi|4160227|emb|AJ132194.1|HSA132194[4160227]

11093: AJ012753
Homo sapiens RAGE gene (partial), exon 2
gi|4034482|emb|AJ012753.1|HSA012753[4034482]

11094: AJ012332
Homo sapiens IL-1R gene cluster PAC contig, centromeric STS, sequence tagged site
gi|4128031|emb|AJ012332.1|HSA012332[4128031]

11095: AJ012331
Homo sapiens IL-1R gene cluster PAC contig, telomeric STS, sequence tagged site gi|4128030|emb|AJ012331.1|HSA012331[4128030]

11097: AJ011701
Homo sapiens TRHR gene promoter and exons 1-2, partial
gi|4128016|emb|AJ011701.1|HSA011701[4128016]

11098: AJ010191
Homo sapiens gababr1 receptor gene, exon 18
gi|3980509|emb|AJ010191.1|HSA010191[3980509]

11099: AJ010190
Homo sapiens gababr1 receptor gene, exon 17
gi|3980507|emb|AJ010190.1|HSA010190[3980507]

11100: AJ010189
Homo sapiens gababr1 receptor gene, exon 16
gi|3980504|emb|AJ010189.1|HSA010189[3980504]

11101: AJ010188
Homo sapiens gababr1 receptor gene, exon 15
gi|3980502|emb|AJ010188.1|HSA010188[3980502]

11102: AJ010187
Homo sapiens gababr1 receptor gene, exon 14
gi|3980500|emb|AJ010187.1|HSA010187[3980500]

11103: AJ010186
Homo sapiens gababr1 receptor gene, exon 13
gi|3980498|emb|AJ010186.1|HSA010186[3980498]

11104: AJ010185
Homo sapiens gababr1 receptor gene, exon 12
gi|3980496|emb|AJ010185.1|HSA010185[3980496]

11105: AJ010184
Homo sapiens gababr1 receptor gene, exon 11
gi|3980494|emb|AJ010184.1|HSA010184[3980494]

11106: AJ010183
Homo sapiens gababr1 receptor gene, exon 10
gi|3980492|emb|AJ010183.1|HSA010183[3980492]

11107: AJ010182
Homo sapiens gababr1 receptor gene, exon 9
gi|3980490|emb|AJ010182.1|HSA010182[3980490]

11108: AJ010181
Homo sapiens gababr1 receptor gene, exon 8
gi|3980488|emb|AJ010181.1|HSA010181[3980488]

11109: AJ010180
Homo sapiens gababr1 receptor gene, exon 7
gi|3980486|emb|AJ010180.1|HSA010180[3980486]

11110: AJ010179
Homo sapiens gababr1 receptor gene, exon 6
gi|3980484|emb|AJ010179.1|HSA010179[3980484]

11111: AJ010178
Homo sapiens gababr1 receptor gene, exon 5
gi|3980482|emb|AJ010178.1|HSA010178[3980482]

11112: AJ010177
Homo sapiens gababr1 receptor gene, exon 4
gi|3980481|emb|AJ010177.1|HSA010177[3980481]

11113: AJ010176
Homo sapiens gababr1 receptor gene, exon 3
gi|3980480|emb|AJ010176.1|HSA010176[3980480]

11114: AJ010175
Homo sapiens gababr1 receptor gene, exon 2
gi|3980479|emb|AJ010175.1|HSA010175[3980479]

11115: AJ010174
Homo sapiens gababr1 receptor gene, exon 1
gi|3980477|emb|AJ010174.1|HSA010174[3980477]

11116: AJ010173
Homo sapiens gababr1 receptor gene, exon 1a4
gi|3980475|emb|AJ010173.1|HSA010173[3980475]

11117: AJ010172
Homo sapiens gababr1 receptor gene, exon 1a3
gi|3980472|emb|AJ010172.1|HSA010172[3980472]

11118: AJ010171
Homo sapiens gababr1 receptor gene, exon 1a2
gi|3980469|emb|AJ010171.1|HSA010171[3980469]

11119: AJ010170
Homo sapiens gababr1 receptor gene, exon 1a1
gi|3980465|emb|AJ010170.1|HSA010170[3980465]

11121: AF061022
Homo sapiens CTH gene, complete cds
gi|4335930|gb|AF061022.1|AF061022[4335930]

11122: AF052041
Homo sapiens olfactory receptor gene cluster, complete sequence
gi|4335873|gb|AF052041.1|AF052041[4335873]

11124: AC006953
Homo sapiens chromosome 19, cosmid R28316, complete sequence
gi|4335701|gb|AC006953.1|AC006953[4335701]

11125: AF105367
Homo sapiens glucagon-like peptide-2 receptor precursor (GLP2R) mRNA, complete cds
gi|4324490|gb|AF105367.1|AF105367[4324490]

11434: AH007439
Homo sapiens chromosome X
gi|4322454|gb|AH007439.1|SEG_HSIL2RGIN[4322454]

11435: AF085452
Homo sapiens interleukin-2 receptor gamma chain (IL2RG) gene, intron 5, partial sequence
gi|4322453|gb|AF085452.1|HSIL2RGIN2[4322453]

11436: AF085451
Homo sapiens interleukin-2 receptor gamma chain (IL2RG) gene, intron 4, partial sequence
gi|4322452|gb|AF085451.1|HSIL2RGIN1[4322452]

11437: AF065213
Homo sapiens advanced glycosylation end product-specific receptor (RAGE) gene, intron 3, partial sequence
gi|4321945|gb|AF065213.1|AF065213[4321945]

11438: AF065212
Homo sapiens patient M1 advanced glycosylation end product-specific receptor (RAGE) gene, exon 3 and partial cds
gi|4321943|gb|AF065212.1|AF065212[4321943]

11439: AF065211
Homo sapiens patient M21 advanced glycosylation end product-specific receptor (RAGE) gene, exon 3 and partial cds
gi|4321941|gb|AF065211.1|AF065211[4321941]

11440: AF065210
Homo sapiens patient M20 advanced glycosylation end product-specific receptor (RAGE) gene, exon 3 and partial cds
gi|4321939|gb|AF065210.1|AF065210[4321939]

11441: AF051305
Homo sapiens beta chemokine receptor (CCR1) gene, promoter region and exon 1
gi|4321648|gb|AF051305.1|AF051305[4321648]

11442: U87223
Homo sapiens contactin associated protein (Caspr) mRNA, complete cds
gi|1857707|gb|U87223.1|HSU87223[1857707]

11443: AF022386
Homo sapiens p53-regulated DNA damage-inducible cell death receptor (killer) mRNA, complete cds
gi|2460427|gb|AF022386.1|AF022386[2460427]

11444: AF011368
Homo sapiens CEV14 mRNA, partial cds
gi|2618824|gb|AF011368.1|AF011368[2618824]

11445: AF016267
Homo sapiens TRAIL receptor 3 mRNA, complete cds
gi|2529564|gb|AF016267.1|AF016267[2529564]

11446: AF020502
Homo sapiens cytotoxic TRAIL receptor-3 (TRAIL-R3) mRNA, complete cds
gi|2443819|gb|AF020502.1|AF020502[2443819]

11447: AF020501
Homo sapiens cytotoxic TRAIL receptor-2 (DR5) mRNA, complete cds
gi|2443817|gb|AF020501.1|AF020501[2443817]

11454: AF075460
Homo sapiens type 1-like ryanodine receptor mRNA, partial cds
gi|3328200|gb|AF075460.1|AF075460[3328200]

11455: AF054830
Homo sapiens interleukin-1 type I receptor mRNA, partial sequence
gi|3003026|gb|AF054830.1|AF054830[3003026]

11456: AF099082
Homo sapiens xenotropic and polytropic murine retrovirus receptor (XPR1) mRNA, complete cds
gi|4176765|gb|AF099082.1|AF099082[4176765]

11501: AF089744
Homo sapiens xenotropic and polytropic murine leukemia virus receptor (X3) mRNA, complete cds
gi|4154282|gb|AF089744.1|AF089744[4154282]

11502: AF001095
Homo sapiens receptor for advanced glycation end products (RAGE) gene, promoter region and exon 1
gi|3093415|gb|AF001095.1|AF001095[3093415]

11503: AF101784
Homo sapiens b-TRCP variant E3RS-IkappaB mRNA, partial cds
gi|4165135|gb|AF101784.1|AF101784[4165135]

11504: AF080586
Homo sapiens galanin receptor type 2 (GALR2) mRNA, complete cds
gi|4165080|gb|AF080586.1|AF080586[4165080]

11505: U71374
Homo sapiens HsPex13p mRNA, complete cds
gi|3738269|gb|U71374.1|HSU71374[3738269]

11506: AF111116
Homo sapiens silencer of death domains (SODD) mRNA, complete cds
gi|4160013|gb|AF111116.1|AF111116[4160013]

11507: AF110314
Homo sapiens herpesvirus immunoglobulin-like receptor HIgR mRNA, complete cds
gi|4154345|gb|AF110314.1|AF110314[4154345]

11518: AF069543
Homo sapiens IL-3/IL-5/GM-CSFR receptor beta chain promoter and exon 1 sequence
gi|4071316|gb|AF069543.1|AF069543[4071316]

11519: U81262
Homo sapiens LERK5 (LERK5) mRNA, complete cds
gi|1809333|gb|U81262.1|HSU81262[1809333]

11520: AF097358
Homo sapiens mast cell function-associated antigen homolog (MAFA) mRNA, complete cds
gi|4139191|gb|AF097358.1|AF097358[4139191]

11521: AF029761
Homo sapiens decoy receptor 2 mRNA, complete cds
gi|4106963|gb|AF029761.1|AF029761[4106963]

11522: AF074483
Homo sapiens GABA-B receptor 2 mRNA, complete cds
gi|4107511|gb|AF074483.1|AF074483[4107511]

11523: AC006293
Homo sapiens chromosome 19, cosmid F15658, complete sequence
gi|4106979|gb|AC006293.1|AC006293[4106979]

11524: AF104419
Homo sapiens decoy receptor 3 (DcR3) mRNA, complete cds
gi|4106877|gb|AF104419.1|AF104419[4106877]

11525: AF046059
Homo sapiens cytokine receptor related protein 4 (CYTOR4) mRNA, complete cds
gi|4105471|gb|AF046059.1|AF046059[4105471]

11526: AF041262
Homo sapiens immunoglobulin-like transcript 8 mRNA, complete cds
gi|4104892|gb|AF041262.1|AF041262[4104892]

11527: AF041261
Homo sapiens immunoglobulin-like transcript 7 mRNA, complete cds
gi|4104890|gb|AF041261.1|AF041261[4104890]

11528: AH007196
Homo sapiens transforming growth factor-beta type I receptor gene, exon 6
gi|4104446|gb|AH007196.1|SEG_HSTGFRBI[4104446]

11529: AF035670
Homo sapiens transforming growth factor-beta type I receptor gene, exon 9, and complete cds
gi|4104445|gb|AF035670.1|HSTGFRBI9[4104445]

11530: AF035669
Homo sapiens transforming growth factor-beta type I receptor gene, exon 8
gi|4104444|gb|AF035669.1|HSTGFRBI8[4104444]

11531: AF035668
Homo sapiens transforming growth factor-beta type I receptor gene, exon 7
gi|4104443|gb|AF035668.1|HSTGFRBI7[4104443]

11532: AF035667
Homo sapiens transforming growth factor-beta type I receptor gene, exon 6
gi|4104442|gb|AF035667.1|HSTGFRBI6[4104442]

11533: AF035666
Homo sapiens transforming growth factor-beta type I receptor gene, exon 5
gi|4104441|gb|AF035666.1|HSTGFRBI5[4104441]

11534: AF035665
Homo sapiens transforming growth factor-beta type I receptor gene, exon 4
gi|4104440|gb|AF035665.1|HSTGFRBI4[4104440]

11535: AF035664
Homo sapiens transforming growth factor-beta type I receptor gene, exon 3
gi|4104439|gb|AF035664.1|HSTGFRBI3[4104439]

11536: AF035663
Homo sapiens transforming growth factor-beta type I receptor gene, exon 2
gi|4104438|gb|AF035663.1|HSTGFRBI2[4104438]

11537: AF035662
Homo sapiens transforming growth factor-beta type I receptor gene, exon 1
gi|4104437|gb|AF035662.1|HSTGFRBI1[4104437]

11538: AF037332
Homo sapiens Eph-like receptor tyrosine kinase hEphB1b (EphB1) mRNA, complete cds
gi|4104412|gb|AF037332.1|AF037332[4104412]

11539: AF037331
Homo sapiens Eph-like receptor tyrosine kinase hEphB1 (EphB1) mRNA, complete cds
gi|4104410|gb|AF037331.1|AF037331[4104410]

11543: AH007119
Homo sapiens killer cell inhibitory receptor KIRCI gene, complete cds
gi|3776473|gb|AH007119.1|SEG_HSKIRCI[3776473]

11544: AF072410
Homo sapiens killer cell inhibitory receptor KIRCI gene, exons 6, 7 and 8 and complete cds
gi|3776472|gb|AF072410.1|HSKIRCI4[3776472]

11545: AF072409
Homo sapiens killer cell inhibitory receptor KIRCI gene, exon 5
gi|3776471|gb|AF072409.1|HSKIRCI3[3776471]

11546: AF072408
Homo sapiens killer cell inhibitory receptor KIRCI gene, exons 2, 3, and 4
gi|3776470|gb|AF072408.1|HSKIRCI2[3776470]

11547: AF072407
Homo sapiens killer cell inhibitory receptor KIRCI gene, exon 1
gi|3776469|gb|AF072407.1|HSKIRCI1[3776469]

11548: AH007118
Homo sapiens immunoglobulin-like transcript 10 protein gene, complete cds
gi|3776467|gb|AH007118.1|SEG_HSILTX[3776467]

11549: AF072101
Homo sapiens immunoglobulin-like transcript 10 protein gene, exons 7 and 8 and complete cds
gi|3776466|gb|AF072101.1|HSILTX2[3776466]

11550: AF072100
Homo sapiens immunoglobulin-like transcript 10 protein gene, exons 1 through 6
gi|3776465|gb|AF072100.1|HSILTX1[3776465]

11551: AF072099
Homo sapiens immunoglobulin-like transcript 3 protein variant 1 gene, complete cds
gi|3776463|gb|AF072099.1|AF072099[3776463]

11553: AF106941
Homo sapiens beta-arrestin 2 mRNA, complete cds
gi|4092782|gb|AF106941.1|AF106941[4092782]

11554: AF104304
Homo sapiens Smad anchor for receptor activation (SARA) mRNA, complete cds
gi|4092766|gb|AF104304.1|AF104304[4092766]

11555: AF034780
Homo sapiens lysosphingolipid receptor Edg5 mRNA, complete cds
gi|4090955|gb|AF034780.1|AF034780[4090955]

11556: AF109401
Homo sapiens neurotrophic factor artemin precursor (ARTN) mRNA, complete cds
gi|4071352|gb|AF109401.1|AF109401[4071352]

11557: AF099148
Homo sapiens GABA-B1a receptor mRNA, complete cds
gi|4063891|gb|AF099148.1|AF099148[4063891]

11558: AF095448
Homo sapiens putative G protein-coupled receptor (RAIG1) mRNA, complete cds
gi|4063889|gb|AF095448.1|AF095448[4063889]

11559: L34689

Homo sapiens somatostatin receptor isoform 2 (SSTR2) gene, partial cds
gi|598233|gb|L34689.1|HUMSOREC2X[598233]

11560: AF100161
Homo sapiens folate receptor type gamma' gene, partial cds
gi|4063392|gb|AF100161.1|AF100161[4063392]

11561: AF082076
Homo sapiens luteinizing hormone receptor (LHR) gene, partial cds
gi|4063365|gb|AF082076.1|AF082076[4063365]

11562: AC006132
Homo sapiens chromosome 19, cosmid R28204, complete sequence
gi|3970930|gb|AC006132.1|AC006132[3970930]

11563: AH007081
Homo sapiens lectin-type oxidized LDL receptor (OLR1) gene, complete cds
gi|4050003|gb|AH007081.1|SEG_HSOLR[4050003]

11564: AF079167
Homo sapiens lectin-type oxidized LDL receptor (OLR1) gene, exons 4, 5, and 6, and complete cds
gi|4050002|gb|AF079167.1|HSOLR4[4050002]

11565: AF079166
Homo sapiens lectin-type oxidized LDL receptor (OLR1) gene, exon 3
gi|4050001|gb|AF079166.1|HSOLR3[4050001]

11566: AF079165
Homo sapiens lectin-type oxidized LDL receptor (OLR1) gene, exon 2
gi|4050000|gb|AF079165.1|HSOLR2[4050000]

11567: AF079164
Homo sapiens lectin-type oxidized LDL receptor (OLR1) gene, exon 1
gi|4049999|gb|AF079164.1|HSOLR1[4049999]

11568: AF099083

Homo sapiens growth hormone secretagogue receptor gene, 5' flanking region and partial cds
gi|4039145|gb|AF099083.1|AF099083[4039145]

11569: AF058390
Homo sapiens neurotrophin 3 receptor truncated isoform (NTRK3) mRNA, partial cds
gi|4027932|gb|AF058390.1|AF058390[4027932]

11570: AF058389
Homo sapiens neurotrophin 3 receptor (NTRK3) mRNA, partial cds
gi|4027930|gb|AF058389.1|AF058389[4027930]

11877: AF029839
Homo sapiens alpha 7 neuronal nicotinic receptor mRNA sequence
gi|3757794|gb|AF029839.1|AF029839[3757794]

11878: AF029838
Homo sapiens alpha 7 neuronal nicotinic receptor mRNA sequence
gi|3757793|gb|AF029838.1|AF029838[3757793]

11880: AH007062
Homo sapiens galanin receptor (GALNR), complete cds
gi|3064074|gb|AH007062.1|SEG_HSGALNRS[3064074]

11881: U90660
Homo sapiens galanin receptor (GALNR) gene, exon 3 and complete cds
gi|3064073|gb|U90660.1|HSGALNRS3[3064073]

11882: U90659
Homo sapiens galanin receptor (GALNR) gene, exon 2
gi|3064072|gb|U90659.1|HSGALNRS2[3064072]

11883: U90658
Homo sapiens galanin receptor (GALNR) gene, exon 1
gi|3064071|gb|U90658.1|HSGALNRS1[3064071]

11884: AF041474
Homo sapiens BAF53a (BAF53a) mRNA, complete cds
gi|4001802|gb|AF041474.1|AF041474[4001802]

11886: AF097942
Homo sapiens monocyte antigen CD14 precursor (CD14) mRNA, complete cds
gi|3983126|gb|AF097942.1|AF097942[3983126]

11887: AH007044
Homo sapiens growth factor receptor (GRB10) gene, alternative splice products, complete cds
gi|3982774|gb|AH007044.1|SEG_HSGRB[3982774]

11904: AF084941
Homo sapiens pre-T cell receptor alpha chain 1 precursor, gene, complete cds
gi|3978459|gb|AF084941.1|AF084941[3978459]

11905: AH007043
Homo sapiens interleukin-7 receptor precursor (IL7R), complete cds
gi|3978161|gb|AH007043.1|SEG_HSIL7R[3978161]

11906: AF043129
Homo sapiens interleukin-7 receptor precursor (IL7R) gene, exons 7 and 8 and complete cds
gi|3978160|gb|AF043129.1|HSIL7R7[3978160]

11907: AF043128
Homo sapiens interleukin-7 receptor precursor (IL7R) gene, exon 6
gi|3978159|gb|AF043128.1|HSIL7R6[3978159]

11908: AF043127
Homo sapiens interleukin-7 receptor precursor (IL7R) gene, exon 5
gi|3978158|gb|AF043127.1|HSIL7R5[3978158]

11909: AF043126
Homo sapiens interleukin-7 receptor precursor (IL7R) gene, exon 4
gi|3978157|gb|AF043126.1|HSIL7R4[3978157]

11910: AF043125
Homo sapiens interleukin-7 receptor precursor (IL7R) gene, exon 3
gi|3978156|gb|AF043125.1|HSIL7R3[3978156]

11911: AF043124
Homo sapiens interleukin-7 receptor precursor (IL7R) gene, exon 2
gi|3978155|gb|AF043124.1|HSIL7R2[3978155]

11912: AF043123
Homo sapiens interleukin-7 receptor precursor (IL7R) gene, exon 1
gi|3978154|gb|AF043123.1|HSIL7R1[3978154]

11913: AH007033
Homo sapiens prostanoid FP receptor (PTGFR), partial cds
gi|3941539|gb|AH007033.1|SEG_HSPTF2AGR[3941539]

11914: AF068679
Homo sapiens prostanoid FP receptor (PTGFR) gene, exon and partial cds
gi|3941538|gb|AF068679.1|HSPTF2AGR4[3941538]

11915: AF068678
Homo sapiens prostanoid FP receptor (PTGFR) gene, exon
gi|3941537|gb|AF068678.1|HSPTF2AGR3[3941537]

11916: AF068677
Homo sapiens prostanoid FP receptor (PTGFR) gene, exon and partial 5'UTR
gi|3941536|gb|AF068677.1|HSPTF2AGR2[3941536]

11917: AF068676
Homo sapiens prostanoid FP receptor (PTGFR) gene, exon
gi|3941535|gb|AF068676.1|HSPTF2AGR1[3941535]

11918: AF035776
Homo sapiens oxidized low-density lipoprotein receptor mRNA, complete cds
gi|3941299|gb|AF035776.1|AF035776[3941299]

11920: AF091501

Homo sapiens receptor protein patched 2 (PTCH2) mRNA, complete cds
gi|3929234|gb|AF091501.1|AF091501[3929234]

11953: X98174
H.sapiens mRNA for MACH-alpha-3 protein
gi|3928273|emb|X98174.1|HSMACHA3[3928273]

11955: X68990
Homo sapiens CR2 mRNA for complement receptor
gi|3928195|emb|X68990.1|HSCR2AA[3928195]

11956: X63128
H.sapiens mRNA for activin receptor
gi|3928172|emb|X63128.1|HSACTREC[3928172]

11958: AF074397
Homo sapiens anti-mullerian hormone type II receptor (AMHR2) gene, promoter region and partial cds
gi|3916231|gb|AF074397.1|AF074397[3916231]

11959: U72648
Homo sapiens alpha2-C4-adrenergic receptor gene, complete cds
gi|3914602|gb|U72648.1|HSU72648[3914602]

11960: Y10148
H.sapiens mRNA for NTR2 receptor
gi|3901027|emb|Y10148.1|HSNTR2REC[3901027]

11961: Y12476
Homo sapiens putative GPR37 gene (exon 1 and joined CDS)
gi|2570029|emb|Y12476.1|HSY12476[2570029]

11962: AJ000479
Homo sapiens mRNA for putative G-protein coupled receptor, EDG6
gi|3805931|emb|AJ000479.1|HSEDG4[3805931]

11963: Y12477

Homo sapiens putative GPR37 gene, exon 2
gi|2570031|emb|Y12477.1|HSY12477[2570031]

11964: X04329
Homo sapiens mRNA fragment for receptor-like furin
gi|31479|emb|X04329.1|HSFUR1[31479]

11965: AH007002
Homo sapiens chromosome 1 map 1q12-q13
gi|3892221|gb|AH007002.1|SEG_HSM1MUSR[3892221]

11966: AF091493
Homo sapiens M1 muscarinic receptor gene, exons 2 and 3
gi|3892220|gb|AF091493.1|HSM1MUSR2[3892220]

11967: AF091492
Homo sapiens M1 muscarinic receptor gene, promoter region and exon 1
gi|3892219|gb|AF091492.1|HSM1MUSR1[3892219]

12129: AF077820
Homo sapiens LDL receptor member LR3 mRNA, complete cds
gi|3831747|gb|AF077820.1|AF077820[3831747]

12130: AF055992
Homo sapiens Duffy antigen/chemokine receptor (FY) gene, FY*X allele, complete cds
gi|3659623|gb|AF055992.1|AF055992[3659623]

12131: U58675
Homo sapiens Chromosome 17p13 Cosmid Clone cos39, complete sequence
gi|3849817|gb|U58675.1|U58675[3849817]

12132: AF077346
Homo sapiens interleukin-18 receptor accessory protein-like mRNA, complete cds
gi|3851059|gb|AF077346.1|AF077346[3851059]

12136: Z17227

Homo sapiens mRNA for transmebrane receptor protein
gi|393378|emb|Z17227.1|HSTRECP[393378]

12137: AF082742
Homo sapiens CC chemokine receptor 5 (CCR5) gene, promoter region and partial sequence
gi|3561057|gb|AF082742.1|AF082742[3561057]

12139: Z34897
H.sapiens mRNA for H1 histamine receptor
gi|510295|emb|Z34897.1|HSHISTR1[510295]

12140: X76786
H.sapiens histamine H1 receptor gene
gi|442517|emb|X76786.1|HSHISH1[442517]

12141: AC005933
Homo sapiens chromosome 19, cosmid F15472, complete sequence
gi|3845348|gb|AC005933.1|AC005933[3845348]

12142: AF094755
Homo sapiens glycine receptor beta subunit precursor (GLRB), variant B mRNA, complete cds
gi|3834636|gb|AF094755.1|AF094755[3834636]

12143: AF094754
Homo sapiens glycine receptor beta subunit precursor (GLRB), variant A mRNA, complete cds
gi|3834634|gb|AF094754.1|AF094754[3834634]

12144: AF091512
Homo sapiens familial mediterranean fever locus genomic sequence
gi|3834584|gb|AF091512.1|AF091512[3834584]

12145: AF065876
Homo sapiens olfactory receptor (OR2D2) gene, partial cds
gi|3831618|gb|AF065876.1|AF065876[3831618]

12147: AF065874
Homo sapiens olfactory receptor (OR10A1) gene, partial cds
gi|3831615|gb|AF065874.1|AF065874[3831615]

12151: AF065870
Homo sapiens olfactory receptor (OR6A1) gene, complete cds
gi|3831610|gb|AF065870.1|AF065870[3831610]

12158: AF065863
Homo sapiens olfactory receptor (OR5F1) gene, partial cds
gi|3831602|gb|AF065863.1|AF065863[3831602]

12160: AF065861
Homo sapiens olfactory receptor (OR5D4) gene, partial cds
gi|3831599|gb|AF065861.1|AF065861[3831599]

12161: AF065860
Homo sapiens olfactory receptor (OR5D3) gene, partial cds
gi|3831597|gb|AF065860.1|AF065860[3831597]

12170: AH006968
Homo sapiens
gi|2828129|gb|AH006968.1|SEG_HSCRFR[2828129]

12171: AF039523
Homo sapiens corticotropin-releasing factor type 1 receptor gene, exon 14 and complete cds
gi|2828128|gb|AF039523.1|HSCRFR14[2828128]

12172: AF039522
Homo sapiens corticotropin-releasing factor type 1 receptor gene, exon 13
gi|2828127|gb|AF039522.1|HSCRFR13[2828127]

12173: AF039521
Homo sapiens corticotropin-releasing factor type 1 receptor gene, exon 12
gi|2828126|gb|AF039521.1|HSCRFR12[2828126]

12174: AF039520
Homo sapiens corticotropin-releasing factor type 1 receptor gene, exon 11
gi|2828125|gb|AF039520.1|HSCRFR11[2828125]

12175: AF039519
Homo sapiens corticotropin-releasing factor type 1 receptor gene, exon 10
gi|2828124|gb|AF039519.1|HSCRFR10[2828124]

12176: AF039518
Homo sapiens corticotropin-releasing factor type 1 receptor gene, exon 9
gi|2828123|gb|AF039518.1|HSCRFR09[2828123]

12177: AF039517
Homo sapiens corticotropin-releasing factor type 1 receptor gene, exon 8
gi|2828122|gb|AF039517.1|HSCRFR08[2828122]

12178: AF039516
Homo sapiens corticotropin-releasing factor type 1 receptor gene, exon 7
gi|2828121|gb|AF039516.1|HSCRFR07[2828121]

12179: AF039515
Homo sapiens corticotropin-releasing factor type 1 receptor gene, exon 6
gi|2828120|gb|AF039515.1|HSCRFR06[2828120]

12180: AF039514
Homo sapiens corticotropin-releasing factor type 1 receptor gene, exon 5
gi|2828119|gb|AF039514.1|HSCRFR05[2828119]

12181: AF039513
Homo sapiens corticotropin-releasing factor type 1 receptor gene, exon 4
gi|2828118|gb|AF039513.1|HSCRFR04[2828118]

12182: AF039512
Homo sapiens corticotropin-releasing factor type 1 receptor gene, exon 3
gi|2828117|gb|AF039512.1|HSCRFR03[2828117]

12183: AF039511
Homo sapiens corticotropin-releasing factor type 1 receptor gene, exon 2
gi|2828116|gb|AF039511.1|HSCRFR02[2828116]

12184: AF039510
Homo sapiens corticotropin-releasing factor type 1 receptor gene, exon 1
gi|2828115|gb|AF039510.1|HSCRFR01[2828115]

12185: AF030186
Homo sapiens glypican-4 (GPC4) mRNA, complete cds
gi|3831546|gb|AF030186.1|AF030186[3831546]

12206: AJ006353
Homo sapiens mRNA for ephrin-A4 protein, soluble form
gi|3821236|emb|AJ006353.1|HSA6353[3821236]

12212: AF055634
Homo sapiens transmembrane receptor UNC5C (UNC5C) mRNA, complete cds
gi|3789764|gb|AF055634.1|AF055634[3789764]

12227: AH006936
Homo sapiens activin receptor type IIB (ACVR2B), complete cds
gi|3769442|gb|AH006936.1|SEG_HSACVR2B[3769442]

12228: AF060202
Homo sapiens activin receptor type IIB (ACVR2B) gene, exon 11 and complete cds
gi|3769441|gb|AF060202.1|HSACVR2B4[3769441]

12229: AF060201
Homo sapiens activin receptor type IIB (ACVR2B) gene, exons 8, 9, and 10
gi|3769440|gb|AF060201.1|HSACVR2B3[3769440]

12230: AF060200
Homo sapiens activin receptor type IIB (ACVR2B) gene, exons 2 through 7
gi|3769439|gb|AF060200.1|HSACVR2B2[3769439]

12231: AF060199

Homo sapiens activin receptor type IIB (ACVR2B) gene, exon 1
gi|3769438|gb|AF060199.1|HSACVR2B1[3769438]

12232: AF037646
Homo sapiens alpha-7 neuronal nicotinic acetylcholine receptor precursor RNA, partial sequence
gi|3757808|gb|AF037646.1|AF037646[3757808]

12233: AF036903
Homo sapiens alpha-7 neuronal nicotinic acetylcholine receptor mRNA, alternatively spliced, partial sequence
gi|3757807|gb|AF036903.1|AF036903[3757807]

12234: AH006931
Homo sapiens lipoprotein receptor-related protein (LRP1) gene, complete cds
gi|3493575|gb|AH006931.1|SEG_HSLRPSS[3493575]

12235: AF058427
Homo sapiens lipoprotein receptor-related protein (LRP1), exons 80 through 89 and complete cds
gi|3493574|gb|AF058427.1|HSLRPSS61[3493574]

12236: AF058426
Homo sapiens lipoprotein receptor-related protein (LRP1), exons 78 and 79
gi|3493573|gb|AF058426.1|HSLRPSS59[3493573]

12237: AF058425
Homo sapiens lipoprotein receptor-related protein (LRP1), exon 77
gi|3493572|gb|AF058425.1|HSLRPSS57[3493572]

12238: AF058424
Homo sapiens lipoprotein receptor-related protein (LRP1), exon 76
gi|3493571|gb|AF058424.1|HSLRPSS55[3493571]

12239: AF058423
Homo sapiens lipoprotein receptor-related protein (LRP1), exons 71 through 75
gi|3493570|gb|AF058423.1|HSLRPSS53[3493570]

12240: AF058422

Homo sapiens lipoprotein receptor-related protein (LRP1), exons 61 through 70
gi|3493569|gb|AF058422.1|HSLRPSS51[3493569]

12241: AF058421

Homo sapiens lipoprotein receptor-related protein (LRP1), exons 59 and 60
gi|3493568|gb|AF058421.1|HSLRPSS49[3493568]

12242: AF058420

Homo sapiens lipoprotein receptor-related protein (LRP1), exons 56, 57, and 58
gi|3493567|gb|AF058420.1|HSLRPSS47[3493567]

12243: AF058419

Homo sapiens lipoprotein receptor-related protein (LRP1), exons 45 through 55
gi|3493566|gb|AF058419.1|HSLRPSS45[3493566]

12244: AF058418

Homo sapiens lipoprotein receptor-related protein (LRP1), exons 43 and 44
gi|3493565|gb|AF058418.1|HSLRPSS43[3493565]

12245: AF058417

Homo sapiens lipoprotein receptor-related protein (LRP1), exon 42
gi|3493564|gb|AF058417.1|HSLRPSS41[3493564]

12246: AF058416

Homo sapiens lipoprotein receptor-related protein (LRP1), exons 39, 40, and 41
gi|3493563|gb|AF058416.1|HSLRPSS39[3493563]

12247: AF058415

Homo sapiens lipoprotein receptor-related protein (LRP1), exons 36, 37, and 38
gi|3493562|gb|AF058415.1|HSLRPSS37[3493562]

12248: AF058414

Homo sapiens lipoprotein receptor-related protein (LRP1), exons 27 through 34
gi|3493561|gb|AF058414.1|HSLRPSS35[3493561]

12249: AF058413
Homo sapiens lipoprotein receptor-related protein (LRP1), exons 25 and 26
gi|3493560|gb|AF058413.1|HSLRPSS33[3493560]

12250: AF058412
Homo sapiens lipoprotein receptor-related protein (LRP1), exons 23 and 24
gi|3493559|gb|AF058412.1|HSLRPSS31[3493559]

12251: AF058411
Homo sapiens lipoprotein receptor-related protein (LRP1), exons 21 and 22
gi|3493558|gb|AF058411.1|HSLRPSS29[3493558]

12252: AF058410
Homo sapiens lipoprotein receptor-related protein (LRP1), exon 20
gi|3493557|gb|AF058410.1|HSLRPSS27[3493557]

12253: AF058409
Homo sapiens lipoprotein receptor-related protein (LRP1), exons 18 and 19
gi|3493556|gb|AF058409.1|HSLRPSS25[3493556]

12254: AF058408
Homo sapiens lipoprotein receptor-related protein (LRP1), exons 16 and 17
gi|3493555|gb|AF058408.1|HSLRPSS23[3493555]

12255: AF058407
Homo sapiens lipoprotein receptor-related protein (LRP1), exons 14 and 15
gi|3493554|gb|AF058407.1|HSLRPSS21[3493554]

12256: AF058406
Homo sapiens lipoprotein receptor-related protein (LRP1), exon 13
gi|3493553|gb|AF058406.1|HSLRPSS19[3493553]

12257: AF058405
Homo sapiens lipoprotein receptor-related protein (LRP1), exon 12
gi|3493552|gb|AF058405.1|HSLRPSS17[3493552]

12258: AF058404

Homo sapiens lipoprotein receptor-related protein (LRP1), exon 11
gi|3493551|gb|AF058404.1|HSLRPSS15[3493551]

12259: AF058403
Homo sapiens lipoprotein receptor-related protein (LRP1), exons 9 and 10
gi|3493550|gb|AF058403.1|HSLRPSS13[3493550]

12260: AF058402
Homo sapiens lipoprotein receptor-related protein (LRP1), exons 7 and 8
gi|3493549|gb|AF058402.1|HSLRPSS11[3493549]

12261: AF058401
Homo sapiens lipoprotein receptor-related protein (LRP1), exons 5 and 6
gi|3493548|gb|AF058401.1|HSLRPSS09[3493548]

12262: AF058400
Homo sapiens lipoprotein receptor-related protein (LRP1), exon 4
gi|3493547|gb|AF058400.1|HSLRPSS07[3493547]

12263: AF058399
Homo sapiens lipoprotein receptor-related protein (LRP1), exon 3
gi|3493546|gb|AF058399.1|HSLRPSS05[3493546]

12264: AF058398
Homo sapiens lipoprotein receptor-related protein (LRP1), exon 2
gi|3493545|gb|AF058398.1|HSLRPSS03[3493545]

12265: AF058397
Homo sapiens lipoprotein receptor-related protein (LRP1), exon 1
gi|3493544|gb|AF058397.1|HSLRPSS01[3493544]

12267: Y11044
Homo sapiens mRNA for GABA-BR1a (hGB1a) receptor
gi|2826760|emb|Y11044.1|HSGTHLA1[2826760]

12277: AF073019
Homo sapiens clone 21 T cell signal transduction molecule SAP mRNA, complete cds gi|3695070|gb|AF073019.1|AF073019[3695070]

12278: AF072930
Homo sapiens clone 14 T cell signal transduction molecule SAP mRNA, complete cds
gi|3695068|gb|AF072930.1|AF072930[3695068]

12279: Y12670
Homo sapiens mRNA for leptin receptor gene-related protein
gi|2266637|emb|Y12670.1|HSOBRGRP[2266637]

12280: AF091890
Homo sapiens G-protein coupled receptor RE2 mRNA, complete cds
gi|3659902|gb|AF091890.1|AF091890[3659902]

12281: Y09586
Homo sapiens mRNA for serotonin 4 receptor (h5-HT4(a)), splice variant
gi|2584764|emb|Y09586.1|HS5HT4SAR[2584764]

12282: X77777
H.sapiens intestinal VIP receptor related protein mRNA
gi|456352|emb|X77777.1|HSVIPRRP[456352]

12283: AJ001383
Homo sapiens activating NK-receptor (NK-p46) mRNA
gi|3647278|emb|AJ001383.1|HSJ001383[3647278]

12284: AJ224901
Homo sapiens mRNA for ZNF198 protein
gi|3647276|emb|AJ224901.1|HSAJ4901[3647276]

12285: AJ006123
Homo sapiens mRNA for NK receptor (NKp46), isoform d
gi|3647272|emb|AJ006123.1|HSA6123[3647272]

12286: AJ006122
Homo sapiens mRNA for NK receptor (NKp46) isoform c
gi|3647270|emb|AJ006122.1|HSA6122[3647270]

12287: AJ006121
Homo sapiens mRNA for NK receptor (NKp46), isoform b
gi|3647268|emb|AJ006121.1|HSA6121[3647268]

12289: X99906
Homo sapiens mRNA for alpha endosulfine
gi|2764973|emb|X99906.1|HSALPEND[2764973]

12292: U52064
Kaposi's sarcoma-associated herpes-like virus ORF73 homolog gene, complete cds
gi|1633571|gb|U52064.1|KSU52064[1633571]

12293: U29343
Homo sapiens hyaluronan receptor (RHAMM) mRNA, complete cds
gi|2959555|gb|U29343.1|HSU29343[2959555]

12294: AF035771
Homo sapiens Na+/H+ exchanger regulatory factor 2 (NHERF-2) mRNA, complete cds
gi|2665825|gb|AF035771.1|AF035771[2665825]

12296: AF023849
Homo sapiens TNF receptor-related receptor for TRAIL mRNA, complete cds
gi|2653844|gb|AF023849.1|AF023849[2653844]

12297: AH006710
Homo sapiens interferon-gamma receptor alpha chain (interferon-gamma receptor alpha chain gene), complete cds
gi|2078444|gb|AH006710.1|SEG_HSINFGRA[2078444]

12298: U19247
Homo sapiens interferon-gamma receptor alpha chain gene, exon 7 and complete cds
gi|632541|gb|U19247.1|HSINFGRA7[632541]

12299: U19246
Homo sapiens interferon-gamma receptor alpha chain gene, exon 6
gi|632540|gb|U19246.1|HSINFGRA6[632540]

12300: U19245
Homo sapiens interferon-gamma receptor alpha chain gene, exon 5
gi|632539|gb|U19245.1|HSINFGRA5[632539]

12301: U19244
Homo sapiens interferon-gamma receptor alpha chain gene, exon 4
gi|632538|gb|U19244.1|HSINFGRA4[632538]

12302: U19243
Homo sapiens interferon-gamma receptor alpha chain gene, exon 3
gi|632537|gb|U19243.1|HSINFGRA3[632537]

12303: U19242
Homo sapiens interferon-gamma receptor alpha chain gene, exon 2
gi|632536|gb|U19242.1|HSINFGRA2[632536]

12304: U19241
Homo sapiens interferon-gamma receptor alpha chain gene, exon 1
gi|632535|gb|U19241.1|HSINFGRA1[632535]

12305: AF027957
Homo sapiens G protein-coupled receptor (GPR35) gene, complete cds
gi|2739108|gb|AF027957.1|AF027957[2739108]

12306: AF027956
Homo sapiens G protein-coupled receptor (GPR30) gene, complete cds
gi|2739106|gb|AF027956.1|AF027956[2739106]

12307: AF016709
Homo sapiens ATP receptor subunit (P2X5) mRNA, complete cds
gi|2731560|gb|AF016709.1|AF016709[2731560]

12308: AF035824
Homo sapiens vesicle soluble NSF attachment protein receptor (VTI1) mRNA, complete cds
gi|2687399|gb|AF035824.1|AF035824[2687399]

12309: U96845
Homo sapiens natual killer cell group 2-F (NKG2-F) mRNA, complete cds
gi|2673988|gb|U96845.1|HSU96845[2673988]

12310: AF022139
Homo sapiens lysosphingolipid receptor (EDG3) mRNA, partial cds
gi|2668611|gb|AF022139.1|AF022139[2668611]

12311: AF022137
Homo sapiens G protein-coupled receptor (EDG1) mRNA, partial cds
gi|2668607|gb|AF022137.1|AF022137[2668607]

12312: AF031556
Homo sapiens clone 17.30 immunoglobulin-like transcript 5 mRNA, complete cds
gi|2665646|gb|AF031556.1|AF031556[2665646]

12313: AF031555
Homo sapiens clone 17.23 immunoglobulin-like transcript 5 mRNA, complete cds
gi|2665644|gb|AF031555.1|AF031555[2665644]

12314: AF031554
Homo sapiens clone 17.18 immunoglobulin-like transcript 5 mRNA, complete cds
gi|2665642|gb|AF031554.1|AF031554[2665642]

12315: AF031553
Homo sapiens clone DC.1 immunoglobulin-like transcript 5 mRNA, complete cds
gi|2665640|gb|AF031553.1|AF031553[2665640]

12316: AF009644
Homo sapiens clone 41 immunoglobulin-like transcript 5 protein mRNA, complete cds
gi|2662447|gb|AF009644.1|AF009644[2662447]

12317: AF009643
Homo sapiens clone 6 immunoglobulin-like transcript 5 protein mRNA, complete cds
gi|2662445|gb|AF009643.1|AF009643[2662445]

12318: AF009642
Homo sapiens clone 40 immunoglobulin-like transcript 5 protein mRNA, complete cds
gi|2662443|gb|AF009642.1|AF009642[2662443]

12319: AF009641
Homo sapiens clone 36 immunoglobulin-like transcript 5 protein mRNA, complete cds
gi|2662441|gb|AF009641.1|AF009641[2662441]

12320: AF009640
Homo sapiens clone 33 immunoglobulin-like transcript 5 protein mRNA, complete cds
gi|2662439|gb|AF009640.1|AF009640[2662439]

12321: AF009639
Homo sapiens clone 31 immunoglobulin-like transcript 5 protein mRNA, complete cds
gi|2662437|gb|AF009639.1|AF009639[2662437]

12322: AF009638
Homo sapiens clone 22 immunoglobulin-like transcript 5 protein mRNA, complete cds
gi|2662435|gb|AF009638.1|AF009638[2662435]

12323: AF009637
Homo sapiens clone 19 immunoglobulin-like transcript 5 protein mRNA, complete cds
gi|2662433|gb|AF009637.1|AF009637[2662433]

12324: AF009636
Homo sapiens clone 17.8 immunoglobulin-like transcript 5 protein mRNA, complete cds
gi|2662431|gb|AF009636.1|AF009636[2662431]

12325: AF009635
Homo sapiens clone 17.7 immunoglobulin-like transcript 5 protein mRNA, complete cds
gi|2662429|gb|AF009635.1|AF009635[2662429]

12326: AF009634
Homo sapiens clone 17.6 immunoglobulin-like transcript 5 protein mRNA, complete cds
gi|2662427|gb|AF009634.1|AF009634[2662427]

12327: AF009633
Homo sapiens clone 17.11 immunoglobulin-like transcript 5 protein mRNA, complete cds
gi|2662425|gb|AF009633.1|AF009633[2662425]

12328: AF009632
Homo sapiens clone 17.10 immunoglobulin-like transcript 5 protein mRNA, complete cds
gi|2662423|gb|AF009632.1|AF009632[2662423]

12329: AF014924
Homo sapiens immunoglobulin-like transcript 6a (ILT6a) mRNA, complete cds
gi|2661224|gb|AF014924.1|AF014924[2661224]

12330: AF014923
Homo sapiens immunoglobulin-like transcript 6 (ILT6) mRNA, complete cds
gi|2661222|gb|AF014923.1|AF014923[2661222]

12331: AF011566
Homo sapiens clone 17 immunoglobulin-like transcript 4 mRNA, complete cds
gi|2660709|gb|AF011566.1|AF011566[2660709]

12332: AF011565
Homo sapiens clone 26 immunoglobulin-like transcript 4 mRNA, complete cds
gi|2660707|gb|AF011565.1|AF011565[2660707]

12333: AF009007
Homo sapiens immunoglobulin-like transcript 2c mRNA, complete cds
gi|2660705|gb|AF009007.1|AF009007[2660705]

12334: AF009006
Homo sapiens immunoglobulin-like transcript 2b mRNA, complete cds
gi|2660703|gb|AF009006.1|AF009006[2660703]

12335: AF009005
Homo sapiens immunoglobulin-like transcript 2a mRNA, complete cds
gi|2660701|gb|AF009005.1|AF009005[2660701]

12336: AH006705
Homo sapiens mu opioid receptor (OPRM1) and mu opioid receptor (OPRM1)s, partial cds
gi|2655104|gb|AH006705.1|SEG_HSOPRMI[2655104]

12338: AF024516
Homo sapiens mu opioid receptor (OPRM1) gene, partial cds, exons 2 and 3, complete IVS2
gi|2655102|gb|AF024516.1|HSOPRMI2[2655102]

12339: AF024515
Homo sapiens mu opioid receptor (OPRM1) gene, partial cds, exon 1
gi|2655101|gb|AF024515.1|HSOPRMI1[2655101]

12410: AF030625
Homo sapiens SCCL vasopressin subtype 1a receptor mRNA, complete cds
gi|2623229|gb|AF030625.1|AF030625[2623229]

12411: AF002986
Homo sapiens platelet activating receptor homolog (H963) mRNA, complete cds
gi|2580587|gb|AF002986.1|AF002986[2580587]

12412: AF023614
Homo sapiens transmembrane activator and CAML interactor (TACI) mRNA, complete cds
gi|2554947|gb|AF023614.1|AF023614[2554947]

12413: AF022860
Homo sapiens neuropilin-2(a17) mRNA, complete cds gi|2547131|gb|AF022860.1|AF022860[2547131]

12414: AF022859
Homo sapiens neuropilin-2(a0) mRNA, complete cds
gi|2547129|gb|AF022859.1|AF022859[2547129]

12415: AF016849
Homo sapiens apoptosis inducing receptor TRAIL-R2 (TRAILR2) mRNA, complete cds
gi|2465585|gb|AF016849.1|AF016849[2465585]

12416: AF013171
Homo sapiens TNF-related ligand TRANCE mRNA, partial cds
gi|2411499|gb|AF013171.1|AF013171[2411499]

12417: AF018956
Homo sapiens neuropilin mRNA, complete cds
gi|2407640|gb|AF018956.1|AF018956[2407640]

12419: AF015257
Homo sapiens flow-induced endothelial G protein-coupled receptor (FEG-1) mRNA, complete cds
gi|2353152|gb|AF015257.1|AF015257[2353152]

12420: U75285
Homo sapiens apoptosis inhibitor survivin gene, complete cds
gi|2315862|gb|U75285.1|HSU75285[2315862]

12421: AF012270
Homo sapiens visual pigment-like receptor peropsin (Rrh) mRNA, complete cds
gi|2307009|gb|AF012270.1|AF012270[2307009]

12422: AH006692
Homo sapiens chromosome 19 clone PAC clone 72N6 map 19q13.42
gi|2290633|gb|AH006692.1|SEG_HSNKAT2A[2290633]

12423: U97180
Homo sapiens NKAT-2a like protein (KIR) gene, exons 8 and 9 and complete cds gi|2290632|gb|U97180.1|HSNKAT2A8[2290632]

12424: U97179
Homo sapiens NKAT-2a like protein (KIR) gene, exon 7
gi|2290631|gb|U97179.1|HSNKAT2A7[2290631]

12425: U97178
Homo sapiens NKAT-2a like protein (KIR) gene, exon 6
gi|2290630|gb|U97178.1|HSNKAT2A6[2290630]

12426: U97177
KIR Homo sapiens NKAT-2a like protein (KIR) gene, exon 5
gi|2290629|gb|U97177.1|HSNKAT2A5[2290629]

12427: U97176
Homo sapiens NKAT-2a like protein (KIR) gene, exon 4
gi|2290628|gb|U97176.1|HSNKAT2A4[2290628]

12429: U97174
KIR Homo sapiens NKAT-2a like protein (KIR) gene, exon 2
gi|2290626|gb|U97174.1|HSNKAT2A2[2290626]

12430: U97173
Homo sapiens NKAT-2a like protein (KIR) gene, exon 1
gi|2290625|gb|U97173.1|HSNKAT2A1[2290625]

12431: U97075
Homo sapiens FLICE-like inhibitory protein short form mRNA, complete cds
gi|2253680|gb|U97075.1|U97075[2253680]

12432: U97074
Homo sapiens FLICE-like inhibitory protein long form mRNA, complete cds
gi|2253678|gb|U97074.1|U97074[2253678]

12688: L76380
Homo sapiens (clone HSNME29) CGRP type 1 receptor mRNA, complete cds
gi|1321593|gb|L76380.1|HUMCGRPB[1321593]

12689: L49241
Homo sapiens fibroblast growth factor 2 (FGFR2) Ser354Cys mutant gene, exon IIIc
gi|1129116|gb|L49241.1|HUMFGF354C[1129116]

12690: L49240
Homo sapiens fibroblast growth factor 2 (FGFR2) Ala344Gly mutant gene, exon IIIc
gi|1129114|gb|L49240.1|HUMFGF344G[1129114]

12691: L49239
Homo sapiens fibroblast growth factor 2 (FGFR2) Cys342Tyr mutant gene, exon IIIc
gi|1129112|gb|L49239.1|HUMFGF342Y[1129112]

12692: L49238
Homo sapiens fibroblast growth factor 2 (FGFR2) Cys342Ser mutant gene, exon IIIc
gi|1129110|gb|L49238.1|HUMFGF342S[1129110]

12693: L49242
Homo sapiens fibroblast growth factor 2 (FGFR2) Gly338Arg mutant gene, exon IIIc
gi|1129108|gb|L49242.1|HUMFGF338R[1129108]

12694: L49237
Homo sapiens fibroblast growth factor 2 (FGFR2) Gln289Pro mutant gene, exon IIIu
gi|1129106|gb|L49237.1|HUMFGF289P[1129106]

12842: L38734
Homo sapiens hepatoma transmembrane kinase ligand (HTK ligand) mRNA, complete cds
gi|769675|gb|L38734.1|HUMHTK[769675]

12843: L40764
Homo sapiens vasoactive intestinal polypeptide receptor 2 (VIPR2) mRNA, complete cds
gi|712836|gb|L40764.1|HUMVIPR2A[712836]

12844: AF068181
Homo sapiens B cell linker protein BLNK-s mRNA, alternatively spliced, complete cds
gi|3406750|gb|AF068181.1|AF068181[3406750]

12845: AF068180
Homo sapiens B cell linker protein BLNK mRNA, alternatively spliced, complete cds
gi|3406748|gb|AF068180.1|AF068180[3406748]

12846: AF064801
Homo sapiens multiple membrane spanning receptor TRC8 (TRC8) mRNA, complete cds
gi|3395786|gb|AF064801.1|AF064801[3395786]

12847: AH006513
Homo sapiens glycine receptor alpha 3 subunit (GLRA3) gene
gi|3342791|gb|AH006513.1|SEG_HSGLRA3S[3342791]

12848: AF017724
Homo sapiens glycine receptor alpha 3 subunit (GLRA3) gene, exon 10n, and complete cds
gi|3342790|gb|AF017724.1|HSGLRA3S10[3342790]

12849: AF017723
Homo sapiens glycine receptor alpha 3 subunit (GLRA3) gene, exon 9n
gi|3342789|gb|AF017723.1|HSGLRA3S09[3342789]

12850: AF017722
Homo sapiens glycine receptor alpha 3 subunit (GLRA3) gene, exon 8
gi|3342788|gb|AF017722.1|HSGLRA3S08[3342788]

12851: AF017721
Homo sapiens glycine receptor alpha 3 subunit (GLRA3) gene, exon 7
gi|3342787|gb|AF017721.1|HSGLRA3S07[3342787]

12852: AF017720
Homo sapiens glycine receptor alpha 3 subunit (GLRA3) gene, exon 6
gi|3342786|gb|AF017720.1|HSGLRA3S06[3342786]

12853: AF017719
Homo sapiens glycine receptor alpha 3 subunit (GLRA3) gene, exon 5
gi|3342785|gb|AF017719.1|HSGLRA3S05[3342785]

12854: AF017718
Homo sapiens glycine receptor alpha 3 subunit (GLRA3) gene, exon 4
gi|3342784|gb|AF017718.1|HSGLRA3S04[3342784]

12855: AF017717
Homo sapiens glycine receptor alpha 3 subunit (GLRA3) gene, exon 3
gi|3342783|gb|AF017717.1|HSGLRA3S03[3342783]

12856: AF017716
Homo sapiens glycine receptor alpha 3 subunit (GLRA3) gene, exon 2
gi|3342782|gb|AF017716.1|HSGLRA3S02[3342782]

12857: AF017715
Homo sapiens glycine receptor alpha 3 subunit (GLRA3) gene, exon 1
gi|3342781|gb|AF017715.1|HSGLRA3S01[3342781]

12858: AF018157
Homo sapiens glycine receptor alpha 3 subunit (GLRA3) mRNA, alternatively spliced, partial cds
gi|3342237|gb|AF018157.1|AF018157[3342237]

12861: AF045764
Homo sapiens orphan G protein-coupled receptor (GPR32) gene, complete cds
gi|3282838|gb|AF045764.1|AF045764[3282838]

12864: AF053004
Homo sapiens class I cytokine receptor (WSX1) mRNA, complete cds
gi|3153240|gb|AF053004.1|AF053004[3153240]

12865: AF055872
Homo sapiens Apo3/DR3 ligand (APO3L) mRNA, complete cds
gi|3108230|gb|AF055872.1|AF055872[3108230]

12866: AF057140
Homo sapiens cargo selection protein TIP47 (TIP47) mRNA, complete cds
gi|3095185|gb|AF057140.1|AF057140[3095185]

12870: AF028785
Homo sapiens phosphatidylinositol 3-kinase p55 gamma regulatory subunit mRNA, complete cds
gi|3046405|gb|AF028785.1|AF028785[3046405]

12872: AF027826
Homo sapiens putative seven pass transmembrane protein (TM7SF1) mRNA, complete cds
gi|2992627|gb|AF027826.1|AF027826[2992627]

12883: AF040630
Homo sapiens galanin receptor GalR2 mRNA, complete cds
gi|2921759|gb|AF040630.1|AF040630[2921759]

12904: U86281
Homo sapiens olfactory receptor (OR7-141) gene, partial cds
gi|2921715|gb|U86281.1|U86281[2921715]

12905: U86280
Homo sapiens olfactory receptor (OR7-140) gene, partial cds
gi|2921713|gb|U86280.1|U86280[2921713]

12906: U86279
Homo sapiens olfactory receptor (OR7-139) gene, partial cds
gi|2921711|gb|U86279.1|U86279[2921711]

12907: U86278
Homo sapiens olfactory receptor (OR7-138) gene, partial cds
gi|2921709|gb|U86278.1|U86278[2921709]

12911: U86274

Homo sapiens olfactory receptor (OR5-85) gene, partial cds
gi|2921704|gb|U86274.1|U86274[2921704]

12915: U86270
Homo sapiens olfactory receptor (OR5-40) gene, partial cds
gi|2921699|gb|U86270.1|U86270[2921699]

12921: U86264
Homo sapiens olfactory receptor (OR3-145) gene, partial cds
gi|2921692|gb|U86264.1|U86264[2921692]

12927: AH006491
Homo sapiens GPI-linked anchor protein (GFRA1), complete cds
gi|2921544|gb|AH006491.1|SEG_HSGFRA1G[2921544]

12928: AF038420
Homo sapiens GPI-linked anchor protein (GFRA1) gene, exon 11 and complete cds
gi|2921543|gb|AF038420.1|HSGFRA1G11[2921543]

12929: AF038419
Homo sapiens GPI-linked anchor protein (GFRA1) gene, exon 10
gi|2921542|gb|AF038419.1|HSGFRA1G10[2921542]

12930: AF038418
Homo sapiens GPI-linked anchor protein (GFRA1) gene, exon 9
gi|2921541|gb|AF038418.1|HSGFRA1G 9[2921541]

12931: AF038417
Homo sapiens GPI-linked anchor protein (GFRA1) gene, exon 8
gi|2921540|gb|AF038417.1|HSGFRA1G 8[2921540]

12932: AF038416
Homo sapiens GPI-linked anchor protein (GFRA1) gene, exon 7
gi|2921539|gb|AF038416.1|HSGFRA1G 7[2921539]

12933: AF038415
Homo sapiens GPI-linked anchor protein (GFRA1) gene, exon 6 gi|2921538|gb|AF038415.1|HSGFRA1G 6[2921538]

12934: AF038414
Homo sapiens GPI-linked anchor protein (GFRA1) gene, exon 5
gi|2921537|gb|AF038414.1|HSGFRA1G 5[2921537]

12935: AF038413
Homo sapiens GPI-linked anchor protein (GFRA1) gene, exon 4
gi|2921536|gb|AF038413.1|HSGFRA1G 4[2921536]

12936: AF038412
Homo sapiens GPI-linked anchor protein (GFRA1) gene, exon 3
gi|2921535|gb|AF038412.1|HSGFRA1G 3[2921535]

12937: AF038411
Homo sapiens GPI-linked anchor protein (GFRA1) gene, exon 2
gi|2921534|gb|AF038411.1|HSGFRA1G 2[2921534]

12938: AF036906
Homo sapiens linker for activation of T cells (LAT) mRNA, alternatively spliced form, complete cds
gi|2828025|gb|AF036906.1|AF036906[2828025]

12939: AF036905
Homo sapiens linker for activation of T cells (LAT) mRNA, complete cds
gi|2828023|gb|AF036905.1|AF036905[2828023]

12940: AF043724
Homo sapiens hepatitis A virus cellular receptor 1 (hHAVcr-1) mRNA, complete cds
gi|2827453|gb|AF043724.1|AF043724[2827453]

12954: U86239
Homo sapiens olfactory receptor (OR16-90) gene, partial cds
gi|2921659|gb|U86239.1|U86239[2921659]

12955: U86238
Homo sapiens olfactory receptor (OR16-89) gene, partial cds gi|2921657|gb|U86238.1|U86238[2921657]

12956: U86237
Homo sapiens olfactory receptor (OR16-88) gene, partial cds
gi|2921655|gb|U86237.1|U86237[2921655]

12957: U86236
Homo sapiens olfactory receptor (OR16-37) gene, partial cds
gi|2921653|gb|U86236.1|U86236[2921653]

12958: U86235
Homo sapiens olfactory receptor (OR16-36) gene, partial cds
gi|2921651|gb|U86235.1|U86235[2921651]

12959: U86234
Homo sapiens olfactory receptor (OR16-35) gene, partial cds
gi|2921649|gb|U86234.1|U86234[2921649]

12971: U86222
Homo sapiens olfactory receptor (OR13-66) gene, partial cds
gi|2921636|gb|U86222.1|U86222[2921636]

12977: U86216
Homo sapiens olfactory receptor (OR1-26) gene, partial cds
gi|2921629|gb|U86216.1|U86216[2921629]

12978: U86215
Homo sapiens olfactory receptor (OR1-25) gene, partial cds
gi|2921627|gb|U86215.1|U86215[2921627]

12979: AF016261
Homo sapiens interleukin-1 receptor accessory protein (IL1RAP) gene, partial cds
gi|2911297|gb|AF016261.1|AF016261[2911297]

12980: AF041245
Homo sapiens orexin receptor-2 mRNA, complete cds
gi|2897127|gb|AF041245.1|AF041245[2897127]

12981: AF041243
Homo sapiens orexin receptor-1 mRNA, complete cds
gi|2897123|gb|AF041243.1|AF041243[2897123]

12982: U97123
Homo sapiens chemokine receptor mRNA, complete cds
gi|2897070|gb|U97123.1|HSU97123[2897070]

12983: AF009014
Homo sapiens glutamate receptor delta-2 subunit (GLURD2) mRNA, complete cds
gi|2853314|gb|AF009014.1|AF009014[2853314]

12984: AF036581
Homo sapiens tumor necrosis factor superfamily member LIGHT mRNA, complete cds
gi|2815623|gb|AF036581.1|AF036581[2815623]

12985: AF040991
Homo sapiens roundabout 2 (robo2) mRNA, partial cds
gi|2804785|gb|AF040991.1|AF040991[2804785]

12986: AF040990
Homo sapiens roundabout 1 (robo1) mRNA, complete cds
gi|2804783|gb|AF040990.1|AF040990[2804783]

12987: AF026070
Homo sapiens death receptor 3 beta (DR3) mRNA, complete cds
gi|2570830|gb|AF026070.1|AF026070[2570830]

12988: AF021818
Homo sapiens putative neurotransmitter receptor mRNA, complete cds
gi|2465431|gb|AF021818.1|AF021818[2465431]

12990: L48211
Homo Sapiens angiotensin II receptor gene, complete cds
gi|1160612|gb|L48211.1|HUMAIR[1160612]

12992: L47169
Homo sapiens neuropeptide Y receptor gene, exon, promoter C
gi|976208|gb|L47169.1|HUMNPYAC[976208]

12993: L47168
Homo sapiens neuropeptide Y receptor gene, exon, promoter B
gi|976207|gb|L47168.1|HUMNPYAB[976207]

12994: L47167
Homo sapiens neuropeptide Y receptor gene, exon, promoter A
gi|976206|gb|L47167.1|HUMNPYAA[976206]

12995: L37086
Homo sapiens FK-506 binding protein (fkbp12.6) gene, complete cds
gi|965467|gb|L37086.1|HUMFK506B[965467]

12996: L36566
Human helodermin-preferring VIP receptor (VIP2/PACAP receptor) mRNA, complete cds
gi|550477|gb|L36566.1|HUMHVRP[550477]

12997: L25647
Homo sapiens fibroblast growth factor receptor gene (located in the central MHC) signal peptide and consecutive exon
gi|457233|gb|L25647.1|HUMFGFRZ[457233]

12998: M85247
H.sapiens dopamine D1A receptor gene, complete exon 1, and exon 2, 5' end
gi|181652|gb|M85247.1|HUMDOPAM[181652]

12999: L21195
Human serotonin 5-HT7 receptor mRNA, complete cds
gi|413865|gb|L21195.1|HUMSHTR[413865]

13000: L22647
Human prostaglandin receptor ep1 subtype mRNA, complete cds
gi|410208|gb|L22647.1|HUMG[410208]

13001: L10822
Human gastrin receptor gene, complete cds
gi|406075|gb|L10822.1|HUMGARE[406075]

13002: L19546
Human (IL2RG) gene, complete cds with repeats
gi|349631|gb|L19546.1|HUMIL2RGA[349631]

13003: M95667
Homo sapiens c-erb B2/neu protein (ERBB2) gene, partial cds
gi|182168|gb|M95667.1|HUMERBB2[182168]

13004: AF087138
Homo sapiens sulfonylurea receptor 1 (SUR1) mRNA, complete cds
gi|3643189|gb|AF087138.1|AF087138[3643189]

13005: AF042782
Homo sapiens galanin receptor type 2 (GALR2) gene, complete cds
gi|3642913|gb|AF042782.1|AF042782[3642913]

13007: AF064548
Homo sapiens low-density lipoprotein receptor-related protein 5 (LRP5) mRNA, complete cds
gi|3641526|gb|AF064548.1|AF064548[3641526]

13008: AF073799
Homo sapiens galanin receptor GALR3 mRNA, complete cds
gi|3608409|gb|AF073799.1|AF073799[3608409]

13009: D10202
Homo sapiens mRNA for platelet-activating factor receptor, complete cds
gi|219975|dbj|D10202.1|HUMPAFRE[219975]

13010: AB017498
Homo sapiens LRP5 mRNA for Lipoprotein Receptor Related Protein 5, complete cds
gi|3582144|dbj|AB017498.1|AB017498[3582144]

13011: AJ011041
Homo sapiens CHRM2 gene, satellite
gi|3581973|emb|AJ011041.1|HSA011041[3581973]

13012: AH006427
Homo sapiens chromosome 12 map 12q13-14
gi|3561040|gb|AH006427.1|SEG_HOMOVDR[3561040]

13013: AF080456
Homo sapiens vitamin D receptor gene, exon 1f
gi|3561039|gb|AF080456.1|HOMOVDR3[3561039]

13014: AF080455
Homo sapiens vitamin D receptor gene, exon 1e
gi|3561038|gb|AF080455.1|HOMOVDR2[3561038]

13015: AF080454
Homo sapiens vitamin D receptor gene, exon 1d
gi|3561037|gb|AF080454.1|HOMOVDR1[3561037]

13025: AJ001689
Homo sapiens NKG2D gene, exon 10
gi|2980867|emb|AJ001689.1|HSAJ1689[2980867]

13026: AJ001688
Homo sapiens NKG2D gene, exons 6-9
gi|2980866|emb|AJ001688.1|HSAJ1688[2980866]

13027: AJ001687
Homo sapiens NKG2D gene, exons 2-5 and joined mRNA and CDS
gi|2980864|emb|AJ001687.1|HSAJ1687[2980864]

13028: AJ001686
Homo sapiens NKG2F gene
gi|2980862|emb|AJ001686.1|HSAJ1686[2980862]

13029: AJ001685
Homo sapiens NKG2E gene
gi|2980860|emb|AJ001685.1|HSAJ1685[2980860]

13030: AJ001684
Homo sapiens NKG2C gene
gi|2980858|emb|AJ001684.1|HSAJ1684[2980858]

13031: AJ001683
Homo sapiens NKG2F mRNA
gi|2980856|emb|AJ001683.1|HSAJ1683[2980856]

13032: Y12546
H.sapiens mRNA for P2Y-like G-protein coupled receptor
gi|2687818|emb|Y12546.1|HSP2YLG[2687818]

13033: AF015525
Homo sapiens putative chemokine receptor (CRAM-B) mRNA, complete cds
gi|3550069|gb|AF015525.1|AF015525[3550069]

13034: AF015524
Homo sapiens putative chemokine receptor (CRAM-A) mRNA, complete cds
gi|3550066|gb|AF015524.1|AF015524[3550066]

13035: AF068868
Homo sapiens TNFR-related death receptor-6 (DR6) mRNA, complete cds
gi|3549262|gb|AF068868.1|AF068868[3549262]

13036: AF052572
Homo sapiens chemokine receptor CXCR4 gene, promoter region and complete cds
gi|3549254|gb|AF052572.1|AF052572[3549254]

13037: AC005625
Homo sapiens chromosome 19, cosmid R27328, complete sequence
gi|3549153|gb|AC005625.1|AC005625[3549153]

13038: AF051152
Homo sapiens Toll/interleukin-1 receptor-like protein 4 (TIL4) mRNA, complete cds
gi|3132527|gb|AF051152.1|AF051152[3132527]

13039: AF051151
Homo sapiens Toll/interleukin-1 receptor-like protein 3 (TIL3) mRNA, complete cds
gi|3132525|gb|AF051151.1|AF051151[3132525]

13040: AC005601
Homo sapiens chromosome 5, BAC clone 343g16 (LBNL H180), complete sequence
gi|3522917|gb|AC005601.1|AC005601[3522917]

13042: U88540
Homo sapiens Toll-like receptor 1 (TLR1) mRNA, complete cds
gi|2459617|gb|U88540.1|HSU88540[2459617]

13066: Z94155
H.sapiens mRNA for P2Y-like G-protein coupled receptor (partial)
gi|2695875|emb|Z94155.1|HSZ94155[2695875]

13067: Z94154
H.sapiens mRNA for P2Y-like G-protein coupled receptor
gi|2695873|emb|Z94154.1|HSZ94154[2695873]

13068: AF074264
Homo sapiens LDL receptor-related protein 6 (LRP6) mRNA, complete cds
gi|3462526|gb|AF074264.1|AF074264[3462526]

13069: AF021233
Homo sapiens TRAIL-R4-B (TRAIL-R4) mRNA, complete cds
gi|3452184|gb|AF021233.1|AF021233[3452184]

13070: AF021232
Homo sapiens TRAIL-R4-A (TRAIL-R4) mRNA, complete cds
gi|3452182|gb|AF021232.1|AF021232[3452182]

13072: X98765
H.sapiens gene encoding secretory component of polymeric immunoglobulin receptor
gi|2546984|emb|X98765.1|HSSC[2546984]

13103: U50062
Homo sapiens RIP protein kinase mRNA, complete cds
gi|3426026|gb|U50062.1|HSU50062[3426026]

13104: AF078925
Homo sapiens P2X1 receptor gene, partial cds
gi|3421366|gb|AF078925.1|AF078925[3421366]

13106: AF061785
Homo sapiens gamma-aminobutyric acid receptor A5 subunit (GABRA5) gene, three alternative first exons and exons 2-3, partial cds
gi|3420025|gb|AF061785.1|AF061785[3420025]

13110: AB009462
Homo sapiens hLRp105 mRNA for LDL receptor related protein 105, complete cds
gi|3413957|dbj|AB009462.1|AB009462[3413957]

13111: AF075590
Homo sapiens MCF-7 peripheral-type benzodiazepine receptor (PBR) mRNA, partial cds
gi|3411164|gb|AF075590.1|AF075590[3411164]

13112: AF075589
Homo sapiens MDA-MB-231 peripheral-type benzodiazepine receptor (PBR) mRNA, partial cds
gi|3411162|gb|AF075589.1|AF075589[3411162]

13113: L39064
Homo sapiens interleukin 9 receptor precursor (IL9R) gene, complete cds
gi|632992|gb|L39064.1|HUMIL9RA[632992]

13114: AJ224878
Homo sapiens mRNA for T-cell receptor interacting molecule (TRIM) protein gi|3402215|emb|AJ224878.1|HSAJ4878[3402215]

13115: AF080214
Homo sapiens protease-activated receptor 4 mRNA, complete cds
gi|3396080|gb|AF080214.1|AF080214[3396080]

13116: AF075005
Homo sapiens full length insert cDNA YH98E06
gi|3377544|gb|AF075005.1|HUMYH98E06[3377544]

13133: AF062006
Homo sapiens orphan G protein-coupled receptor HG38 mRNA, complete cds
gi|3366801|gb|AF062006.1|AF062006[3366801]

13134: Y12815
H.sapiens mRNA for chemokine receptor D6
gi|2204204|emb|Y12815.1|HSY12815[2204204]

13135: AC005338
Homo sapiens chromosome 19, cosmid R31646, complete sequence
gi|3355457|gb|AC005338.1|AC005338[3355457]

13137: AF078530
Homo sapiens receptor interacting protein 2 (RIP2) mRNA, complete cds
gi|3342909|gb|AF078530.1|AF078530[3342909]

13138: AF077526
Homo sapiens parathyroid hormone-related protein receptor gene, partial cds
gi|3342553|gb|AF077526.1|AF077526[3342553]

13139: AH006311
Homo sapiens chromosome 11 gastrin\cholecystokinin brain receptor (CCKBR), partial cds
gi|3342089|gb|AH006311.1|SEG_HSCCKBR[3342089]

13140: AF074029

Homo sapiens gastrin\cholecystokinin brain receptor (CCKBR) gene, exons 4 and 5 and partial cds
gi|3342088|gb|AF074029.1|HSCCKBR2[3342088]

13141: AF074035
Homo sapiens gastrin\cholecystokinin brain receptor (CCKBR) gene, exons 2 and 3
gi|3342087|gb|AF074035.1|HSCCKBR1[3342087]

13142: U44132
Homo sapiens lung cancer suppressor region LCR11.1 satellite DNA
gi|1174163|gb|U44132.1|HSU44132[1174163]

13143: Y14930
Homo sapiens TCRAV28 gene, allele A4, partial
gi|2664276|emb|Y14930.1|HSY14930[2664276]

13144: Y14931
Homo sapiens TCRAV28 gene, allele A5, partial
gi|2661832|emb|Y14931.1|HSY14931[2661832]

13145: Y14929
Homo sapiens TCRAV28 gene, allele A3, partial
gi|2661828|emb|Y14929.1|HSY14929[2661828]

13146: AF074087
Homo sapiens killer cell inhibitory receptor short form (KIR2DS2) mRNA, alternatively spliced, partial cds
gi|3328178|gb|AF074087.1|AF074087[3328178]

13147: Y12507
H.sapiens mRNA for serotonin receptor 5-HT4D, splice variant
gi|3326990|emb|Y12507.1|HSY12507[3326990]

13148: Y12506
H.sapiens mRNA for serotonin receptor 5-HT4C, splice variant
gi|3326988|emb|Y12506.1|HSY12506[3326988]

13151: D85242
Homo sapiens mRNA for NOR-1 3'-variant, partial cds
gi|3168581|dbj|D85242.1|D85242[3168581]

13152: D85241
Homo sapiens mRNA for NOR-1beta, partial cds
gi|3168579|dbj|D85241.1|D85241[3168579]

13153: AF034633
Homo sapiens orphan G protein-coupled receptor (GPR39) mRNA, complete cds
gi|2654160|gb|AF034633.1|AF034633[2654160]

13154: AF034632
Homo sapiens orphan G protein-coupled receptor (GPR38) gene, complete cds
gi|2654158|gb|AF034632.1|AF034632[2654158]

13155: AF054633
Homo sapiens thrombin receptor gene, exon 1 and partial cds
gi|3309036|gb|AF054633.1|AF054633[3309036]

13156: AF073792
Homo sapiens CGRP-receptor component protein mRNA, complete cds
gi|3300101|gb|AF073792.1|AF073792[3300101]

13157: AF007575
Homo sapiens ES/130-related protein mRNA, partial cds
gi|3299886|gb|AF007575.1|AF007575[3299886]

13158: AF055917
Homo sapiens protease-activated receptor 4 mRNA, complete cds
gi|3293321|gb|AF055917.1|AF055917[3293321]

13160: AC005255
Homo sapiens chromosome 19, CIT-HSP-146e8, complete sequence
gi|3289998|gb|AC005255.1|AC005255[3289998]

13165: AB012724

Homo sapiens gene for endothelin-A receptor, cis_element region
gi|3273319|dbj|AB012724.1|AB012724[3273319]

13166: AB015745
Homo sapiens mRNA for human prolactin-releasing peptide receptor, complete cds
gi|3273224|dbj|AB015745.1|AB015745[3273224]

13167: AF020498
Homo sapiens P2X1 purinoceptor (P2X) mRNA, complete cds
gi|3258622|gb|AF020498.1|AF020498[3258622]

13170: AF051767
Homo sapiens GDNF family receptor alpha 3 (GFRA3) mRNA, complete cds
gi|2961631|gb|AF051767.1|AF051767[2961631]

13171: AH006188
Homo sapiens GABA-A receptor pi subunit (GABRP), partial cds
gi|3252851|gb|AH006188.1|SEG_HSGABRP[3252851]

13172: AF009702
Homo sapiens GABA-A receptor pi subunit gene (GABRP), exon 10 and complete cds
gi|3252850|gb|AF009702.1|HSGABRP10[3252850]

13173: AF009701
Homo sapiens GABA-A receptor pi subunit gene (GABRP), exon 9
gi|3252849|gb|AF009701.1|HSGABRP09[3252849]

13174: AF009700
Homo sapiens GABA-A receptor pi subunit gene (GABRP), exon 8
gi|3252848|gb|AF009700.1|HSGABRP08[3252848]

13175: AF009699
Homo sapiens GABA-A receptor pi subunit gene (GABRP), exon 7
gi|3252847|gb|AF009699.1|HSGABRP07[3252847]

13176: AF009698
Homo sapiens GABA-A receptor pi subunit gene (GABRP), exon 6 gi|3252846|gb|AF009698.1|HSGABRP06[3252846]

13177: AF009697
Homo sapiens GABA-A receptor pi subunit gene (GABRP), exon 5
gi|3252845|gb|AF009697.1|HSGABRP05[3252845]

13178: AF009696
Homo sapiens GABA-A receptor pi subunit gene (GABRP), exon 4
gi|3252844|gb|AF009696.1|HSGABRP04[3252844]

13179: AF009695
Homo sapiens GABA-A receptor pi subunit gene (GABRP), exon 3
gi|3252843|gb|AF009695.1|HSGABRP03[3252843]

13180: AF009694
Homo sapiens GABA-A receptor pi subunit gene (GABRP), exon 2
gi|3252842|gb|AF009694.1|HSGABRP02[3252842]

13181: AF009693
Homo sapiens GABA-A receptor pi subunit gene (GABRP), exon 1
gi|3252841|gb|AF009693.1|HSGABRP01[3252841]

13182: E13909
cDNA encoding human MCP-1 receptor protein
gi|3252676|dbj|E13909.1|E13909[3252676]

13183: E13892
cDNA encoding human novel G protein-coupling receptor protein
gi|3252659|dbj|E13892.1|E13892[3252659]

13184: E13385
cDNA encoding human MIP-1 alpha /RANTES receptor
gi|3252190|dbj|E13385.1|E13385[3252190]

13185: E13006
cDNA encoding human G-protein coupling receptor protein
gi|3251830|dbj|E13006.1|E13006[3251830]

13186: E13005
cDNA encoding human G-protein-coupling receptor protein
gi|3251829|dbj|E13005.1|E13005[3251829]

13187: E12979
cDNA encoding human interleukin-6 receptor
gi|3251803|dbj|E12979.1|E12979[3251803]

13188: E12916
Human cDNA encoding a denatured low-density lipoprotein receptor
gi|3251747|dbj|E12916.1|E12916[3251747]

13189: E12845
cDNA encoding melatonin receptor
gi|3251677|dbj|E12845.1|E12845[3251677]

13190: E12752
A novel human Corticotropin Releasing Factor 2 (CRF2) receptor mRNA, complete cds
gi|3251584|dbj|E12752.1|E12752[3251584]

13191: E12750
A novel human Corticotropin Releasing Factor 2 (CRF2) receptor mRNA, complete cds
gi|3251582|dbj|E12750.1|E12750[3251582]

13192: E12703
cDNA encoding asialoglycoprotein receptor L-H2, AGPR L-H2
gi|3251535|dbj|E12703.1|E12703[3251535]

13193: E12702
cDNA encoding asialoglycoprotein receptor H1, AGPR H1
gi|3251534|dbj|E12702.1|E12702[3251534]

13197: E12658
cDNA encoding galanin receptor gi|3251490|dbj|E12658.1|E12658[3251490]

13198: E12487
Human cDNA encoding a G protein-coupled receptor
gi|3251320|dbj|E12487.1|E12487[3251320]

13199: E12484
Human cDNA encoding a G protein-coupled receptor
gi|3251317|dbj|E12484.1|E12484[3251317]

13200: E12354
cDNA encoding receptor of luteinizing hormone-releasing hormone,LH-RH receptor
gi|3251188|dbj|E12354.1|E12354[3251188]

13201: E12281
cDNA encoding human growth hormone-releasing hormone receptor
gi|3251115|dbj|E12281.1|E12281[3251115]

13202: E12186
A novel ligand for receptor type tyrosine kinase
gi|3251020|dbj|E12186.1|E12186[3251020]

13203: E12185
cDNA encoding a receptor type tyrosine kinase
gi|3251019|dbj|E12185.1|E12185[3251019]

13204: AF009962
Homo sapiens CC-chemokine receptor (CCR-5) gene, delta-32 allele, complete cds
gi|3243092|gb|AF009962.1|AF009962[3243092]

13205: AF050525
Homo sapiens proteinase activated receptor-3 (PAR-3) gene, 5' regulatory sequence
gi|3241996|gb|AF050525.1|AF050525[3241996]

13206: U33328
Homo sapiens killer cell Ig-like receptor variant (KIR3DL1) mRNA, complete cds gi|995756|gb|U33328.1|HSU33328[995756]

13207: U31416
Homo sapiens killer cell Ig-like receptor (KIR3DL1) mRNA, complete cds
gi|973405|gb|U31416.1|HSU31416[973405]

13208: U50748
Homo sapiens leptin receptor short form (db) mRNA, complete cds
gi|3236285|gb|U50748.1|HSU50748[3236285]

13215: Y14838
Homo sapiens ChemR23 gene
gi|3219597|emb|Y14838.1|HSCHEMR23[3219597]

13216: Y12505
H.sapiens mRNA for serotonin receptor 5-HT4B, splice variant
gi|2661756|emb|Y12505.1|HSY12505[2661756]

13217: Y08756
H.sapiens mRNA for serotonin receptor 5-HT4
gi|2661732|emb|Y08756.1|HS5HT4AR[2661732]

13218: X85785
H.sapiens DARC gene
gi|929624|emb|X85785.1|HSDARC[929624]

13219: AH006173
Homo sapiens Type II integral membrane protein (NKG2-F), complete cds
gi|2674028|gb|AH006173.1|SEG_HSNKG2F0[2674028]

13220: AF001298
Homo sapiens type II integral membrane protein (NKG2-D) gene, exons 9-13
gi|2674027|gb|AF001298.1|HSNKG2F02[2674027]

13221: AF001297
Homo sapiens type II integral membrane protein (NKG2-D) gene, exons 5-8
gi|2674026|gb|AF001297.1|HSNKG2F01[2674026]

13222: AF048704
Homo sapiens lamin B receptor homolog TM7SF2 gene, complete cds
gi|3211743|gb|AF048704.1|AF048704[3211743]

13223: AF023676
Homo sapiens lamin B receptor homolog TM7SF2 (TM7SF2) mRNA, complete cds
gi|3211721|gb|AF023676.1|AF023676[3211721]

13224: AJ001016
Homo sapiens mRNA encoding RAMP3
gi|3171913|emb|AJ001016.1|HSRAMP3[3171913]

13236: Y13584
Homo sapiens mRNA for serotin receptor 4, short splice variant
gi|3183985|emb|Y13584.1|HSY13584[3183985]

13237: AF030339
Homo sapiens receptor for viral semaphorin protein (VESPR) mRNA, complete cds
gi|3176761|gb|AF030339.1|AF030339[3176761]

13239: AC004782
Homo sapiens chromosome 5, BAC clone 205e20 (LBNL H170), complete sequence
gi|3172145|gb|AC004782.1|AC004782[3172145]

13240: AF009662
Homo sapiens T cell receptor beta locus, TCRBV13S1 to TCRBV6S9 region
gi|2275573|gb|AF009662.1|HSTCRBB27[2275573]

13241: AJ001015
Homo sapiens mRNA encoding RAMP2
gi|3171911|emb|AJ001015.1|HSRAMP2[3171911]

13242: AJ001014
Homo sapiens mRNA encoding RAMP1
gi|3171909|emb|AJ001014.1|HSRAMP1[3171909]

13243: AF011333
Homo sapiens DEC-205 mRNA, complete cds
gi|3165456|gb|AF011333.1|AF011333[3165456]

13244: AJ001902
Homo sapiens mRNA for TRIP6 (thyroid receptor interacting protein)
gi|2558591|emb|AJ001902.1|HSTRIP6[2558591]

13245: AF002216
AF002216 AP20 melanoma mRNA Homo sapiens cDNA, mRNA sequence
gi|2895065|gb|AF002216.1|AF002216[2895065]

13246: AF002215
AF002215 AP20 melanoma mRNA Homo sapiens cDNA, mRNA sequence
gi|2895064|gb|AF002215.1|AF002215[2895064]

13247: AF002214
AF002214 AP20 melanoma mRNA Homo sapiens cDNA, mRNA sequence
gi|2895063|gb|AF002214.1|AF002214[2895063]

13248: AC002411
Arabidopsis thaliana chromosome 1 BAC F20D22 sequence, complete sequence
gi|2570223|gb|AC002411.1|F20D22[2570223]

13249: AF058927
Homo sapiens clone hvRNA92 vRNA sequence
gi|3138979|gb|AF058927.1|AF058927[3138979]

13250: AF058926
Homo sapiens clone hvRNA82 vRNA sequence
gi|3138978|gb|AF058926.1|AF058926[3138978]

13252: AC004699
Homo sapiens chromosome 19, cosmid R31973, complete sequence
gi|3138892|gb|AC004699.1|AC004699[3138892]

13253: Y13472
Homo sapiens mRNA for FIM protein
gi|3135791|emb|Y13472.1|HSRIMP[3135791]

13254: AF015452
Homo sapiens Usurpin-gamma mRNA, complete cds
gi|3133284|gb|AF015452.1|AF015452[3133284]

13255: AF015451
Homo sapiens Usurpin-beta mRNA, complete cds
gi|3133282|gb|AF015451.1|AF015451[3133282]

13256: AF015450
Homo sapiens Usurpin-alpha mRNA, complete cds
gi|3133280|gb|AF015450.1|AF015450[3133280]

13257: AF063658
Homo sapiens vascular endothelial growth factor receptor 2 (KDR) mRNA, complete cds
gi|3132832|gb|AF063658.1|AF063658[3132832]

13258: AJ224869
Homo sapiens CXCR4 gene encoding receptor CXCR4
gi|3059119|emb|AJ224869.1|HSA224869[3059119]

13259: AH006106
Homo sapiens apoptosis signaling receptor FAS (FAS) and apoptosis signaling receptor FAS (FAS)s, partial cds
gi|3128402|gb|AH006106.1|SEG_HSASRFAS[3128402]

13260: AF061979
Homo sapiens apoptosis signaling receptor FAS (FAS) gene, exon 7 and partial cds
gi|3128401|gb|AF061979.1|HSASRFAS2[3128401]

13261: AF061978
Homo sapiens apoptosis signaling receptor FAS (FAS) gene, exons 6 and 7 and partial cds gi|3128400|gb|AF061978.1|HSASRFAS1[3128400]

13262: AH006105
Homo sapiens sulfonylurea receptor type (SUR2) gene, alternative splice products, complete cds
gi|3127174|gb|AH006105.1|SEG_HSSUR2G[3127174]

13263: AF061324
Homo sapiens sulfonylurea receptor 2B (SUR2) gene, alternatively spliced product, exon 38b and complete cds
gi|3127173|gb|AF061324.1|HSSUR2G71[3127173]

13264: AF061323
Homo sapiens sulfonylurea receptor 2A (SUR2) gene, alternatively spliced product, exon 38a and complete cds
gi|3127172|gb|AF061323.1|HSSUR2G69[3127172]

13265: AF061322
Homo sapiens sulfonylurea receptor (SUR2) gene, exon 37
gi|3127171|gb|AF061322.1|HSSUR2G67[3127171]

13266: AF061321
Homo sapiens sulfonylurea receptor (SUR2) gene, exon 36
gi|3127170|gb|AF061321.1|HSSUR2G65[3127170]

13267: AF061320
Homo sapiens sulfonylurea receptor (SUR2) gene, exon 35
gi|3127169|gb|AF061320.1|HSSUR2G63[3127169]

13268: AF061319
Homo sapiens sulfonylurea receptor (SUR2) gene, exon 34
gi|3127168|gb|AF061319.1|HSSUR2G61[3127168]

13269: AF061318
Homo sapiens sulfonylurea receptor (SUR2) gene, exon 33
gi|3127167|gb|AF061318.1|HSSUR2G59[3127167]

13270: AF061317
Homo sapiens sulfonylurea receptor (SUR2) gene, exon 32
gi|3127166|gb|AF061317.1|HSSUR2G57[3127166]

13271: AF061316
Homo sapiens sulfonylurea receptor (SUR2) gene, exon 31
gi|3127165|gb|AF061316.1|HSSUR2G55[3127165]

13272: AF061315
Homo sapiens sulfonylurea receptor (SUR2) gene, exon 30
gi|3127164|gb|AF061315.1|HSSUR2G53[3127164]

13273: AF061314
Homo sapiens sulfonylurea receptor (SUR2) gene, exon 29
gi|3127163|gb|AF061314.1|HSSUR2G51[3127163]

13274: AF061313
Homo sapiens sulfonylurea receptor (SUR2) gene, exon 28
gi|3127162|gb|AF061313.1|HSSUR2G49[3127162]

13275: AF061312
Homo sapiens sulfonylurea receptor (SUR2) gene, exon 27
gi|3127161|gb|AF061312.1|HSSUR2G47[3127161]

13276: AF061311
Homo sapiens sulfonylurea receptor (SUR2) gene, exons 25 and 26
gi|3127160|gb|AF061311.1|HSSUR2G45[3127160]

13277: AF061310
Homo sapiens sulfonylurea receptor (SUR2) gene, exon 24
gi|3127159|gb|AF061310.1|HSSUR2G43[3127159]

13278: AF061309
Homo sapiens sulfonylurea receptor (SUR2) gene, exon 23
gi|3127158|gb|AF061309.1|HSSUR2G41[3127158]

13279: AF061308

Homo sapiens sulfonylurea receptor (SUR2) gene, exons 21 and 22
gi|3127157|gb|AF061308.1|HSSUR2G39[3127157]

13280: AF061307
Homo sapiens sulfonylurea receptor (SUR2) gene, exon 20
gi|3127156|gb|AF061307.1|HSSUR2G37[3127156]

13281: AF061306
Homo sapiens sulfonylurea receptor (SUR2) gene, exon 19
gi|3127155|gb|AF061306.1|HSSUR2G35[3127155]

13282: AF061305
Homo sapiens sulfonylurea receptor (SUR2) gene, exon 18
gi|3127154|gb|AF061305.1|HSSUR2G33[3127154]

13283: AF061304
Homo sapiens sulfonylurea receptor (SUR2) gene, exon 17
gi|3127153|gb|AF061304.1|HSSUR2G31[3127153]

13284: AF061303
Homo sapiens sulfonylurea receptor (SUR2) gene, exon 16
gi|3127152|gb|AF061303.1|HSSUR2G29[3127152]

13285: AF061302
Homo sapiens sulfonylurea receptor (SUR2) gene, exon 15
gi|3127151|gb|AF061302.1|HSSUR2G27[3127151]

13286: AF061301
Homo sapiens sulfonylurea receptor (SUR2) gene, exon 14
gi|3127150|gb|AF061301.1|HSSUR2G25[3127150]

13287: AF061300
Homo sapiens sulfonylurea receptor (SUR2) gene, exon 13
gi|3127149|gb|AF061300.1|HSSUR2G23[3127149]

13288: AF061299
Homo sapiens sulfonylurea receptor (SUR2) gene, exon 12 gi|3127148|gb|AF061299.1|HSSUR2G21[3127148]

13289: AF061298
Homo sapiens sulfonylurea receptor (SUR2) gene, exon 11
gi|3127147|gb|AF061298.1|HSSUR2G19[3127147]

13290: AF061297
Homo sapiens sulfonylurea receptor (SUR2) gene, exon 10
gi|3127146|gb|AF061297.1|HSSUR2G17[3127146]

13291: AF061296
Homo sapiens sulfonylurea receptor (SUR2) gene, exon 9
gi|3127145|gb|AF061296.1|HSSUR2G15[3127145]

13292: AF061295
Homo sapiens sulfonylurea receptor (SUR2) gene, exons 7 and 8
gi|3127144|gb|AF061295.1|HSSUR2G13[3127144]

13293: AF061294
Homo sapiens sulfonylurea receptor (SUR2) gene, exon 6
gi|3127143|gb|AF061294.1|HSSUR2G11[3127143]

13294: AF061293
Homo sapiens sulfonylurea receptor (SUR2) gene, exon 5
gi|3127142|gb|AF061293.1|HSSUR2G09[3127142]

13295: AF061292
Homo sapiens sulfonylurea receptor (SUR2) gene, exon 4
gi|3127141|gb|AF061292.1|HSSUR2G07[3127141]

13296: AF061291
Homo sapiens sulfonylurea receptor (SUR2) gene, exon 3
gi|3127140|gb|AF061291.1|HSSUR2G05[3127140]

13297: AF061290
Homo sapiens sulfonylurea receptor (SUR2) gene, exon 2
gi|3127139|gb|AF061290.1|HSSUR2G03[3127139]

13298: AF061289
Homo sapiens sulfonylurea receptor (SUR2) gene, exon 1
gi|3127138|gb|AF061289.1|HSSUR2G01[3127138]

13299: U77783
Homo sapiens N-methyl-D-aspartate receptor 2D subunit precursor (NMDAR2D) mRNA, complete cds
gi|2444025|gb|U77783.1|HSU77783[2444025]

13300: AJ001515
Homo sapiens mRNA for ryanodine receptor 3, complete CDS
gi|3123583|emb|AJ001515.1|HSRYR3[3123583]

13302: AJ002512
Homo sapiens mRNA for ryanodine receptor 3, partial
gi|2582750|emb|AJ002512.1|HSAJ2512[2582750]

13303: AJ002511
Homo sapiens mRNA for ryanodine receptor 2, partial
gi|2582748|emb|AJ002511.1|HSAJ2511[2582748]

13315: Z81148
H.sapiens mRNA for gonadotropin-releasing hormone receptor, splice variant
gi|1628389|emb|Z81148.1|HSGTRHSV[1628389]

13316: U71092
Homo sapiens somatostatin receptor-like protein (GPR24) gene, complete cds
gi|1737178|gb|U71092.1|HSU71092[1737178]

13317: AH006056
Homo sapiens chromosome 10 clone BAC 73106 map 10q25-q26
gi|3068782|gb|AH006056.1|SEG_HSGFRA1H[3068782]

13318: AF058999
Homo sapiens glial cell line-derived neurotrophic factor receptor alpha (GFRA1) gene, exon 11 and complete cds gi|3068781|gb|AF058999.1|HSGFRA1H10[3068781]

13319: AF058998
Homo sapiens glial cell line-derived neurotrophic factor receptor alpha (GFRA1) gene, exon 10
gi|3068780|gb|AF058998.1|HSGFRA1H09[3068780]

13320: AF058997
Homo sapiens glial cell line-derived neurotrophic factor receptor alpha (GFRA1) gene, exon 9
gi|3068779|gb|AF058997.1|HSGFRA1H08[3068779]

13321: AF058996
Homo sapiens glial cell line-derived neurotrophic factor receptor alpha (GFRA1) gene, exon 8
gi|3068778|gb|AF058996.1|HSGFRA1H07[3068778]

13322: AF058995
Homo sapiens glial cell line-derived neurotrophic factor receptor alpha (GFRA1) gene, exon 7
gi|3068777|gb|AF058995.1|HSGFRA1H06[3068777]

13323: AF058994
Homo sapiens glial cell line-derived neurotrophic factor receptor alpha (GFRA1) gene, exon 6
gi|3068776|gb|AF058994.1|HSGFRA1H05[3068776]

13324: AF058993
Homo sapiens glial cell line-derived neurotrophic factor receptor alpha (GFRA1) gene, exon 5
gi|3068775|gb|AF058993.1|HSGFRA1H04[3068775]

13325: AF058992
Homo sapiens glial cell line-derived neurotrophic factor receptor alpha (GFRA1) gene, exon 4
gi|3068774|gb|AF058992.1|HSGFRA1H03[3068774]

13326: AF058991

Homo sapiens glial cell line-derived neurotrophic factor receptor alpha (GFRA1) gene, exon 3
gi|3068773|gb|AF058991.1|HSGFRA1H02[3068773]

13327: AF058990
Homo sapiens glial cell line-derived neurotrophic factor receptor alpha (GFRA1) gene, exon 2
gi|3068772|gb|AF058990.1|HSGFRA1H01[3068772]

13328: AF044197
Homo sapiens B lymphocyte chemoattractant BLC mRNA, complete cds
gi|2911375|gb|AF044197.1|AF044197[2911375]

13329: Y16280
Homo sapiens mRNA for G protein-coupled receptor ETBR-LP-2
gi|3059117|emb|Y16280.1|HSETBRLP2[3059117]

13330: U16260
Neisseria gonorrheae lactoferrin receptor precursor (lbpA) gene, complete cds
gi|915277|gb|U16260.1|NGU16260[915277]

13331: AF057177
Homo sapiens T-cell receptor gamma V1 gene region
gi|3047019|gb|AF057177.1|AF057177[3047019]

13333: AF057168
Homo sapiens type II interleukin-1 receptor antagonist (IL-1ra3) gene, partial cds
gi|3046605|gb|AF057168.1|AF057168[3046605]

13334: L06155
Homo sapiens melanocortin receptor gene, complete cds
gi|188673|gb|L06155.1|HUMMR[188673]

13335: L27490
Homo sapiens prostanoid EP3-I receptor mRNA, complete cds
gi|440313|gb|L27490.1|HUMPEIRB[440313]

13336: L27489
Homo sapiens prostanoid EP3-III receptor mRNA, complete cds
gi|440311|gb|L27489.1|HUMPEIRA[440311]

13337: L27488
Homo sapiens prostanoid EP3-II receptor mRNA, complete cds
gi|440309|gb|L27488.1|HUMPEIR[440309]

13338: AF009664
Homo sapiens T cell receptor beta locus, 3' trypsinogen repeats
gi|2275594|gb|AF009664.1|HSTCRB1H[2275594]

13339: AF009660
Homo sapiens T cell receptor beta locus, TCRBV7S3A2 to TCRBV12S2 region
gi|2275560|gb|AF009660.1|HSTCRBK17[2275560]

13340: AB006537
Homo sapiens mRNA for interleukin 1 receptor accessory protein, complete cds
gi|3041772|dbj|AB006537.1|AB006537[3041772]

13341: AF016098
Homo sapiens vascular endothelial cell growth factor 165 receptor 2 (VEGF165R2) mRNA, complete cds
gi|2978561|gb|AF016098.1|AF016098[2978561]

13342: AF016050
Homo sapiens vascular endothelial cell growth factor 165 receptor/neuropilin (VEGF165) mRNA, complete cds
gi|2978559|gb|AF016050.1|AF016050[2978559]

13343: U90941
Homo sapiens cell-type natural killer cells Fc gamma receptor RIIc4 (Fc-gammaRIIC) mRNA, complete cds
gi|2149631|gb|U90941.1|HSU90941[2149631]

13344: U90940
Homo sapiens cell-type natural killer cells Fc gamma receptor IIc3

(Fc-gammaRIIC) mRNA, complete cds
gi|2149629|gb|U90940.1|HSU90940[2149629]

13345: U90939
Homo sapiens cell-type natural killer cells Fc gamma receptor IIc2
(Fc-gammaRIIC) mRNA, complete cds
gi|2149627|gb|U90939.1|HSU90939[2149627]

13346: U90938
Homo sapiens cell-type natural killer cells Fc gamma receptor IIc1
(Fc-gammaRIIC) mRNA, complete cds
gi|2149625|gb|U90938.1|HSU90938[2149625]

13348: Y14739
Homo sapiens CXCR4 gene
gi|3021393|emb|Y14739.1|HSCXCR4[3021393]

13349: Y07683
H.sapiens mRNA for P2X3 purinoceptor
gi|2370146|emb|Y07683.1|HSP2X3PC[2370146]

13350: AF027390
Homo sapiens 7q telomere, complete sequence
gi|3004858|gb|AF027390.1|AF027390[3004858]

13351: U04357
Homo sapiens arginine vasopressin receptor type II, V2 antidiuretic hormone
receptor (AVPR2) gene, complete cds
gi|3004498|gb|U04357.1|HSU04357[3004498]

13352: AH006005
Homo sapiens TGF-beta type I receptor (TGFBR1), complete cds
gi|3003037|gb|AH006005.1|SEG_HSTGFBR1G[3003037]

13353: AF054598
Homo sapiens TGF-beta type I receptor (TGFBR1) gene, exon 9 and complete cds
gi|3003036|gb|AF054598.1|HSTGFBR1G9[3003036]

13354: AF054597
Homo sapiens TGF-beta type I receptor (TGFBR1) gene, exon 8
gi|3003035|gb|AF054597.1|HSTGFBR1G8[3003035]

13355: AF054596
Homo sapiens TGF-beta type I receptor (TGFBR1) gene, exon 7
gi|3003034|gb|AF054596.1|HSTGFBR1G7[3003034]

13356: AF054595
Homo sapiens TGF-beta type I receptor (TGFBR1) gene, exon 6
gi|3003033|gb|AF054595.1|HSTGFBR1G6[3003033]

13357: AF054594
Homo sapiens TGF-beta type I receptor (TGFBR1) gene, exon 5
gi|3003032|gb|AF054594.1|HSTGFBR1G5[3003032]

13358: AF054593
Homo sapiens TGF-beta type I receptor (TGFBR1) gene, exon 4
gi|3003031|gb|AF054593.1|HSTGFBR1G4[3003031]

13359: AF054592
Homo sapiens TGF-beta type I receptor (TGFBR1) gene, exon 3
gi|3003030|gb|AF054592.1|HSTGFBR1G3[3003030]

13360: AF054591
Homo sapiens TGF-beta type I receptor (TGFBR1) gene, exon 2
gi|3003029|gb|AF054591.1|HSTGFBR1G2[3003029]

13361: AF054590
Homo sapiens TGF-beta type I receptor (TGFBR1) gene, exon 1
gi|3003028|gb|AF054590.1|HSTGFBR1G1[3003028]

13362: L12406
Homo sapiens chemoattractant receptor (fMLP) gene sequence
gi|348164|gb|L12406.1|HUMCR[348164]

13363: AC004510
Homo sapiens chromosome 19, cosmid R30385, complete sequence
gi|2996651|gb|AC004510.1|AC004510[2996651]

13364: U84721
Homo sapiens interferon gamma receptor 1 gene, microsatellite sequence
gi|2982188|gb|U84721.1|HSU84721[2982188]

13365: AF013261
Homo sapiens alpha 1A adrenergic receptor isoform 4 mRNA, complete cds
gi|2978555|gb|AF013261.1|AF013261[2978555]

13369: AF014794
Homo sapiens TNF related TRAIL receptor (TRAIL-R3) mRNA, complete cds
gi|2957263|gb|AF014794.1|AF014794[2957263]

13372: AC003658
Homo sapiens Xp22 BAC GS-607H18 (Genome Systems Human BAC library) complete sequence
gi|2935592|gb|AC003658.1|AC003658[2935592]

13375: AH005897
Homo sapiens type I sigma receptor, complete cds
gi|2914739|gb|AH005897.1|SEG_HSTIRG[2914739]

13376: AF001977
Homo sapiens type I sigma receptor gene, exon 4 and complete cds
gi|2914738|gb|AF001977.1|HSTIRG3[2914738]

13377: AF001976
Homo sapiens type I sigma receptor gene, exons 1, 2 and 3
gi|2914737|gb|AF001976.1|HSTIRG2[2914737]

13486: U78192
Homo sapiens Edg-2 receptor mRNA, complete cds
gi|1688304|gb|U78192.1|HSU78192[1688304]

13488: AF044492
Homo sapiens olfactory receptor-like protein (OLFR42A) gene, allele 9092.1, partial cds
gi|2828698|gb|AF044492.1|AF044492[2828698]

13489: AF044491
Homo sapiens olfactory receptor-like protein (OLFR42A) gene, allele 9004.14, partial cds
gi|2828696|gb|AF044491.1|AF044491[2828696]

13490: AF042078
Homo sapiens olfactory receptor-like protein (OLFR42A) gene, OLFR42A-9026.2 allele, partial cds
gi|2828681|gb|AF042078.1|AF042078[2828681]

13491: AB010710
Homo sapiens mRNA for lectin-like oxidized LDL receptor, complete cds
gi|2828355|dbj|AB010710.1|AB010710[2828355]

13492: AF041462
Homo sapiens I-FLICE isoform 5 mRNA, complete cds
gi|2827297|gb|AF041462.1|AF041462[2827297]

13493: AF041461
Homo sapiens I-FLICE isoform 4 mRNA, complete cds
gi|2827295|gb|AF041461.1|AF041461[2827295]

13494: AF041460
Homo sapiens I-FLICE isoform 3 mRNA, complete cds
gi|2827293|gb|AF041460.1|AF041460[2827293]

13495: AF041459
Homo sapiens I-FLICE isoform 2 mRNA, complete cds
gi|2827291|gb|AF041459.1|AF041459[2827291]

13496: AF041458
Homo sapiens I-FLICE mRNA, complete cds gi|2827289|gb|AF041458.1|AF041458[2827289]

13497: Z73157
H.sapiens mRNA for C3a anaphylatoxin receptor
gi|2826756|emb|Z73157.1|HSC3AAREC[2826756]

13498: U58917
Homo sapiens IL-17 receptor mRNA, complete cds
gi|2826475|gb|U58917.1|HSU58917[2826475]

13524: Y16282
Homo sapiens mRNA for nicotinic acetylcholine receptor alpha6 subunit precursor
gi|2815224|emb|Y16282.1|HSY16282[2815224]

13525: Y16281
Homo sapiens mRNA for nicotinic acetylcholine receptor alpha2 subunit precursor
gi|2815222|emb|Y16281.1|HSY16281[2815222]

13526: X98858
H.sapiens mRNA for HLA-C specific activatory NK receptor
gi|1419593|emb|X98858.1|HSNKREC[1419593]

13527: M76676
Homo sapiens leukocyte platelet-activating factor receptor mRNA, complete cds
gi|2810988|gb|M76676.1|HUMNPIIY20[2810988]

13528: Y08420
H.sapiens mRNA for nicotinic acetylcholine receptor alpha7 subunit precursor
gi|2808623|emb|Y08420.1|HSNACHRA7[2808623]

13529: Y08419
H.sapiens mRNA for nicotinic acetylcholine receptor alpha5 subunit precursor
gi|1702913|emb|Y08419.1|HSNACHRA5[1702913]

13530: Y08421
H.sapiens mRNA for nicotinic acetylcholine receptor alpha4 subunit precursor
gi|1702911|emb|Y08421.1|HSNACHRA4[1702911]

13531: Y08417

H.sapiens mRNA for nicotinic acetylcholine receptor beta3 subunit precursor
gi|1702909|emb|Y08417.1|HSNACHR3B[1702909]

13532: Y08416

H.sapiens mRNA for nicotinic acetylcholine receptor beta4 subunit precursor
gi|1702919|emb|Y08416.1|HSNACHRB4[1702919]

13533: Y08415

H.sapiens mRNA for nicotinic acetylcholine receptor beta2 subunit precursor
gi|1702917|emb|Y08415.1|HSNACHRB2[1702917]

13534: Y08418

H.sapiens mRNA for nicotinic acetylcholine receptor alpha3 subunit precursor
gi|1702907|emb|Y08418.1|HSNACHR3A[1702907]

13536: AF042077

Homo sapiens olfactory receptor-like protein (OLFR 42B) gene, OLFR 42B-9079.6
allele, partial cds
gi|2801710|gb|AF042077.1|AF042077[2801710]

13537: AF042076

Homo sapiens olfactory receptor-like protein (OLFR 42B) gene, OLFR 42B-9108.1
allele, partial cds
gi|2801708|gb|AF042076.1|AF042076[2801708]

13538: AF042075

Homo sapiens olfactory receptor-like protein (OLFR 42B) gene, OLFR 42B-9110
allele, partial cds
gi|2801706|gb|AF042075.1|AF042075[2801706]

13539: AF042074

Homo sapiens olfactory receptor-like protein (OLFR 42A) gene, OLFR 42A-9079.3
allele, partial cds
gi|2801704|gb|AF042074.1|AF042074[2801704]

13540: AF042073
Homo sapiens olfactory receptor-like protein (OLFR 42A) gene, OLFR 42A-9049 allele, partial cds
gi|2801702|gb|AF042073.1|AF042073[2801702]

13600: Y10530
H.sapiens gene encoding putative olfactory receptor (clone htpcr2)
gi|2792017|emb|Y10530.1|HSHTPCR2[2792017]

13601: Y10529
H.sapiens mRNA for putative olfactory receptor (clone ht2)
gi|2792015|emb|Y10529.1|HSHT2[2792015]

13614: Z26876
H.sapiens gene for ribosomal protein L38
gi|407422|emb|Z26876.1|HSRPL38[407422]

13615: Z50150
H.sapiens mRNA for tyrosine kinase activator protein 1 (TKA-1)
gi|1246762|emb|Z50150.1|HSTKA1MR[1246762]

13616: Y13055
Homo sapiens mRNA for NKG2-CII activating NK receptor
gi|2765292|emb|Y13055.1|HSNKG2CII[2765292]

13617: Y13054
Homo sapiens mRNA for NK receptor, clone GR #29
gi|2765290|emb|Y13054.1|HSNKREC29[2765290]

13618: Y10437
H.sapiens mRNA for serotonin receptor 4
gi|2765076|emb|Y10437.1|HSSERR4[2765076]

13619: AJ002105
Homo sapiens mRNA for NK receptor, clone library TG14#13
gi|2764706|emb|AJ002105.1|HSAJ2105[2764706]

13620: AJ002104
Homo sapiens mRNA for NK receptor, clone library TG14#6
gi|2764704|emb|AJ002104.1|HSAJ2104[2764704]

13621: AJ002103
Homo sapiens mRNA for NK receptor, clone library TG14#35
gi|2764702|emb|AJ002103.1|HSAJ2103[2764702]

13622: AJ002102
Homo sapiens mRNA for NK receptor, clone library TG14#8
gi|2764700|emb|AJ002102.1|HSAJ2102[2764700]

13623: AJ000001
Homo sapiens mRNA for CD94-B NK receptor
gi|2764393|emb|AJ000001.1|HSCD94B[2764393]

13624: Y10141
H.sapiens DAT1 gene, partial, VNTR
gi|1752665|emb|Y10141.1|HSDAT1[1752665]

13625: Z97213
Homo sapiens mRNA for T-cell receptor
gi|2239129|emb|Z97213.1|HSTCRBV2S[2239129]

13627: AF026263
Homo sapiens muscarinic receptor (CHRM5) mRNA, complete cds
gi|2605721|gb|AF026263.1|AF026263[2605721]

13628: AF026261
Homo sapiens histamine H1 receptor mRNA, complete cds
gi|2605717|gb|AF026261.1|AF026261[2605717]

13629: AF026260
Homo sapiens vitamin D receptor (VDR) mRNA, complete cds
gi|2605715|gb|AF026260.1|AF026260[2605715]

13630: AH005786

Homo sapiens CC chemokine receptor 5 (CCR5) gene, complete cds
gi|2739498|gb|AH005786.1|SEG_HSCCR5AB[2739498]

13631: AF031237
Homo sapiens CC chemokine receptor 5 (CCR5) gene, complete cds
gi|2739497|gb|AF031237.1|HSCCR5AB3[2739497]

13633: AH005782
Homo sapiens chromosome X map Xq28
gi|2735348|gb|AH005782.1|SEG_HSGABRE[2735348]

13634: AF037334
Homo sapiens Eph-like receptor tyrosine kinase hEphB1d (EphB1) mRNA, complete cds
gi|2739209|gb|AF037334.1|AF037334[2739209]

13635: AF037333
Homo sapiens Eph-like receptor tyrosine kinase hEphB1c (EphB1) mRNA, complete cds
gi|2739207|gb|AF037333.1|AF037333[2739207]

13636: AF011406
Homo sapiens corticotropin releasing hormone receptor type 2 beta isoform (CRH2R) mRNA, complete cds
gi|2738557|gb|AF011406.1|AF011406[2738557]

13637: U59632
Homo sapiens H5 mRNA, partial cds; and platelet glycoprotein Ib beta chain mRNA, complete cds
gi|1809264|gb|U59632.1|HSU59632[1809264]

13638: D86864
Homo sapiens mRNA for acetyl LDL receptor, complete cds
gi|2723468|dbj|D86864.1|D86864[2723468]

13639: AF027208
Homo sapiens AC133 antigen mRNA, complete cds
gi|2688948|gb|AF027208.1|AF027208[2688948]

13640: AB001025
Homo sapiens mRNA for brain ryanodine receptor, complete cds
gi|2696014|dbj|AB001025.1|AB001025[2696014]

13641: D00017
Homo sapiens mRNA for lipocortin II, complete cds
gi|219909|dbj|D00017.1|HUMLIC[219909]

13642: Y08236
H.sapiens LRP gene, polymorphisms in intron 24
gi|2125808|emb|Y08236.1|HSLRPIN24[2125808]

13644: AF025998
Homo sapiens atrial natriuretic peptide clearance receptor (ANPRC) mRNA, complete cds
gi|2570851|gb|AF025998.1|AF025998[2570851]

13645: AD000671
Homo sapiens DNA from chromosome 19-cosmid f24109 containing HRX2, genomic sequence
gi|1905893|gb|AD000671.1|AD000671[1905893]

13646: Z49119
H.sapiens mRNA for serotonin 6 receptor (5-HT6; partial)
gi|984128|emb|Z49119.1|HS5HT6[984128]

13647: Z48150
H.sapiens 5-HT4 mRNA for serotonin 4 receptor (5-HT4)
gi|984126|emb|Z48150.1|HS5HT4[984126]

13648: Y15743
Homo sapiens RET proto-oncogene, exon 13 containing two mutations
gi|2665353|emb|Y15743.1|HSRET13[2665353]

13649: AF000575
Homo sapiens clone 16 immunoglobulin-like transcript 5 mRNA, complete cds gi|2264428|gb|AF000575.1|AF000575[2264428]

13650: AF000574
Homo sapiens clone 1 immunoglobulin-like transcript 4 mRNA, complete cds
gi|2264426|gb|AF000574.1|AF000574[2264426]

13651: Z26652
H.sapiens FLT3 mRNA for FLT3 receptor tyrosine kinase
gi|406322|emb|Z26652.1|HSFLT3RTK[406322]

13653: X82208
H.sapiens mRNA for beta-centractin (ATCC# HHCPJ76)
gi|563887|emb|X82208.1|HSBCENTR[563887]

13654: AF035261
Homo sapiens thyroid stimulating hormone receptor (TSHR) mRNA, partial cds
gi|2654195|gb|AF035261.1|HSTSHR[2654195]

13655: AF032388
Homo sapiens vasopressin receptor type 2 mRNA, alternatively spliced, complete cds
gi|2654030|gb|AF032388.1|AF032388[2654030]

13656: AF025534
Homo sapiens leucocyte immunoglobulin-like receptor-8 (LIR-8) mRNA, complete cds
gi|2653874|gb|AF025534.1|AF025534[2653874]

13657: AF025533
Homo sapiens leucocyte immunoglobulin-like receptor-3 (LIR-3) mRNA, complete cds
gi|2653872|gb|AF025533.1|AF025533[2653872]

13658: AF025532
Homo sapiens leucocyte immunoglobulin-like receptor-5 (LIR-5) mRNA, complete cds
gi|2653870|gb|AF025532.1|AF025532[2653870]

13659: AF025531
Homo sapiens leucocyte immunoglobulin-like receptor-7 (LIR-7) mRNA, complete cds gi|2653868|gb|AF025531.1|AF025531[2653868]

13660: AF025530
Homo sapiens leucocyte immunoglobulin-like receptor-6a (LIR-6) mRNA, complete cds
gi|2653866|gb|AF025530.1|AF025530[2653866]

13661: AF025529
Homo sapiens leucocyte immunoglobulin-like receptor-6b (LIR-6) mRNA, complete cds
gi|2653864|gb|AF025529.1|AF025529[2653864]

13662: AF025528
Homo sapiens leucocyte immunoglobulin-like receptor-2 (LIR-2) mRNA, complete cds
gi|2653862|gb|AF025528.1|AF025528[2653862]

13663: AF025527
Homo sapiens leucocyte immunoglobulin-like receptor-4 (LIR-4) mRNA, complete cds
gi|2653860|gb|AF025527.1|AF025527[2653860]

13664: Y13583
Homo sapiens mRNA for G-protein coupled receptor
gi|2652933|emb|Y13583.1|HSGPCP[2652933]

13665: Y13367
H.sapiens mRNA for phosphoinositide 3-kinase
gi|2143259|emb|Y13367.1|HSPHOSI3K[2143259]

13666: X82207
H.sapiens mRNA for beta-centractin (PC3)
gi|563885|emb|X82207.1|HSBCENT[563885]

13667: AF033854
Homo sapiens lymphocyte inhibitor of TRAIL (LIT) mRNA, complete cds
gi|2645841|gb|AF033854.1|AF033854[2645841]

13668: X81882

H.sapiens mRNA for for vasopressin activated calcium mobilizing receptor-like protein
gi|1628414|emb|X81882.1|HSVACM1[1628414]

13669: AF024690
Homo sapiens putative G protein-coupled receptor (GPR43) gene, complete cds
gi|2612951|gb|AF024690.1|AF024690[2612951]

13670: AF024689
Homo sapiens putative G protein-coupled receptor (GPR42) gene, complete cds
gi|2612949|gb|AF024689.1|AF024689[2612949]

13671: AF024688
Homo sapiens putative G protein-coupled receptor (GPR41) gene, complete cds
gi|2612947|gb|AF024688.1|AF024688[2612947]

13672: AF024687
Homo sapiens putative G protein-coupled receptor (GPR40) gene, complete cds
gi|2612945|gb|AF024687.1|AF024687[2612945]

13673: D87513
Homo sapiens mRNA for Grb7 protein, partial cds
gi|1526534|dbj|D87513.1|D87513[1526534]

13674: D49919
Homo sapiens mRNA for C-C chemokine receptor type 2, complete cds
gi|2626807|dbj|D49919.1|D49919[2626807]

13675: AF030512
Homo sapiens small cell vasopressin subtype 1b receptor mRNA, complete cds
gi|2613124|gb|AF030512.1|AF030512[2613124]

13676: Y12852
Homo sapiens P2X7 gene, exon 2 and 3
gi|2612788|emb|Y12852.1|HSP2X7E23[2612788]

13677: Y12851

Homo sapiens P2X7 gene, exon 1 and joined CDS
gi|2597926|emb|Y12851.1|HSP2X7EX1[2597926]

13678: Y12854
Homo sapiens P2X7 gene, exon 9-11
gi|2612787|emb|Y12854.1|HSP2X7911[2612787]

13679: Y12853
Homo sapiens P2X7 gene, exon 4-8
gi|2612786|emb|Y12853.1|HSP2X748[2612786]

13680: Y12855
Homo sapiens P2X7 gene, exon 12 and 13
gi|2612785|emb|Y12855.1|HSP2X7123[2612785]

13681: AB005520
Homo sapiens ppar gamma2 gene for peroxisome proliferator activated-receptor gamma, partial cds and 5' flanking
gi|2605488|dbj|AB005520.1|AB005520[2605488]

13682: Y09765
Homo sapiens mRNA for putative GABA receptor epsilon subunit
gi|2285960|emb|Y09765.1|HSY09765[2285960]

13683: Y09764
Homo sapiens GABRE gene, exon 2-8
gi|2285959|emb|Y09764.1|HSY09764[2285959]

13684: Y09763
Homo sapiens GABRE gene, exon 1 (and joined CDS)
gi|2285957|emb|Y09763.1|HSY09763[2285957]

13685: AF026535
Homo sapiens chemokine receptor (CCR3) mRNA, complete cds
gi|2582565|gb|AF026535.1|AF026535[2582565]

13686: AF026071

Homo sapiens soluble death receptor 3 beta (DR3) mRNA, complete cds
gi|2570832|gb|AF026071.1|AF026071[2570832]

13687: AF022956
Homo sapiens beta2-adrenergic receptor (ADRB2) gene, complete cds
gi|2570532|gb|AF022956.1|AF022956[2570532]

13688: AF022955
Homo sapiens beta2-adrenergic receptor (ADRB2) gene, complete cds
gi|2570530|gb|AF022955.1|AF022955[2570530]

13689: AF022954
Homo sapiens beta2-adrenergic receptor (ADRB2) gene, complete cds
gi|2570528|gb|AF022954.1|AF022954[2570528]

13690: AF022953
Homo sapiens beta2-adrenergic receptor (ADRB2) gene, complete cds
gi|2570526|gb|AF022953.1|AF022953[2570526]

13691: AF014958
Homo sapiens chemokine receptor X (CKRX) mRNA, complete cds
gi|2305263|gb|AF014958.1|AF014958[2305263]

13692: AB000712
Homo sapiens hCPE-R mRNA for CPE-receptor, complete cds
gi|2570124|dbj|AB000712.1|AB000712[2570124]

13693: X94609
H.sapiens mRNA for activatory NK receptor/KKA3 p50.3
gi|1495414|emb|X94609.1|HSANKRMR[1495414]

13694: AF025375
Homo sapiens chemokine receptor-4 (CXCR4) mRNA, complete cds
gi|2565335|gb|AF025375.1|AF025375[2565335]

13695: AF000380
Homo sapiens folate binding protein mRNA, complete cds gi|2565193|gb|AF000380.1|HSAF000380[2565193]

13696: U35875
Homo sapiens B2 bradykinin receptor mRNA, 5' sequence
gi|1353391|gb|U35875.1|HSU35875[1353391]

13697: AF010193
Homo sapiens MAD-related gene SMAD7 (SMAD7) mRNA, complete cds
gi|2252821|gb|AF010193.1|AF010193[2252821]

13698: X94634
H.sapiens CD97 gene exon 7
gi|1165087|emb|X94634.1|HSX94634[1165087]

13699: X94633
H.sapiens CD97 gene exon 4
gi|1165086|emb|X94633.1|HSX94633[1165086]

13700: X94632
H.sapiens CD97 gene exon 3
gi|1165085|emb|X94632.1|HSX94632[1165085]

13702: AF007892
Homo sapiens P2Y6 receptor, long splice variant mRNA, complete cds
gi|2258421|gb|AF007892.1|[2258421]

13703: AF007891
Homo sapiens P2Y6 receptor, short splice variant mRNA, complete cds
gi|2258419|gb|AF007891.1|[2258419]

13704: AF022383
Homo sapiens complexin I mRNA, complete cds
gi|2465458|gb|AF022383.1|AF022383[2465458]

13709: X89860
H.sapiens mRNA for T-cell receptor alpha chain
gi|927420|emb|X89860.1|HSNP7TCR2[927420]

13710: Y08456
H.sapiens ChemR1 gene
gi|2465081|emb|Y08456.1|HSCHEMR1[2465081]

13711: U95025
Homo sapiens metabotropic glutamate receptor 8 (GRM8) mRNA, complete cds
gi|2435409|gb|U95025.1|HSU95025[2435409]

13712: AF021799
Homo sapiens interleukin 17 receptor-like mRNA sequence
gi|2460201|gb|AF021799.1|AF021799[2460201]

13714: U73443
Homo sapiens 5HT3 serotonin receptor gene, partial cds
gi|2459549|gb|U73443.1|MMU73443[2459549]

13715: AB000520
Homo sapiens mRNA for APS, complete cds
gi|2447035|dbj|AB000520.1|AB000520[2447035]

13716: X98172
H.sapiens mRNA for MACH-alpha-1 protein
gi|1403318|emb|X98172.1|HSMACHA1[1403318]

13728: AH005567
Homo sapiens chromosome 4 map 4q13
gi|2290767|gb|AH005567.1|SEG_HSGNRHR[2290767]

13729: AF001952
Homo sapiens gonadotropin releasing hormone receptor (GNRHR) gene, exon 3 and complete cds
gi|2290766|gb|AF001952.1|HSGNRHR3[2290766]

13730: AF001951
Homo sapiens gonadotropin releasing hormone receptor (GNRHR) gene, exon 2
gi|2290765|gb|AF001951.1|HSGNRHR2[2290765]

13731: AF001950

Homo sapiens gonadotropin releasing hormone receptor (GNRHR) gene, exon 1
gi|2290764|gb|AF001950.1|HSGNRHR1[2290764]

13733: AF020201

Homo sapiens Jagged 2 mRNA, complete cds
gi|2432001|gb|AF020201.1|AF020201[2432001]

13734: Y14442

Homo sapiens mRNA for olfactory receptor protein, partial
gi|2370144|emb|Y14442.1|HSOLFMF[2370144]

13736: AF017061

Homo sapiens vasopressin-activated calcium mobilizing putative receptor protein
(VACM-1) mRNA, complete cds
gi|2394273|gb|AF017061.1|AF017061[2394273]

13737: AF017262

Homo sapiens putative G protein-coupled receptor mRNA, complete cds
gi|2388705|gb|AF017262.1|AF017262[2388705]

13738: AF016917

Homo sapiens GABA-A receptor delta subunit (GABRD) mRNA, complete cds
gi|2388692|gb|AF016917.1|AF016917[2388692]

13739: Y13248

Homo sapiens mRNA for orphan chemokine receptor TYMSTR
gi|2370179|emb|Y13248.1|HSY13248[2370179]

13740: D83492

Homo sapiens mRNA for Eph-family protein, complete cds
gi|2281007|dbj|D83492.1|D83492[2281007]

13741: AB002058

Homo sapiens mRNA for HUMAN P2XM, complete cds
gi|2350846|dbj|AB002058.1|AB002058[2350846]

13742: AF015251
Homo sapiens breast cancer-related unknown protein mRNA, partial cds
gi|2345090|gb|AF015251.1|AF015251[2345090]

13743: AF004231
Homo sapiens monocyte/macrophage Ig-related receptor MIR-10 (MIR cl-10) mRNA, complete cds
gi|2343110|gb|AF004231.1|AF004231[2343110]

13744: AF004230
Homo sapiens monocyte/macrophage Ig-related receptor MIR-7 (MIR cl-7) mRNA, complete cds
gi|2343108|gb|AF004230.1|AF004230[2343108]

13745: X90563
H.sapiens mRNA for peroxisome proliferactor activated receptor gamma
gi|1480099|emb|X90563.1|HSPPARGAM[1480099]

13746: AF012629
Homo sapiens antagonist decoy receptor for TRAIL/Apo-2L (TRID) mRNA, complete cds
gi|2338430|gb|AF012629.1|AF012629[2338430]

13747: AF012628
Homo sapiens death domain containing receptor for TRAIL/Apo-2L (DR5) mRNA, complete cds
gi|2338428|gb|AF012628.1|AF012628[2338428]

13748: AF012536
Homo sapiens decoy receptor 1 (DcR1) mRNA, complete cds
gi|2338421|gb|AF012536.1|AF012536[2338421]

13749: AF012535
Homo sapiens death receptor 5 (DR5) mRNA, complete cds
gi|2338419|gb|AF012535.1|AF012535[2338419]

13750: AF012903
Homo sapiens P2X4 ATP-gated cation channel protein mRNA, partial cds
gi|2331043|gb|AF012903.1|AF012903[2331043]

13751: X69316
H.sapiens KIT proto-oncogene for mast/stem cell growth factor receptor, exon 21
gi|34105|emb|X69316.1|HSKITPO16[34105]

13752: X69315
H.sapiens KIT proto-oncogene for mast/stem cell growth factor receptor, exons 18, 19, 20
gi|34104|emb|X69315.1|HSKITPO15[34104]

13753: X69314
H.sapiens KIT proto-oncogene for mast/stem cell growth factor receptor, exon 17
gi|34103|emb|X69314.1|HSKITPO14[34103]

13754: X69313
H.sapiens KIT proto-oncogene for mast/stem cell growth factor receptor, exon 16
gi|34102|emb|X69313.1|HSKITPO13[34102]

13755: X69312
H.sapiens KIT proto-oncogene for mast/stem cell growth factor receptor, exon 15
gi|34101|emb|X69312.1|HSKITPO12[34101]

13756: X69311
H.sapiens KIT proto-oncogene for mast/stem cell growth factor receptor, exon 14
gi|34100|emb|X69311.1|HSKITPO11[34100]

13757: X69310
H.sapiens KIT proto-oncogene for mast/stem cell growth factor receptor, exons 10, 11, 12, 13
gi|34099|emb|X69310.1|HSKITPO10[34099]

13758: X69309
H.sapiens KIT proto-oncogene for mast/stem cell growth factor receptor, exon 9
gi|34098|emb|X69309.1|HSKITPO09[34098]

13759: X69308
H.sapiens KIT proto-oncogene for mast/stem cell growth factor receptor, exon 8
gi|34097|emb|X69308.1|HSKITPO08[34097]

13760: X69307
H.sapiens KIT proto-oncogene for mast/stem cell growth factor receptor, exon 7
gi|34096|emb|X69307.1|HSKITPO07[34096]

13761: X69306
H.sapiens KIT proto-oncogene for mast/stem cell growth factor receptor, exon 6
gi|34095|emb|X69306.1|HSKITPO06[34095]

13762: X69305
H.sapiens KIT proto-oncogene for mast/stem cell growth factor receptor, exon 5
gi|34094|emb|X69305.1|HSKITPO05[34094]

13763: AF005419
Homo sapiens P2Y5-like receptor gene, complete cds
gi|2240034|gb|AF005419.1|AF005419[2240034]

13764: L42324
Homo sapiens (clone GPCR W) G protein-linked receptor gene (GPCR) gene, 5' end of cds
gi|1066730|gb|L42324.1|HUMFRCG[1066730]

13766: AF015910
Homo sapiens unknown protein mRNA, partial cds
gi|2286201|gb|AF015910.1|AF015910[2286201]

13767: X99250
H.sapiens mRNA for endothelin-B receptor splice variant
gi|2285955|emb|X99250.1|HSX99250[2285955]

13768: AF007545
Homo sapiens SIV/HIV receptor Bonzo (Bonzo) mRNA, complete cds
gi|2253421|gb|AF007545.1|AF007545[2253421]

13769: Z79783
H.sapiens G protein-coupled receptor CKR-L2
gi|2281709|emb|Z79783.1|HSCKRL2[2281709]

13778: Z49994
H.sapiens partial gene for proteinase-activated receptor 2 (1289 BP)
gi|1008086|emb|Z49994.1|HSPAR2B[1008086]

13779: AF007555
Homo sapiens IAR/receptor-like protein-tyrosine phosphatase precursor mRNA, complete cds
gi|2262074|gb|AF007555.1|AF007555[2262074]

13780: AF008556
Homo sapiens interleukin-2 receptor mRNA, alternatively spliced, partial cds
gi|2266932|gb|AF008556.1|AF008556[2266932]

13891: Y10152
H.sapiens mRNA for CRF2 receptor, beta isoform, aberrantly spliced, (94bp deletion)
gi|1785640|emb|Y10152.1|HSCRF294[1785640]

13892: Y10153
H.sapiens mRNA for CRF2 receptor, beta isoform, aberrantly spliced, (227bp insertion)
gi|1785639|emb|Y10153.1|HSCRF2227[1785639]

13893: Y10151
H.sapiens mRNA for CRF2 receptor, beta isoform, partial
gi|1785637|emb|Y10151.1|HSCRF2[1785637]

13894: M17325
Homo sapiens T-cell receptor gamma-chain constant region (TCRGC1) mRNA, partial cds
gi|2072752|gb|M17325.1|HUMTCGCJ[2072752]

13895: M17324

Homo sapiens T-cell receptor gamma-chain constant region (TCRGC2) mRNA, partial cds
gi|2072751|gb|M17324.1|HUMTCGCI[2072751]

13896: M17323
Homo sapiens T-cell receptor gamma-chain constant region (TCRGC2) mRNA, partial cds
gi|2072750|gb|M17323.1|HUMTCGCH[2072750]

13897: AF004327
Homo sapiens angiopoietin-2 mRNA, complete cds
gi|2257932|gb|AF004327.1|AF004327[2257932]

13898: AF004021
Homo sapiens prostaglandin F2 alpha receptor mRNA, complete cds
gi|2257849|gb|AF004021.1|AF004021[2257849]

13899: AF006464
Homo sapiens muscle specific tyrosine kinase receptor (MUSK) mRNA, complete cds
gi|2253311|gb|AF006464.1|AF006464[2253311]

13900: AF005637
Homo sapiens endothelin A receptor gene, 5' flanking region and exon 1
gi|2253289|gb|AF005637.1|AF005637[2253289]

13902: Z24461
H.sapiens MTCP-1 gene
gi|406866|emb|Z24461.1|HSMTCP1I[406866]

13903: Z24463
H.sapiens MTCP-1 gene
gi|406865|emb|Z24463.1|HSMTCP1H[406865]

13904: Z24457
H.sapiens of TCRA gene MTCP-1 gene
gi|406860|emb|Z24457.1|HSMTCP1D[406860]

13905: Z24456
H.sapiens of MTCP-1 gene MTCP-1 gene
gi|406859|emb|Z24456.1|HSMTCP1C[406859]

13906: U45984
Homo sapiens CCR6 chemokine receptor (CMKBR6) gene, complete cds
gi|2246432|gb|U45984.1|HSU45984[2246432]

13908: AF005900
Homo sapiens alpha2B-adrenergic receptor (alpha2C2AR) gene, complete cds
gi|2245627|gb|AF005900.1|AF005900[2245627]

13909: AF005210
Homo sapiens CC chemokine receptor CCR8 (CMKBR8) mRNA, partial cds
gi|2245579|gb|AF005210.1|AF005210[2245579]

13524: Y16282
Homo sapiens mRNA for nicotinic acetylcholine receptor alpha6 subunit precursor
gi|2815224|emb|Y16282.1|HSY16282[2815224]

13525: Y16281
Homo sapiens mRNA for nicotinic acetylcholine receptor alpha2 subunit precursor
gi|2815222|emb|Y16281.1|HSY16281[2815222]

13526: X98858
H.sapiens mRNA for HLA-C specific activatory NK receptor
gi|1419593|emb|X98858.1|HSNKREC[1419593]

13527: M76676
Homo sapiens leukocyte platelet-activating factor receptor mRNA, complete cds
gi|2810988|gb|M76676.1|HUMNPIIY20[2810988]

13528: Y08420
H.sapiens mRNA for nicotinic acetylcholine receptor alpha7 subunit precursor
gi|2808623|emb|Y08420.1|HSNACHRA7[2808623]

13529: Y08419

H.sapiens mRNA for nicotinic acetylcholine receptor alpha5 subunit precursor
gi|1702913|emb|Y08419.1|HSNACHRA5[1702913]

13530: Y08421
H.sapiens mRNA for nicotinic acetylcholine receptor alpha4 subunit precursor
gi|1702911|emb|Y08421.1|HSNACHRA4[1702911]

13531: Y08417
H.sapiens mRNA for nicotinic acetylcholine receptor beta3 subunit precursor
gi|1702909|emb|Y08417.1|HSNACHR3B[1702909]

13532: Y08416
H.sapiens mRNA for nicotinic acetylcholine receptor beta4 subunit precursor
gi|1702919|emb|Y08416.1|HSNACHRB4[1702919]

13533: Y08415
H.sapiens mRNA for nicotinic acetylcholine receptor beta2 subunit precursor
gi|1702917|emb|Y08415.1|HSNACHRB2[1702917]

13534: Y08418
H.sapiens mRNA for nicotinic acetylcholine receptor alpha3 subunit precursor
gi|1702907|emb|Y08418.1|HSNACHR3A[1702907]

13535: AF001985
Homo sapiens CD38 gene, 5' upstream sequence
gi|2804672|gb|AF001985.1|AF001985[2804672]

13536: AF042077
Homo sapiens olfactory receptor-like protein (OLFR 42B) gene, OLFR 42B-9079.6 allele, partial cds
gi|2801710|gb|AF042077.1|AF042077[2801710]

13537: AF042076
Homo sapiens olfactory receptor-like protein (OLFR 42B) gene, OLFR 42B-9108.1 allele, partial cds
gi|2801708|gb|AF042076.1|AF042076[2801708]

13538: AF042075
Homo sapiens olfactory receptor-like protein (OLFR 42B) gene, OLFR 42B-9110 allele, partial cds
gi|2801706|gb|AF042075.1|AF042075[2801706]

13539: AF042074
Homo sapiens olfactory receptor-like protein (OLFR 42A) gene, OLFR 42A-9079.3 allele, partial cds
gi|2801704|gb|AF042074.1|AF042074[2801704]

13540: AF042073
Homo sapiens olfactory receptor-like protein (OLFR 42A) gene, OLFR 42A-9049 allele, partial cds
gi|2801702|gb|AF042073.1|AF042073[2801702]

13600: Y10530
H.sapiens gene encoding putative olfactory receptor (clone htpcr2)
gi|2792017|emb|Y10530.1|HSHTPCR2[2792017]

13601: Y10529
H.sapiens mRNA for putative olfactory receptor (clone ht2)
gi|2792015|emb|Y10529.1|HSHT2[2792015]

13614: Z26876
H.sapiens gene for ribosomal protein L38
gi|407422|emb|Z26876.1|HSRPL38[407422]

13615: Z50150
H.sapiens mRNA for tyrosine kinase activator protein 1 (TKA-1)
gi|1246762|emb|Z50150.1|HSTKA1MR[1246762]

13616: Y13055
Homo sapiens mRNA for NKG2-CII activating NK receptor
gi|2765292|emb|Y13055.1|HSNKG2CII[2765292]

13617: Y13054
Homo sapiens mRNA for NK receptor, clone GR #29
gi|2765290|emb|Y13054.1|HSNKREC29[2765290]

13618: Y10437
H.sapiens mRNA for serotonin receptor 4
gi|2765076|emb|Y10437.1|HSSERR4[2765076]

13619: AJ002105
Homo sapiens mRNA for NK receptor, clone library TG14#13
gi|2764706|emb|AJ002105.1|HSAJ2105[2764706]

13620: AJ002104
Homo sapiens mRNA for NK receptor, clone library TG14#6
gi|2764704|emb|AJ002104.1|HSAJ2104[2764704]

13621: AJ002103
Homo sapiens mRNA for NK receptor, clone library TG14#35
gi|2764702|emb|AJ002103.1|HSAJ2103[2764702]

13622: AJ002102
Homo sapiens mRNA for NK receptor, clone library TG14#8
gi|2764700|emb|AJ002102.1|HSAJ2102[2764700]

13623: AJ000001
Homo sapiens mRNA for CD94-B NK receptor
gi|2764393|emb|AJ000001.1|HSCD94B[2764393]

13624: Y10141
H.sapiens DAT1 gene, partial, VNTR
gi|1752665|emb|Y10141.1|HSDAT1[1752665]

13625: Z97213
Homo sapiens mRNA for T-cell receptor
gi|2239129|emb|Z97213.1|HSTCRBV2S[2239129]

13627: AF026263
Homo sapiens muscarinic receptor (CHRM5) mRNA, complete cds
gi|2605721|gb|AF026263.1|AF026263[2605721]

13628: AF026261
Homo sapiens histamine H1 receptor mRNA, complete cds
gi|2605717|gb|AF026261.1|AF026261[2605717]

13629: AF026260
Homo sapiens vitamin D receptor (VDR) mRNA, complete cds
gi|2605715|gb|AF026260.1|AF026260[2605715]

13630: AH005786
Homo sapiens CC chemokine receptor 5 (CCR5) gene, complete cds
gi|2739498|gb|AH005786.1|SEG_HSCCR5AB[2739498]

13631: AF031237
Homo sapiens CC chemokine receptor 5 (CCR5) gene, complete cds
gi|2739497|gb|AF031237.1|HSCCR5AB3[2739497]

13633: AH005782
Homo sapiens chromosome X map Xq28
gi|2735348|gb|AH005782.1|SEG_HSGABRE[2735348]

13634: AF037334
Homo sapiens Eph-like receptor tyrosine kinase hEphB1d (EphB1) mRNA, complete cds
gi|2739209|gb|AF037334.1|AF037334[2739209]

13635: AF037333
Homo sapiens Eph-like receptor tyrosine kinase hEphB1c (EphB1) mRNA, complete cds
gi|2739207|gb|AF037333.1|AF037333[2739207]

13636: AF011406
Homo sapiens corticotropin releasing hormone receptor type 2 beta isoform (CRH2R) mRNA, complete cds
gi|2738557|gb|AF011406.1|AF011406[2738557]

13637: U59632
Homo sapiens H5 mRNA, partial cds; and platelet glycoprotein Ib beta chain mRNA, complete cds
gi|1809264|gb|U59632.1|HSU59632[1809264]

13638: D86864
Homo sapiens mRNA for acetyl LDL receptor, complete cds
gi|2723468|dbj|D86864.1|D86864[2723468]

13639: AF027208
Homo sapiens AC133 antigen mRNA, complete cds
gi|2688948|gb|AF027208.1|AF027208[2688948]

13640: AB001025
Homo sapiens mRNA for brain ryanodine receptor, complete cds
gi|2696014|dbj|AB001025.1|AB001025[2696014]

13641: D00017
Homo sapiens mRNA for lipocortin II, complete cds
gi|219909|dbj|D00017.1|HUMLIC[219909]

13644: AF025998
Homo sapiens atrial natriuretic peptide clearance receptor (ANPRC) mRNA, complete cds
gi|2570851|gb|AF025998.1|AF025998[2570851]

13645: AD000671
Homo sapiens DNA from chromosome 19-cosmid f24109 containing HRX2, genomic sequence
gi|1905893|gb|AD000671.1|AD000671[1905893]

13646: Z49119
H.sapiens mRNA for serotonin 6 receptor (5-HT6; partial)
gi|984128|emb|Z49119.1|HS5HT6[984128]

13647: Z48150
H.sapiens 5-HT4 mRNA for serotonin 4 receptor (5-HT4)
gi|984126|emb|Z48150.1|HS5HT4[984126]

13648: Y15743
Homo sapiens RET proto-oncogene, exon 13 containing two mutations
gi|2665353|emb|Y15743.1|HSRET13[2665353]

13649: AF000575
Homo sapiens clone 16 immunoglobulin-like transcript 5 mRNA, complete cds
gi|2264428|gb|AF000575.1|AF000575[2264428]

13650: AF000574
Homo sapiens clone 1 immunoglobulin-like transcript 4 mRNA, complete cds
gi|2264426|gb|AF000574.1|AF000574[2264426]

13651: Z26652
H.sapiens FLT3 mRNA for FLT3 receptor tyrosine kinase
gi|406322|emb|Z26652.1|HSFLT3RTK[406322]

13653: X82208
H.sapiens mRNA for beta-centractin (ATCC# HHCPJ76)
gi|563887|emb|X82208.1|HSBCENTR[563887]

13654: AF035261
Homo sapiens thyroid stimulating hormone receptor (TSHR) mRNA, partial cds
gi|2654195|gb|AF035261.1|HSTSHR[2654195]

13655: AF032388
Homo sapiens vasopressin receptor type 2 mRNA, alternatively spliced, complete cds
gi|2654030|gb|AF032388.1|AF032388[2654030]

13656: AF025534
Homo sapiens leucocyte immunoglobulin-like receptor-8 (LIR-8) mRNA, complete cds
gi|2653874|gb|AF025534.1|AF025534[2653874]

13657: AF025533
Homo sapiens leucocyte immunoglobulin-like receptor-3 (LIR-3) mRNA, complete cds
gi|2653872|gb|AF025533.1|AF025533[2653872]

13658: AF025532
Homo sapiens leucocyte immunoglobulin-like receptor-5 (LIR-5) mRNA, complete cds
gi|2653870|gb|AF025532.1|AF025532[2653870]

13659: AF025531
Homo sapiens leucocyte immunoglobulin-like receptor-7 (LIR-7) mRNA, complete cds
gi|2653868|gb|AF025531.1|AF025531[2653868]

13660: AF025530
Homo sapiens leucocyte immunoglobulin-like receptor-6a (LIR-6) mRNA, complete cds
gi|2653866|gb|AF025530.1|AF025530[2653866]

13661: AF025529
Homo sapiens leucocyte immunoglobulin-like receptor-6b (LIR-6) mRNA, complete cds
gi|2653864|gb|AF025529.1|AF025529[2653864]

13662: AF025528
Homo sapiens leucocyte immunoglobulin-like receptor-2 (LIR-2) mRNA, complete cds
gi|2653862|gb|AF025528.1|AF025528[2653862]

13663: AF025527
Homo sapiens leucocyte immunoglobulin-like receptor-4 (LIR-4) mRNA, complete cds
gi|2653860|gb|AF025527.1|AF025527[2653860]

13664: Y13583
Homo sapiens mRNA for G-protein coupled receptor
gi|2652933|emb|Y13583.1|HSGPCP[2652933]

13665: Y13367
H.sapiens mRNA for phosphoinositide 3-kinase
gi|2143259|emb|Y13367.1|HSPHOSI3K[2143259]

13666: X82207
H.sapiens mRNA for beta-centractin (PC3)
gi|563885|emb|X82207.1|HSBCENT[563885]

13667: AF033854
Homo sapiens lymphocyte inhibitor of TRAIL (LIT) mRNA, complete cds
gi|2645841|gb|AF033854.1|AF033854[2645841]

13668: X81882
H.sapiens mRNA for for vasopressin activated calcium mobilizing receptor-like protein
gi|1628414|emb|X81882.1|HSVACM1[1628414]

13669: AF024690
Homo sapiens putative G protein-coupled receptor (GPR43) gene, complete cds
gi|2612951|gb|AF024690.1|AF024690[2612951]

13670: AF024689
Homo sapiens putative G protein-coupled receptor (GPR42) gene, complete cds
gi|2612949|gb|AF024689.1|AF024689[2612949]

13671: AF024688
Homo sapiens putative G protein-coupled receptor (GPR41) gene, complete cds
gi|2612947|gb|AF024688.1|AF024688[2612947]

13672: AF024687
Homo sapiens putative G protein-coupled receptor (GPR40) gene, complete cds
gi|2612945|gb|AF024687.1|AF024687[2612945]

13673: D87513
Homo sapiens mRNA for Grb7 protein, partial cds
gi|1526534|dbj|D87513.1|D87513[1526534]

13674: D49919
Homo sapiens mRNA for C-C chemokine receptor type 2, complete cds
gi|2626807|dbj|D49919.1|D49919[2626807]

13675: AF030512
Homo sapiens small cell vasopressin subtype 1b receptor mRNA, complete cds
gi|2613124|gb|AF030512.1|AF030512[2613124]

13676: Y12852
Homo sapiens P2X7 gene, exon 2 and 3
gi|2612788|emb|Y12852.1|HSP2X7E23[2612788]

13677: Y12851
Homo sapiens P2X7 gene, exon 1 and joined CDS
gi|2597926|emb|Y12851.1|HSP2X7EX1[2597926]

13678: Y12854
Homo sapiens P2X7 gene, exon 9-11
gi|2612787|emb|Y12854.1|HSP2X7911[2612787]

13679: Y12853
Homo sapiens P2X7 gene, exon 4-8
gi|2612786|emb|Y12853.1|HSP2X748[2612786]

13680: Y12855
Homo sapiens P2X7 gene, exon 12 and 13
gi|2612785|emb|Y12855.1|HSP2X7123[2612785]

13681: AB005520
Homo sapiens ppar gamma2 gene for peroxisome proliferator activated-receptor gamma, partial cds and 5' flanking
gi|2605488|dbj|AB005520.1|AB005520[2605488]

13682: Y09765
Homo sapiens mRNA for putative GABA receptor epsilon subunit
gi|2285960|emb|Y09765.1|HSY09765[2285960]

13683: Y09764
Homo sapiens GABRE gene, exon 2-8
gi|2285959|emb|Y09764.1|HSY09764[2285959]

13684: Y09763
Homo sapiens GABRE gene, exon 1 (and joined CDS)
gi|2285957|emb|Y09763.1|HSY09763[2285957]

13685: AF026535

Homo sapiens chemokine receptor (CCR3) mRNA, complete cds
gi|2582565|gb|AF026535.1|AF026535[2582565]

13686: AF026071

Homo sapiens soluble death receptor 3 beta (DR3) mRNA, complete cds
gi|2570832|gb|AF026071.1|AF026071[2570832]

13687: AF022956

Homo sapiens beta2-adrenergic receptor (ADRB2) gene, complete cds
gi|2570532|gb|AF022956.1|AF022956[2570532]

13688: AF022955

Homo sapiens beta2-adrenergic receptor (ADRB2) gene, complete cds
gi|2570530|gb|AF022955.1|AF022955[2570530]

13689: AF022954

Homo sapiens beta2-adrenergic receptor (ADRB2) gene, complete cds
gi|2570528|gb|AF022954.1|AF022954[2570528]

13690: AF022953

Homo sapiens beta2-adrenergic receptor (ADRB2) gene, complete cds
gi|2570526|gb|AF022953.1|AF022953[2570526]

13691: AF014958

Homo sapiens chemokine receptor X (CKRX) mRNA, complete cds
gi|2305263|gb|AF014958.1|AF014958[2305263]

13692: AB000712

Homo sapiens hCPE-R mRNA for CPE-receptor, complete cds
gi|2570124|dbj|AB000712.1|AB000712[2570124]

13693: X94609

H.sapiens mRNA for activatory NK receptor/KKA3 p50.3
gi|1495414|emb|X94609.1|HSANKRMR[1495414]

13694: AF025375
Homo sapiens chemokine receptor-4 (CXCR4) mRNA, complete cds
gi|2565335|gb|AF025375.1|AF025375[2565335]

13695: AF000380
Homo sapiens folate binding protein mRNA, complete cds
gi|2565193|gb|AF000380.1|HSAF000380[2565193]

13696: U35875
Homo sapiens B2 bradykinin receptor mRNA, 5' sequence
gi|1353391|gb|U35875.1|HSU35875[1353391]

13697: AF010193
Homo sapiens MAD-related gene SMAD7 (SMAD7) mRNA, complete cds
gi|2252821|gb|AF010193.1|AF010193[2252821]

13698: X94634
H.sapiens CD97 gene exon 7
gi|1165087|emb|X94634.1|HSX94634[1165087]

13699: X94633
H.sapiens CD97 gene exon 4
gi|1165086|emb|X94633.1|HSX94633[1165086]

13700: X94632
H.sapiens CD97 gene exon 3
gi|1165085|emb|X94632.1|HSX94632[1165085]

13702: AF007892
Homo sapiens P2Y6 receptor, long splice variant mRNA, complete cds
gi|2258421|gb|AF007892.1|[2258421]

13703: AF007891
Homo sapiens P2Y6 receptor, short splice variant mRNA, complete cds
gi|2258419|gb|AF007891.1|[2258419]

13704: AF022383
Homo sapiens complexin I mRNA, complete cds gi|2465458|gb|AF022383.1|AF022383[2465458]

13709: X89860
H.sapiens mRNA for T-cell receptor alpha chain
gi|927420|emb|X89860.1|HSNP7TCR2[927420]

13710: Y08456
H.sapiens ChemR1 gene
gi|2465081|emb|Y08456.1|HSCHEMR1[2465081]

13711: U95025
Homo sapiens metabotropic glutamate receptor 8 (GRM8) mRNA, complete cds
gi|2435409|gb|U95025.1|HSU95025[2435409]

13712: AF021799
Homo sapiens interleukin 17 receptor-like mRNA sequence
gi|2460201|gb|AF021799.1|AF021799[2460201]

13714: U73443
Homo sapiens 5HT3 serotonin receptor gene, partial cds
gi|2459549|gb|U73443.1|MMU73443[2459549]

13715: AB000520
Homo sapiens mRNA for APS, complete cds
gi|2447035|dbj|AB000520.1|AB000520[2447035]

13716: X98172
H.sapiens mRNA for MACH-alpha-1 protein
gi|1403318|emb|X98172.1|HSMACHA1[1403318]

13727: X92883
H.sapiens mRNA for T cell receptor alpha (clone XPHC46IV)
gi|1061141|emb|X92883.1|HSPHC46A1[1061141]

13728: AH005567
Homo sapiens chromosome 4 map 4q13
gi|2290767|gb|AH005567.1|SEG_HSGNRHR[2290767]

13729: AF001952
Homo sapiens gonadotropin releasing hormone receptor (GNRHR) gene, exon 3 complete cds
gi|2290766|gb|AF001952.1|HSGNRHR3[2290766]

13730: AF001951
Homo sapiens gonadotropin releasing hormone receptor (GNRHR) gene, exon 2
gi|2290765|gb|AF001951.1|HSGNRHR2[2290765]

13731: AF001950
Homo sapiens gonadotropin releasing hormone receptor (GNRHR) gene, exon 1
gi|2290764|gb|AF001950.1|HSGNRHR1[2290764]

13732: AF017263
Homo sapiens putative G protein-coupled receptor gene, partial intron sequence
gi|2435439|gb|AF017263.1|AF017263[2435439]

13733: AF020201
Homo sapiens Jagged 2 mRNA, complete cds
gi|2432001|gb|AF020201.1|AF020201[2432001]

13734: Y14442
Homo sapiens mRNA for olfactory receptor protein, partial
gi|2370144|emb|Y14442.1|HSOLFMF[2370144]

13735: AF017264
Homo sapiens putative G protein-coupled receptor gene, intronic sequence
gi|2407224|gb|AF017264.1|AF017264[2407224]

13736: AF017061
Homo sapiens vasopressin-activated calcium mobilizing putative receptor protein (VACM-1) mRNA, complete cds
gi|2394273|gb|AF017061.1|AF017061[2394273]

13737: AF017262 gi|2388705|gb|AF017262.1|AF017262[2388705]

13738: AF016917
Homo sapiens GABA-A receptor delta subunit (GABRD) mRNA, complete cds
gi|2388692|gb|AF016917.1|AF016917[2388692]

13739: Y13248
Homo sapiens mRNA for orphan chemokine receptor TYMSTR
gi|2370179|emb|Y13248.1|HSY13248[2370179]

13740: D83492
Homo sapiens mRNA for Eph-family protein, complete cds
gi|2281007|dbj|D83492.1|D83492[2281007]

13741: AB002058
Homo sapiens mRNA for HUMAN P2XM, complete cds
gi|2350846|dbj|AB002058.1|AB002058[2350846]

13742: AF015251
Homo sapiens breast cancer-related unknown protein mRNA, partial cds
gi|2345090|gb|AF015251.1|AF015251[2345090]

13743: AF004231
Homo sapiens monocyte/macrophage Ig-related receptor MIR-10 (MIR cl-10) mRNA, complete cds
gi|2343110|gb|AF004231.1|AF004231[2343110]

13744: AF004230
Homo sapiens monocyte/macrophage Ig-related receptor MIR-7 (MIR cl-7) mRNA, complete cds
gi|2343108|gb|AF004230.1|AF004230[2343108]

13745: X90563
H.sapiens mRNA for peroxisome proliferactor activated receptor gamma
gi|1480099|emb|X90563.1|HSPPARGAM[1480099]

13746: AF012629

Homo sapiens antagonist decoy receptor for TRAIL/Apo-2L (TRID) mRNA, complete cds
gi|2338430|gb|AF012629.1|AF012629[2338430]

13747: AF012628
Homo sapiens death domain containing receptor for TRAIL/Apo-2L (DR5) mRNA, complete cds
gi|2338428|gb|AF012628.1|AF012628[2338428]

13748: AF012536
Homo sapiens decoy receptor 1 (DcR1) mRNA, complete cds
gi|2338421|gb|AF012536.1|AF012536[2338421]

13749: AF012535
Homo sapiens death receptor 5 (DR5) mRNA, complete cds
gi|2338419|gb|AF012535.1|AF012535[2338419]

13750: AF012903
Homo sapiens P2X4 ATP-gated cation channel protein mRNA, partial cds
gi|2331043|gb|AF012903.1|AF012903[2331043]

13751: X69316
H.sapiens KIT proto-oncogene for mast/stem cell growth factor receptor, exon 21
gi|34105|emb|X69316.1|HSKITPO16[34105]

13752: X69315
H.sapiens KIT proto-oncogene for mast/stem cell growth factor receptor, exons 18, 19, 20
gi|34104|emb|X69315.1|HSKITPO15[34104]

13753: X69314
H.sapiens KIT proto-oncogene for mast/stem cell growth factor receptor, exon 17
gi|34103|emb|X69314.1|HSKITPO14[34103]

13754: X69313
H.sapiens KIT proto-oncogene for mast/stem cell growth factor receptor, exon 16
gi|34102|emb|X69313.1|HSKITPO13[34102]

13755: X69312
H.sapiens KIT proto-oncogene for mast/stem cell growth factor receptor, exon 15
gi|34101|emb|X69312.1|HSKITPO12[34101]

13756: X69311
H.sapiens KIT proto-oncogene for mast/stem cell growth factor receptor, exon 14
gi|34100|emb|X69311.1|HSKITPO11[34100]

13757: X69310
H.sapiens KIT proto-oncogene for mast/stem cell growth factor receptor, exons 10, 11, 12, 13
gi|34099|emb|X69310.1|HSKITPO10[34099]

13758: X69309
H.sapiens KIT proto-oncogene for mast/stem cell growth factor receptor, exon 9
gi|34098|emb|X69309.1|HSKITPO09[34098]

13759: X69308
H.sapiens KIT proto-oncogene for mast/stem cell growth factor receptor, exon 8
gi|34097|emb|X69308.1|HSKITPO08[34097]

13760: X69307
H.sapiens KIT proto-oncogene for mast/stem cell growth factor receptor, exon 7
gi|34096|emb|X69307.1|HSKITPO07[34096]

13761: X69306
H.sapiens KIT proto-oncogene for mast/stem cell growth factor receptor, exon 6
gi|34095|emb|X69306.1|HSKITPO06[34095]

13762: X69305
H.sapiens KIT proto-oncogene for mast/stem cell growth factor receptor, exon 5
gi|34094|emb|X69305.1|HSKITPO05[34094]

13763: AF005419
Homo sapiens P2Y5-like receptor gene, complete cds
gi|2240034|gb|AF005419.1|AF005419[2240034]

13764: L42324
Homo sapiens (clone GPCR W) G protein-linked receptor gene (GPCR) gene, 5' end of cds
gi|1066730|gb|L42324.1|HUMFRCG[1066730]

13766: AF015910
Homo sapiens unknown protein mRNA, partial cds
gi|2286201|gb|AF015910.1|AF015910[2286201]

13767: X99250
H.sapiens mRNA for endothelin-B receptor splice variant
gi|2285955|emb|X99250.1|HSX99250[2285955]

13768: AF007545
Homo sapiens SIV/HIV receptor Bonzo (Bonzo) mRNA, complete cds
gi|2253421|gb|AF007545.1|AF007545[2253421]

13769: Z79783
H.sapiens G protein-coupled receptor CKR-L2
gi|2281709|emb|Z79783.1|HSCKRL2[2281709]

13778: Z49994
H.sapiens partial gene for proteinase-activated receptor 2 (1289 BP)
gi|1008086|emb|Z49994.1|HSPAR2B[1008086]

13779: AF007555
Homo sapiens IAR/receptor-like protein-tyrosine phosphatase precursor mRNA, complete cds
gi|2262074|gb|AF007555.1|AF007555[2262074]

13780: AF008556
Homo sapiens interleukin-2 receptor mRNA, alternatively spliced, partial cds
gi|2266932|gb|AF008556.1|AF008556[2266932]

13891: Y10152
H.sapiens mRNA for CRF2 receptor, beta isoform, aberrantly spliced, (94bp deletion)

gi|1785640|emb|Y10152.1|HSCRF294[1785640]

13892: Y10153
H.sapiens mRNA for CRF2 receptor, beta isoform, aberrantly spliced, (227bp insertion)
gi|1785639|emb|Y10153.1|HSCRF2227[1785639]

13893: Y10151
H.sapiens mRNA for CRF2 receptor, beta isoform, partial
gi|1785637|emb|Y10151.1|HSCRF2[1785637]

13894: M17325
Homo sapiens T-cell receptor gamma-chain constant region (TCRGC1) mRNA, partial cds
gi|2072752|gb|M17325.1|HUMTCGCJ[2072752]

13895: M17324
Homo sapiens T-cell receptor gamma-chain constant region (TCRGC2) mRNA, partial cds
gi|2072751|gb|M17324.1|HUMTCGCI[2072751]

13896: M17323
Homo sapiens T-cell receptor gamma-chain constant region (TCRGC2) mRNA, partial cds
gi|2072750|gb|M17323.1|HUMTCGCH[2072750]

13897: AF004327
Homo sapiens angiopoietin-2 mRNA, complete cds
gi|2257932|gb|AF004327.1|AF004327[2257932]

13898: AF004021
Homo sapiens prostaglandin F2 alpha receptor mRNA, complete cds
gi|2257849|gb|AF004021.1|AF004021[2257849]

13899: AF006464
Homo sapiens muscle specific tyrosine kinase receptor (MUSK) mRNA, complete cds
gi|2253311|gb|AF006464.1|AF006464[2253311]

13900: AF005637
Homo sapiens endothelin A receptor gene, 5' flanking region and exon 1
gi|2253289|gb|AF005637.1|AF005637[2253289]

13902: Z24461
H.sapiens MTCP-1 gene
gi|406866|emb|Z24461.1|HSMTCP1I[406866]

13903: Z24463
H.sapiens MTCP-1 gene
gi|406865|emb|Z24463.1|HSMTCP1H[406865]

13904: Z24457
H.sapiens of TCRA gene MTCP-1 gene
gi|406860|emb|Z24457.1|HSMTCP1D[406860]

13905: Z24456
H.sapiens of MTCP-1 gene MTCP-1 gene
gi|406859|emb|Z24456.1|HSMTCP1C[406859]

13906: U45984
Homo sapiens CCR6 chemokine receptor (CMKBR6) gene, complete cds
gi|2246432|gb|U45984.1|HSU45984[2246432]

13908: AF005900
Homo sapiens alpha2B-adrenergic receptor (alpha2C2AR) gene, complete cds
gi|2245627|gb|AF005900.1|AF005900[2245627]

13909: AF005210
Homo sapiens CC chemokine receptor CCR8 (CMKBR8) mRNA, partial cds
gi|2245579|gb|AF005210.1|AF005210[2245579]

14010: Y13758
Homo sapiens mRNA for transient receptor potential related channel 3 protein
gi|2225936|emb|Y13758.1|HSY13758[2225936]

14012: AF000546
Homo sapiens purinergic receptor P2Y5 mRNA, complete cds
gi|2232068|gb|AF000546.1|HSAF000546[2232068]

14013: U45983
Homo sapiens CCR8 chemokine receptor (CMKBR8) gene, complete cds
gi|2231165|gb|U45983.1|HSU45983[2231165]

14015: X63819
H.sapiens mRNA for Lipoxin A4 receptor
gi|31460|emb|X63819.1|HSLIPA4R[31460]

14016: X15274
H.sapiens TRGV9 gene, allele V9*A2
gi|1848091|emb|X15274.1|HSTRGV9F[1848091]

14020: X80282
H.sapiens gene for oxytocin receptor
gi|609014|emb|X80282.1|HSOXYTOC[609014]

14021: X81086
H. sapiens PCaR1 gene
gi|599819|emb|X81086.1|HSPCAR1[599819]

14023: X65857
H.sapiens HGMP07E gene for olfactory receptor
gi|425220|emb|X65857.1|HSHGM07EG[425220]

14024: X65858
H.sapiens gene for high affinity IL-8 receptor
gi|312046|emb|X65858.1|HSHAIL8G[312046]

14026: Z69640
H.sapiens fgfr2 gene (exon 5)
gi|1200062|emb|Z69640.1|HSFGFR2UB[1200062]

14027: Z69641
H.sapiens fgfr2 gene
gi|1200061|emb|Z69641.1|HSFGFR2UA[1200061]

14029: Z70243
H.sapiens enhancer region for interleukin-2 receptor alpha chain
gi|1769435|emb|Z70243.1|HSENHREG1[1769435]

14030: Z38109
H.sapiens DNA for CD69, exon 1
gi|793837|emb|Z38109.1|HSCD69X1[793837]

14031: AC002306
Homo sapiens DNA from chromosome 19-cosmid R33799, genomic sequence, complete sequence
gi|2213634|gb|AC002306.1|AC002306[2213634]

14032: AF002256
Homo sapiens killer cell inhibitory receptor homolog cl-9 mRNA, complete cds
gi|2197058|gb|AF002256.1|AF002256[2197058]

14033: AF002255
Homo sapiens killer cell inhibitory receptor cl-17 mRNA, complete cds
gi|2197056|gb|AF002255.1|AF002255[2197056]

14034: D89079
Homo sapiens mRNA for leukotriene b4 receptor, complete cds
gi|2196450|dbj|D89079.1|D89079[2196450]

14035: D89078
Homo sapiens mRNA for leukotriene b4 receptor, complete cds
gi|2196448|dbj|D89078.1|D89078[2196448]

14036: AB004662
Homo sapiens mRNA for adenosine A1-receptor, complete cds
gi|2196442|dbj|AB004662.1|AB004662[2196442]

14037: Y07909
H.sapiens mRNA for Progression Associated Protein
gi|1542882|emb|Y07909.1|HSPAPR[1542882]

14038: L17411
Human complement receptor type 1 (alleles S and F) gene, exon 40
gi|1199855|gb|L17411.1|HUMCR1SF34[1199855]

14039: L17425
Human complement receptor type 1 (allele S) gene, exon 11
gi|451301|gb|L17425.1|HUMCR1SF10[451301]

14040: L17418
Human complement receptor type 1 (alleles S and F) gene, exon 47 and complete cds's
gi|306678|gb|L17418.1|HUMCR1SF41[306678]

14041: L17417
Human complement receptor type 1 (alleles S and F) gene, exon 46
gi|306677|gb|L17417.1|HUMCR1SF40[306677]

14042: L17416
Human complement receptor type 1 (alleles S and F) gene, exon 45
gi|306676|gb|L17416.1|HUMCR1SF39[306676]

14043: L17415
Human complement receptor type 1 (alleles S and F) gene, exon 44
gi|306675|gb|L17415.1|HUMCR1SF38[306675]

14044: L17414
Human complement receptor type 1 (alleles S and F) gene, exon 43
gi|306674|gb|L17414.1|HUMCR1SF37[306674]

14045: L17413
Human complement receptor type 1 (alleles S and F) gene, exon 42
gi|306673|gb|L17413.1|HUMCR1SF36[306673]

14046: L17412
Human complement receptor type 1 (alleles S and F) gene, exon 41
gi|306672|gb|L17412.1|HUMCR1SF35[306672]

14047: L17410
Human complement receptor type 1 (alleles S and F) gene, exons 38 and 39
gi|306670|gb|L17410.1|HUMCR1SF33[306670]

14048: L17408
Human complement receptor type 1 (alleles S and F) gene, exon 37
gi|306669|gb|L17408.1|HUMCR1SF32[306669]

14049: L17407
Human complement receptor type 1 (alleles S and F) gene, exon 36
gi|306668|gb|L17407.1|HUMCR1SF31[306668]

14050: L17406
Human complement receptor type 1 (alleles S and F) gene, exon 35
gi|306667|gb|L17406.1|HUMCR1SF30[306667]

14051: L17405
Human complement receptor type 1 (alleles S and F) gene, exon 34
gi|306666|gb|L17405.1|HUMCR1SF29[306666]

14052: L17404
Human complement receptor type 1 (alleles S and F) gene, exon 33
gi|306665|gb|L17404.1|HUMCR1SF28[306665]

14053: L17403
Human complement receptor type 1 (alleles S and F) gene, exon 32
gi|306664|gb|L17403.1|HUMCR1SF27[306664]

14054: L17402
Human complement receptor type 1 (alleles S and F) gene, exons 30 and 31
gi|306663|gb|L17402.1|HUMCR1SF26[306663]

14055: L17401
Human complement receptor type 1 (alleles S and F) gene, exon 29
gi|306662|gb|L17401.1|HUMCR1SF25[306662]

14056: L17400
Human complement receptor type 1 (alleles S and F) gene, exon 28
gi|306661|gb|L17400.1|HUMCR1SF24[306661]

14057: L17398
Human complement receptor type 1 (alleles S and F) gene, exons 26 and 27
gi|306660|gb|L17398.1|HUMCR1SF23[306660]

14058: L17397
Human complement receptor type 1 (alleles S and F) gene, exon 25
gi|306659|gb|L17397.1|HUMCR1SF22[306659]

14059: L17396
Human complement receptor type 1 (alleles S and F) gene, exon 24
gi|306658|gb|L17396.1|HUMCR1SF21[306658]

14060: L17395
Human complement receptor type 1 (alleles S and F) gene, exons 22 and 23
gi|306657|gb|L17395.1|HUMCR1SF20[306657]

14061: L17394
Human complement receptor type 1 (alleles S and F) gene, exon 21
gi|306656|gb|L17394.1|HUMCR1SF19[306656]

14062: L17393
Human complement receptor type 1 (alleles S and F) gene, exon 20
gi|306655|gb|L17393.1|HUMCR1SF18[306655]

14063: L17392
Human complement receptor type 1 (alleles S and F) gene, exon 19
gi|306654|gb|L17392.1|HUMCR1SF17[306654]

14064: L17391

Human complement receptor type 1 (alleles S and F) gene, exon 18
gi|306653|gb|L17391.1|HUMCR1SF16[306653]

14065: L17430
Human complement receptor type 1 (allele S) gene, exon 17
gi|306652|gb|L17430.1|HUMCR1SF15[306652]

14066: L17429
Human complement receptor type 1 (allele S) gene, exon 16
gi|306651|gb|L17429.1|HUMCR1SF14[306651]

14067: L17428
Human complement receptor type 1 (allele S) gene, exons 14 and 15
gi|306650|gb|L17428.1|HUMCR1SF13[306650]

14068: L17427
Human complement receptor type 1 (allele S) gene, exon 13
gi|306649|gb|L17427.1|HUMCR1SF12[306649]

14069: L17426
Human complement receptor type 1 (allele S) gene, exon 12
gi|306648|gb|L17426.1|HUMCR1SF11[306648]

14070: L17424
Human complement receptor type 1 (allele S) gene, exon 10
gi|306646|gb|L17424.1|HUMCR1SF09[306646]

14071: L17423
Human complement receptor type 1 (alleles S and F) gene, exon 9
gi|306645|gb|L17423.1|HUMCR1SF08[306645]

14072: L17422
Human complement receptor type 1 (alleles S and F) gene, exon 8
gi|306644|gb|L17422.1|HUMCR1SF07[306644]

14073: L17421
Human complement receptor type 1 (alleles S and F) gene, exons 6 and 7 gi|306643|gb|L17421.1|HUMCR1SF06[306643]

14074: L17420
Human complement receptor type 1 (alleles S and F) gene, exon 5
gi|306642|gb|L17420.1|HUMCR1SF05[306642]

14075: L17419
Human complement receptor type 1 (alleles S and F) gene, exon 4
gi|306641|gb|L17419.1|HUMCR1SF04[306641]

14076: L17409
Human complement receptor type 1 (alleles S and F) gene, exon 3
gi|306640|gb|L17409.1|HUMCR1SF03[306640]

14077: L17399
Human complement receptor type 1 (alleles S and F) gene, exon 2
gi|306639|gb|L17399.1|HUMCR1SF02[306639]

14078: L17390
Human complement receptor type 1 (alleles S and F) gene, enhancer and exon 1
gi|306638|gb|L17390.1|HUMCR1SF01[306638]

14081: M14764
Human nerve growth factor receptor mRNA, complete cds
gi|189204|gb|M14764.1|HUMNGFR[189204]

14082: M11025
Human asialoglycoprotein receptor H2 mRNA, complete cds
gi|179080|gb|M11025.1|HUMASGPR2[179080]

14083: L31772
Human alpha-1a/d adrenergic receptor mRNA, complete cds
gi|666894|gb|L31772.1|HUMA1DA[666894]

14084: L31774
Human alpha-1C-adrenergic receptor mRNA, complete cds
gi|666892|gb|L31774.1|HUMA1ARA[666892]

14085: L31773
Human alpha-1B-adrenergic receptor mRNA, complete cds
gi|666890|gb|L31773.1|HUMA1AR[666890]

14093: L07868
Homo sapiens receptor tyrosine kinase (ERBB4) gene, complete cds
gi|337359|gb|L07868.1|HUMRETYKIN[337359]

14094: L19593
Homo sapiens interleukin 8 receptor beta (IL8RB) mRNA, complete cds
gi|559053|gb|L19593.1|HUMIL8RB[559053]

14095: L19591
Homo sapiens interleukin 8 receptor alpha (IL8RA) mRNA, complete cds
gi|559049|gb|L19591.1|HUMIL8RAA[559049]

14096: M69229
Human insulin-like growth factor I receptor gene, promoter region and 5' end
gi|184837|gb|M69229.1|HUMIGFR1PR[184837]

14097: L03840
Human fibroblast growth factor receptor 4 (FGFR4) mRNA, complete cds
gi|182570|gb|L03840.1|HUMFGFR4X[182570]

14098: L13268
Homo sapiens N-methyl-d-aspartate receptor (NR1-3) mRNA, 3' end
gi|292286|gb|L13268.1|HUMMARB[292286]

14099: L13266
Homo sapiens N-methyl-d-aspartate receptor (NR1-1) mRNA, complete cds
gi|292282|gb|L13266.1|HUMMAR[292282]

14100: Y13426
Homo sapiens TCRDV2 gene, partial
gi|2181879|emb|Y13426.1|HSTCRDV2[2181879]

14101: Y08768
H.sapiens mRNA for IL-13 receptor
gi|1877211|emb|Y08768.1|HSIL13[1877211]

14102: Y08110
H.sapiens mRNA for mosaic protein LR11
gi|1552323|emb|Y08110.1|HSLR11[1552323]

14103: E08844
Histamine H1 receptor gene
gi|2176948|dbj|E08844.1|E08844[2176948]

14104: E08843
cDNA encoding Histamine H1 receptor
gi|2176947|dbj|E08843.1|E08843[2176947]

14106: E07873
cDNA encoding cholecystokinin B/gastrin receptor
gi|2176006|dbj|E07873.1|E07873[2176006]

14107: E07650
cDNA encoding endothelin receptor,ETB-receptor
gi|2175785|dbj|E07650.1|E07650[2175785]

14108: E07649
cDNA encoding endothelin receptor,ETA-receptor
gi|2175784|dbj|E07649.1|E07649[2175784]

14109: E07358
gDNA encoding adrenaline alpha2CII receptor
gi|2175498|dbj|E07358.1|E07358[2175498]

14110: E07278
cDNA encoding human cholecystokinin(CCK) receptor
gi|2175419|dbj|E07278.1|E07278[2175419]

14111: E06799
DNA encoding human Interleukin-5 receptor
gi|2174981|dbj|E06799.1|E06799[2174981]

14112: E06798
DNA encoding human Interleukin-5 receptor
gi|2174980|dbj|E06798.1|E06798[2174980]

14113: E06797
DNA encoding human Interleukin-5 receptor
gi|2174979|dbj|E06797.1|E06797[2174979]

14114: E06796
DNA encoding human Interleukin-5 receptor
gi|2174978|dbj|E06796.1|E06796[2174978]

14115: E05678
cDNA encoding human LH-hCG(luteinizing hormone-human choriogonadotropic hormone)receptor
gi|2173865|dbj|E05678.1|E05678[2173865]

14116: E05211
DNA encoding human scavenger receptor II
gi|2173401|dbj|E05211.1|E05211[2173401]

14117: E05210
DNA encoding human scavenger receptor I
gi|2173400|dbj|E05210.1|E05210[2173400]

14118: E05109
cDNA encoding human oxytocin receptor
gi|2173303|dbj|E05109.1|E05109[2173303]

14189: E04823
cDNA encoding interleukin 6 receptor
gi|2173019|dbj|E04823.1|E04823[2173019]

14190: E03879
cDNA encoding platelet activating factor receptor
gi|2172093|dbj|E03879.1|E03879[2172093]

14191: E03829
cDNA encoding human thromboxane receptor
gi|2172043|dbj|E03829.1|E03829[2172043]

14192: E03378
DNA encoding N-terminal fragment of human growth hormone receptor
gi|2171595|dbj|E03378.1|E03378[2171595]

14193: E03377
DNA encoding C-terminal fragment of human growth hormone receptor
gi|2171594|dbj|E03377.1|E03377[2171594]

14194: E03335
Human b-FGF receptor gene
gi|2171552|dbj|E03335.1|E03335[2171552]

14195: E03268
cDNA sequence coding for human scavenger receptor,type II
gi|2171485|dbj|E03268.1|E03268[2171485]

14196: E03267
cDNA sequence coding for human scavenger receptor,type I
gi|2171484|dbj|E03267.1|E03267[2171484]

14197: E02673
cDNA encoding human B cell stimulating factor 2 receptor protein
gi|2170901|dbj|E02673.1|E02673[2170901]

14198: E02541
cDNA encoding human Interleukin-2 receptor L chain
gi|2170771|dbj|E02541.1|E02541[2170771]

14199: E02151

Terminal sequence of constant region of T cell receptor beta chain(c beta-1)
gi|2170389|dbj|E02151.1|E02151[2170389]

14200: E01646
cDNA encoding Fc epsilon receptor
gi|2169899|dbj|E01646.1|E01646[2169899]

14201: E01052
DNA encoding human mature TNF
gi|2169311|dbj|E01052.1|E01052[2169311]

14202: E00999
cDNA encoding human insulin receptor
gi|2169258|dbj|E00999.1|E00999[2169258]

14203: E00990
cDNA encoding alpha chain of T-cell receptor
gi|2169251|dbj|E00990.1|E00990[2169251]

14204: E00727
cDNA encoding human IL-2 receptor
gi|2169004|dbj|E00727.1|E00727[2169004]

14205: E00723
cDNA encoding human interleukin-2 receptor
gi|2169000|dbj|E00723.1|E00723[2169000]

14206: E00685
cDNA encoding human T-cell antigen receptor protein
gi|2168964|dbj|E00685.1|E00685[2168964]

14207: D31833
Human mRNA for vasopressin V1b receptor, complete cds
gi|563981|dbj|D31833.1|HUMVV1BR[563981]

14208: D16845
Human mRNA for thyrotropin-releasing hormone receptor, complete cds gi|577631|dbj|D16845.1|HUMTRHR1[577631]

14209: D28131
Human mRNA for TGF-beta receptor type IIB, partial sequence
gi|456708|dbj|D28131.1|HUMTGFBRII[456708]

14211: D17517
Human sky mRNA for Sky, complete cds
gi|624880|dbj|D17517.1|HUMSKY[624880]

14214: D30780
Human mRNA for phospholipase A2 receptor, partial cds
gi|565645|dbj|D30780.1|HUMPLA2IR[565645]

14215: D38299
Homo sapiens mRNA for prostaglandin E receotor EP3 subtype 2 isoform, complete cds
gi|1389574|dbj|D38299.1|HUMPEREFC[1389574]

14216: D38298
Homo sapiens mRNA for prostaglandin E receotor EP3 subtype 1b isoform, complete cds
gi|1389573|dbj|D38298.1|HUMPEREEB[1389573]

14217: D38301
Homo sapiens mRNA for prostaglandin E receptor EP3 subtype 3 isoform, complete cds
gi|1389572|dbj|D38301.1|HUMPERECE[1389572]

14218: D38300
Homo sapiens mRNA for prostaglandin E receotor EP3 subtype 4 isoform, complete cds
gi|1389571|dbj|D38300.1|HUMPEREBD[1389571]

14219: D38297
Homo sapiens mRNA for prostaglandin E receotor EP3 subtype 1a isoform, complete cds
gi|1389570|dbj|D38297.1|HUMPEREA[1389570]

14220: D28538
Human mRNA for metabotropic glutamate receptor subtype 5a, complete cds
gi|1408051|dbj|D28538.1|HUMMGRS5A[1408051]

14221: D14872
Human DNA for fibroblast growth factor receptor 2 (K-sam-II) exon C3, partial sequence
gi|511927|dbj|D14872.1|HUMKSAMC3[511927]

14222: D50582
Human gene for inward rectifier K channel, complete cds
gi|1088444|dbj|D50582.1|HUMIRKCB[1088444]

14223: D26070
Human mRNA for type 1 inositol 1,4,5-trisphosphate receptor, complete cds
gi|559322|dbj|D26070.1|HUMINSP3R1[559322]

14232: D26156
Human mRNA for transcriptional activator hSNF2b, complete cds
gi|505087|dbj|D26156.1|HUMHSNF2B[505087]

14233: D26155
Human mRNA for transcriptional activator hSNF2a, complete cds
gi|505086|dbj|D26155.1|HUMHSNF2A[505086]

14234: D26351
Human mRNA for type 3 inositol 1,4,5-trisphosphate receptor, complete cds
gi|450470|dbj|D26351.1|HUMHT3I[450470]

14235: D26350
Human mRNA for type 2 inositol 1,4,5-trisphosphate receptor, complete cds
gi|450468|dbj|D26350.1|HUMHT2I[450468]

14236: D25418
Human mRNA for prostacyclin receptor, complete cds
gi|467509|dbj|D25418.1|HUMHPR[467509]

14237: D10924
Human mRNA for HM89
gi|219868|dbj|D10924.1|HUMHM89[219868]

14238: D10923
Human mRNA for HM74
gi|219866|dbj|D10923.1|HUMHM74[219866]

14239: D10922
Human mRNA for FMLP-related receptor (HM63)
gi|219864|dbj|D10922.1|HUMHM63[219864]

14240: D10925
Human mRNA for HM145
gi|219862|dbj|D10925.1|HUMHM145[219862]

14241: D28481
Human mRNA for histamine H1 receptor, complete cds
gi|457654|dbj|D28481.1|HUMHH1R[457654]

14242: D10995
Human gene for serotonin 1B receptor, complete cds
gi|219678|dbj|D10995.1|HUMHGCR[219678]

14243: D38449
Human mRNA for G protein-coupled receptor, complete cds
gi|556519|dbj|D38449.1|HUMGPCRAA[556519]

14245: D37827
Homo sapiens mRNA for large erk/cek5 tyrosine kinase, partial cds
gi|1060894|dbj|D37827.1|HUMERK1P[1060894]

14246: D13305
Human mRNA for brain cholecystokinin receptor
gi|436039|dbj|D13305.1|HUMBRACHRE[436039]

14247: D32201
Human mRNA for alpha 1C adrenergic receptor isoform 3, complete cds
gi|927210|dbj|D32201.1|HUMA1CAR3[927210]

14248: D16354
Human mRNA for Ah receptor, complete cds
gi|464179|dbj|D16354.1|HUMAHRE[464179]

14249: D25235
Human mRNA for alpha1C adrenergic receptor, complete cds
gi|433200|dbj|D25235.1|HUMACAR[433200]

14250: D13538
Human alpha2CII-adrenergic receptor gene, complete cds
gi|219405|dbj|D13538.1|HUMA2CIIA[219405]

14251: D32202
Human mRNA for alpha 1C adrenergic receptor isoform 2, complete cds
gi|927208|dbj|D32202.1|HUMA1CAR2[927208]

14253: D86519
Human mRNA for neuropeptide y/peptide YY Y6 receptor, complete cds
gi|1731789|dbj|D86519.1|D86519[1731789]

14254: D50683
Homo sapiens mRNA for TGF-betaIIR alpha, complete cds
gi|1827474|dbj|D50683.1|D50683[1827474]

14255: D50682
Homo sapiens mRNA for TGF-betaIIR beta, partial cds
gi|1827472|dbj|D50682.1|D50682[1827472]

14256: D28472
Human mRNA for prostaglandin E receptor EP4 subtype, complete cds
gi|1486234|dbj|D28472.1|D28472[1486234]

14257: D29634
Human lung mRNA for receptor for prostacyclin, complete cds
gi|577629|dbj|D29634.1|D29634[577629]

14258: D28539
Human mRNA for metabotropic glutamate receptor subtype 5b, complete cds
gi|1408053|dbj|D28539.1|HUMMGRS5B[1408053]

14259: Y09479
H.sapiens mRNA for G protein-coupled receptor Edg-2
gi|1679601|emb|Y09479.1|HSEDG2[1679601]

14260: U97197
Homo sapiens asialoglycoprotein receptor (ASGPR) mRNA, complete cds
gi|2121249|gb|U97197.1|HSU97197[2121249]

14261: X81892
H.sapiens mRNA for HE6 Tm7 receptor
gi|2117160|emb|X81892.1|HSHE6[2117160]

14262: Y07619
H.sapiens mRNA for peroxisome proliferator-activated receptor alpha
gi|1514594|emb|Y07619.1|HSPPARAGE[1514594]

14263: D16815
Homo sapiens mRNA for EAR-1r, complete cds
gi|2116671|dbj|D16815.1|D16815[2116671]

14264: X95876
H.sapiens mRNA for G-protein coupled receptor
gi|1552845|emb|X95876.1|HSGPCRIN8[1552845]

14265: AF000545
Homo sapiens putative purinergic receptor P2Y10 gene, complete cds
gi|2104786|gb|AF000545.1|HSAF000545[2104786]

14267: U95626

Homo sapiens ccr2b (ccr2), ccr2a (ccr2), ccr5 (ccr5) and ccr6 (ccr6) genes, complete cds, and lactoferrin (lactoferrin) gene, partial cds, complete sequence
gi|2104517|gb|U95626.1|HSU95626[2104517]

14268: U77352
Homo sapiens MAP kinase-activating death domain protein (MADD) mRNA, complete cds
gi|2102697|gb|U77352.1|HSU77352[2102697]

14269: D86098
Homo sapiens mRNA for prostaglandin EP3 receptor subtype isoform, complete cds
gi|2102646|dbj|D86098.1|D86098[2102646]

14270: D86097
Homo sapiens mRNA for prostaglandin EP3 receptor subtype isoform, complete cds
gi|2102644|dbj|D86097.1|D86097[2102644]

14271: X98510
H.sapiens mRNA for G protein-coupled receptor
gi|1894788|emb|X98510.1|HSX98510[1894788]

14272: D89675
Homo sapiens mRNA for bone morphogenetic protein type IB receptor, complete cds
gi|2055308|dbj|D89675.1|D89675[2055308]

14273: D43772
Human squamous cell carcinoma of esophagus mRNA for GRB-7 SH2 domain protein, complete cds
gi|601890|dbj|D43772.1|HUMGRB7[601890]

14274: X89677
H.sapiens mRNA for TPCR92 protein
gi|902337|emb|X89677.1|HSTPCR92P[902337]

14275: X89676
H.sapiens mRNA for TPCR86 protein
gi|902335|emb|X89676.1|HSTPCR86P[902335]

14276: X89675
H.sapiens mRNA for TPCR85 protein
gi|902333|emb|X89675.1|HSTPCR85P[902333]

14277: X89674
H.sapiens mRNA for TPCR27 protein
gi|902331|emb|X89674.1|HSTPCR27P[902331]

14278: X89673
H.sapiens mRNA for TPCR26 protein
gi|902329|emb|X89673.1|HSTPCR26P[902329]

14279: X89672
H.sapiens mRNA for TPCR25 protein
gi|902327|emb|X89672.1|HSTPCR25P[902327]

14280: X89671
H.sapiens mRNA for TPCR24 protein
gi|902325|emb|X89671.1|HSTPCR24P[902325]

14281: X89670
H.sapiens mRNA for TPCR16 protein
gi|902323|emb|X89670.1|HSTPCR16P[902323]

14282: X89669
H.sapiens mRNA for TPCR120 protein
gi|902321|emb|X89669.1|HSTPCR120[902321]

14283: X89668
H.sapiens mRNA for TPCR110 protein
gi|902319|emb|X89668.1|HSTPCR110[902319]

14284: X89667
H.sapiens mRNA for TPCR106 protein
gi|902317|emb|X89667.1|HSTPCR106[902317]

14285: X89666
H.sapiens mRNA for TPCR100 protein
gi|902315|emb|X89666.1|HSTPCR100[902315]

14291: X73617
H.sapiens mRNA for T-cell receptor delta
gi|402624|emb|X73617.1|HSTCRDE[402624]

14292: Z79612
H.sapiens DNA for muscle nicotinic acetylcholine receptor gene promotor, clone DBLambda20
gi|1922318|emb|Z79612.1|HSMNAR3[1922318]

14293: Z79611
H.sapiens DNA for muscle nicotinic acetylcholine receptor gene promotor, clone DBLambda23
gi|1922317|emb|Z79611.1|HSMNAR2[1922317]

14294: Z79610
H.sapiens DNA for muscle nicotinic acetylcholine receptor gene promotor, clone ICRFc105F02104
gi|1922316|emb|Z79610.1|HSMNAR1[1922316]

14295: Y09852
H.sapiens FGFR3 gene, partial
gi|1922307|emb|Y09852.1|HSFGFR3I2[1922307]

14309: Z46223
H.sapiens DNA for immunoglobulin G Fc receptor IIIB
gi|559446|emb|Z46223.1|HSIGGRE3B[559446]

14310: Z46222
H.sapiens DNA for immunoglobulin G Fc receptor IIIA
gi|559445|emb|Z46222.1|HSIGGRE3A[559445]

14311: Y09561
H.sapiens mRNA for P2X7 receptor
gi|1854511|emb|Y09561.1|HSP2X7[1854511]

14312: Y09328
H.sapiens mRNA for IL13 receptor alpha-1 chain
gi|1885307|emb|Y09328.1|HSIL13RA1[1885307]

14313: Y07593
H.sapiens mRNA for 46 kDa coxsackievirus and adenovirus receptor (CAR) protein
gi|1881446|emb|Y07593.1|HS46KDA[1881446]

14314: X07205
H.sapiens TRGV9 gene, allele V9*A1
gi|1848089|emb|X07205.1|HSTRGV9[1848089]

14315: X15272
H.sapiens TRGV4F gene
gi|1841921|emb|X15272.1|HSTRGV4F[1841921]

14316: Y11227
H.sapiens TRGV11 gene
gi|1848086|emb|Y11227.1|HSTRGV11G[1848086]

14317: X74798
H.sapiens TRGV10 gene, allele V10*A2
gi|1848083|emb|X74798.1|HSTRGV[1848083]

14321: X80878
H.sapiens R kappa B mRNA
gi|695578|emb|X80878.1|HSRKAPB[695578]

14324: X70070
H.sapiens mRNA for neurotensin receptor
gi|35020|emb|X70070.1|HSNEURA[35020]

14325: X94552
H.sapiens mRNA for metabotropic glutamate receptor type 7
gi|1370110|emb|X94552.1|HSMGLU7[1370110]

14326: X89105
H.sapiens krag-like mRNA
gi|939922|emb|X89105.1|HSKRAGGEN[939922]

14327: X92562
H.sapiens mRNA for myeloid IgA Fc receptor, CD89 (539bp)
gi|1296655|emb|X92562.1|HSIGAFCR5[1296655]

14328: X92561
H.sapiens mRNA for myeloid IgA Fc receptor, CD89 (585bp)
gi|1296654|emb|X92561.1|HSIGAFCR4[1296654]

14329: X92560
H.sapiens mRNA for myeloid IgA Fc receptor, CD89 (807bp)
gi|1296653|emb|X92560.1|HSIGAFCR3[1296653]

14330: X92559
H.sapiens mRNA for myeloid IgA Fc receptor, CD89 (771bp)
gi|1296652|emb|X92559.1|HSIGAFCR2[1296652]

14331: X92558
H.sapiens mRNA for myeloid IgA Fc receptor, CD89 (837bp)
gi|1296651|emb|X92558.1|HSIGAFCR1[1296651]

14332: Z50197
H.sapiens FGFR2, Bek gene (partial; mutation C)
gi|929635|emb|Z50197.1|HSFGFR2XC[929635]

14333: Z50196
H.sapiens FGFR2, Bek gene (partial; mutation B)
gi|929634|emb|Z50196.1|HSFGFR2XB[929634]

14334: Z50201
H.sapiens FGFR2 gene (partial; mutation A)
gi|929633|emb|Z50201.1|HSFGFR2XA[929633]

14335: X72304
H.sapiens mRNA for corticotrophin releasing factor receptor
gi|436118|emb|X72304.1|HSCRFA[436118]

14336: X86169
H.sapiens B2-bradykinin receptor gene, exon 2, C allele
gi|1220165|emb|X86169.1|HSB2BRX2C[1220165]

14342: X03131
H.sapiens interleukin 2 receptor gene 5' flanking region and exon 1 (and joined CDS)
gi|33818|emb|X03131.1|HSIL2RG1[33818]

14343: X57740
H.sapiens rearranged T-cell receptor gamma chain gene, V3RS-J1 (hybrid joint)
gi|505478|emb|X57740.1|HSTCRHJD[505478]

14344: X01719
H.sapiens gene fragment for the acetylcholine receptor gamma subunit (exon 7 and 8)
gi|28278|emb|X01719.1|HSACHG5[28278]

14345: X01715
H.sapiens gene fragment for the acetylcholine receptor gamma subunit precursor (exons 1 and 2)
gi|28268|emb|X01715.1|HSACHG1[28268]

14535: Z30429
H.sapiens gene for early lymphocyte activation antigen CD69, exon 4
gi|534947|emb|Z30429.1|HSLACD694[534947]

14536: X89744
H.sapiens mRNA for neuronal acetylcholine receptor alpha-4 subunit, exon 4
gi|1279462|emb|X89744.1|HSCHRNA44[1279462]

14537: X87765
H.sapiens CD89 gene, exon TM/C
gi|963045|emb|X87765.1|HSCD89EX5[963045]

14538: X87766
H.sapiens CD89 gene, exon EC2
gi|963044|emb|X87766.1|HSCD89EX4[963044]

14539: X87769
H.sapiens CD89 gene, exon EC1
gi|963043|emb|X87769.1|HSCD89EX3[963043]

14540: X87768
H.sapiens CD89 gene, exon S2
gi|963042|emb|X87768.1|HSCD89EX2[963042]

14541: X87767
H.sapiens CD89 gene, exon S1
gi|963041|emb|X87767.1|HSCD89EX1[963041]

14542: AH004970
Homo sapiens (clone Q-2OD3) interferon receptor (IFNAR2) gene
gi|995299|gb|AH004970.1|SEG_HUMIFNAM0[995299]

14543: L42243
Homo sapiens (clone 51H8) alternatively spliced interferon receptor (IFNAR2) gene, exon 9 and complete cds's
gi|995298|gb|L42243.1|HUMIFNAM08[995298]

14544: L41944
Homo sapiens interferon receptor ifnar2-1 (splice variant IFNAR2-1) mRNA, complete cds
gi|995296|gb|L41944.1|HUMIFNAL[995296]

14545: L41943
Homo sapiens interferon receptor ifnar2-3 (splice variant IFNAR2-3) mRNA, complete cds
gi|995294|gb|L41943.1|HUMIFNAK[995294]

14546: L41942

Homo sapiens interferon receptor ifnar2-2 (splice variant IFNAR2-2) mRNA, complete cds
gi|995292|gb|L41942.1|HUMIFNAJ[995292]

14547: L42242
Homo sapiens (clone Q-2OD3) interferon receptor (IFNAR2) gene, exon 8
gi|994722|gb|L42242.1|HUMIFNAM07[994722]

14548: L42241
Homo sapiens (clone Q-2OD3) interferon receptor (IFNAR2) gene, exon 7
gi|994721|gb|L42241.1|HUMIFNAM06[994721]

14549: L42323
Homo sapiens (clone 20D3) interferon receptor (IFNAR2) gene, exon 6
gi|994720|gb|L42323.1|HUMIFNAM05[994720]

14550: L42240
Homo sapiens (clone Q-2OD3) interferon receptor (IFNAR2) gene, exon 5
gi|994719|gb|L42240.1|HUMIFNAM04[994719]

14551: L42239
Homo sapiens (clone Q-2OD3) interferon receptor (IFNAR2) gene, exons 3-4
gi|994718|gb|L42239.1|HUMIFNAM03[994718]

14552: L42238
Homo sapiens (clone Q-2OD3) interferon receptor (IFNAR2) gene, exon 2
gi|994717|gb|L42238.1|HUMIFNAM02[994717]

14553: L42237
Homo sapiens (clone Q-2OD3) interferon receptor (IFNAR2) gene, exon 1
gi|994716|gb|L42237.1|HUMIFNAM01[994716]

14557: X94647
H.sapiens CD97 gene exon 20
gi|1165083|emb|X94647.1|HSX94647[1165083]

14558: X94630

H.sapiens CD97 gene exon 1 (and joined CDS)
gi|1165073|emb|X94630.1|HSX94630[1165073]

14560: X91747
H.sapiens gene for FSH receptor (exon 10)
gi|1009412|emb|X91747.1|HSFSHRX10[1009412]

14561: X74979
H.sapiens TRK E mRNA
gi|400462|emb|X74979.1|HSTRKE[400462]

14562: Y10100
H.sapiens ACTH receptor promoter & exon 1
gi|1743254|emb|Y10100.1|HSACTHPRO[1743254]

14563: Y09028
H.sapiens NTRK1 gene, exon 1 (and joined mRNA)
gi|1785644|emb|Y09028.1|HSNTRK11[1785644]

14564: Y07684
H.sapiens mRNA for P2X4 purinoceptor
gi|1781008|emb|Y07684.1|HSP2X4PC[1781008]

14565: X95712
H.sapiens mRNA for receptor protein tyrosine phosphatase
gi|1666422|emb|X95712.1|HSRPTYRPH[1666422]

14568: X97232
H.sapiens mRNA for NK receptor, clone library D97.10
gi|1770483|emb|X97232.1|HSNKRD9[1770483]

14569: X97233
H.sapiens mRNA for NK receptor, clone library C97.12#5
gi|1770481|emb|X97233.1|HSNKRC9[1770481]

14570: X97231
H.sapiens mRNA for NK receptor, clone library 59C/K3 gi|1770479|emb|X97231.1|HSNKR59[1770479]

14571: X97230
H.sapiens mRNA for NK receptor, clone library 4M1#6
gi|1770477|emb|X97230.1|HSNKR4M[1770477]

14572: X97229
H.sapiens mRNA for NK receptor, clone library 15.212
gi|1770475|emb|X97229.1|HSNKR15[1770475]

14573: X99481
H.sapiens mRNA for NK receptor, clone GR #19
gi|1770473|emb|X99481.1|HSNKGR19[1770473]

14574: X99480
H.sapiens mRNA for NK receptor, clone NK3.3 #27
gi|1770471|emb|X99480.1|HSNK3327[1770471]

14575: X99479
H.sapiens mRNA for NK receptor, clone 12.11C
gi|1770469|emb|X99479.1|HSNK1211C[1770469]

14576: X98118
H.sapiens GRK4A gene
gi|1770421|emb|X98118.1|HSGRK4AGE[1770421]

14589: X83864
H.sapiens EDG-3 gene
gi|1770395|emb|X83864.1|HSEDG3[1770395]

14590: Z48923
H.sapiens mRNA for BMPR-II
gi|1009409|emb|Z48923.1|HSBMPRII[1009409]

14592: X84939
H.sapiens mRNA for fibroblast growth factor receptor-3
gi|695548|emb|X84939.1|HSFGFR3EX[695548]

14593: X89604
H.sapiens mRNA for metallothionein-III
gi|914850|emb|X89604.1|HSMTIII[914850]

14594: Z70276
H.sapiens mRNA for fibroblast growth factor 12 (partial)
gi|1749790|emb|Z70276.1|HSFGF12CR[1749790]

14595: Z70275
H.sapiens mRNA for fibroblast growth factor 11 (partial)
gi|1749788|emb|Z70275.1|HSFGF11CR[1749788]

14596: Y09392
H.sapiens mRNA for WSL-LR, WSL-S1 and WSL-S2 proteins
gi|1669690|emb|Y09392.1|HSWSL1[1669690]

14597: X99031
H.sapiens gene encoding discoidin receptor tyrosine kinase, exon 14
gi|1480251|emb|X99031.1|HSDRTK14[1480251]

14598: X99029
H.sapiens gene encoding discoidin receptor tyrosine kinase, exon 11
gi|1480247|emb|X99029.1|HSDRTK11[1480247]

14599: Y08162
H.sapiens mRNA for heptahelix receptor
gi|1707499|emb|Y08162.1|HSHHR[1707499]

14600: X98194
H.sapiens gene encoding serotonin receptor, 5-HT7, exon 3
gi|1707470|emb|X98194.1|HS5HT73[1707470]

14601: X99025
H.sapiens gene encoding discoidin receptor tyrosine kinase, exons 6 & 7
gi|1480257|emb|X99025.1|HSDRTK6[1480257]

14615: X98147
H.sapiens gene encoding serotonin receptor, 5-HT7, exon 2
gi|1707469|emb|X98147.1|HS5HT72[1707469]

14616: X98193
H.sapiens gene encoding serotonin receptor, 5-HT7, exon 1 (and joined CDS)
gi|1707467|emb|X98193.1|HS5HT71[1707467]

14617: X90753
H.sapiens mRNA for alternatively spliced IgA Fc receptor (CD89)
gi|951268|emb|X90753.1|HSIGAFCGN[951268]

14618: X70812
H.sapiens gene for beta 3 adrenergic receptor
gi|312398|emb|X70812.1|HSBARED[312398]

14619: Z22971
H.sapiens mRNA for M130 antigen extracellular variant
gi|312147|emb|Z22971.1|HSM130AE[312147]

14620: Z22970
H.sapiens mRNA for M130 antigen cytoplasmic variant 2
gi|312145|emb|Z22970.1|HSM130AC2[312145]

14621: Z22969
H.sapiens mRNA for M130 antigen cytoplasmic variant 1
gi|312143|emb|Z22969.1|HSM130AC1[312143]

14622: Z22968
H.sapiens mRNA for M130 antigen
gi|312141|emb|Z22968.1|HSM130A[312141]

14623: X69680
H.sapiens mRNA for bradykinin receptor
gi|288798|emb|X69680.1|HSBKR[288798]

14624: Z79784
H.sapiens G protein-coupled receptor CKR-L3
gi|1668737|emb|Z79784.1|HSCKRL3[1668737]

14625: Z79782
H.sapiens G protein-coupled receptor CKR-L1
gi|1668735|emb|Z79782.1|HSCKRL1[1668735]

14626: X94374
H.sapiens mRNA for HLA class I inhibitory NK receptor (AMC5)
gi|1495480|emb|X94374.1|HSNKRAMC5[1495480]

14627: X94373
H.sapiens mRNA for HLA class I inhibitory NK receptor (1.1)
gi|1495478|emb|X94373.1|HSNKR11[1495478]

14628: X93596
H.sapiens mRNA for HLA specific NK receptor
gi|1495476|emb|X93596.1|HSNKI8[1495476]

14629: X93595
H.sapiens mRNA for NK receptor (clone 17.1C)
gi|1495474|emb|X93595.1|HSNKI7[1495474]

14630: X94262
H.sapiens mRNA for HLA-Bw4 specific inhibitory NK cell receptor
gi|1495472|emb|X94262.1|HSNKCRMR[1495472]

14631: X89772
H.sapiens mRNA for interferon alpha/beta receptor (long form)
gi|1620400|emb|X89772.1|HSRNAIABR[1620400]

14632: X69516
H.sapiens gene for folate receptor
gi|288876|emb|X69516.1|HSFOLA[288876]

14633: X97671

H.sapiens mRNA for erythropoietin receptor
gi|1310666|emb|X97671.1|HSERYTHR[1310666]

14639: X97874
H.sapiens EP4 prostaglandin receptor gene, exon III
gi|1359732|emb|X97874.1|HSEP4EX3[1359732]

14640: X97873
H.sapiens EP4 prostaglandin receptor gene, exons I & II (and joined CDS)
gi|1359730|emb|X97873.1|HSEP4EX12[1359730]

14646: X99404
H.sapiens mRNA for early response gene, Berg36
gi|1480242|emb|X99404.1|HSBERG36[1480242]

14647: Z49205
H.sapiens mRNA for purinergic receptor
gi|798835|emb|Z49205.1|HSATPRMR[798835]

14650: X89066
H.sapiens mRNA for TRPC1 protein
gi|1370118|emb|X89066.1|HSTRPC1GN[1370118]

14671: Y08218
H.sapiens mRNA for ryanodine receptor 2
gi|1561613|emb|Y08218.1|HSRYAN2[1561613]

14678: X96586
H.sapiens mRNA for FAN protein
gi|1556398|emb|X96586.1|HSFAN[1556398]

14679: Z48226
H.sapiens partial gene for receptor-type protein tyrosine phosphatase IA-2
gi|667014|emb|Z48226.1|HSPTPAIA2[667014]

14680: X91665
H.sapiens B2-bradykinin receptor gene (allele BE-R33)
gi|1216151|emb|X91665.1|HSB2BER33[1216151]

14681: L05424
Human cell surface glycoprotein CD44 (CD44) gene, 3' end of long tailed isoform
gi|337956|gb|L05424.1|HUMSCG19[337956]

14682: L05423
Human cell surface glycoprotein CD44 (CD44) gene, exon 18, 3' end of short tailed isoform
gi|337955|gb|L05423.1|HUMSCG18[337955]

14683: L05422
Human cell surface glycoprotein CD44 (CD44) gene, exon 17
gi|337954|gb|L05422.1|HUMSCG17[337954]

14684: L05421
Human cell surface glycoprotein CD44 (CD44) gene, exon 16
gi|337953|gb|L05421.1|HUMSCG16[337953]

14685: L05420
Human cell surface glycoprotein CD44 (CD44) gene, exon 15
gi|337952|gb|L05420.1|HUMSCG15[337952]

14686: L05419
Human cell surface glycoprotein CD44 (CD44) gene, exon 14
gi|337951|gb|L05419.1|HUMSCG14[337951]

14687: L05418
Human cell surface glycoprotein CD44 (CD44) gene, exon 13
gi|337950|gb|L05418.1|HUMSCG13[337950]

14688: L05417
Human cell surface glycoprotein CD44 (CD44) gene, exon 12
gi|337949|gb|L05417.1|HUMSCG12[337949]

14689: L05416
Human cell surface glycoprotein CD44 (CD44) gene, exon 11
gi|337948|gb|L05416.1|HUMSCG11[337948]

14690: L05415
Human cell surface glycoprotein CD44 (CD44) gene, exon 10
gi|337947|gb|L05415.1|HUMSCG10[337947]

14691: L05414
Human cell surface glycoprotein CD44 (CD44) gene, exon 9
gi|337946|gb|L05414.1|HUMSCG09[337946]

14692: L05413
Human cell surface glycoprotein CD44 (CD44) gene, exon 8
gi|337945|gb|L05413.1|HUMSCG08[337945]

14693: L05412
Human cell surface glycoprotein CD44 (CD44) gene, exon 7
gi|337944|gb|L05412.1|HUMSCG07[337944]

14694: L05411
Human cell surface glycoprotein CD44 (CD44) gene, exon 6
gi|337943|gb|L05411.1|HUMSCG06[337943]

14695: L05410
Human cell surface glycoprotein CD44 (CD44) gene, exon 5
gi|337942|gb|L05410.1|HUMSCG05[337942]

14696: L05409
Human cell surface glycoprotein CD44 (CD44) gene, exon 4
gi|337941|gb|L05409.1|HUMSCG04[337941]

14697: L05408
Human cell surface glycoprotein CD44 (CD44) gene, exon 3
gi|337940|gb|L05408.1|HUMSCG03[337940]

14698: L05407
Human cell surface glycoprotein CD44 (CD44) gene, exon 2
gi|337939|gb|L05407.1|HUMSCG02[337939]

14699: M69215
Human hyaluronate receptor (CD44) gene, exon 1
gi|180127|gb|M69215.1|HUMSCG01[180127]

14700: X91492
H.sapiens ChemR13 gene
gi|1262810|emb|X91492.1|HSCCCKR4G[1262810]

14701: X91742
H.sapiens gene for FSH receptor (exon 5)
gi|1051149|emb|X91742.1|HSFSHRX5[1051149]

14702: X91746
H.sapiens gene for FSH receptor (exon 9)
gi|1009420|emb|X91746.1|HSFSHRX9[1009420]

14703: X91745
H.sapiens gene for FSH receptor (exon 8)
gi|1009419|emb|X91745.1|HSFSHRX8[1009419]

14704: X91744
H.sapiens gene for FSH receptor (exon 7)
gi|1009418|emb|X91744.1|HSFSHRX7[1009418]

14705: X91743
H.sapiens gene for FSH receptor (exon 6)
gi|1009417|emb|X91743.1|HSFSHRX6[1009417]

14706: X91741
H.sapiens gene for FSH receptor (exon 4)
gi|1009415|emb|X91741.1|HSFSHRX4[1009415]

14707: X91740
H.sapiens gene for FSH receptor (exon 3)
gi|1009414|emb|X91740.1|HSFSHRX3[1009414]

14708: X91739
H.sapiens gene for FSH receptor (exon 2)
gi|1009413|emb|X91739.1|HSFSHRX2[1009413]

14709: X91738
H.sapiens gene for FSH receptor (exon 1)
gi|1009411|emb|X91738.1|HSFSHRX1[1009411]

14710: A34990
H.sapiens TSH receptor
gi|1568335|emb|A34990.1|A34990[1568335]

14729: A23337
H.sapiens mRNA for 5-HT2 receptor
gi|1566776|emb|A23337.1|A23337[1566776]

14730: X95095
H.sapiens mRNA for PDGFRalpha protein
gi|1403334|emb|X95095.1|HSPDGFRAL[1403334]

14731: X91875
H.sapiens IGF2R gene exon & intron 1
gi|1017421|emb|X91875.1|HSIGF2R1[1017421]

14733: L40636
Homo sapiens (clone FBK III 16) protein tyrosine kinase (NET PTK) mRNA, complete cds
gi|1100111|gb|L40636.1|HUMEPHT2R[1100111]

14734: X55077
H.sapiens mRNA fragment for alpha-2 macroglobulin receptor
gi|24762|emb|X55077.1|HSA2MR[24762]

14735: X98330
H.sapiens mRNA for ryanodine receptor 2
gi|1526977|emb|X98330.1|HSRR2[1526977]

14737: X80038
H.sapiens PRR2 mRNA
gi|1524087|emb|X80038.1|HSPRR2[1524087]

14738: Z15017
H.sapiens mRNA for glycoprotein 39 (gp39)
gi|38483|emb|Z15017.1|HSGP39MR[38483]

14740: Z36748
H.sapiens mRNA for serotonin receptor
gi|558382|emb|Z36748.1|HSSERRC[558382]

14741: X97198
H.sapiens mRNA for receptor phosphate PCP-2
gi|1502342|emb|X97198.1|HSRECPCP2[1502342]

14742: X81870
H.sapiens DNA for macrophage stimulating protein receptor
gi|1491705|emb|X81870.1|HSDNAMSPR[1491705]

14743: Z11168
H.sapiens 5HT1A receptor region
gi|1033027|emb|Z11168.1|HS5HT1A[1033027]

14744: M75105
Human neurokinin-2 receptor (TAC2R) gene, exon 5
gi|189219|gb|M75105.1|HUMNK25[189219]

14745: M75104
Human neurokinin-2 receptor (NK-2) gene, exon 4
gi|189218|gb|M75104.1|HUMNK24[189218]

14746: M75103
Human neurokinin-2 receptor (NK-2) gene, exon 3
gi|189217|gb|M75103.1|HUMNK23[189217]

14747: M75102

Human neurokinin-2 receptor (NK-2) gene, exon 2
gi|189216|gb|M75102.1|HUMNK22[189216]

14748: M75101
Human neurokinin-2 receptor (TAC2R) gene, exon 1
gi|189215|gb|M75101.1|HUMNK21[189215]

14750: X76981
H.sapiens mRNA for adenosin receptor A3
gi|440547|emb|X76981.1|HSRADRA3[440547]

14751: X95302
H.sapiens mRNA for IL13 receptor
gi|1483349|emb|X95302.1|HSIL13REC[1483349]

14752: X51469
H.sapiens cell receptor gamma-chain J1-C1 DNA fragment (Raji cell line)
gi|1480294|emb|X51469.1|HSRAJI[1480294]

14753: X99027
H.sapiens gene encoding discoidin receptor tyrosine kinase, exon 9
gi|1480259|emb|X99027.1|HSDRTK9[1480259]

14754: X99026
H.sapiens gene encoding discoidin receptor tyrosine kinase, exon 8
gi|1480258|emb|X99026.1|HSDRTK8[1480258]

14755: X99024
H.sapiens gene encoding discoidin receptor tyrosine kinase, exon 5
gi|1480256|emb|X99024.1|HSDRTK5[1480256]

14756: X99023
H.sapiens gene encoding discoidin receptor tyrosine kinase, exon 4
gi|1480255|emb|X99023.1|HSDRTK4[1480255]

14757: X99034
H.sapiens gene encoding discoidin receptor tyrosine kinase, exon 17 gi|1480254|emb|X99034.1|HSDRTK17[1480254]

14758: X99033
H.sapiens gene encoding discoidin receptor tyrosine kinase, exon 16
gi|1480253|emb|X99033.1|HSDRTK16[1480253]

14759: X99032
H.sapiens gene encoding discoidin receptor tyrosine kinase, exon 15
gi|1480252|emb|X99032.1|HSDRTK15[1480252]

14760: X98208
H.sapiens gene encoding discoidin receptor tyrosine kinase, exons 1,2,3 and joined CDS
gi|1480249|emb|X98208.1|HSDRTK123[1480249]

14761: X99030
H.sapiens gene encoding discoidin receptor tyrosine kinase, exons 12 & 13
gi|1480248|emb|X99030.1|HSDRTK12[1480248]

14762: X99028
H.sapiens gene encoding discoidin receptor tyrosine kinase, exon 10
gi|1480246|emb|X99028.1|HSDRTK10[1480246]

14763: X51470
H.sapiens T-cell receptor gamma-chain J1-C1 DNA fragment (D-PLL cell line)
gi|1480245|emb|X51470.1|HSDPLL[1480245]

14764: L76631
Homo sapiens metabotropic glutamate receptor 1 beta (mGluR1beta) mRNA, complete cds
gi|1477389|gb|L76631.1|HUMMGLUB[1477389]

14765: L76627
Homo sapiens metabotropic glutamate receptor 1 alpha (mGluR1alpha) mRNA, complete cds
gi|1477387|gb|L76627.1|HUMMGLUA[1477387]

14766: L57508
Homo sapiens Cak receptor kinase mRNA, complete cds
gi|1160924|gb|L57508.1|HUMCAKA[1160924]

14767: L38019
Homo sapiens (clone HUM-IP3R1) inositol 1,4,5-trisphosphate receptor type 1 mRNA, complete cds
gi|1464750|gb|L38019.1|HUMITR[1464750]

14768: X77748
H.sapiens mRNA for metabotropic glutamate receptor type 3
gi|1171563|emb|X77748.1|HSMGLUR3[1171563]

14769: M26016
Human CR2/CD21/C3d/Epstein-Barr virus receptor gene, exon IC
gi|181935|gb|M26016.1|HUMEBUR13[181935]

14770: X63717
H.sapiens mRNA for APO-1 cell surface antigen
gi|28741|emb|X63717.1|HSAPO1[28741]

14771: L03718
Human G protein-coupled receptor (kinase-like) gene, complete cds
gi|183598|gb|L03718.1|HUMGPRKLG[183598]

14773: X99269
H.sapiens NPYY1 gene
gi|1430810|emb|X99269.1|HSNPYY1[1430810]

14774: X95536
H.sapiens ear1 gene
gi|1418937|emb|X95536.1|HSREOR[1418937]

14775: X63745
H.sapiens ERD2.2 mRNA for KDEL receptor
gi|31217|emb|X63745.1|HSERD22[31217]

14777: X98133
H.sapiens gene encoding histamine H2 receptor
gi|1359758|emb|X98133.1|HSH2R[1359758]

14778: X89893
H.sapiens mRNA for NK receptor (183 ActI)
gi|1103680|emb|X89893.1|HSNKRECT2[1103680]

14779: X89892
H.sapiens mRNA for NK receptor (Eb6 ActI)
gi|1103678|emb|X89892.1|HSNKRECT1[1103678]

14780: X98178
H.sapiens mRNA for MACH-beta-4 protein
gi|1403330|emb|X98178.1|HSMACHB4[1403330]

14781: X98177
H.sapiens mRNA for MACH-beta-3 protein
gi|1403328|emb|X98177.1|HSMACHB3[1403328]

14782: X98175
H.sapiens mRNA for MACH-beta-2 protein
gi|1403326|emb|X98175.1|HSMACHB2[1403326]

14783: X98176
H.sapiens mRNA for MACH-beta-1 protein
gi|1403324|emb|X98176.1|HSMACHB1[1403324]

14784: X98173
H.sapiens mRNA for MACH-alpha-2 protein
gi|1403320|emb|X98173.1|HSMACHA2[1403320]

14785: X67594
H.sapiens mRNA for MSH receptor
gi|1405733|emb|X67594.1|HSMSHRECA[1405733]

14786: X96597

H.sapiens gene encoding G protein coupled receptor
gi|1296631|emb|X96597.1|HSGPCRE[1296631]

14789: M88714
Human bradykinin receptor (BK-2) mRNA, complete cds
gi|1387999|gb|M88714.1|HUMBK2A[1387999]

14790: AH003589
Homo sapiens sulfonylurea receptor (SUR1) gene
gi|1374918|gb|AH003589.1|SEG_HUMSUR1G[1374918]

14791: L78243
Homo sapiens sulfonylurea receptor (SUR1) gene, exon 39
gi|1374917|gb|L78243.1|HUMSUR1G38[1374917]

14792: L78242
Homo sapiens sulfonylurea receptor (SUR1) gene, exon 38
gi|1374916|gb|L78242.1|HUMSUR1G37[1374916]

14793: L78241
Homo sapiens sulfonylurea receptor (SUR1) gene, exon 37
gi|1374915|gb|L78241.1|HUMSUR1G36[1374915]

14794: L78240
Homo sapiens sulfonylurea receptor (SUR1) gene, exons 34, 35, and 36
gi|1374914|gb|L78240.1|HUMSUR1G35[1374914]

14795: L78239
Homo sapiens sulfonylurea receptor (SUR1) gene, exon 33
gi|1374913|gb|L78239.1|HUMSUR1G34[1374913]

14796: L78238
Homo sapiens sulfonylurea receptor (SUR1) gene, exon 32
gi|1374912|gb|L78238.1|HUMSUR1G33[1374912]

14797: L78237
Homo sapiens sulfonylurea receptor (SUR1) gene, exon 31 gi|1374911|gb|L78237.1|HUMSUR1G32[1374911]

14798: L78236
Homo sapiens sulfonylurea receptor (SUR1) gene, exon 30
gi|1374910|gb|L78236.1|HUMSUR1G31[1374910]

14799: L78235
Homo sapiens sulfonylurea receptor (SUR1) gene, exon 29
gi|1374909|gb|L78235.1|HUMSUR1G30[1374909]

14800: L78234
Homo sapiens sulfonylurea receptor (SUR1) gene, exon 28
gi|1374908|gb|L78234.1|HUMSUR1G29[1374908]

14801: L78233
Homo sapiens sulfonylurea receptor (SUR1) gene, exon 27
gi|1374907|gb|L78233.1|HUMSUR1G28[1374907]

14802: L78232
Homo sapiens sulfonylurea receptor (SUR1) gene, exon 26
gi|1374906|gb|L78232.1|HUMSUR1G27[1374906]

14803: L78231
Homo sapiens sulfonylurea receptor (SUR1) gene, exon 25
gi|1374905|gb|L78231.1|HUMSUR1G26[1374905]

14804: L78230
Homo sapiens sulfonylurea receptor (SUR1) gene, exon 24
gi|1374904|gb|L78230.1|HUMSUR1G25[1374904]

14805: L78229
Homo sapiens sulfonylurea receptor (SUR1) gene, exon 23
gi|1374903|gb|L78229.1|HUMSUR1G24[1374903]

14806: L78228
Homo sapiens sulfonylurea receptor (SUR1) gene, exon 22
gi|1374902|gb|L78228.1|HUMSUR1G23[1374902]

14807: L78227
Homo sapiens sulfonylurea receptor (SUR1) gene, exon 21
gi|1374901|gb|L78227.1|HUMSUR1G22[1374901]

14808: L78226
Homo sapiens sulfonylurea receptor (SUR1) gene, exon 20
gi|1374900|gb|L78226.1|HUMSUR1G21[1374900]

14809: L78254
Homo sapiens sulfonylurea receptor (SUR1) gene, exon 19
gi|1374899|gb|L78254.1|HUMSUR1G20[1374899]

14810: L78225
Homo sapiens sulfonylurea receptor (SUR1) gene, exon 18
gi|1374898|gb|L78225.1|HUMSUR1G19[1374898]

14811: L78224
Homo sapiens sulfonylurea receptor (SUR1) gene, exon 17 (alternative)
gi|1374897|gb|L78224.1|HUMSUR1G18[1374897]

14812: L78223
Homo sapiens sulfonylurea receptor (SUR1) gene, exon 17
gi|1374896|gb|L78223.1|HUMSUR1G17[1374896]

14813: L78222
Homo sapiens sulfonylurea receptor (SUR1) gene, exon 16
gi|1374895|gb|L78222.1|HUMSUR1G16[1374895]

14814: L78221
Homo sapiens sulfonylurea receptor (SUR1) gene, exon 15
gi|1374894|gb|L78221.1|HUMSUR1G15[1374894]

14815: L78220
Homo sapiens sulfonylurea receptor (SUR1) gene, exon 14
gi|1374893|gb|L78220.1|HUMSUR1G14[1374893]

14816: L78219
Homo sapiens sulfonylurea receptor (SUR1) gene, exon 13
gi|1374892|gb|L78219.1|HUMSUR1G13[1374892]

14817: L78218
Homo sapiens sulfonylurea receptor (SUR1) gene, exon 12
gi|1374891|gb|L78218.1|HUMSUR1G12[1374891]

14818: L78217
Homo sapiens sulfonylurea receptor (SUR1) gene, exon 11
gi|1374890|gb|L78217.1|HUMSUR1G11[1374890]

14819: L78216
Homo sapiens sulfonylurea receptor (SUR1) gene, exon 10
gi|1374889|gb|L78216.1|HUMSUR1G10[1374889]

14820: L78215
Homo sapiens sulfonylurea receptor (SUR1) gene, exon 9
gi|1374888|gb|L78215.1|HUMSUR1G09[1374888]

14821: L78214
Homo sapiens sulfonylurea receptor (SUR1) gene, exon 8
gi|1374887|gb|L78214.1|HUMSUR1G08[1374887]

14822: L78213
Homo sapiens sulfonylurea receptor (SUR1) gene, exon 7
gi|1374886|gb|L78213.1|HUMSUR1G07[1374886]

14823: L78255
Homo sapiens sulfonylurea receptor (SUR1) gene, exon 6
gi|1374885|gb|L78255.1|HUMSUR1G06[1374885]

14824: L78212
Homo sapiens sulfonylurea receptor (SUR1) gene, exon 5
gi|1374884|gb|L78212.1|HUMSUR1G05[1374884]

14825: L78211
Homo sapiens sulfonylurea receptor (SUR1) gene, exon 4
gi|1374883|gb|L78211.1|HUMSUR1G04[1374883]

14826: L78210
Homo sapiens sulfonylurea receptor (SUR1) gene, exon 3
gi|1374882|gb|L78210.1|HUMSUR1G03[1374882]

14827: L78209
Homo sapiens sulfonylurea receptor (SUR1) gene, exon 2
gi|1374881|gb|L78209.1|HUMSUR1G02[1374881]

14828: L78208
Homo sapiens sulfonylurea receptor (SUR1) gene, exon 1
gi|1374880|gb|L78208.1|HUMSUR1G01[1374880]

14829: L78207
Homo sapiens sulfonylurea receptor (SUR1) mRNA, complete cds
gi|1374674|gb|L78207.1|HUMSUR1RNA[1374674]

14830: X80818
H.sapiens mRNA for metabotropic glutamate receptor type 4
gi|1160182|emb|X80818.1|HSMGLUR4[1160182]

14831: X89068
H.sapiens mRNA for TRPC3 protein
gi|1019789|emb|X89068.1|HSTRPC3GN[1019789]

14832: X85740
H.sapiens mRNA for C-C chemokine receptor-4
gi|1370103|emb|X85740.1|HSCCCR3[1370103]

14833: X72924
H.sapiens STS in the vicinity of the ADRA2C gene, sequence tagged site
gi|458814|emb|X72924.1|HSADRASTS[458814]

14834: A27282

H.sapiens TGR-CL3C
gi|1247129|emb|A27282.1|A27282[1247129]

14835: A27278
H.sapiens TGR-CL5
gi|1247127|emb|A27278.1|A27278[1247127]

14836: A27276
H.sapiens TGR-CL1
gi|1247125|emb|A27276.1|A27276[1247125]

14837: A27270
H.sapiens TGR-CL10C
gi|1247123|emb|A27270.1|A27270[1247123]

14838: A10542
H.sapiens low affinity Fc-epsilon-receptor
gi|489152|emb|A10542.1|A10542[489152]

14839: X84700
H.sapiens mRNA for leucocyte antigen CD97
gi|840770|emb|X84700.1|HSCD97[840770]

14841: X56794
H.sapiens CD44R mRNA
gi|29798|emb|X56794.1|HSCD441[29798]

14842: Z22924
H.sapiens of CD36 gene, partial CDS
gi|397604|emb|Z22924.1|HSCD36AA[397604]

14843: X81121
H.sapiens mRNA for central cannabinoid receptor, short isoform
gi|736238|emb|X81121.1|HSCB1A[736238]

14844: X74328
H.sapiens mRNA for CB2 (peripheral) cannabinoid receptor
gi|407806|emb|X74328.1|HSCB2CANR[407806]

14852: X81120
H.sapiens mRNA for central cannabinoid receptor
gi|736236|emb|X81120.1|HSCANN6[736236]

14853: X82466
H.sapiens mRNA for calcitonin receptor
gi|565026|emb|X82466.1|HSCALRECR[565026]

14854: X69920
H.sapiens mRNA for calcitonin receptor
gi|474931|emb|X69920.1|HSCALRE[474931]

14855: Z22672
H.sapiens cacnl1a3 gene encoding skeletal muscle dhp-receptor alpha 1 subunit
gi|297467|emb|Z22672.1|HSCACN1A[297467]

14856: Z35761
H.sapiens TEL/ABL fusion protien
gi|601903|emb|Z35761.1|HSBREAKP3[601903]

14862: X62515
H.sapiens mRNA for basement membrane heparan sulfate proteoglycan
gi|29469|emb|X62515.1|HSBMHSP[29469]

14887: X70811
H.sapiens mRNA for beta 3 adrenergic receptor
gi|312396|emb|X70811.1|HSBARE[312396]

14888: X69117
H.sapiens mRNA for beta-adrenergic kinase 2
gi|312394|emb|X69117.1|HSBADRK2[312394]

14889: X61157
H.sapiens mRNA for beta-adrenergic receptor kinase
gi|288307|emb|X61157.1|HSBARK[288307]

14891: X77584
H.sapiens mRNA for ATL-derived factor/thiredoxin
gi|453963|emb|X77584.1|HSATLRED[453963]

14894: X70297
H.sapiens mRNA for neuronal nicotinic acetylcholine receptor alpha-7 subunit
gi|496606|emb|X70297.1|HSARA7A[496606]

14901: Z11162
H.sapiens gene for angiotensin II
gi|28709|emb|Z11162.1|HSANTENII[28709]

14902: X91162
H.sapiens anti-mullerian hormone type II receptor exon 9
gi|1107682|emb|X91162.1|HSAMREXO9[1107682]

14903: X91164
H.sapiens anti-mullerian hormone type II receptor exon 11
gi|1107681|emb|X91164.1|HSAMREX11[1107681]

14904: X91163
H.sapiens anti-mullerian hormone type II receptor exon 10
gi|1107680|emb|X91163.1|HSAMREX10[1107680]

14905: X91161
H.sapiens anti-mullerian hormone type II receptor exon 8
gi|1107679|emb|X91161.1|HSAMREX08[1107679]

14906: X91160
H.sapiens anti-mullerian hormone type II receptor exon 7
gi|1107678|emb|X91160.1|HSAMREX07[1107678]

14907: X91159
H.sapiens anti-mullerian hormone type II receptor exon 6
gi|1107677|emb|X91159.1|HSAMREX06[1107677]

14908: X91158
H.sapiens anti-mullerian hormone type II receptor exon 5
gi|1107676|emb|X91158.1|HSAMREX05[1107676]

14909: X91157
H.sapiens anti-mullerian hormone type II receptor exon 4
gi|1107675|emb|X91157.1|HSAMREX04[1107675]

14910: X91165
H.sapiens anti-mullerian hormone type II receptor exon 3
gi|1107674|emb|X91165.1|HSAMREX03[1107674]

14911: X91166
H.sapiens anti-mullerian hormone type II receptor exon 2
gi|1107673|emb|X91166.1|HSAMREX02[1107673]

14912: X65699
H.sapiens mRNA for angiotensin II receptor
gi|510983|emb|X65699.1|HSANGII[510983]

14913: X91156
H.sapiens anti-mullerian hormone type II receptor exon 1
gi|1107671|emb|X91156.1|HSAMREX01[1107671]

14914: Z22533
H.sapiens ALK-1 mRNA
gi|402196|emb|Z22533.1|HSALK1A[402196]

14915: Z22536
Homo sapiens ALK-4 mRNA, complete CDS
gi|402188|emb|Z22536.1|HSALK4A[402188]

14916: Z22535
H.sapiens ALK-3 mRNA
gi|402186|emb|Z22535.1|HSALK3A[402186]

14917: Z22534

H.sapiens ALK-2 mRNA
gi|402184|emb|Z22534.1|HSALK2A[402184]

14918: X59684
H.sapiens DNA for alpha2-1.8 adrenergic receptor gene
gi|28635|emb|X59684.1|HSALPH218[28635]

14919: Z11687
H.sapiens mRNA for antidiuretic hormone receptor
gi|28417|emb|Z11687.1|HSADHRMR[28417]

14920: X77533
H.sapiens mRNA for activin type II receptor
gi|825619|emb|X77533.1|HSACTIIRE[825619]

14921: X62381
H.sapiens mRNA for activin receptor
gi|28347|emb|X62381.1|HSACTR[28347]

14922: X65633
H.sapiens ACTH-R gene for adrenocorticotropic hormone receptor
gi|28343|emb|X65633.1|HSACTHR[28343]

14923: X55019
H.sapiens mRNA for acetylcholine receptor delta subunit
gi|297401|emb|X55019.1|HSACHRG[297401]

14924: X02508
H.sapiens gene fragment for acetylcholine receptor (AChR) alpha subunit exons 8, 9 and 3' flanking region
gi|28306|emb|X02508.1|HSACHR8[28306]

14925: X02507
H.sapiens gene fragment for acetylcholine receptor (AChR) alpha subunit exon 7
gi|28304|emb|X02507.1|HSACHR7[28304]

14926: X02506

H.sapiens gene fragment for acetylcholine receptor (AChR) alpha-subunit exon 6
gi|28302|emb|X02506.1|HSACHR6[28302]

14927: X83956
H.sapiens ACCA gene
gi|1061125|emb|X83956.1|HSACCAGEN[1061125]

14928: X66403
H.sapiens mRNA for acetylcholine receptor (epsilon subunit)
gi|560152|emb|X66403.1|HSACETR[560152]

14929: X02505
H.sapiens gene fragment for acetylcholine receptor (AChR) alpha subunit exon 5
gi|28300|emb|X02505.1|HSACHR5[28300]

14930: X02504
H.sapiens gene fragment for acetylcholine receptor (AChR) alpha-subunit exon 4
gi|28298|emb|X02504.1|HSACHR4[28298]

14931: X02503
H.sapiens gene fragment for acetylcholine receptor (AChR) alpha-subunit exons 2 and 3
gi|28293|emb|X02503.1|HSACHR2[28293]

14932: X02502
H.sapiens gene fragment for acetylcholine receptor (AChR) alpha-subunit exon 1
gi|28291|emb|X02502.1|HSACHR[28291]

14933: X04759
H.sapiens gene fragment for the acetylcholine receptor gamma subunit (exon 12)
gi|28288|emb|X04759.1|HSACHG8[28288]

14934: X01721
H.sapiens gene fragment for the acetylcholine receptor gamma subunit (exons 10 and 11)
gi|28286|emb|X01721.1|HSACHG7[28286]

14935: X01720
H.sapiens gene fragment for the acetylcholine receptor gamma subunit (exon 9)
gi|28283|emb|X01720.1|HSACHG6[28283]

14936: X01718
H.sapiens gene fragment for the acetylcholine receptor gamma subunit (exon 6)
gi|28276|emb|X01718.1|HSACHG4[28276]

14937: X01717
H.sapiens gene fragment for the acetylcholine receptor gamma subunit (exon 5)
gi|28274|emb|X01717.1|HSACHG3[28274]

14938: X01716
H.sapiens gene fragment for the acetylcholine receptor gamma subunit (exon 3 and 4)
gi|28271|emb|X01716.1|HSACHG2[28271]

14939: X77018
H.sapiens mRNA for anti-acetylcholine receptor monoclonal autoantibody V lambda region
gi|441251|emb|X77018.1|HSAARMA2[441251]

14941: X68487
H.sapiens mRNA for A2b adenosine receptor
gi|400453|emb|X68487.1|HSA2BREC[400453]

14942: X68486
H.sapiens mRNA for A2a adenosine receptor
gi|400451|emb|X68486.1|HSA2AREC[400451]

14943: X68485
H.sapiens mRNA for A1 adenosine receptor
gi|400449|emb|X68485.1|HSA1ADREC[400449]

14948: X87197
H.sapiens mRNA for 6.3 gene
gi|854083|emb|X87197.1|HS63MRNAG[854083]

14949: X81412
H.sapiens DNA for 5-HT5A exon2
gi|541777|emb|X81412.1|HS5HT5A2[541777]

14950: X81411
H.sapiens DNA for 5-HT5A exon1
gi|541776|emb|X81411.1|HS5HT5A1[541776]
14952: X77307
H.sapiens mRNA for 5-HT2B serotonin receptor
gi|475197|emb|X77307.1|HS5HT2BSR[475197]

14968: X75299
H.sapiens HIVR mRNA for vasoactive intestinal peptide (VIP) receptor
gi|407461|emb|X75299.1|HSVIPRE[407461]

14969: X94216
H.sapiens mRNA for VEGF-C protein
gi|1177488|emb|X94216.1|HSVEGFC[1177488]

14971: X67482
H.sapiens mRNA for 1,25-dihydroxyvitamin D-3 receptor
gi|37653|emb|X67482.1|HSVD3R[37653]

14976: Z46797
H.sapiens gene for urokinase receptor (partial)
gi|732804|emb|Z46797.1|HSUPAR5[732804]

14977: X74039
H.sapiens mRNA for urokinase plasminogen activator receptor
gi|456192|emb|X74039.1|HSUPAR[456192]

14984: X51675
H.sapiens urokinase plasminogen activator surface receptor (uPAR) mRNA
gi|37604|emb|X51675.1|HSUPARAA[37604]

14985: X76498
H.sapiens gene for uterine bombesin receptor gi|468753|emb|X76498.1|HSUBR[468753]

14986: X66029
H.sapiens mRNA for tyrosine kinase receptor
gi|37596|emb|X66029.1|HSUFOR[37596]

14987: X66030
Homo sapiens partial ufo gene encoding tyrosine kinase receptor
gi|37594|emb|X66030.1|HSUFOD[37594]

14998: X72089
H.sapiens mRNA for TRH receptor
gi|440155|emb|X72089.1|HSTRHREC[440155]

15005: X72018
H.sapiens hTGR 1 mRNA
gi|1200088|emb|X72018.1|HSTGR1[1200088]

15006: X69178
H.sapiens mRNA for thyrotropin receptor, partial
gi|288212|emb|X69178.1|HSTHREC[288212]

15007: X69177
H.sapiens mRNA for thyrotropin receptor, partial
gi|288211|emb|X69177.1|HSTHRE[288211]

15246: X65181
H.sapiens gene for substance P receptor (exon 5)
gi|36640|emb|X65181.1|HSSUBP5G[36640]

15247: X65180
H.sapiens gene for substance P receptor (exon 4)
gi|36639|emb|X65180.1|HSSUBP4G[36639]

15248: X65179
H.sapiens gene for substance P receptor (exon 3)
gi|36638|emb|X65179.1|HSSUBP3G[36638]

15249: X65177
H.sapiens gene for substance P receptor (exon 1)
gi|36636|emb|X65177.1|HSSUBP1G[36636]

15253: X62156
H.sapiens mRNA for soluble interleukin-5 receptor
gi|36465|emb|X62156.1|HSSILR5[36465]

15254: X57830
H.sapiens serotonin 5-HT2 receptor mRNA
gi|36430|emb|X57830.1|HSSERR52[36430]

15255: Z11166
H.sapiens S31 gene for serotonin receptor
gi|36264|emb|Z11166.1|HSS31G[36264]

15256: X91869
H.sapiens mRNA for ryanodine receptor
gi|1022320|emb|X91869.1|HSRYR2[1022320]

15257: X74269
H.sapiens RYR3 mRNA for ryanodine receptor type 3 (partial)
gi|405718|emb|X74269.1|HSRYR3MR[405718]

15258: X74270
H.sapiens RYR3 gene for ryanodine receptor type 3 (partial)
gi|405716|emb|X74270.1|HSRYR3G[405716]

15261: Z27409
H.sapiens mRNA for receptor tyrosine kinase eph (partial)
gi|482916|emb|Z27409.1|HSRTKEPH[482916]

15262: X74764
H.sapiens mRNA for receptor protein tyrosine kinase
gi|433337|emb|X74764.1|HSRPTK[433337]

15265: X59155
H.sapiens retroviral receptor mRNA
gi|36160|emb|X59155.1|HSRRMRNA[36160]

15267: X70040
H.sapiens RON mRNA for tyrosine kinase
gi|36109|emb|X70040.1|HSRON[36109]

15268: X75071
H.sapiens mRNA for human thyrotropin-releasing hormone receptor
gi|404157|emb|X75071.1|HSRNAHTRH[404157]

15269: X86446
H.sapiens mRNA for 55.11 binding protein
gi|1008088|emb|X86446.1|HSRNA5511[1008088]

15270: Z29093
H.sapiens EDDR1 gene for receptor tyrosine kinase
gi|732799|emb|Z29093.1|HSRETYK1[732799]

15274: X64123
H.sapiens PVR gene for poliovirus receptor (exon 8)
gi|35819|emb|X64123.1|HSPVR8G[35819]

15275: X64122
H.sapiens PVR gene for poliovirus receptor (exon 7)
gi|35818|emb|X64122.1|HSPVR7G[35818]

15276: X64121
H.sapiens PVR gene for poliovirus receptor (exon 6)
gi|35817|emb|X64121.1|HSPVR6G[35817]

15277: X64120
H.sapiens PVR gene for poliovirus receptor (exon 5)
gi|35816|emb|X64120.1|HSPVR5G[35816]

15278: X64119
H.sapiens PVR gene for poliovirus receptor (exon 4)
gi|35815|emb|X64119.1|HSPVR4G[35815]

15279: X64118
H.sapiens PVR gene for poliovirus receptor (exon 3)
gi|35814|emb|X64118.1|HSPVR3G[35814]

15280: X64117
H.sapiens PVR gene for poliovirus receptor (exon 2)
gi|35813|emb|X64117.1|HSPVR2G[35813]

15281: X64116
H.sapiens PVR gene for poliovirus receptor (exon 1)
gi|35809|emb|X64116.1|HSPVR1G[35809]

15283: X75208
H.sapiens HEK2 mRNA for protein tyrosine kinase receptor
gi|406867|emb|X75208.1|HSPTKR[406867]

15284: X65178
H.sapiens gene for substance P receptor (exon 2)
gi|35653|emb|X65178.1|HSPREC2G[35653]

15285: X94226
H.sapiens poliovirus receptor gene
gi|1185121|emb|X94226.1|HSPOLR[1185121]

15288: X73079
Homo sapiens encoding Polymeric immunoglobulin receptor
gi|456345|emb|X73079.1|HSPIR[456345]

15291: X68596
H.sapiens mRNA for parathyroid hormone receptor
gi|396812|emb|X68596.1|HSPHR[396812]

15302: X76079

H.sapiens mRNA for platelet derived growth factor alpha receptor
gi|433494|emb|X76079.1|HSPDGF[433494]

15311: Z49993
H.sapiens partial gene for proteinase-activated receptor 2 (292 BP)
gi|1008084|emb|Z49993.1|HSPAR2A[1008084]

15321: X80022
H.sapiens p75 TNF receptor, exon 2
gi|666045|emb|X80022.1|HSP75NFR2[666045]

15322: X80021
H.sapiens p75 TNF receptor, exon 1
gi|666044|emb|X80021.1|HSP75NFR1[666044]

15323: X69810
H.sapiens gene for p55 tumor necrosis factor receptor, exon 1
gi|288493|emb|X69810.1|HSP55TNF[288493]

15324: X83688
H.sapiens mRNA for ATP receptor
gi|1166437|emb|X83688.1|HSP2XRCPR[1166437]

15325: X77130
H.sapiens mRNA for ORL1 receptor
gi|471316|emb|X77130.1|HSORL1[471316]

15327: X71635
H.sapiens mRNA for neuropeptide Y-like receptor
gi|297099|emb|X71635.1|HSNPYRLA[297099]

15328: X71445
H.sapiens partial NTRK1 gene, involved in oncogenic rearrangements
gi|296536|emb|X71445.1|HSNTRK1[296536]

15329: X66945
H.sapiens N-sam mRNA for fibroblast growth factor receptor gi|35109|emb|X66945.1|HSNSAMTK[35109]

15330: X75918
H.sapiens mRNA for NOT
gi|415822|emb|X75918.1|HSNOT[415822]

15331: Z32774
H.sapiens gene for N-methyl-D-aspartate receptor R1 exons 6-21
gi|807894|emb|Z32774.1|HSNMDAR1C[807894]

15332: Z32773
H.sapiens gene for N-methyl-D-aspartate receptor R1 exons 3, 4, 5
gi|807893|emb|Z32773.1|HSNMDAR1B[807893]

15333: Z32772
H.sapiens gene for N-methyl-D-aspartate receptor R1, exon1, exon2
gi|807892|emb|Z32772.1|HSNMDAR1A[807892]

15334: X68275
H.sapiens mRNA for nicotinic receptor beta 4 subunit
gi|35054|emb|X68275.1|HSNICRB[35054]

15335: X65176
H.sapiens gene for neuromedin K receptor (exon 5)
gi|35027|emb|X65176.1|HSNEURK5[35027]

15336: X65175
H.sapiens gene for neuromedin K receptor (exon 4)
gi|35026|emb|X65175.1|HSNEURK4[35026]

15337: X65174
H.sapiens gene for neuromedin K receptor (exon 3)
gi|35025|emb|X65174.1|HSNEURK3[35025]

15338: X65173
H.sapiens gene for neuromedin K receptor (exon 2)
gi|35024|emb|X65173.1|HSNEURK2[35024]

15339: X65172
H.sapiens gene for neuromedin K receptor (exon 1)
gi|35022|emb|X65172.1|HSNEURK1[35022]

15340: X87629
H.sapiens mRNA for nicotinic acetylcholine receptor alpha4 subunit
gi|854158|emb|X87629.1|HSNACRA4G[854158]

15341: X70108
H.sapiens gene for nicotinic acetylcholine receptor alpha subunit, partial
gi|312470|emb|X70108.1|HSNACHRA[312470]

15342: X67513
H.sapiens mRNA for neuronal nAChR beta-3 subunit
gi|34987|emb|X67513.1|HSNACHRB3[34987]

15343: X53559
H.sapiens Hachr alpha-3 mRNA for mature neuronal nicotinic acetylcholine receptor alpha-3 subunit
gi|34985|emb|X53559.1|HSNACHRA3[34985]

15344: X63131
H.sapiens Myl (PML) mRNA
gi|34813|emb|X63131.1|HSMY1[34813]

15345: X65634
H.sapiens MSH-R gene for melanocyte stimulating hormone receptor
gi|34790|emb|X65634.1|HSMSHR[34790]

15346: X64878
H.sapiens mRNA for oxytocin receptor
gi|34764|emb|X64878.1|HSMRNAOXY[34764]

15347: X84709
H.sapiens mRNA for mediator of receptor-induced toxicity
gi|791037|emb|X84709.1|HSMRINTX[791037]

15348: X55635
H.sapiens mRNA for macrophage mannose receptor
gi|34702|emb|X55635.1|HSMMR[34702]

15349: Z25470
H.sapiens melanocortin 5 receptor gene, complete CDS
gi|939924|emb|Z25470.1|HSMELRECA[939924]

15350: X68829
H.sapiens mRNA for MDR15 protein
gi|840783|emb|X68829.1|HSMDCR[840783]

15351: X61615
H.sapiens mRNA for leukemia inhibitory factor (LIF) receptor
gi|34365|emb|X61615.1|HSLIFR[34365]

15374: X86128
H.sapiens mRNA for ood T lymphocyte
gi|1197254|emb|X86128.1|HSLAB2725[1197254]

15375: Z30428
H.sapiens gene for early lymphocyte activation antigen CD69, exon 5
gi|536775|emb|Z30428.1|HSLACD695[536775]

15376: Z30430
H.sapiens gene for early lymphocyte activation antigen CD69, exon 2
gi|535122|emb|Z30430.1|HSLACD692[535122]

15398: X69304
H.sapiens KIT proto-oncogene for mast/stem cell growth factor receptor, exon 4
gi|34093|emb|X69304.1|HSKITPO04[34093]

15399: X69303
H.sapiens KIT proto-oncogene for mast/stem cell growth factor receptor, exon 3
gi|34092|emb|X69303.1|HSKITPO03[34092]

15400: X69302
H.sapiens KIT proto-oncogene for mast/stem cell growth factor receptor, exon 2
gi|34091|emb|X69302.1|HSKITPO02[34091]

15401: X69301
H.sapiens KIT proto-oncogene for mast/stem cell growth factor receptor, exon 1
gi|34089|emb|X69301.1|HSKITPO01[34089]

15405: X03138
H.sapiens interleukin 2 receptor gene exon 8 and 3' untranslated region
gi|33830|emb|X03138.1|HSIL2RG8[33830]

15406: X03137
H.sapiens interleukin 2 receptor gene exon 7
gi|33829|emb|X03137.1|HSIL2RG7[33829]

15407: X03136
H.sapiens interleukin 2 receptor gene exon 6
gi|33827|emb|X03136.1|HSIL2RG6[33827]

15408: X03135
H.sapiens interleukin 2 receptor gene exon 5
gi|33825|emb|X03135.1|HSIL2RG5[33825]

15409: X03134
H.sapiens interleukin 2 receptor gene exon 4
gi|33823|emb|X03134.1|HSIL2RG4[33823]

15410: X03133
H.sapiens interleukin 2 receptor gene exon 3
gi|33822|emb|X03133.1|HSIL2RG3[33822]

15411: X03132
H.sapiens interleukin 2 receptor gene exon 2
gi|33820|emb|X03132.1|HSIL2RG2[33820]

15412: X84348
H.sapiens mRNA for intracellular IL-1 receptor antagonist type II
gi|1008970|emb|X84348.1|HSIL1RAII[1008970]

15413: Z46595
H.sapiens mRNA for interleukin 11 receptor isoform (incomplete)
gi|995655|emb|Z46595.1|HSIL11RR[995655]

15414: Z38102
H.sapiens mRNA for interleukin-11 receptor
gi|995653|emb|Z38102.1|HSIL11RM[995653]

15415: Z46596
H.sapiens gene for interleukin 11 receptor
gi|995652|emb|Z46596.1|HSIL11RGN[995652]

15416: X59770
H.sapiens IL-1R2 mRNA for type II interleukin-1 receptor, (cell line CB23)
gi|33796|emb|X59770.1|HSIL1R2II[33796]

15421: X77722
H.sapiens mRNA for interferon alpha/beta receptor
gi|488363|emb|X77722.1|HSIFNABR[488363]

15423: X53296
H.sapiens mRNA for IRAP
gi|32578|emb|X53296.1|HSI1RAP[32578]

15424: X52015
H.sapiens mRNA for interleukin-1 receptor antagonist
gi|32576|emb|X52015.1|HSI1RA[32576]

15425: X64993
H.sapiens mRNA HTPCRX19 for olfactory receptor
gi|32523|emb|X64993.1|HSHTPRX19[32523]

15426: X64992

H.sapiens mRNA HTPCRX18 for olfactory receptor
gi|32522|emb|X64992.1|HSHTPRX18[32522]

15427: X64991
H.sapiens mRNA HTPCRX17 for olfactory receptor
gi|32521|emb|X64991.1|HSHTPRX17[32521]

15428: X64990
H.sapiens mRNA HTPCRX16 for olfactory receptor
gi|32520|emb|X64990.1|HSHTPRX16[32520]

15429: X64989
H.sapiens mRNA HTPCRX15 for olfactory receptor
gi|32519|emb|X64989.1|HSHTPRX15[32519]

15430: X64988
H.sapiens mRNA HTPCRX14 for olfactory receptor
gi|32518|emb|X64988.1|HSHTPRX14[32518]

15431: X64987
H.sapiens mRNA HTPCRX13 for olfactory receptor
gi|32517|emb|X64987.1|HSHTPRX13[32517]

15432: X64986
H.sapiens mRNA HTPCRX12 for olfactory receptor
gi|32516|emb|X64986.1|HSHTPRX12[32516]

15433: X64985
H.sapiens mRNA HTPCRX11 for olfactory receptor
gi|32515|emb|X64985.1|HSHTPRX11[32515]

15434: X64984
H.sapiens mRNA HTPCRX10 for olfactory receptor
gi|32514|emb|X64984.1|HSHTPRX10[32514]

15435: X64983
H.sapiens mRNA HTPCRX09 for olfactory receptor gi|32513|emb|X64983.1|HSHTPRX09[32513]

15436: X64982
H.sapiens mRNA HTPCRX06 for olfactory receptor
gi|32512|emb|X64982.1|HSHTPRX06[32512]

15437: X64981
H.sapiens mRNA HTPCRX03 for olfactory receptor
gi|32511|emb|X64981.1|HSHTPRX03[32511]

15438: X64980
H.sapiens mRNA HTPCRX02 for olfactory receptor
gi|32510|emb|X64980.1|HSHTPRX02[32510]

15439: X64979
H.sapiens mRNA HTPCRX01 for olfactory receptor
gi|32509|emb|X64979.1|HSHTPRX01[32509]

15440: X64974
H.sapiens mRNA HTPCRH02 for olfactory receptor
gi|32508|emb|X64974.1|HSHTPRHO2[32508]

15441: X64978
H.sapiens mRNA HTPCRH07 for olfactory receptor
gi|32507|emb|X64978.1|HSHTPRH07[32507]

15442: X64977
H.sapiens mRNA HTPCRH06 for olfactory receptor
gi|32506|emb|X64977.1|HSHTPRH06[32506]

15443: X64976
H.sapiens mRNA HTPCRH04 for olfactory receptor
gi|32505|emb|X64976.1|HSHTPRH04[32505]

15444: X64975
H.sapiens mRNA HTPCRH03 for olfactory receptor
gi|32504|emb|X64975.1|HSHTPRH03[32504]

15445: X58288
H.sapiens hR-PTPu gene for protein tyrosine phosphatase
gi|32455|emb|X58288.1|HSHRPTPU[32455]

15449: X64995
H.sapiens HGMP07J gene for olfactory receptor
gi|32092|emb|X64995.1|HSHGMP07J[32092]

15450: X64994
H.sapiens HGMP07I gene for olfactory receptor
gi|32085|emb|X64994.1|HSHGM071[32085]

15451: X17653
H.sapiens hFcRII-C isoform mRNA for IgG Fc receptor hFcRII
gi|32076|emb|X17653.1|HSHFCRIIC[32076]

15452: X17652
H.sapiens hFcRII-B isoform mRNA for IgG Fc receptor hFcRII
gi|32073|emb|X17652.1|HSHFCRIIB[32073]

15453: X53364
H.sapiens HePTP mRNA for tyrosine phosphatase
gi|32066|emb|X53364.1|HSHEPTP[32066]

15454: X64830
H.sapiens mRNA for GLU-R2 glutamate receptor subunit, 'flop' exon
gi|31911|emb|X64830.1|HSGRSFLOP[31911]

15455: X64829
H.sapiens mRNA for GLU-R2 glutamate receptor subunit, 'flip' exon
gi|31910|emb|X64829.1|HSGRSFLIP[31910]

15456: X75897
H.sapiens mRNA for G-protein coupled kinase 4
gi|483764|emb|X75897.1|HSGRK4[483764]

15460: X52009
H.sapiens alpha-1 strychnine binding subunit of inhibitory glycine receptor mRNA
gi|31850|emb|X52009.1|HSGLYRA2[31850]

15461: X52008
H.sapiens alpha-2 strychnine binding subunit of inhibitory glycine receptor mRNA
gi|31848|emb|X52008.1|HSGLYRA1[31848]

15462: X82068
H.sapiens mRNA for glutamate receptor subunit GluRC
gi|558587|emb|X82068.1|HSGLURC[558587]

15463: X58633
H.sapiens mRNA for glutamate receptor GLUR1
gi|414892|emb|X58633.1|HSGLUR1[414892]

15464: X81832
H.sapiens mRNA for glucose-dependant insulinotropic polypeptide receptor gene
gi|1030050|emb|X81832.1|HSGDIPR[1030050]

15465: X61656
H.sapiens mRNA for growth factor receptor tyrosine kinase
gi|31717|emb|X61656.1|HSGFRTK[31717]

15466: X55037
H.sapiens GATA-3 mRNA
gi|31661|emb|X55037.1|HSGATA3[31661]

15467: X63670
H.sapiens DNA sequence for polymorphism at the GABA receptor B3
gi|31638|emb|X63670.1|HSGABRB3[31638]

15472: Z34260
H.sapiens DNA for follicle stimulating hormone (FSH) receptor
gi|1052701|emb|Z34260.1|HSFSHX1[1052701]

15473: X68044
H.sapiens mRNA for follicle-stimulating hormone receptor
gi|31473|emb|X68044.1|HSFSTHR[31473]

15474: Z46619
H.sapiens mRNA for immunoglobulin kappa chain (fsa10)
gi|575235|emb|Z46619.1|HSFSA10KA[575235]

15475: Z46615
H.sapiens DNA for immunoglobulin kappa chain (fsa10glk)
gi|575234|emb|Z46615.1|HSFSA10GL[575234]

15476: Z32633
H.sapiens FRGAMMA' mRNA for folate receptor (817bp)
gi|474060|emb|Z32633.1|HSFRGAM2[474060]

15477: Z32564
H.sapiens FRGAMMA mRNA (819bp) for folate receptor
gi|473235|emb|Z32564.1|HSFRGAM1[473235]

15478: X69878
H.sapiens Flt4 mRNA for transmembrane tyrosine kinase
gi|297049|emb|X69878.1|HSFLT4X[297049]

15479: X68203
H.sapiens mRNA for FLT4, class III receptor tyrosine kinase
gi|31433|emb|X68203.1|HSFLT4[31433]

15480: X62573
H.sapiens RNA for Fc receptor, TC9
gi|31339|emb|X62573.1|HSFCTC6[31339]

15481: X66187
H.sapiens FceRI mRNA, partial CDS
gi|396463|emb|X66187.1|HSFCERIGB[396463]

15482: X62572

H.sapiens RNA for Fc receptor, PC23
gi|31328|emb|X62572.1|HSFCPC23[31328]

15483: Z46618
H.sapiens mRNA for immunoglobulin lambda chain (f29)
gi|575230|emb|Z46618.1|HSF29LAM[575230]

15484: Z46634
H.sapiens mRNA for immunoglobulin kappa chain (f29)
gi|575228|emb|Z46634.1|HSF29KAP[575228]

15485: X61950
H.sapiens mRNA for endothelin-1 receptor
gi|288312|emb|X61950.1|HSET1R[288312]

15486: X83863
H.sapiens mRNA for prostaglandin E receptor (EP3f)
gi|633219|emb|X83863.1|HSEP3F[633219]

15487: X83862
H.sapiens mRNA for prostaglandin E receptor (EP3e)
gi|633217|emb|X83862.1|HSEP3E[633217]

15488: X83861
H.sapiens mRNA for prostaglandin E receptor (EP3d)
gi|633215|emb|X83861.1|HSEP3D[633215]

15489: X83860
H.sapiens mRNA for prostaglandin E receptor (EP3c)
gi|633213|emb|X83860.1|HSEP3C[633213]

15490: X83859
H.sapiens mRNA for prostaglandin E receptor (EP3b)
gi|633211|emb|X83859.1|HSEP3B[633211]

15491: X83858
H.sapiens mRNA for prostaglandin E receptor (EP3a2)

gi|633209|emb|X83858.1|HSEP3A2[633209]

15492: X83857
H.sapiens mRNA for prostaglandin E receptor (EP3a1)
gi|633207|emb|X83857.1|HSEP3A1[633207]

15493: X83868
H.sapiens mRNA for EP2 prostaglandin receptor
gi|633205|emb|X83868.1|HSEP2PR[633205]

15494: X81479
H.sapiens mRNA for EMR1 hormone receptor
gi|784993|emb|X81479.1|HSEMR1[784993]

15518: Z28613
H.sapiens (dhpa215) cacnl2a gene for dihydropyridine receptor alpha-2 subunit
gi|472953|emb|Z28613.1|HSDPRA25[472953]

15519: Z28609
H.sapiens (dhpa22hd) cacnl2a gene for dihydropyridine receptor alpha 2-subunit
gi|472952|emb|Z28609.1|HSDPRA24[472952]

15520: Z28605
H.sapiens (dhpa23) cacnl2a gene for dihydropyridine receptor alpha2 subunit
gi|472951|emb|Z28605.1|HSDPRA23[472951]

15521: Z28602
H.sapiens (dhpa21hb) cacnl2a gene for dihydropyridine receptor alpha 2-subunit
gi|472950|emb|Z28602.1|HSDPRA22[472950]

15522: Z28599
H.sapiens (a225eh) cacnl2a gene for dihydropyridine receptor alpha2 subunit
gi|472949|emb|Z28599.1|HSDPRA21[472949]

15526: X55758
H.sapiens dopamine D1 receptor gene
gi|288931|emb|X55758.1|HSDOPD1[288931]

15529: Z23025
H.sapiens cacn11a3 gene encoding skeletal muscle DHP-receptor alpha 1 subunit (exon)
gi|312285|emb|Z23025.1|HSDHPRA1S[312285]

15530: X84076
H.sapiens mRNA for DGCR2
gi|809021|emb|X84076.1|HSDGCR2[809021]

15532: X63523
H.sapiens mRNA DAUDI6 3'-region
gi|30449|emb|X63523.1|HSDAUDI63[30449]

15533: X66171
H.sapiens CMRF35 mRNA, complete CDS
gi|396169|emb|X66171.1|HSCMRF35A[396169]

15534: Z23141
H.sapiens CHRNA7 mRNA, 3' end
gi|457736|emb|Z23141.1|HSCHRNA7A[457736]

15550: X56777
H.sapiens mRNA for ZP3 gene
gi|297790|emb|X56777.1|HSZP3G[297790]

15551: X77155
H.sapiens genomic DNA (YAC end 63 with high affinity Fc-receptor for IgG)
gi|450533|emb|X77155.1|HSYACFC[450533]

15582: M31165
Human tumor necrosis factor-inducible (TSG-6) mRNA fragment, adhesion receptor CD44 putative CDS
gi|339994|gb|M31165.1|HUMTSG6A[339994]

15594: A31613

H.sapiens beta-adrenergic receptor gene
gi|1247565|emb|A31613.1|A31613[1247565]

15595: A29216
H.sapiens DNA for bFGF receptor from patent WO9111459
gi|1247528|emb|A29216.1|A29216[1247528]

15596: A29103
H.sapiens mRNA for TNF-binding polypeptide from patent EP0393438
gi|1247517|emb|A29103.1|A29103[1247517]

15597: A28489
H.sapiens mRNA for IL-2R-beta-chain from patent EP0395853
gi|1247509|emb|A28489.1|A28489[1247509]

15598: A28003
H.sapiens HEK gene
gi|1247486|emb|A28003.1|A28003[1247486]

15599: A27284
H.sapiens TGR-CLH
gi|1247482|emb|A27284.1|A27284[1247482]

15600: A27280
H.sapiens TGR-CL3
gi|1247480|emb|A27280.1|A27280[1247480]

15601: A27274
H.sapiens TGR-CL11/TGR-C15
gi|1247478|emb|A27274.1|A27274[1247478]

15602: A27272
H.sapiens TGR-CL11
gi|1247476|emb|A27272.1|A27272[1247476]

15603: A27268
H.sapiens TGR-CL10 gi|1247474|emb|A27268.1|A27268[1247474]

15604: A27266
H.sapiens TGR-CL7
gi|1247472|emb|A27266.1|A27266[1247472]

15605: A27264
H.sapiens TGR-CL6
gi|1247470|emb|A27264.1|A27264[1247470]

15606: A27262
H.sapiens TGR-CL5bis
gi|1247468|emb|A27262.1|A27262[1247468]

15607: A27260
H.sapiens TGR-CL4
gi|1247466|emb|A27260.1|A27260[1247466]

15608: A27258
H.sapiens TGR-CL1bis
gi|1247464|emb|A27258.1|A27258[1247464]

15609: A19671
H.sapiens DNA for D3 receptor fragment
gi|579581|emb|A19671.1|A19671[579581]

15610: A19670
H.sapiens DNA for D3 receptor fragment
gi|579580|emb|A19670.1|A19670[579580]

15611: A19667
H.sapiens gene for dopaminergic receptor D-3
gi|579578|emb|A19667.1|A19667[579578]

15612: A09781
H.sapiens (clone 18-4-3) mRNA interferon-gamma receptor segment
gi|412192|emb|A09781.1|A09781[412192]

15613: A09779
H.sapiens (clone 15-21-1) mRNA for interferon-gamma receptor segment binding interferon-gamma
gi|412190|emb|A09779.1|A09779[412190]

15614: A07799
H.sapiens IL-2R-beta mRNA for interleukin-2 beta-chain
gi|1247399|emb|A07799.1|A07799[1247399]

15615: A07801
H.sapiens IL-2R-beta mRNA for interleukin-2 beta-chain
gi|490067|emb|A07801.1|A07801[490067]

15616: A07795
H.sapiens IL-2R-beta mRNA for interleukin-2 receptor beta-chain
gi|412175|emb|A07795.1|A07795[412175]

15617: L11573
Human surfactant protein B mRNA, complete cds
gi|1220354|gb|L11573.1|HUMPSPBQ[1220354]

15618: L40625
Homo sapiens sulfonylurea receptor (SUR) mRNA, 3' end of cds
gi|784881|gb|L40625.1|HUMSUR[784881]

15620: L34579
Homo sapiens (clone HC1) angiotensin II type-2 receptor (AGTR2) gene, complete cds
gi|510700|gb|L34579.1|HUMAIRS[510700]

15621: X97058
H.sapiens mRNA for P2Y6 receptor
gi|1296659|emb|X97058.1|HSP2Y6[1296659]

15622: X96588
H.sapiens mRNA for H-RYK receptor tyrosine kinase gi|1296649|emb|X96588.1|HSHRYKG[1296649]

15623: X80391
H.sapiens OR17-40 gene
gi|516319|emb|X80391.1|HSOR1740[516319]

15624: L41690
Homo sapiens TNF receptor-1 associated protein (TRADD) mRNA, 3' end of cds
gi|808914|gb|L41690.1|HUMTRADD[808914]

15630: X89746
H.sapiens mRNA for neuronal acetylcholine receptor alpha-4 subunit, exon 6
gi|1279464|emb|X89746.1|HSCHRNA46[1279464]

15631: X89745
H.sapiens mRNA for neuronal acetylcholine receptor alpha-4 subunit, exon 5
gi|1279463|emb|X89745.1|HSCHRNA45[1279463]

15632: X89743
H.sapiens mRNA for neuronal acetylcholine receptor alpha-4 subunit, exon 3
gi|1279461|emb|X89743.1|HSCHRNA43[1279461]

15633: X89742
H.sapiens mRNA for neuronal acetylcholine receptor alpha-4 subunit, exon 2
gi|1279460|emb|X89742.1|HSCHRNA42[1279460]

15634: X89741
H.sapiens mRNA for neuronal acetylcholine receptor alpha-4 subunit, exon 1
gi|1279458|emb|X89741.1|HSCHRNA41[1279458]

15644: M21574
Human platelet-derived growth factor receptor alpha (PDGFRA) mRNA, complete cds
gi|189733|gb|M21574.1|HUMPDGFRAA[189733]

15645: X94635
H.sapiens CD97 gene exon 8
gi|4379070|emb|X94635.1|HSX94635[4379070]

15646: X94638
H.sapiens CD97 gene exon 11
gi|1165091|emb|X94638.1|HSX94638[1165091]

15647: X94637
H.sapiens CD97 gene exon 10
gi|1165090|emb|X94637.1|HSX94637[1165090]

15648: X94636
H.sapiens CD97 gene exon 9
gi|1165089|emb|X94636.1|HSX94636[1165089]

15649: X94631
H.sapiens CD97 gene exon 2
gi|1165084|emb|X94631.1|HSX94631[1165084]

15650: X94646
H.sapiens CD97 gene exon 19
gi|1165082|emb|X94646.1|HSX94646[1165082]

15651: X94645
H.sapiens CD97 gene exon 18
gi|1165081|emb|X94645.1|HSX94645[1165081]

15652: X94644
H.sapiens CD97 gene exon 17
gi|1165080|emb|X94644.1|HSX94644[1165080]

15653: X94643
H.sapiens CD97 gene exon 16
gi|1165079|emb|X94643.1|HSX94643[1165079]

15654: X94642
H.sapiens CD97 gene exon 15
gi|1165078|emb|X94642.1|HSX94642[1165078]

15655: X94641
H.sapiens CD97 gene exon 14
gi|1165077|emb|X94641.1|HSX94641[1165077]

15656: X94640
H.sapiens CD97 gene exon 13
gi|1165076|emb|X94640.1|HSX94640[1165076]

15657: X94639
H.sapiens CD97 gene exon 12
gi|1165075|emb|X94639.1|HSX94639[1165075]

15658: L40949
Homo sapiens (clone AT7-5eu) opioid-receptor-like protein mRNA, 5' end
gi|725265|gb|L40949.1|HUMOPRLP[725265]

15659: X57282
H.sapiens mRNA for soluble erythropoietin receptor
gi|36426|emb|X57282.1|HSSER[36426]

15660: Z66526
H.sapiens pancreatic polypeptide receptor PP1 gene
gi|1107699|emb|Z66526.1|HSPP1GN[1107699]

15661: X89013
H.sapiens gene for anti-mullerian hormone type II receptor
gi|1212943|emb|X89013.1|HSDNAAMHI[1212943]

15662: X86163
H.sapiens mRNA for B2-bradykinin receptor, 3'
gi|1220163|emb|X86163.1|HSB2BRRNA[1220163]

15663: X86165
H.sapiens mRNA for B2-bradykinin receptor, R14 allele
gi|1220160|emb|X86165.1|HSB2BRR14[1220160]

15664: X86164
H.sapiens mRNA for B2-bradykinin receptor, C14 allele
gi|1220155|emb|X86164.1|HSB2BRC14[1220155]

15665: L08187
Human cytokine receptor (EBI3) mRNA, complete cds
gi|632973|gb|L08187.1|HUMEBI3X[632973]

15666: L41147
Homo sapiens 5-HT6 serotonin receptor mRNA, complete cds
gi|1162923|gb|L41147.1|HUM5HSR[1162923]

15698: X84755
H.sapiens LHCGR gene, exon 3
gi|1225986|emb|X84755.1|HSLHCGRX3[1225986]

15699: L25829
Human platelet-derived growth factor alpha-receptor (PDGFRA) mRNA, exons 13-16
gi|1220351|gb|L25829.1|HUMPDGFRAX[1220351]

15700: L07746
Human cholecystokinin B receptor (CCK-B) mRNA, complete cds
gi|1220298|gb|L07746.1|HUMCCKBR[1220298]

15701: X86172
H.sapiens B2-bradykinin receptor gene, exon 3, allele R48
gi|1220162|emb|X86172.1|HSB2BRR48[1220162]

15702: X86180
H.sapiens B2-bradykinin receptor gene, promoter region and exon 1
gi|1220159|emb|X86180.1|HSB2BRPX1[1220159]

15703: X86173
H.sapiens B2-bradykinin receptor gene, promotor region and exon 1
gi|1220158|emb|X86173.1|HSB2BREX1[1220158]

15704: X86162

H.sapiens B2-bradykinin receptor gene, 3'
gi|1220157|emb|X86162.1|HSB2BRDNA[1220157]

15705: X86171
H.sapiens B2-bradykinin receptor gene, exon 3, BE3-R43 allele
gi|1220154|emb|X86171.1|HSB2BRBE3[1220154]

15706: X86170
H.sapiens B2-bradykinin receptor gene, exon 2, T allele
gi|1220153|emb|X86170.1|HSB2BRAXT[1220153]

15707: X86168
H.sapiens B2-bradykinin receptor gene, exon 1, 3T allele
gi|1220152|emb|X86168.1|HSB2BR3T[1220152]

15708: X86167
H.sapiens B2-bradykinin receptor gene, exon 1, 3G allele
gi|1220151|emb|X86167.1|HSB2BR3G[1220151]

15709: X86166
H.sapiens B2-bradykinin receptor gene, exon 1, 2G allele
gi|1220150|emb|X86166.1|HSB2BR2G[1220150]

15710: Z69891
H.sapiens mRNA (clone ICRFp507G10101)
gi|1213610|emb|Z69891.1|HSBRN3B2[1213610]

15711: L18983
Homo sapiens tyrosine phosphatase (IA-2/PTP) mRNA, complete cds
gi|662362|gb|L18983.1|HUMTYROPHO[662362]

15712: L76224
Homo sapiens NMDA receptor mRNA, complete cds
gi|1196448|gb|L76224.1|HUMNMRE[1196448]

15715: M73481
Human gastrin releasing peptide receptor (GRPR) mRNA, complete cds gi|183649|gb|M73481.1|HUMGRPR[183649]

15717: M30625
Human dopamine D2 receptor, mRNA, complete cds
gi|181431|gb|M30625.1|HUMD2A[181431]

15718: J02960
Human beta-2-adrenergic receptor gene, complete cds
gi|178203|gb|J02960.1|HUMADRBRA[178203]

15719: M15169
Human beta-2-adrenergic receptor mRNA, complete cds
gi|178201|gb|M15169.1|HUMADRBR[178201]

15720: L18973
Human acetylcholine receptor mRNA, partial cds
gi|441143|gb|L18973.1|HUMACETYL[441143]

15723: M73969
Human interleukin-8 receptor type B (IL8RB) mRNA, complete cds
gi|186516|gb|M73969.1|HUMINTLEU8[186516]

15752: L35233
Homo sapiens autocrine motility factor receptor (AMFR) mRNA, complete cds
gi|521220|gb|L35233.1|HUMNGP78A[521220]

15754: U35399
Human G protein-coupled receptor mRNA, complete cds
gi|1015420|gb|U35399.1|HSU35399[1015420]

15755: L35318
Human rearranged metabotropic glutamate receptor type II (GLUR2) mRNA, complete cds
gi|999415|gb|L35318.1|HUMGLUR2A[999415]

15756: M11730
Human tyrosine kinase-type receptor (HER2) mRNA, complete cds gi|183986|gb|M11730.1|HUMHER2A[183986]

15759: U33017
Human signaling lymphocytic activation molecule (SLAM) mRNA, complete cds
gi|984968|gb|U33017.1|HSU33017[984968]

15761: L47220
Homo sapiens inositol triphosphate receptor type 1 gene fragment
gi|976275|gb|L47220.1|HUMITRT1F[976275]

15762: M37722
Human shorter form basic fibroblast growth factor (bFGF) receptor mRNA, complete cds
gi|179413|gb|M37722.1|HUMBFGFS[179413]

15765: L09753
Homo sapiens CD30 ligand mRNA, complete cds
gi|349277|gb|L09753.1|HUMCD30[349277]

15767: L36645
Homo sapiens receptor protein-tyrosine kinase (HEK8) mRNA, complete cds
gi|551613|gb|L36645.1|HUMRPTKC[551613]

15768: L36644
Homo sapiens receptor protein-tyrosine kinase (HEK7) mRNA, 3' end
gi|551611|gb|L36644.1|HUMRPTKB[551611]

15769: L36643
Homo sapiens receptor protein-tyrosine kinase (HEK5) mRNA, 3' end
gi|551609|gb|L36643.1|HUMRPTKA[551609]

15770: L36642
Homo sapiens receptor protein-tyrosine kinase (HEK11) mRNA, complete cds
gi|551607|gb|L36642.1|HUMRPTK[551607]

15771: L31581

Human G protein-coupled receptor (EBI 1) mRNA, complete cds
gi|468319|gb|L31581.1|HUMEBI1CDN[468319]

15772: L29301
Homo sapiens opioid receptor mRNA, complete cds
gi|459831|gb|L29301.1|HUMOPIOIDA[459831]

15773: L32831
Homo sapiens G protein-coupled receptor (GPR3) gene, complete cds
gi|602311|gb|L32831.1|HUMGPCRD[602311]

15774: L32830
Homo sapiens G protein-coupled receptor (GPR3) gene, exon
gi|602310|gb|L32830.1|HUMGPCRC[602310]

15775: M88461
Human neuropeptide Y peptide YY receptor mRNA, complete cds
gi|189155|gb|M88461.1|HUMNEYPEPY[189155]

15779: M73747
Homo sapiens thyroid stimulating hormone receptor (TSHR) mRNA, complete cds
gi|903759|gb|M73747.1|HUMTSHR[903759]

15780: M73746
Homo sapiens lutropin/choriogonadotropin receptor (LHCGR) mRNA, complete cds
gi|903745|gb|M73746.1|HUMLHCGR[903745]

15781: M90103
Human (clones 18, 23, 27, 24) c-myeloproliferative leukemia virus type K
(c-mpl-K) mRNA, complete cds
gi|184262|gb|M90103.1|HSHMPLK[184262]

15782: M90102
Human (clones 15, 39, 41) c-myeloproliferative leukemia virus type P (c-mpl-P)
mRNA, complete cds
gi|184260|gb|M90102.1|HSHMPLP[184260]

15796: M98512
Human NFG genomic fragment
gi|292359|gb|M98512.1|HUMNF1FRAG[292359]

15797: M98511
Human NFE genomic fragment
gi|292358|gb|M98511.1|HUMNF1FRAE[292358]

15798: M98510
Human NFC genomic fragment
gi|292357|gb|M98510.1|HUMNF1FRAC[292357]

15799: M98508
Human NFA genomic fragment
gi|292355|gb|M98508.1|HUMNF1FRAA[292355]

15801: L32662
Human prostaglandin E2 receptor EP3 subtype isoform IV mRNA, complete cds
gi|484163|gb|L32662.1|HUMEP3IV[484163]

15802: L32661
Human prostaglandin E2 receptor EP3 subtype isoform III mRNA, 3' end
gi|484161|gb|L32661.1|HUMEP3III[484161]

15803: L32660
Human prostaglandin E2 receptor EP3 subtype isoform II mRNA, partial cds
gi|484159|gb|L32660.1|HUMEP3II[484159]

15822: L07594
Human transforming growth factor-beta type III receptor (TGF-beta) mRNA, complete cds
gi|818001|gb|L07594.1|HUMTGFB3C[818001]

15823: M83181
Human serotonin receptor gene, complete cds
gi|808000|gb|M83181.1|HUMHTRB[808000]

15824: M33602
Human T-cell leukemia t(10:14)(q24:q11) chromosomal translocation
gi|339907|gb|M33602.1|HUMTRANSX[339907]

15828: L37112
Homo sapiens vasopressin V3 receptor mRNA, complete cds
gi|791151|gb|L37112.1|HUMVVR[791151]

15829: L35901
Human nicotinic acetylcholine receptor alpha 4 subunit (nAChR) mRNA, complete cds
gi|755647|gb|L35901.1|HUMNACHR4A[755647]

15830: U13666
Human G protein-coupled receptor (GPR1) gene, complete cds
gi|577412|gb|U13666.1|HSU13666[577412]

15831: L35903
Human dopamine D3 receptor gene, exon 6
gi|532478|gb|L35903.1|UMDOPD30S2[532478]

15832: L35902
Human dopamine D3 receptor gene, exon 5
gi|532477|gb|L35902.1|UMDOPD30S1[532477]

15833: L37362
Homo sapiens (clone d2-115) kappa opioid receptor (OPRK1) mRNA, complete cds
gi|722617|gb|L37362.1|HUMOPRK1B[722617]

15834: L35545
Homo sapiens endothelial cell protein C/APC receptor (EPCR) mRNA, complete cds
gi|565267|gb|L35545.1|HUMECPC[565267]

15835: L36130
Homo sapiens kappa opiate receptor mRNA, partial cds
gi|598184|gb|L36130.1|HUMKOR[598184]

15836: L36150
Homo sapiens G protein-coupled receptor (GPR6) gene, complete cds
gi|598156|gb|L36150.1|HUMGPR6A[598156]

15837: L36148
Homo sapiens G protein-coupled receptor (GPR4) gene, complete cds
gi|598152|gb|L36148.1|HUMGPR4A[598152]

15839: L36149
Homo sapiens G protein-coupled receptor (GPR5) gene, complete cds
gi|598154|gb|L36149.1|HUMGPR5A[598154]

15840: M64749
Human homologue of the canine orphan receptor (RDC1) mRNA, 5' end
gi|292418|gb|M64749.1|HUMRDC1A[292418]

15841: L35848
Homo sapiens IgE receptor beta chain (HTm4) mRNA, complete cds
gi|561638|gb|L35848.1|HUMIERB[561638]

16011: L22431
Human very low density lipoprotein receptor, complete cds
gi|437386|gb|L22431.1|HUMVLDLRX[437386]

16012: M90366
Human zona pellucida glycoprotein 2 (ZP2) mRNA, complete cds
gi|292939|gb|M90366.1|HUMZP2GP[292939]

16015: M76125
Human tyrosine kinase receptor (axl) mRNA, complete cds
gi|292869|gb|M76125.1|HUMTYRKINR[292869]

16016: L04489
Homo sapiens (clone NCD18) tumor necrosis factor receptor related protein mRNA, complete exon and repeat region
gi|340022|gb|L04489.1|HUMTUMNEC[340022]

16017: M31163
Human tumor necrosis factor-inducible (TSG-12) mRNA fragment
gi|339990|gb|M31163.1|HUMTSG12A[339990]

16019: M75866
Human tumor necrosis factor receptor 1 (TNFR1) gene, complete cds
gi|339748|gb|M75866.1|HUMTNFR103[339748]

16020: M75865
Human tumor necrosis factor receptor 1 (TNFR1) gene, exons 2-5
gi|339747|gb|M75865.1|HUMTNFR102[339747]

16021: M75864
Human tumor necrosis factor receptor 1 (TNFR1) gene, exon 1
gi|339746|gb|M75864.1|HUMTNFR101[339746]

16026: M85079
Human TGF-beta type II receptor mRNA, complete cds
gi|339569|gb|M85079.1|HUMTGFBIIR[339569]

16027: L06139
Homo sapiens receptor protein-tyrosine kinase (TEK) mRNA, complete cds
gi|292823|gb|L06139.1|HUMTEKRPTK[292823]

16204: L29349
Homo sapiens granulocyte-macrophage colony-stimulating factor receptor alpha-subunit 3 (GM-CSF-RA3) mRNA, complete cds
gi|460284|gb|L29349.1|HUMGMCSA[460284]

16205: L29348
Homo sapiens granulocyte-macrophage colony-stimulating factor receptor alpha-subunit soluble isoform 2 (GM-CSF-RAS2) mRNA, complete cds
gi|460282|gb|L29348.1|HUMGMCS[460282]

16270: M74290
Human substance P receptor protein mRNA
gi|338612|gb|M74290.1|HUMSUBPRA[338612]

16271: M96738
Human somatostatin receptor subtype 3 (SSTR3) gene, complete cds
gi|338498|gb|M96738.1|HUMSSTR3X[338498]

16272: L13033
Homo sapiens somatostatin receptor isoform 2 gene, alternatively spliced exon
gi|292515|gb|L13033.1|HUMSSTR23X[292515]

16273: L07833
Homo sapiens somatostatin receptor (SSTR4) gene, complete cds
gi|307429|gb|L07833.1|HUMSOMATA[307429]

16274: L10126
Human serine/threonine kinase receptor-2-3 (SKR2-3) mRNA, complete cds
gi|558102|gb|L10126.1|HUMSKR23A[558102]

16275: L10125
Human serine/threonine kinase receptor-2-2 (SKR2-2) mRNA, complete cds
gi|558101|gb|L10125.1|HUMSKR22A[558101]

16276: J04132
Human T cell receptor zeta-chain mRNA, complete cds
gi|623041|gb|J04132.1|HUMTCRZCN[623041]

16277: M93221
Human macrophage mannose receptor (MRC1) gene, exon 30
gi|187332|gb|M93221.1|HUMMANR30[187332]

16278: M93220
Human macrophage mannose receptor (MRC1) gene, exon 29
gi|187331|gb|M93220.1|HUMMANR29[187331]

16279: M93219
Human macrophage mannose receptor (MRC1) gene, exon 28
gi|187330|gb|M93219.1|HUMMANR28[187330]

16280: M93218
Human macrophage mannose receptor (MRC1) gene, exon 27
gi|187329|gb|M93218.1|HUMMANR27[187329]

16281: M93217
Human macrophage mannose receptor (MRC1) gene, exon 26
gi|187328|gb|M93217.1|HUMMANR26[187328]

16282: M93216
Human macrophage mannose receptor (MRC1) gene, exon 25
gi|187327|gb|M93216.1|HUMMANR25[187327]

16283: M93215
Human macrophage mannose receptor (MRC1) gene, exon 24
gi|187326|gb|M93215.1|HUMMANR24[187326]

16284: M93214
Human macrophage mannose receptor (MRC1) gene, exon 23
gi|187325|gb|M93214.1|HUMMANR23[187325]

16285: M93213
Human macrophage mannose receptor (MRC1) gene, exon 22
gi|187324|gb|M93213.1|HUMMANR22[187324]

16286: M93212
Human macrophage mannose receptor (MRC1) gene, exon 21
gi|187323|gb|M93212.1|HUMMANR21[187323]

16287: M93211
Human macrophage mannose receptor (MRC1) gene, exon 20
gi|187322|gb|M93211.1|HUMMANR20[187322]

16288: M93210
Human macrophage mannose receptor (MRC1) gene, exon 19
gi|187321|gb|M93210.1|HUMMANR19[187321]

16289: M93209

Human macrophage mannose receptor (MRC1) gene, exon 18
gi|187320|gb|M93209.1|HUMMANR18[187320]

16290: M93208
Human macrophage mannose receptor (MRC1) gene, exon 17
gi|187319|gb|M93208.1|HUMMANR17[187319]

16291: M93207
Human macrophage mannose receptor (MRC1) gene, exon 16
gi|187318|gb|M93207.1|HUMMANR16[187318]

16292: M93206
Human macrophage mannose receptor (MRC1) gene, exon 15
gi|187317|gb|M93206.1|HUMMANR15[187317]

16293: M93205
Human macrophage mannose receptor (MRC1) gene, exon 14
gi|187316|gb|M93205.1|HUMMANR14[187316]

16294: M93204
Human macrophage mannose receptor (MRC1) gene, exon 13
gi|187315|gb|M93204.1|HUMMANR13[187315]

16295: M93203
Human macrophage mannose receptor (MRC1) gene, exon 12
gi|187314|gb|M93203.1|HUMMANR12[187314]

16296: M93202
Human macrophage mannose receptor (MRC1) gene, exon 11
gi|187313|gb|M93202.1|HUMMANR11[187313]

16297: M93201
Human macrophage mannose receptor (MRC1) gene, exon 10
gi|187312|gb|M93201.1|HUMMANR10[187312]

16298: M93200
Human macrophage mannose receptor (MRC1) gene, exon 9 gi|187311|gb|M93200.1|HUMMANR09[187311]

16299: M93199
Human macrophage mannose receptor (MRC1) gene, exon 8
gi|187310|gb|M93199.1|HUMMANR08[187310]

16300: M93198
Human macrophage mannose receptor (MRC1) gene, exon 7
gi|187309|gb|M93198.1|HUMMANR07[187309]

16301: M93197
Human macrophage mannose receptor (MRC1) gene, exon 6
gi|187308|gb|M93197.1|HUMMANR06[187308]

16302: M93196
Human macrophage mannose receptor (MRC1) gene, exon 5
gi|187307|gb|M93196.1|HUMMANR05[187307]

16303: M93195
Human macrophage mannose receptor (MRC1) gene, exon 4
gi|187306|gb|M93195.1|HUMMANR04[187306]

16304: M93194
Human macrophage mannose receptor (MRC1) gene, exon 3
gi|187305|gb|M93194.1|HUMMANR03[187305]

16305: M93193
Human macrophage mannose receptor (MRC1) gene, exon 2
gi|187304|gb|M93193.1|HUMMANR02[187304]

16306: M93192
Human macrophage mannose receptor (MRC1) gene, exon 1
gi|187303|gb|M93192.1|HUMMANR01[187303]

16307: L05198
Homo sapiens insulin receptor substrate 1 (IRS1) gene, repeat polymorphism
gi|307396|gb|L05198.1|HUMIRS1RPT[307396]

16308: M15365
Human low density lipoprotein receptor mutant gene recombination site
gi|187107|gb|M15365.1|HUMLDLRM[187107]

16309: M80637
Human keratinocyte growth factor receptor gene, exon K
gi|186758|gb|M80637.1|HUMKKGFRA[186758]

16310: M81778
Human serotonin 5-HT1C receptor mRNA, complete cds
gi|338027|gb|M81778.1|HUMSER5R[338027]

16311: M81590
Homo sapiens serotonin 1D receptor (5-HT1D~) mRNA, complete cds
gi|338025|gb|M81590.1|HUMSER1DRB[338025]

16312: M81589
Homo sapiens serotonin 1D receptor (5-HT1D`) mRNA, complete cds
gi|338023|gb|M81589.1|HUMSER1DRA[338023]

16313: M91455
Human ryanodine receptor (RYR1) gene, exons 17 and 18
gi|337723|gb|M91455.1|HUMRYR1[337723]

16316: M97639
Human transmembrane receptor (ror2) mRNA, complete cds
gi|337466|gb|M97639.1|HUMROR2A[337466]

16317: M97675
Human transmembrane receptor (ror1) mRNA, complete cds
gi|337464|gb|M97675.1|HUMROR1A[337464]

16318: M74721
Human B-cell antigen receptor (MB-1) mRNA, complete cds
gi|337419|gb|M74721.1|HUMRIGMAMB[337419]

16319: M89796
Human high affinity IgE receptor beta chain gene, complete cds
gi|337417|gb|M89796.1|HUMRIGBCHA[337417]

16329: L09247
Human receptor-type protein tyrosine phosphatase gamma (PTPRG) mRNA, complete cds
gi|292410|gb|L09247.1|HUMPTPRG[292410]

16330: M93426
Human protein tyrosine phosphatase zeta-polypeptide (PTPRZ) mRNA, complete cds
gi|190743|gb|M93426.1|HUMPTPRZ[190743]

16331: M88177
Human platelet activating factor receptor (PTAFR) gene, complete cds
gi|190697|gb|M88177.1|HUMPTAFR[190697]

16332: L16862
Homo sapiens G protein-coupled receptor kinase (GRK6) mRNA, complete cds
gi|388766|gb|L16862.1|HUMPROCRKI[388766]

16333: M86528
Human neurotrophin-4 (NT-4) gene, complete cds
gi|190264|gb|M86528.1|HUMPPNT4P[190264]

16334: L07334
Human platelet-activating factor receptor mRNA, complete cds
gi|190014|gb|L07334.1|HUMPLACTFR[190014]

16335: L26976
Human prostaglandin receptor (PGE-2) mRNA, complete cds
gi|473428|gb|L26976.1|HUMPGE2REP[473428]

16336: M88107
Human formyl peptide receptor (FPR2) mRNA, complete cds
gi|189862|gb|M88107.1|HUMPFPR2A[189862]

16337: M76674
Human platelet activating factor receptor (PAFR) mRNA, complete cds
gi|456293|gb|M76674.1|HUMPAFRX[456293]

16338: M80436
Human platelet activating factor receptor mRNA, complete cds
gi|189537|gb|M80436.1|HUMPAFR[189537]

16339: L26079
Homo sapiens (clone hSR4-1) kappa opioid receptor (OPRK1) gene, complete exon
gi|416143|gb|L26079.1|HUMOPRK1A[416143]

16340: L07615
Human neuropeptide Y receptor Y1 (NPYY1) mRNA, exon 2-3 and complete cds
gi|189284|gb|L07615.1|HUMNPYY1A2[189284]

16341: L07614
Human neuropeptide Y receptor Y1 (NPYY1) mRNA, exon 1
gi|189283|gb|L07614.1|HUMNPYY1A1[189283]

16342: M37981
Human alpha-3 neuronal nicotinic acetylcholine receptor subunit mRNA, complete cds
gi|189252|gb|M37981.1|HUMNNAR[189252]

16343: M73482
Human neuromedin B receptor (NMB-R) mRNA, complete cds
gi|189241|gb|M73482.1|HUMNMBR[189241]

16344: M76675
Human neurokinin 1 receptor (NKIR) mRNA, complete cds
gi|189231|gb|M76675.1|HUMNKIRX[189231]

16345: M81797
Human NK-1 receptor mRNA, complete cds
gi|189213|gb|M81797.1|HUMNK1A[189213]

16346: M32315
Human tumor necrosis factor receptor mRNA, complete cds
gi|189185|gb|M32315.1|HUMNFR[189185]

16347: M84755
Human neuropeptide y receptor mRNA, complete cds
gi|189153|gb|M84755.1|HUMNEUYREC[189153]

16348: M83246
Human monocyte activation antigen (Mo3) mRNA, complete cds
gi|188623|gb|M83246.1|HUMMO3A[188623]

16350: L27080
Human melanocortin 5 receptor (MC5R) gene, complete cds
gi|435599|gb|L27080.1|HUMMC5R[435599]

16351: M28219
Homo sapiens low density lipoprotein receptor (FH 10 mutant causing familial hypercholesterolemia) mRNA, 3' end
gi|619785|gb|M28219.1|HUMLDLRFMT[619785]

16352: M12626
Human low density lipoprotein receptor gene, FH381 (deletion mutant) allele
gi|187103|gb|M12626.1|HUMLDLRFH[187103]

16353: M93189
Human acetylated low density lipoprotein (AcLDL) receptor (LDLR) gene, promoter and exon 1
gi|187100|gb|M93189.1|HUMLDLRAC[187100]

16354: M87772
Human secreted fibroblast growth factor receptor (K-sam-IV) mRNA, complete cds
gi|186783|gb|M87772.1|HUMKSAMIV[186783]

16355: M87771
Human secreted fibroblast growth factor receptor (K-sam-III) mRNA, complete cds
gi|186781|gb|M87771.1|HUMKSAMIII[186781]

16356: M87770
Human fibroblast growth factor receptor (K-sam) mRNA, complete cds
gi|186779|gb|M87770.1|HUMKSAMI[186779]

16357: L04947
Homo sapiens (clones BT3.081.8, BT3.129.5 and BT4.169) receptor tyrosine kinase (KDR) mRNA, 3' end cds
gi|186674|gb|L04947.1|HUMKDRZ[186674]

16358: M32972
Human insulin receptor (INSR) gene, exon 22, clones lambda-hINSR-(1-13)
gi|186462|gb|M32972.1|HUMINSR22[186462]

16359: M32842
Human insulin receptor (INSR) gene, exon 21, clones lambda-hINSR-(1-13)
gi|186461|gb|M32842.1|HUMINSR21[186461]

16360: M32841
Human insulin receptor (INSR) gene, exon 20, clones lambda-hINSR-(1-13)
gi|186460|gb|M32841.1|HUMINSR20[186460]

16361: M32840
Human insulin receptor (INSR) gene, exon 19, clones lambda-hINSR-(1-13)
gi|186459|gb|M32840.1|HUMINSR19[186459]

16362: M32839
Human insulin receptor (INSR) gene, exon 18, clones lambda-hINSR-(1-13)
gi|186458|gb|M32839.1|HUMINSR18[186458]

16363: M32838
Human insulin receptor (hINSR) gene, exon 17, clones lambda-hINSR-(1-13)
gi|186457|gb|M32838.1|HUMINSR17[186457]

16364: M32837
Human insulin receptor (INSR) gene, exon 16, clones lambda-hINSR-(1-13)
gi|186456|gb|M32837.1|HUMINSR16[186456]

16365: M32836
Human insulin receptor (INSR) gene, exon 15, clones lambda-hINSR-(1-13)
gi|186455|gb|M32836.1|HUMINSR15[186455]

16366: M32835
Human insulin receptor (INSR) gene, exon 14, clones lambda-hINSR-(1-13)
gi|186454|gb|M32835.1|HUMINSR14[186454]

16367: M32834
Human insulin receptor (INSR) gene, exon 13, clones lambda-hINSR-(1-13)
gi|186453|gb|M32834.1|HUMINSR13[186453]

16368: M32833
Human insulin receptor (INSR) gene, exon 12, clones lambda-hINSR-(1-13)
gi|186452|gb|M32833.1|HUMINSR12[186452]

16369: M32832
Human insulin receptor (INSR) gene, exon 11, clones lambda-hINSR-(1-13)
gi|186451|gb|M32832.1|HUMINSR11[186451]

16370: M32831
Human insulin receptor (INSR) gene, exon 10, clones lambda-hINSR-(1-13)
gi|186450|gb|M32831.1|HUMINSR10[186450]

16371: M32830
Human insulin receptor (hINSR) gene, exon 9, clones lambda-hINSR-(1-13)
gi|186449|gb|M32830.1|HUMINSR09[186449]

16372: M32829
Human insulin receptor (INSR) gene, exon 8, clones lambda-hINSR-(1-13)
gi|186448|gb|M32829.1|HUMINSR08[186448]

16373: M32828
Human insulin receptor (INSR) gene, exon 7, clones lambda-hINSR-(1-13)
gi|186447|gb|M32828.1|HUMINSR07[186447]

16374: M32827
Human insulin receptor (INSR) gene, exon 6, clones lambda-hINSR-(1-13)
gi|186446|gb|M32827.1|HUMINSR06[186446]

16375: M32826
Human insulin receptor (INSR) gene, exon 5, clones lambda-hINSR-(1-13)
gi|186445|gb|M32826.1|HUMINSR05[186445]

16376: M32825
Human insulin receptor (INSR) gene, exon 4, clones lambda-hINSR-(1-13)
gi|186444|gb|M32825.1|HUMINSR04[186444]

16377: M32824
Human insulin receptor (INSR) gene, exon 3, clones lambda-hINSR-(1-13)
gi|186443|gb|M32824.1|HUMINSR03[186443]

16378: M32823
Human insulin receptor (INSR) gene, exon 2, clones lambda-hINSR-(1-13)
gi|186442|gb|M32823.1|HUMINSR02[186442]

16379: M23100
Human insulin receptor (INSR) gene, exon 1, clones lambda-hINSR-(1-13)
gi|186441|gb|M23100.1|HUMINSR01[186441]

16380: J05043
Human insulin receptor (IR) gene, exon 1
gi|186556|gb|J05043.1|HUMIRSRE[186556]

16381: M24555
Human insulin receptor (INSR) mRNA, partial cds
gi|186480|gb|M24555.1|HUMINSRZ[186480]

16382: L07782
Human insulin receptor gene, last exon
gi|186475|gb|L07782.1|HUMINSRE[186475]

16383: J03466
Human insulin receptor gene, exon 1, clone p-lambda EA2
gi|186469|gb|J03466.1|HUMINSRB[186469]

16384: L19592
Homo sapiens interleukin 8 receptor alpha (IL8RA) gene, complete cds
gi|559051|gb|L19592.1|HUMIL8RAB[559051]

16385: M15864
Human interleukin-2 receptor alpha (IL2R-alpha) gene, exon 1 and promoter region
gi|186375|gb|M15864.1|HUMILA2R1A[186375]

16387: M68932
Human IL-8 receptor mRNA, complete cds
gi|186369|gb|M68932.1|HUMIL8RA[186369]

16388: L12183
Human interleukin 2 receptor gamma chain (IL2RG) gene, exon 8 and complete cds
gi|307056|gb|L12183.1|HUMIL2RG08[307056]

16389: L12182
Human interleukin 2 receptor gamma chain (IL2RG) gene, exon 7
gi|307055|gb|L12182.1|HUMIL2RG07[307055]

16390: L12181
Human interleukin 2 receptor gamma chain (IL2RG) gene, exon 6
gi|307054|gb|L12181.1|HUMIL2RG06[307054]

16391: L12180
Human interleukin 2 receptor gamma chain (IL2RG) gene, exon 5
gi|307053|gb|L12180.1|HUMIL2RG05[307053]

16392: L12179
Human interleukin 2 receptor gamma chain (IL2RG) gene, exon 4
gi|307052|gb|L12179.1|HUMIL2RG04[307052]

16393: L12177
Human interleukin 2 receptor gamma chain (IL2RG) gene, exon 3
gi|307051|gb|L12177.1|HUMIL2RG03[307051]

16394: L12176
Human interleukin 2 receptor gamma chain (IL2RG) gene, exon 2
gi|307050|gb|L12176.1|HUMIL2RG02[307050]

16395: L12178
Human interleukin 2 receptor gamma chain (IL2RG) gene, exon 1 and promoter region
gi|307049|gb|L12178.1|HUMIL2RG01[307049]

16396: M96652
Human interleukin 5 receptor alpha-subunit (IL5R) mRNA, complete cds
gi|186344|gb|M96652.1|HUMIL5RB[186344]

16397: M96651
Human interleukin 5 receptor alpha-subunit (IL5R) mRNA, complete cds
gi|186342|gb|M96651.1|HUMIL5RA[186342]

16398: M74782
Human interleukin 3 receptor (hIL-3Ra) mRNA, complete cds
gi|186330|gb|M74782.1|HUMIL3B[186330]

16405: M84967
Human acrosin-trypsin inhibitor (HUSI-II) gene
gi|553347|gb|M84967.1|HUMHUSIIIA[553347]

16406: M84747
Human interleukin 9 receptor mRNA, complete cds
gi|184508|gb|M84747.1|HUMI9R[184508]

16407: M75128
Human serotonin 1Db receptor (HTR1D) gene, complete cds
gi|184459|gb|M75128.1|HUMHTR1DB[184459]

16408: M64799
Human histamine H2 receptor gene, complete cds
gi|184087|gb|M64799.1|HUMHISH2R[184087]

16409: M83941
Human receptor tyrosine kinase (HEK) mRNA, complete cds
gi|183931|gb|M83941.1|HUMHEK[183931]

16410: L20814
Human glutamate receptor 2 (HBGR2) mRNA, complete cds
gi|493133|gb|L20814.1|HUMHBGR2A[493133]

16412: L09237
growth hormone releasing hormone receptor, human, G-protein coupled receptor, secretin family
gi|337134|gb|L09237.1|HUMGRFREC1[337134]

16413: L15388
Human G protein-coupled receptor kinase (GRK5) mRNA, complete cds
gi|306804|gb|L15388.1|HUMGRK5A[306804]

16415: L08176
Human Epstein-Barr virus induced G-protein coupled receptor mRNA, complete cds
gi|183484|gb|L08176.1|HUMGPCRA[183484]

16416: M64752
Human glutamate receptor subunit (GluH1) mRNA, complete cds
gi|183280|gb|M64752.1|HUMGLURS[183280]

16417: L34075
Human FKBP-rapamycin associated protein (FRAP) mRNA, complete cds
gi|508481|gb|L34075.1|HUMFRAPX[508481]

16418: L08485
Human GABA-benzodiazepine receptor alpha-5-subunit (GABRA5) mRNA, complete cds
gi|182915|gb|L08485.1|HUMGABRA5Y[182915]

16419: M93435
Human gamma-aminobutyric acid receptor A5 subunit (GABRA5) gene
gi|182914|gb|M93435.1|HUMGABRA5X[182914]

16421: M76673
Human RMLP-related receptor I (RMLP R I) mRNA, complete cds
gi|182668|gb|M76673.1|HUMFMLPY[182668]

16422: M76672
Human FMLP-related receptor II (FMLP R II) mRNA, complete cds
gi|182666|gb|M76672.1|HUMFMLPX[182666]

16423: M64347
Human novel growth factor receptor mRNA, 3' cds
gi|182564|gb|M64347.1|HUMFGFLR[182564]

16424: M74921
Human endothelin receptor mRNA, complete cds
gi|182275|gb|M74921.1|HUMETSR[182275]

16427: M96995
Homo sapiens epidermal growth factor receptor-binding protein GRB2 (EGFRBP-GRB2) mRNA sequence
gi|181975|gb|M96995.1|HUMEGFGRBA[181975]

16428: L06622
Homo sapiens endothelin receptor type A (EDNRA) mRNA, complete cds
gi|181956|gb|L06622.1|HUMEDNRA[181956]

16434: M26317
Homo sapiens (clone lambda-6.11) complement receptor 2 (CR2) allele, mRNA fragment
gi|541647|gb|M26317.1|HUMCR2ALLE[541647]

16435: M25785
Homo sapiens transmembrane glycoprotein (c-fms) gene, exon 1, and platelet-derived growth factor receptor (PDGF) gene, 3'UTR
gi|349453|gb|M25785.1|HUMCFMS01[349453]

16436: M91555
Human Fc gamma receptor type I (CD64) gene, exon 6
gi|180160|gb|M91555.1|HUMCD6406[180160]

16437: M91554
Human Fc gamma receptor type I (CD64) gene, exon 5
gi|180159|gb|M91554.1|HUMCD6405[180159]

16438: M91553
Human Fc gamma receptor type I (CD64) gene, exon 4
gi|180158|gb|M91553.1|HUMCD6404[180158]

16439: M91552
Human Fc gamma receptor type I (CD64) gene, exon 3
gi|180157|gb|M91552.1|HUMCD6403[180157]

16440: M91551
Human Fc gamma receptor type I (CD64) gene, exon 2
gi|180156|gb|M91551.1|HUMCD6402[180156]

16441: M91550
Human Fc gamma receptor type I (CD64) gene, exon 1
gi|180155|gb|M91550.1|HUMCD6401[180155]

16442: M63928
Homo sapiens T cell activation antigen (CD27) mRNA, complete cds
gi|180084|gb|M63928.1|HUMCD27A[180084]

16443: M95293
Homo sapiens integrin beta subunit (CD18) gene, exon 1
gi|180022|gb|M95293.1|HUMCD18EX[180022]

16444: M76724
Human leukocyte adhesion receptor alpha subunit (CD11b) gene, 5' end gi|180018|gb|M76724.1|HUMCD11B[180018]

16447: L09230
Human C-C chemokine receptor type 1 (C-C CKR-1) mRNA, complete cds
gi|179984|gb|L09230.1|HUMCCCKR1A[179984]

16448: M81886
Human glutamate receptor type 1 (HBGR1) mRNA, complete cds
gi|179441|gb|M81886.1|HUMBGR1A[179441]

16449: M80776
Human beta-adrenergic receptor kinase 1 mRNA, complete cds
gi|179334|gb|M80776.1|HUMBARK1A[179334]

16450: L25259
Human CTLA4 counter-receptor (B7-2) mRNA, complete cds
gi|416368|gb|L25259.1|HUMB72A[416368]

16451: M93394
Human angiotensin II type-1 receptor (AT1) mRNA, complete cds
gi|178680|gb|M93394.1|HUMANTIIR[178680]

16452: M83712
H.sapiens nicotinic receptor alpha 5 subunit mRNA, complete cds
gi|177925|gb|M83712.1|HUMA5NICRC[177925]

16453: M97370
Human adenosine receptor (A2) gene, complete cds
gi|177891|gb|M97370.1|HUMA2XXX[177891]

16454: M92826
Human serotonin receptor (5-HTR1E) gene, complete cds
gi|177777|gb|M92826.1|HUM5HTR1E[177777]

16455: M86841
Human serotonin receptor type 2 (5HT2) mRNA, complete cds
gi|177775|gb|M86841.1|HUM5HT2A[177775]

16456: M91467
Human serotonin receptor (5HT1E) mRNA, complete cds
gi|177773|gb|M91467.1|HUM5HT1E[177773]

16457: M81830
Human somatostatin receptor isoform 2 (SSTR2) gene, complete cds
gi|307435|gb|M81830.1|HUMSRI2A[307435]

16458: M81829
Human somatostatin receptor isoform 1 gene, complete cds
gi|307433|gb|M81829.1|HUMSRI1A[307433]

16463: L20470
Human very low density lipoprotein receptor mRNA, complete cds
gi|409425|gb|L20470.1|HUMVLDLR[409425]

16464: L20316
Human glucagon receptor mRNA, complete cds
gi|405189|gb|L20316.1|HUMGLUCREC[405189]

16465: M24853
Homo sapiens (clone H12) low affinity IgG receptor CD16 (FcGRIII) mRNA, 3' end
gi|184849|gb|M24853.1|HUMIGGRLA[184849]

16466: M80635
Human fibroblast growth factor receptor-2 (FGFR2) gene, exon B
gi|182572|gb|M80635.1|HUMFGFRA[182572]

16467: L31848
Homo sapiens serine/threonine kinase receptor 2 (SKR2) gene, 3 alternative splices, 3' ends
gi|576680|gb|L31848.1|HUMSKR2[576680]

16472: M29066
Human dopamine D2 receptor (DRD2) mRNA, complete cds
gi|181828|gb|M29066.1|HUMDRD2A[181828]

16473: M85289
Human heparan sulfate proteoglycan (HSPG2) mRNA, complete cds
gi|184426|gb|M85289.1|HUMHSPG2B[184426]

16474: L02931
Human hepatocyte growth factor heavy chain (HGF) gene mRNA, complete cds
gi|184033|gb|L02931.1|HUMHGFX[184033]

16475: L19058
Human glutamate receptor (GLUR5) mRNA, complete cds
gi|455447|gb|L19058.1|HUMGLUR5X[455447]

16476: L20859
Human leukemia virus receptor 1 (GLVR1) mRNA, complete cds
gi|306769|gb|L20859.1|HUMGLVR1X[306769]

16477: M82919
Human gamma amino butyric acid (GABAA) receptor beta-3 subunit mRNA, complete cds
gi|182924|gb|M82919.1|HUMGABRB3A[182924]

16478: M86868
Human gamma amino butyric acid (GABA rho2) gene mRNA, complete cds
gi|182912|gb|M86868.1|HUMGABARHO[182912]

16479: L14061
Human N-formyl receptor-like 2 protein (FPRL2) gene, complete cds
gi|292034|gb|L14061.1|HUMFRPL2[292034]

16480: M95489
H.sapiens follicle stimulating hormone receptor mRNA, complete cds
gi|182772|gb|M95489.1|HUMFSHREC[182772]

16481: M84562
Human formyl peptide receptor-like receptor (FPRL1) mRNA, complete cds
gi|182741|gb|M84562.1|HUMFPRL1A[182741]

16482: M97193
Homo sapiens fibroblast growth factor receptor 2 IIIb (FGFR2) mRNA, complete cds
gi|182566|gb|M97193.1|HUMFGFR2A[182566]

16483: M23562
Human IgE Fc-epsilon-RIIa gene, exon 2, and Fc-epsilon-RIIb gene, exon 1
gi|182444|gb|M23562.1|HUMFCEIIA[182444]

16484: M76595
Human erythropoietin receptor mRNA sequence derived from DNA, 5' end
gi|182147|gb|M76595.1|HUMEPR[182147]

16485: M77244
H.sapiens erythropoietin receptor (EPOR) gene, 5' end
gi|182133|gb|M77244.1|HUMEPOR[182133]

16486: M24736
Human endothelial leukocyte adhesion molecule 1 (ELAM-1) mRNA, complete cds
gi|537523|gb|M24736.1|HUMELAM1A[537523]

16487: L37361
Homo sapiens (clone hELK-L) ELK receptor tyrosine kinase ligand (EFL-3) mRNA, complete cds
gi|567005|gb|L37361.1|HUMEFL3[567005]

16488: L37360
Homo sapiens (clone hEHK1-L) EHK1 receptor tyrosine kinase ligand (EFL-2) mRNA, complete cds
gi|567003|gb|L37360.1|HUMEFL2[567003]

16489: K03193
Human aberrant (short) epidermal growth factor receptor mRNA, complete cds
gi|181984|gb|K03193.1|HUMEGFRS[181984]

16490: M11234
Human epidermal growth factor receptor (EGFR) gene, exon 1 gi|181981|gb|M11234.1|HUMEGFRG[181981]

16491: L06623
Homo sapiens endothelin receptor type B (EDNRB) mRNA, complete cds
gi|181958|gb|L06623.1|HUMEDNRB[181958]

16494: M67439
Human D5 dopamine receptor (DRD5) gene, complete cds
gi|181830|gb|M67439.1|HUMDRD5A[181830]

16495: M77250
Human dopamine D2 receptor gene, intron 6/exon 7 boundary
gi|181825|gb|M77250.1|HUMDRD24[181825]

16496: M77249
Human dopamine D2 receptor gene, exon 3
gi|181824|gb|M77249.1|HUMDRD23[181824]

16497: M77247
Human dopamine D2 receptor gene, exon 2
gi|181823|gb|M77247.1|HUMDRD22[181823]

16498: M77248
Human dopamine D2 receptor gene, exon 1
gi|181822|gb|M77248.1|HUMDRD21[181822]

16499: M33210
Human colony stimulating factor 1 receptor (CSF1R) gene, exon 5
gi|532591|gb|M33210.1|HUMCSF1R03[532591]

16500: M33209
Human colony stimulating factor 1 receptor (CSF1R) gene, exon 4
gi|532590|gb|M33209.1|HUMCSF1R02[532590]

16501: M33208
Human colony stimulating factor 1 receptor (CSF1R) gene, exon 2
gi|532589|gb|M33208.1|HUMCSF1R01[532589]

16502: M83328
Human cell surface glycoprotein CD44 mRNA, (variant F) exons 1, 2, 3, and 5
gi|180135|gb|M83328.1|HUMCD44J[180135]

16503: M83327
Human cell surface glycoprotein CD44 mRNA, (variant E) exons 1, 2, 3, and 4
gi|180134|gb|M83327.1|HUMCD44I[180134]

16504: M83326
Human cell surface glycoprotein CD44 mRNA, (variant D) exon 1, 2, and 3
gi|180133|gb|M83326.1|HUMCD44H[180133]

16505: M83325
Human cell surface glycoprotein CD44 mRNA, (variant C) exons 1 and 2
gi|180132|gb|M83325.1|HUMCD44G[180132]

16506: M83324
Human cell surface glycoprotein CD44 mRNA, (variant B) exon 1
gi|180131|gb|M83324.1|HUMCD44F[180131]

16507: M83554
H.sapiens lymphocyte activation antigen CD30 mRNA, complete cds
gi|180095|gb|M83554.1|HUMCD30A[180095]

16512: M97759
Human adenosine A2b receptor (ADORA2) mRNA, complete cds
gi|178149|gb|M97759.1|HUMADORA1[178149]

16513: M80333
Human m5 muscarinic acetylcholine receptor gene, complete cds
gi|177987|gb|M80333.1|HUMACHRM[177987]

16527: L34339
Human galanin receptor mRNA, complete cds
gi|559047|gb|L34339.1|HUMGALAREC[559047]

16528: L17033
Human heparin-binding epidermal growth factor gene sequence
gi|348176|gb|L17033.1|HUMHBEGFF[348176]

16529: L17032
Human heparin-binding epidermal growth factor gene sequence
gi|348175|gb|L17032.1|HUMHBEGFE[348175]

16530: L17031
Human heparin-binding epidermal growth factor gene, 3' end
gi|348173|gb|L17031.1|HUMHBEGFD[348173]

16531: L17030
Human heparin-binding epidermal growth factor gene, partial cds
gi|348171|gb|L17030.1|HUMHBEGFC[348171]

16532: L17029
Human heparin-binding epidermal growth factor gene, partial cds
gi|348169|gb|L17029.1|HUMHBEGFB[348169]

16533: L17028
Human heparin-binding epidermal growth factor gene, 5' end
gi|348168|gb|L17028.1|HUMHBEGFA[348168]

16534: L13288
Human vasoactive intestial peptide receptor mRNA, complete cds
gi|292903|gb|L13288.1|HUMVIPR[292903]

16545: M31164
Human tumor necrosis factor-inducible (TSG-37) mRNA fragment
gi|339993|gb|M31164.1|HUMTSG37A[339993]

16547: L04270
Homo sapiens (clone CD18) tumor necrosis factor receptor 2 related protein mRNA, complete cds
gi|339761|gb|L04270.1|HUMTNFRRP[339761]

16548: M58286
Homo sapiens tumor necrosis factor receptor mRNA, complete cds
gi|339753|gb|M58286.1|HUMTNFRB[339753]

16562: L07062
Human somatostatin receptor 3 (SSTR3) gene
gi|348713|gb|L07062.1|HUMSSTR3Y[348713]

16563: L07061
Human somatostatin receptor 4 (SSTR4) gene
gi|348712|gb|L07061.1|HUMSSTR4Z[348712]

16564: M73489
Human heat-stable enterotoxin receptor mRNA, complete cds
gi|338501|gb|M73489.1|HUMSTAR[338501]

16565: L04962
Homo sapiens serotonin receptor (HTR1F) gene, complete cds
gi|338464|gb|L04962.1|HUMSRCPT1F[338464]

16566: M84426
Homo sapiens substance P receptor (short form) mRNA, complete cds
gi|338435|gb|M84426.1|HUMSPRSHOR[338435]

16567: M84425
Homo sapiens substance P receptor (long form) mRNA, complete cds
gi|338427|gb|M84425.1|HUMSPRLONG[338427]

16568: M97190
Human Sp2 protein mRNA, complete cds
gi|338300|gb|M97190.1|HUMSP2A[338300]

16569: L05521
Human somatostatin receptor subtype 2 gene related dinucleotide repeat
gi|292502|gb|L05521.1|HUMSOMREPB[292502]

16570: L05520
Human somatostatin receptor subtype 1 gene related dinucleotide repeat
gi|292501|gb|L05520.1|HUMSOMREPA[292501]

16571: L14856
Human somatostatin receptor gene, complete cds
gi|292499|gb|L14856.1|HUMSOMAT[292499]

16572: L02911
Human novel serine kinase receptor mRNA, complete cds
gi|338218|gb|L02911.1|HUMSKRN[338218]

16573: L05597
Human serotonin receptor gene, complete cds
gi|307419|gb|L05597.1|HUMSEROTON[307419]

16576: L10918
Homo sapiens macrophage inflammatory protein-1-alpha/RANTES receptor mRNA, complete cds
gi|292416|gb|L10918.1|HUMRANTES[292416]

16577: L28824
Homo sapiens protein tyrosine kinase (Syk) mRNA, complete cds
gi|479012|gb|L28824.1|HUMPTK[479012]

16578: L04308
Human parathyroid hormone receptor mRNA, complete cds
gi|190721|gb|L04308.1|HUMPTHR[190721]

16579: L02932
Human peroxisome proliferator activated receptor mRNA, complete cds
gi|307340|gb|L02932.1|HUMPPAR[307340]

16580: L07592
Human peroxisome proliferator activated receptor mRNA, complete cds
gi|190229|gb|L07592.1|HUMPPARA[190229]

16581: L29016
Homo sapiens prostanoid IP receptor, complete cds
gi|495042|gb|L29016.1|HUMPIR[495042]

16582: L25124
Homo sapiens prostaglandin E2 receptor mRNA, complete cds
gi|435049|gb|L25124.1|HUMPGE2R[435049]

16583: L28175
Homo sapiens prostaglandin E2 receptor EP2 subtype mRNA, complete cds
gi|452495|gb|L28175.1|HUMPERE[452495]

16584: M84986
Human DNA sequence from 5-hydroxytryptamine 1B receptor region
gi|189401|gb|M84986.1|HUMORFZ[189401]

16585: M84605
Human putative opioid receptor mRNA, complete cds
gi|189391|gb|M84605.1|HUMOPIODRE[189391]

16587: M89473
Human neurokinin 3 receptor (NK3R) mRNA, complete cds
gi|189223|gb|M89473.1|HUMNK3R[189223]

16588: L12214
Human N-formyl receptor gene
gi|189182|gb|L12214.1|HUMNFORECB[189182]

16589: L12213
Human N-formyl receptor gene
gi|189181|gb|L12213.1|HUMNFORECA[189181]

16590: L13267
Homo sapiens N-methyl-d-aspartate receptor (NR1-2) mRNA, 3' end
gi|292284|gb|L13267.1|HUMMARA[292284]

16591: M80634

Human keratinocyte growth factor receptor mRNA, complete cds
gi|186740|gb|M80634.1|HUMKGFRA[186740]

16592: M80638
Human keratinocyte growth factor receptor and fibroblast growth factor receptor-2 gene, exon
gi|186737|gb|M80638.1|HUMKFGFRB[186737]

16593: M80636
Human keratinocyte growth factor receptor and fibroblast growth factor receptor-2 gene, exon
gi|186736|gb|M80636.1|HUMKFGFRA[186736]

16594: M59911
Human integrin alpha-3 chain mRNA, complete cds
gi|186496|gb|M59911.1|HUMINTA3A[186496]

16595: M75914
Human interleukin 5 receptor alpha mRNA, complete cds
gi|186387|gb|M75914.1|HUMILSRAA[186387]

16596: M73724
Human insulin-like growth factor-I receptor gene, exon 1
gi|186383|gb|M73724.1|HUMILGFIR[186383]

16597: M94582
Human interleukin 8 receptor B mRNA, complete cds
gi|186377|gb|M94582.1|HUMILEU8R[186377]

16599: M24559
Human poly-Ig receptor transmembrane secretory component mRNA, 3' end
gi|514365|gb|M24559.1|HUMIGRPOLY[514365]

16600: L03418
Human Fc-gamma receptor I A1 mRNA, complete cds
gi|184840|gb|L03418.1|HUMIGGFCIA[184840]

16601: M73780
Human integrin beta-8 subunit mRNA, complete cds
gi|184520|gb|M73780.1|HUMIB8SUA[184520]

16602: L09732
Homo sapiens 5-hydroxytryptamine 1D receptor gene, complete cds
gi|184467|gb|L09732.1|HUMHTRD1A[184467]

16603: M83180
Human serotonin receptor gene, complete cds
gi|184463|gb|M83180.1|HUMHTRA[184463]

16605: M63889
Human heparin-binding growth factor receptor (HBGF-R-alpha-a3) mRNA, complete cds
gi|183882|gb|M63889.1|HUMHBGFC[183882]

16606: L22607
Homo sapiens A3 adenosine receptor mRNA, complete cds
gi|413863|gb|L22607.1|HUMHAAR[413863]

16607: M82819
Human DNA sequence
gi|183778|gb|M82819.1|HUMHAIGGR[183778]

16608: L13436
Homo sapiens guanylate cyclase mRNA, complete mature peptide
gi|292071|gb|L13436.1|HUMGUANCYC[292071]

16609: L08177
Human EBV induced G-protein coupled receptor (EBI2) mRNA, complete cds
gi|292056|gb|L08177.1|HUMGPCRB[292056]

16610: L07949
Homo sapiens GnRH receptor mRNA, complete cds
gi|292052|gb|L07949.1|HUMGNRHR[292052]

16611: L03380
Human gonadotropin-releasing hormone receptor mRNA, complete cds
gi|183421|gb|L03380.1|HUMGNRHREC[183421]

16612: M73832
Human GM-CSF receptor (GM-CSF receptor) mRNA, complete cds
gi|306773|gb|M73832.1|HUMGMCSFRA[306773]

16613: M64445
Human GM-CSF receptor mRNA, complete cds
gi|183361|gb|M64445.1|HUMGMCSF[183361]

16614: L24751
Homo sapiens glucagon receptor gene, partial cds
gi|404723|gb|L24751.1|HUMGLCGNR[404723]

16615: L01406
Human growth hormone-releasing hormone receptor mRNA, complete cds
gi|183172|gb|L01406.1|HUMGHRHREC[183172]

16616: L08109
Human low-affinity Fc-gamma receptor IIC gene, exons 4-7
gi|183090|gb|L08109.1|HUMGFCIIC[183090]

16617: L08108
Human low-affinity Fc-receptor IIB gene, exons 4-7
gi|183089|gb|L08108.1|HUMGFCIIB[183089]

16618: L08107
Human low-affinity Fc-gamma receptor IIA gene, exons 4-7
gi|183088|gb|L08107.1|HUMGFCIIA[183088]

16619: M69106
Human Gata3 enhancer-binding protein mRNA, complete cds
gi|182999|gb|M69106.1|HUMGATA3BP[182999]

16620: M59216

Human gamma-aminobutyric acid-A (GABA-A) receptor beta-1 subunit, exon 9
gi|182921|gb|M59216.1|HUMGABRB15[182921]

16621: M59215
Human gamma-aminobutyric acid-A (GABA-A) receptor beta-1 subunit, exons 6, 7 and 8
gi|182920|gb|M59215.1|HUMGABRB14[182920]

16622: M59214
Human gamma-aminobutyric acid-A (GABA-A) receptor beta-1 subunit, exon 5
gi|182919|gb|M59214.1|HUMGABRB13[182919]

16623: M59213
Human gamma-aminobutyric acid-A (GABA-A) receptor beta-1 subunit, exon 4
gi|182918|gb|M59213.1|HUMGABRB12[182918]

16624: M59212
Human gamma-aminobutyric acid-A (GABA-A) receptor beta-1 subunit, exons 1, 2 and 3
gi|182917|gb|M59212.1|HUMGABRB11[182917]

16625: M11067
Human c-fms proto-oncogene, exon 2, partial cds
gi|182674|gb|M11067.1|HUMFMSB[182674]

16626: M91647
Human high-affinity Fc IgG receptor gamma polypeptide (FcgammaRI) gene
gi|182486|gb|M91647.1|HUMFCIGGHC[182486]

16627: M91646
Human high-affinity Fc IgG receptor gamma polypeptide (FcgammaRI) gene
gi|182485|gb|M91646.1|HUMFCIGGHB[182485]

16628: M91645
Human high-affinity Fc IgG receptor gamma polypeptide (FcgammaRI) gene
gi|182484|gb|M91645.1|HUMFCIGGHA[182484]

16629: L03420
Human Fc-gamma receptor I B2 mRNA, complete cds
gi|182461|gb|L03420.1|HUMFCGR1BB[182461]

16630: L03419
Human Fc-gamma receptor I B1 mRNA, complete cds
gi|182460|gb|L03419.1|HUMFCGR1B[182460]

16632: L08603
Human melanocortin 4 receptor gene, complete cds
gi|291977|gb|L08603.1|HUMEL4REC[291977]

16633: M93111
Human endothelial cell-derived thrombin receptor cDNA, 5' additional sequence
gi|181945|gb|M93111.1|HUMECTR[181945]

16635: M94915
Human dinucleotide repeat polymorphism gene
gi|181836|gb|M94915.1|HUMDRP[181836]

16636: L12116
Homo sapiens dinucleotide polymorphism in the G-protein coupled receptor gene (d20s32e)
gi|181631|gb|L12116.1|HUMDNP[181631]

16637: M25945
Human DNA sequence, C-beta locus
gi|181627|gb|M25945.1|HUMDNAZ[181627]

16639: L22303
Human dopamine receptor D2 gene, repeat polymorphism
gi|441061|gb|L22303.1|HUMD2RP[441061]

16640: L23333
Human corticotropin releasing factor receptor mRNA, complete cds
gi|408691|gb|L23333.1|HUMCRFRB[408691]

16641: L23332
Human corticotropin releasing factor receptor mRNA, complete cds
gi|408689|gb|L23332.1|HUMCRFRA[408689]

16642: M73238
Human ciliary neurotrophic factor receptor (CNTFR) mRNA, complete cds
gi|180710|gb|M73238.1|HUMCNTFR[180710]

16643: M63835
Human IgG Fc receptor I gene, exon 6 and complete cds
gi|180277|gb|M63835.1|HUMCFCGRI6[180277]

16644: M63834
Human IgG Fc receptor I gene, exon 5
gi|180276|gb|M63834.1|HUMCFCGRI5[180276]

16645: M63833
Human IgG Fc receptor I gene, exon 4
gi|180275|gb|M63833.1|HUMCFCGRI4[180275]

16646: M63832
Human IgG Fc receptor I gene, exon 3
gi|180274|gb|M63832.1|HUMCFCGRI3[180274]

16647: M63831
Human IgG Fc receptor I gene, exon 2
gi|180273|gb|M63831.1|HUMCFCGRI2[180273]

16648: M63830
Human IgG Fc receptor I gene, exon 1
gi|180272|gb|M63830.1|HUMCFCGRI1[180272]

16649: L13605
Human cholecystokinin A receptor mRNA, complete cds
gi|306490|gb|L13605.1|HUMCCKAR[306490]

16650: L08112

Human brain cholecystokinin-B/gastrin receptor mRNA, complete cds
gi|306488|gb|L08112.1|HUMCCBGR[306488]

16651: L04473
Human cholecystokinin receptor mRNA, complete cds
gi|179997|gb|L04473.1|HUMCCKR[179997]

16652: L00587
Human calcitonin receptor mRNA, complete cds
gi|179879|gb|L00587.1|HUMCALREC[179879]

16653: L08893
Human bombesin receptor subtype-3 mRNA, complete cds
gi|291876|gb|L08893.1|HUMBOMB3S[291876]

16654: L27594
Homo sapiens bradykinin B2 receptor gene sequence
gi|508475|gb|L27594.1|HUMBB2R[508475]

16656: M28639
Human autoimmune thyroid disease-related antigen mRNA
gi|291864|gb|M28639.1|HUMATDRAGA[291864]

16657: M91464
Human angiotensinogen II type-1A receptor gene, complete cds
gi|179121|gb|M91464.1|HUMAT1A[179121]

16658: M87290
Human angiotensin II type 1 receptor mRNA, complete cds
gi|178682|gb|M87290.1|HUMANTIR[178682]

16659: M26228
Human anti-angiotensinogen mRNA, partial cds
gi|178641|gb|M26228.1|HUMANGA[178641]

16661: M99590
Homo sapiens (clone pmt2-huma1b) alpha-1B adrenergic receptor gene sequence gi|178211|gb|M99590.1|HUMADRENB[178211]

16663: M93415
Human activin type II receptor mRNA, complete cds
gi|178049|gb|M93415.1|HUMACTIIA[178049]

16664: M74954
Human alpha-5-beta-1 fibronectin receptor
gi|177940|gb|M74954.1|HUMABFIREC[177940]

16665: L25827
Human a7 nicotinic acetylcholine receptor mRNA
gi|438616|gb|L25827.1|HUMA7NAR[438616]

16666: M76446
Human alpha-A1-adrenergic receptor mRNA, complete cds
gi|177806|gb|M76446.1|HUMA1AADR[177806]

16667: M89955
Human 5-HT1D-type serotonin receptor gene, complete cds
gi|177771|gb|M89955.1|HUM5HT1DA[177771]

16668: M89478
Human 5-HT1B serotonin receptor gene
gi|177770|gb|M89478.1|HUM5HT1BSR[177770]

16669: L36162
Homo sapiens (clone TH3L) receptor tyrosine kinase type III (DID) mRNA
gi|537326|gb|L36162.1|HUM3RTK[537326]

16670: L05666
Homo sapiens NMDA receptor subunit (NR1) mRNA, complete cds
gi|307302|gb|L05666.1|HUMNMDAREC[307302]

16671: L14865
Human somatostatin receptor (SST) gene, complete cds
gi|431094|gb|L14865.1|HUMSST28A[431094]

16672: L24894
Human myelin protein zero (PO) gene, exon 1
gi|454413|gb|L24894.1|HUMAAC01[454413]

16673: L24893
Human myelin protein zero (PO) gene, exons 2, 3, 4, 5, and 6
gi|454412|gb|L24893.1|HUMAAC02[454412]

16674: L25119
Human Mu opiate receptor (MOR1) mRNA, complete cds
gi|452072|gb|L25119.1|HUMMOR1X[452072]

16676: L24804
Human (p23) mRNA, complete cds
gi|438651|gb|L24804.1|HUMPRA[438651]

16677: L21954
Human peripheral benzodiazepine receptor gene, exon 4
gi|483405|gb|L21954.1|HSPBR4[483405]

16678: L21953
Human peripheral benzodiazepine receptor gene, exon 3
gi|483404|gb|L21953.1|HSPBR3[483404]

16679: L21952
Human peripheral benzodiazepine receptor gene, exon 2
gi|483403|gb|L21952.1|HSPBR2[483403]

16680: L21951
Human peripheral benzodiazepine receptor gene, exon 1
gi|483402|gb|L21951.1|HSPBR1[483402]

16681: L21950
Human peripheral benzodiazepine receptor related mRNA sequence
gi|483401|gb|L21950.1|HUMBENZA[483401]

16682: L20817
Homo sapiens tyrosine protein kinase (CAK) gene, complete cds
gi|306474|gb|L20817.1|HUMCAK[306474]

16683: L20852
Human leukemia virus receptor 2 (GLVR2) mRNA, complete cds
gi|306771|gb|L20852.1|HUMGLVR2X[306771]

16684: L24470
Homo sapiens prostanoid FP receptor mRNA, complete cds
gi|456563|gb|L24470.1|HUMPF2AR[456563]

16685: L22214
Human adenosine A1 receptor (ADORA1) mRNA exons 1-6, complete cds
gi|347520|gb|L22214.1|HUMADORA1X[347520]

16687: L23503
Human glucagon-like peptide-1 receptor (GLP-1) mRNA, complete cds
gi|402480|gb|L23503.1|HUMGLP1R[402480]

16689: L10820
Human N-formyl peptide receptor (FPR1) gene, complete cds and Alu repeats
gi|182739|gb|L10820.1|HUMFPR1A[182739]

16690: M99293
Homo sapiens seven transmembrane segment receptor mRNA, complete cds
gi|292516|gb|M99293.1|HUMSTSR[292516]

16691: L01639
Human (clone HSY3RR) neuropeptide Y receptor (NPYR) mRNA, complete cds
gi|189313|gb|L01639.1|HUMNYRECA[189313]

16692: L20463
Human A3 adenosine receptor mRNA, complete cds
gi|349448|gb|L20463.1|HUMA3ADENR[349448]

16693: L19872
Human AH-receptor mRNA, complete cds
gi|416141|gb|L19872.1|HUMAHREC[416141]

16694: L17075
Human TGF-b superfamily receptor type I mRNA, complete cds
gi|425147|gb|L17075.1|HUMTGFBRS[425147]

16695: L14075
Homo sapiens immunoglobulin receptor alpha chain gene, complete cds
gi|410211|gb|L14075.1|HUMIGERA[410211]

16696: L11695
Human activin receptor-like kinase (ALK-5) mRNA, complete cds
gi|431034|gb|L11695.1|HUMALK5A[431034]

16697: L22206
Human vasopressin receptor V2 gene, complete cds
gi|347522|gb|L22206.1|HUMV2R[347522]

16698: M91211
Human receptor for advanced glycosylation end products (RAGE) mRNA, partial cds
gi|190845|gb|M91211.1|HUMRAGE[190845]

16699: L20469
Human truncated dopamine D3 receptor mRNA, complete cds
gi|306688|gb|L20469.1|HUMD3DR[306688]

16701: L11315
Homo sapiens receptor tyrosine kinase mRNA, complete cds
gi|403386|gb|L11315.1|HUMRTK[403386]

16702: L19315
Human cholecystokinin A receptor mRNA, complete cds
gi|306595|gb|L19315.1|HUMCHOLREC[306595]

16724: L15310

Homo sapiens glucagon-like peptide-1 receptor gene
gi|292051|gb|L15310.1|HUMGLP1RGA[292051]

16725: M99624
Human epidermal growth factor receptor-related gene, 5' end
gi|178251|gb|M99624.1|HUMAGGCRB[178251]

The invention claimed is:

1. A method of modulating in a subject a cellular immune response to an antigen, comprising administering to the subject a composition comprising a nucleic acid molecule encoding a polypeptide comprising said antigen, a secretory sequence, and an amino acid sequence which comprises a ligand that binds to a cell surface molecule of an antigen presenting cell of monocytic lineage in an amount effective to modulate a cellular immune response.

2. The method of claim 1, in which said amino acid sequence which comprises a ligand that binds to a cell surface molecule comprises an antigen presenting cell (APC) binding domain of an opsonin.

3. The method of claim 2, wherein said APC binding domain of said opsonin is a domain of an opsonin selected from the group of opsonins consisting of: Fibronectin, C3, a collectin, alpha-2 macroglobulin, C-reactive protein, complement component C1q, complement fragment C3b, complement component C4b, mannose binding protein, conglutinin, surfactant protein A, and surfactant protein D.

4. The method of claim 2, wherein said APC binding domain of an opsonin comprises an opsonin.

5. The method of claim 1, wherein said antigen is selected from the group consisting of: a bacterial antigen, a viral antigen, a tumor antigen, an antigen that is associated with an autoimmune disease, and an antigen that is associated with an allergy.

6. The method of claim 1, wherein said subject is a human.

7. The method of claim 1, wherein said composition comprises naked DNA.

8. The method of claim 1, wherein said composition comprises a vector.

* * * * *

SEQUENCE LISTING

<160> NUMBER OF SEQ ID NOS: 9

<210> SEQ ID NO 1
<211> LENGTH: 148
<212> TYPE: DNA
<213> ORGANISM: Artificial
<220> FEATURE:
<223> OTHER INFORMATION: GTX-5: Synthetic oligonucleotide encoding GPI
      modification signal sequence found on the human Thy-1 protein

<400> SEQUENCE: 1
aattccgcgc cggcacagtg ctcagagaca aactggtcaa gtgtgagggc atcagcctgc      60
tggctcagaa cacctcgtgg ctgctgctgc tcctgctgtc cctctccctc ctccaggcca     120
cggatttcat gtccctgtga ctgggtac                                        148

<210> SEQ ID NO 2
<211> LENGTH: 140
<212> TYPE: DNA
<213> ORGANISM: Artificial
<220> FEATURE:
<223> OTHER INFORMATION: GTX-6: Complementary sequence to GTX-5

<400> SEQUENCE: 2
ccagtcacag ggacatgaaa tccgtggcct ggaggaggga gagggacagc aggagcagca      60
gcagccacga ggtgttctga gccagcaggc tgatgccctc acacttgacc agtttgtctc     120
tgagcactgt gccggcgcgg                                                 140

<210> SEQ ID NO 3
<211> LENGTH: 58
<212> TYPE: DNA
<213> ORGANISM: Artificial
<220> FEATURE:
<223> OTHER INFORMATION: Upstream primer

<400> SEQUENCE: 3
gcgaattccg cctaggagtg aattggagga agacataatt ccagaagaag atattatc       58

<210> SEQ ID NO 4
<211> LENGTH: 47
<212> TYPE: DNA
<213> ORGANISM: Artificial
<220> FEATURE:
<223> OTHER INFORMATION: Downstream primer

<400> SEQUENCE: 4
tagccggcgt tgggacaacc ataaaccacc atagattctg tgaatgc                   47

<210> SEQ ID NO 5
<211> LENGTH: 10
<212> TYPE: PRT
<213> ORGANISM: Artificial
<220> FEATURE:
<223> OTHER INFORMATION: Linker

<400> SEQUENCE: 5

Gly Gly Gly Gly Ser Gly Gly Gly Gly Ser
1               5                   10

<210> SEQ ID NO 6
<211> LENGTH: 58
<212> TYPE: DNA
<213> ORGANISM: Artificial

```
-continued

<220> FEATURE:
<223> OTHER INFORMATION: Primer

<400> SEQUENCE: 6
gcgaattcgc gccggcatga ggtctttgct aatcttggtg ctttgcttcc tgcccctg        58

<210> SEQ ID NO 7
<211> LENGTH: 61
<212> TYPE: DNA
<213> ORGANISM: Artificial
<220> FEATURE:
<223> OTHER INFORMATION: Primer

<400> SEQUENCE: 7
ggaagcttgc cctaggtcac agccggcagc ctctgatcca cgcctggacg tcggtaccct      60
t                                                                      61

<210> SEQ ID NO 8
<211> LENGTH: 86
<212> TYPE: DNA
<213> ORGANISM: Artificial
<220> FEATURE:
<223> OTHER INFORMATION: GTX-7: Synthetic oligonucleotide coding for
      the mouse IL2 secretory sequence

<400> SEQUENCE: 8
aattcatgta cagcatgcag ctcgcatcct gtgtcacatt gacacttgtg ctccttgtca      60
acagcgctag ccagtggtac cgttat                                           86

<210> SEQ ID NO 9
<211> LENGTH: 86
<212> TYPE: DNA
<213> ORGANISM: Artificial
<220> FEATURE:
<223> OTHER INFORMATION: GTX-8: Synthetic oligonucleotide coding for
      the mouse IL2 secretory sequence

<400> SEQUENCE: 9
ctagataacg gtaccactgg ctagcgctgt tgacaaggag cacaagtgtc aatgtgacac      60
aggatgcgag ctgcatgctg tacatg                                           86
```